(12) United States Patent
Kudo et al.

(10) Patent No.: US 10,703,762 B2
(45) Date of Patent: Jul. 7, 2020

(54) COMPOUND, MATERIAL FOR ORGANIC ELECTROLUMINESCENCE DEVICE, ORGANIC ELECTROLUMINESCENCE DEVICE AND ELECTRONIC APPARATUS

(71) Applicant: IDEMITSU KOSAN CO., LTD., Tokyo (JP)

(72) Inventors: Yu Kudo, Sodegaura (JP); Yumiko Mizuki, Sodegaura (JP); Masahiro Kawamura, Sodegaura (JP); Tomoki Kato, Sodegaura (JP); Hirokatsu Ito, Sodegaura (JP); Tasuku Haketa, Sodegaura (JP); Yuichi Nishimae, Basel (CH); Annemarie Wolleb, Fehren (CH)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 15/329,167

(22) PCT Filed: Aug. 26, 2016

(86) PCT No.: PCT/JP2016/075100
§ 371 (c)(1),
(2) Date: Jan. 25, 2017

(87) PCT Pub. No.: WO2017/038728
PCT Pub. Date: Mar. 9, 2017

(65) Prior Publication Data
US 2018/0339994 A1 Nov. 29, 2018

(30) Foreign Application Priority Data

Aug. 28, 2015 (JP) .................. 2015-168514

(51) Int. Cl.
| | | |
|---|---|---|
| *C07D 491/22* | (2006.01) | |
| *C07D 491/147* | (2006.01) | |
| *C09K 11/06* | (2006.01) | |
| *H01L 51/50* | (2006.01) | |
| *H01L 51/00* | (2006.01) | |

(52) U.S. Cl.
CPC ....... *C07D 491/22* (2013.01); *C07D 491/147* (2013.01); *C09K 11/06* (2013.01); *H01L 51/0071* (2013.01); *C09K 2211/1007* (2013.01); *C09K 2211/1029* (2013.01); *C09K 2211/1033* (2013.01); *C09K 2211/1044* (2013.01); *C09K 2211/1088* (2013.01); *C09K 2211/185* (2013.01); *H01L 51/5012* (2013.01)

(58) Field of Classification Search
None
See application file for complete search history.

(56) References Cited

U.S. PATENT DOCUMENTS

| | | | |
|---|---|---|---|
| 9,040,172 | B2 | 5/2015 | Parham et al. |
| 9,768,394 | B2 | 9/2017 | Kang et al. |
| 9,859,507 | B2 | 1/2018 | Kang et al. |
| 10,319,918 | B2 | 6/2019 | Kang et al. |
| 2012/0238105 | A1 | 9/2012 | Anémian et al. |
| 2013/0026422 | A1 | 1/2013 | Parham et al. |
| 2013/0087768 | A1 | 4/2013 | Kim et al. |
| 2013/0320269 | A1 | 12/2013 | Cocherel et al. |
| 2014/0014940 | A1 | 1/2014 | Pflumm et al. |
| 2014/0048745 | A1 | 2/2014 | Anémian et al. |
| 2014/0225046 | A1 | 8/2014 | Jatsch et al. |
| 2014/0275530 | A1 | 9/2014 | Jatsch et al. |
| 2015/0034914 | A1 | 2/2015 | Lee et al. |
| 2015/0053938 | A1 | 2/2015 | Zeng et al. |
| 2015/0053939 | A1 | 2/2015 | Adamovich et al. |
| 2015/0228904 | A1 | 8/2015 | Kawamura et al. |
| 2015/0228909 | A1 | 8/2015 | Kim et al. |
| 2015/0270496 | A1 | 9/2015 | Nakano et al. |
| 2015/0318478 | A1 | 11/2015 | Pflumm et al. |
| 2015/0364689 | A1 | 12/2015 | Anémian et al. |
| 2015/0380663 | A1 | 12/2015 | Kim et al. |
| 2016/0013419 | A1 | 1/2016 | Yoshida et al. |
| 2016/0130225 | A1 | 5/2016 | Tasaki et al. |
| 2016/0172599 | A1 | 6/2016 | Ogiwara et al. |
| 2016/0172601 | A1 | 6/2016 | Kawamura et al. |
| 2016/0172602 | A1 | 6/2016 | Ogiwara et al. |
| 2016/0190469 | A1 | 6/2016 | Ogiwara et al. |
| 2016/0211462 | A1 | 7/2016 | Ogiwara et al. |
| 2016/0254456 | A1 | 9/2016 | Heil et al. |
| 2016/0380206 | A1 | 12/2016 | Kim et al. |
| 2017/0047528 | A1 | 2/2017 | Kang et al. |
| 2017/0141326 | A1 | 5/2017 | Kang et al. |
| 2017/0352814 | A1 | 12/2017 | Kang et al. |

FOREIGN PATENT DOCUMENTS

| | | |
|---|---|---|
| CN | 101220034 A | 7/2008 |
| CN | 104718210 A | 6/2015 |
| CN | 104829626 A | 8/2015 |
| CN | 106232601 A | 12/2016 |
| CN | 106459074 A | 2/2017 |

(Continued)

OTHER PUBLICATIONS

International Search Report dated Nov. 9, 2016 in PCT/JP2016/075100.

(Continued)

*Primary Examiner* — Samantha L Shterengarts
(74) *Attorney, Agent, or Firm* — Foley & Lardner LLP

(57) ABSTRACT

A compound represented by the following formula (1):

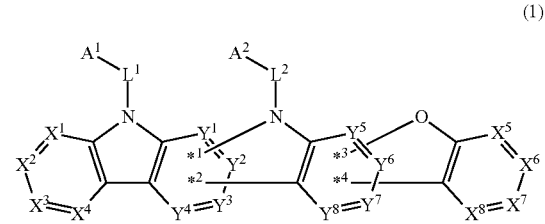

(1)

35 Claims, No Drawings

(56) References Cited

FOREIGN PATENT DOCUMENTS

| | | |
|---|---|---|
| JP | 2013-82662 A | 5/2013 |
| JP | 2015-151399 A | 8/2015 |
| JP | 2015-153911 A | 8/2015 |
| JP | 2016-025203 A | 2/2016 |
| KR | 10-2011-0102055 A | 9/2011 |
| KR | 10-2014-0097044 A | 8/2014 |
| KR | 10-2014-0136722 A | 12/2014 |
| KR | 10-2016-0028737 A | 3/2016 |
| KR | 10-2016-0016078 A | 4/2016 |
| KR | 10-2016-0046077 A | 4/2016 |
| WO | WO-2012/141273 A1 | 10/2012 |
| WO | WO-2013/154325 A1 | 10/2013 |
| WO | WO 2014/057684 A1 | 4/2014 |
| WO | WO 2014/142467 A1 | 9/2014 |
| WO | WO 2015/108325 A1 | 7/2015 |
| WO | WO-2015/165563 A1 | 11/2015 |
| WO | WO 2015/182994 A1 | 12/2015 |
| WO | WO-2015/192941 A1 | 12/2015 |
| WO | WO-2016/024637 A1 | 2/2016 |
| WO | WO-2016/031703 A1 | 3/2016 |
| WO | WO 2016/036171 A1 | 3/2016 |
| WO | WO-2016/125807 A1 | 8/2016 |
| WO | WO-2016/129536 A1 | 8/2016 |
| WO | WO-2016/149608 A1 | 9/2016 |

OTHER PUBLICATIONS

Office Action dated Mar. 27, 2020 for corresponding Chinese Patent Application No. 201680002131.0.

COMPOUND, MATERIAL FOR ORGANIC ELECTROLUMINESCENCE DEVICE, ORGANIC ELECTROLUMINESCENCE DEVICE AND ELECTRONIC APPARATUS

CROSS-REFERENCE TO RELATED APPLICATIONS

The present application is a U.S. national stage application claiming the benefit of International Patent Application No. PCT/JP2016/075100, filed Aug. 26, 2016, which claims the benefit of priority to Japanese Patent Application No. 2015-168514, filed Aug. 28, 2015, the entireties of which are hereby incorporated by reference.

TECHNICAL FIELD

The invention relates to a novel compound, a material for an organic electroluminescence device, an organic electroluminescence device and an electronic apparatus.

BACKGROUND ART

Increase in luminous efficiency, lowering in driving voltage and prolonged lifetime of a phosphorescent organic EL device is a universal object, and various materials have been developed in order to attain this object.

It is known that a compound having a fused ring structure in which an aromatic six-membered ring and a five-membered ring are fused alternately and repeatedly is used as a host material of an emitting layer of a phosphorescent organic EL device (Patent Document 1, for example).

Patent Document 1 discloses a compound having a structure in which a benzene ring, a nitrogen-containing five-membered ring, a benzene ring, a nitrogen-containing five-membered ring, a benzene ring, a sulfur-containing five-membered ring and a benzene ring are fused in this order (claim 1) (hereinafter, referred to as the compound disclosed in Patent Document 1).

RELATED ART DOCUMENT

Patent Document

Patent Document 1: WO2014/142467A1

SUMMARY OF THE INVENTION

As for a host material for a phosphorescent organic electroluminescence device, many of conventional host materials allow holes to be flown rather than electrons. Therefore, a conventional host material is difficult in adjusting carrier balance, and hence, is not satisfactory in lifetime.

An object of the invention is to provide a novel compound that is useful as a material for a phosphorescent organic electroluminescence device.

Another object of the invention is to provide an organic electroluminescence device that is obtained by using the compound.

According to one aspect of the invention, the following compound, material for an organic electroluminescence device, organic electroluminescence device and electronic apparatus are provided.

The compound according to one aspect of the invention is characterized in that it is represented by the following formula (1):

(1)

$$\begin{array}{c} A^1\diagdown_{L^1} \quad A^2\diagdown_{L^2} \\ \text{[structure]} \end{array}$$

wherein in the formula (1), $A^1$ and $A^2$ are independently a substituted or unsubstituted aryl group including 6 to 50 carbon atoms that form a ring (hereinafter referred to as "ring carbon atoms") or a substituted or unsubstituted heteroaryl group including 5 to 50 atoms that form a ring (hereinafter referred to as "ring atoms");

$L^1$ and $L^2$ are independently a single bond, a substituted or unsubstituted arylene group including 6 to 60 ring carbon atoms or a substituted or unsubstituted heteroarylene group including 5 to 50 ring atoms;

$X^1$ to $X^8$ are independently CH, C($R^a$) or N;

*1 to *4 are independently an atomic bonding that forms a single bond;

any adjacent two of $Y^1$ to $Y^4$ are Cs that independently form a single bond with *1 and *2, and remaining two of $Y^1$ to $Y^4$ are independently CH, C($R^a$) or N;

any adjacent two of $Y^5$ to $Y^8$ are Cs that independently form a single bond with *3 and *4, and remaining two of $Y^5$ to $Y^8$ are independently CH, C($R^a$) or N; and $R^a$ is a substituent, and when plural $R^a$s are present, the plural $R^a$s are independently the same as or different from each other, and two selected from the plural $R^a$s may be bonded to each other to form a ring.

The material for an organic electroluminescence device according to one aspect of the invention is characterized in that it comprises the compound according to one aspect of the invention which is represented by the above formula (1).

The organic electroluminescence device according to one aspect of the invention is an organic electroluminescence device comprising a cathode, an anode and one or more organic thin film layers between the cathode and the anode, wherein the one or more organic thin film layers include an emitting layer, and at least one layer of the one or more organic thin film layers comprises the compound represented by the formula (1) according to one aspect of the invention.

The electronic apparatus according to one aspect of the invention is characterized in that it is provided with the organic electroluminescence device according to one aspect of the invention.

According to one aspect of the invention, it is possible to provide a novel compound that is useful as a material for a phosphorescent organic electroluminescence device.

According to one aspect of the invention, it is possible to provide an organic electroluminescence device obtained by using the compound.

MODE FOR CARRYING OUT THE INVENTION

A. Compound

The compound according to one aspect of the invention is represented by the following formula (1) (hereinafter simply referred to as "the compound represented by the formula (1)").

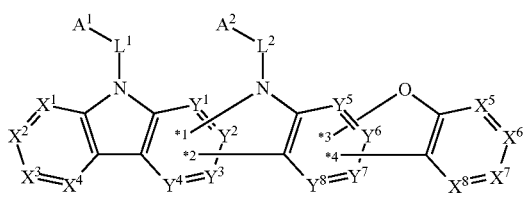

wherein in the formula (1), $A^1$ and $A^2$ are independently a substituted or unsubstituted aryl group including 6 to 50 ring carbon atoms or a substituted or unsubstituted heteroaryl group including 5 to 50 ring atoms;

$L^1$ and $L^2$ are independently a single bond, a substituted or unsubstituted arylene group including 6 to 60 ring carbon atoms or a substituted or unsubstituted heteroarylene group including 5 to 50 ring atoms;

$X^1$ to $X^8$ are independently CH, $C(R^a)$ or N;

*1 to *4 are independently an atomic bonding that forms a single bond;

any adjacent two of $Y^1$ to $Y^4$ are Cs that respectively form a single bond with *1 and *2, and remaining two of $Y^1$ to $Y^4$ are independently CH, $C(R^a)$ or N;

any adjacent two of $Y^5$ to $Y^8$ are Cs that respectively form a single bond with *3 and *4, and remaining two f$Y^5$ to $Y^8$ are independently CH, $C(R^a)$ or N;

$R^a$ is a substituent, and when plural $R^a$s are present, they may be the same as or different from each other, and two selected from the plural $R^a$s may be bonded with each other to form a ring.

Many of conventional host materials for a phosphorescent organic EL device containing the compound disclosed in Patent Document 1 tend to allow holes to be flown easily rather than electrons. Therefore, a conventional host material is difficult in adjusting carrier balance, and hence, is not satisfactory in lifetime.

The compound represented by the formula (1) has a structure in which an aromatic six-membered ring, a nitrogen-containing five-membered ring, an aromatic six-membered ring, a nitrogen-containing five-membered ring, an aromatic six-membered ring, a nitrogen-containing five-membered ring and an aromatic six-membered ring are fused in this order. This structure has a high planarity, and hence, the molecular orbit is widened to transport holes well. Further, contrary to conventional materials, it has a property that it allows electrons to be flown easily than holes. Further, it can contribute to lowering in driving voltage of the device.

The compound represented by the formula (1) can prolong the device life as compared with the compound disclosed in Patent Document 1. The reason therefor is supposed to be that oxygen atoms are hardly oxidized as compared with sulfur atoms, and hence hardly deteriorated.

As compared with the compound disclosed in Patent Document 1 or a compound having a structure in which an aromatic six-membered ring, a nitrogen-containing five-membered ring, an aromatic six-membered ring, a nitrogen-containing five-membered ring, an aromatic six-membered ring, a nitrogen-containing five-membered ring and an aromatic six-membered ring are fused in this order, the compound represented by the formula (1) has a high energy in the lowest triplet excited state (T1), and hence can realize a high luminous efficiency.

Further, in the compound represented by the formula (1), the structure in which an aromatic six-membered ring, a nitrogen-containing five-membered ring, an aromatic six-membered ring, a nitrogen-containing five-membered ring, an aromatic six-membered ring, an oxygen-containing five-membered ring and an aromatic six-membered ring are fused in this order constitutes a donor unit. Due to presence of an acceptor substituent in the nitrogen atom, a high luminous efficiency can be realized.

By using the compound represented by the formula (1), carrier balance adjustment of a phosphorescent organic EL device can be facilitated, whereby the efficiency of the device can be increased. Further, due to adjusted carrier balance, deterioration of each material constituting the device can be prevented, whereby device life can be prolonged.

The compound represented by the formula (1) is useful as a host material of a phosphorescent emitting layer. Further, it has excellent carrier transporting property, and hence, is useful as a carrier transporting material (hole-transporting material, electron-transporting material, or the like).

The compound represented by the formula (1) is more preferably selected from the compounds represented by the following formulas (1-a) to (1-d):

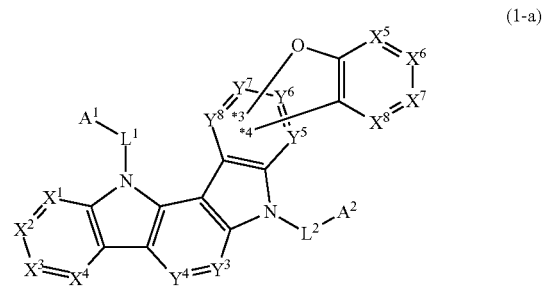

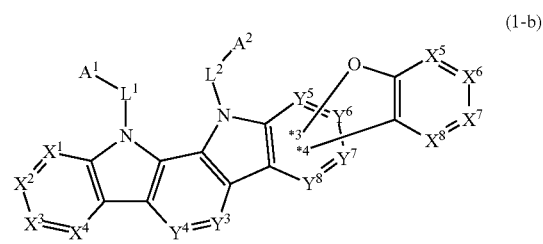

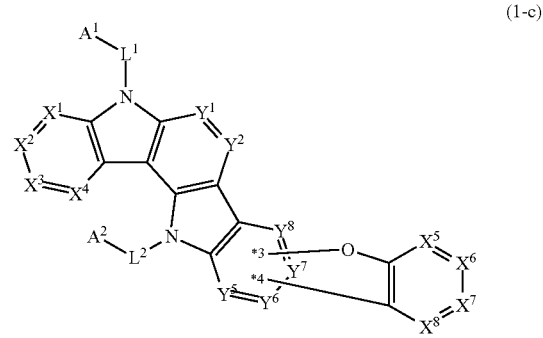

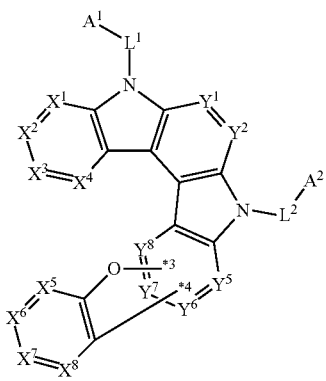

(1-d)

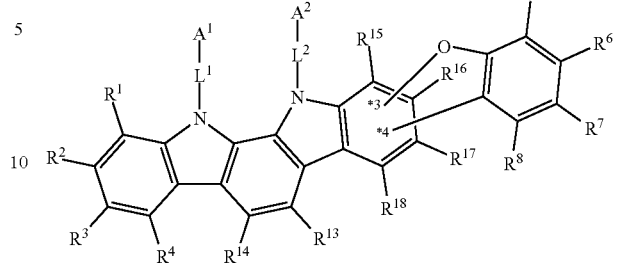

(3-1)

wherein in the formulas (1-a) to (1-d), $A^1, A^2, L^1, L^2, X^1$ to $X^8, Y^1$ to $Y^8$, *3 and *4 are as defined in the formula (1).

Among the compounds represented by the formula (1), as compared with compounds in which the bonding position of *1 and *2 are $Y^2$ and $Y^3$, compounds in which the bonding position of *1 and *2 are $Y^1$ and $Y^2$, or $Y^3$ and $Y^4$ have a higher luminous efficiency and have a prolonged lifetime.

It is preferred that the compound represented by the formula (1) be a compound represented by the following formula (2):

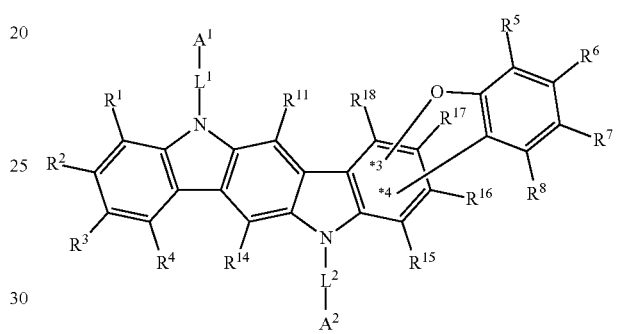

(3-2)

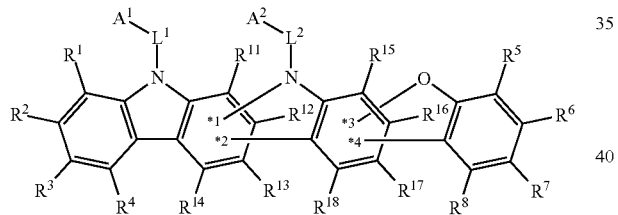

(2)

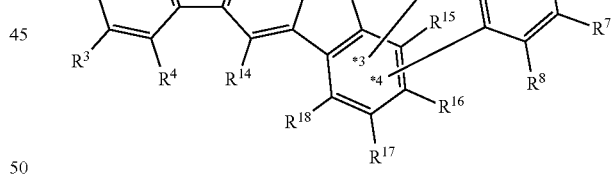

(3-3)

wherein in the formula (2), $A^1, A^2, L^1, L^2$, and *1 to *4 are as defined in the formula (1); $R^1$ to $R^8$ are independently a hydrogen atom or a substituent $R^a$;

any adjacent two of $R^{11}$ to $R^{14}$ form a single bond with *1 and *2, and remaining two of $R^{11}$ to $R^{14}$ are independently a hydrogen atom or a substituent $R^a$;

any adjacent two of $R^{15}$ to $R^{18}$ form a single bond with *3 and *4, and remaining two of $R^{15}$ to $R^{18}$ are independently a hydrogen atom or a substituent $R^a$; and $R^a$ is as defined in the formula (1).

It is preferred that $R^1$ to $R^8$ be a hydrogen atom in the formula (2).

It is preferred that the compound represented by the formula (2) be selected from a group consisting of compounds represented by the following formulas (3-1) to (3-6). It is further preferred that the compound be selected from a group consisting of compounds represented by the following formulas (3-1) and (3-4) to (3-6).

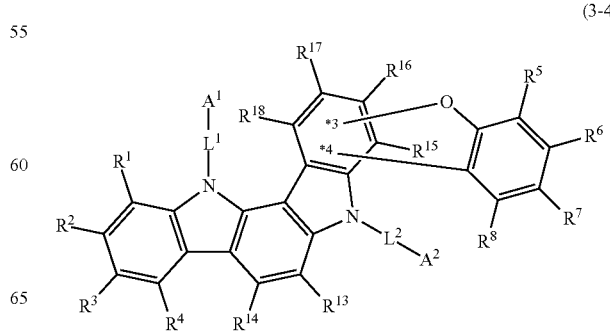

(3-4)

(3-5)

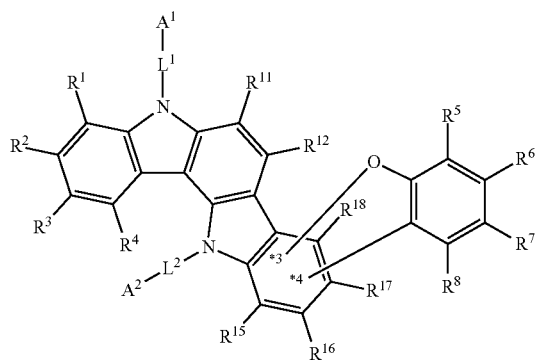

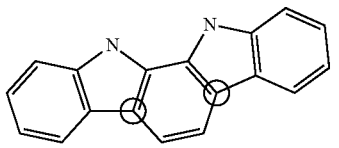

Para-fusion-1

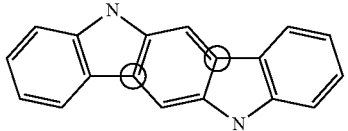

Para-fusion-2

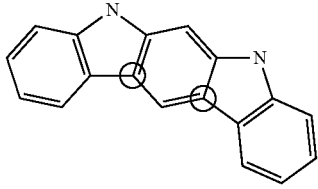

Meta-fusion-1

(3-6)

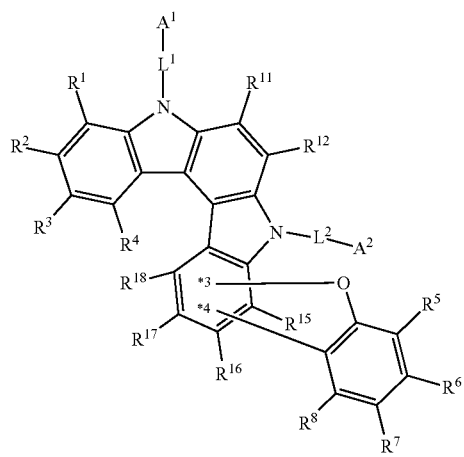

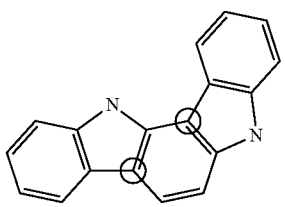

Meta-fusion-2

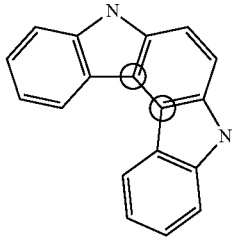

Ortho-fusion wherein in the formulas (3-1) to (3-6), $A^1$, $A^2$, $L^1$, $L^2$, *3 and *4 are as defined in the formula (1); and $R^1$ to $R^8$ and $R^{11}$ to $R^{18}$ are as defined in the formula (2).

The formulas (3-1) to (3-6) respectively specify the bonding positions of *1 and *2 in the formula (2).

In the formulas (3-1) and (3-4) to (3-6), it is preferred that $R^1$ to $R^8$ be a hydrogen atom.

In the present specification, the relationship of the position at which each aromatic six-membered ring and each five-membered ring containing a nitrogen atom or an oxygen atom are fused in the compound represented by the formula (1) is represented as follows. An explanation is made taking as an example an indolocarbazole skeleton. Note the benzene ring that is fused between two nitrogen-containing five-membered rings. The two positions at which the respective two nitrogen-containing five-membered ring is bonded with adjacent benzene rings without bonding with the nitrogen atoms in the two five-membered rings are in any of the para (p), the meta (m) and ortho (o) positional relationships, and the fusion is referred to as the para-fusion (p-fusion), meta-fusion (m-fusion) and ortho-fusion (o-fusion). Specifically, this positional relationship is shown by using the indolocarbazole skeleton as follows.

In the compound represented by the formula (1), a benzofuro skeleton is further fused to the indolocarbazole skeleton. The position of fusion of a benzofuro skeleton is shown as above. For example, a benzofuro skeleton is fused to the indolocarbazole skeleton of the above-mentioned para-fusion-1, the following structure can be taken.

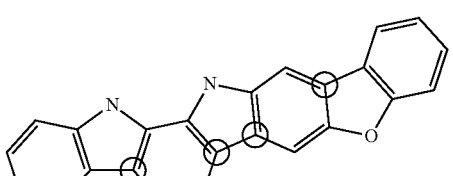

Para-para-fusion 1

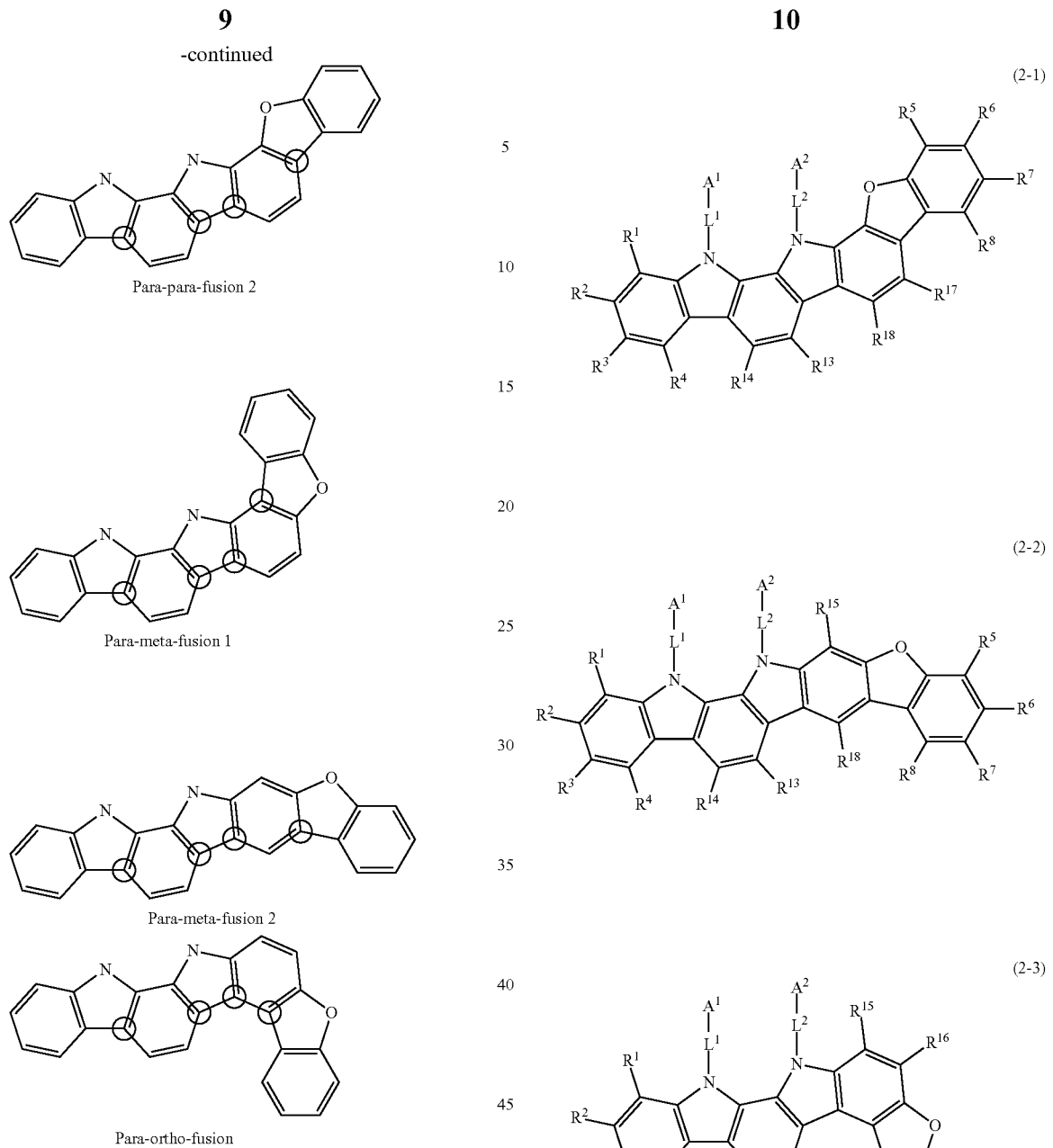

In the present specification, the fusion mode of the compound represented by the formula (1) is abbreviated, for example, as "p-p fused" or "p-p", in the case of a para-para fusion.

Among the compounds represented by the formula (1), the fusion mode of o-o, o-m, o-p, m-o, m-m, m-p, p-o and p-m are preferable since the lowest triplet excited state (T1) is high, and hence luminous efficiency is improved.

Among the compounds represented by the formula (1), the fusion mode of m-m, m-p and p-m are preferable since it enables hole transportability to be high.

The compounds represented by the formulas (3-1) and (3-2) are selected from the group consisting of compounds represented by the following formulas (2-1) to (2-12). The compounds represented by the formula (3-1) are selected from the group consisting of the compounds represented by the following formulas (2-1) to (2-6).

(2-5)

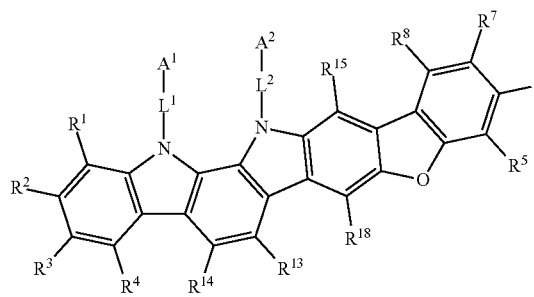

(2-6)

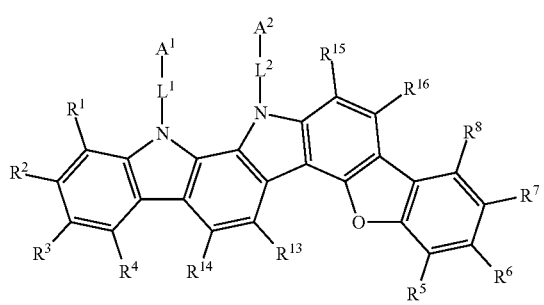

(2-7)

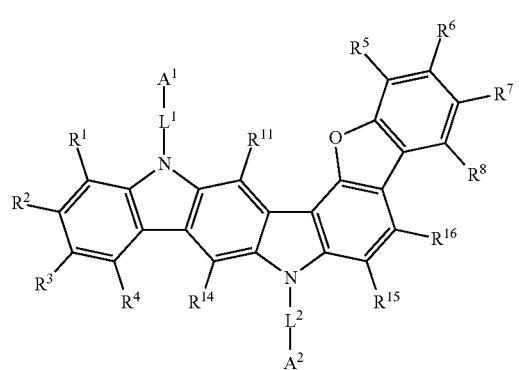

(2-8)

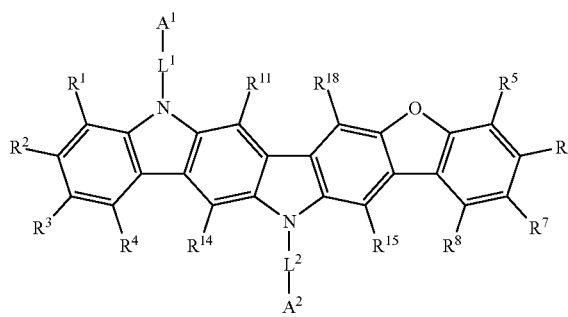

(2-9)

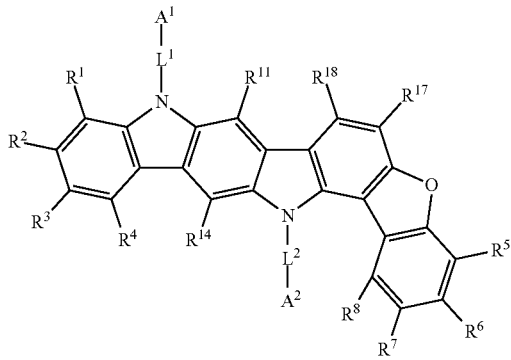

(2-10)

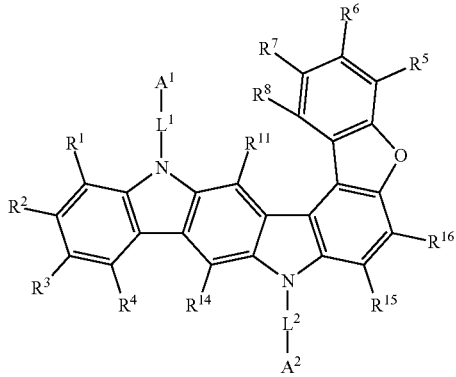

(2-11)

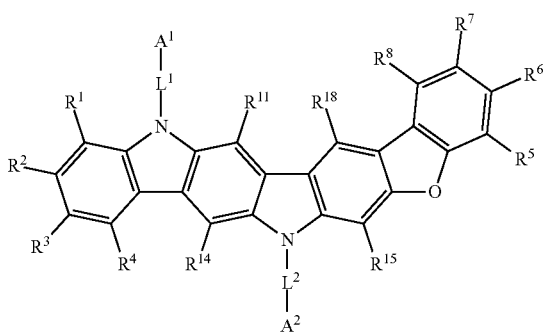

(2-12)

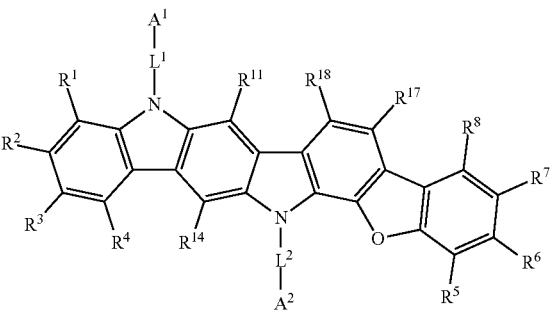

wherein in the formulas (2-1) to (2-12),
$A^1$, $A^2$, $L^1$ and $L^2$ are as defined in the formula (1); and $R^1$ to $R^8$ and $R^{11}$ to $R^{18}$ are as defined in the formula (2).

Among the compounds represented by the formulas (2-1) to (2-12), the compound is preferably selected from the group consisting of the compounds represented by the formulas (2-1) to (2-6), more preferably selected from the group consisting of the compounds represented by the formulas (2-2) to (2-4), (2-6), (2-7) and (2-9) to (2-11), and further preferably selected from the group consisting of the compounds represented by the formulas (2-2) to (2-4) and (2-6).

The compounds represented by the formulas (3-3) to (3-5) are selected from the group consisting of compounds represented by the following formulas (2-13) to (2-30). The compounds represented by the formulas (3-4) and (3-5) are selected from the group consisting of the compounds represented by the following formulas (2-19) to (2-30).

(2-13)

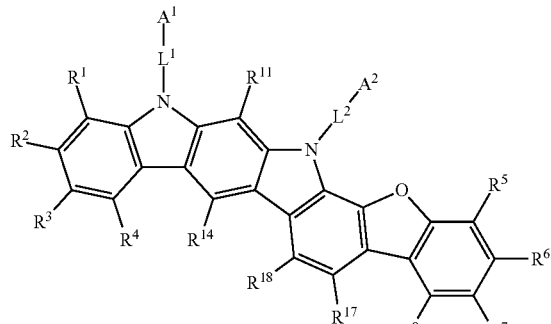

(2-14)

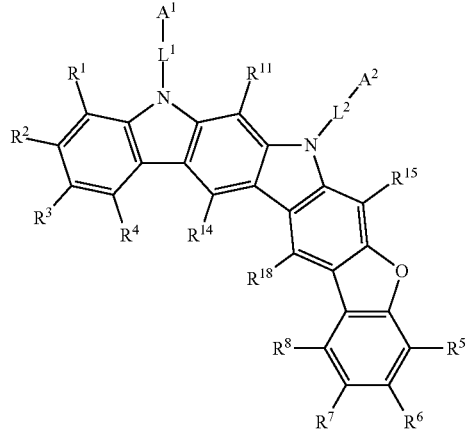

(2-15)

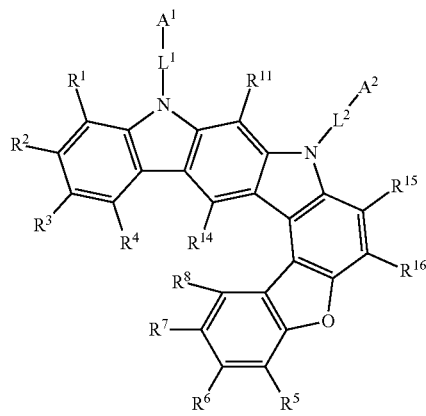

(2-16)

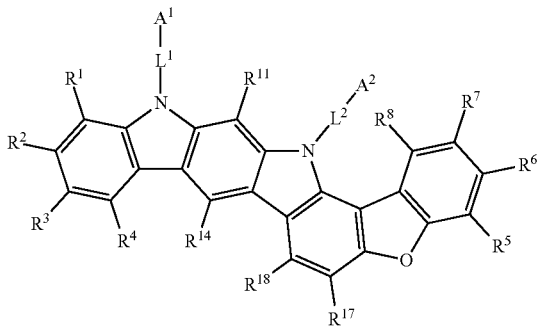

(2-17)

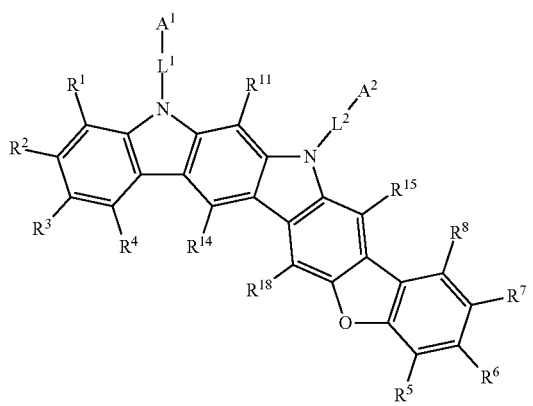

(2-18)

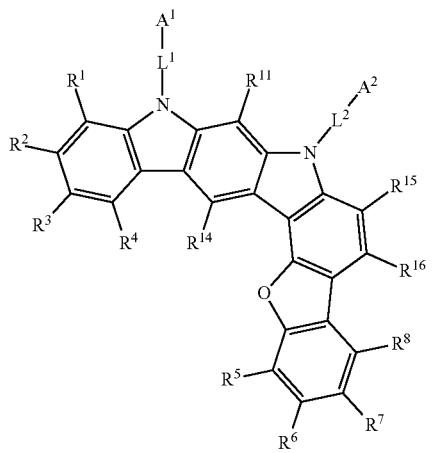

(2-19)

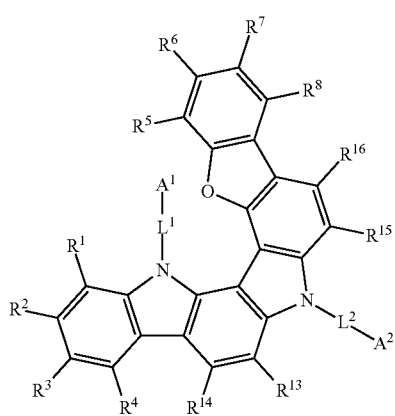

(2-20)
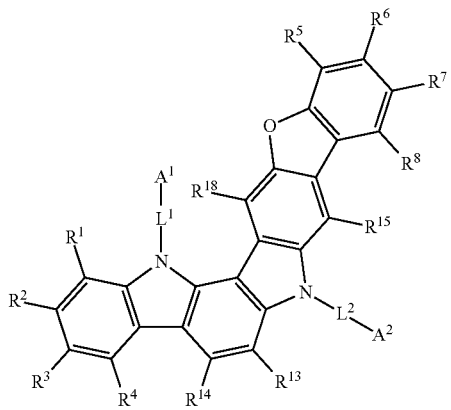
(2-21)
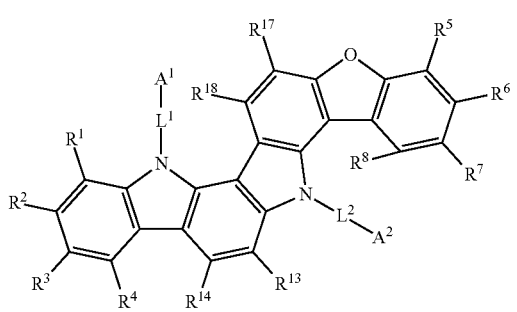
(2-22)
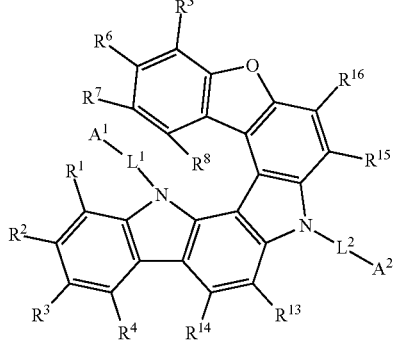
(2-23)
(2-24)
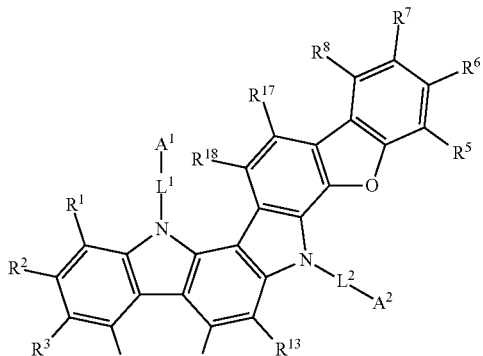
(2-25)
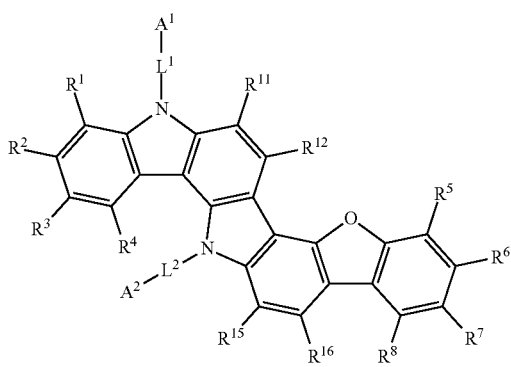
(2-26)
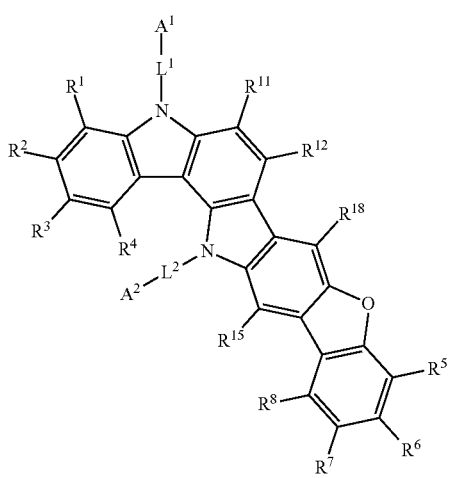

(2-27)
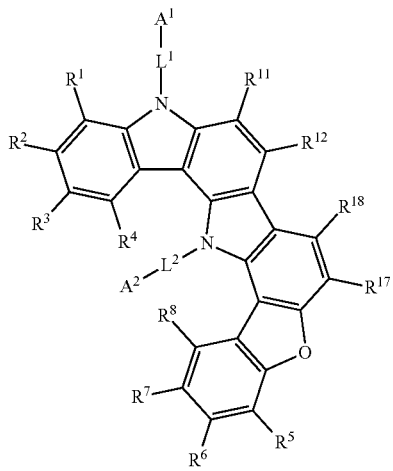
(2-28)
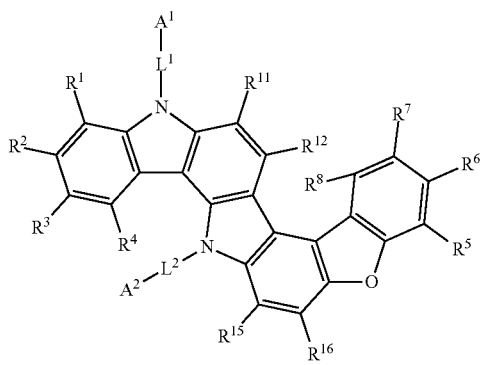
(2-29)
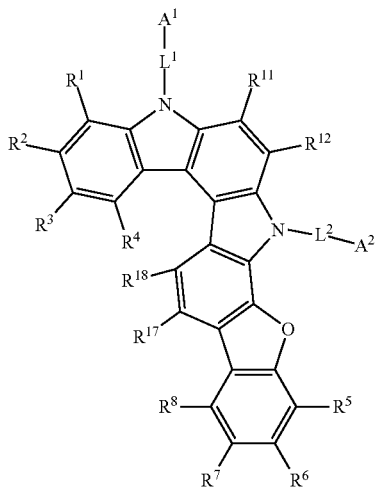
(2-30)
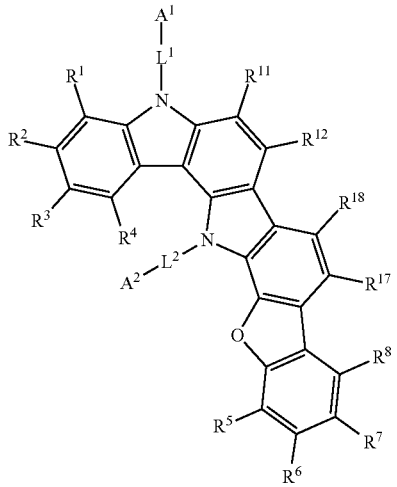
wherein in the formulas (2-13) to (2-30),
$A^1$, $A^2$, $L^1$ and $L^2$ are as defined in the formula (1); and
$R^1$ to $R^8$ and $R^{11}$ to $R^{18}$ are as defined in the formula (2).
The compound represented by the formula (3-6) is selected from the group consisting of compounds represented by the following formulas (2-31) to (2-36).
(2-31)

(2-32)

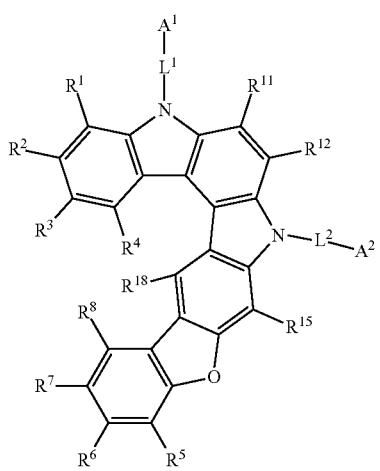

(2-33)

(2-34)

(2-35)

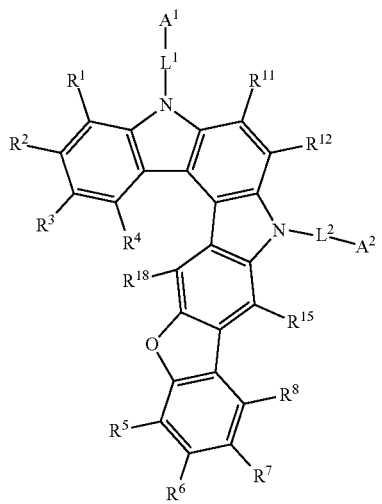

(2-36)

wherein in the formulas (2-31) to (2-36),
A¹, A², L¹ and L² are as defined in the formula (1); and R¹ to R⁸ and R¹¹ to R¹⁸ are as defined in the formula (2).

In the formulas (2-1) to (2-6) and (2-19) to (2-36), it is preferred that R¹ to R⁸ be a hydrogen atom.

In the formulas (2-1) to (2-6), (2-7) to (2-12), (2-13) to (2-18), (2-19) to (2-24), (2-25) to (2-30) and (2-31) to (2-36) respectively specify the bonding positions of *3 and *4 in the formulas (3-1) to (3-6).

It is preferred that the compounds represented by the formulas (3-1) and (3-2) be respectively compounds represented by the following formulas (3-1-1) and (3-2-1). The compound represented by the formula (3-1) is more preferably a compound represented by the following formula (3-1-1).

(3-1-1)

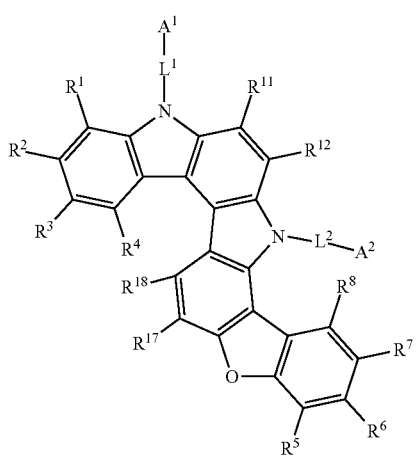

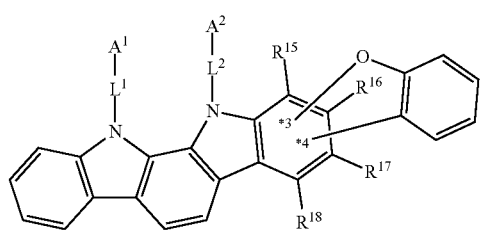

-continued

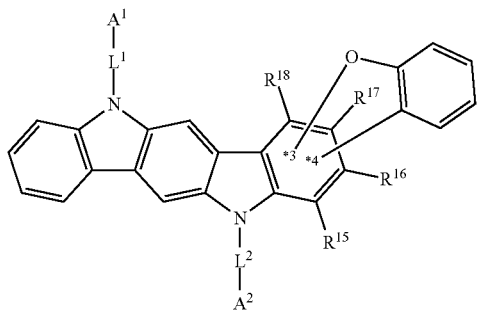
(3-2-1)

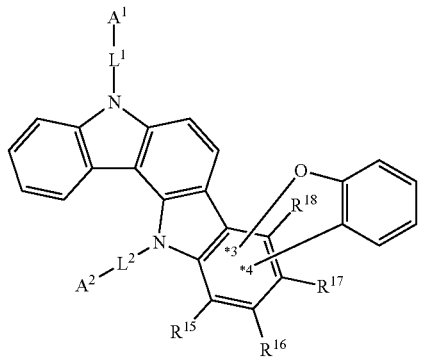
(3-5-1)

wherein in the formulas (3-1-1) and (3-2-1), $A^1, A^2, L^1, L^2$, *3 and *4 are as defined in the formula (1); and $R^{15}$ to $R^{18}$ are as defined in the formula (2), and any one selected from $R^{15}$, $R^7$ and $R^{18}$ forms a single bond with *4.

It is preferred that the compounds represented by the formulas (3-3) to (3-5) be respectively compounds represented by the following formulas (3-3-1) to (3-5-1). It is preferred that the compound represented by the formulas (3-4) and (3-5) be respectively compounds represented by the following formulas (3-4-1) and (3-5-1).

wherein in the formulas (3-3-1) to (3-5-1), $A^1, A^2, L^1, L^2$, *3 and *4 are as defined in the formula (1); and $R^{15}$ to $R^{18}$ are as defined in the formula (2), and any one selected from $R^{15}$, $R^{11}$ and $R^{18}$ forms a single bond with *4.

It is preferred that the compound represented by the formula (3-6) be a compound represented by the following formula (3-6-1).

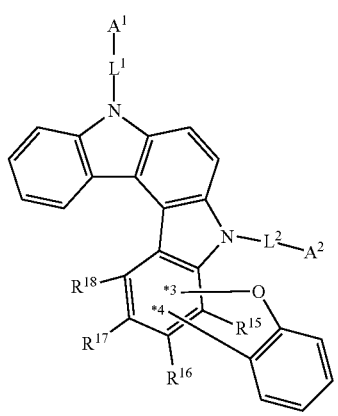
(3-6-1)

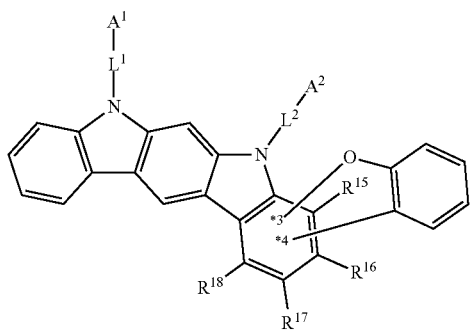
(3-3-1)

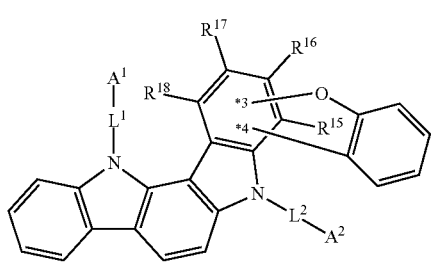
(3-4-1)

wherein in the formula (3-6-1), $A^1, A^2, L^1, L^2$, *3 and *4 are as defined in the formula (1); and $R^{15}$ to $R^{18}$ are as defined in the formula (2), and any one selected from $R^{15}$, $R^{17}$ and $R^{18}$ forms a single bond with *4.

Here, the "any one selected from $R^{15}$, $R^7$ and $R^{18}$ forms a single bond with *4" means as follows. When *4 forms a single bond with $R^{15}$, *3 forms a single bond with $R^{16}$. When *4 forms a single bond with $R^{17}$, *3 forms a single bond with $R^{16}$ or $R^{18}$. When *4 forms a single bond with $R^{18}$, *3 forms a single bond with $R^{17}$.

It is preferred that A and $A^2$ in the formula (1) be independently a substituted or unsubstituted aryl group including 6 to 24 ring carbon atoms or a substituted or unsubstituted heteroaryl group including 5 to 24 ring atoms which include, as the ring atom, one or more atoms selected from the group consisting of a nitrogen atom, an oxygen atom and a sulfur atom.

It is preferred that the substituted or unsubstituted aryl group including 6 to 24 ring carbon atoms in $A^1$ and $A^2$ be independently a substituted or unsubstituted fused aryl group including 10 to 24 ring carbon atoms.

It is preferred that the substituted or unsubstituted fused aryl group including 10 to 24 ring carbon atoms in A1 and $A^2$ be a monovalent residue of the compound represented by the following formula (a1-1) or (a1-2).

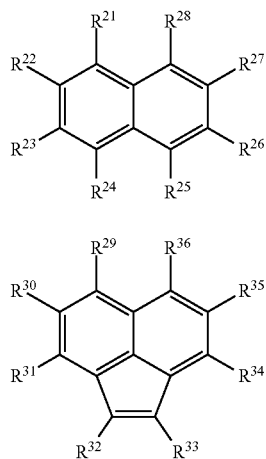

(a1-1)

(a1-2)

wherein in the formulas (a1-1) and (a1-2), $R^{21}$ to $R^{36}$ are independently a hydrogen atom or a substituent $R^b$, and when plural $R^b$s are present, the plural $R^b$s may be the same as or different from each other. Two selected from the plural $R^b$s may be bonded to each other to form a ring.

As the residue for forming the substituted or unsubstituted fused ring including 10 to 24 ring carbon atoms in the compound represented by the formula (a1-1), the following fused aromatic rings can be given, for example. Among them, a fused aromatic ring group formed by fusion of 4 or more rings is preferable. Specifically, a triphenylenyl group or the like can be given.

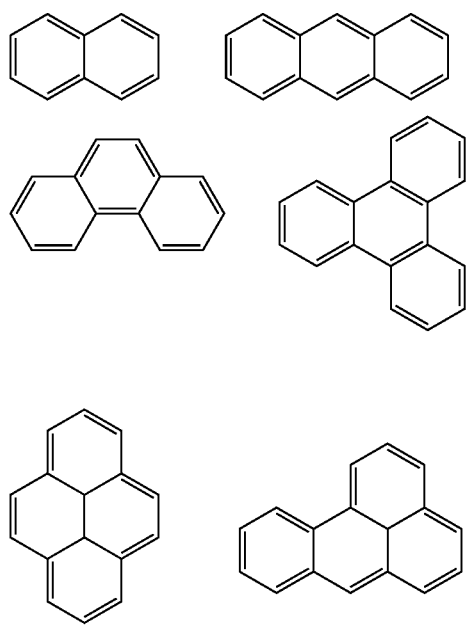

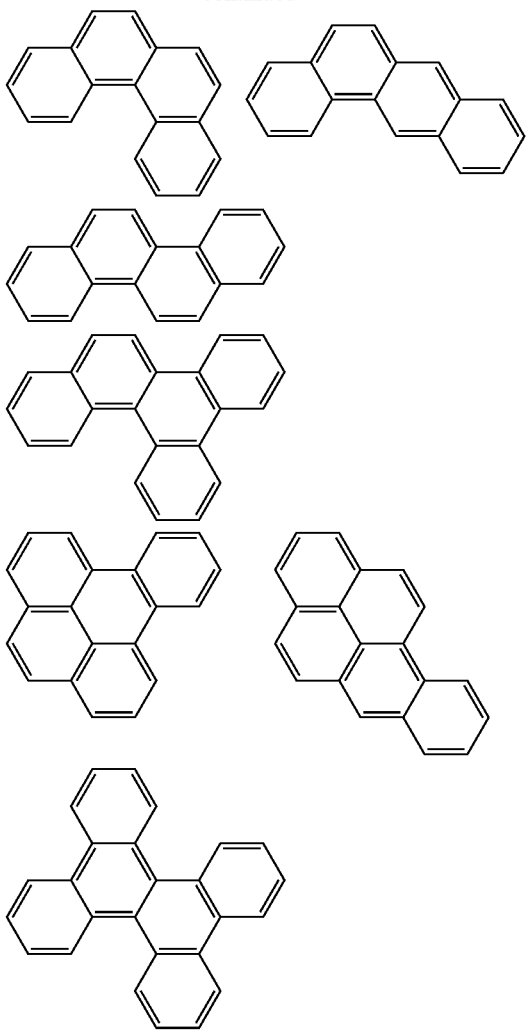

As the residue for forming the substituted or unsubstituted fused ring including 10 to 24 ring carbon atom in the compound represented by the formula (a1-2), the following compound can be given, for example. A residue for forming a fused ring formed by fusion of 4 or more rings is preferable. Specifically, a fluororanthenyl group or the like can be given.

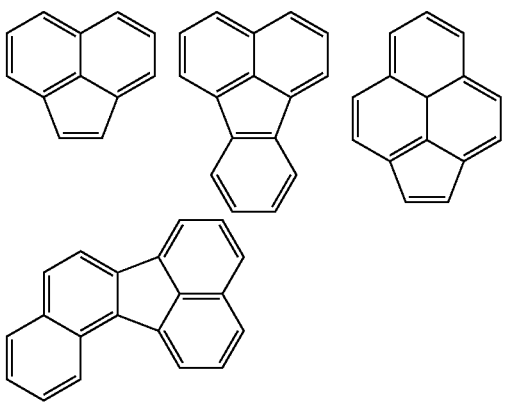

-continued

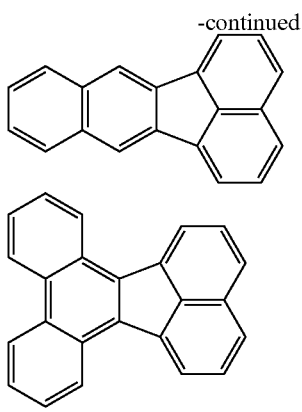

In one embodiment, it is preferred that the substituted or unsubstituted fused aryl group including 10 to 24 ring atoms in A and $A^2$ be independently selected from a group consisting of fused rings formed of 4 or more rings.

In another embodiment, it is preferred that the substituted or unsubstituted heteroaryl group including 5 to 24 ring atoms in $A^1$ and $A^2$ and containing one or more atoms selected from the group consisting of a nitrogen atom, an oxygen atom and a sulfur atom be independently a monovalent residue of the compound represented by the following formula (a2).

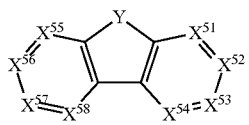 (a2)

wherein in the formula (a2),
$X^{51}$ to $X^{58}$ are independently CH, C($R^b$) or N;
$R^b$ is a substituent, when plural $R^b$s are present, the $R^b$s may be the same as or different from each other, and two selected from the plural $R^b$s may be bonded to each other to form a ring;
Y is an oxygen atom, a sulfur atom, —$NR^d$ or —C($R^e$)($R^f$); and
$R^d$, $R^e$ and $R^f$ are independently a hydrogen atom or a substituent $R^b$, and when both $R^e$ and $R^f$ are $R^b$, they may be bonded to each other to form a ring.

It is preferred that the monovalent residue of the compound represented by the formula (a2) be a monovalent residue of the compound represented by the following formula (a2-1).

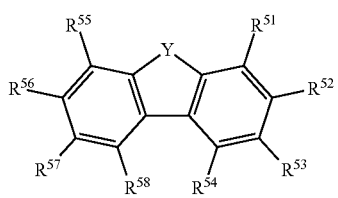 (a2-1)

wherein in the formula (a2-1),
Y is as defined in the formula (a2);
$R^{51}$ to $R^{58}$ are independently a hydrogen atom or a substituent $R^b$, and when plural $R^b$s are present, the plural $R^b$s may be the same as or different from each other, and two selected from the plural $R^b$s may be bonded to each other to form a ring.

In the compound represented by the formula (a2-1), Y is preferably an oxygen atom, a sulfur atom, NH or C(CH$_3$)$_2$, for example.

It is preferred that any of $R^{51}$ to $R^{58}$ form a single bond with $L^1$ or $L^2$.

It is preferred that the substituted or unsubstituted heteroaryl group including 5 to 24 ring atoms and containing one or more atoms selected from the group consisting of a nitrogen atom, an oxygen atom and a sulfur atom as the ring atom in A and $A^2$ be a monovalent residue of the compound represented by the following formula (a3).

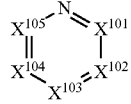 (a3)

wherein in the formula (a3),
$X^{101}$ to $X^{105}$ are independently CH, C($R^b$) or a nitrogen atom;
$R^b$ is a substituent, and when plural $R^b$s are present, the plural $R^b$s may be the same as or different from each other, and two selected from the plural $R^b$s may be bonded with each other to form a ring.

It is preferred that the monovalent residue represented by the formula (a3) be a monovalent residue of the compound represented by the following formula (a3-1).

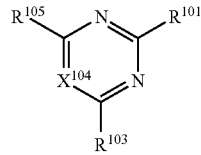 (a3-1)

wherein in the formula (a3-1),
$X^{104}$ is as defined in the formula (a3);
$R^{101}$, $R^{103}$ and $R^{105}$ are independently a hydrogen atom or a substituent $R^b$.

In one embodiment, in the formula (a3-1), $X^{14}$ is preferably CH or a nitrogen atom. It is preferred that any of $R^{101}$, $R^{103}$ and $R^{105}$ form a single bond with $L^1$ or $L^2$, and remaining two of $R^{101}$, $R^{103}$ and $R^{105}$ be independently a substituted or unsubstituted aryl group including 6 to 24 ring carbon atoms.

In another embodiment, $X^{104}$ is C($R^b$) in the formula (a3-1). As examples thereof, those represented by the following formulas (a3-1-1) and (a3-1-2) are preferable.

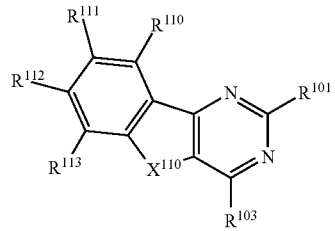 (a3-1-1)

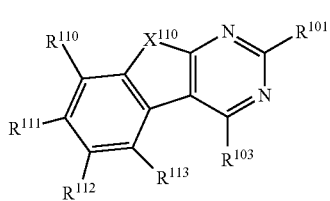

(a3-1-2)

wherein in the formulas (a3-1-1) and (a3-1-2), $X^{110}$ is an oxygen atom or a sulfur atom; and $R^{110}$ to $R^{113}$ are independently a hydrogen atom or a substituent $R^b$.

In this case, it is preferred that any one of $R^{101}$ and $R^{10}$ form a single bond with $L^1$ or $L^2$, and the remaining one of $R^{101}$ and $R^{103}$ be independently a substituted or unsubstituted aryl group including 6 to 24 ring carbon atoms.

It is preferred that the monovalent residue of the compound represented by the formula (a3) be a monovalent residue of the compound represented by the following formula (a3-2).

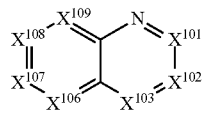

(a3-2)

wherein in the formula (a3-2), $X^{101}$ to $X^{103}$ and $X^{106}$ to $X^{109}$ are independently CH, $C(R^b)$ or N; and $R^b$ is a substituent, and when plural $R^b$s are present, the plural $R^b$s may be the same as or different from each other, and two selected from the plural $R^b$s may be bonded with each other to form a ring.

It is preferred that the monovalent residue of the compound represented by the formula (a3-2) be a monovalent residue of the compound represented by the following formula (a3-2-1).

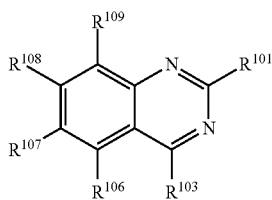

(a3-2-1)

wherein in the formula (a3-2-1), $R^{101}$, $R^{103}$ and $R^{106}$ to $R^{109}$ are independently a hydrogen atom or a substituent $R^b$, and when plural $R^b$s are present, the plural $R^b$s may be the same as or different from each other, and two selected from the plural $R^b$s may be bonded with each other to form a ring.

In the formula (a3-2-1), it is preferred that any of $R^{101}$, $R^{103}$ and $R^{106}$ to $R^{109}$ form a single bond with $L^1$ or $L^2$ and that remaining five of $R^{101}$, $R^{103}$ and $R^{106}$ to $R^{109}$ be hydrogen atoms.

According to one embodiment, it is preferred that $A^2$ be a substituted or unsubstituted heteroaryl group including 5 to 50 ring atoms. Specifically, it is preferred that $A^2$ be represented by the formula (a3), (a3-1), (a3-2) or (a3-2-1).

It is more preferred that $A^2$ be a substituted or unsubstituted heteroaryl group including 5 to 24 ring atoms and containing one or more atoms selected from the group consisting of a nitrogen atom, an oxygen atom and a sulfur atom as the ring atom.

The compound represented by the formula (2) is preferably a compound represented by the following formula (3), and more preferably a compound selected from the group consisting of compounds represented by the following formulas (3-a) to (3-d):

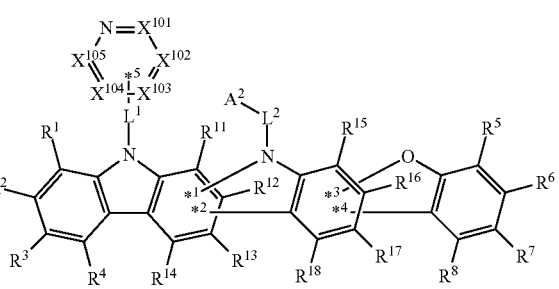

(3)

wherein in the formula (3), $A^2$, $L^1$, $L^2$ and *1 to *4 are as defined in the formula (1);

$R^1$ to $R^8$ and $R^{11}$ to $R^{18}$ are as defined in the formula (2);

$X^{101}$ to $X^{105}$ are as defined in the formula (a3); and

*5 is an atomic bonding that forms a single bond with any of $X^{101}$ to $X^{105}$.

It is preferred that the compound represented by the formula (3) be a compound represented by the following formula (4). It is preferred that the compounds represented by the formulas (3-a) to (3-d) be independently a compound represented by the following formulas (4-a) to (4-d):

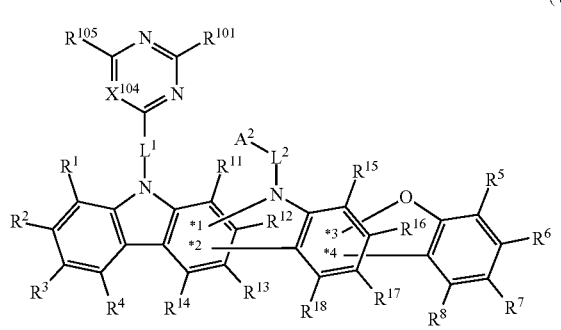

(4)

(4-a)

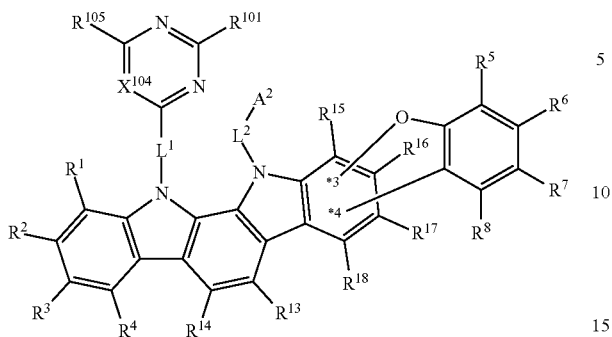

(4-b)

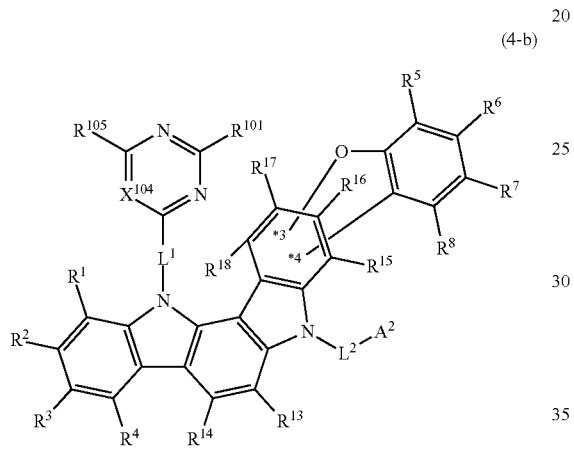

(4-c)

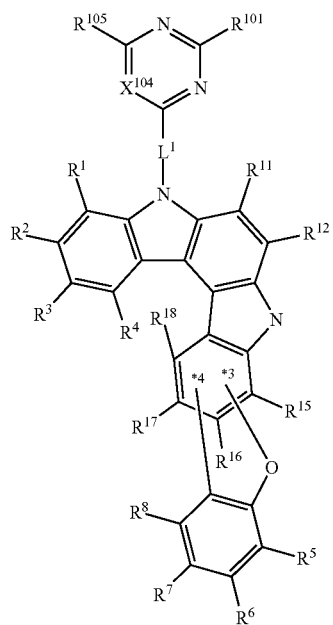

(4-d)

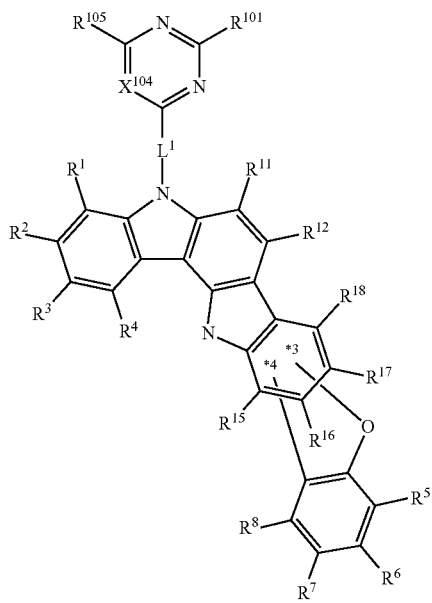

wherein in the formulas (4) and (4-a) to (4-d), $A^2$, $L^2$, $L^2$ and *1 to *4 are as defined in the formula (1);

$R^1$ to $R^8$ and $R^{11}$ to $R^{18}$ are as defined in the formula (2);

$X^{104}$ is as defined in the formula (a3); and $R^{101}$ and $R^{105}$ are as defined in the formula (a3-1).

In the formula (1), it is preferred that $L^1$ and $L^2$ be independently a single bond or a group selected from the group consisting of groups represented by the following formulas (i) to (vii):

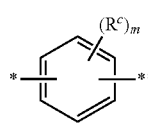

(i)

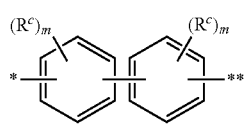

(ii)

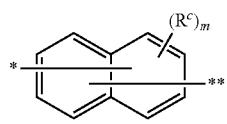

(iii)

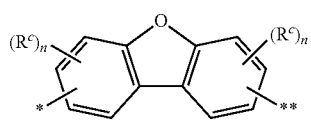

(iv)

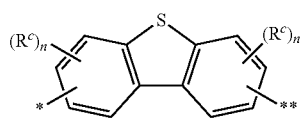

(v)

-continued

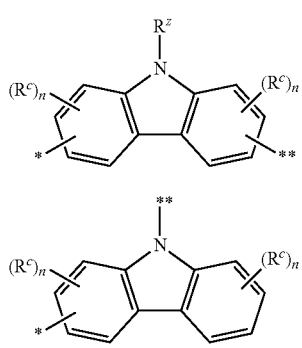

(vi)

(vii)

wherein in the formulas (i) to (vi),
* and ** are independently an atomic bonding that forms a single bond with N and either one of $A^1$ and $A^2$ in the formula (1);
$R^c$ is a substituent, and when plural $R^c$s are present, the plural $R^c$s may be the same as or different from each other, and two selected from the plural $R^c$s may be bonded to each other to form a ring structure;
$R^z$ is a hydrogen atom or a substituent $R^c$; and
m are independently an integer of 0 to 4, and n are independently an integer of 0 to 3.

In one embodiment, $L^1$ is preferably a substituted or unsubstituted arylene group including 6 to 60 ring carbon atoms and $L^1$ is further preferably selected from the group consisting of compounds represented by the formulas (i) to (iii).

It is preferred that the substituents $R^a$, $R^b$ and $R^c$ and the substituent in the expression "substituted or unsubstituted" be independently a group selected from the group consisting of an alkyl group including 1 to 50 carbon atoms, a cycloalkyl group including 3 to 50 ring carbon atoms, an aryl group having 6 to 50 ring carbon atoms, an aralkyl group including 7 to 51 carbon atoms that include an aryl group including 6 to 50 ring carbon atoms, an amino group, a mono- or di-substituted amino group including a substituent selected from an alkyl group including 1 to 50 carbon atoms and an aryl group including 6 to 50 ring carbon atoms, an alkoxy group including an alkyl group including 1 to 50 carbon atoms, an aryloxy group including an aryl group including 6 to 50 ring carbon atoms, a heteroaryloxy group including a heteroaryl group including 5 to 50 ring atoms, a mono-, di- or tri-substituted silyl group including a substituent selected from an alkyl group including 1 to 50 carbon atoms, an alkoxy group including 1 to 50 carbon atoms and an aryl group including 6 to 50 ring carbon atoms, a heteroaryl group including 5 to 50 ring atoms, a haloalkyl group including 1 to 50 carbon atoms, a halogen atom, a cyano group, a nitro group, an arylthio group including an aryl group including 6 to 50 carbon atoms, a heteroarylthio group including a heteroaryl group including 5 to 50 ring atoms, a sulfonyl group including a substituent selected from an alkyl group including 1 to 50 carbon atoms and an aryl group including 6 to 50 ring carbon atoms, a di-substituted phosphoryl group including a substituent selected from an alkyl group including 1 to 50 carbon atoms and an aryl group including 6 to 50 ring carbon atoms, an alkylsulfonyloxy group including an alkyl group including 1 to 50 carbon atoms, an arylsulfonyloxy group including an aryl group including 6 to 50 ring carbon atoms, an alkylcarbonyloxy group including an alkyl group including 1 to 50 carbon atoms, an arylcarbonyloxy group including an aryl group including 6 to 50 ring carbon atoms, a silicon-containing group, a hydroxy group, a substituted carbonyl group including a substituent selected from an alkyl group including 1 to 50 carbon atoms and an aryl group including 6 to 50 ring carbon atoms, a carboxyl group, a vinyl group, a (meth)acryloyl group, an epoxy group, and an oxetanyl group.

Preferably, $R^a$ is independently an aryl group including 6 to 20 ring carbon atoms, a heteroaryl group including 5 to 20 ring atoms, a cyano group, a fluorine atom, a straight-chain, branched or cyclic alkyl group including 1 to 20 carbon atoms, a straight-chain, branched or cyclic alkenyl-containing group including 2 to 20 carbon atoms, a straight-chain, branched or cyclic alkynyl-containing group including 2 to 20 carbon atoms, an alkoxy group including 1 to 20 carbon atoms, an aryloxy group including 6 to 20 ring carbon atoms, an arylthio group including 6 to 20 ring carbon atoms, a heteroaryloxy group including 5 to 20 ring atoms, a heteroarylthio group including 5 to 20 ring atoms, a mono-, di- or tri-substituted silyl group including a substituent selected from an alkyl group including 1 to 10 carbon atoms, an alkoxy group including 1 to 10 carbon atoms and an aryl group including 6 to 20 ring carbon atoms, a mono- or di-substituted amino group including a substituent selected from an alkyl group including 1 to 20 carbon atoms in which an aryl group including 6 to 20 ring carbon atoms or a heterocyclic group including 3 to 20 ring atoms is mono-, di- or tri-substituted, an aryl group including 6 to 20 ring carbon atoms and a heterocyclic group including 3 to 20 ring atoms. More preferably, $R^a$ is an alkyl group including 1 to 10 carbon atoms, an aryl group including 6 to 20 ring carbon atoms, an aryloxy group including 6 to 20 ring carbon atoms, a heteroaryl group including 5 to 20 ring atoms, a fluorine atom, a mono-, di- or tri-substituted silyl group including a substituent selected from an alkyl group including 1 to 10 carbon atoms, an alkoxy group including 1 to 10 carbon atoms and an aryl group including 6 to 20 ring carbon atoms, and a mono- or di-substituted amino group including a substituent selected from an alkyl group including 1 to 10 carbon atoms and an aryl group including 6 to 20 ring carbon atoms. When plural $R^a$s are present, the plural $R^a$s may be the same as or different from each other, and two selected from the plural $R^a$s may be bonded to each other to form a ring.

$R^b$ is independently an aryl group including 6 to 20 ring carbon atoms, a heteroaryl group including 5 to 20 ring atoms, a cyano group, a fluorine atom, a straight-chain, branched or cyclic alkyl group including 1 to 20 carbon atoms, a straight-chain, branched or cyclic alkenyl-containing group including 2 to 20 carbon atoms, a straight-chain, branched or cyclic alkynyl-containing group including 2 to 20 carbon atoms, an alkoxy group including 1 to 20 carbon atoms, an aryloxy group including 6 to 20 ring carbon atoms, an arylthio group including 6 to 20 ring carbon atoms, a heteroaryloxy group including 5 to 20 ring atoms, a heteroarylthio group including 5 to 20 ring atoms, a mono-, di- or tri-substituted silyl group including a substituent selected from an alkyl group including 1 to 10 carbon atoms, an alkoxy group including 1 to 10 carbon atoms and an aryl group including 6 to 20 ring carbon atoms, and a mono- or di-substituted amino group including a substituent selected from an alkyl group including 1 to 20 carbon atoms in which an aryl group including 6 to 20 ring carbon atoms or a heterocyclic group including 3 to 20 ring atoms is mono-, di- or tri-substituted, an aryl group including 6 to 20 ring carbon atoms and a heterocyclic group including 3 to 20 ring carbon atoms. When plural $R^b$s are present, the plural $R^b$s may be the same as or different from each other. Two selected from the plural $R^b$s may be bonded to each other to form a ring.

$R^c$ is preferably an aryl group including 6 to 20 ring carbon atoms, a heteroaryl group including 5 to 20 ring atoms, a cyano group, a fluorine atom, a straight-chain, branched or cyclic alkyl group including 1 to 20 carbon atoms, a straight-chain, branched or cyclic alkenyl-containing group including 2 to 20 carbon atoms, a straight-chain, branched or cyclic alkynyl-containing group including 2 to 20 carbon atoms, an alkoxy group including 1 to 20 carbon atoms, an aryloxy group including 6 to 20 ring carbon atoms, an arythio group including 6 to 20 ring carbon atoms, a heteroaryloxy group including 5 to 20 ring atoms, a heteroarylthio group including 5 to 20 ring atoms, a mono-, di- or tri-substituted silyl group including a substituent selected from an alkyl group including 1 to 10 carbon atoms, an alkoxy group including 1 to 10 carbon atoms and an aryl group including 6 to 20 ring carbon atoms, or a mono- or di-substituted amino group including a substituent selected from an alkyl group including 1 to 20 carbon atoms in which an aryl group including 6 to 20 ring carbon atoms or a heterocyclic group including 3 to 20 ring atoms is mono-, di- or tri-substituted, an aryl group including 6 to 20 ring carbon atoms or a heterocyclic group including 3 to 20 ring atoms. When plural $R^c$s are present, the plural $R^c$s may be the same as or different from each other, and two selected from the plural $R^c$s may be bonded to each other to form a ring.

The substituent in the "substituted or unsubstituted" is preferably a substituent selected from the group of the preferable substituents described with referring to the $R^a$, $R^b$ and $R^c$ mentioned above.

The substituent in the "substituted or unsubstituted" may be further substituted by the above-mentioned substituents. These substituents may be bonded to form a ring. In another embodiment, these substituents are not bonded to each other, and hence do not necessarily form a ring.

In the present specification, the number of "ring carbon atoms" mean the number of carbon atoms among atoms constituting a ring of a compound in which atoms are bonded in the form of a ring (for example, a monocyclic compound, a fused ring compound, a cross-linked compound, a carbocyclic compound, a heterocyclic compound). When the ring is substituted by a substituent, the carbon contained in the substituent is not included in the number of ring carbon atoms. The same is applied to the "ring carbon atoms" mentioned below, unless otherwise indicated. For example, a benzene ring includes 6 ring carbon atoms, a naphthalene ring includes 10 ring carbon atoms, a pyridinyl group includes 5 ring carbon atoms, and a furanyl group includes 4 ring carbon atoms. When a benzene ring or a naphthalene ring is substituted by an alkyl group, for example, the number of carbon atoms of the alkyl group is not included in the number of ring carbon atoms. When a fluorene ring is bonded with a fluorene ring as a substituent (including a spirofluorene ring), for example, the number of carbon atoms of the fluorene ring as a substituent is not included in the number of ring carbon atoms.

In the present specification, the number of "ring atoms" means the number of atoms among atoms constituting a ring of a compound in which atoms are bonded in the form of a ring (for example, a monocycle, a fused ring, a ring assembly) (for example, a monocyclic compound, a fused ring compound, a cross-linked compound, a carbocyclic compound, a heterocyclic compound). Atoms that do not constitute a ring or atoms included in a substituent when the ring is substituted by a substituent are not included in the number of ring atoms. The same is applied to the "ring atoms" mentioned below unless otherwise indicated. For example, a pyridine ring includes 6 ring atoms, a quanazoline ring includes 10 ring atoms and a furan ring includes 5 ring atoms. The hydrogen atom bonded with the carbon atom of the pyridine ring or the quinazoline ring, respectively, or atoms that constitute a substituent are not included in number of the ring atoms. When a fluorene ring is bonded with a fluorene ring as a substituent (including a spirofluorene ring), for example, the number of atoms of the fluorene ring as a substituent is not included in the number of ring atoms.

In the present specification, the "XX to YY carbon atoms" in the "substituted or unsubstituted ZZ group including XX to YY carbon atoms" means the number of carbon atoms when the ZZ group is unsubstituted. The number of carbon atoms of a substituent when the group is substituted is not included.

In the present specification, the "XX to YY atoms" in the "substituted or unsubstituted ZZ group including XX to YY atoms" means the number of carbon atoms when the ZZ group is unsubstituted. The number of atoms of a substituent when the group is substituted is not included.

The "unsubstituted" in the "substituted or unsubstituted" means bonding of a hydrogen atom, not substitution by the substituent mentioned above.

In the present specification, a hydrogen atom includes isomers differing in number of neutrons, i.e. protium, deuterium and tritium.

An explanation will be given on specific examples of the substituent in the above formulas and the substituent in the "substituted or unsubstituted".

As specific examples of the alkyl group including 1 to 50 carbon atoms, a methyl group, an ethyl group, a n-propyl group, an isopropyl group, an n-butyl group, a s-butyl group, an isobutyl group, a t-butyl group, a n-pentyl group, a n-hexyl group, a n-heptyl group, a n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitroethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group or the like can be given.

As examples of the alkyl group including 1 to 20 carbon atoms, those including 1 to 20 carbon atoms can be given among those mentioned above. As examples of the alkyl group including 1 to 10 carbon atoms, those including 1 to 10 carbon atoms can be given among those mentioned above.

A preferable alkyl group is selected from a n-propyl group, an isopropyl group, a n-butyl group, a s-butyl group, an isobutyl group, a t-butyl group, a n-pentyl group and a n-hexyl group.

The number of carbon atoms of the alkyl group is preferably 1 to 20, more preferably 1 to 10, and further preferably 1 to 6.

As examples of the cycloalkyl group including 3 to 50 ring carbon atoms, a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group or the like can be given.

The number of ring carbon atoms of a cycloalkyl group is preferably 3 to 10, more preferably 3 to 8, and further more preferably 3 to 6.

As the halogen atom, fluorine, chlorine, bromine, iodine or the like can be given, with fluorine being preferable.

The haloalkyl group including 1 to 50 carbon atoms is a group in which one or more hydrogen atoms in the alkyl group including 1 to 50 carbon atoms and the cycloalkyl group including 3 to 50 ring carbon atoms are substituted by the above-mentioned halogen atom.

The alkoxy group including 1 to 50 carbon atoms is a group represented by —$OY^{10}$. As examples of $Y^{10}$, the same groups as those exemplified above as the alkyl group including 1 to 50 carbon atoms and the cycloalkyl group including 3 to 50 ring carbon atoms can be given.

The alkoxy group including 1 to 20 carbon atoms is a group represented by —$OY^{10A}$. As examples of $Y^{10A}$, among the groups exemplified above as the alkyl group including 1 to 50 carbon atoms and the cycloalkyl group including 3 to 50 ring carbon atoms, an alkyl group including 1 to 20 carbon atoms or a cycloalkyl group can be given.

The alkoxy group including 1 to 10 carbon atoms is a group represented by —$OY^{10B}$. As examples of $Y^{10B}$, among the groups exemplified above as the alkyl group including 1 to 50 carbon atoms and the cycloalkyl group including 3 to 50 ring carbon atoms, an alkyl group including 1 to 10 carbon atoms or a cycloalkyl group can be given.

The alkylcarbonyloxy group including an alkyl group including 1 to 50 carbon atoms is a group represented by —O—(C=O)—$Y^{10}$, and examples of $Y^{10}$ are as mentioned above.

As examples of an aryl group including 6 to 50 ring carbon atoms, a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-pyrenyl group, a 2-pyrenyl group, a 4-pyrenyl group, a 6-chrysenyl group, a 1-benzo[c]phenanthryl group, a 2-benzo[c]phenanthryl group, a 3-benzo[c]phenanthryl group, a 4-benzo[c]phenanthryl group, a 5-benzo[c]phenanthryl group, a 6-benzo[c]phenanthryl group, a 1-benzo[g]chrysenyl group, a 2-benzo[g]chrysenyl group, a 3-benzo[g]chrysenyl group, a 4-benzo[g]chrysenyl group, a 5-benzo[g]chrysenyl group, a 6-benzo[g]chrysenyl group, a 7-benzo[g]chrysenyl group, a 8-benzo[g]chrysenyl group, a 9-benzo[g]chrysenyl group, a 10-benzo[g]chrysenyl group, a 11-benzo[g]chrysenyl group, a 12-benzo[g]chrysenyl group, a 13-benzo[g]chrysenyl group, a 14-benzo[g]chrysenyl group, a 1-benzo[a]anthryl group, a 2-benzo[a]anthryl group, a 3-benzo[a]anthryl group, a 4-benzo[a]anthryl group, a 5-benzo[a]anthryl group, a 6-benzo[a]anthryl group, a 7-benzo[a]anthryl group, a 8-benzo[a]anthryl group, a 9-benzo[a]anthryl group, a 10-benzo[a]anthryl group, a 11-benzo[a]anthryl group, a 12-benzo[a]anthryl group, a 13-benzo[a]anthryl group, a 14-benzo[a]anthryl group, a 1-triphenyl group, a 2-triphenyl group, a 1-fluorenyl group, a 2-fluorenyl group, a 3-fluorenyl group, a 4-fluorenyl group, a benzofluorenyl group, a dibenzofluorenyl group, a fluoranthenyl group, a benzofluoranthenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, or the like can be given.

As examples of the aryl group including 6 to 24 ring carbon atoms, among those exemplified above, those including 6 to 24 ring carbon atoms can be given. As examples of the aryl group including 6 to 20 ring carbon atoms, among those exemplified above, those including 6 to 20 ring carbon atoms can be given.

As the aryl group, a phenyl group, a 1-naphthyl group, a 2-naphthyl group, a 1-phenanthryl group, a 2-phenanthryl group, a 3-phenanthryl group, a 4-phenanthryl group, a 9-phenanthryl group, a 1-fluorenyl group, a 2-fluorenyl group, a 3-fluorenyl group, a 4-fluorenyl group, a 5-benzo[c]phenanthryl group, a 4-benzo[a]anthryl group, a 7-benzo[a]anthryl group, a 1-triphenyl group, a 2-triphenyl group and a fluoranthenyl group are preferable.

As the aryl group, preferably one including 6 to 24 ring carbon atoms, more preferably one including 6 to 20 ring carbon atoms can be given.

The arylene group including 6 to 50 ring carbon atoms and the arylene group including 6 to 60 ring carbon atoms are a residue $Y^{21}$ obtained by further removing one hydrogen atom or one substituent from the aryl group including 6 to 50 ring carbon atoms.

The aralkyl group including 7 to 51 carbon atoms including an aryl group including 6 to 50 ring carbon atoms is represented by —$Y^{11}$-$Y^{20}$. As examples of $Y^{11}$, a residue (alkylene group or cycloalkylene group) obtained by further removing one hydrogen atom or one substituent from those mentioned as the alkyl group including 1 to 50 carbon atoms and the cycloalkyl group including 3 to 50 ring carbon atoms can be given. As examples of $Y^{20}$, the aryl group including 6 to 50 ring carbon atoms can be given.

The aryloxy group including 6 to 50 ring carbon atoms is represented by —$OY^{20}$. As examples of $Y^{20}$, the same as those exemplified above as the aryl group including 6 to 50 ring carbon atoms can be given.

The aryloxy group including 6 to 20 ring carbon atoms is represented by —$OY^{20A}$. As examples of $Y^{20A}$, the same as those exemplified above as the aryl group including 6 to 20 ring carbon atoms can be given.

The heteroaryloxy including 5 to 50 ring atoms is represented by —$OY^{21}$. As examples of $Y^{21}$, the same as those exemplified above as the heteroaryl group including 5 to 50 ring atoms can be given.

The heteroaryloxy including 5 to 20 ring atoms is represented by —$OY^{21A}$. As examples of $Y^{21A}$, the same as those exemplified above as the heteroaryl group including 5 to 20 ring atoms can be given.

The arythio group including 6 to 50 ring carbon atoms is represented by —$SY^{22}$. As examples of $Y^{22}$, the same as those exemplified above as the aryl group including 6 to 50 ring carbon atoms can be given.

The arythio group including 6 to 20 ring carbon atoms is represented by —$SY^{22A}$. As examples of $Y^{22}$, the same as those exemplified above as the aryl group including 6 to 20 ring carbon atoms can be given.

The heteroarythio group including 5 to 50 ring atoms is represented by —$SY^{23}$. As examples of $Y^{23}$, the same as those exemplified above as the heteroaryl group including 5 to 50 ring atoms can be given.

The heteroarythio group including 5 to 20 ring atoms is represented by —$SY^{23A}$. As examples of $Y^{23A}$, the same as those exemplified above as the heteroaryl group including 5 to 20 ring atoms can be given.

The arylcarbonyloxy group including an aryl group including 6 to 50 ring carbon atoms is represented by —O—(C=O)—$Y^{20}$, and examples of $Y^{20}$ are as mentioned above.

The substituted carbonyl group including a substituent selected from the alkyl group including 1 to 50 carbon atoms and the aryl group including 6 to 50 ring carbon atoms is represented by —(C=O)—$Y^{10}$ or —(C=O)—$Y^{20}$, and examples of $Y^{10}$ and $Y^{20}$ are as exemplified above.

As examples of the heteroaryl group including 5 to 50 ring atoms, a 1-pyrrolyl group, 2-pyrrolyl group, 3-pyrrolyl group, pyrazinyl group, 2-pyridinyl group, 3-pyridinyl group, 4-pyridinyl group, pyrimidinyl group, triazinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, carbazolyl group, benzocarbazolyl group, azadibenzofuranyl group, azadibenzothiophenyl group, diazadibenzofuranyl group, diazadibenzothiophenyl group, naphthobenzofuranyl group, naphthobenzothiophenyl group, diazaphenanthryl group, 2-benzothiophenyl group, 3-benzothiophenyl group, 4-benzothiophenyl group, 5-benzothiophenyl group, 6-benzothiophenyl group, 7-benzothiophenyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 2-quinazolinyl group, 4-quinazolinyl group, 5-quinazolinyl group, 6-quinazolinyl group, 7-quinazolinyl group, 8-quinazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiadinyl group, 2-phenothiadinyl group, 3-phenothiadinyl group, 4-phenothiadinyl group, 10-phenothiadinyl group, 1-phenoxadinyl group, 2-phenoxadinyl group, 3-phenoxadinyl group, 4-phenoxadinyl group, 10-phenoxadinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 1-benzoimidazoyl group, 2-benzimidazolyl group, 4-benzimidazolyl group, 5-benzimidazolyl group, 6-benzimidazolyl group, 7-benzimidazolyl group, 2-imidazo[1,2-a]pyridinyl group, 3-imidazo[1,2-a]pyridinyl group, 5-imidazo[1,2-a]pyridinyl group, 6-imidazo[1,2-a]pyridinyl group, 7-imidazo[1,2-a]pyridinyl group, 8-imidazo[1,2-a]pyridinyl group, benzimidazol-2-on-1-yl group, benzimidazol-2-on-3-yl group, benzimidazol-2-on-4-yl, benzimidazol-2-on-5-yl group, benzimidazol-2-on-6-yl group, benzimidazol-2-on-7-yl group or the like can be given.

As examples of the heteroaryl group including 5 to 24 ring atoms, among those exemplified above, those including 5 to 24 ring atoms can be given. As examples of the heteroaryl group including 5 to 20 ring atoms, among those exemplified above, those including 5 to 20 ring atoms can be given.

As the preferable heteroaryl group, pyrazinyl group, 2-pyridinyl group, 3-pyridinyl group, 4-pyridinyl group, pyrimidinyl group, triazinyl group, quinazolinyl group, diazadibenzofuranyl group, diazadibenzothiophenyl group, carbazolyl group, 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group or 4-dibenzothiophenyl group can be given.

The number of ring atoms of the heteroaryl group is preferably 5 to 24, more preferably 5 to 18. As the atoms that constitute the ring of the heteroaryl group, it is preferred that an atom selected from the group consisting of a nitrogen atom, an oxygen atom and a sulfur atom be contained.

The heteroarylene group including 5 to 50 ring atoms is a group $Y^{31}$ obtained by further removing one hydrogen atom or one substituent from the heteroaryl group including 5 to 50 ring atoms.

The mono-substituted amino group including a substituent selected from the alkyl group including 1 to 50 carbon atoms and the aryl group including 6 to 50 ring carbon atoms is represented by —NH($Y^{10}$) or —NH($Y^{20}$), and examples of $Y^{10}$ and $Y^{20}$ are as exemplified above.

The di-substituted amino group including a substituent selected from the alkyl group including 1 to 50 carbon atoms and the aryl group including 6 to 50 ring carbon atoms is represented by —N(Y¹⁰)₂, —N(Y²⁰)₂ or —N(Y¹⁰)(Y²⁰), and examples of Y¹⁰ and Y²⁰ are as exemplified above. If two Y¹⁰s or two Y²⁰s are present, they may be the same as or different from each other.

The mono-substituted silyl group including a substituent selected from the alkyl group including 1 to 50 carbon atoms, an alkoxy group including 1 to 50 carbon atoms and an aryl group including 6 to 50 ring carbon atoms is represented by —SiH₂(Y¹⁰), —SiH₂(OY¹⁰) or —SiH₂(Y²).

The di-substituted silyl group including a substituent selected from the alkyl group including 1 to 50 carbon atoms, an alkoxy group including 1 to 50 carbon atoms and an aryl group including 6 to 50 ring carbon atoms is represented by —SiH(Y¹⁰)₂, —SiH(OY¹⁰)₂, —SiH(Y²⁰)₂, —SiH(Y¹⁰)(Y²⁰), —SiH(Y¹⁰)(OY¹⁰), or —SiH(OY¹⁰)(Y²⁰).

The tri-substituted silyl group including a substituent selected from the alkyl group including 1 to 50 carbon atoms, an alkoxy group including 1 to 50 carbon atoms and an aryl group including 6 to 50 ring carbon atoms is represented by —Si(Y¹⁰)₃, —Si(OY¹⁰)₃, —Si(Y²⁰)₃, —Si(Y¹⁰)₂(OY¹⁰), —Si(OY¹⁰)₂(Y¹⁰), —Si(Y¹⁰)₂(Y²⁰), —Si(OY¹⁰)₂(Y²⁰), —Si(Y²⁰)₂(OY¹⁰), —Si(Y¹⁰)(Y²⁰)₂ or —Si(Y¹⁰)(OY¹⁰)(Y²⁰). Y¹⁰ and Y²⁰ are as exemplified above, and if plural Y¹⁰ and Y²⁰ are as exemplified above, and if plural Y¹⁰ and Y²⁰ are present, they may be the same as or different from each other.

As the tri-substituted silyl group, a triarylsilyl group, a monoalkyl diarylsilyl group and a dialkyl monoarylsilyl group can be given. Specific examples include a trimethylsilyl group, a triethylsilyl group, a tributylsilyl group, a trioctylsilyl group, a triisobutylsilyl group, a dimethylethylsilyl group, a dimethylisopropylsilyl group, a dimethylpropylsilyl group, a dimethylbutylsilyl group, a dimethyltertiarybutylsilyl group, a diethyl isopropylsilyl group, a phenyldimethylsilyl group, a diphenylmethylsilyl group, a diphenyftertiarybutyl group, a triphenylsilyl group orthe like. Among them, a trimethylsilyl group, a triethylsilyl group and a tributylsilyl group can be given.

The sulfonyl group including a substituent selected from the alkyl group including 1 to 50 carbon atoms and the aryl group including 6 to 50 ring carbon atoms is represented by —S(=O)—Y¹⁰ or —S(=O)₂—Y²⁰. Y¹⁰ and Y²⁰ are as defined above.

The di-substituted phosphoryl group including a substituent selected from the alkyl group including 1 to 50 carbon atoms and the aryl group including 6 to 50 ring carbon atoms is represented by —O—P(=O)(Y¹⁰)₂, —O—P(=O)(Y²⁰)₂ or —O—P(=O)(Y¹⁰)(Y²⁰). Y¹⁰ and Y²⁰ are as defined above. If two Y¹⁰s or two Y²⁰s are present, they may be the same as or different from each other.

The alkylsulfonyloxy group including the alkyl group including 1 to 50 carbon atoms is represented by —O—S(=O)₂(Y¹⁰), and Y¹⁰ are as defined above.

The arylsulfonyloxy group including a substituent selected from the aryl group including 6 to 50 ring carbon atoms is represented by —O—S(=O)₂(Y²⁰). Y²⁰ are as defined above.

The (meth)acryloyl group includes an acryloyl group and a methacryloyl group.

Specific examples of the compound represented by the formula (1) according to one aspect of the invention are given below.

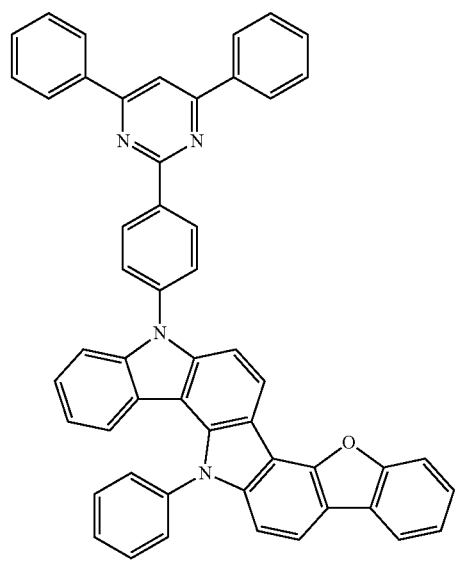

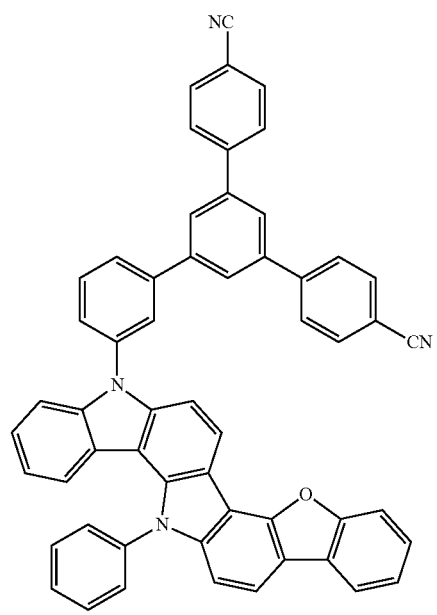

41
-continued
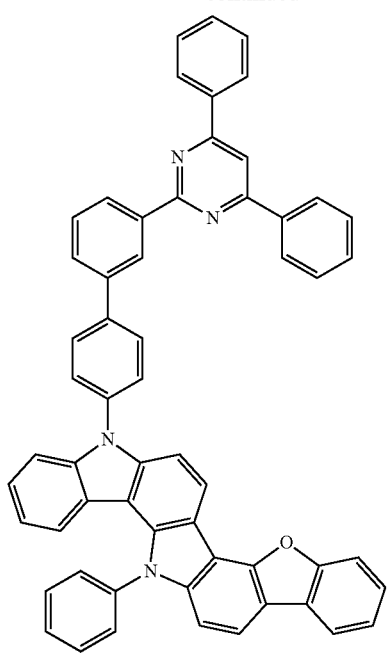
42
-continued
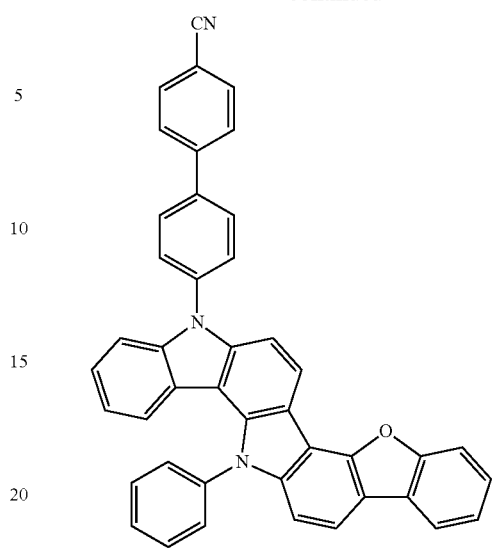
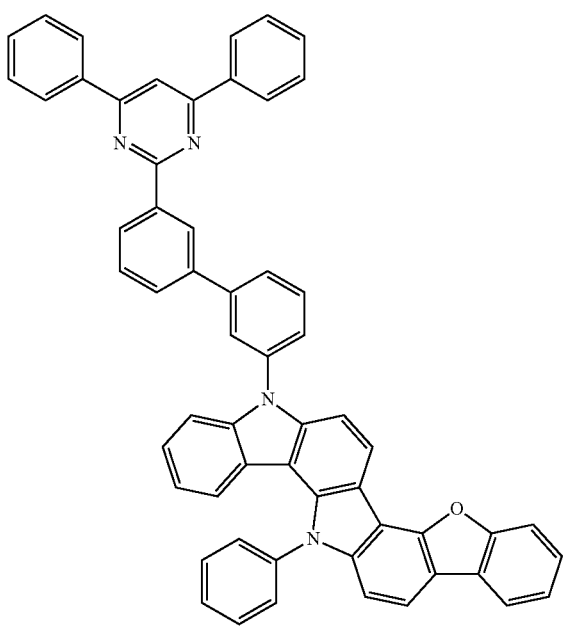
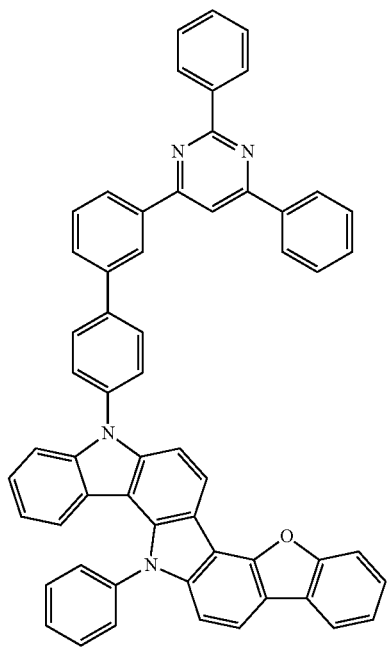

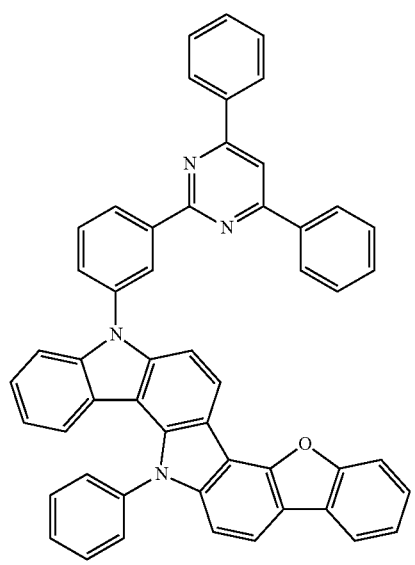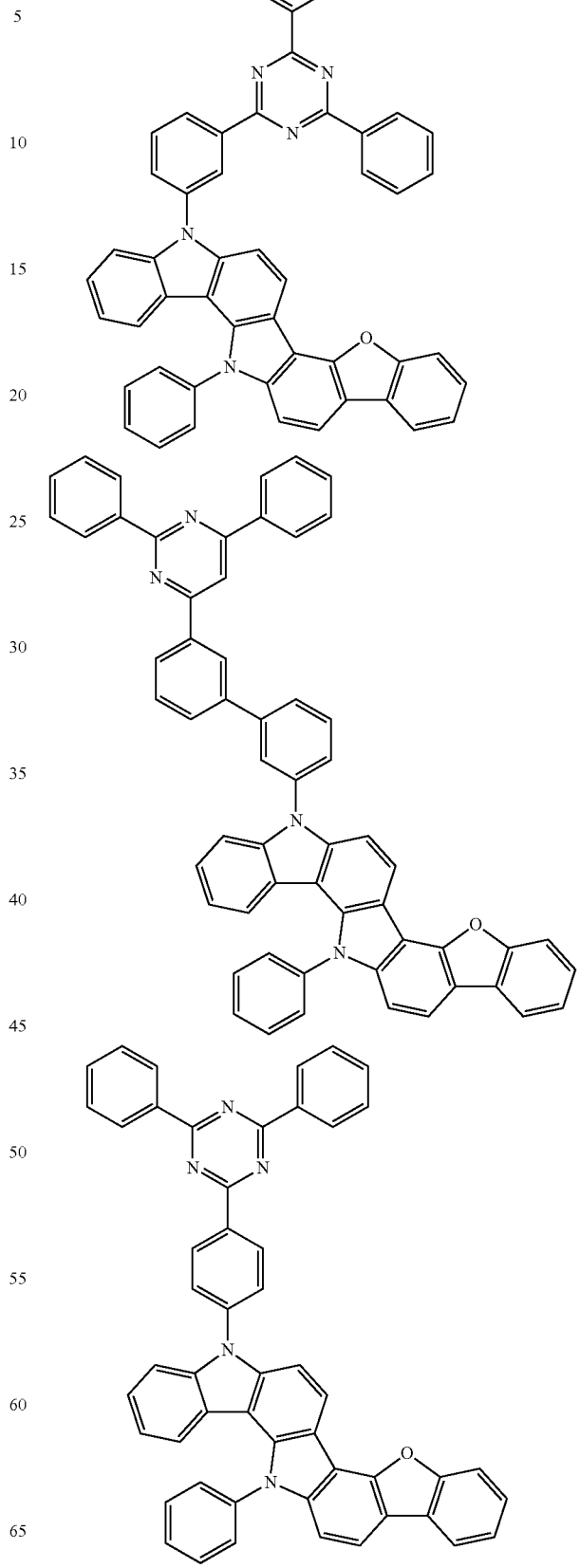

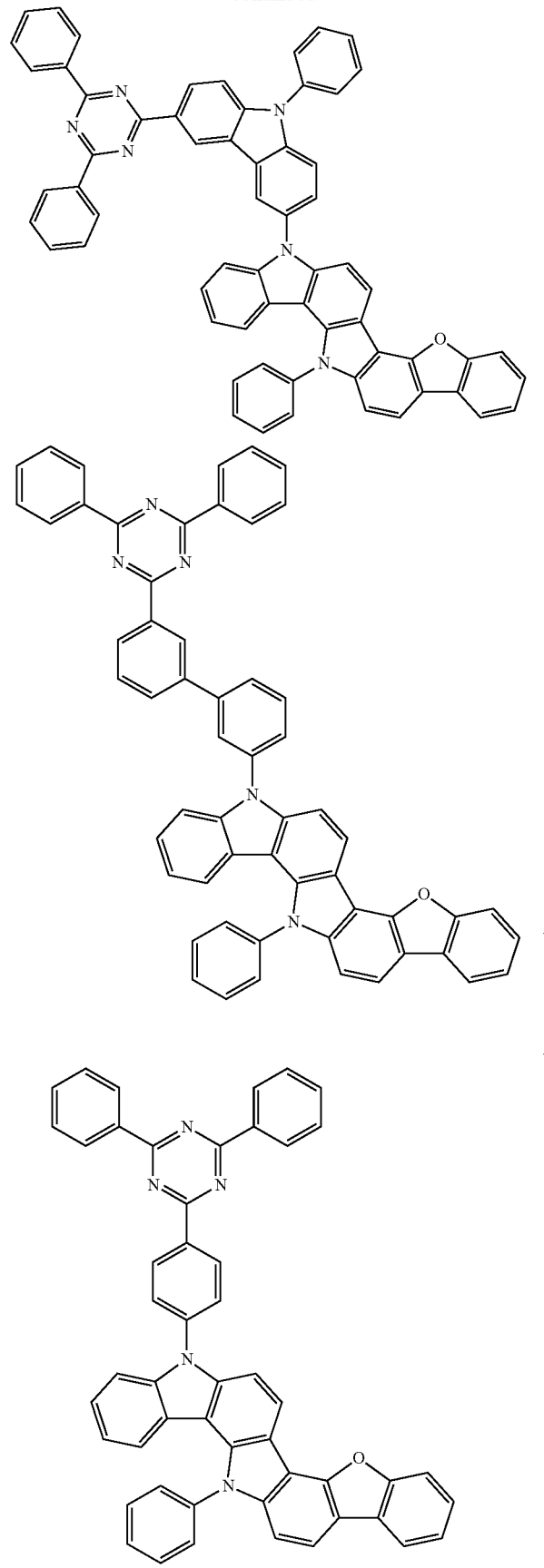
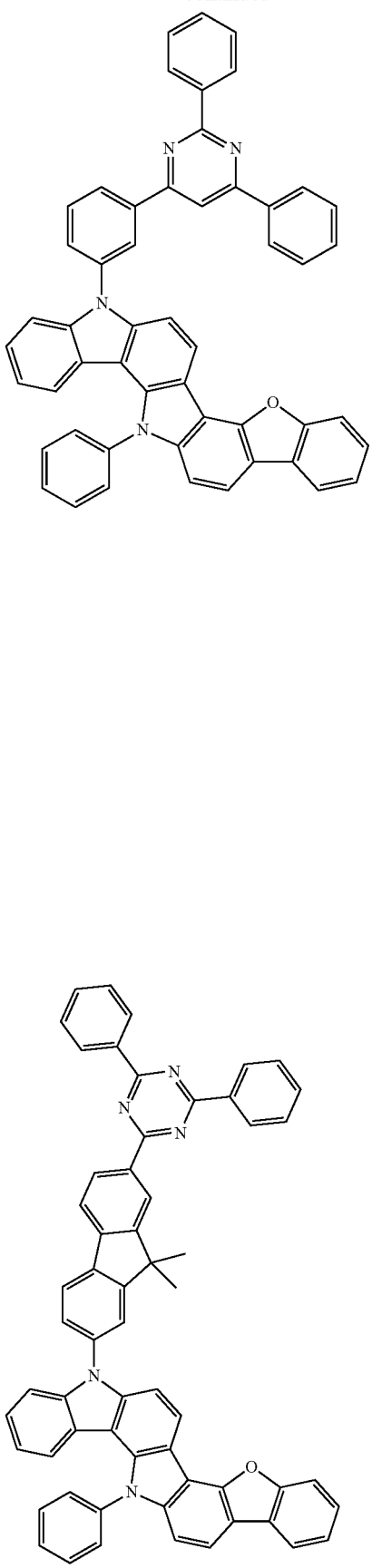

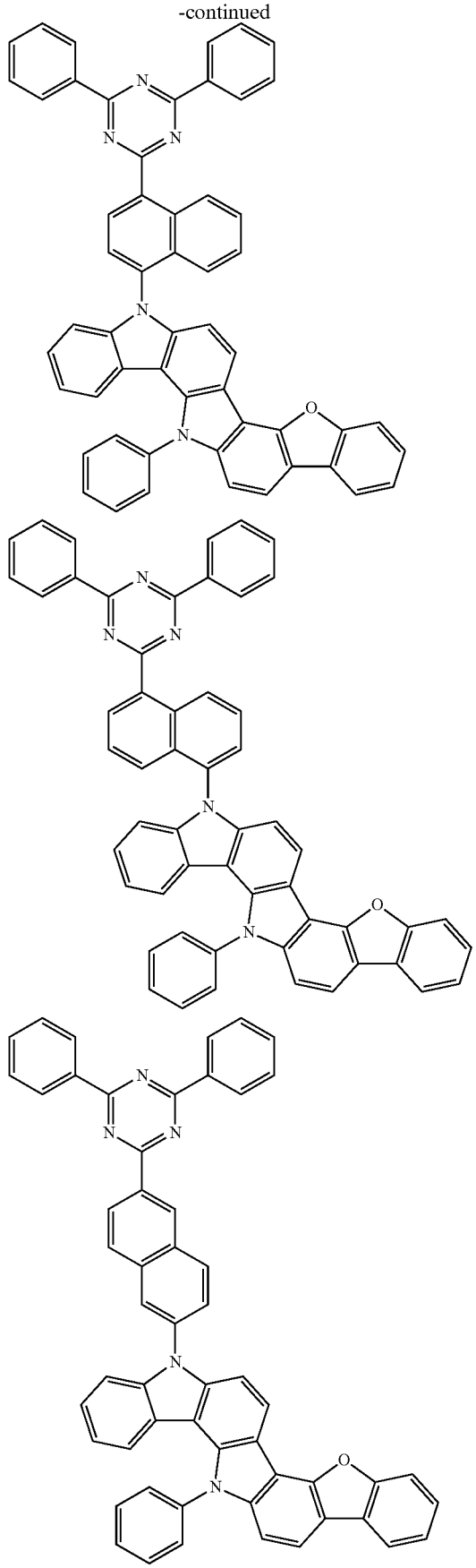
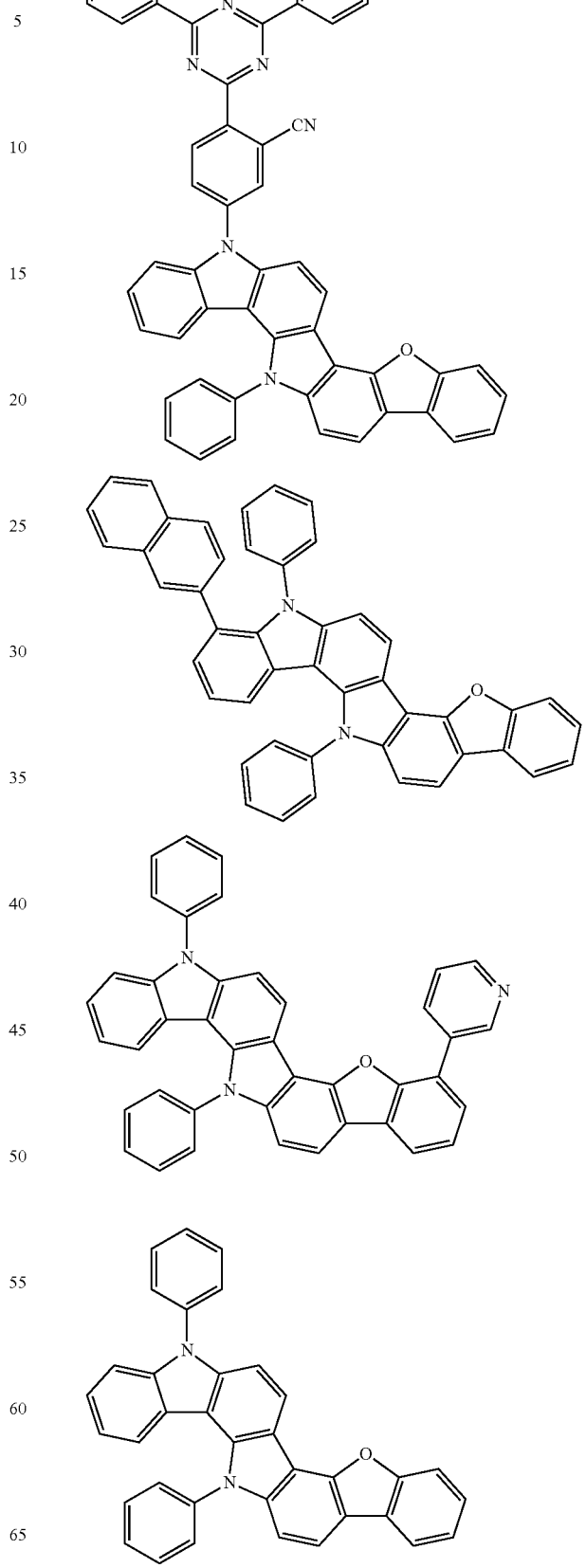

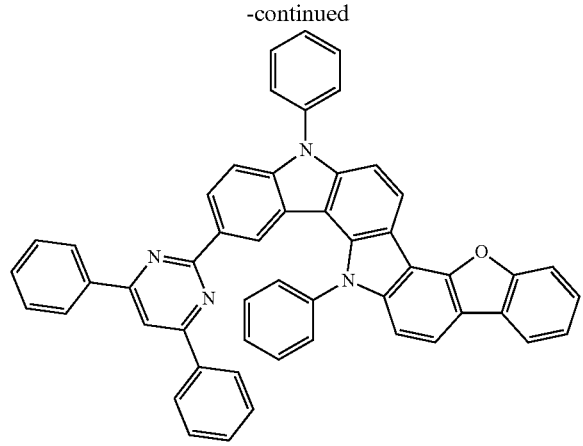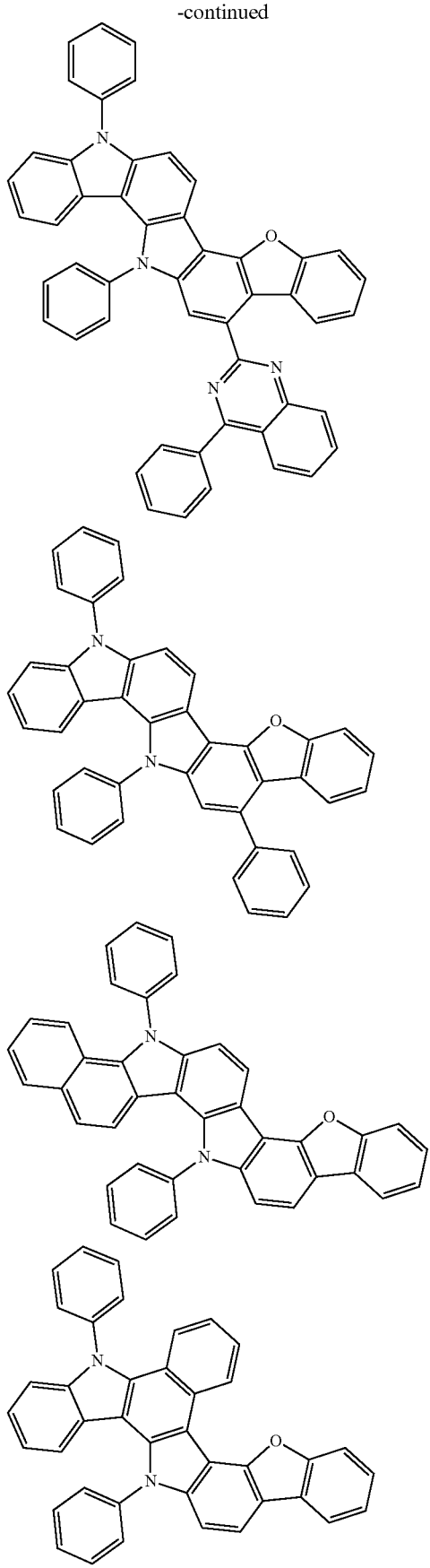

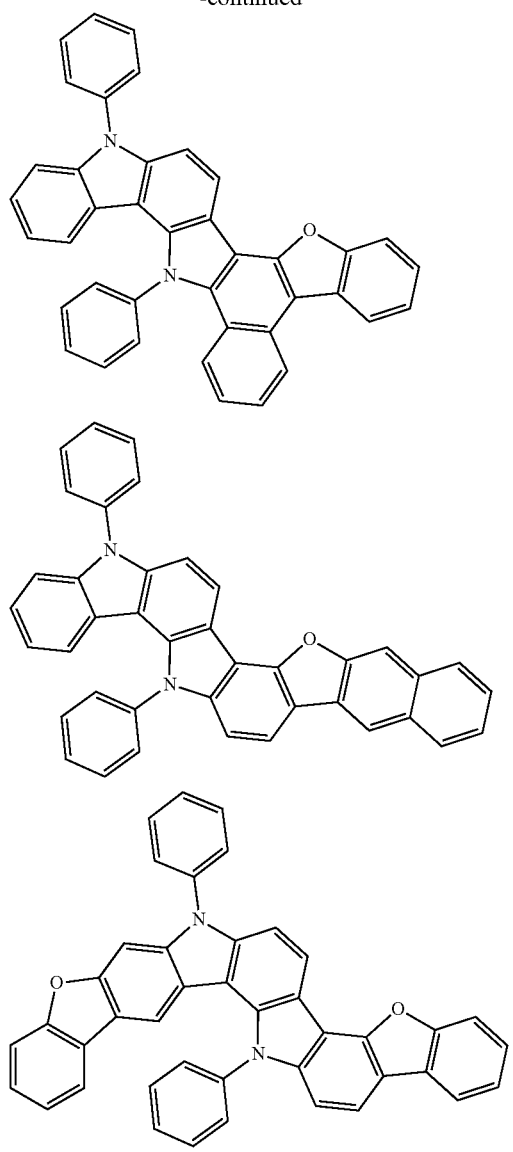
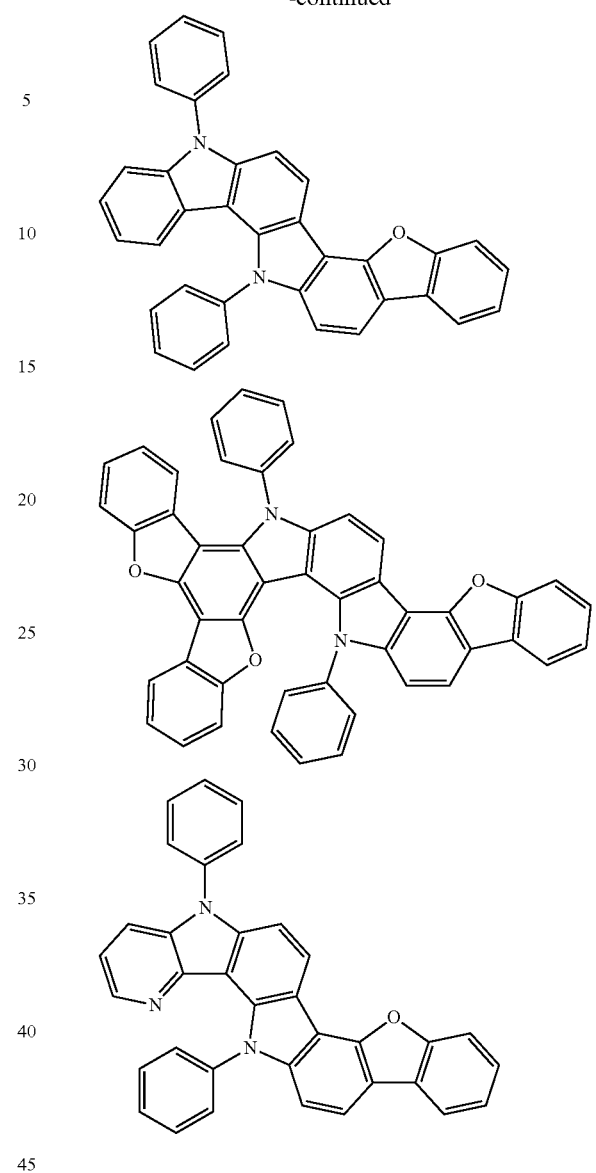
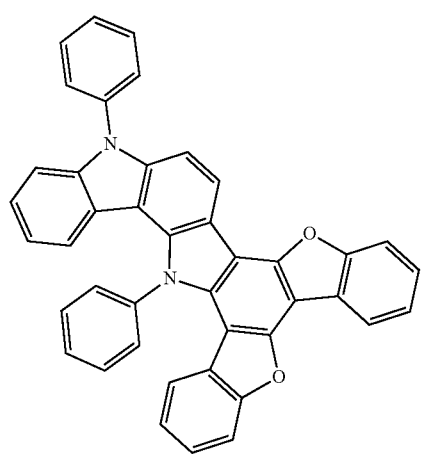
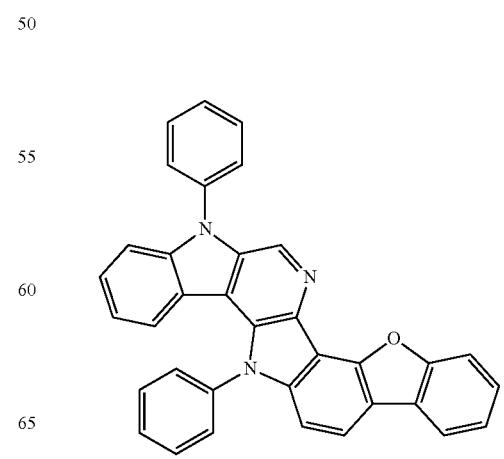

53
-continued
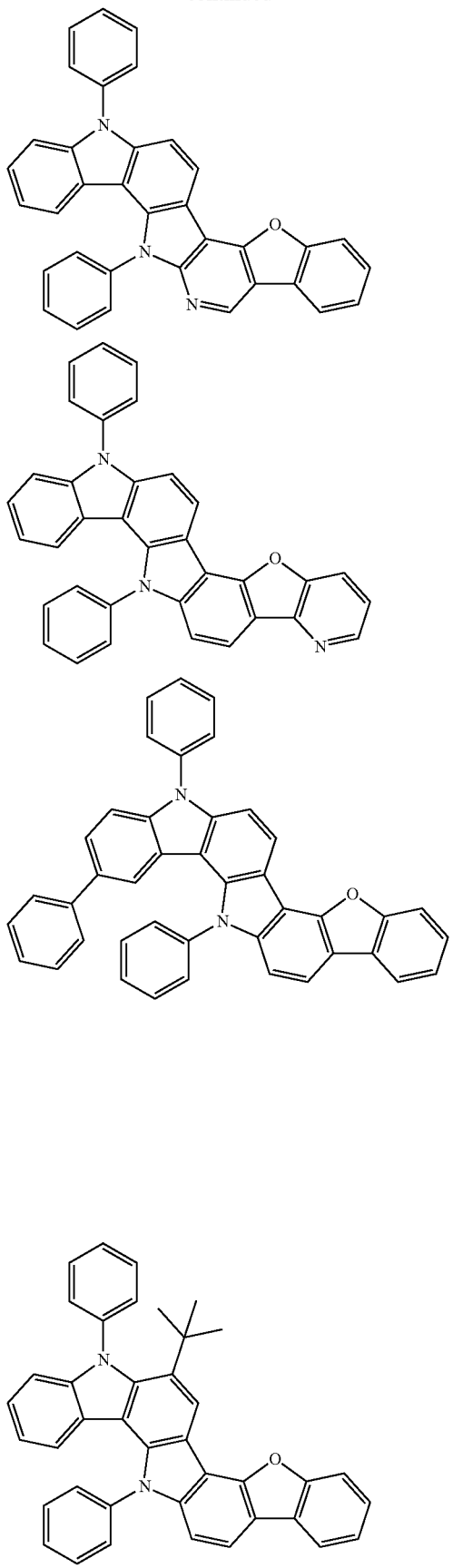
54
-continued
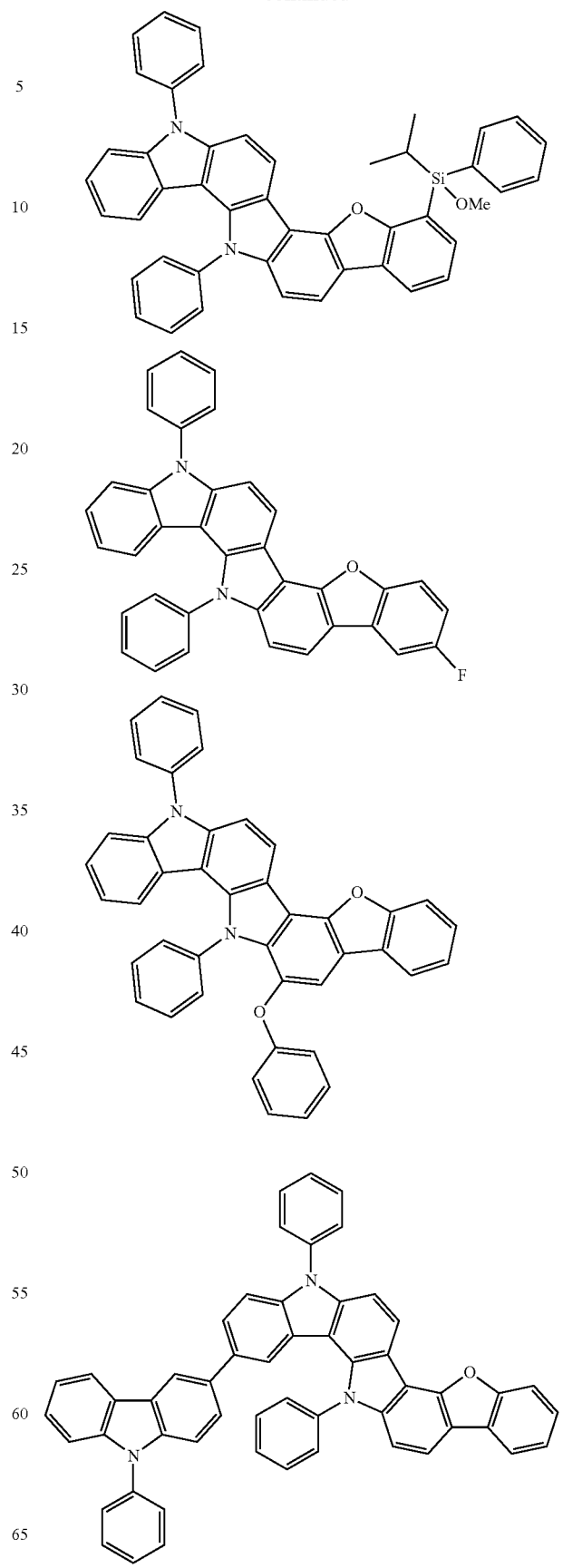

55
-continued
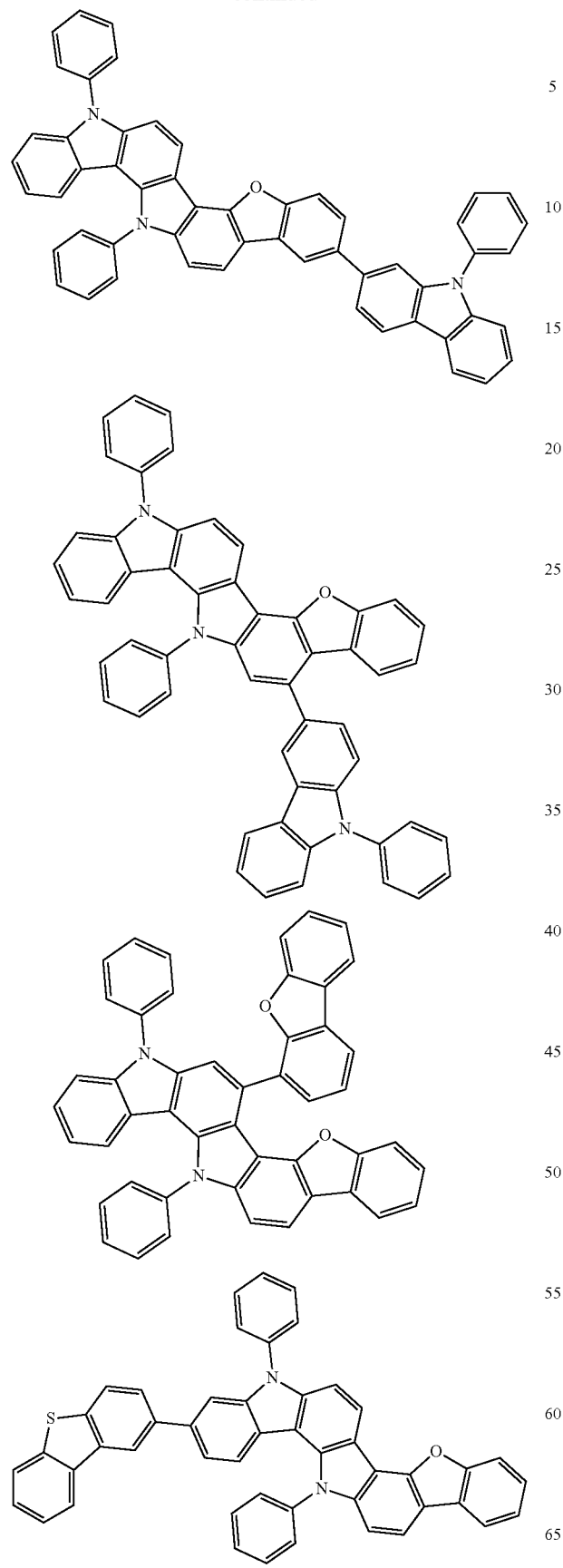
56
-continued
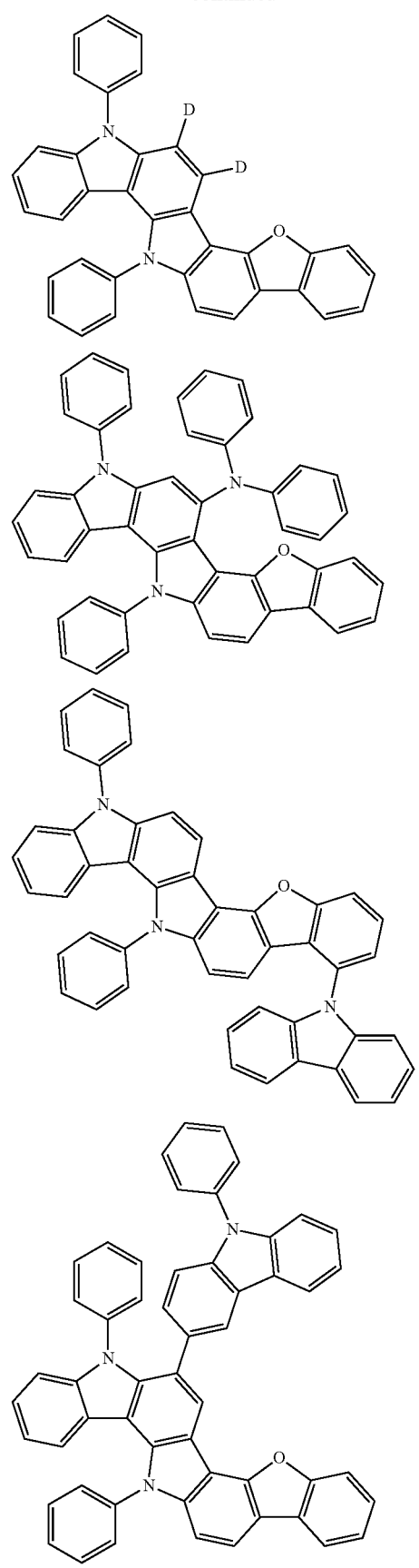

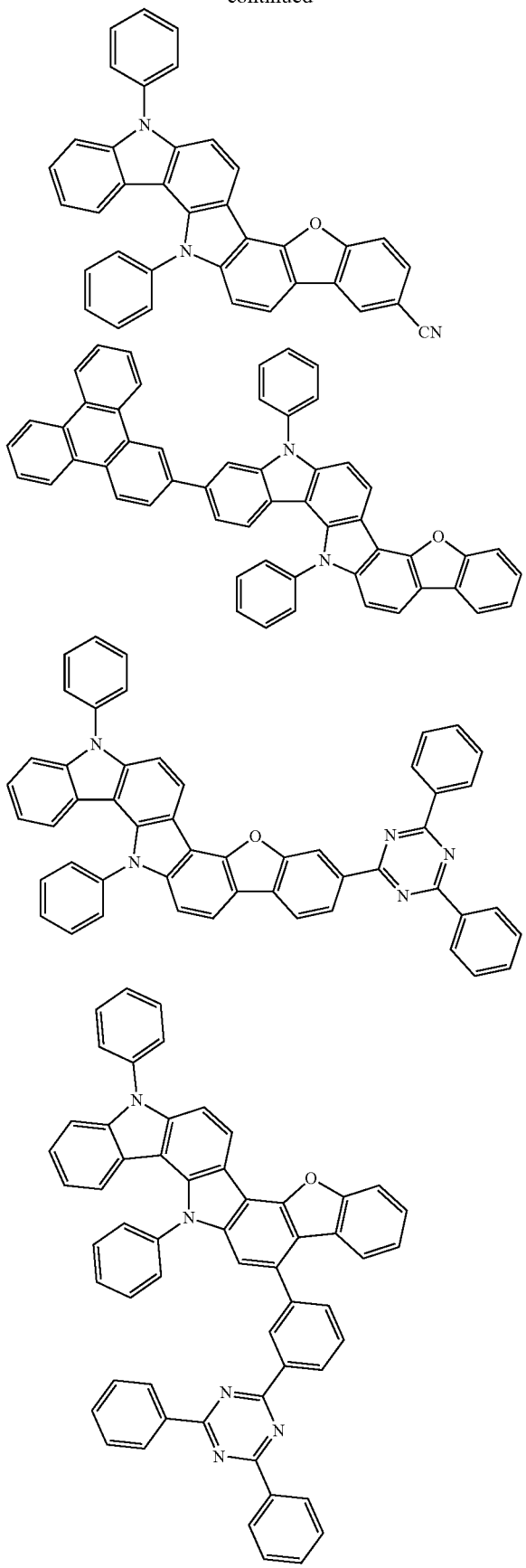
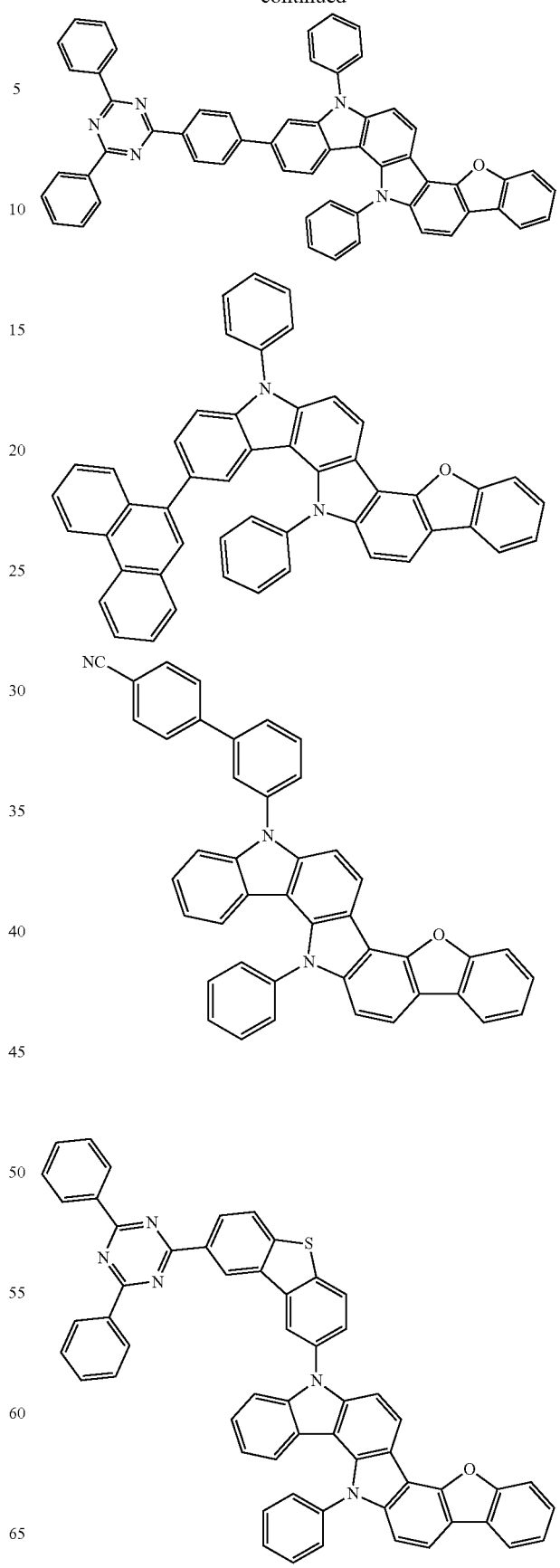

59
-continued
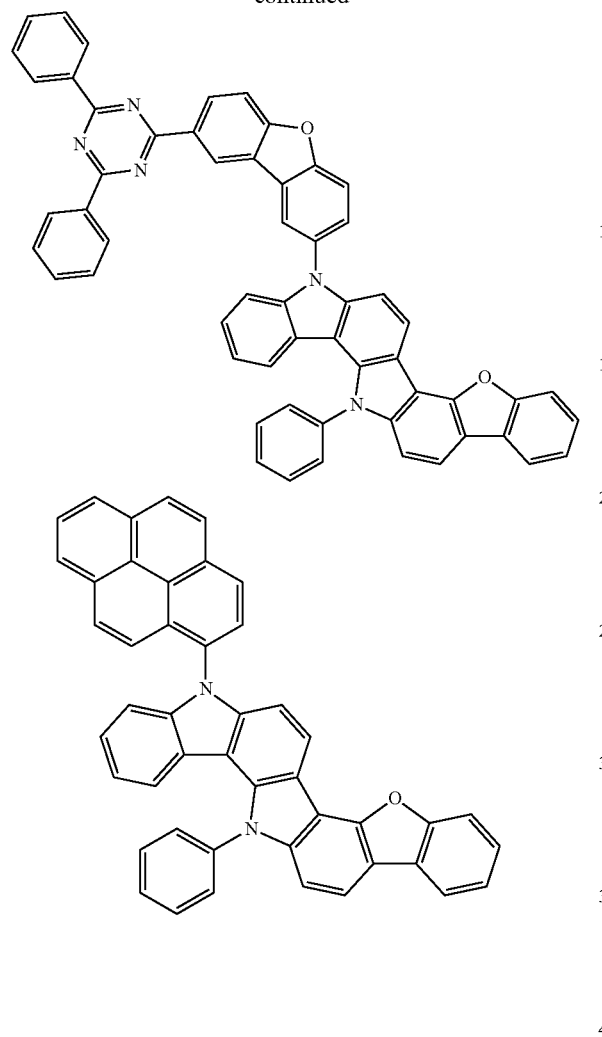
60
-continued
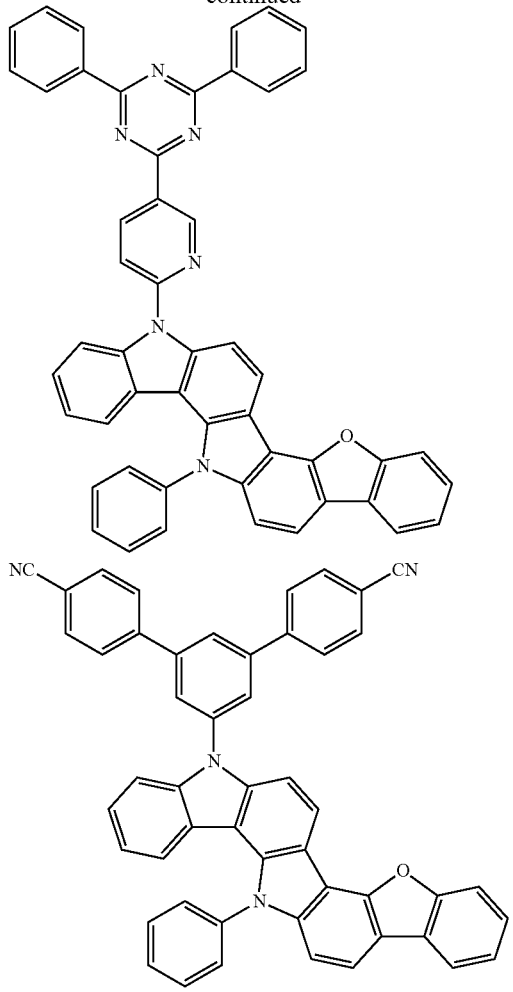
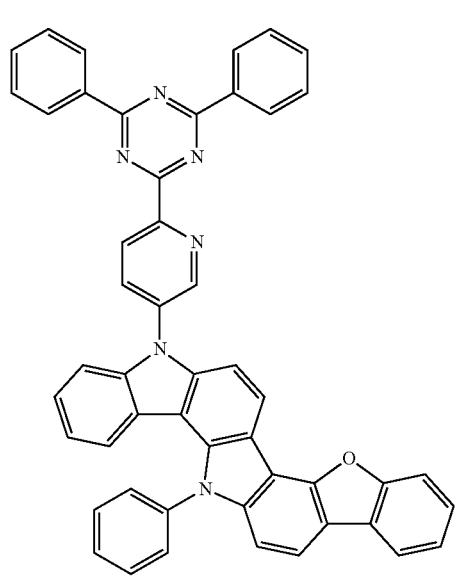
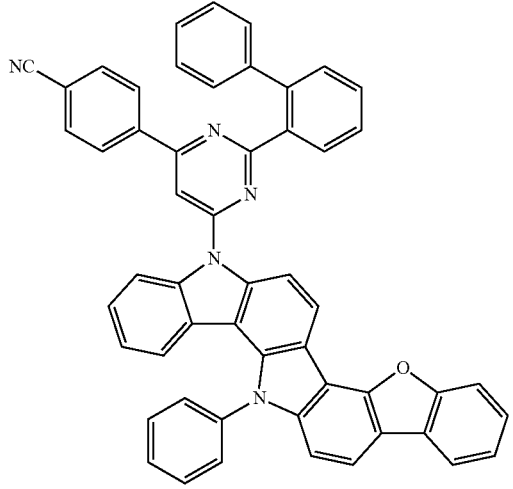

61
-continued
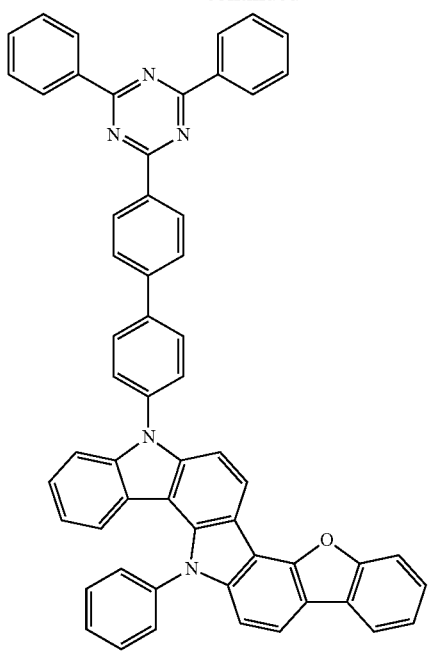
62
-continued
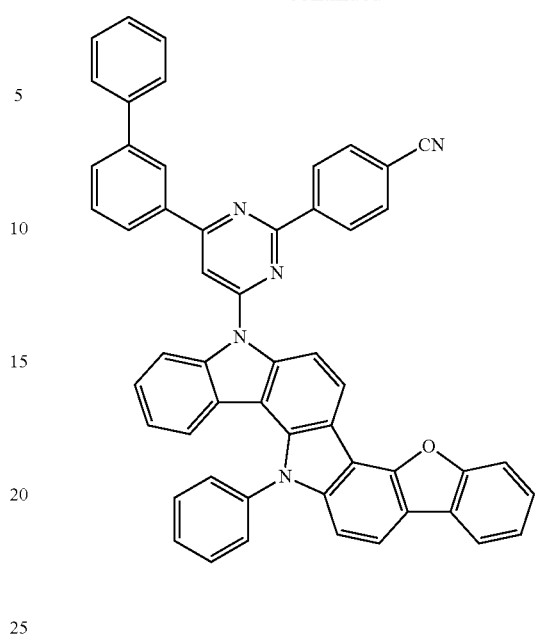
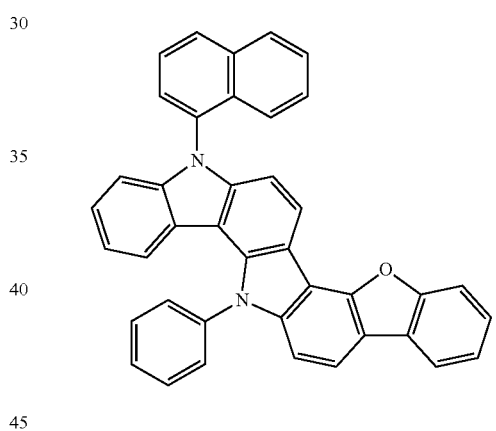
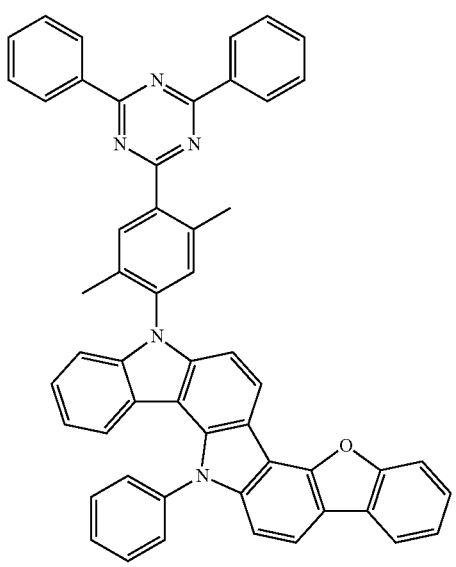
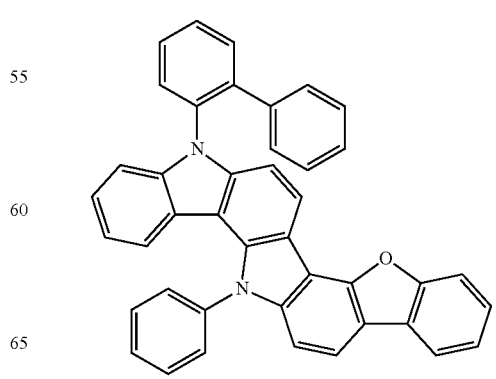

63
-continued
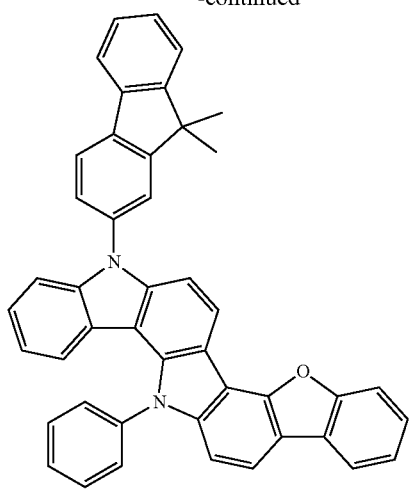
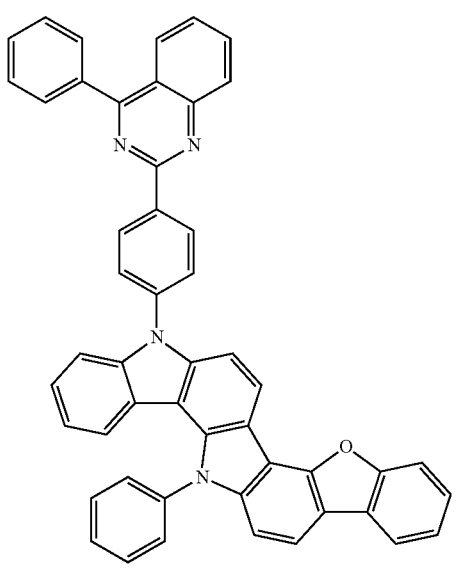
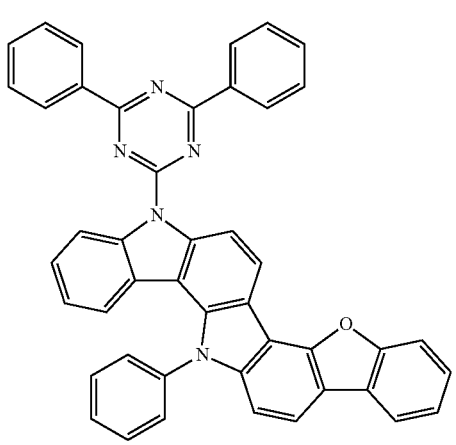
64
-continued
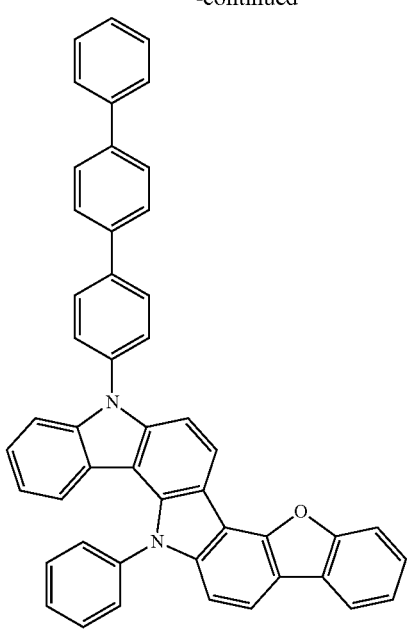
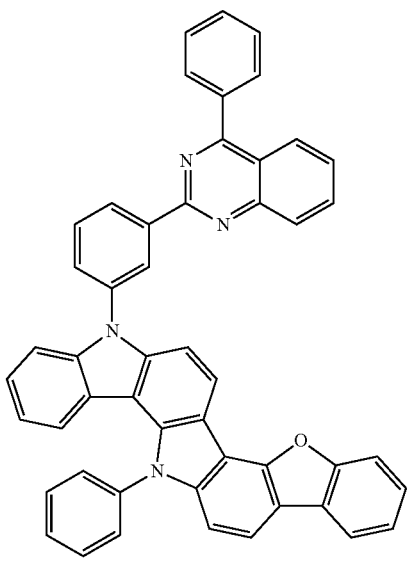

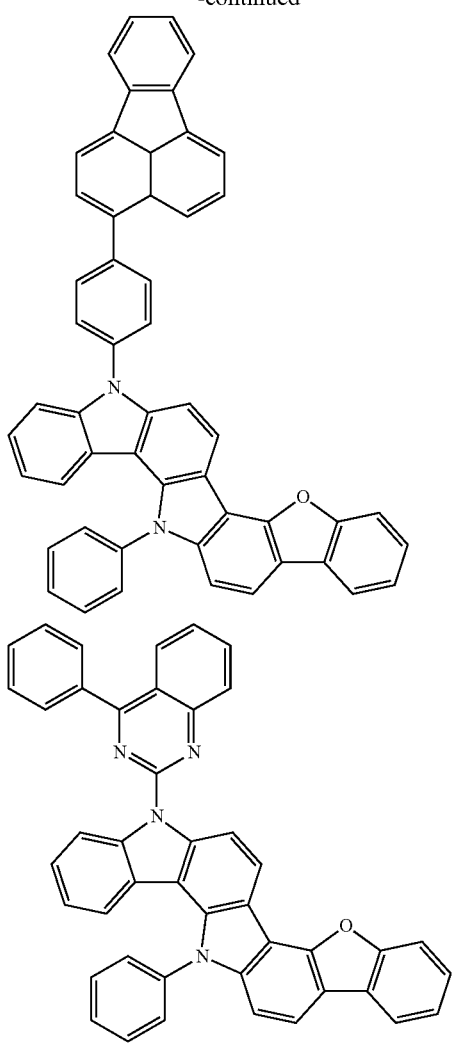
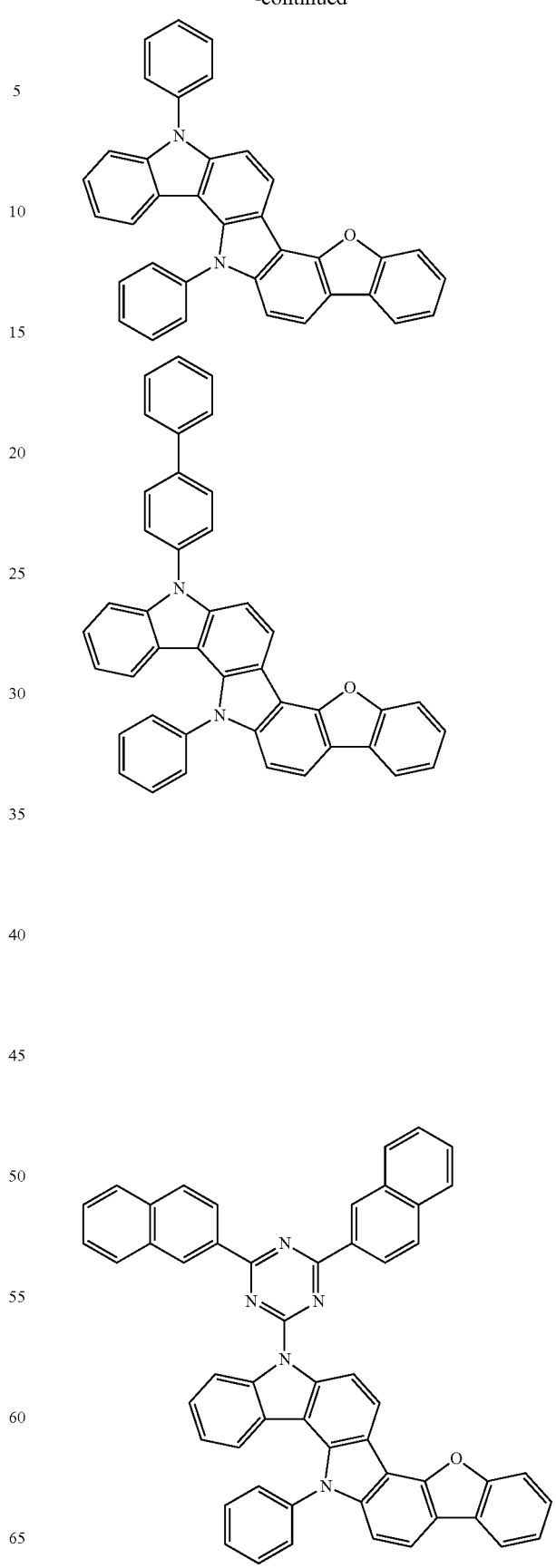

67
-continued
68
-continued
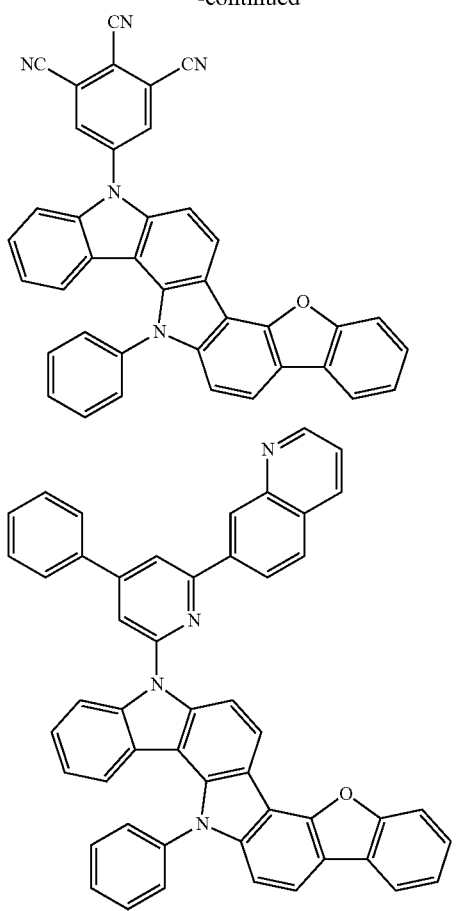
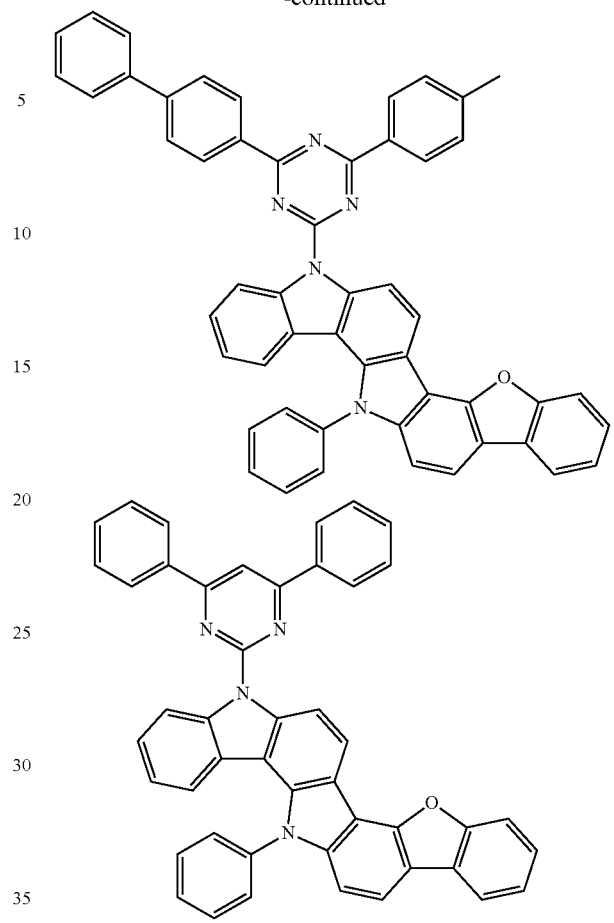
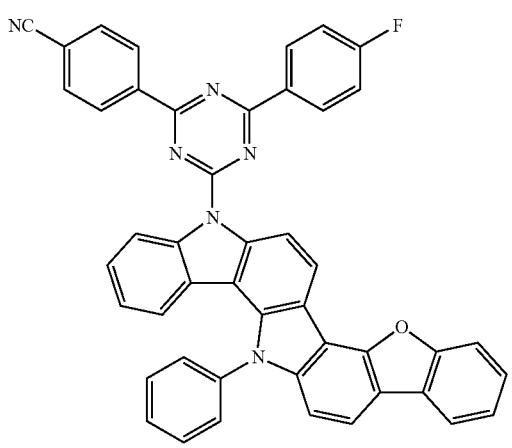
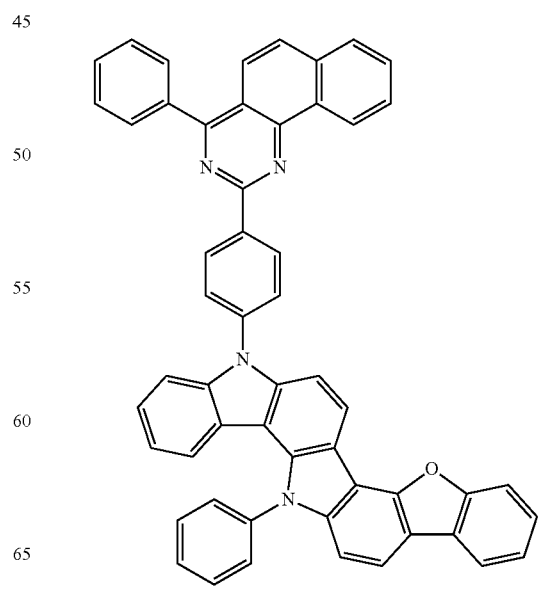

69
-continued
70
-continued
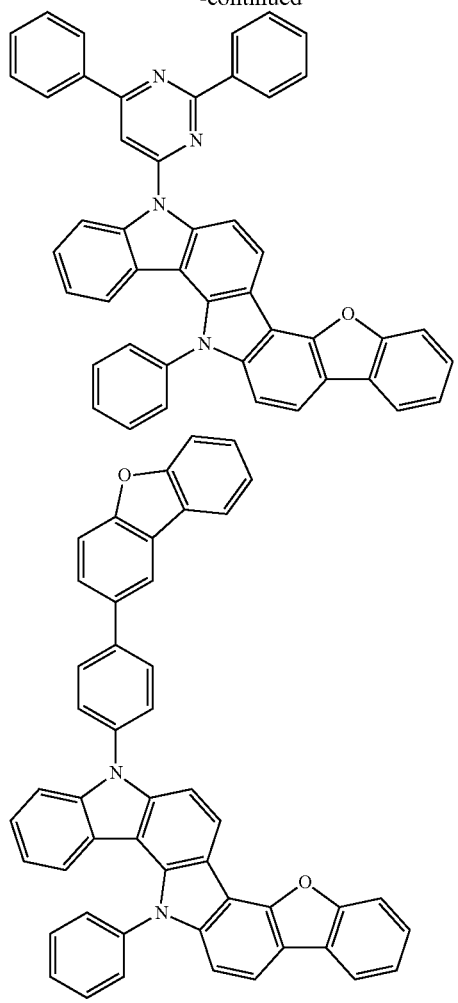
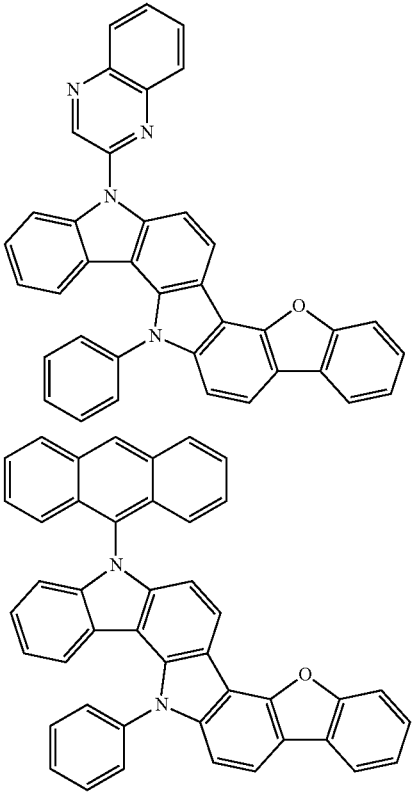
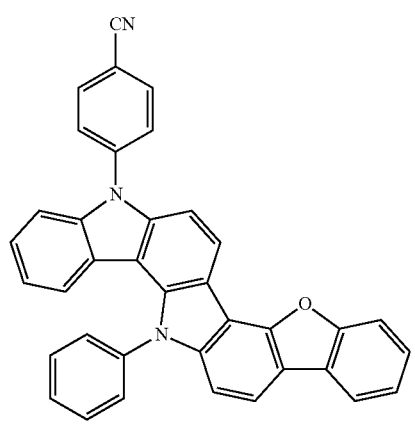
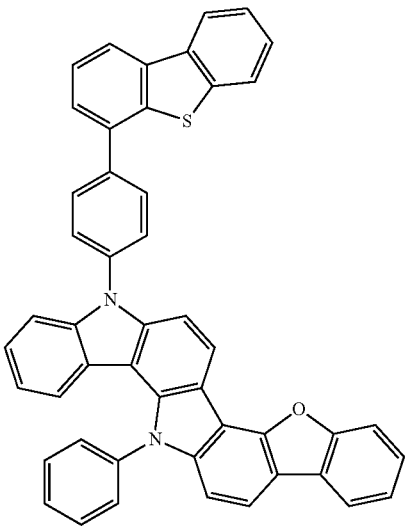

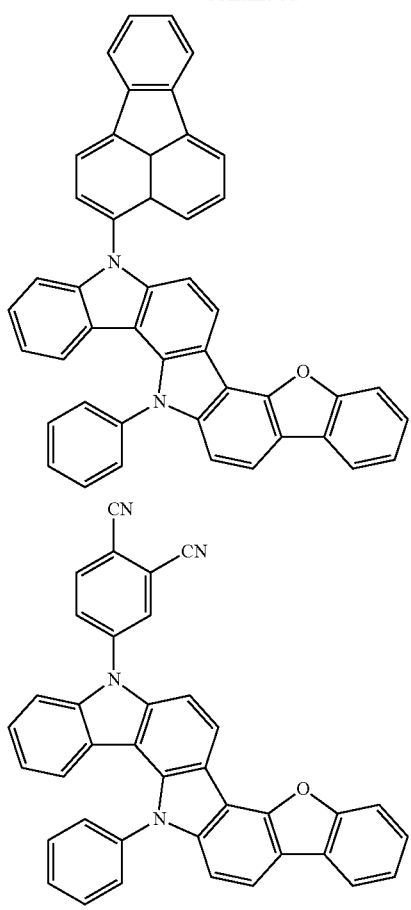
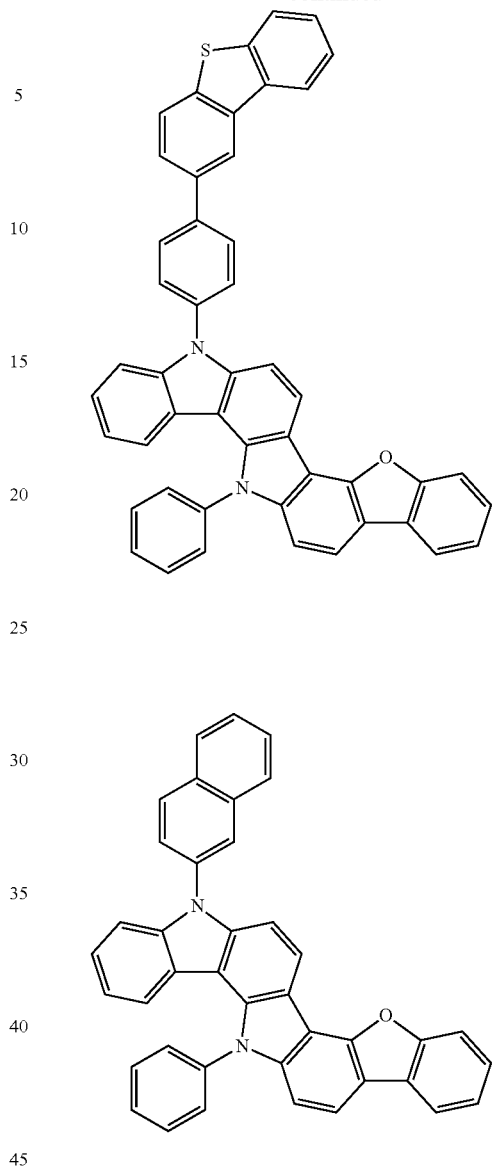
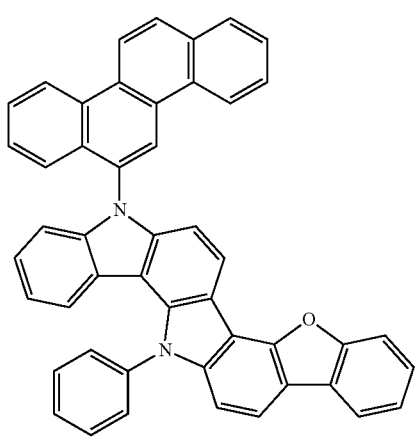
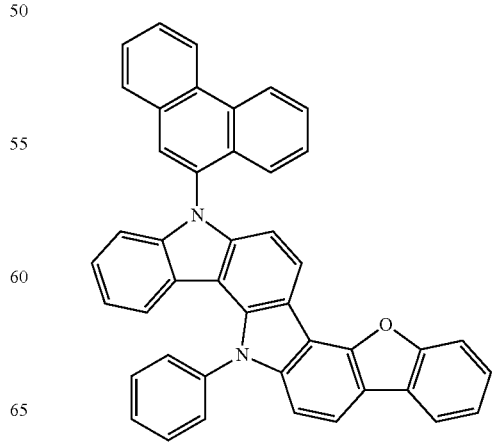

73
-continued
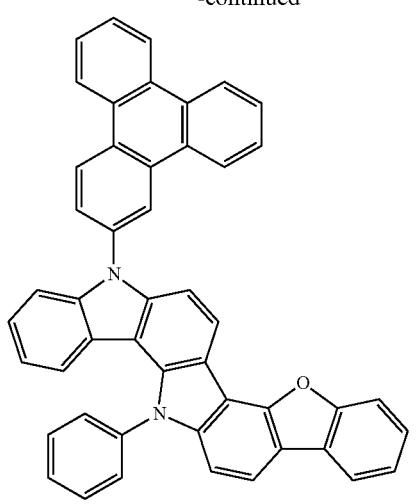
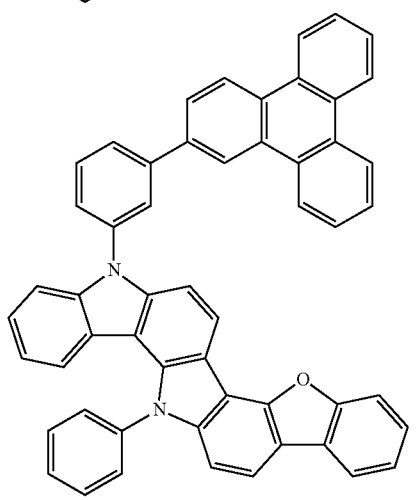
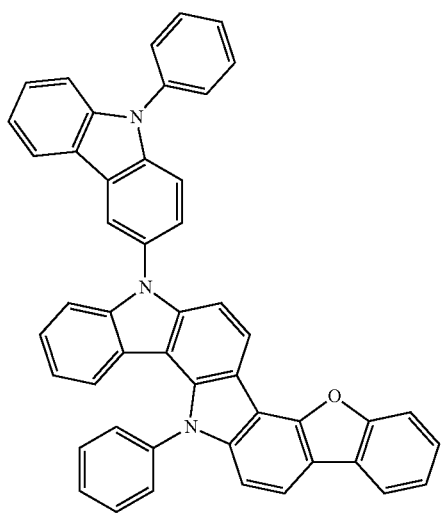
74
-continued
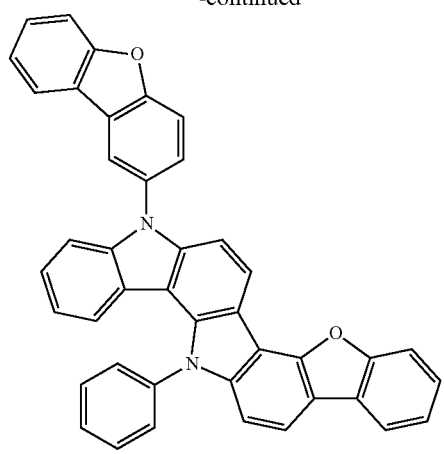
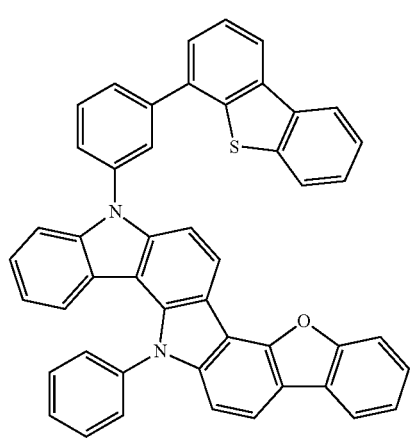
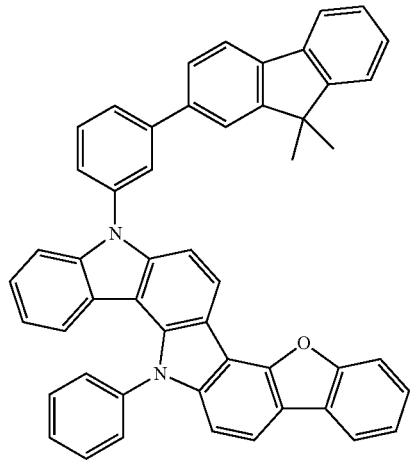

-continued
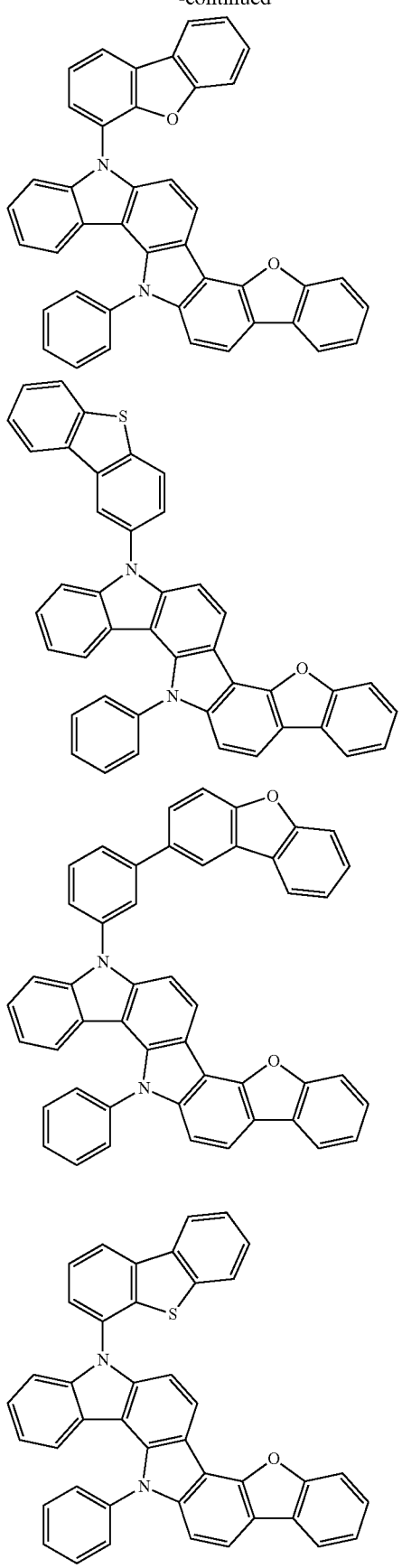
-continued
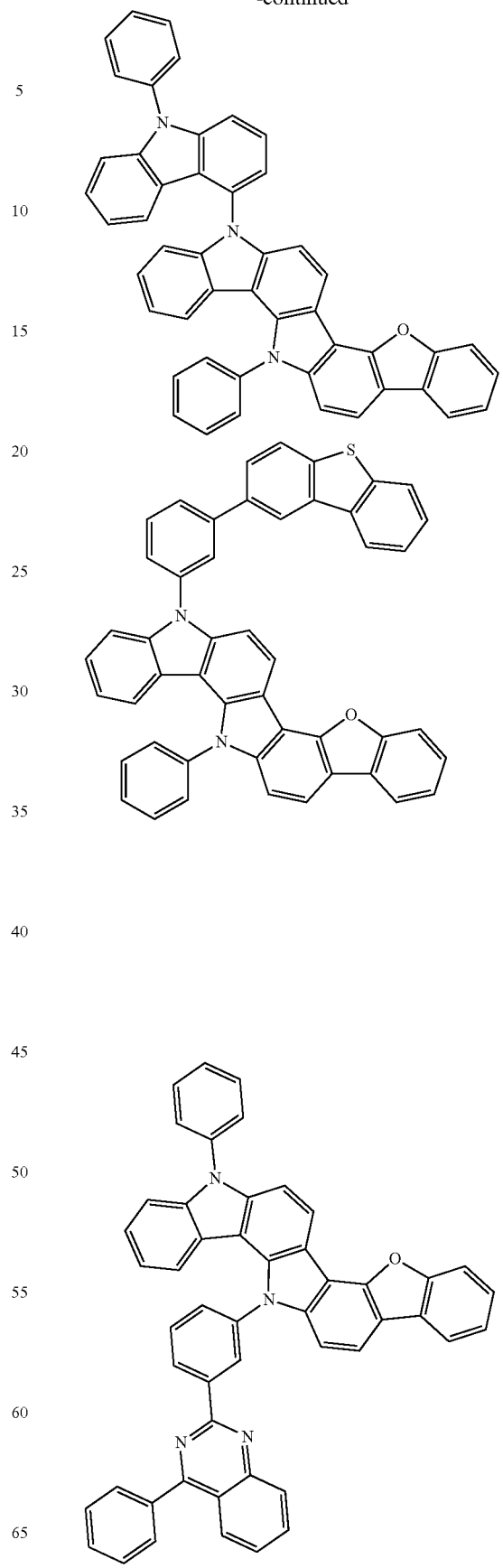

77
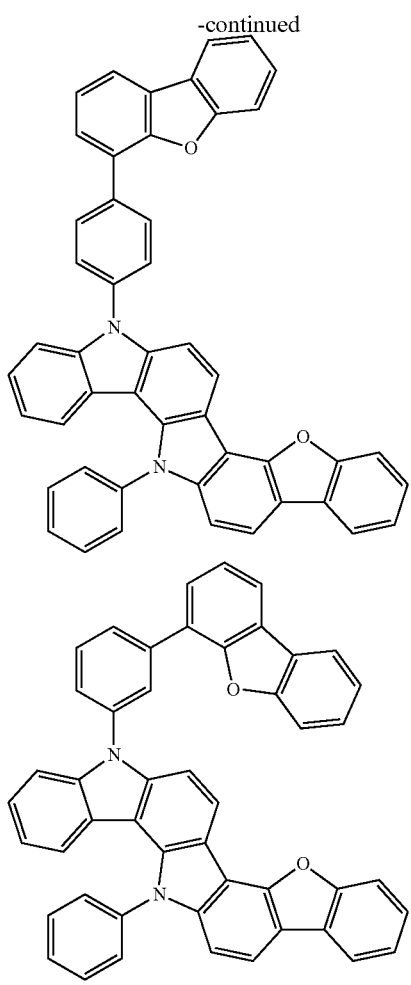
78
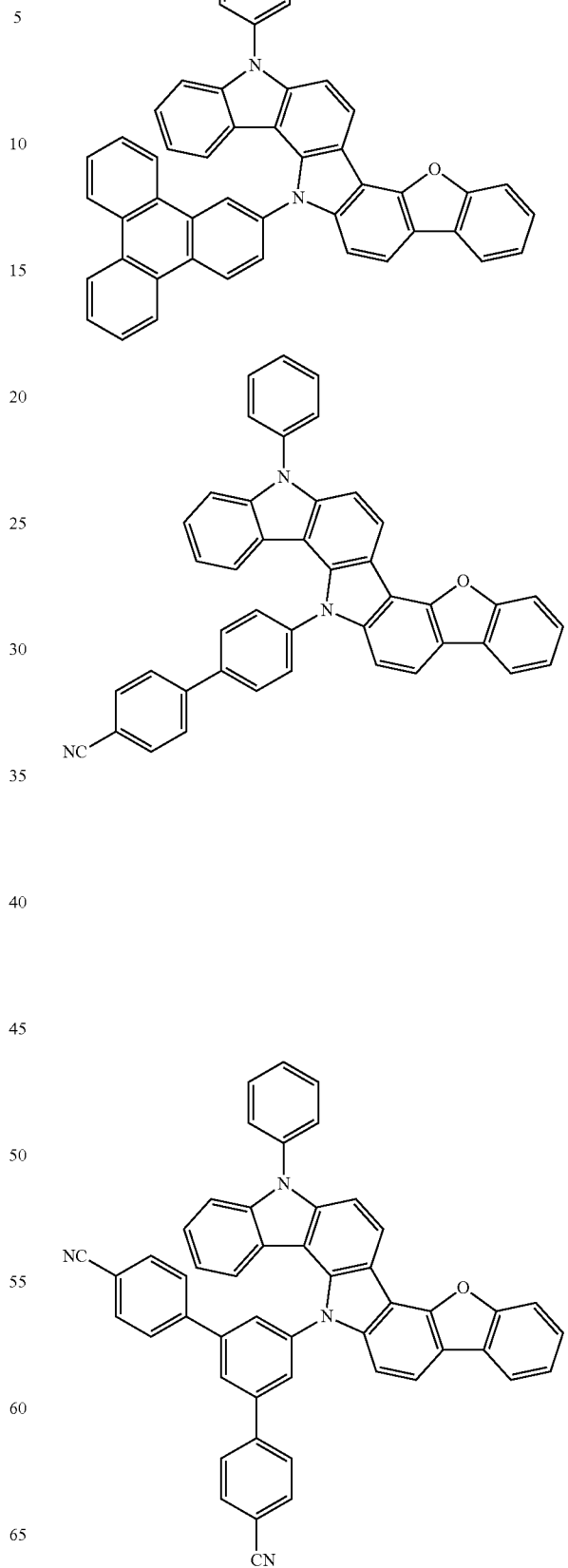

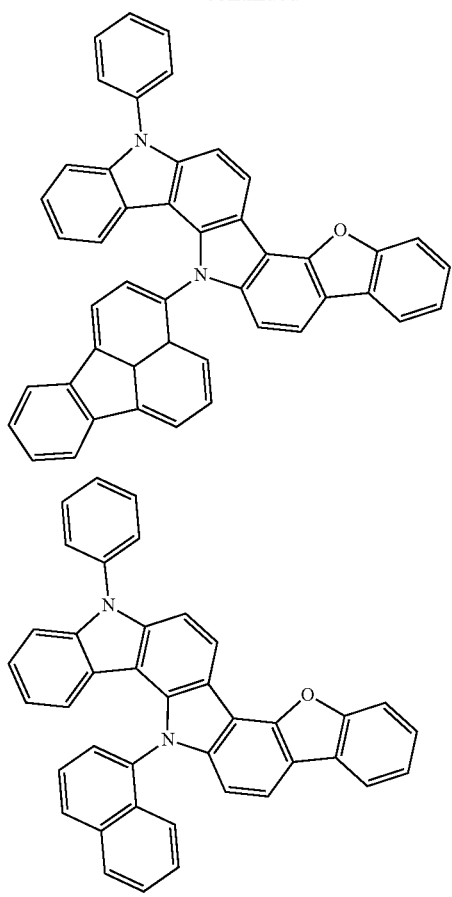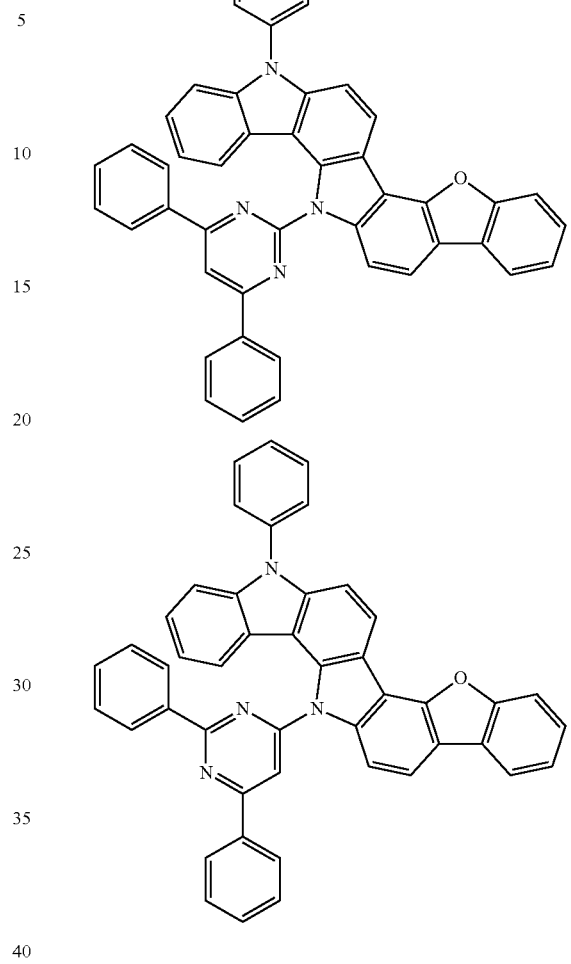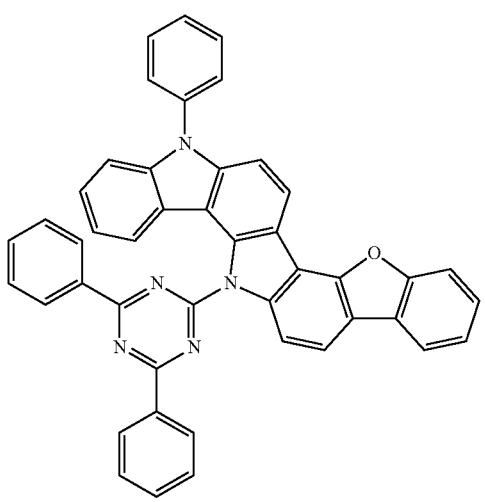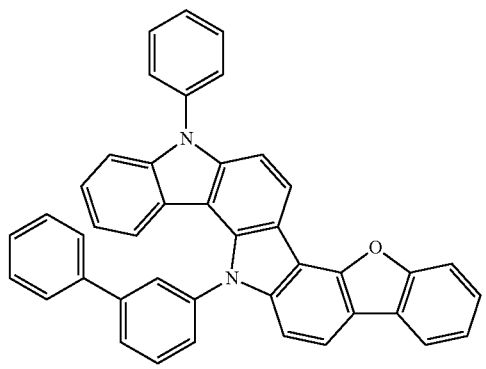

81
-continued
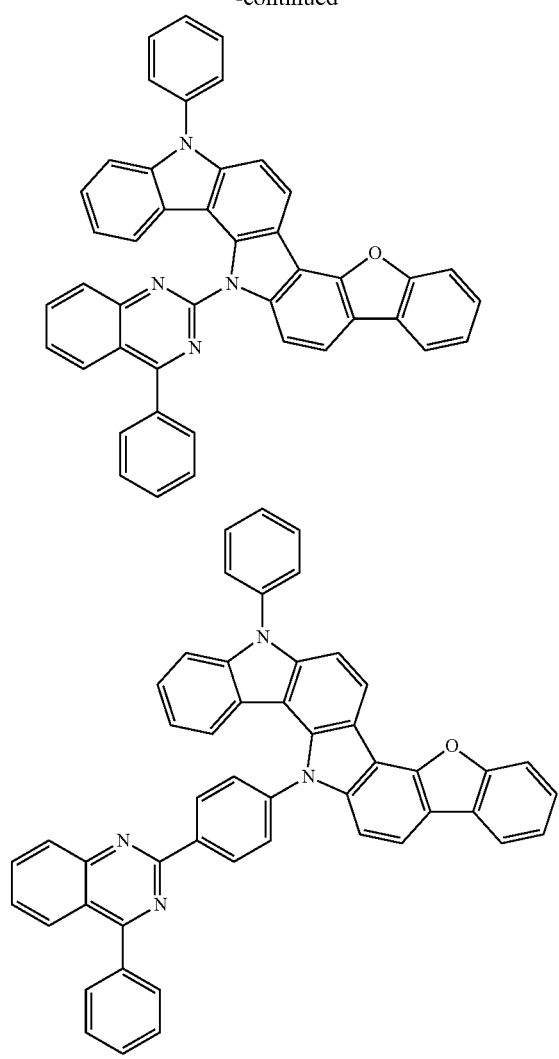
82
-continued
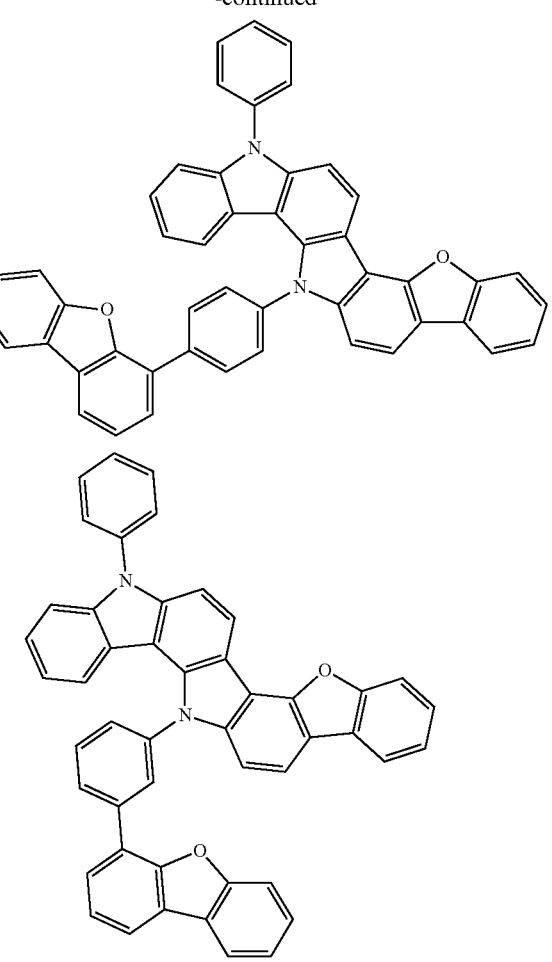
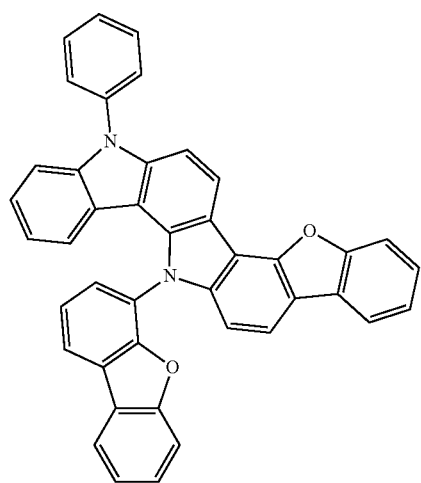
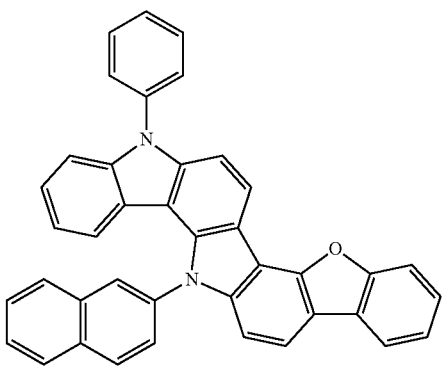

83
-continued
84
-continued
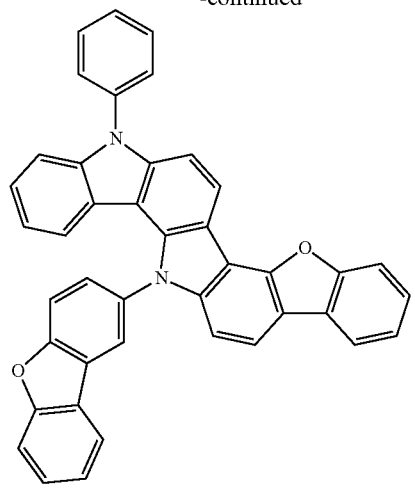
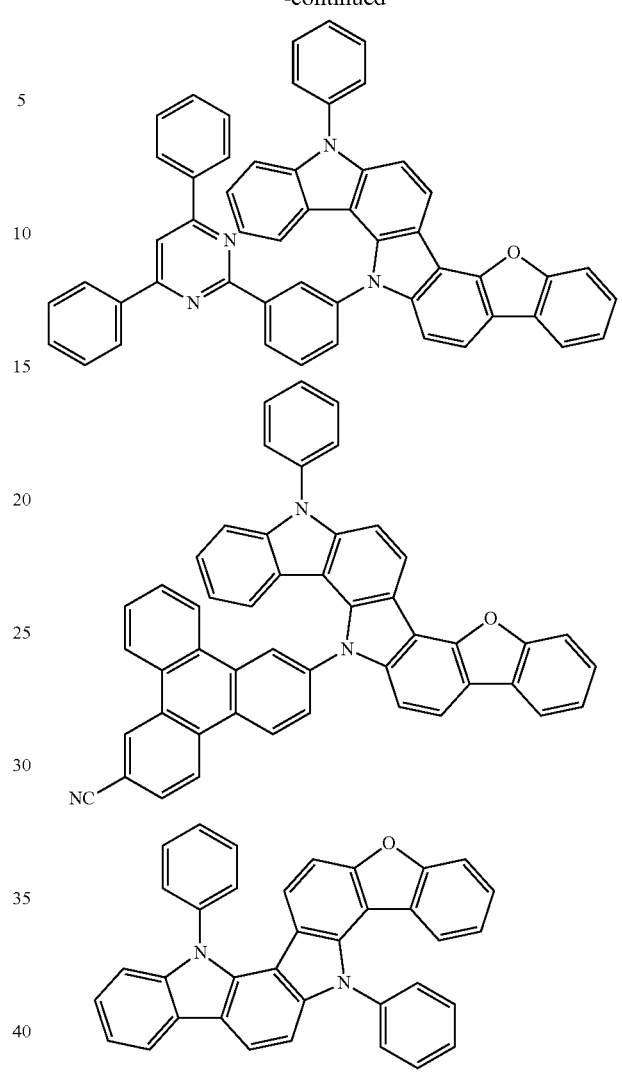
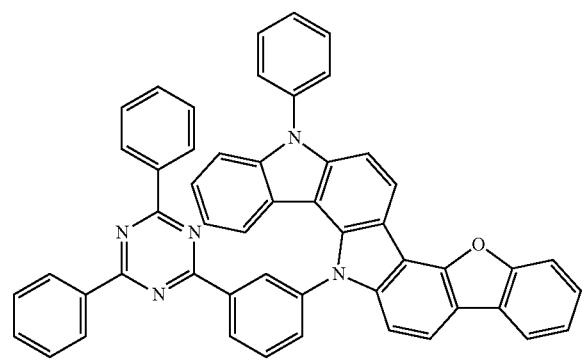
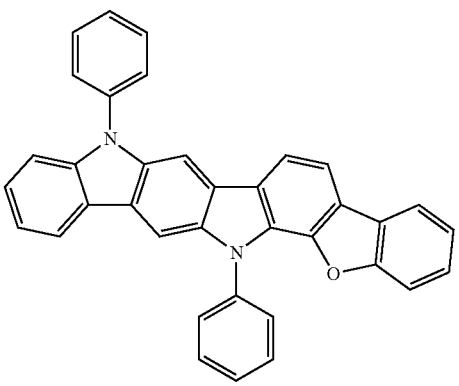

85
-continued
86
-continued
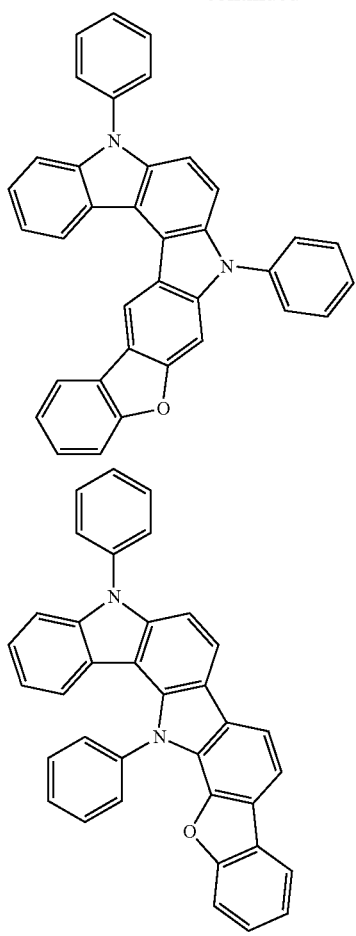
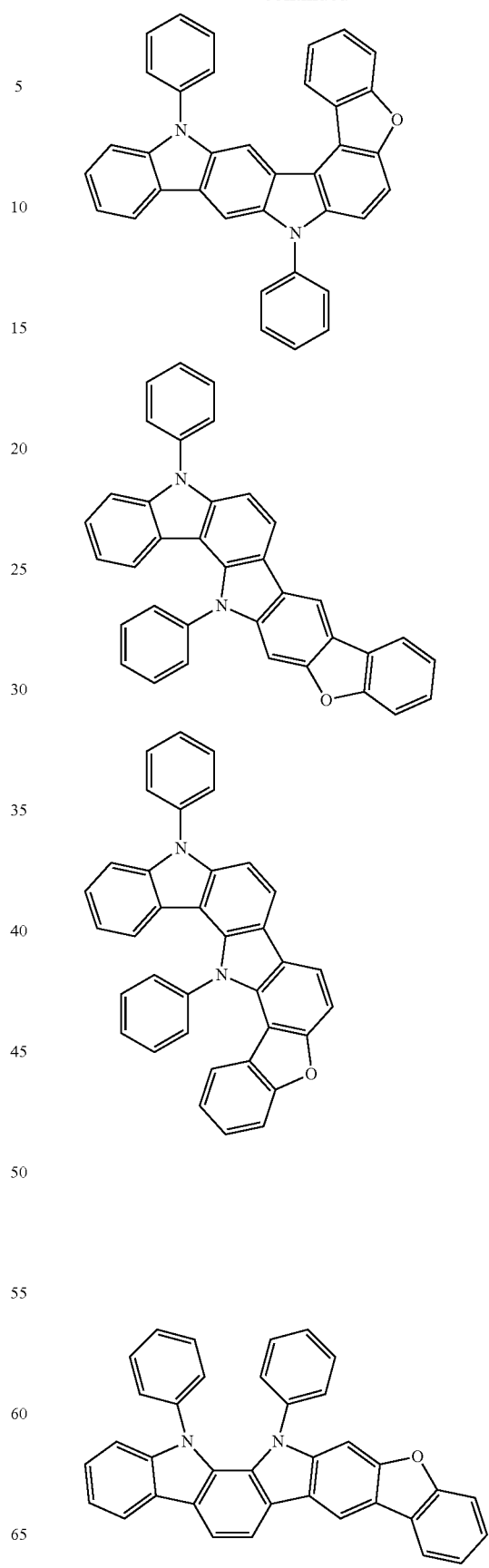

87
-continued
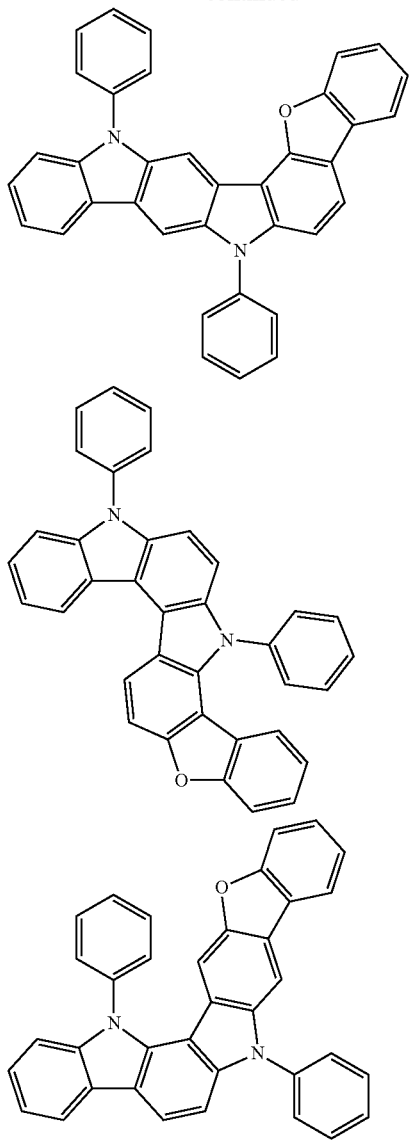
88
-continued
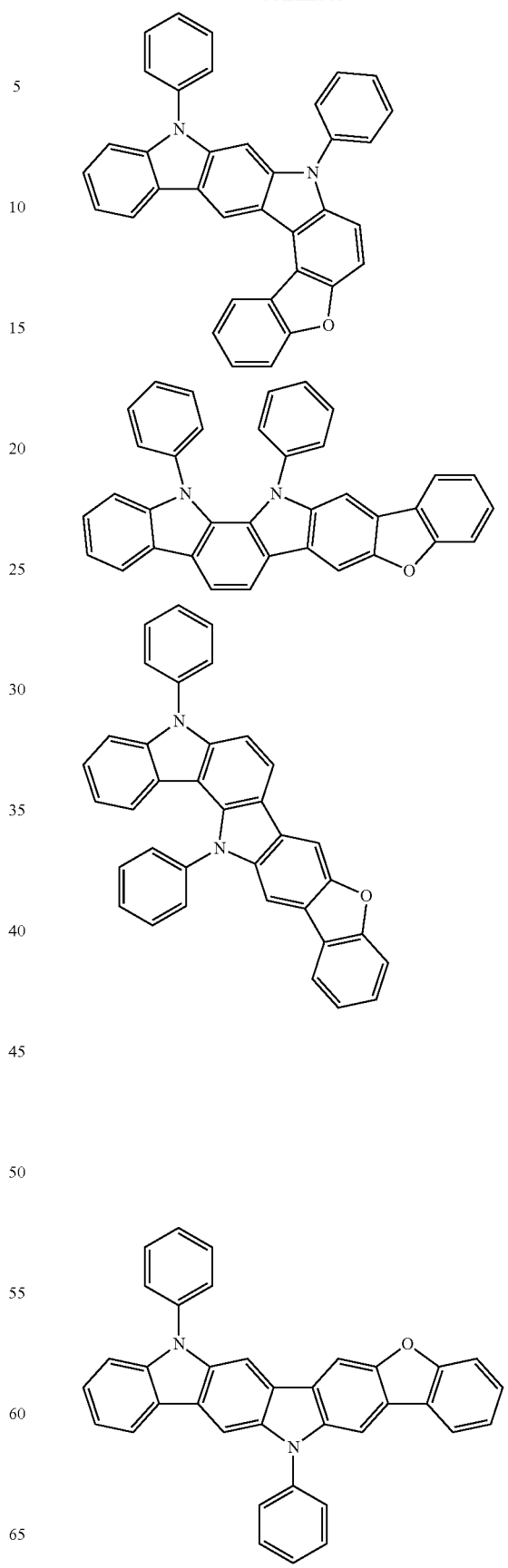

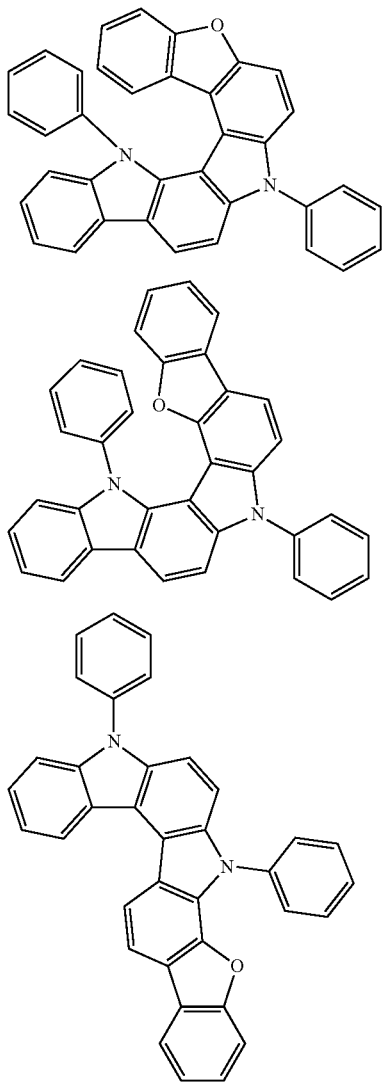
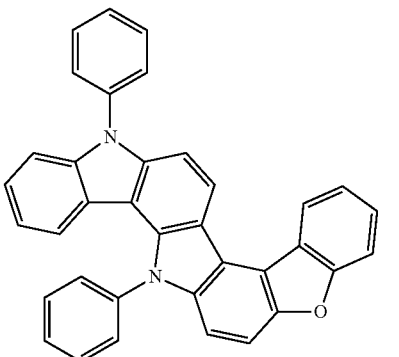
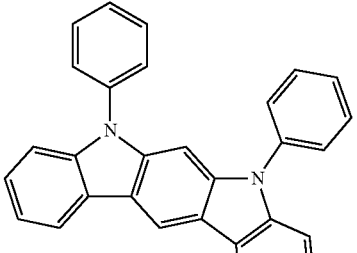
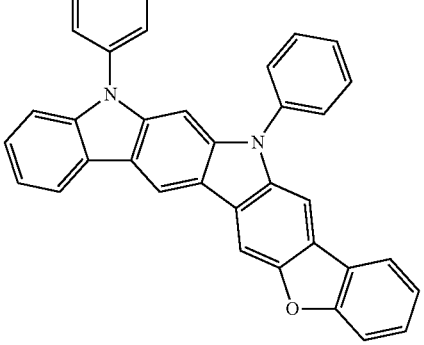
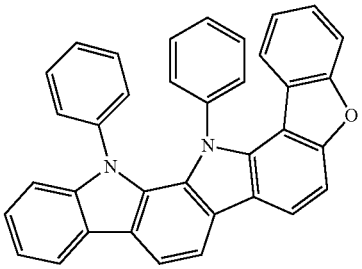
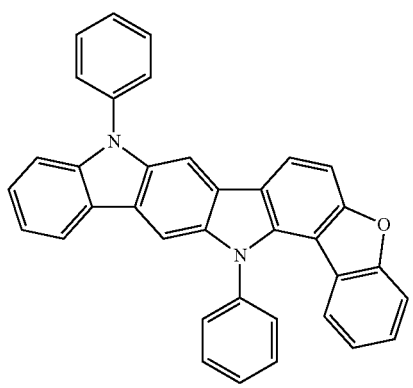
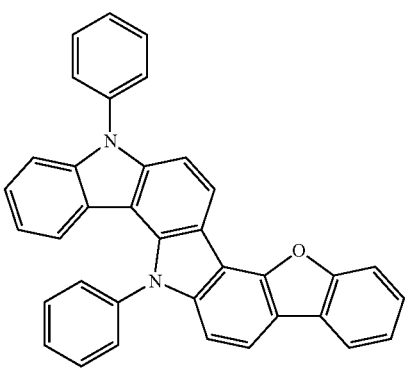

91
-continued
92
-continued
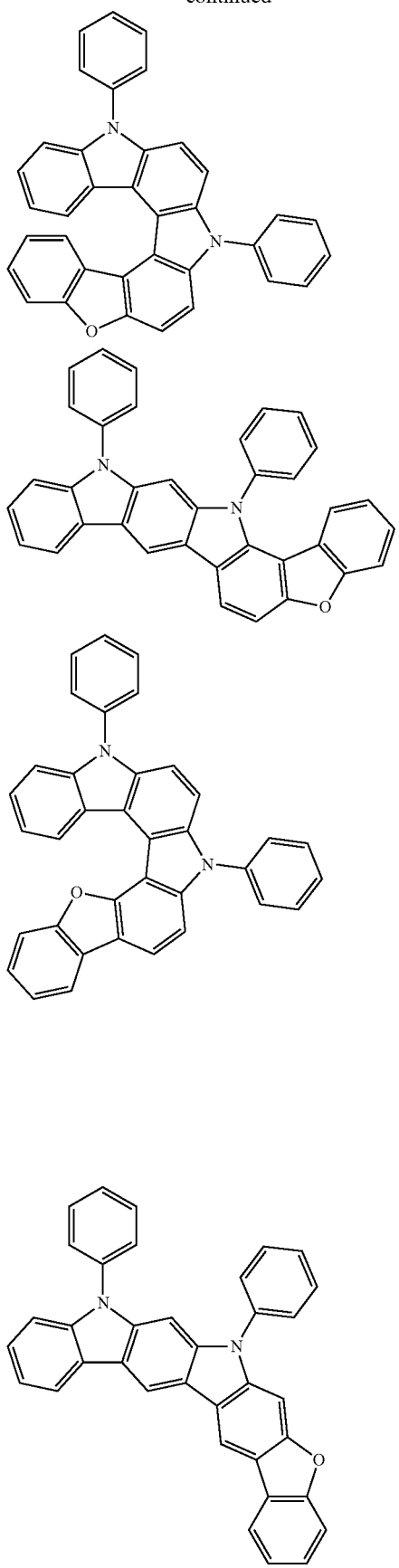
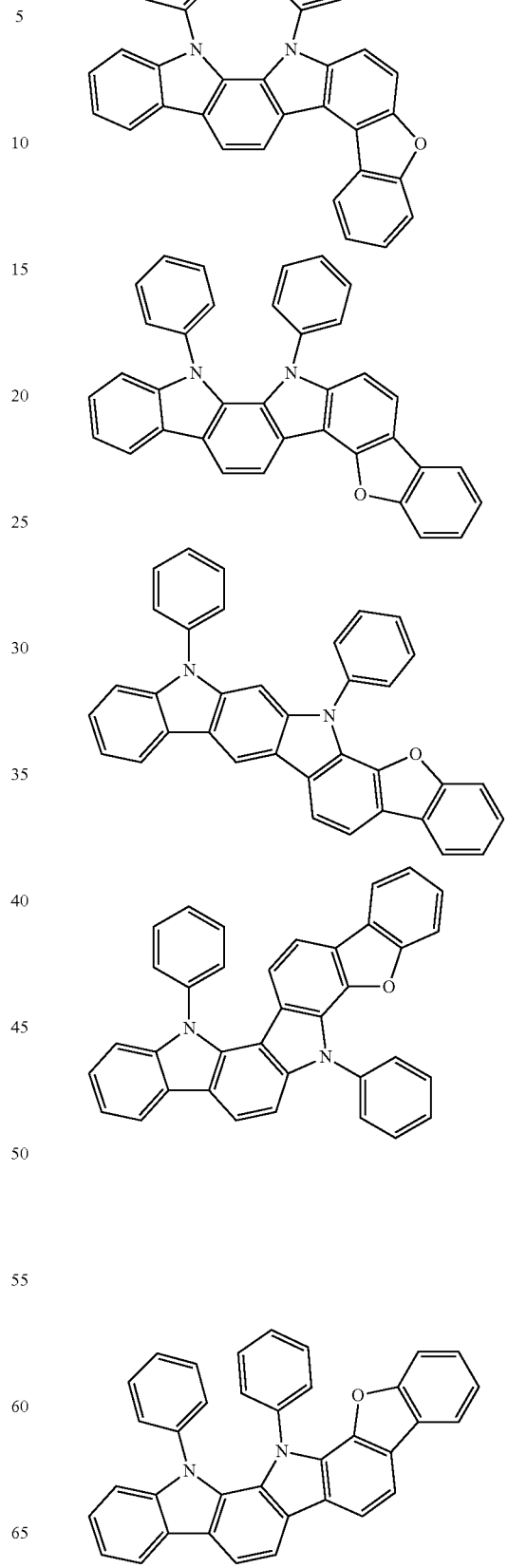

-continued
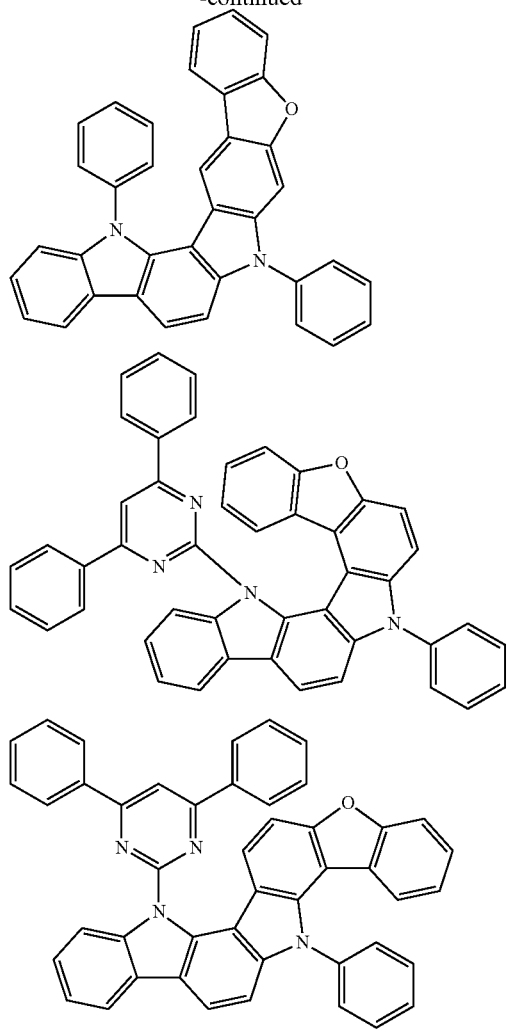
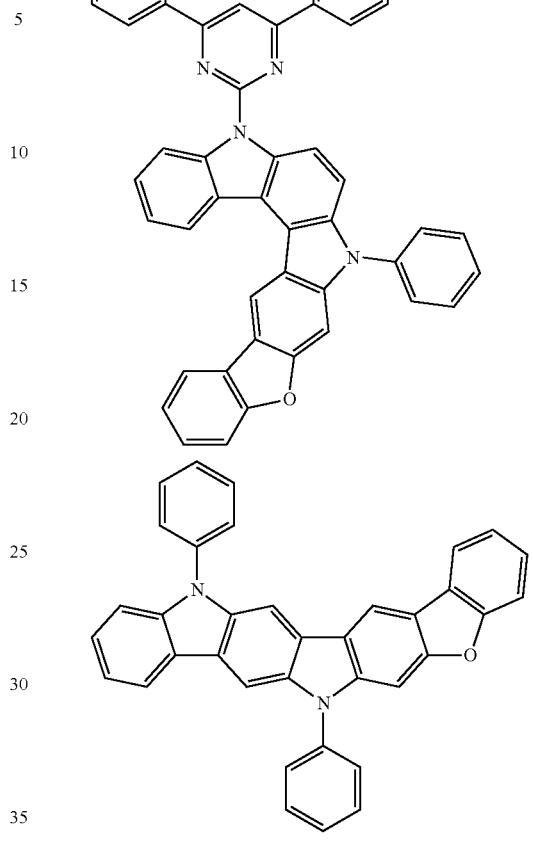
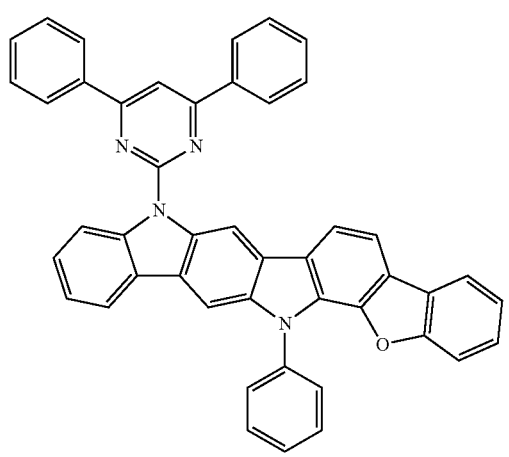
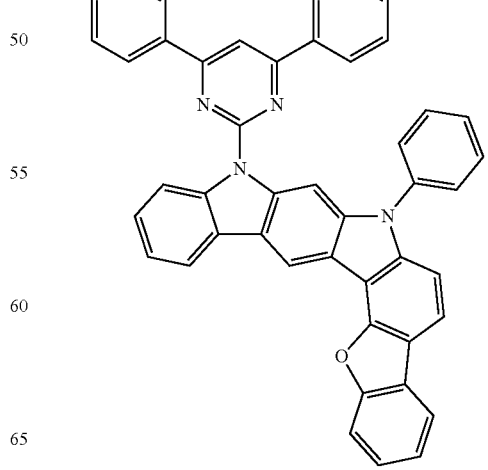

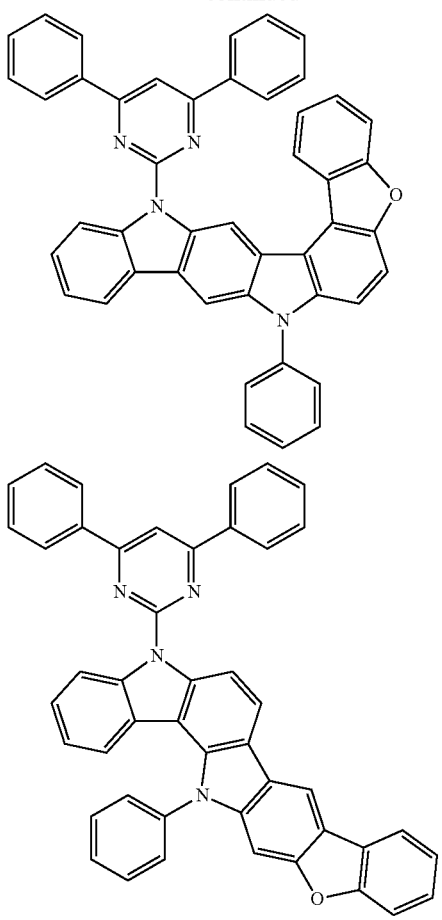
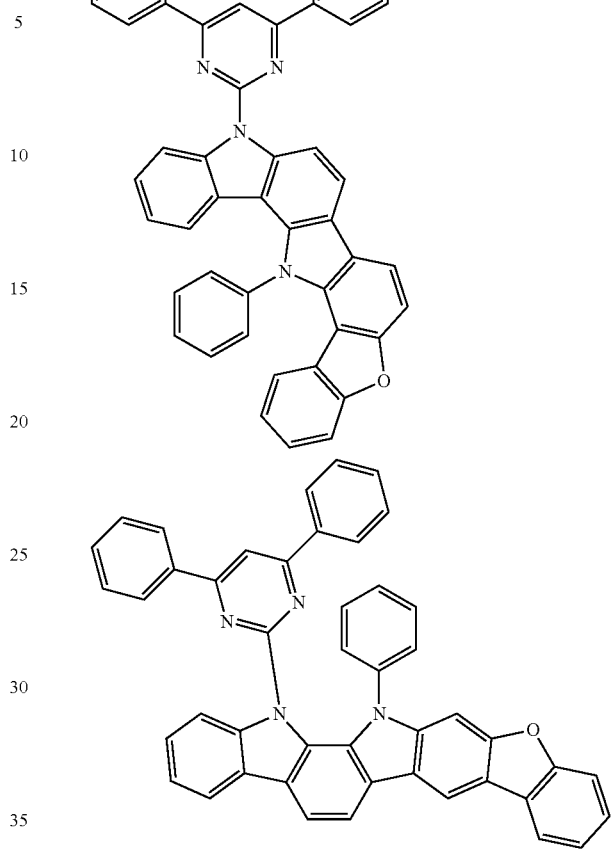
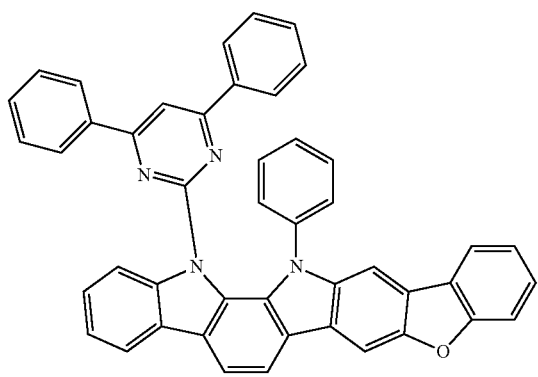
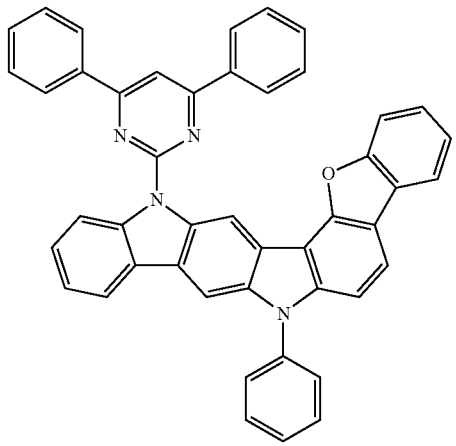

97
-continued
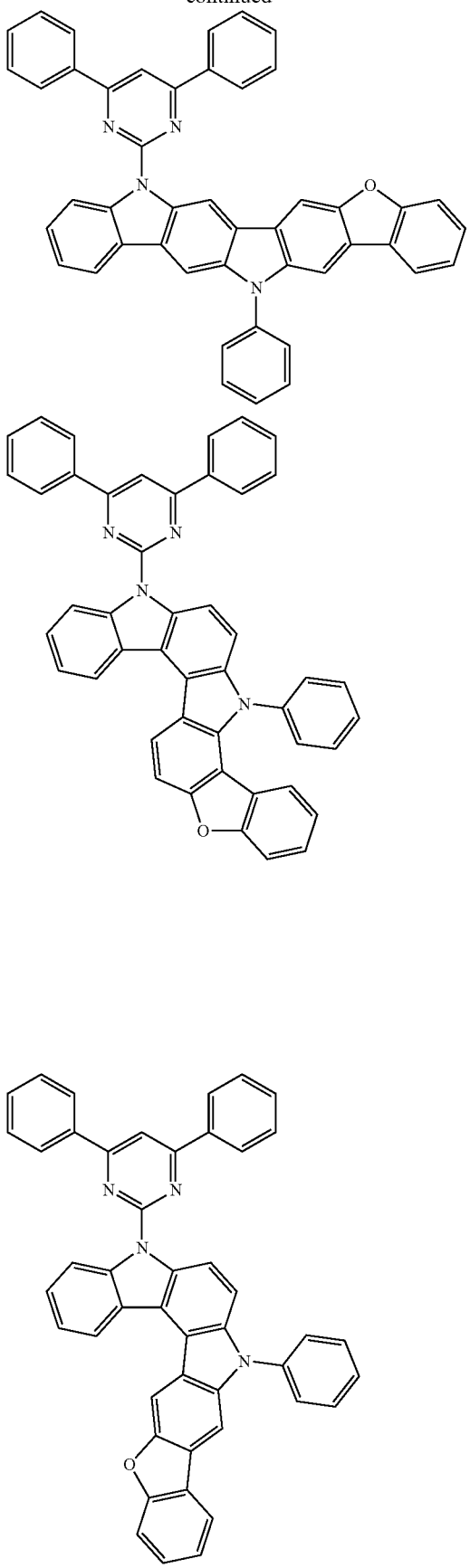
98
-continued
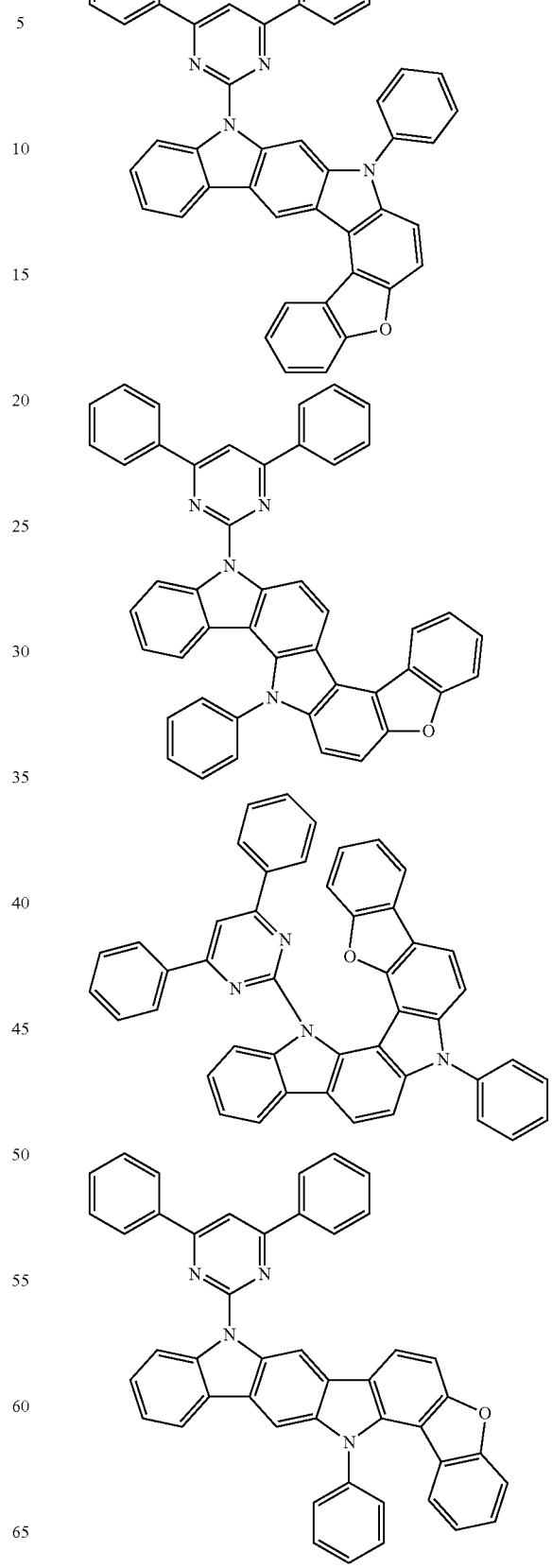

99
-continued
100
-continued
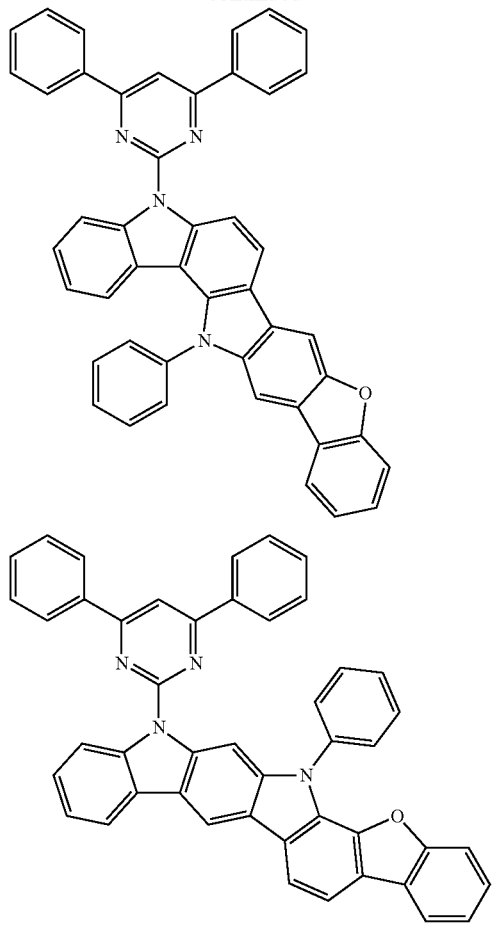
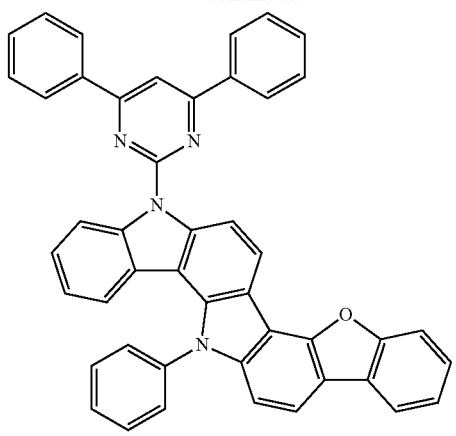
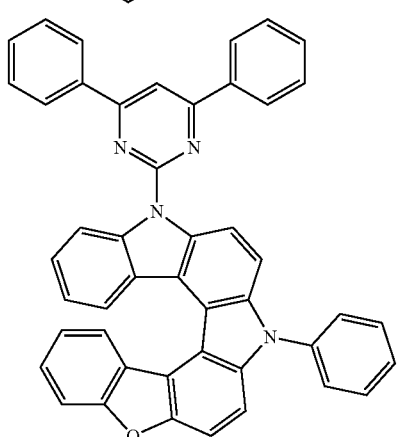
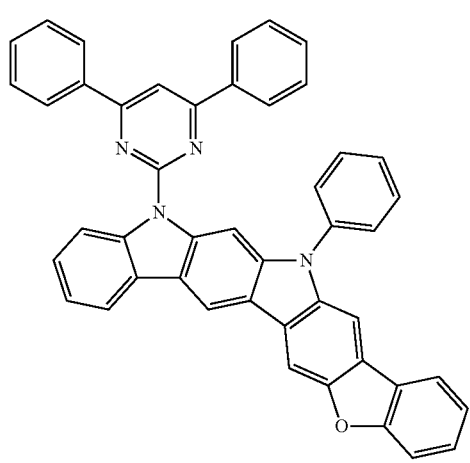
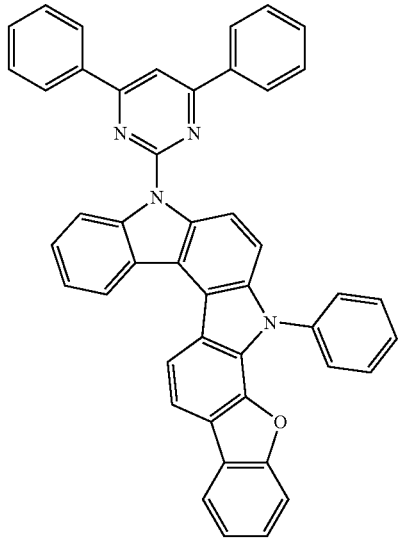

101
-continued
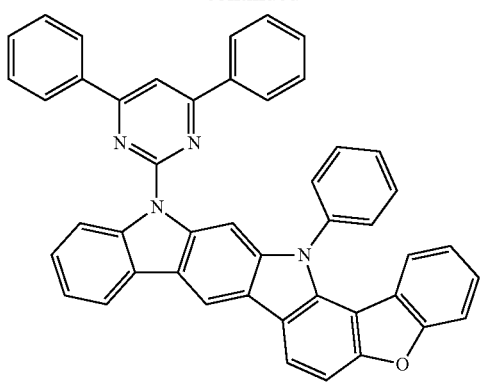
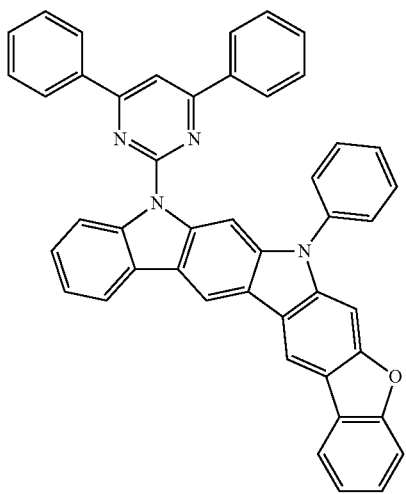
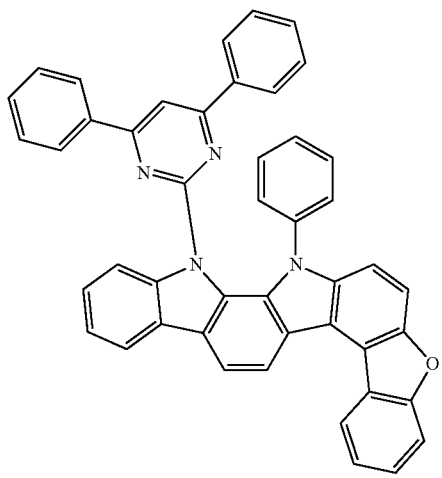
102
-continued
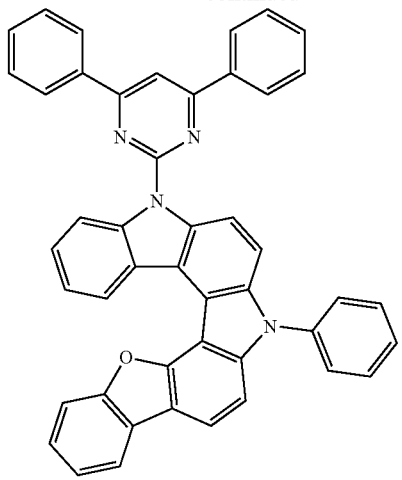
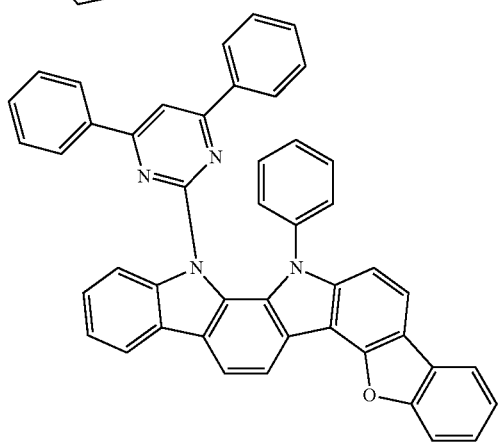
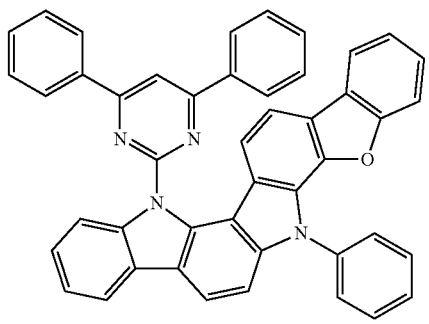
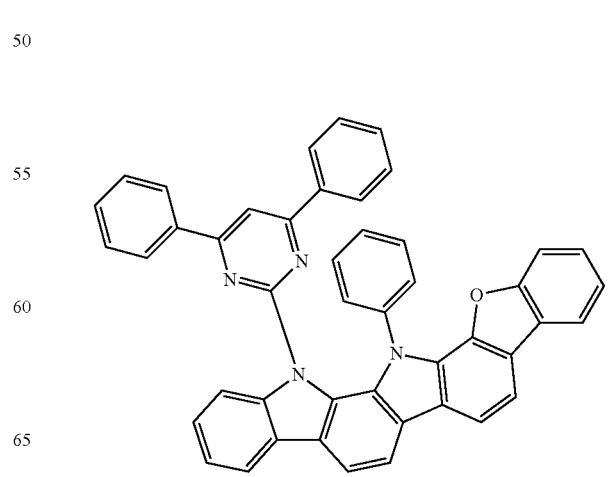

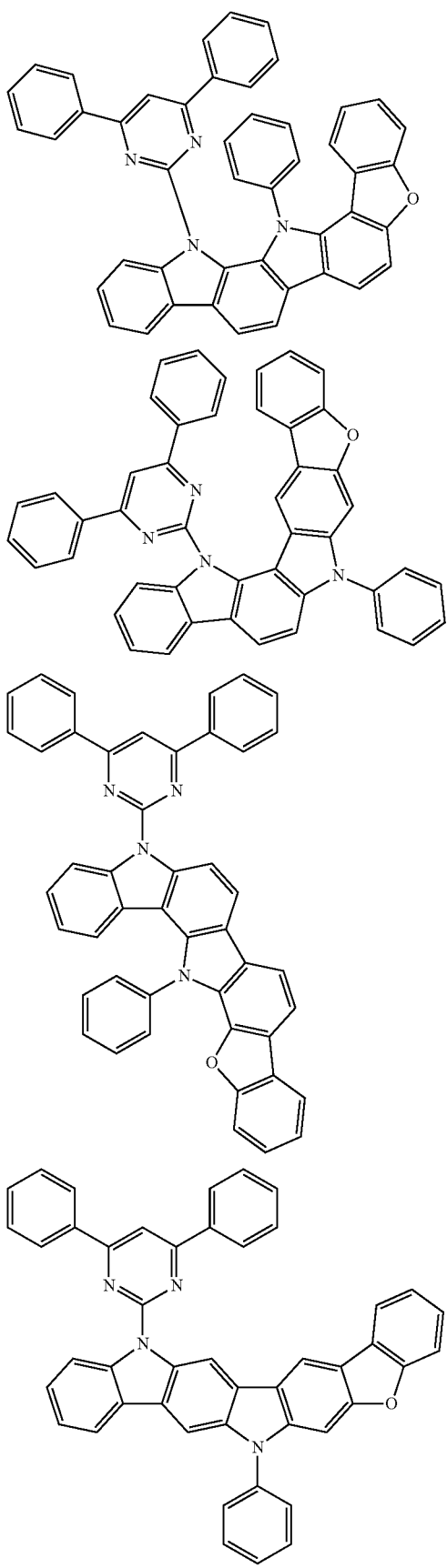
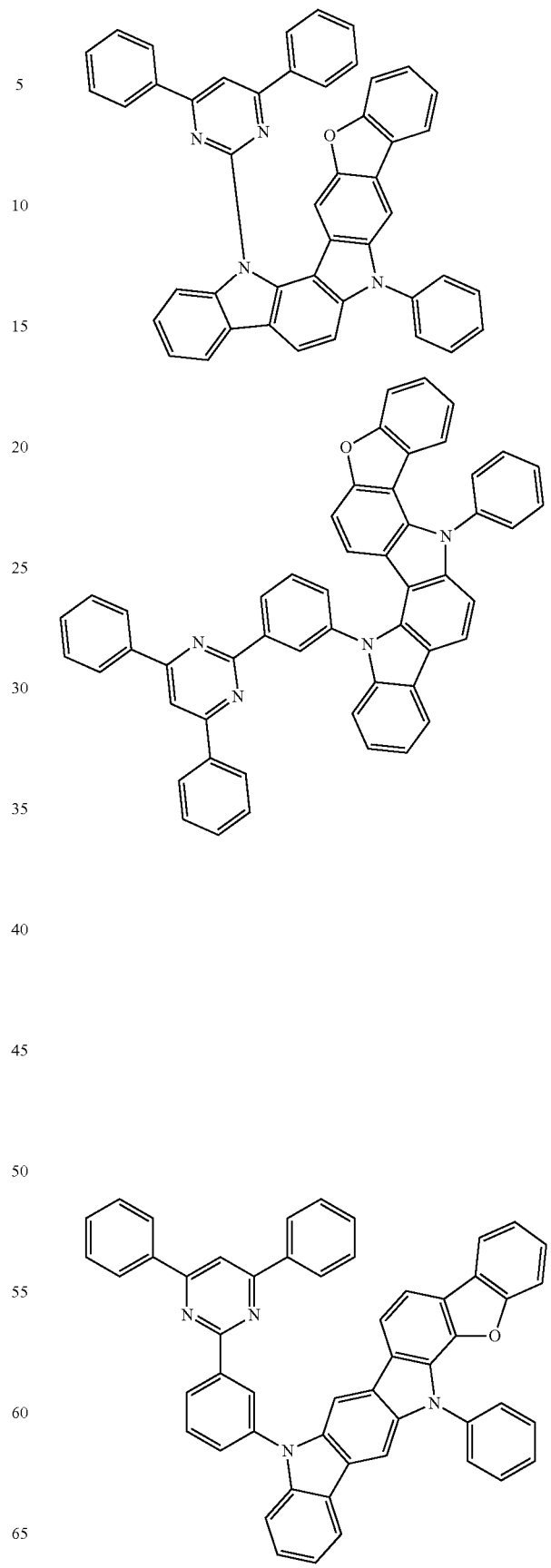

105
-continued
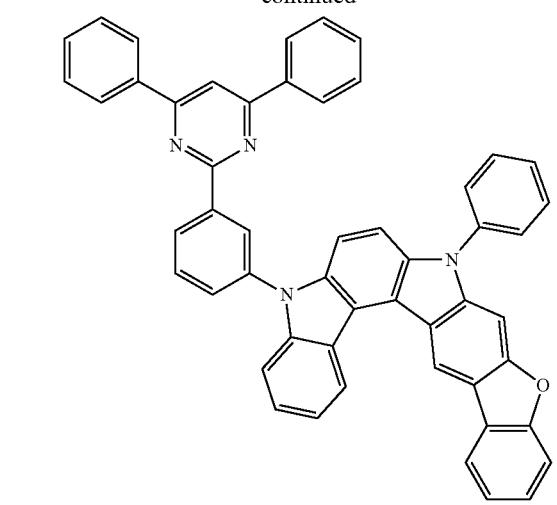
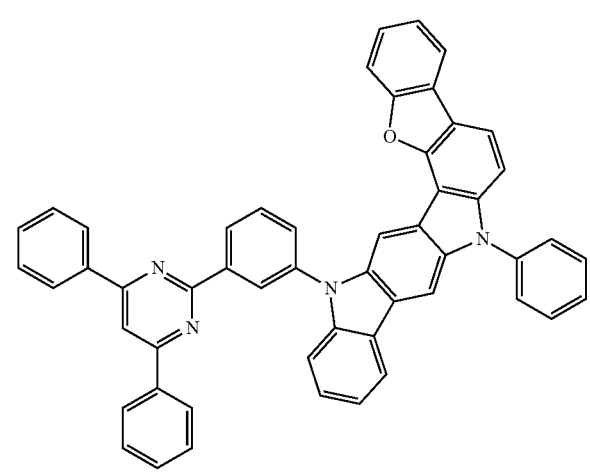
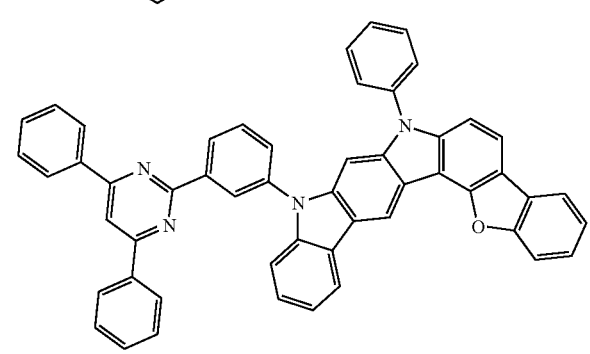
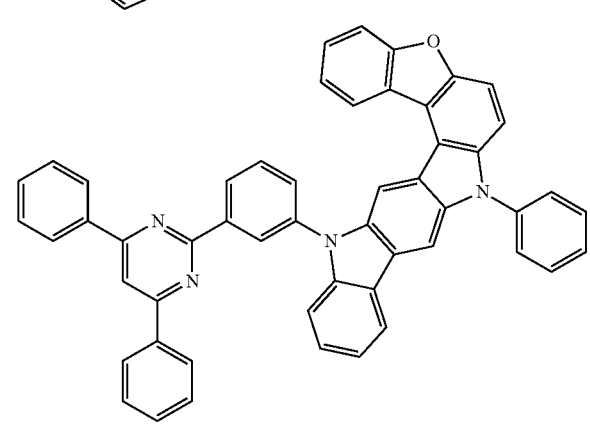
106
-continued
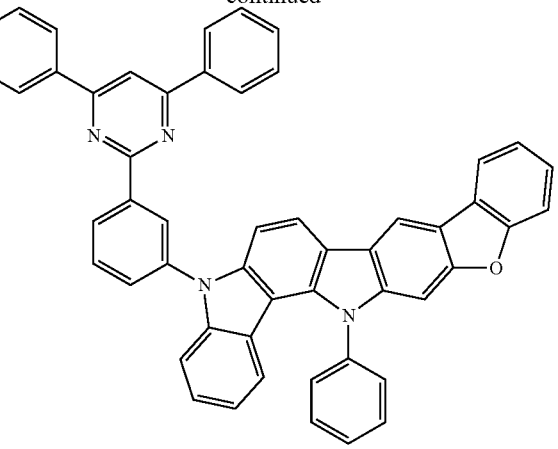
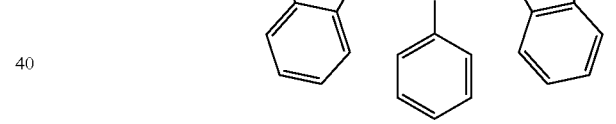
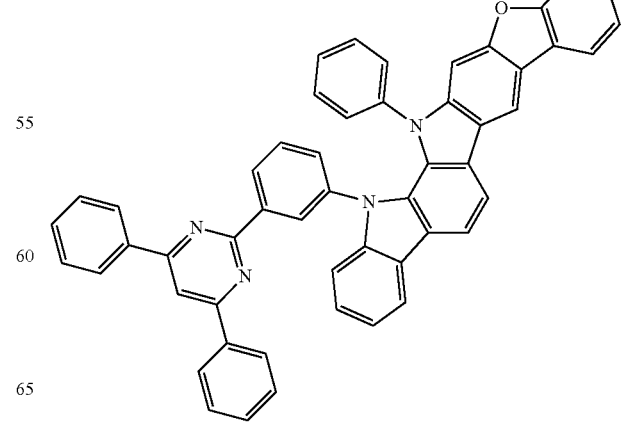

107
-continued
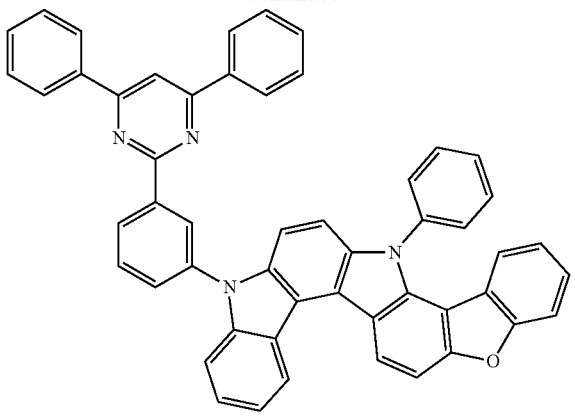
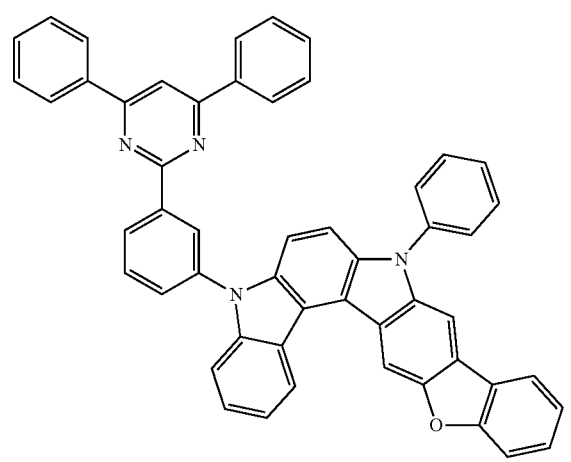
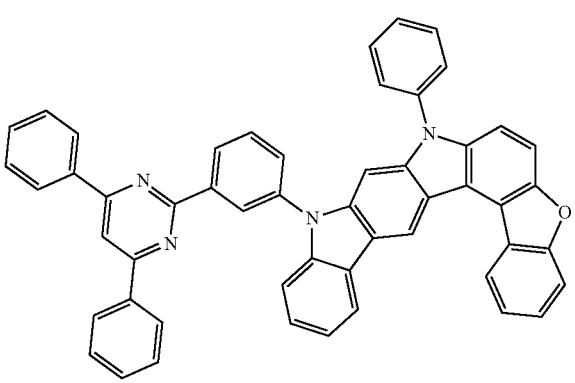
108
-continued
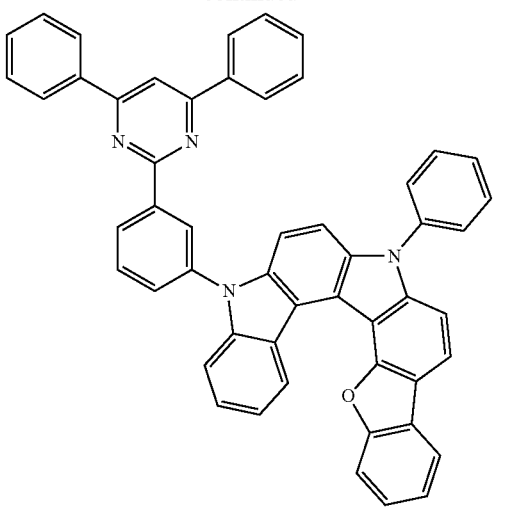
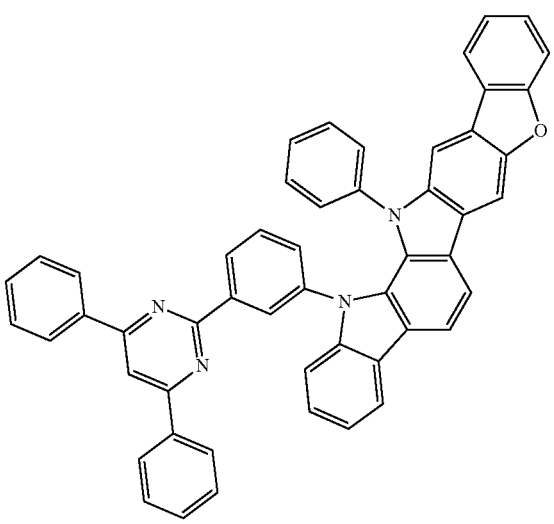
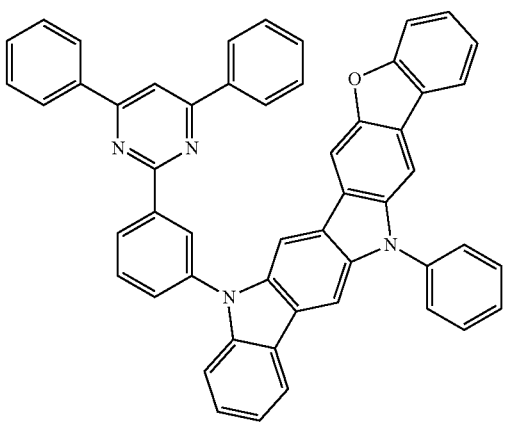

109
-continued
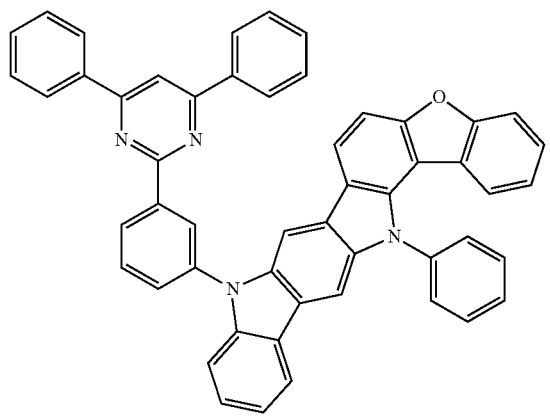
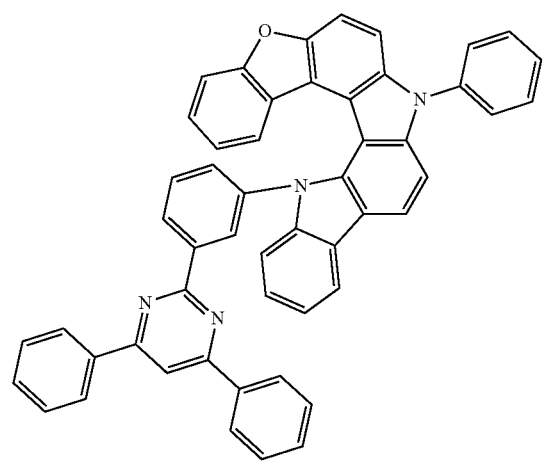
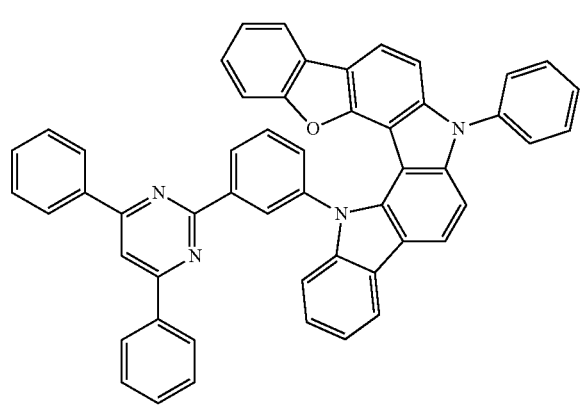
110
-continued
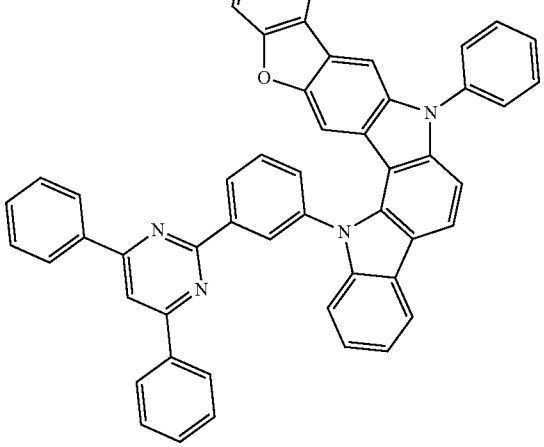
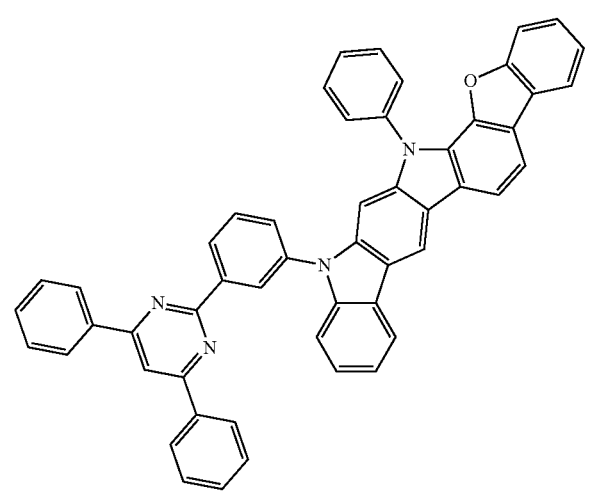
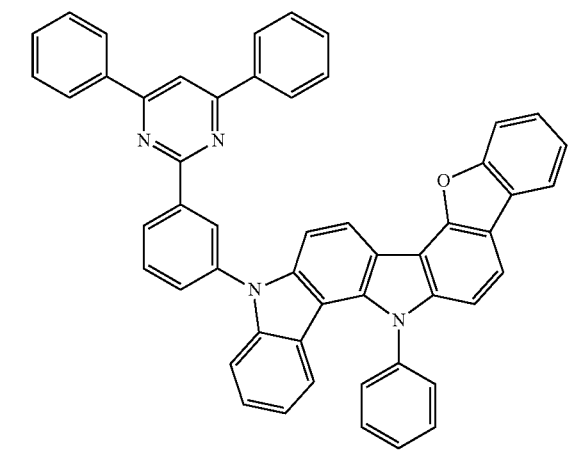

111
-continued
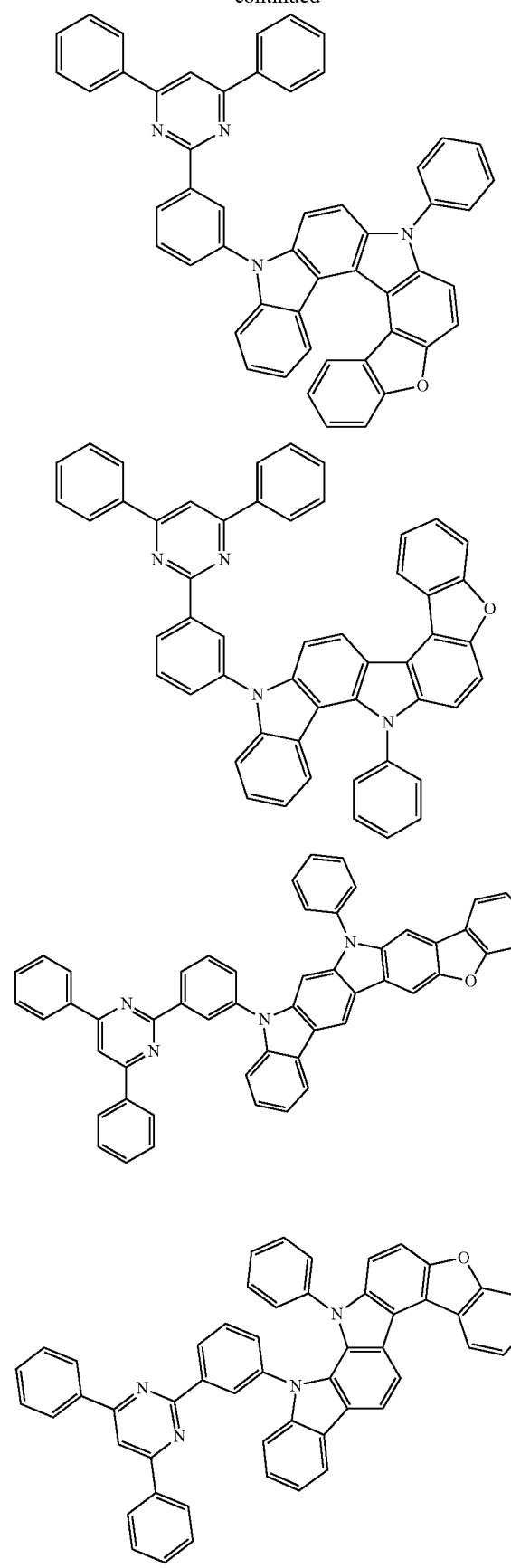
112
-continued
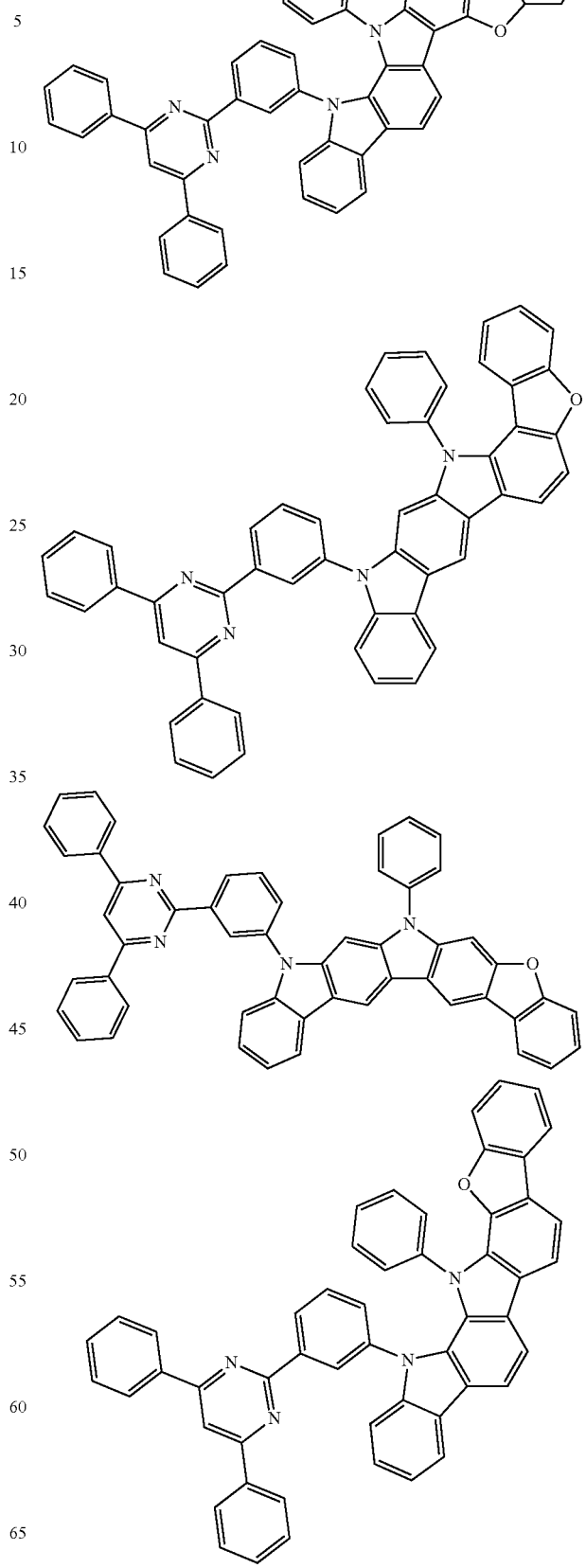

113
-continued
114
-continued
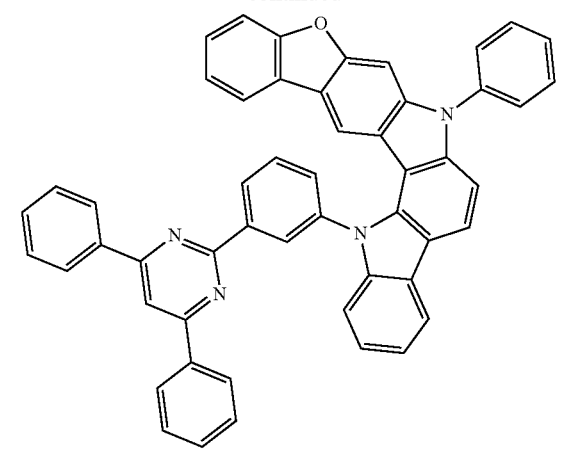
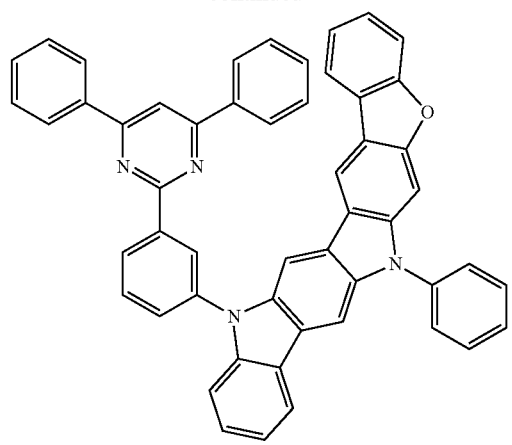
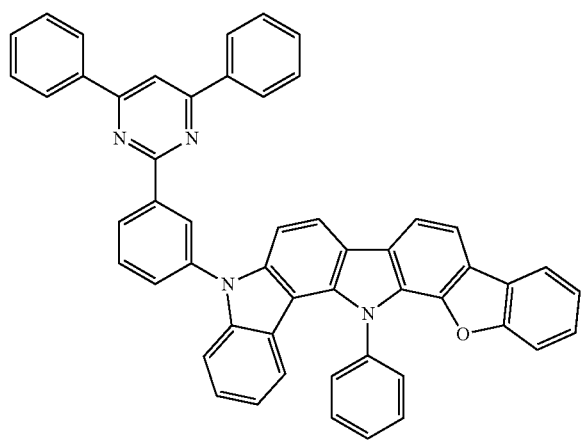
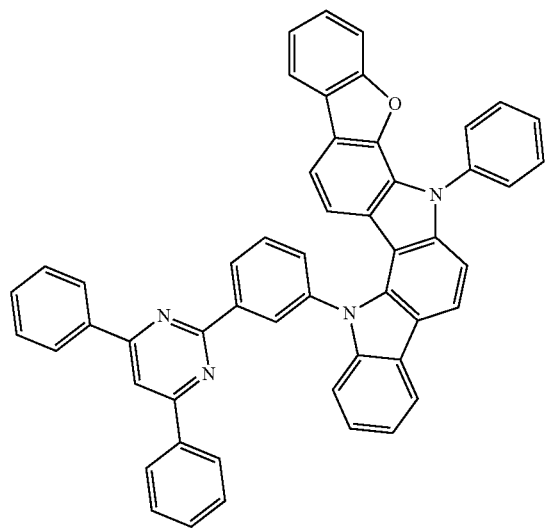
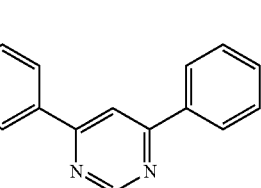
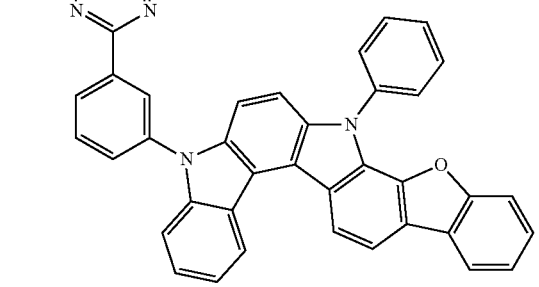

115
-continued
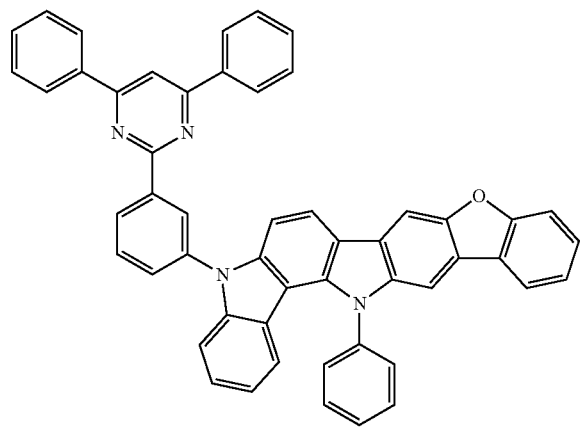
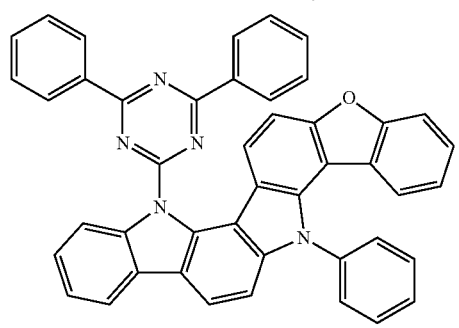
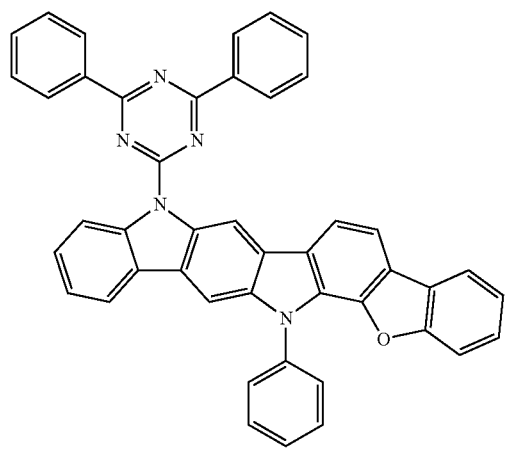
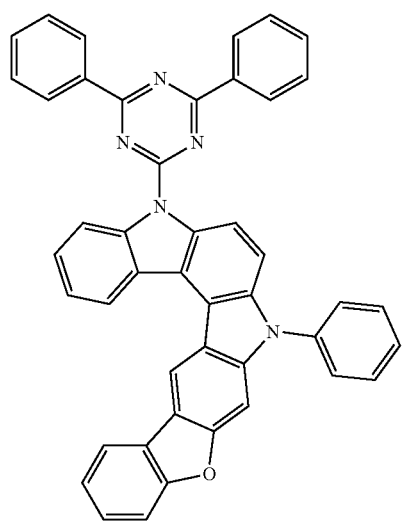
116
-continued
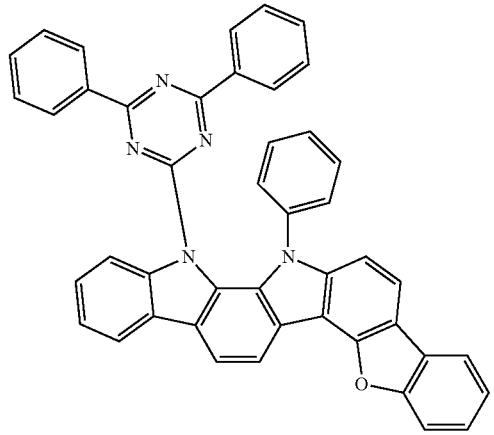
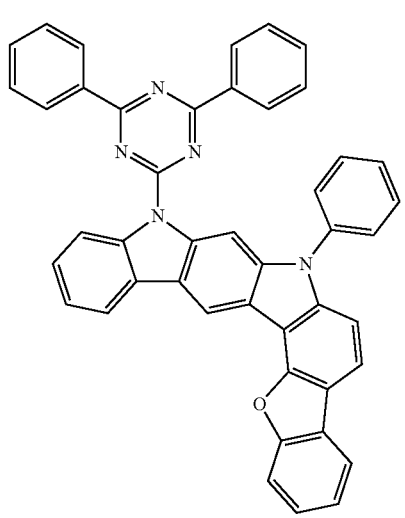
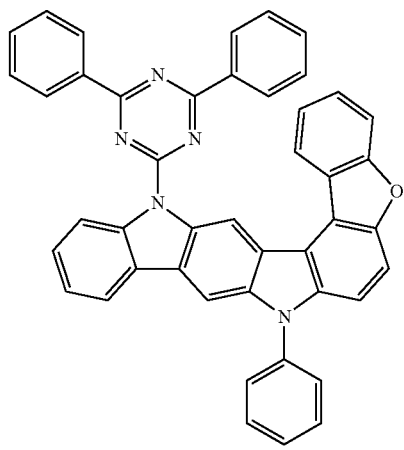

117
-continued
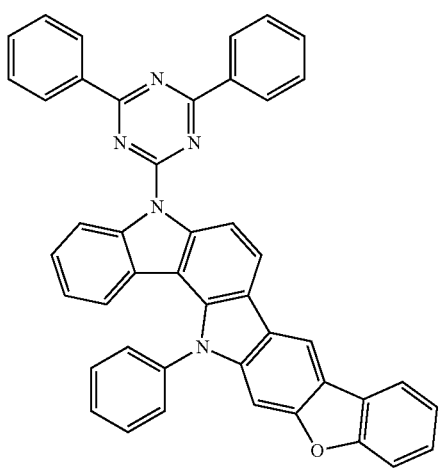
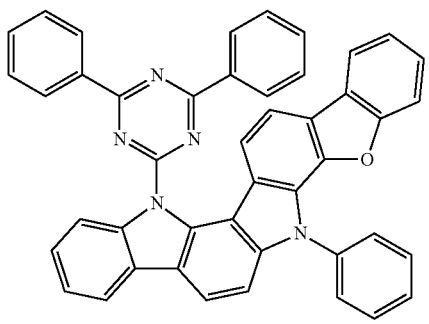
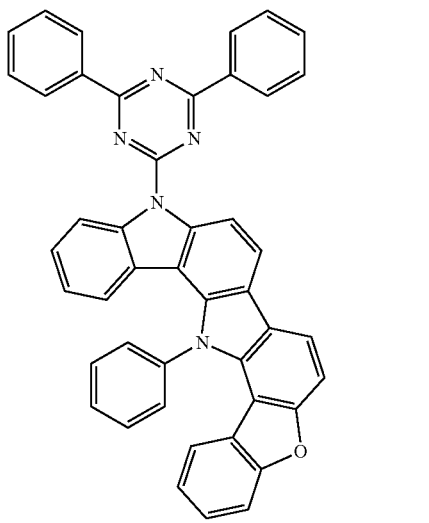
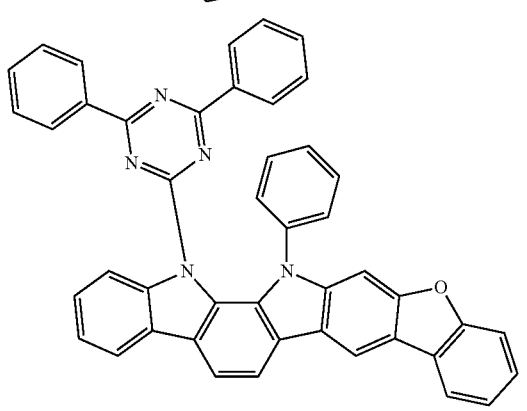
118
-continued
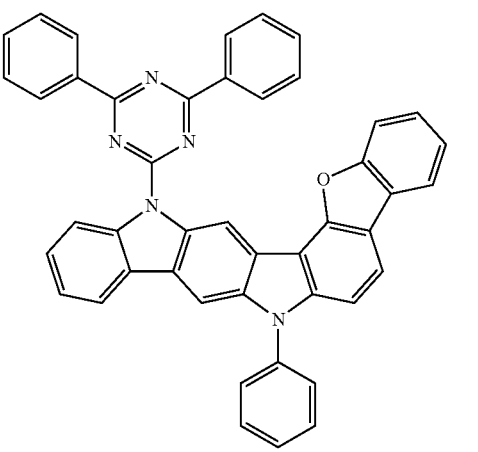
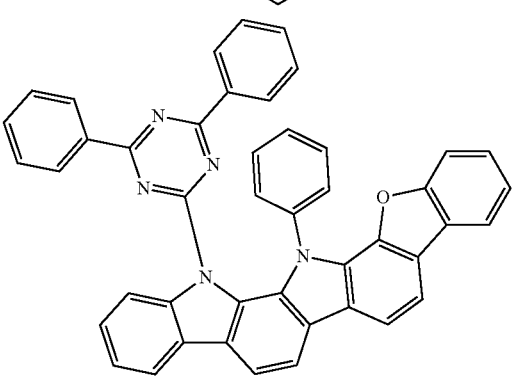
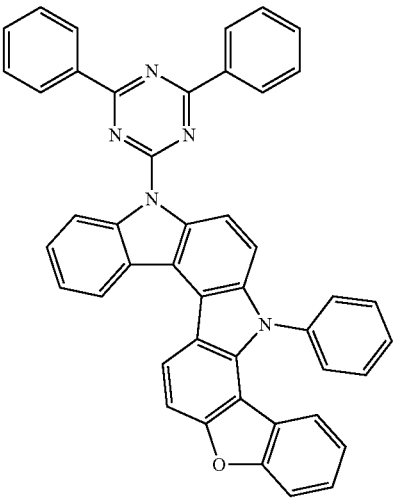

-continued
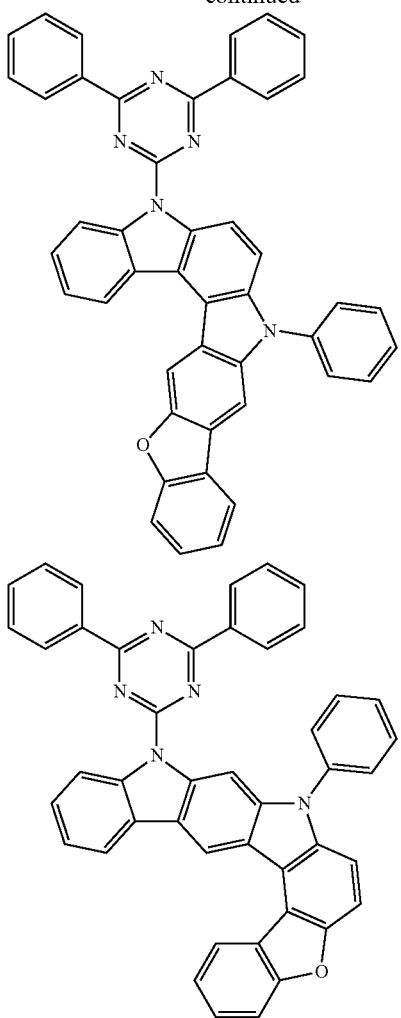
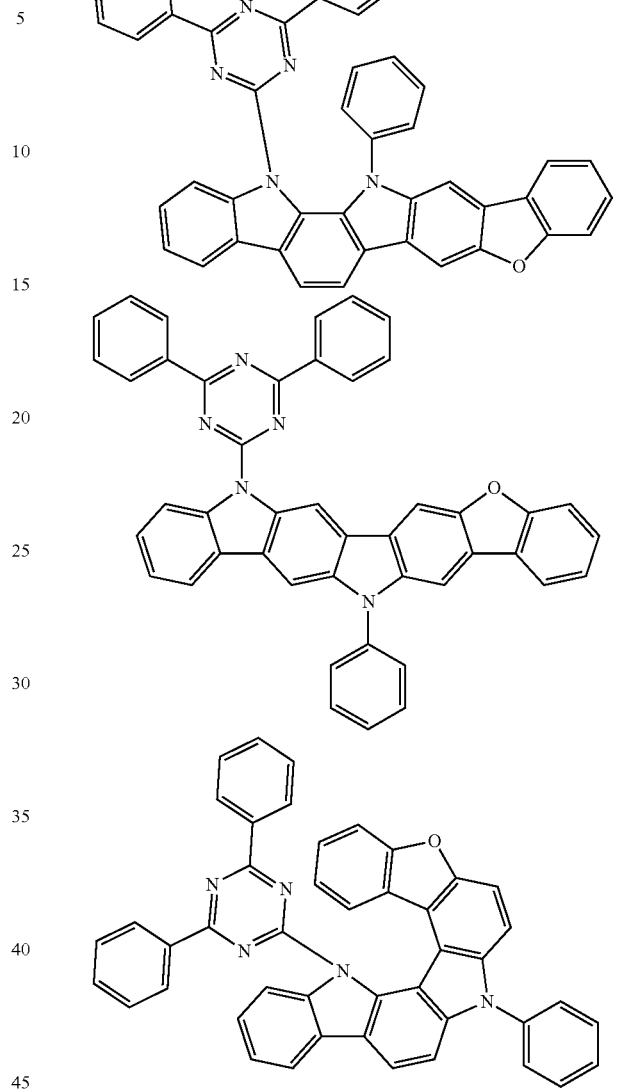
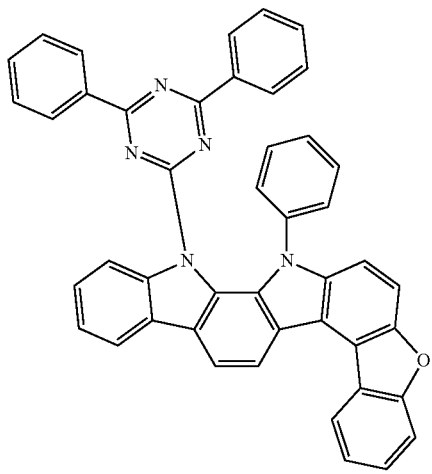
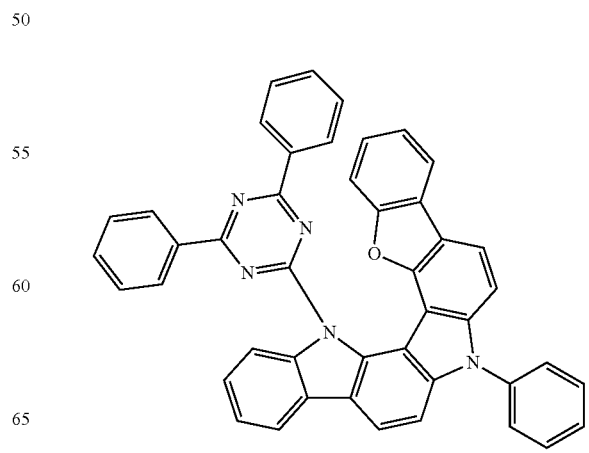

121
-continued
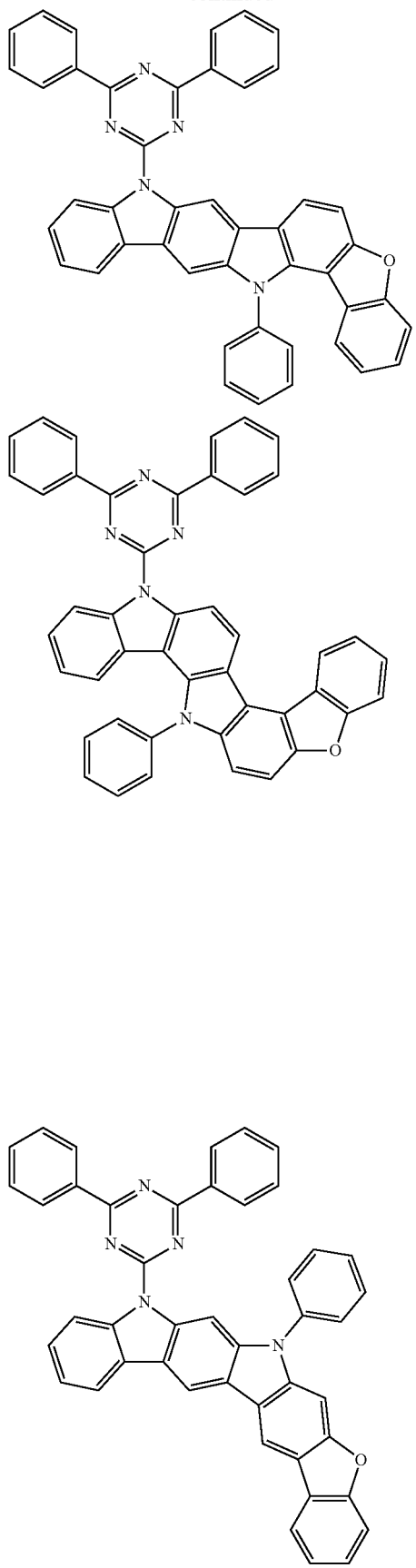
122
-continued
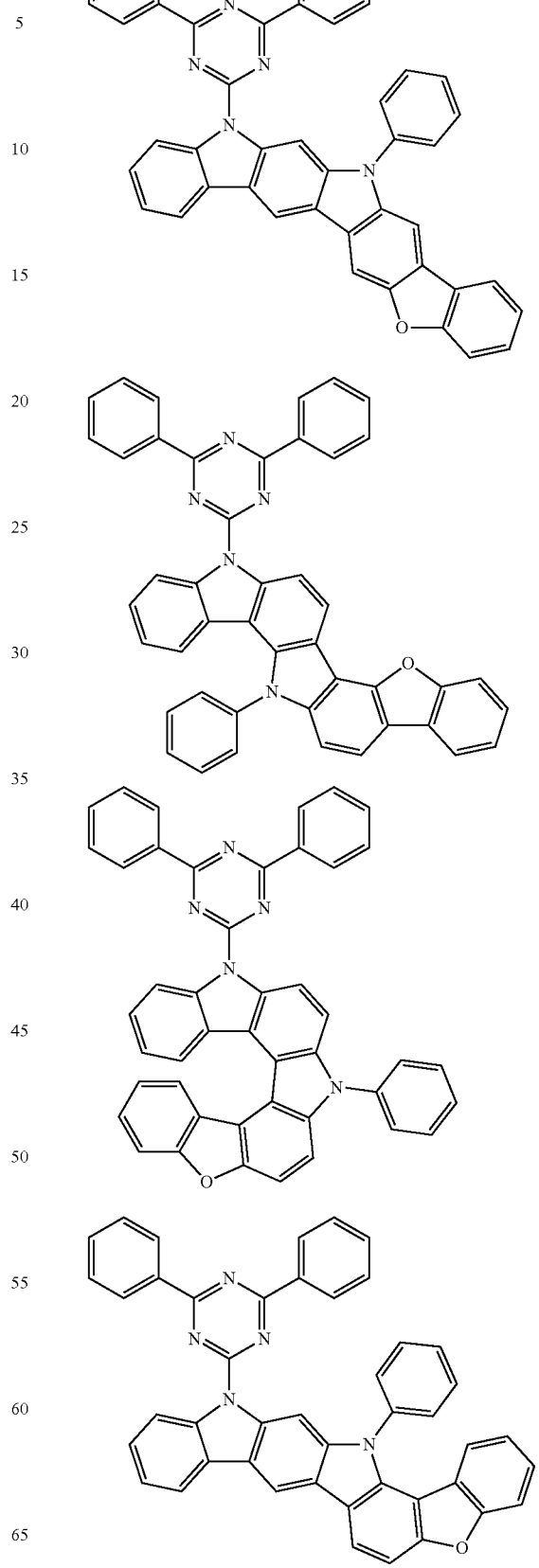

123
-continued
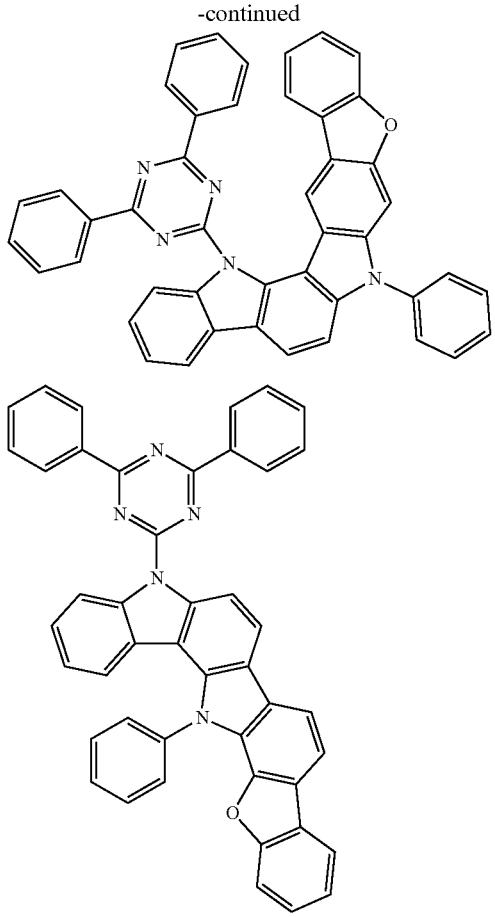
124
-continued
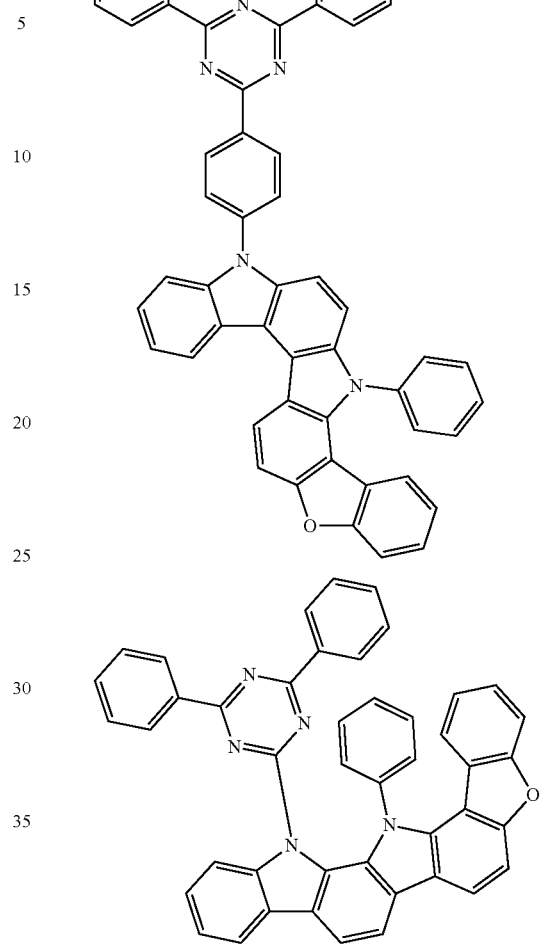
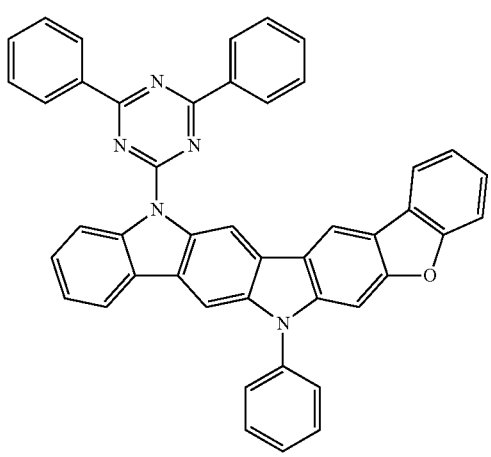
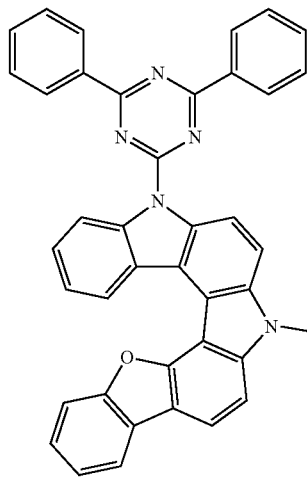

125
-continued
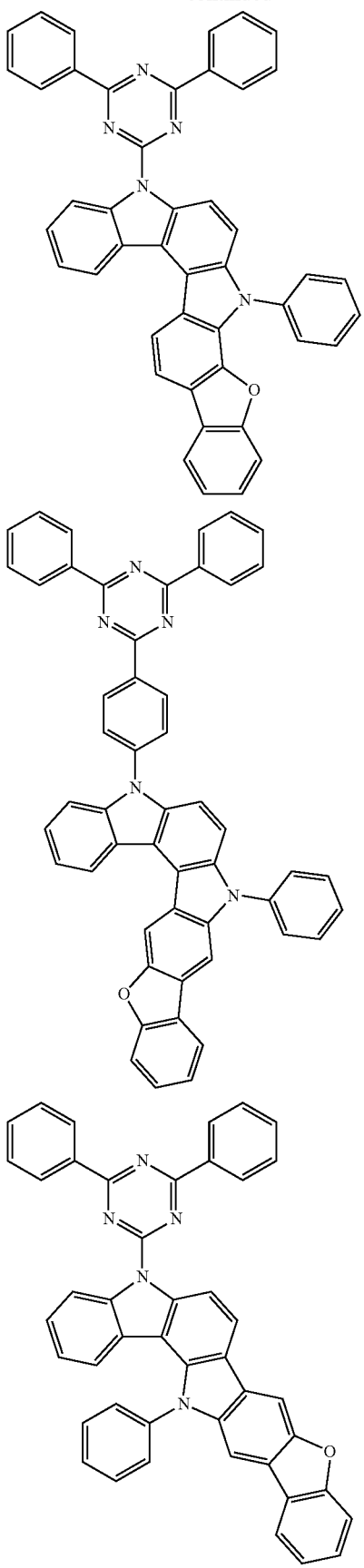
126
-continued
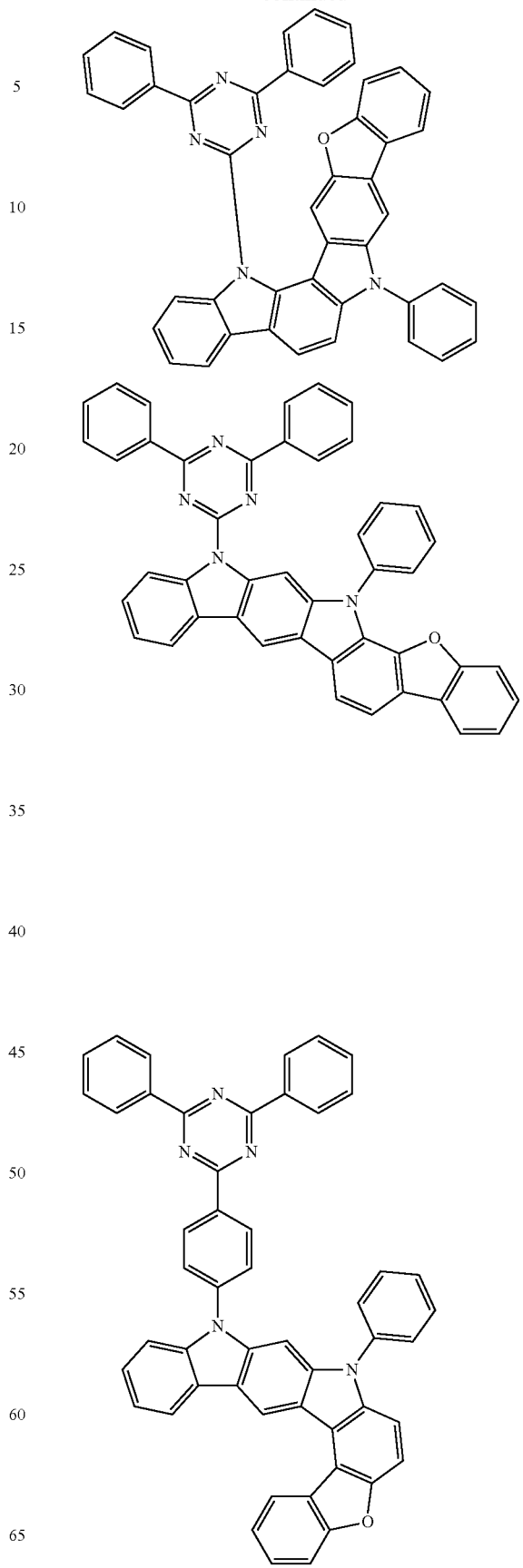

127
-continued
128
-continued
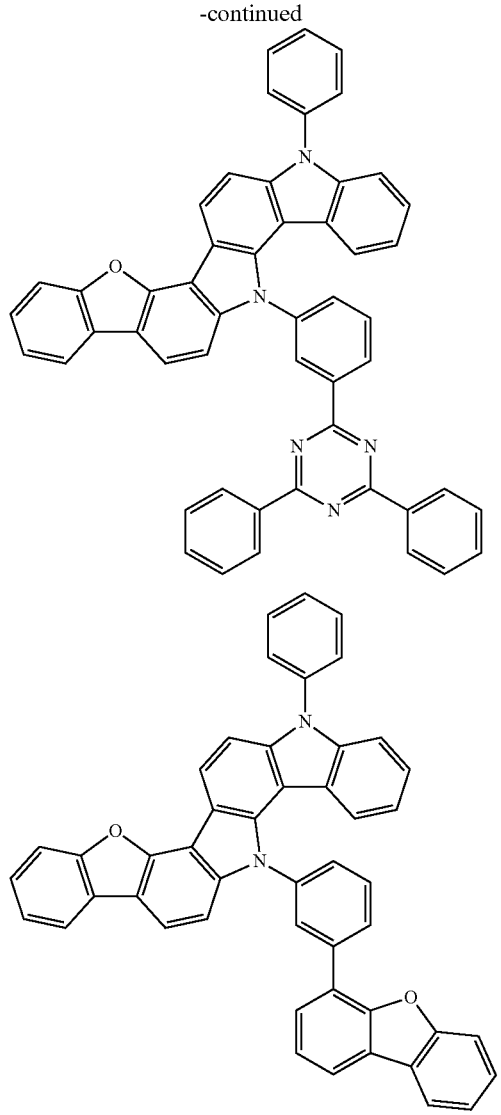
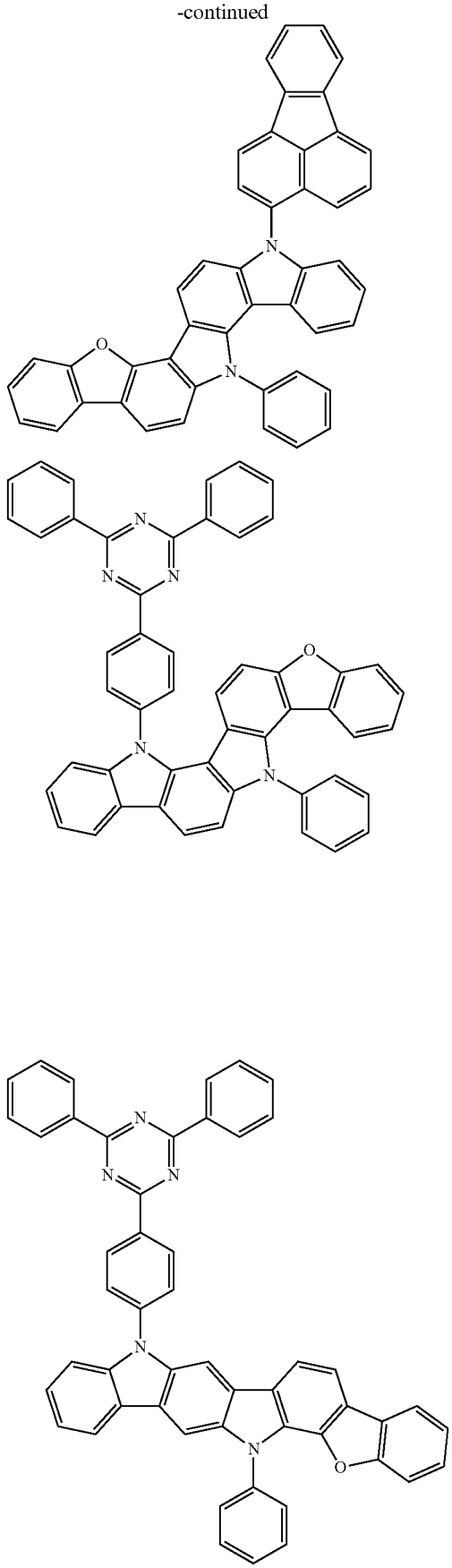

129
-continued
130
-continued
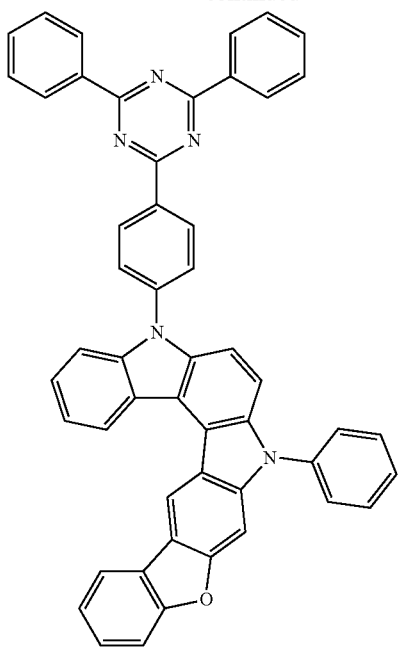
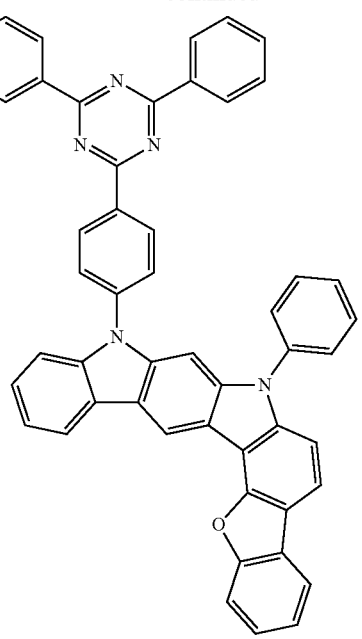
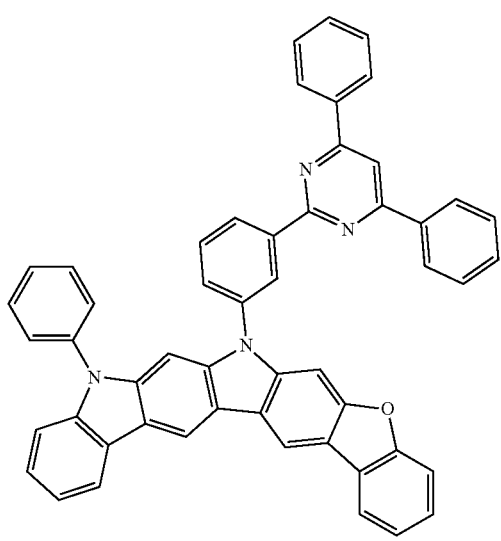

131
-continued
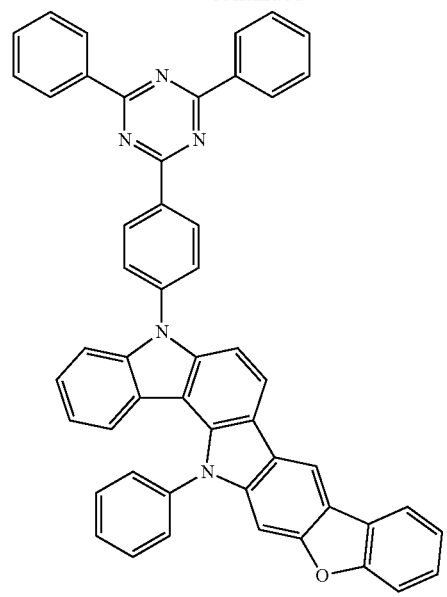
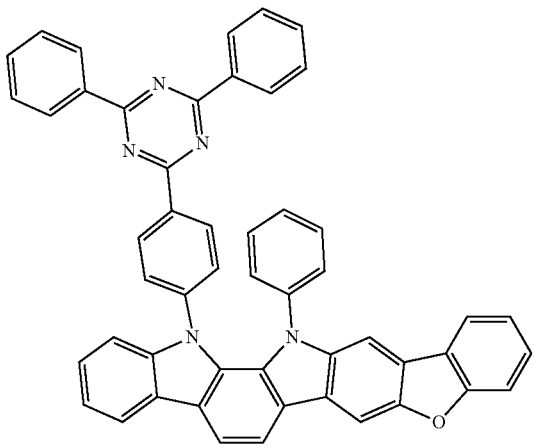
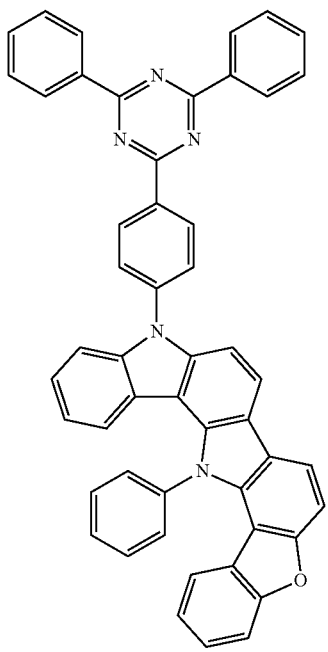
132
-continued
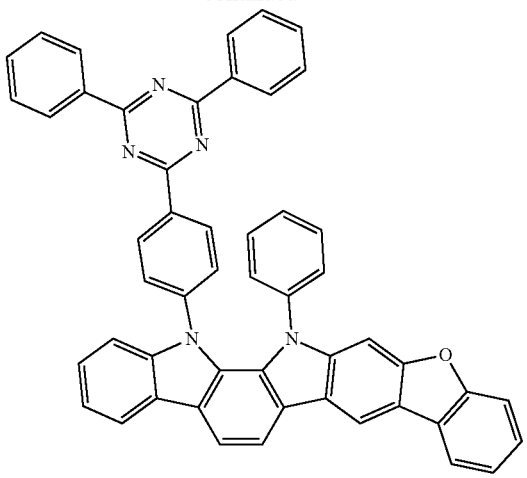
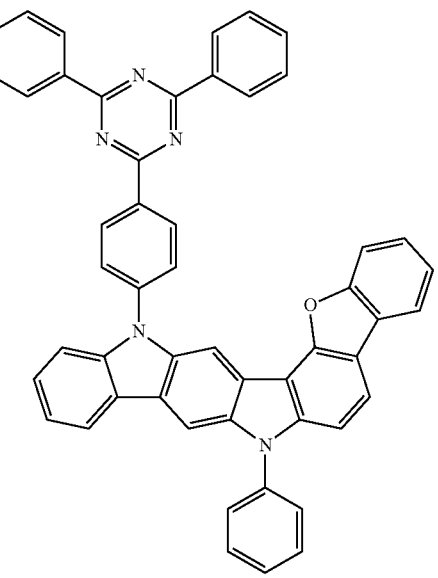
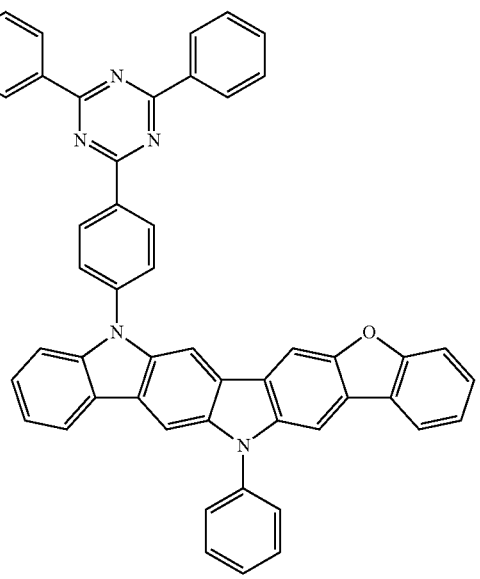

133
-continued
134
-continued
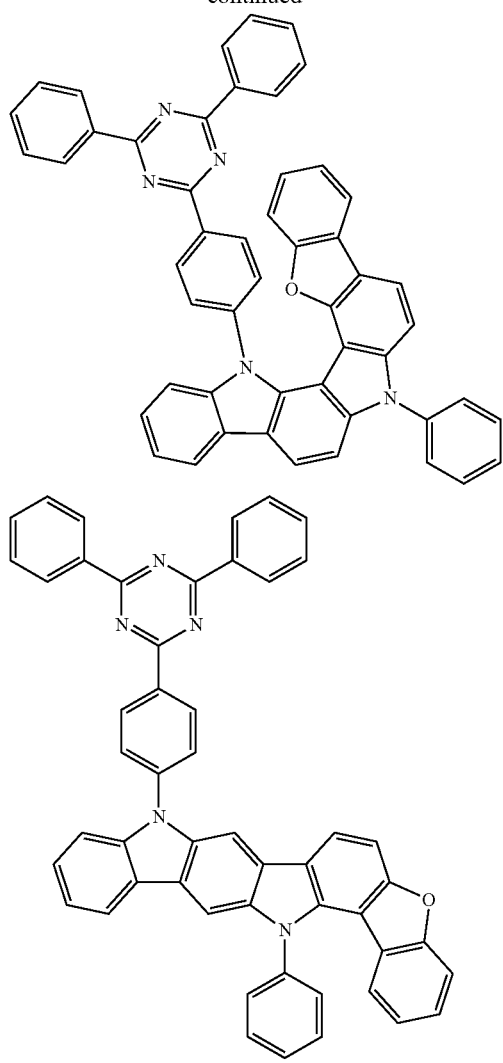
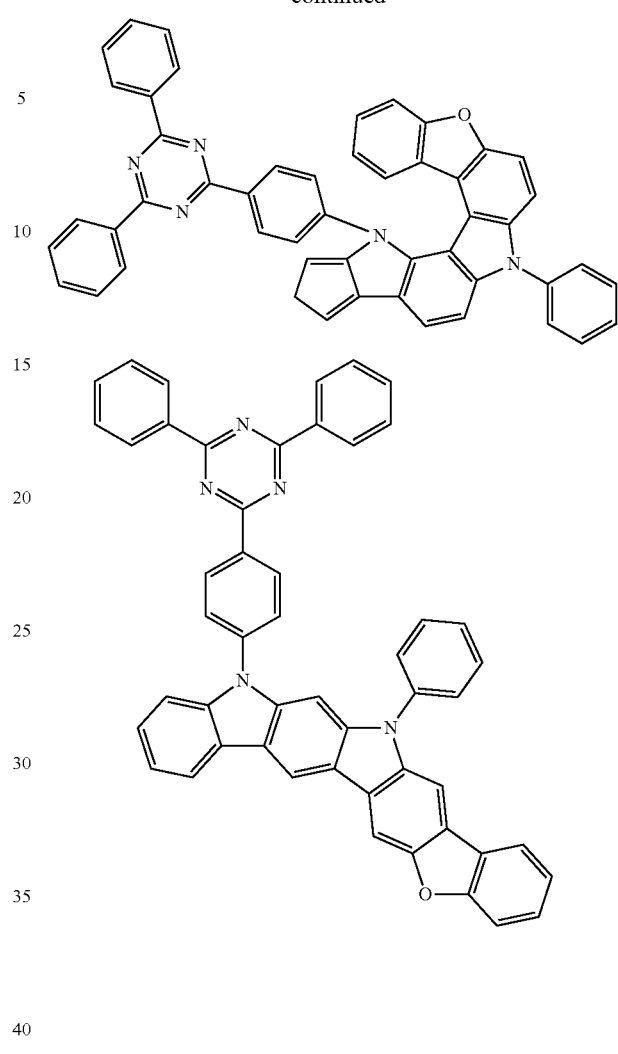
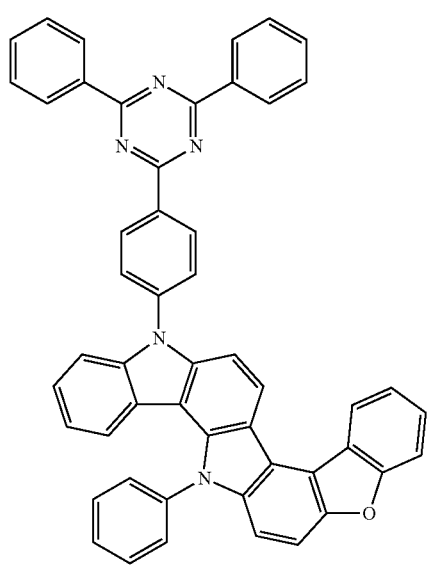
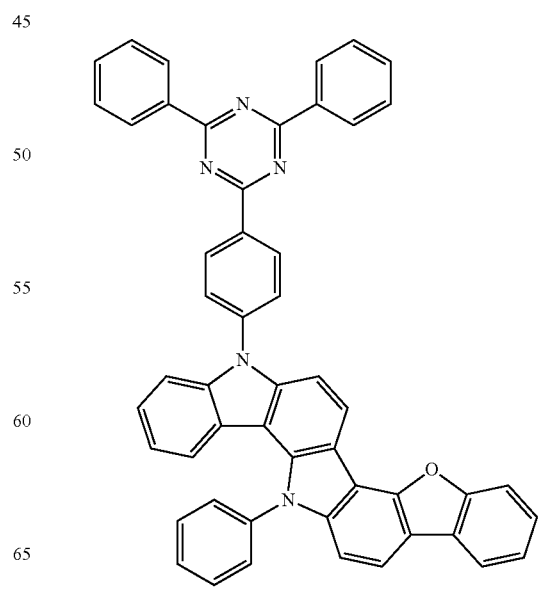

135
-continued
136
-continued
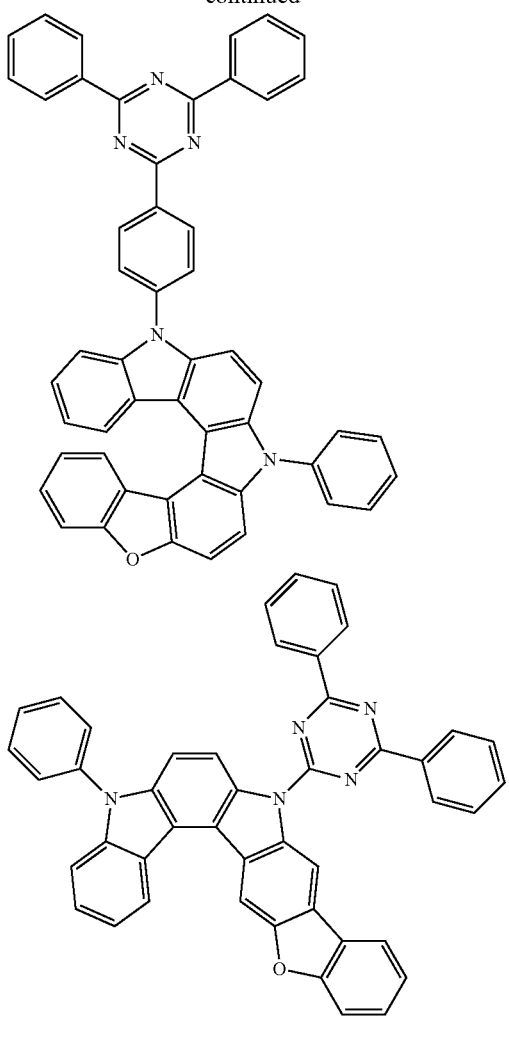
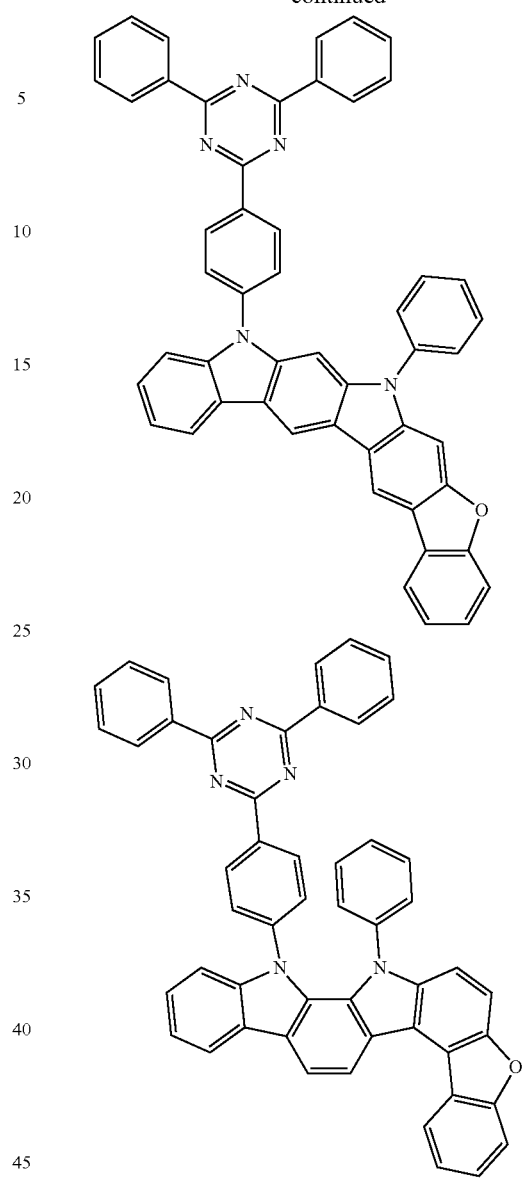
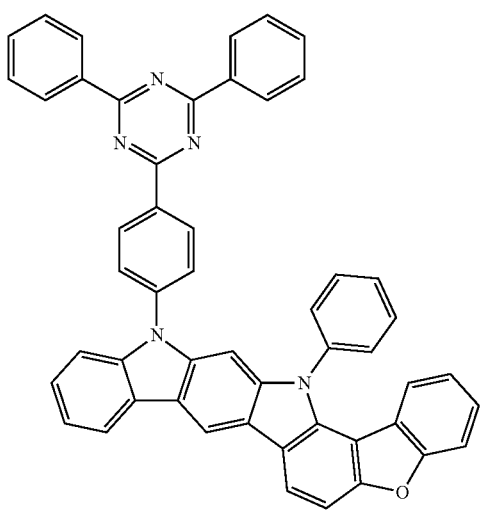
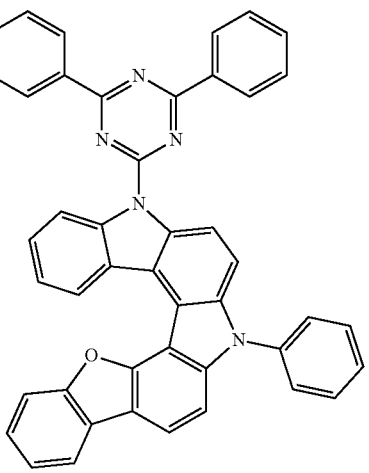

137
-continued
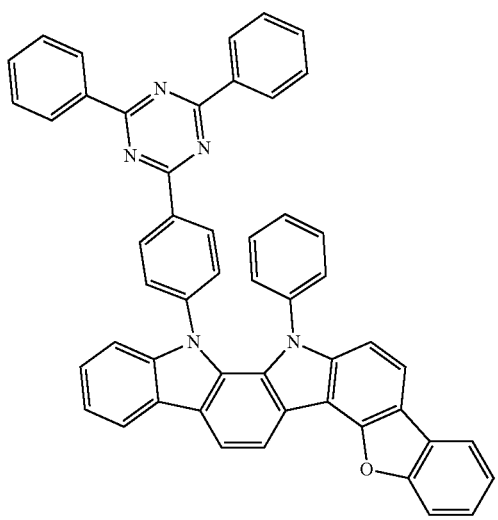
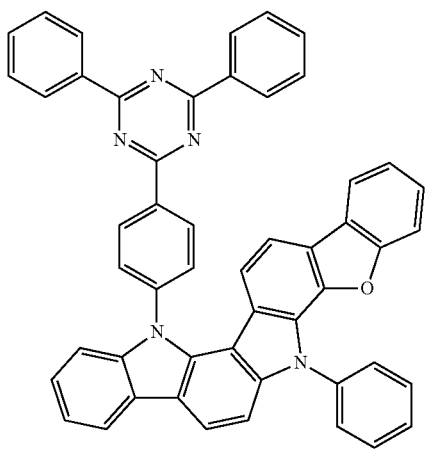
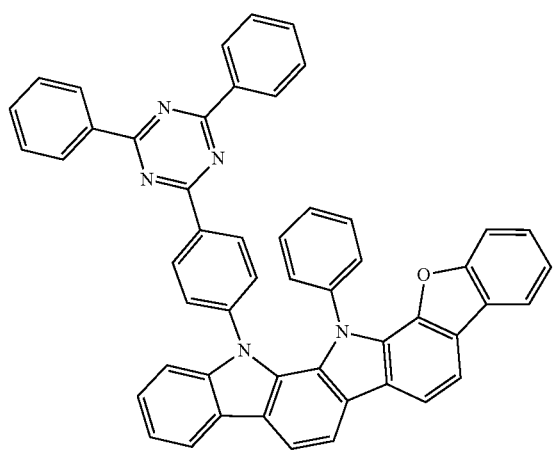
138
-continued
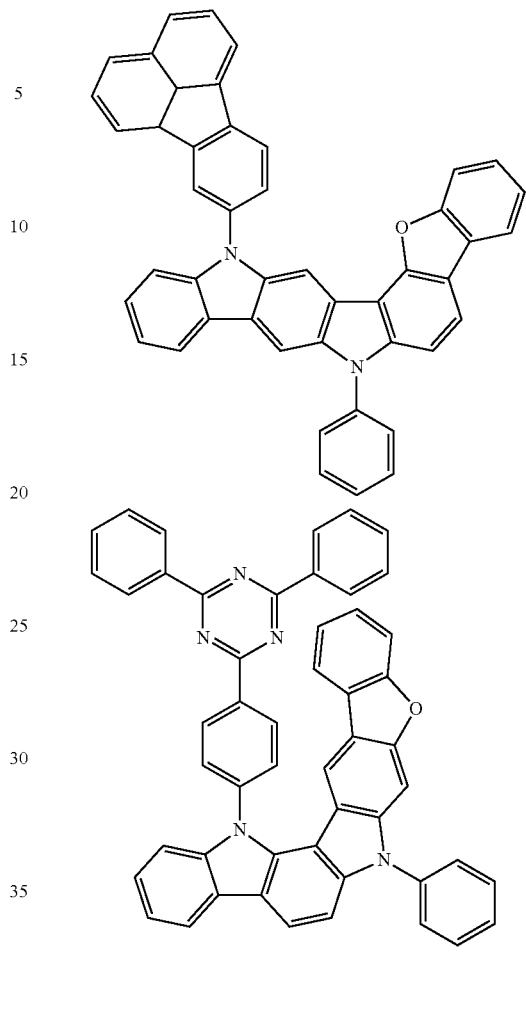
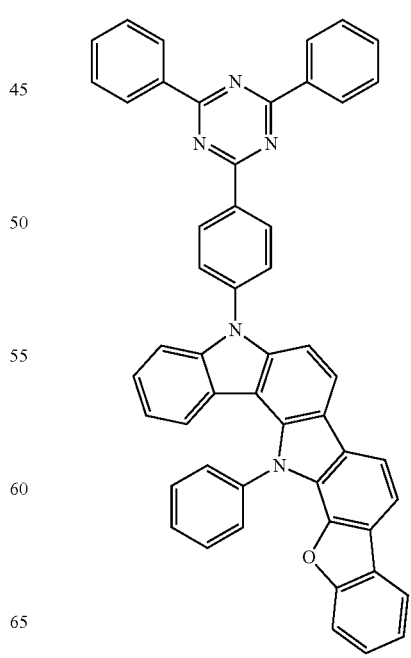

139
-continued
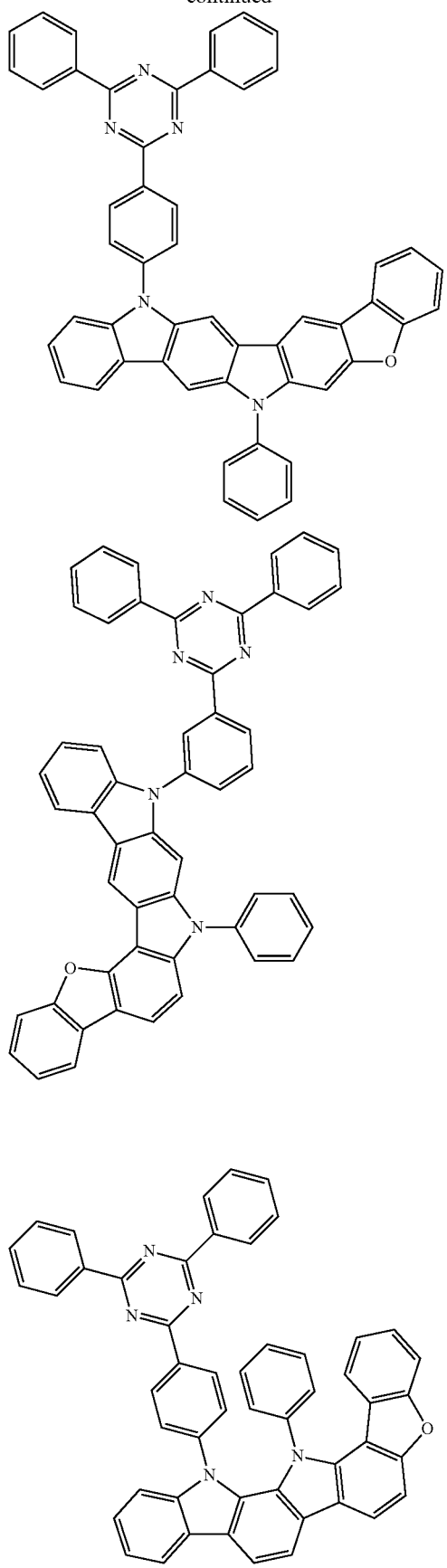
140
-continued
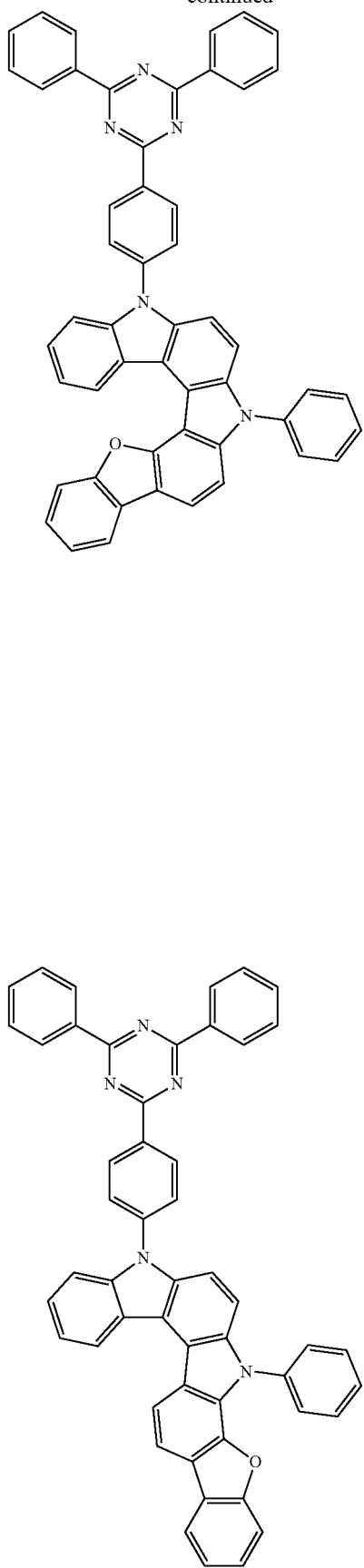

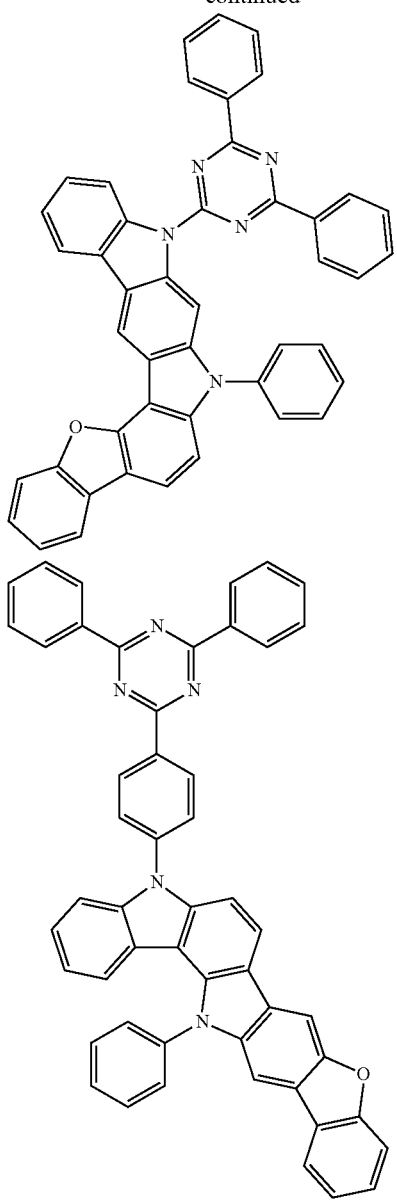
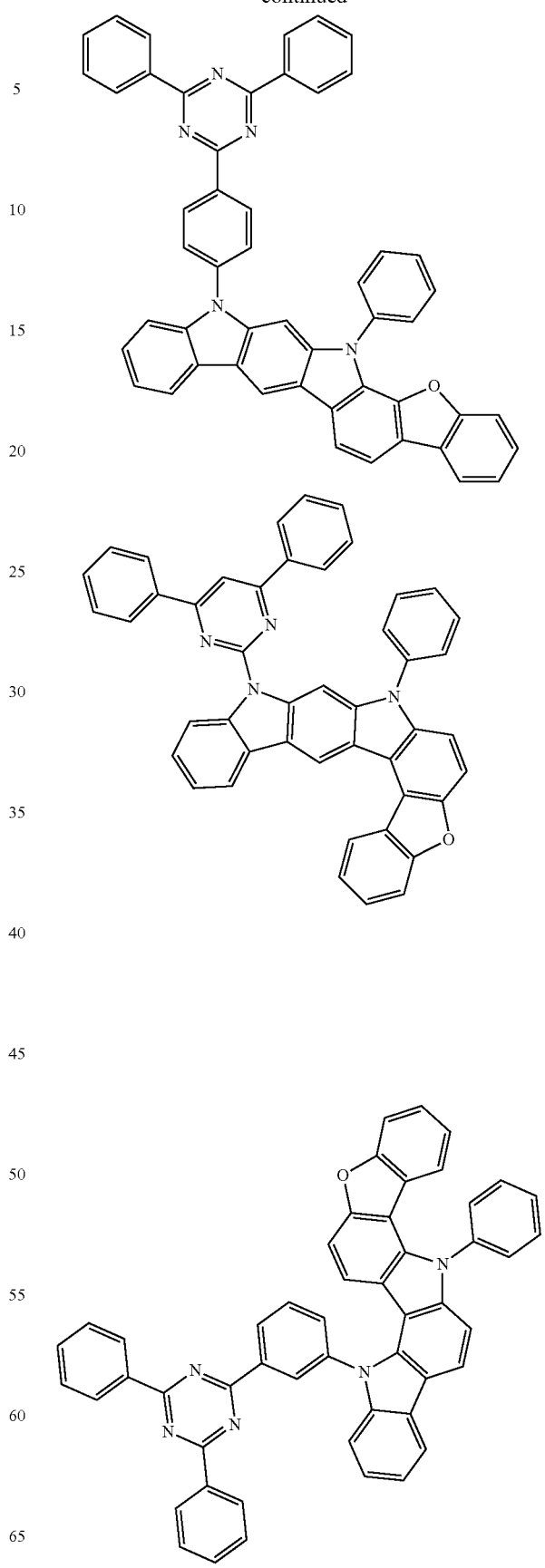

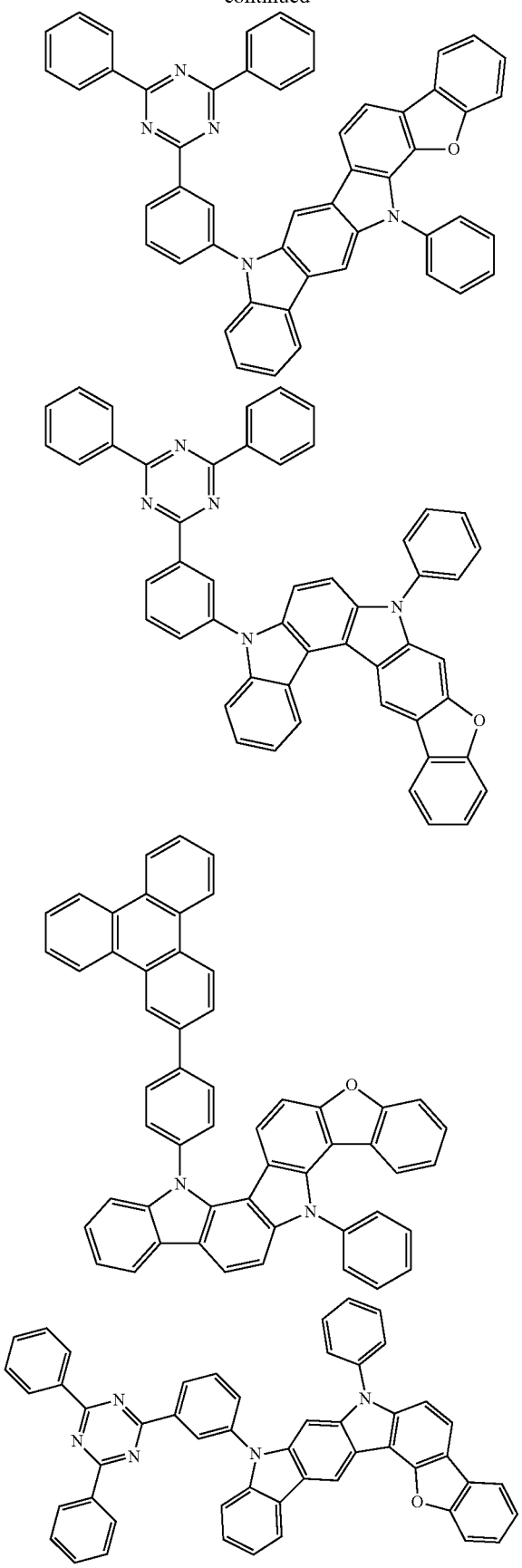

145
-continued
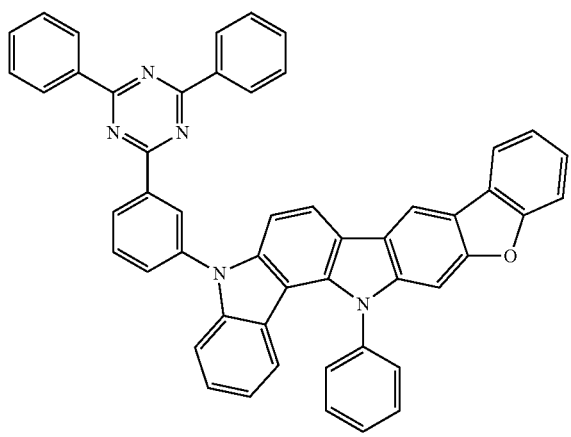
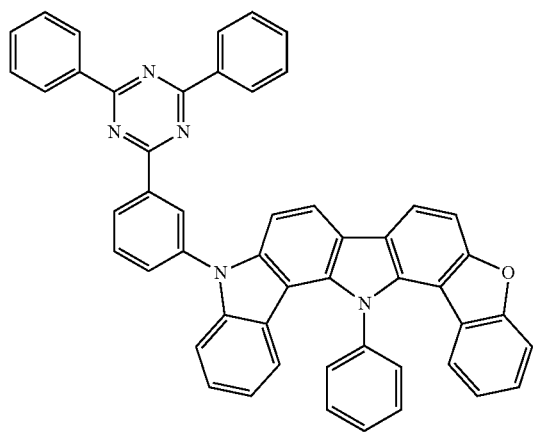
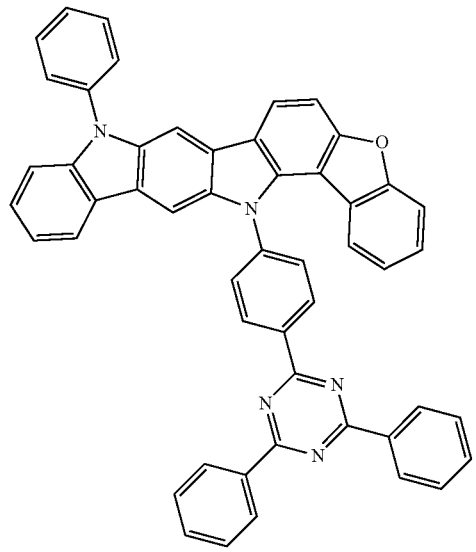
146
-continued
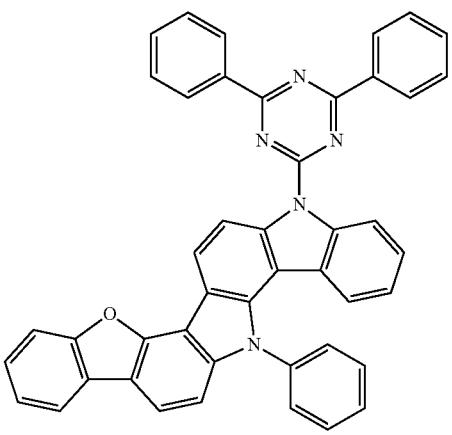
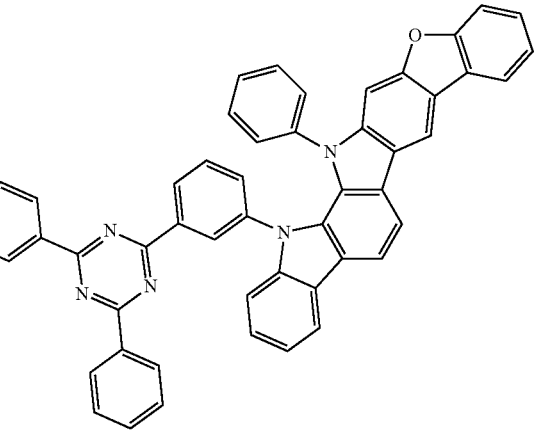
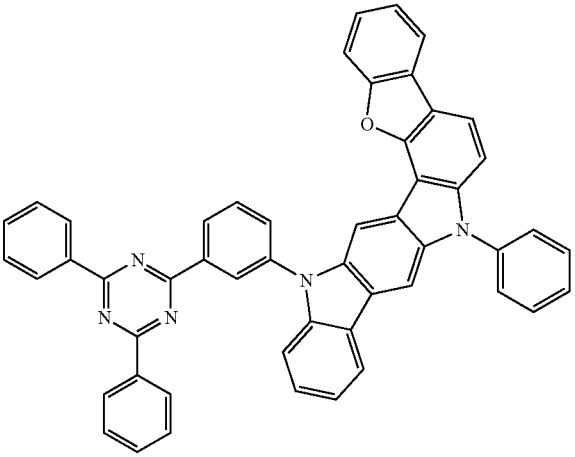

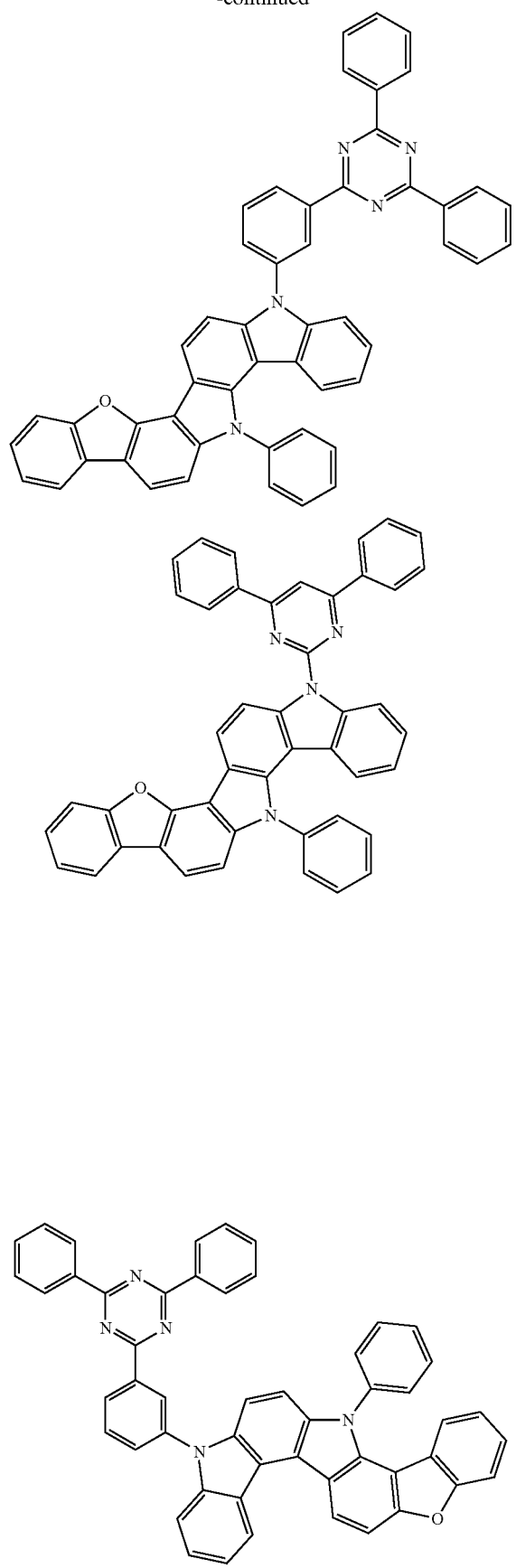
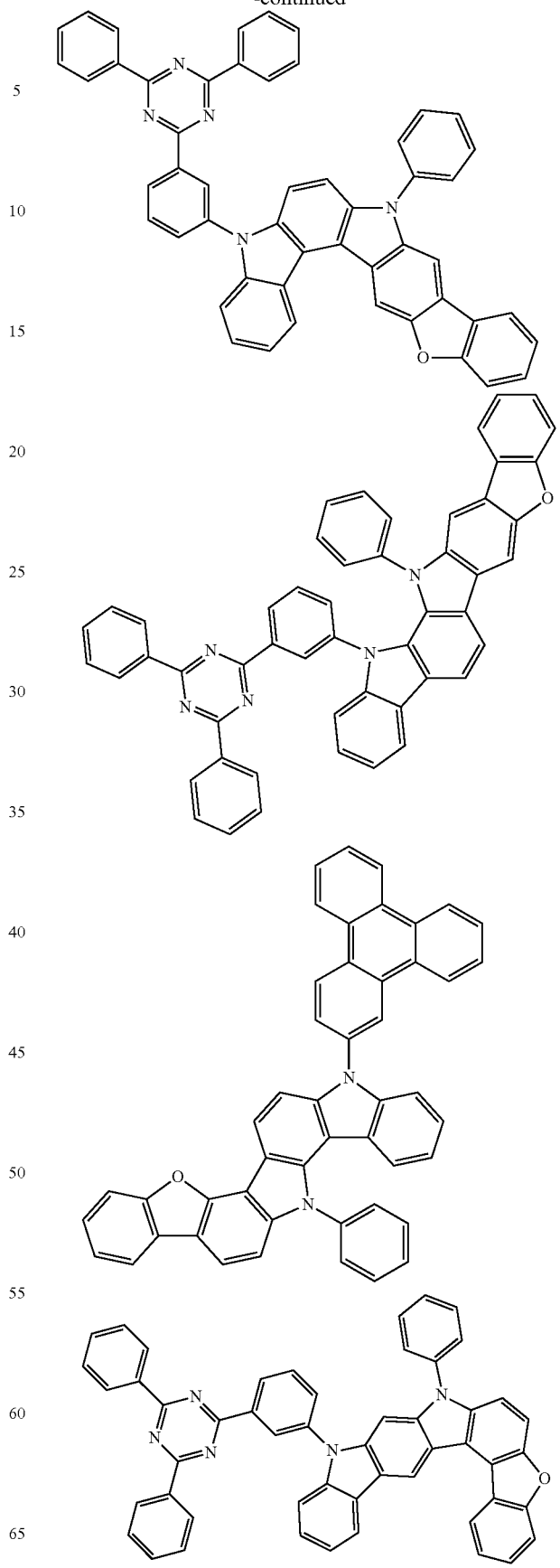

149
-continued
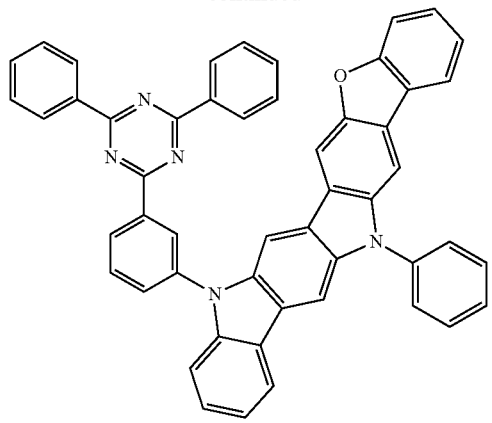
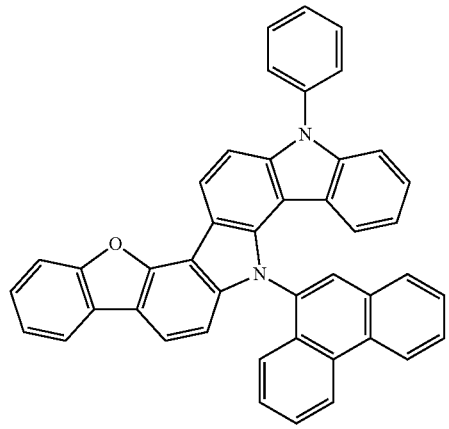
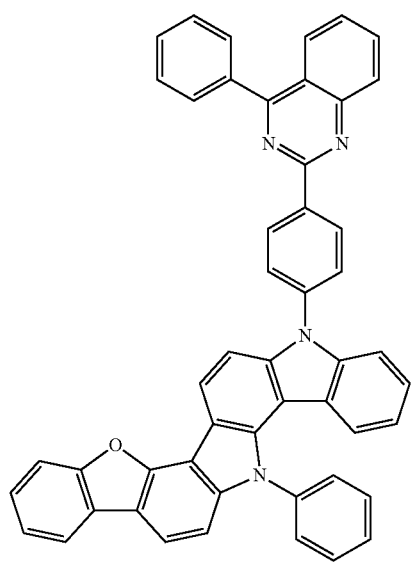
150
-continued
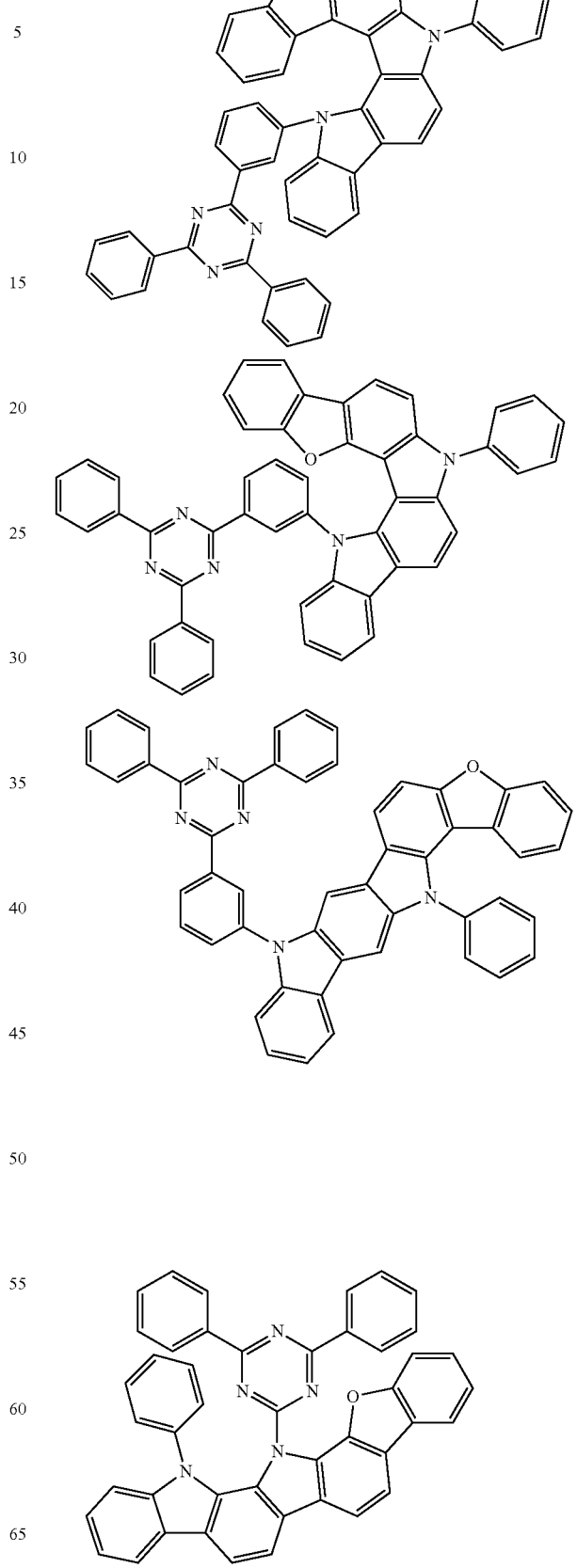

151
-continued
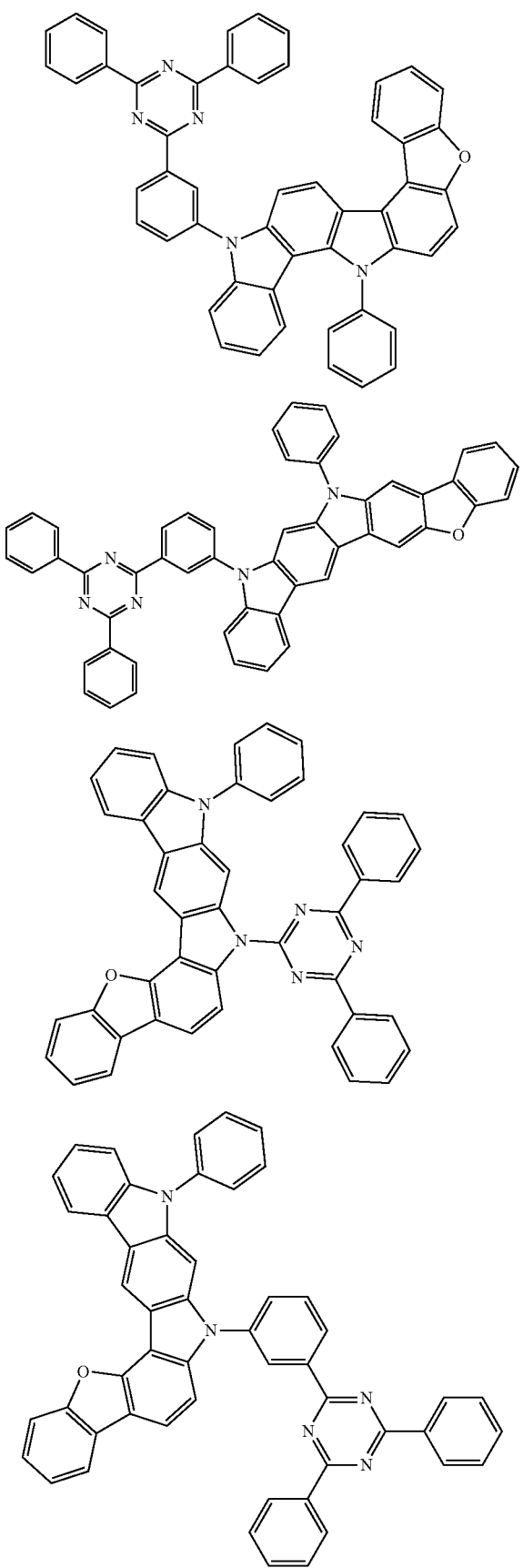
152
-continued
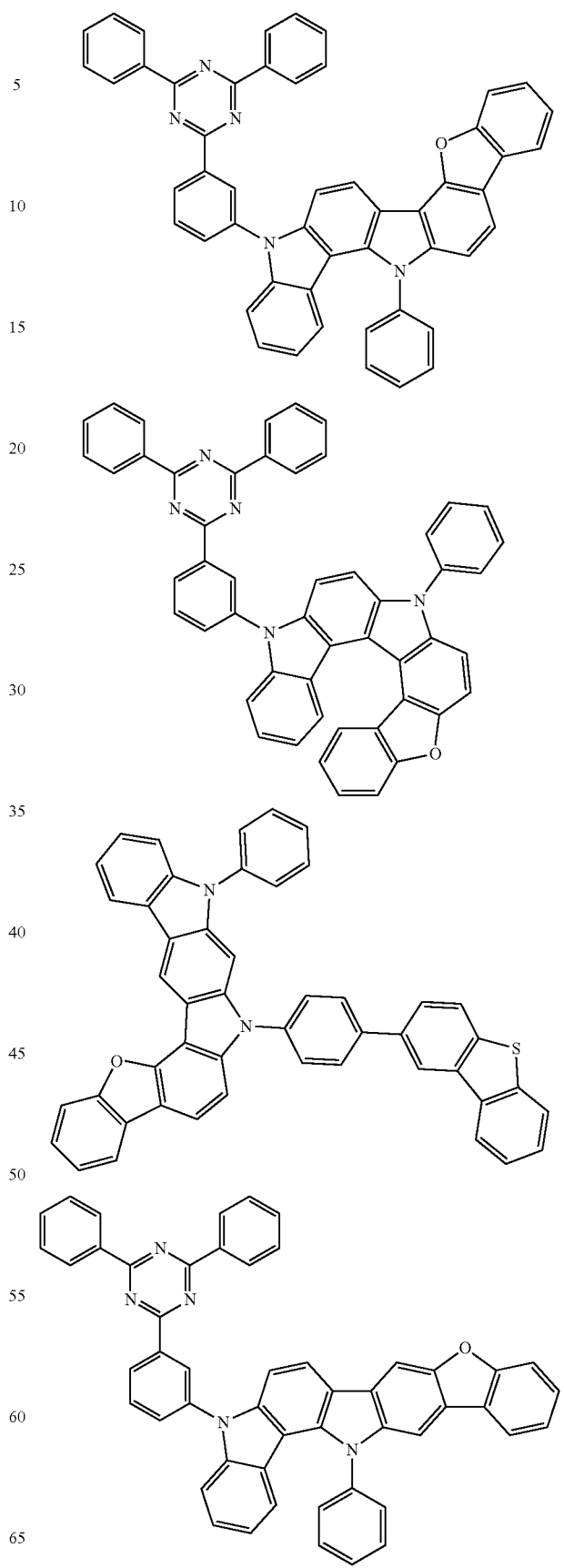

153
-continued
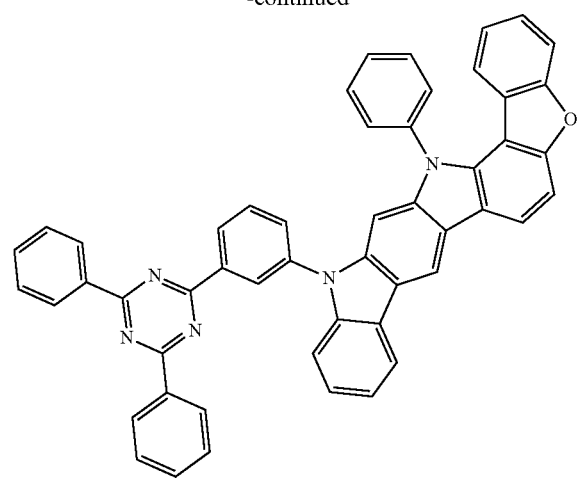
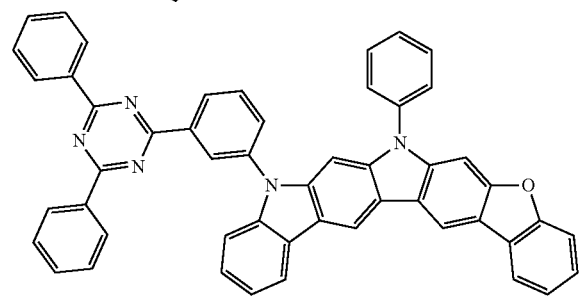
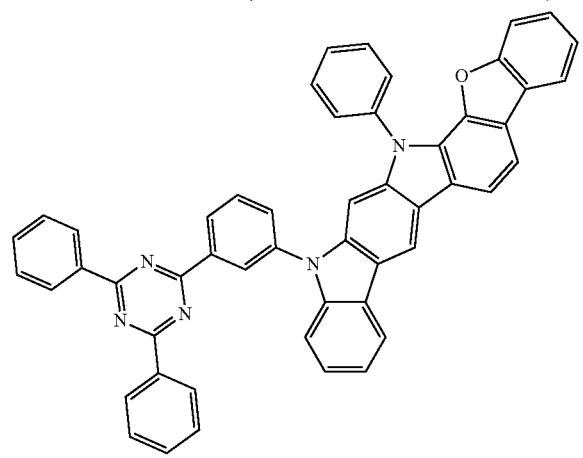
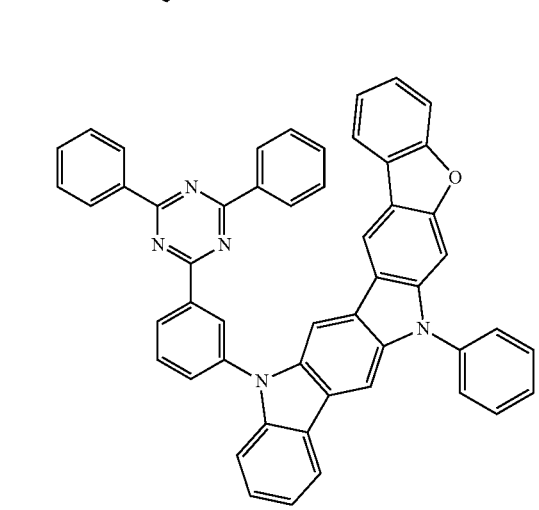
154
-continued
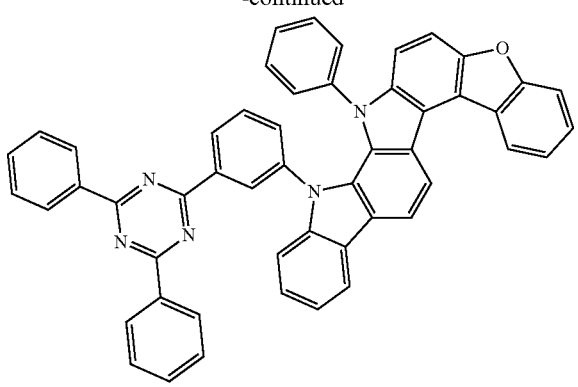
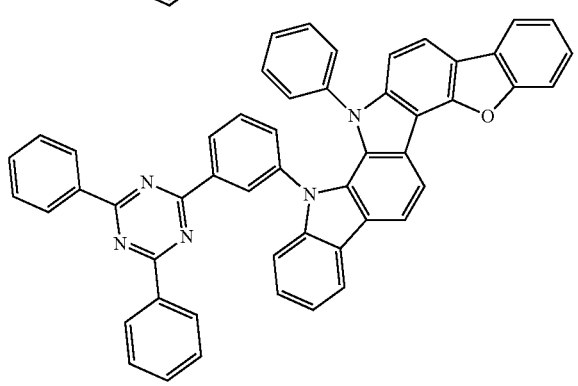
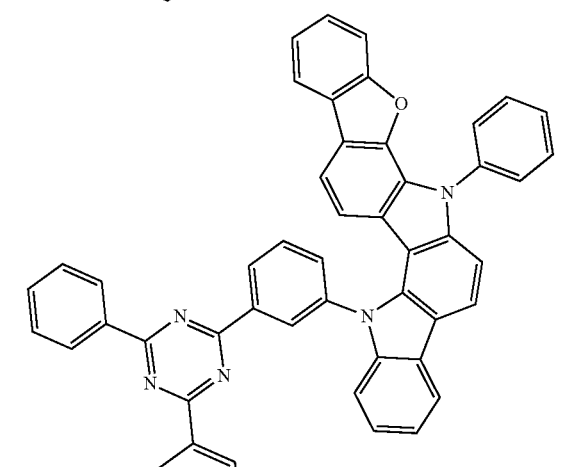
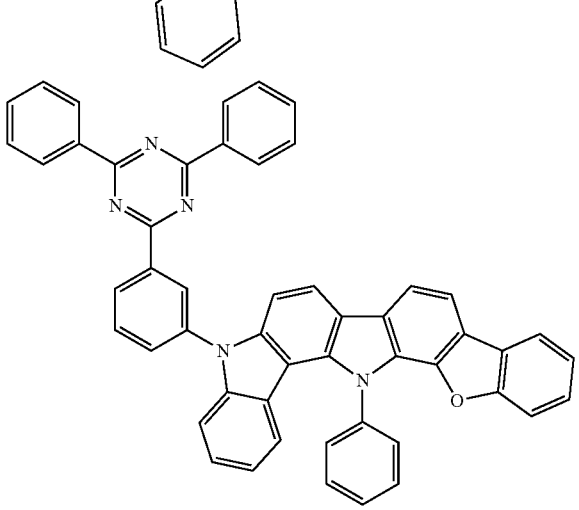

155
-continued
156
-continued
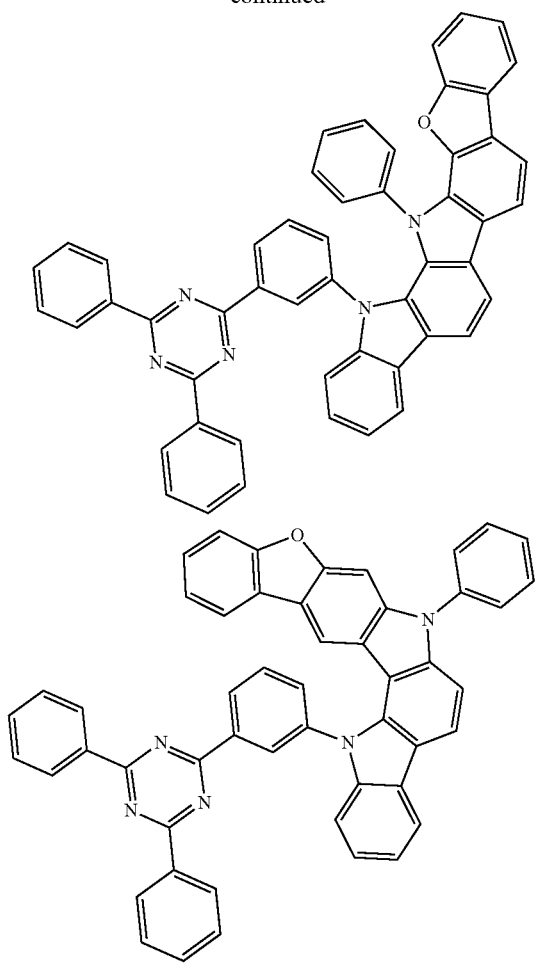
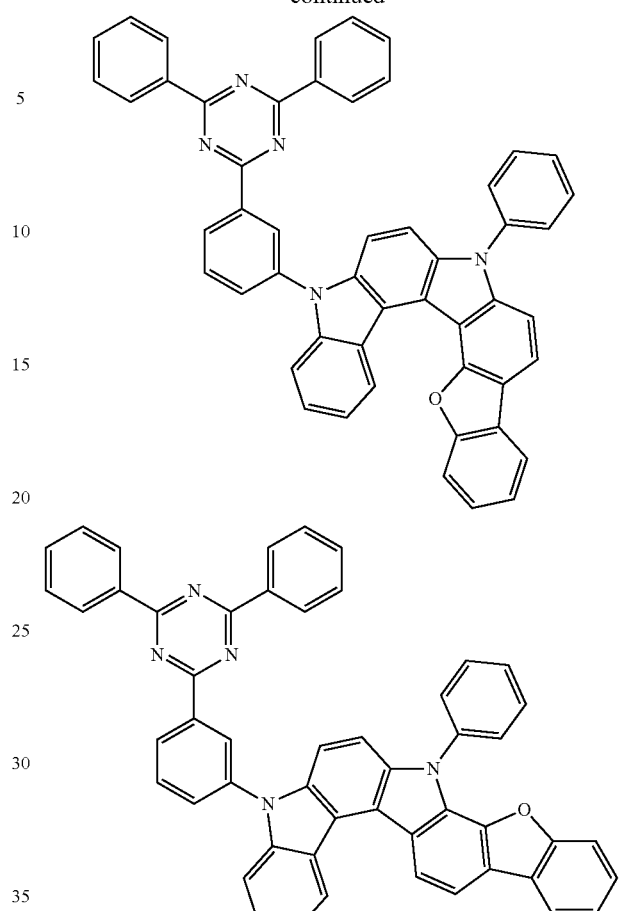
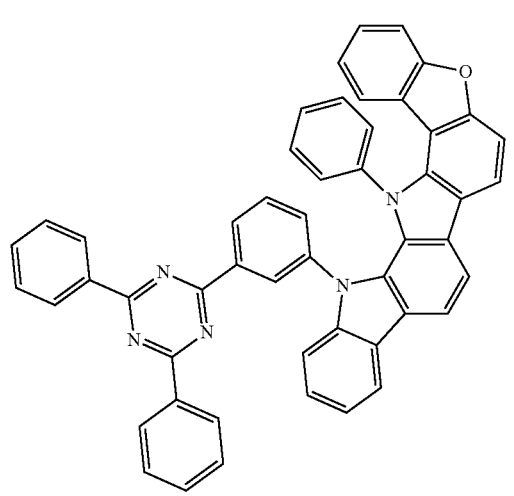
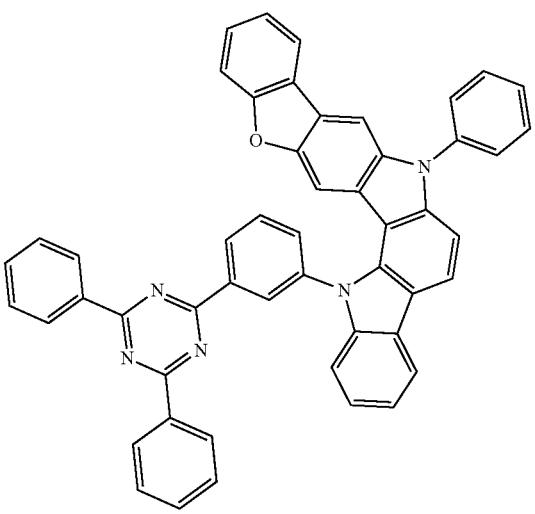

157
-continued
158
-continued
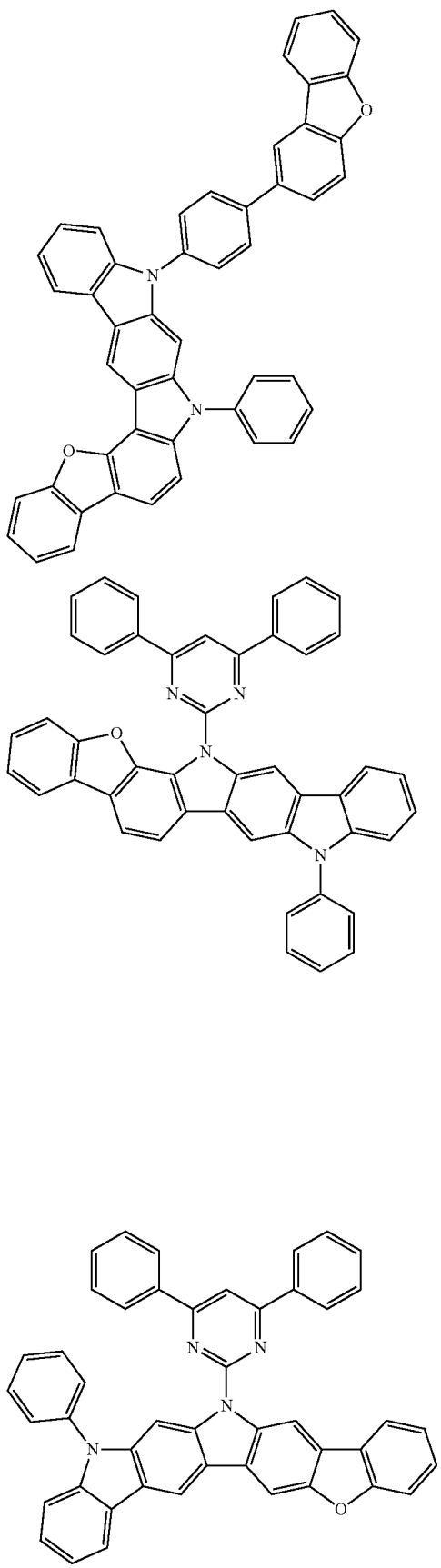
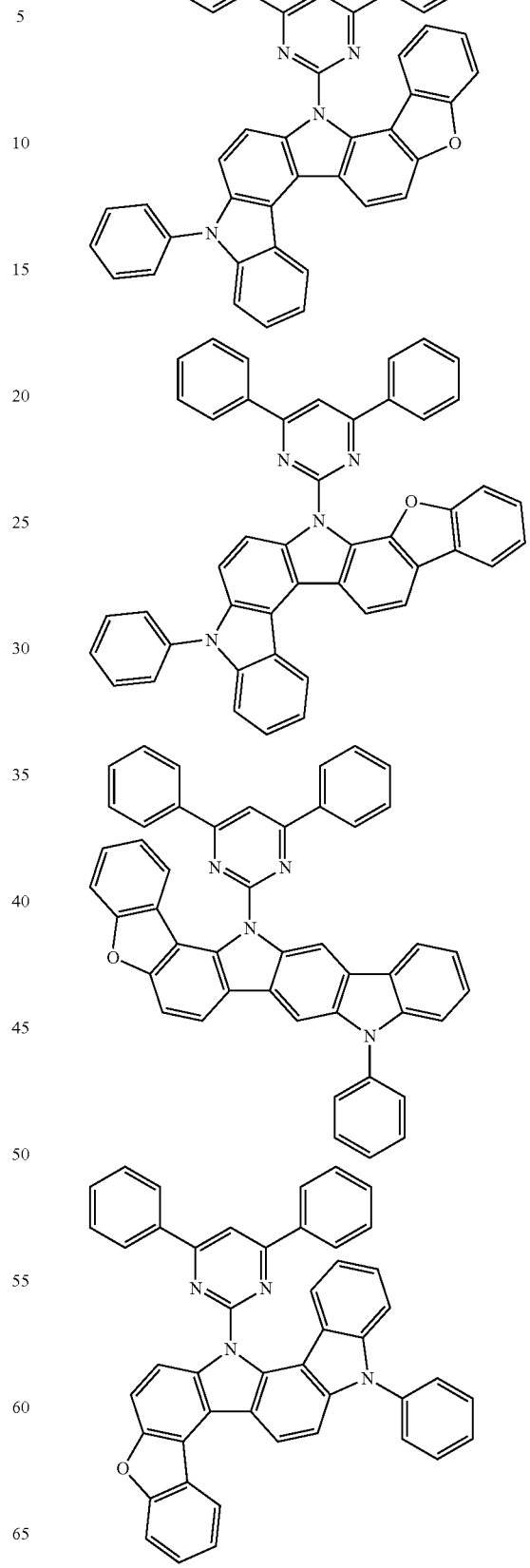

159
-continued
160
-continued
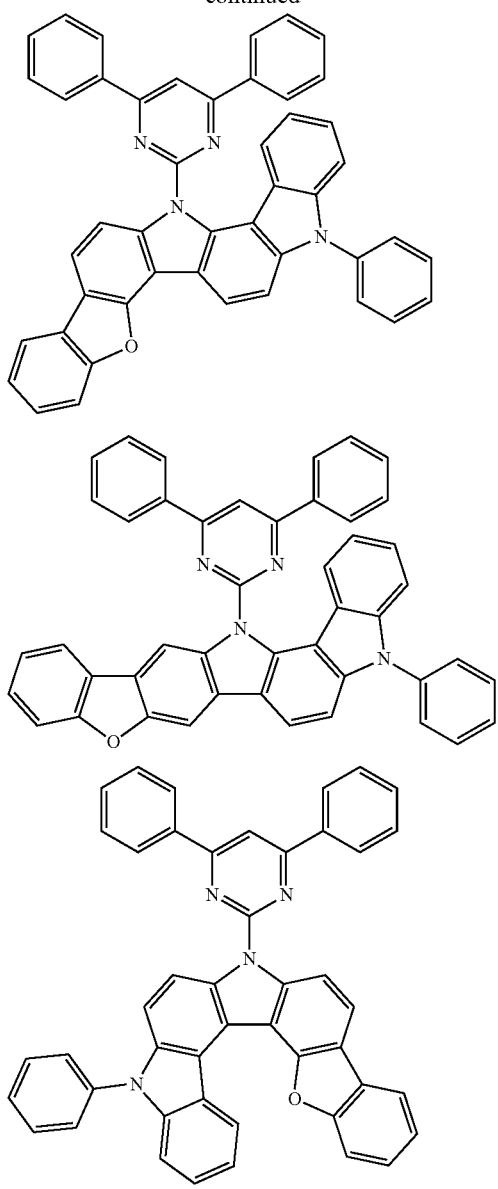
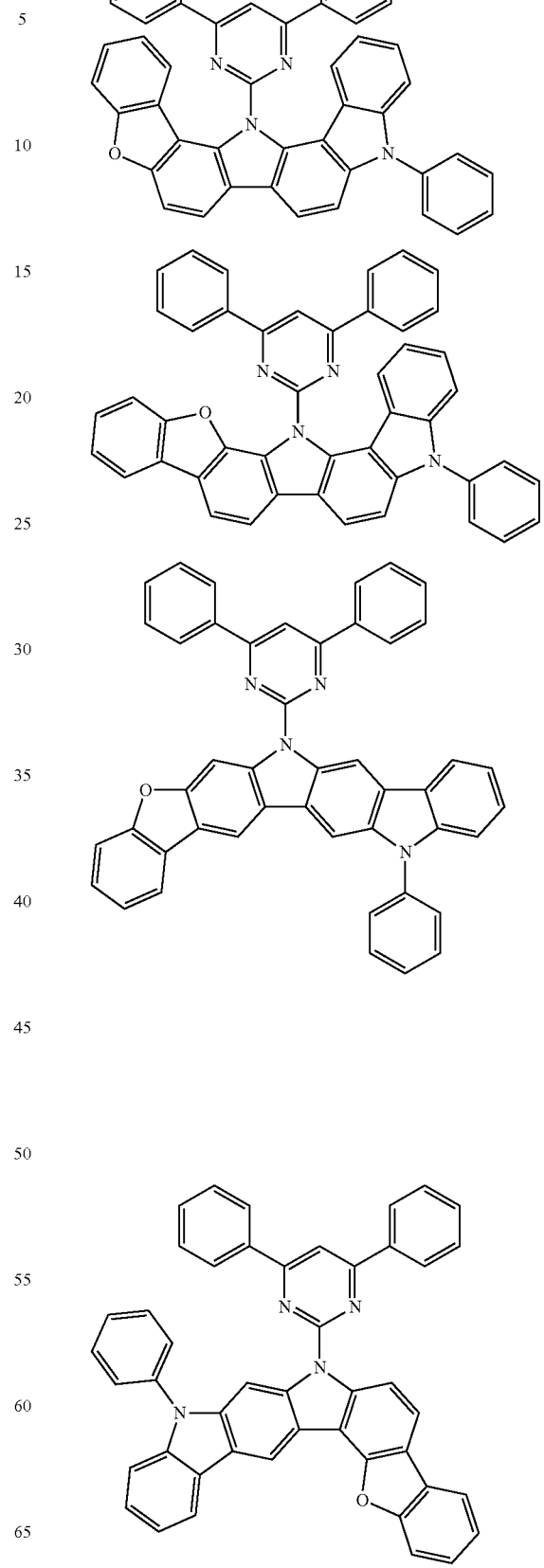

161
-continued
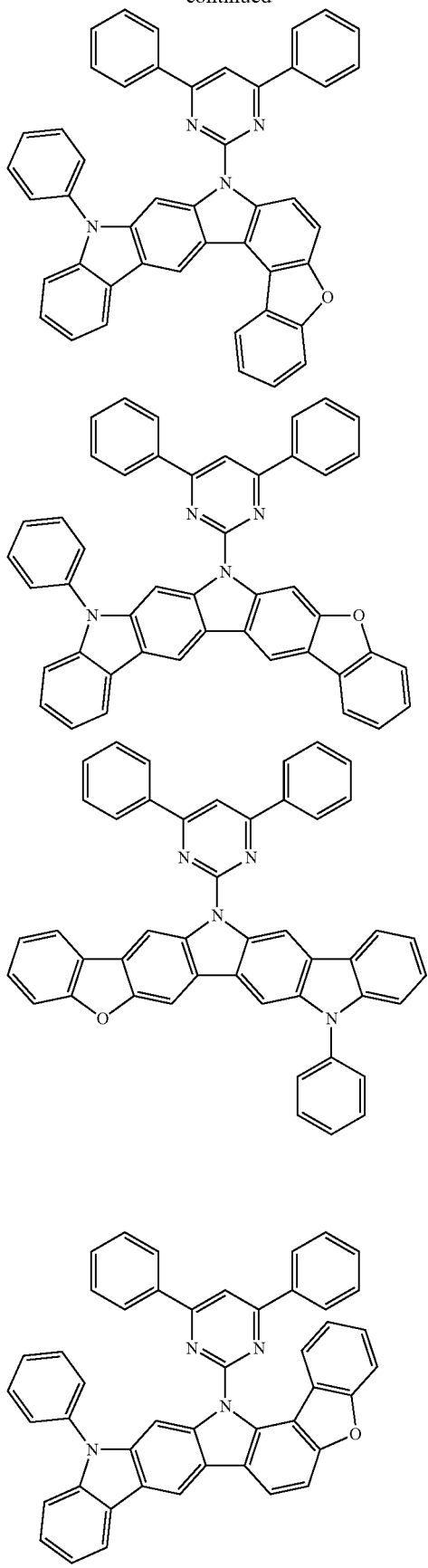
162
-continued
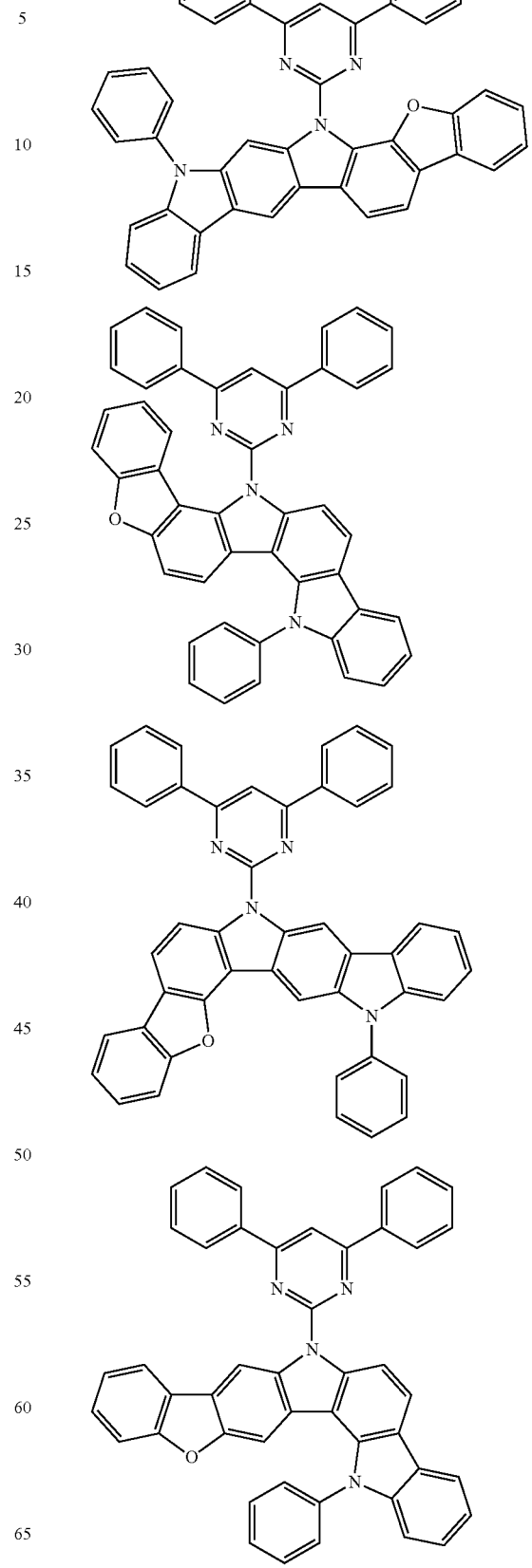

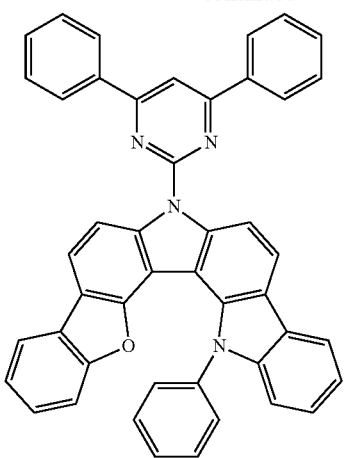
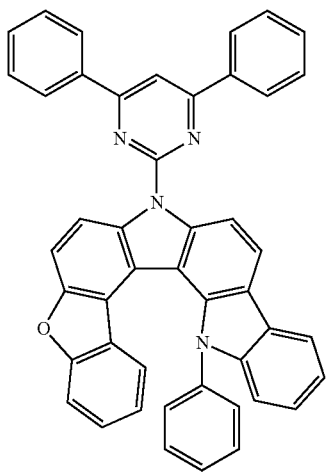
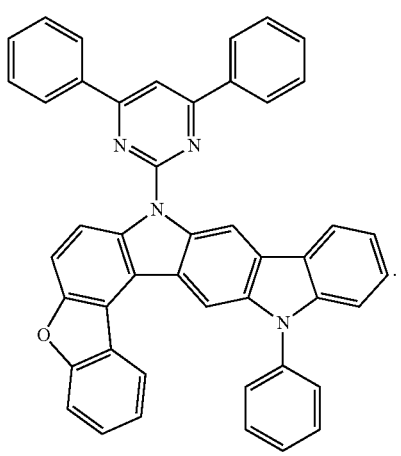
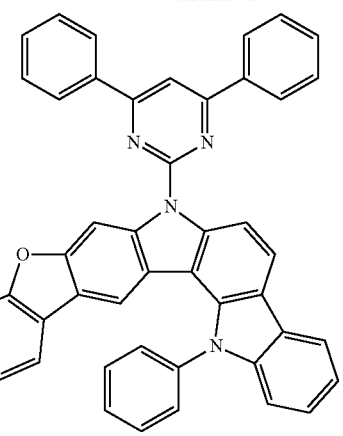
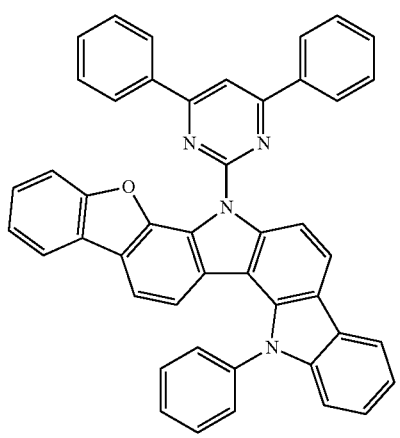
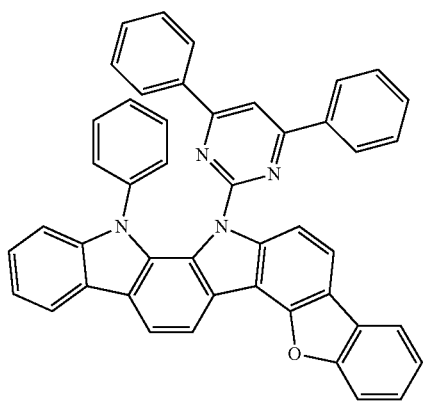
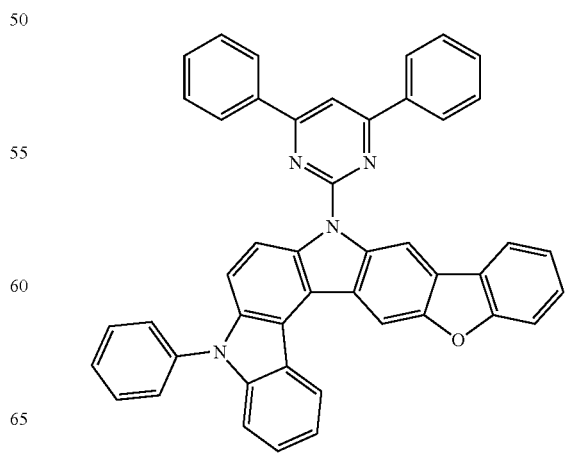

165
-continued
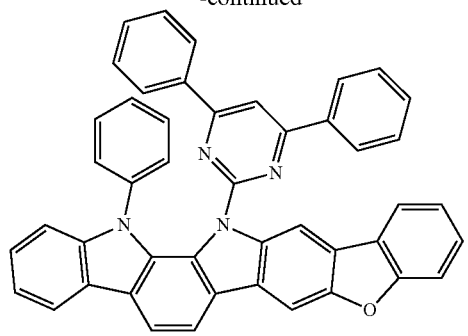
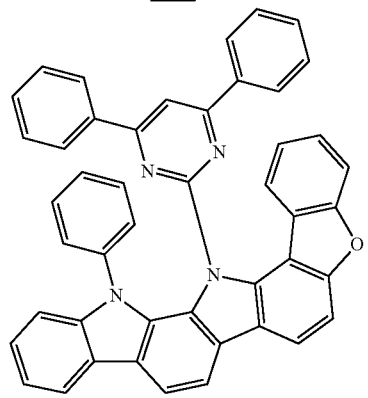
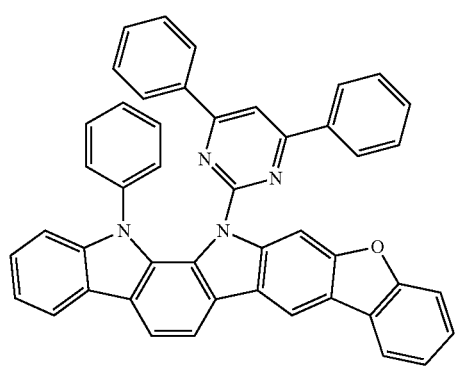
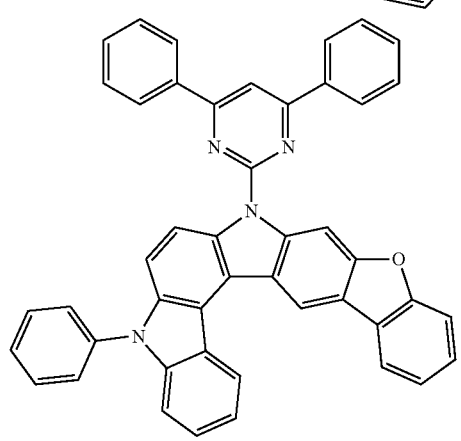
166
-continued
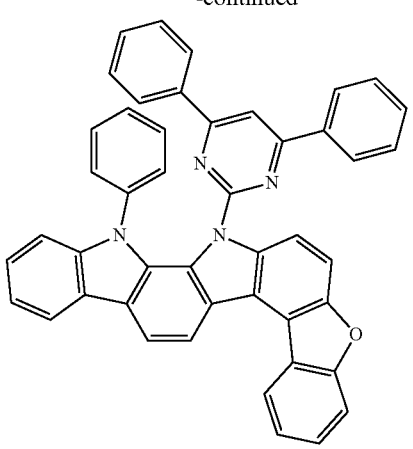
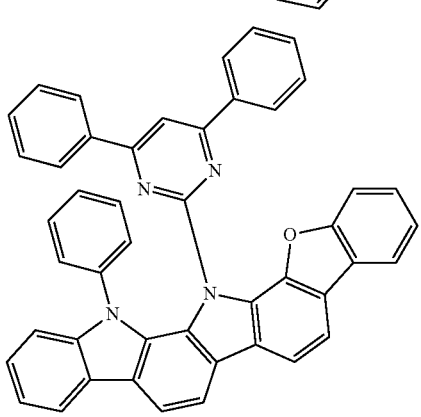
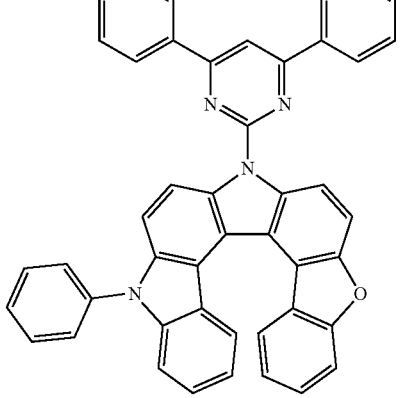
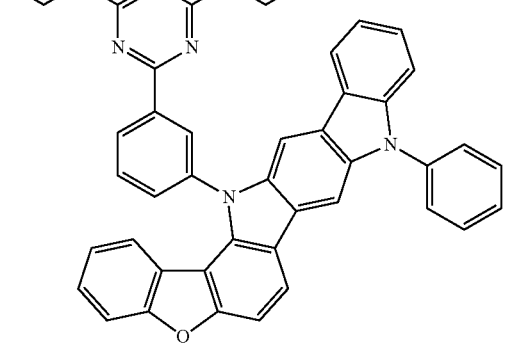

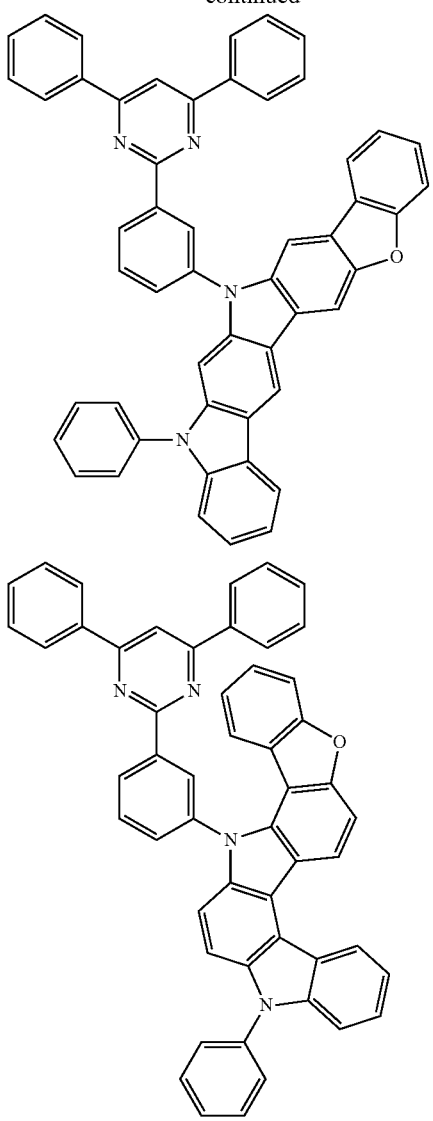
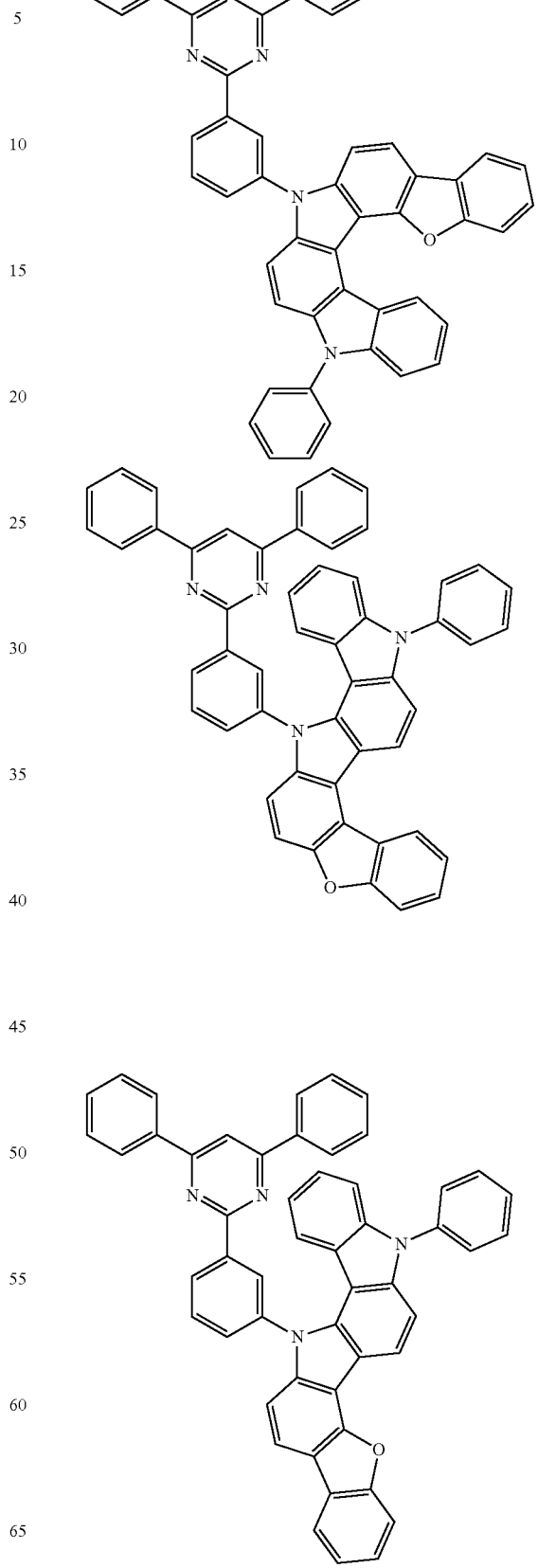

169
-continued
170
-continued
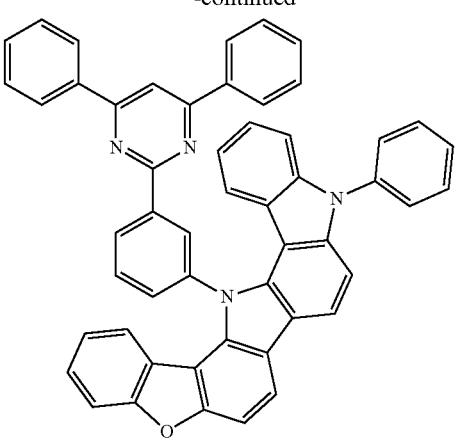
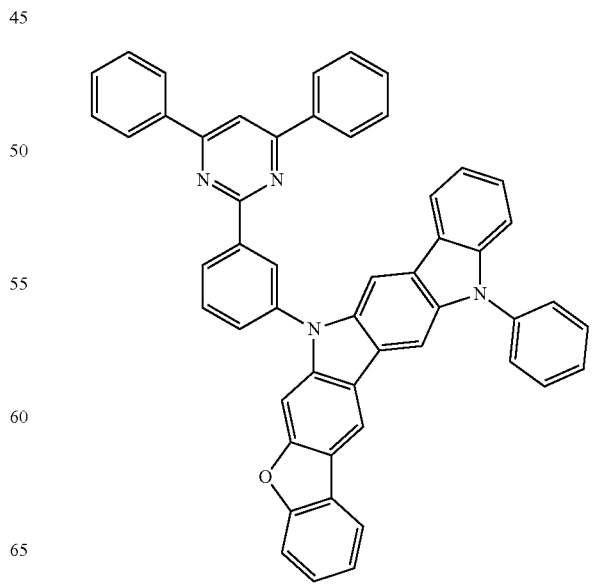

171
-continued
172
-continued
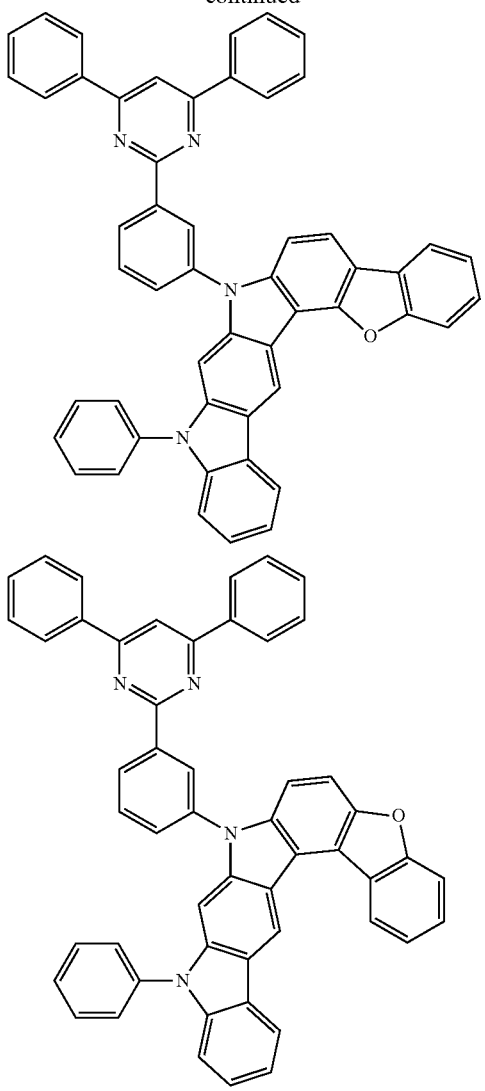
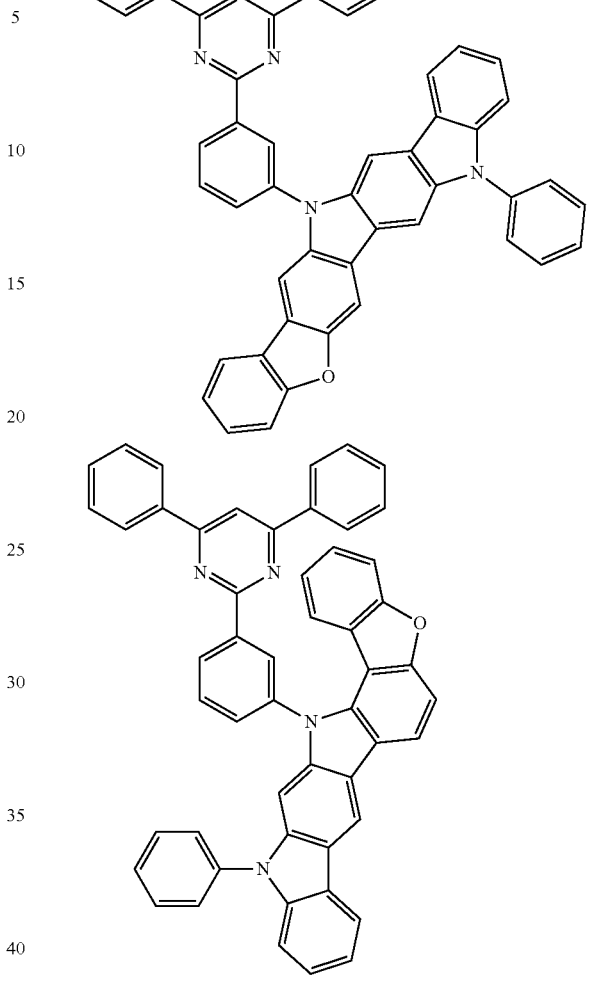
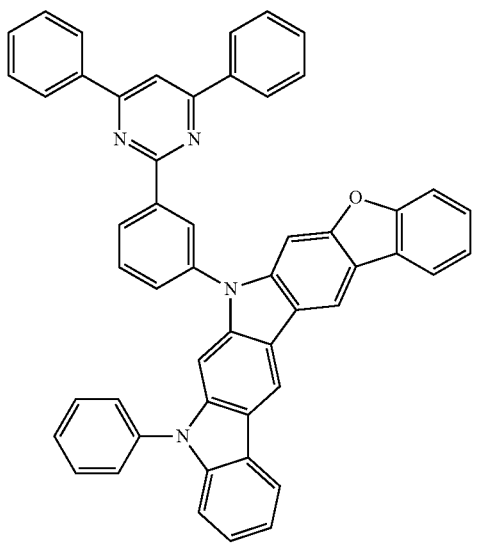

173
-continued
174
-continued
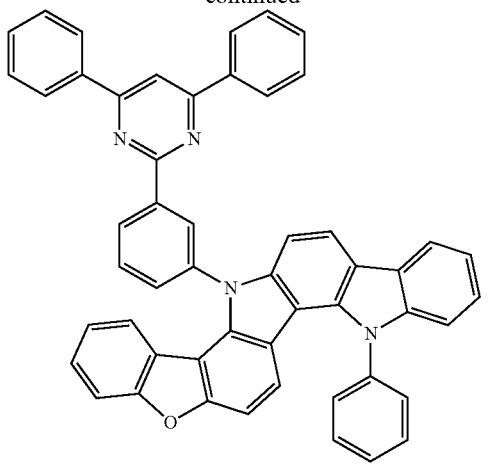
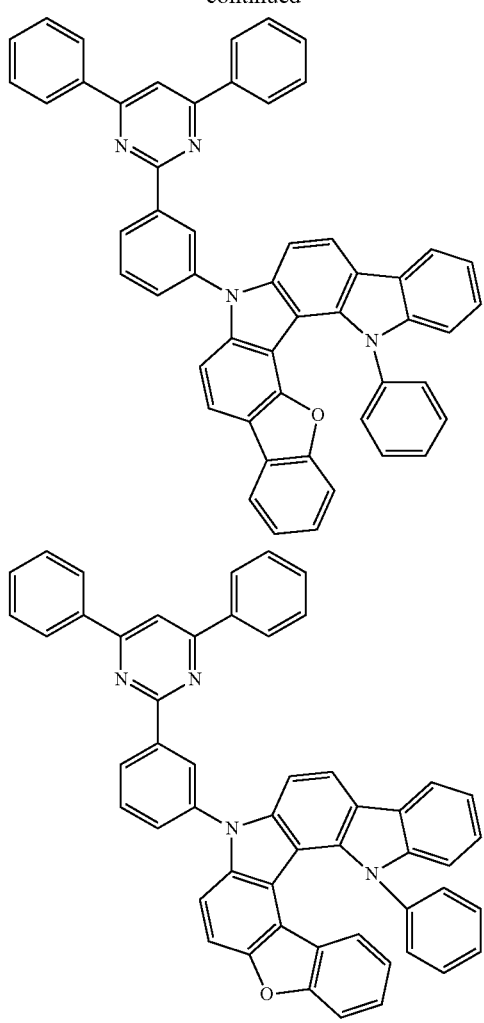
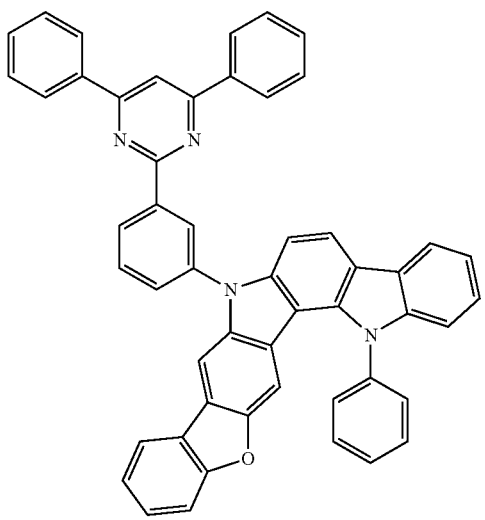
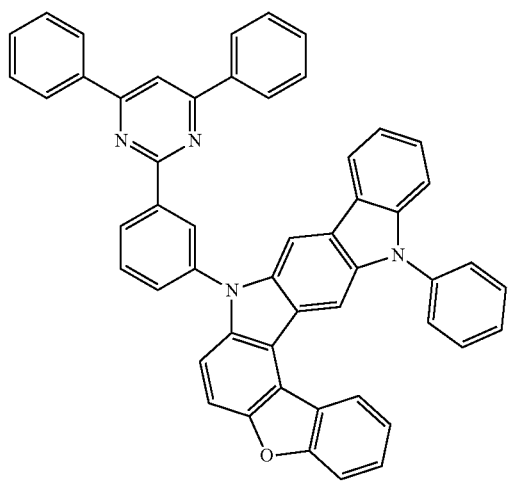

175
-continued
176
-continued
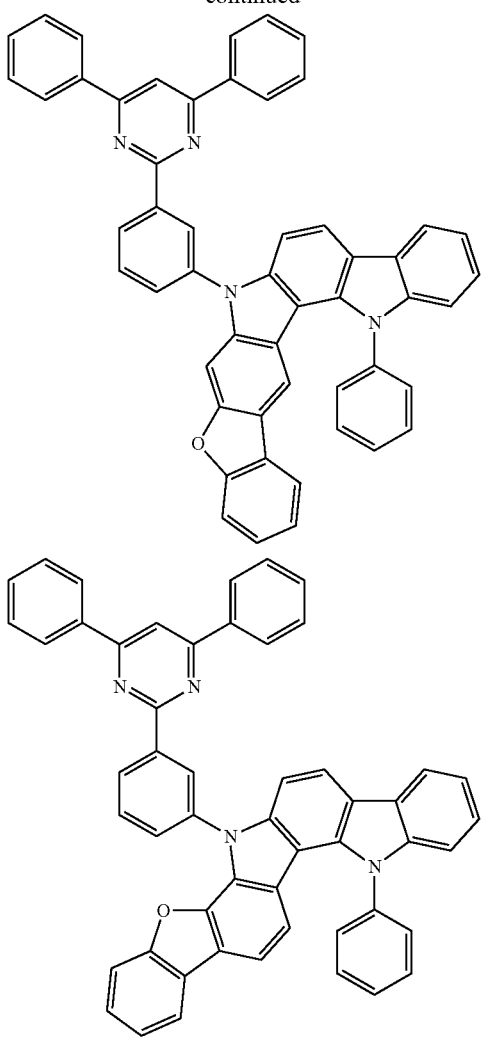
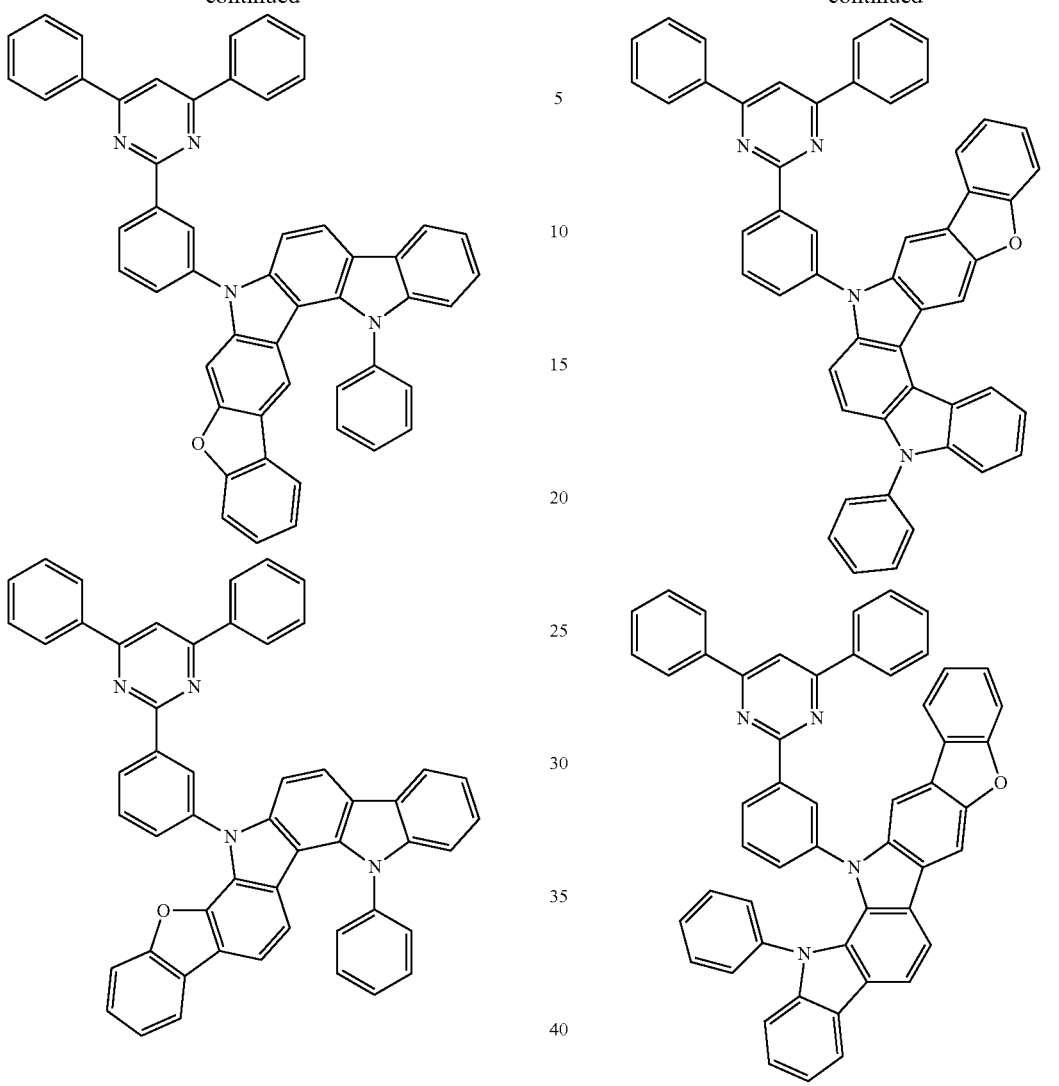

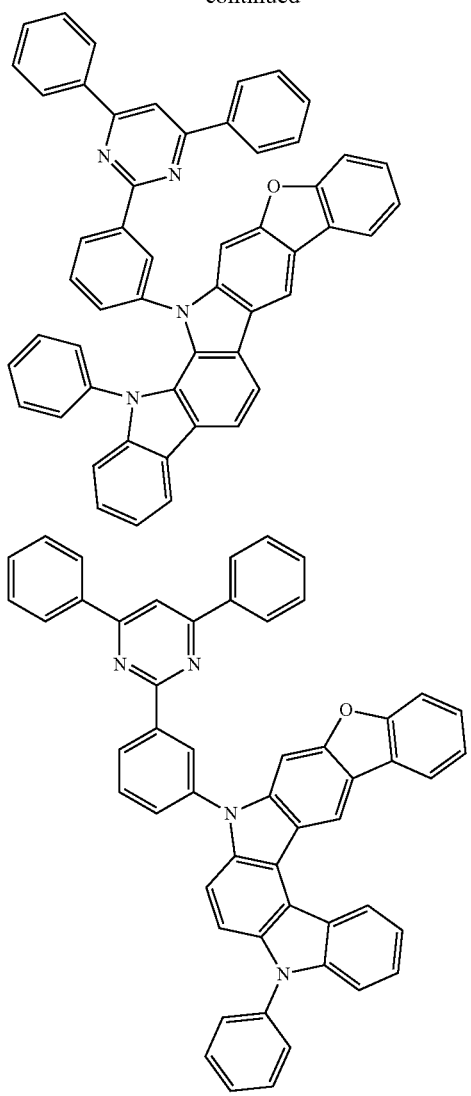
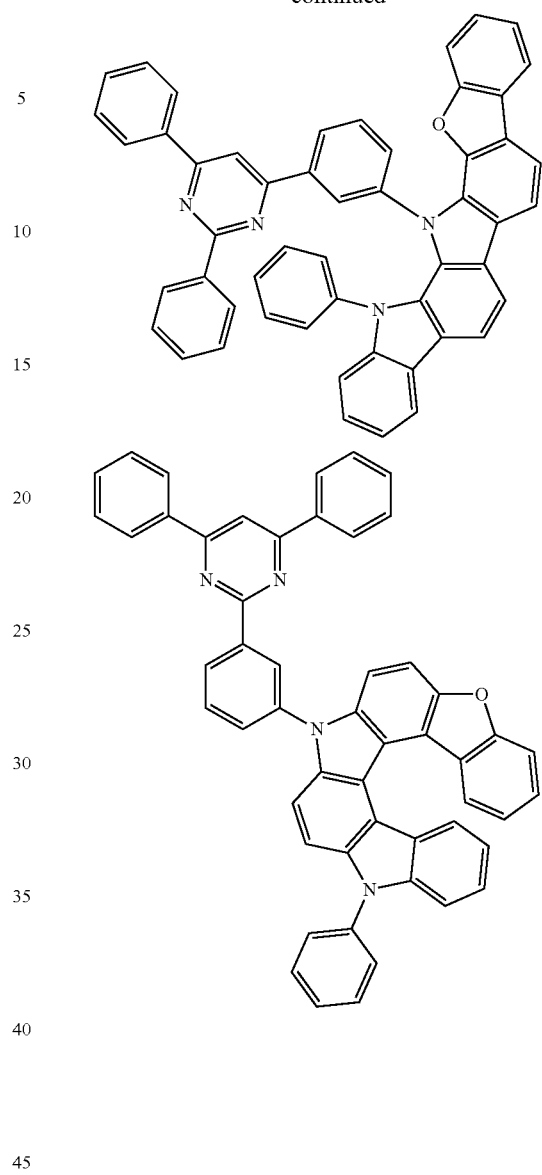
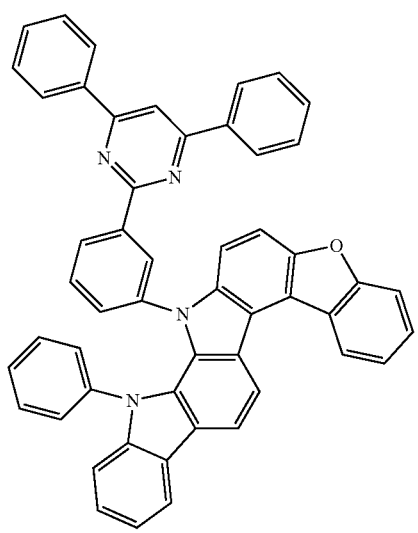
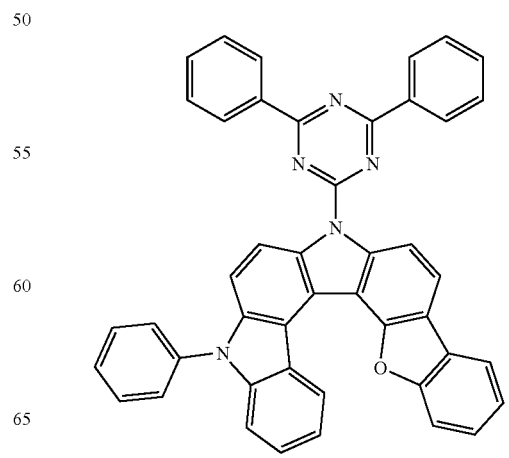

179
-continued
180
-continued
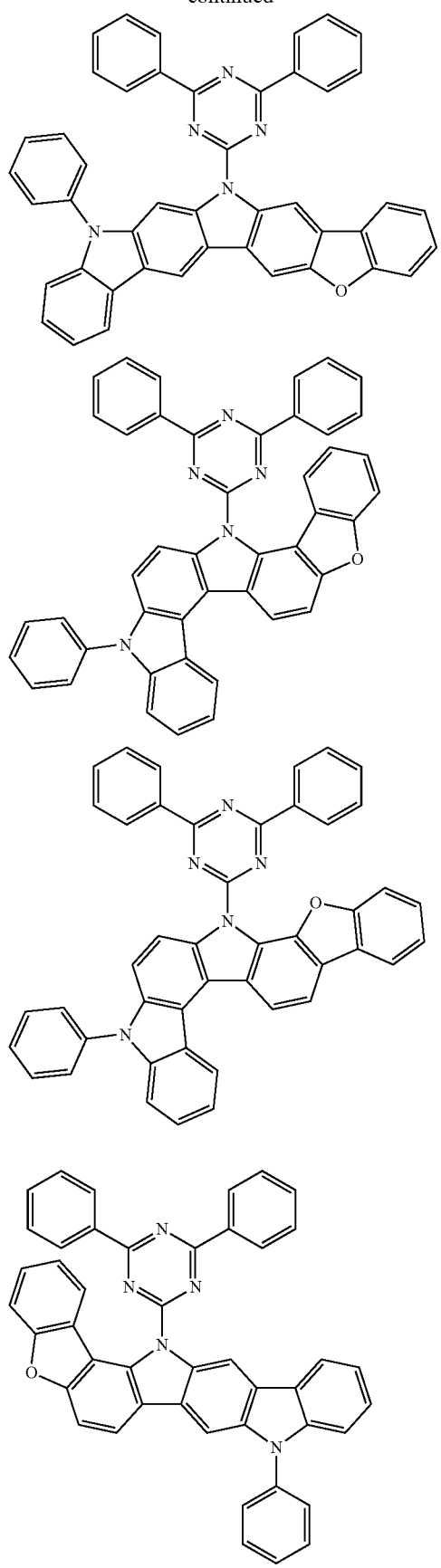
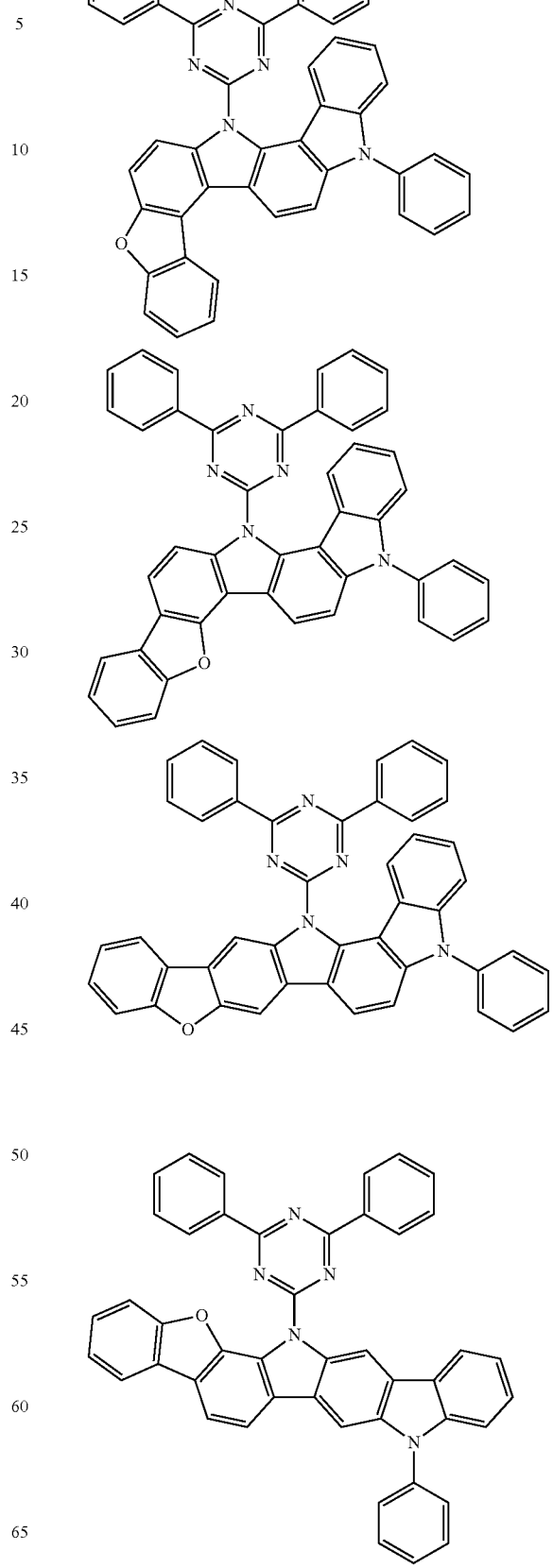

181
-continued
182
-continued
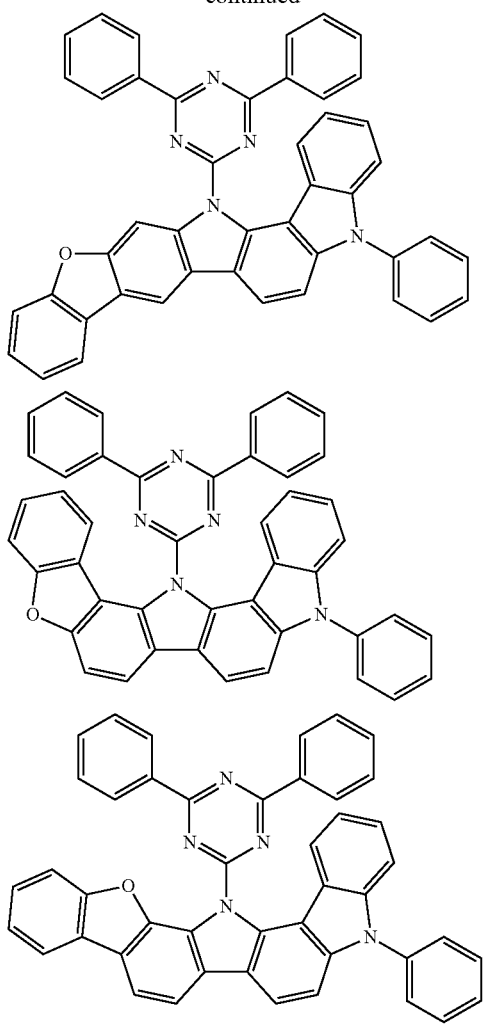
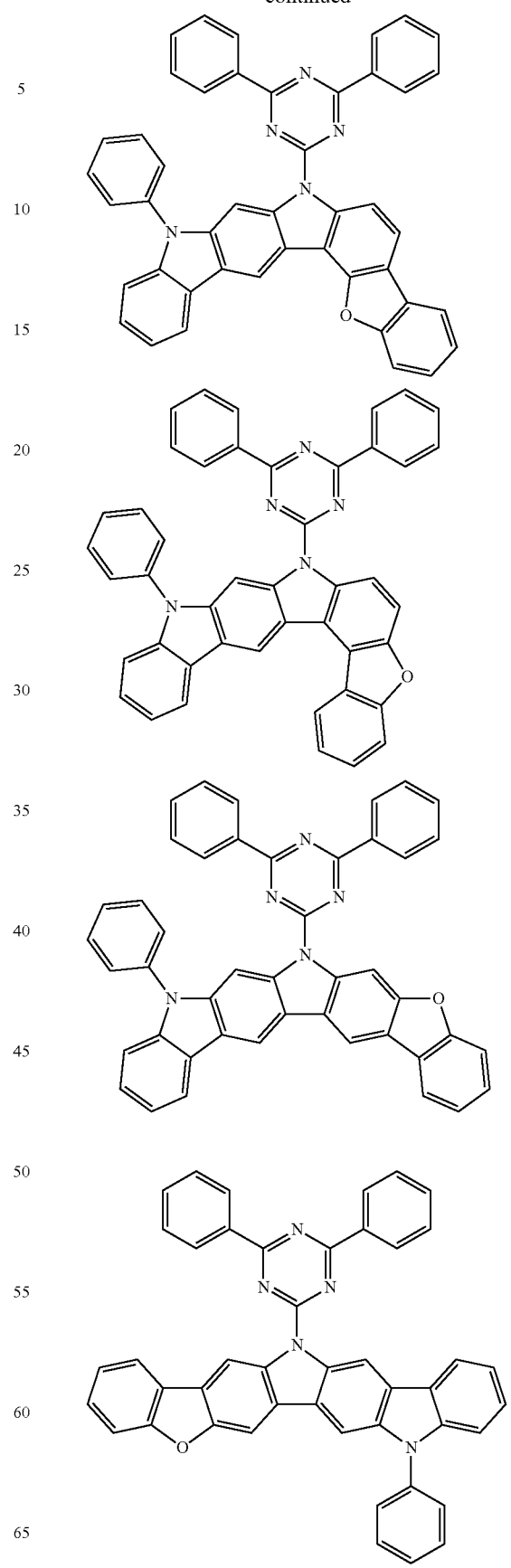
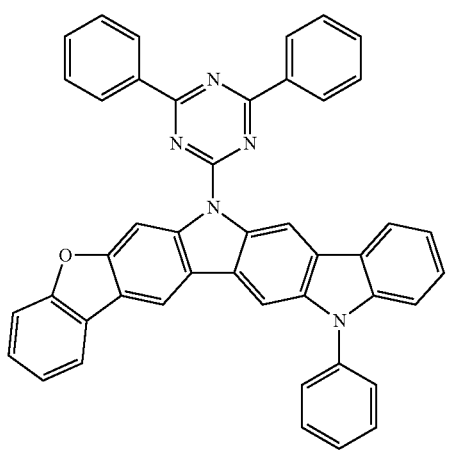

-continued
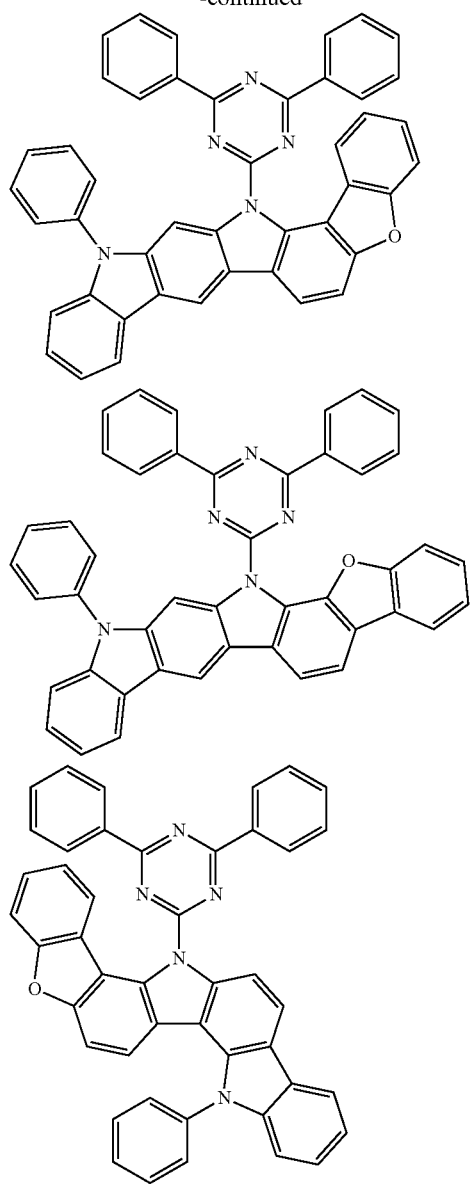
-continued
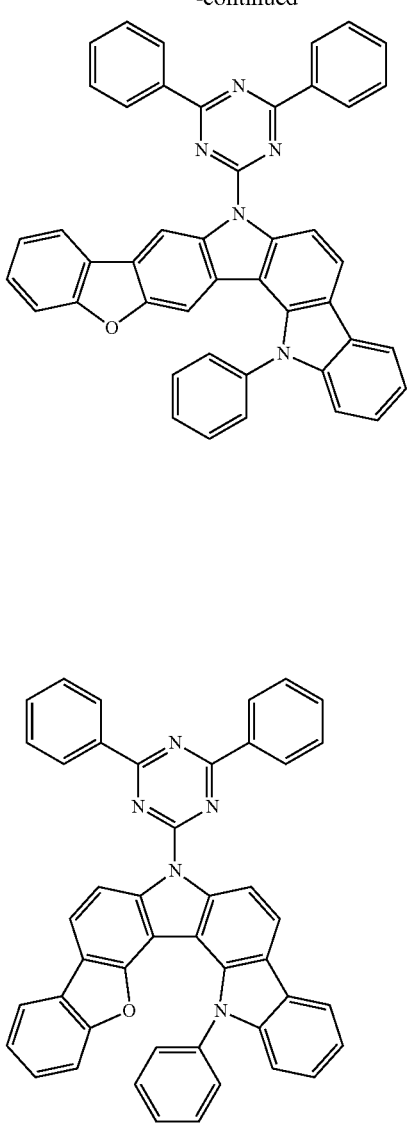
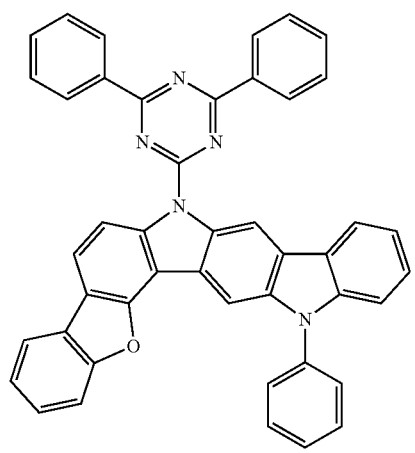
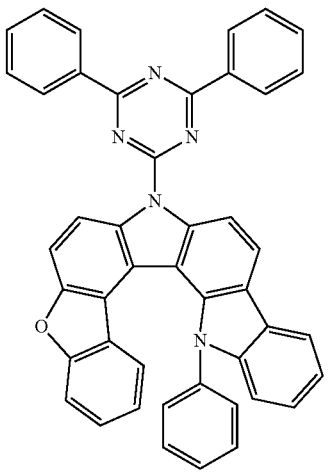

185
-continued
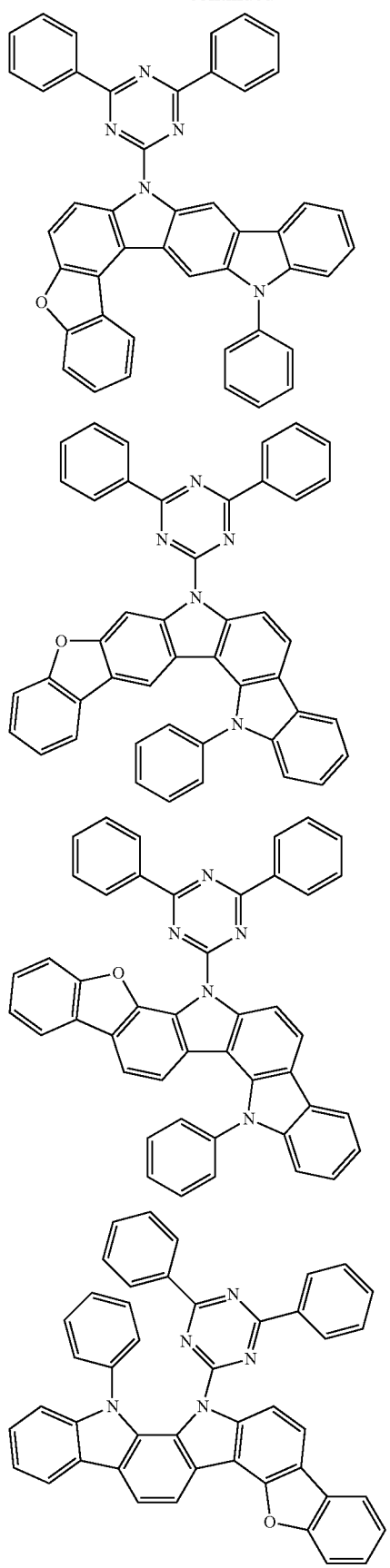
186
-continued
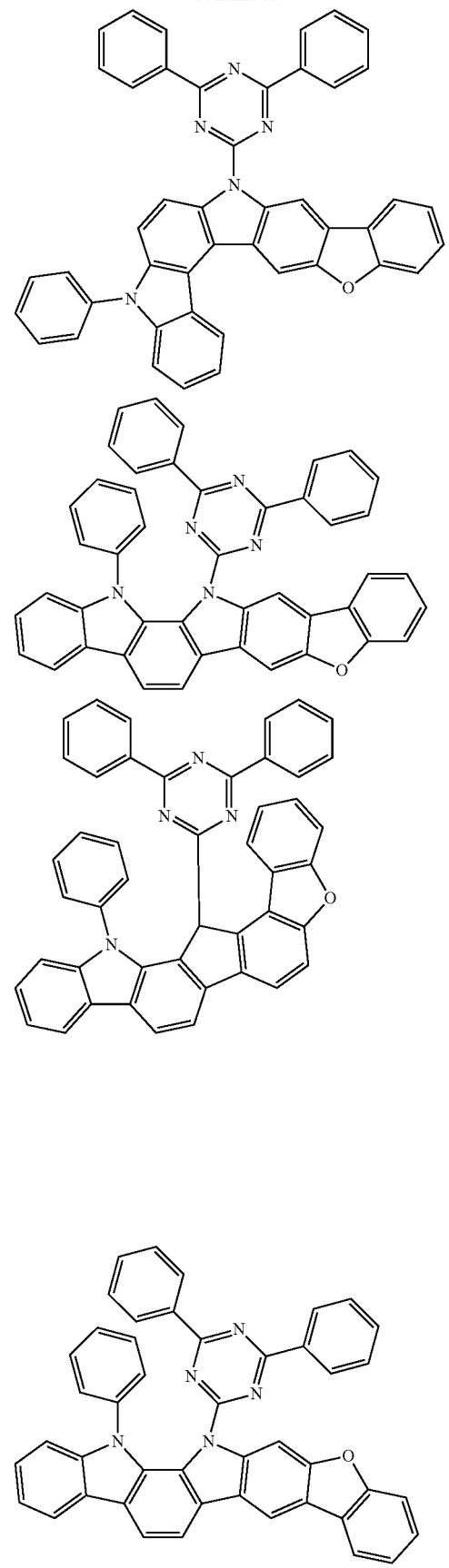

187
-continued
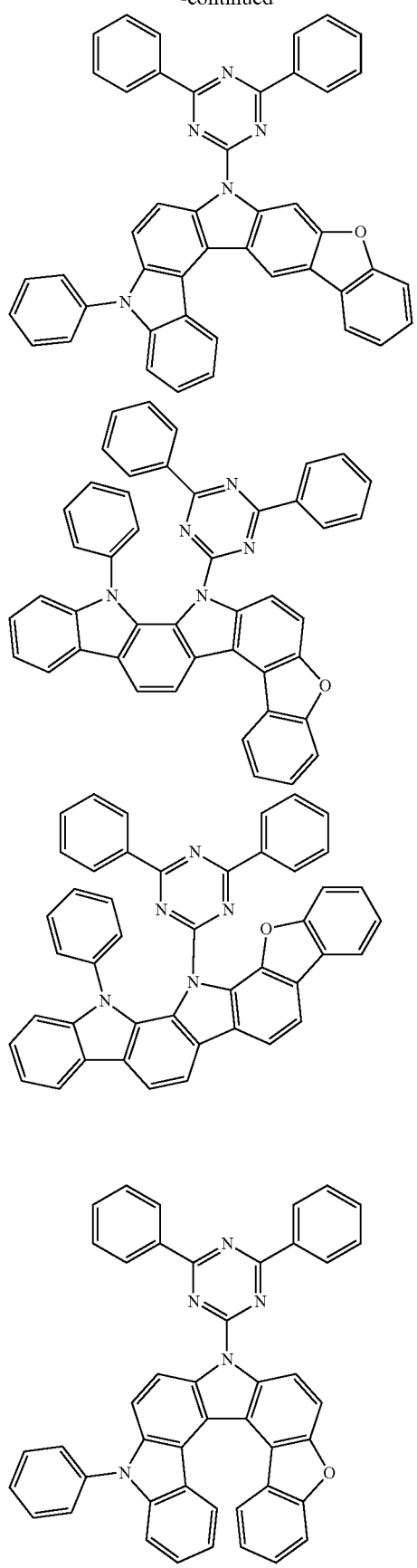
188
-continued
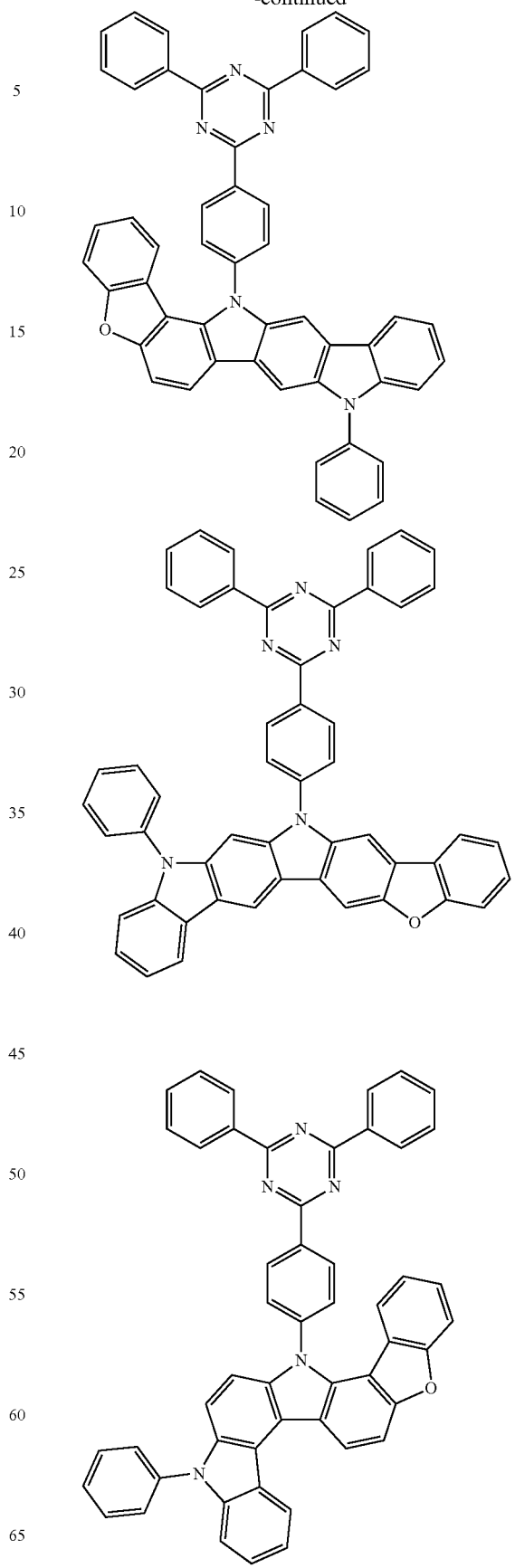

189
-continued
190
-continued
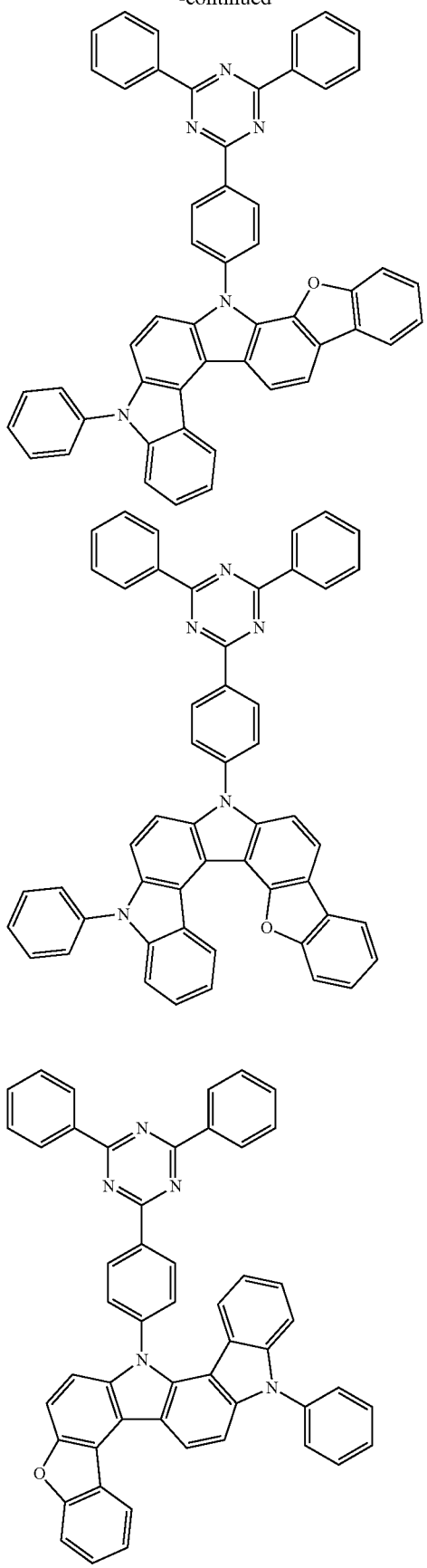
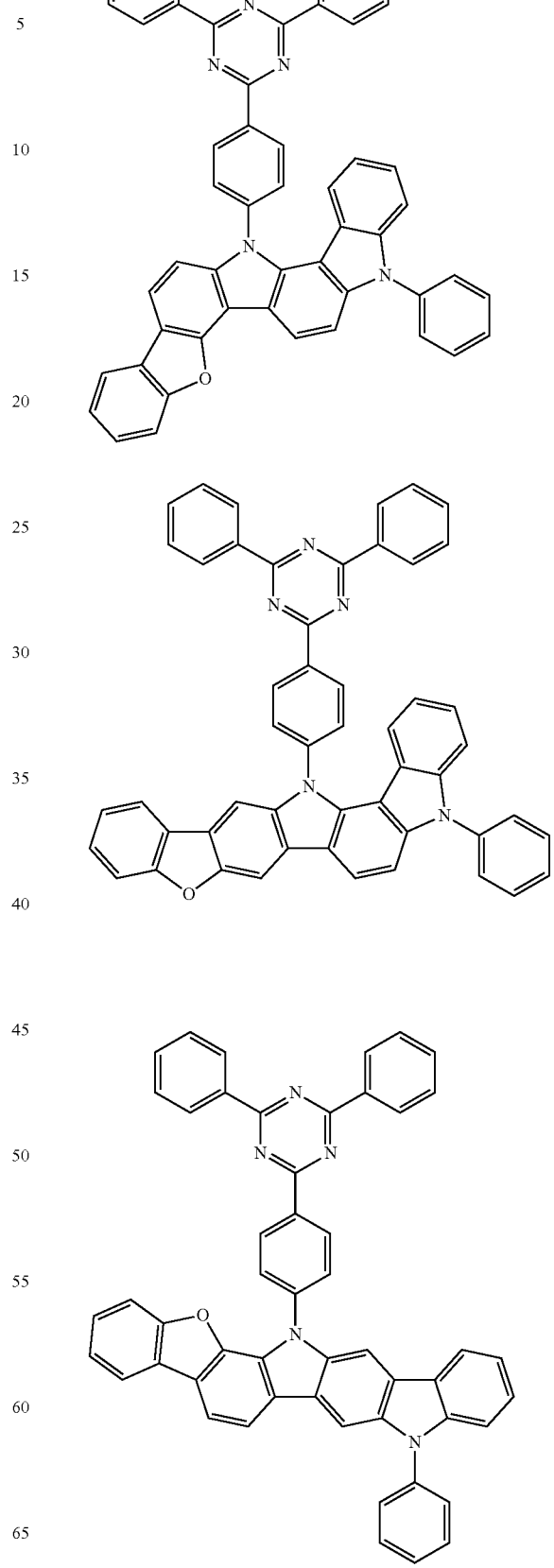

191
-continued
192
-continued
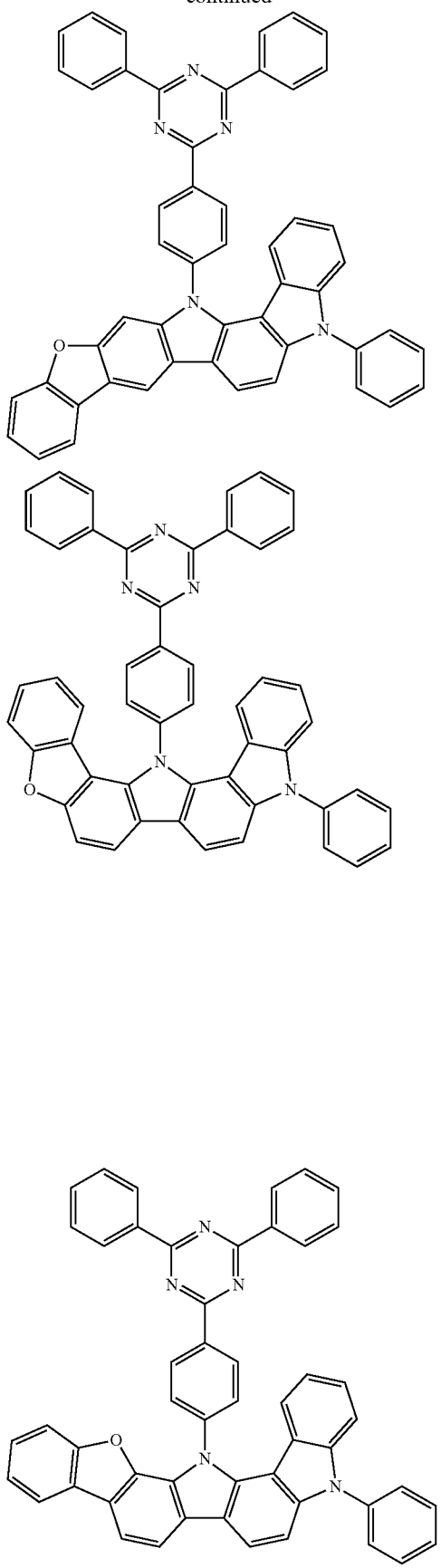
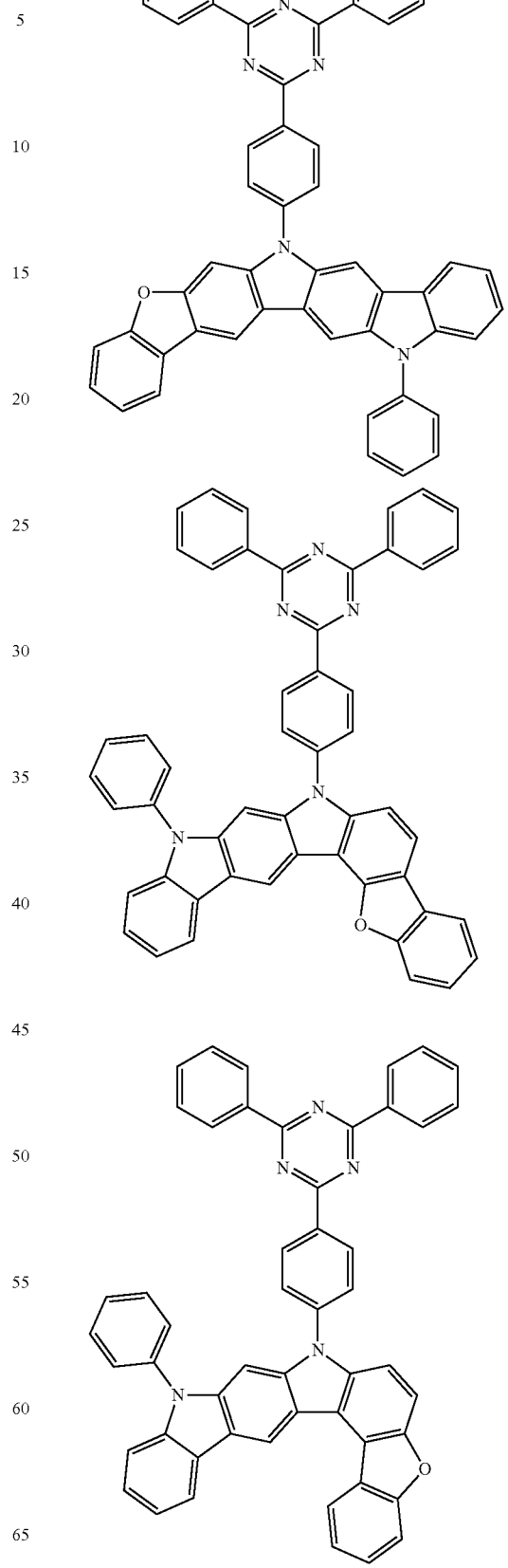

193
-continued
194
-continued
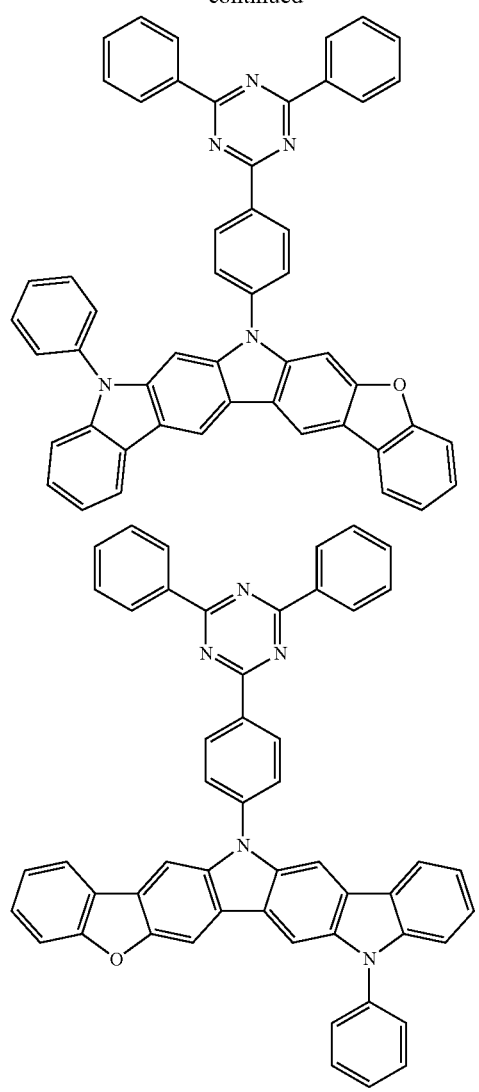
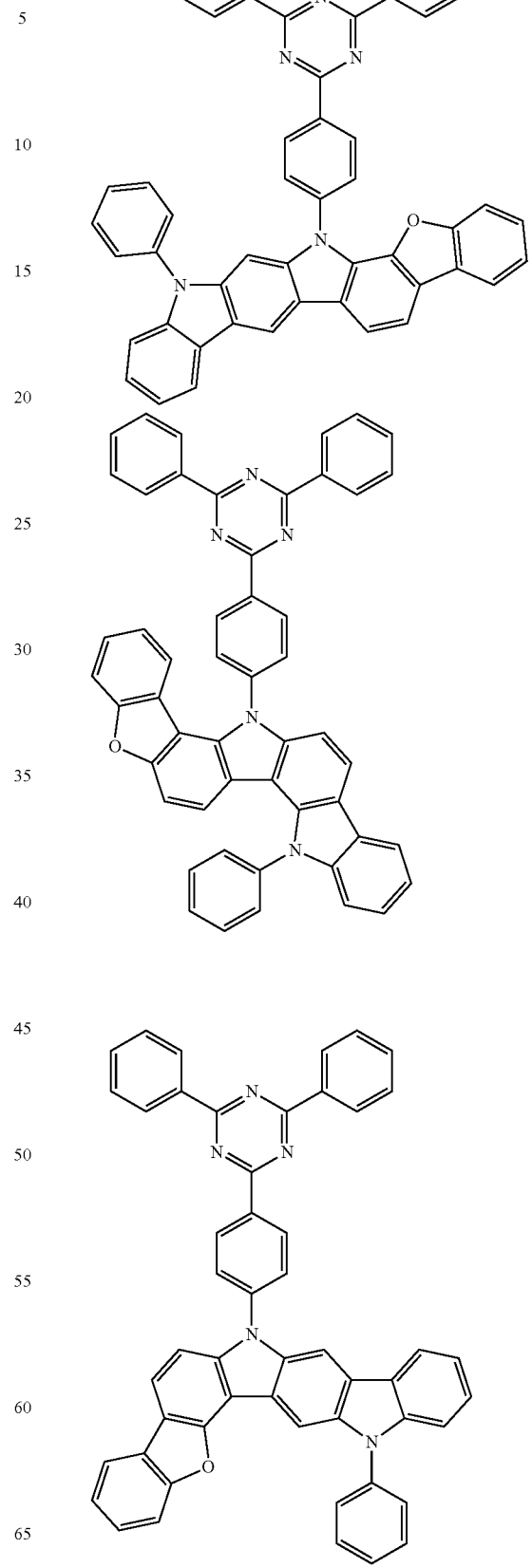

195
-continued
196
-continued
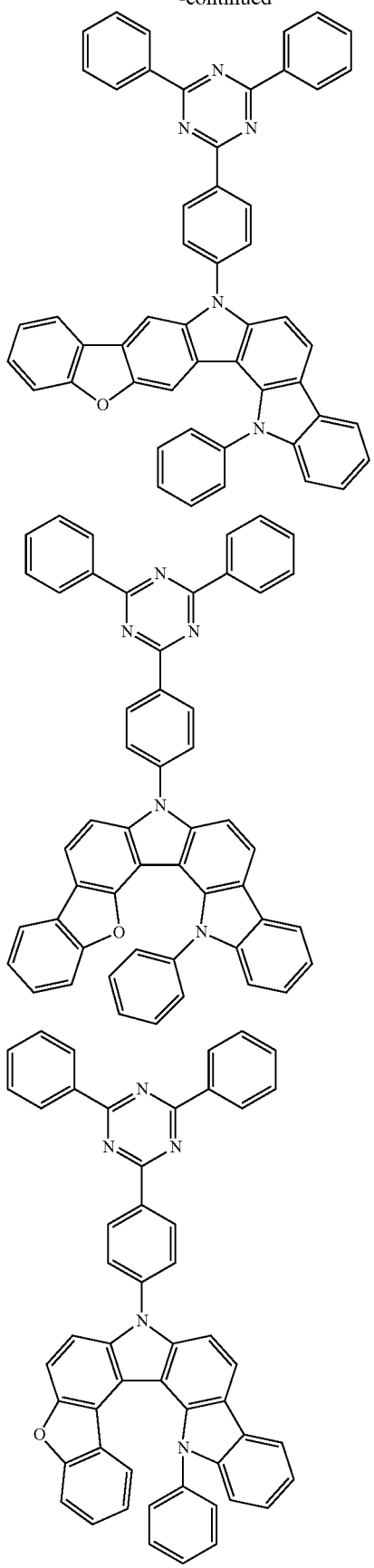
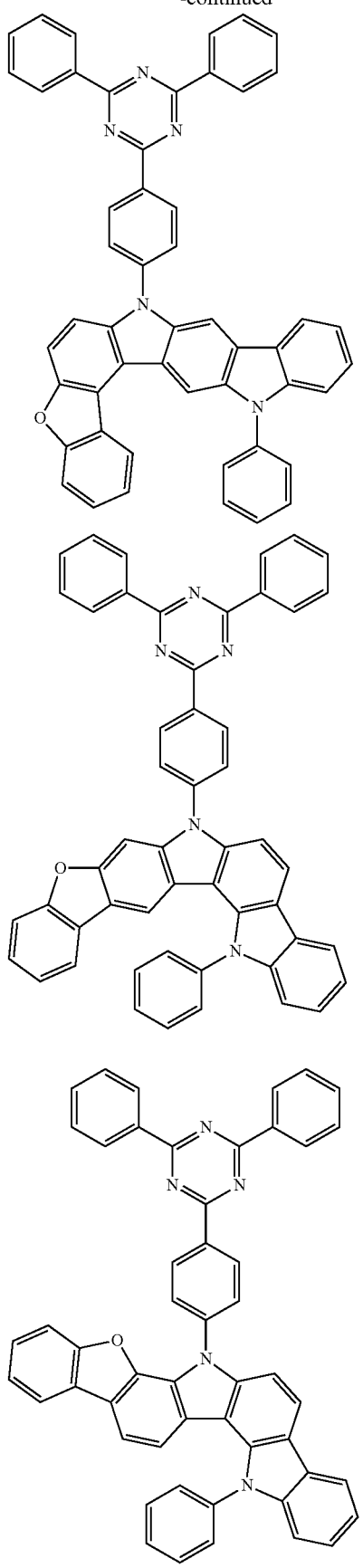

197
-continued
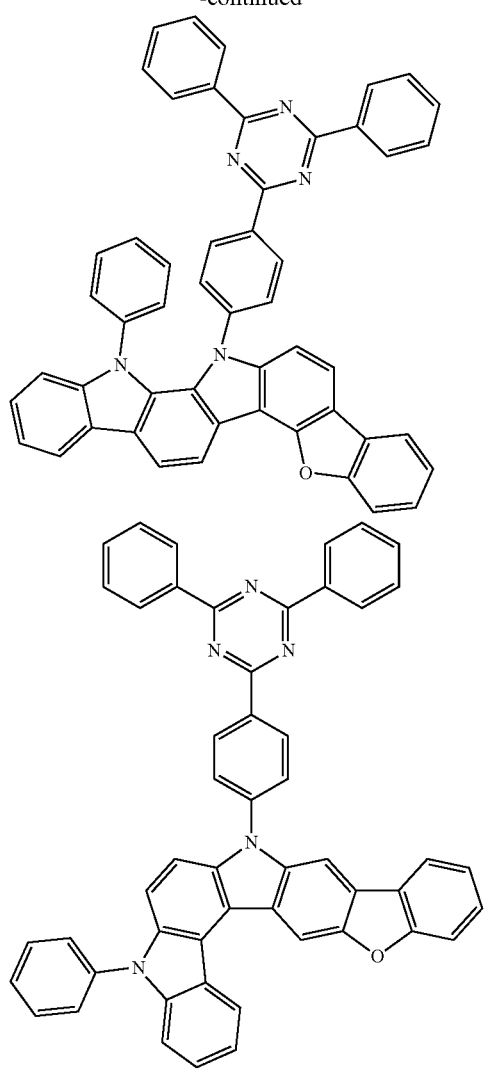
198
-continued
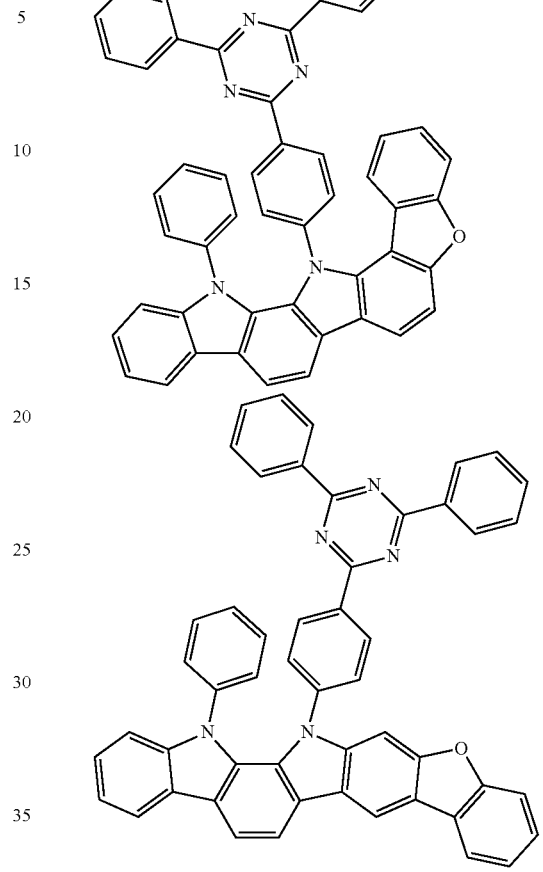
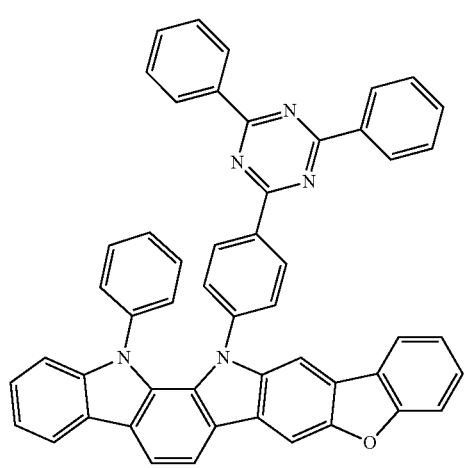
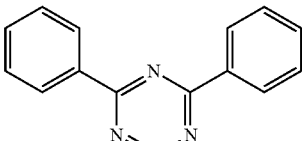
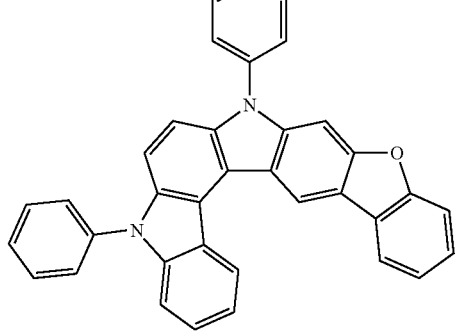

199
-continued
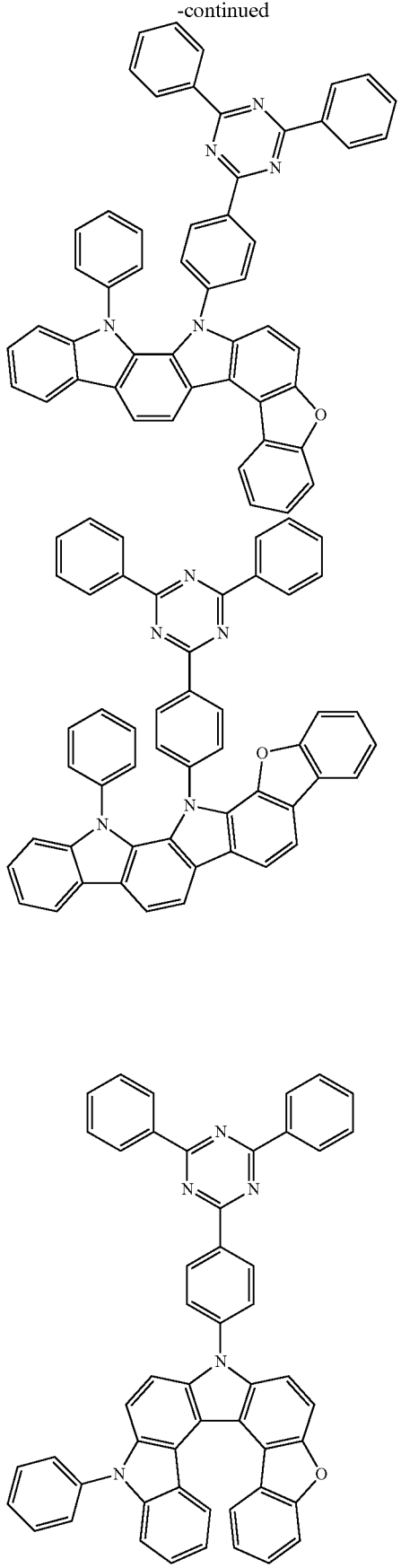
200
-continued
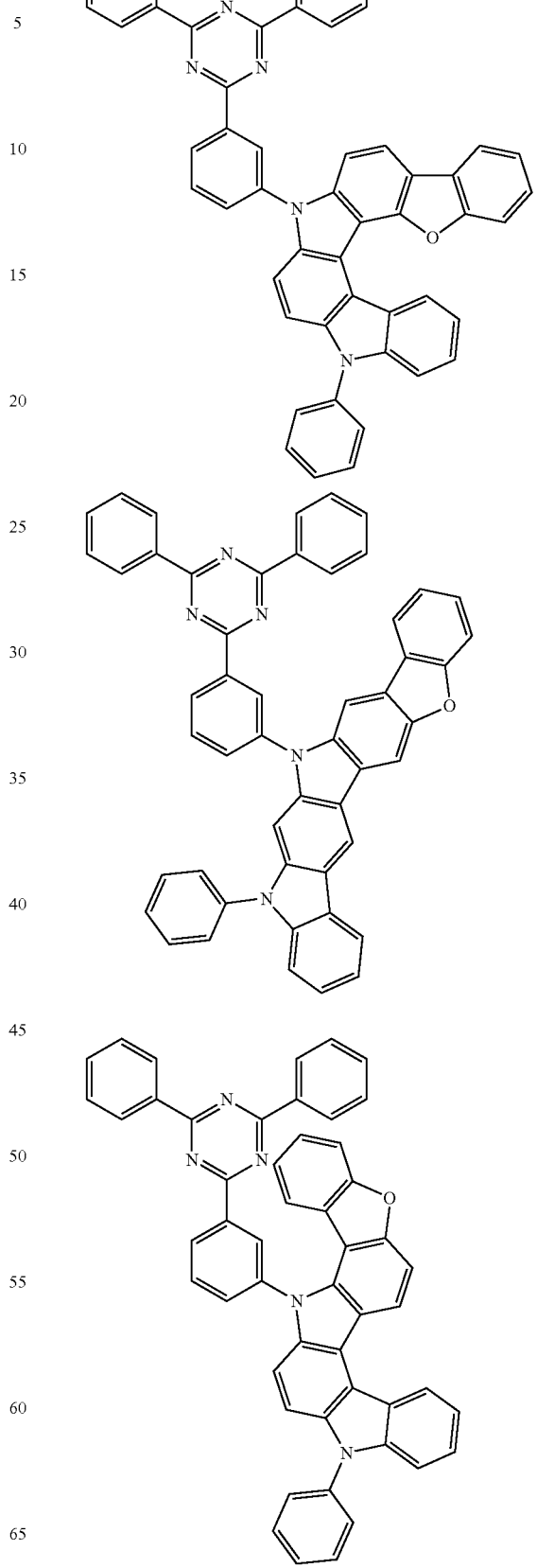

201
-continued
202
-continued
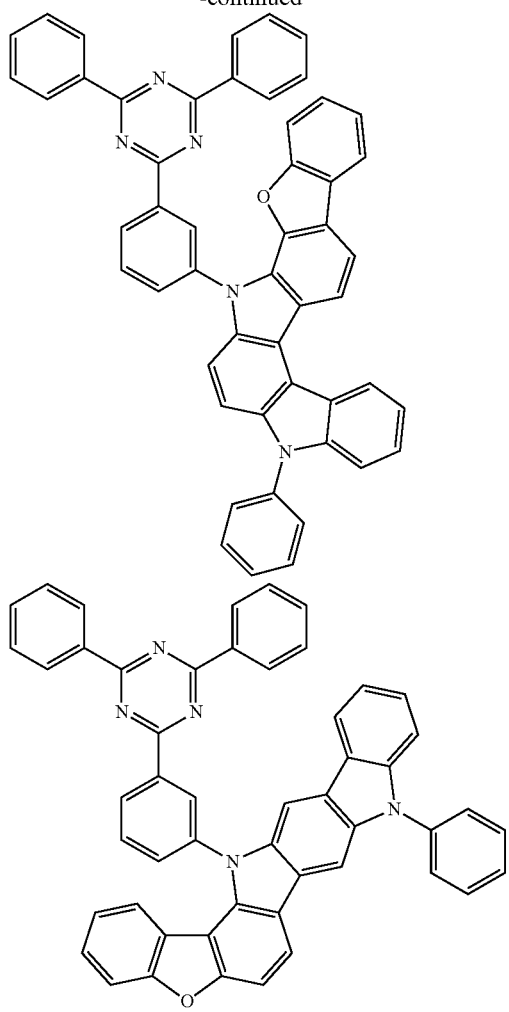
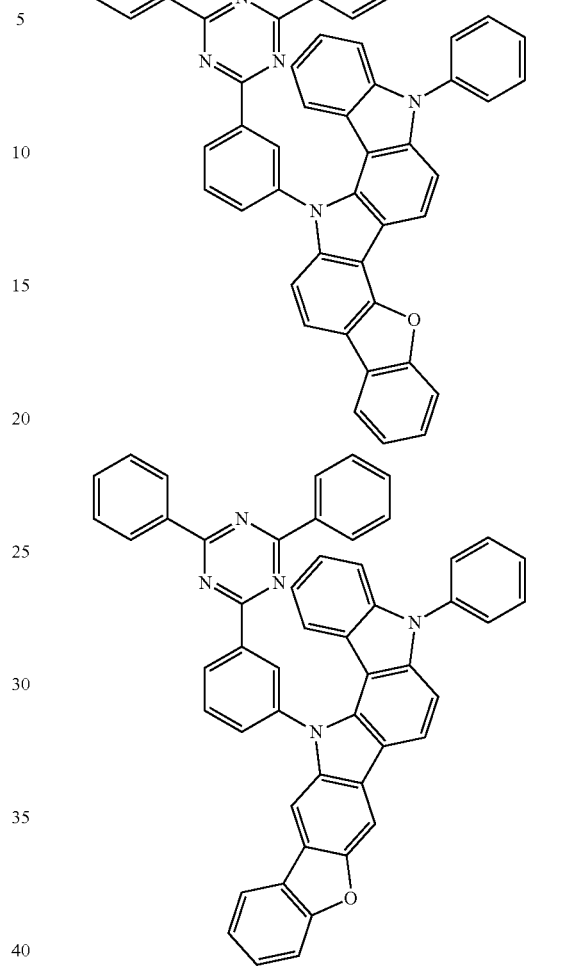
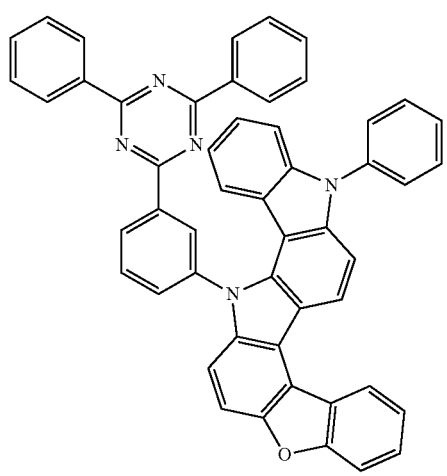
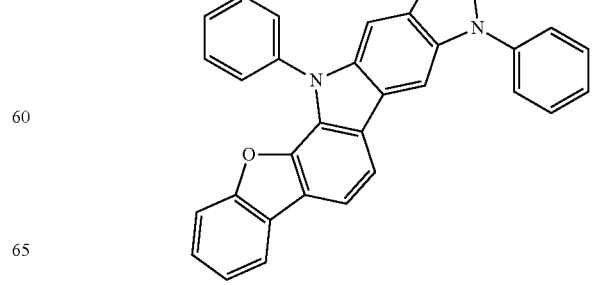

203
-continued
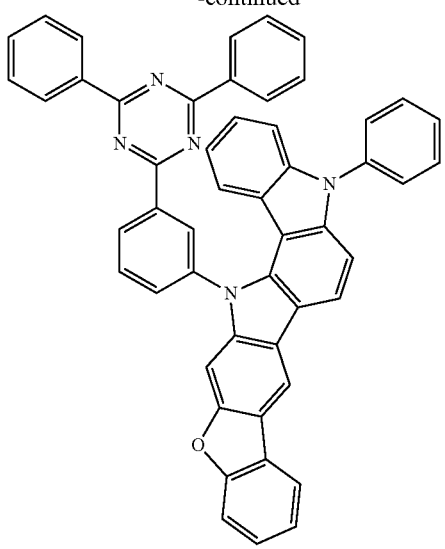
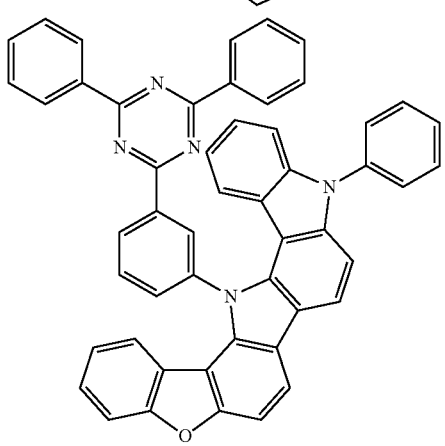
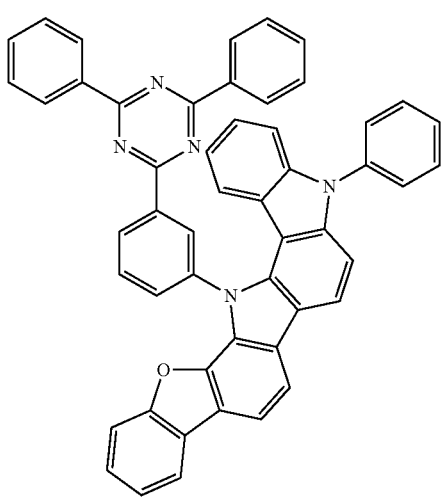
204
-continued
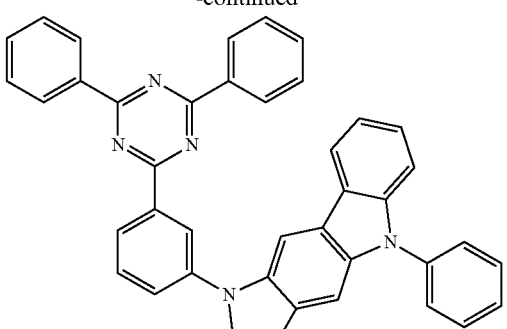
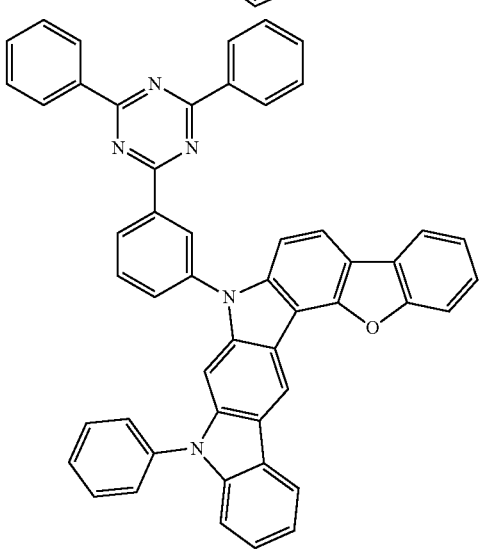

205
-continued
206
-continued
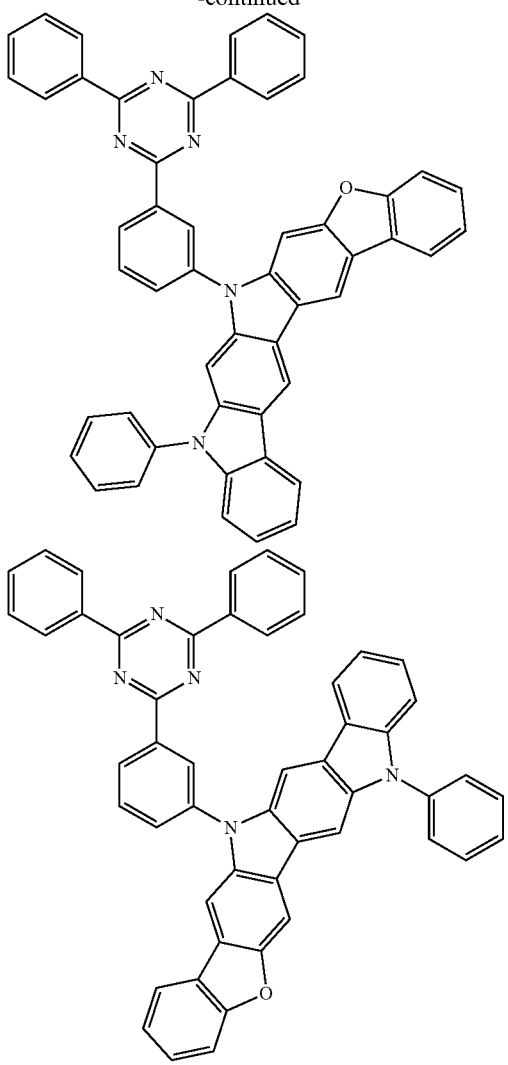
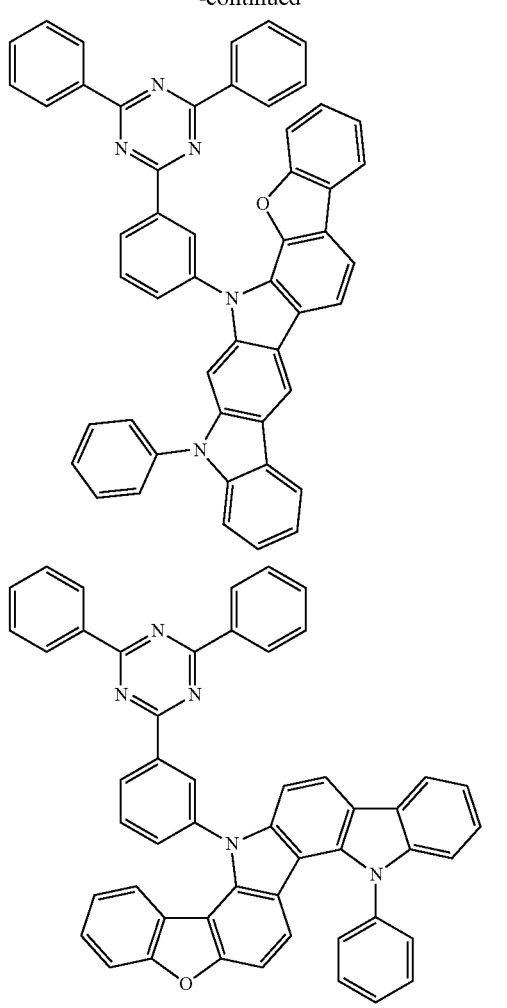
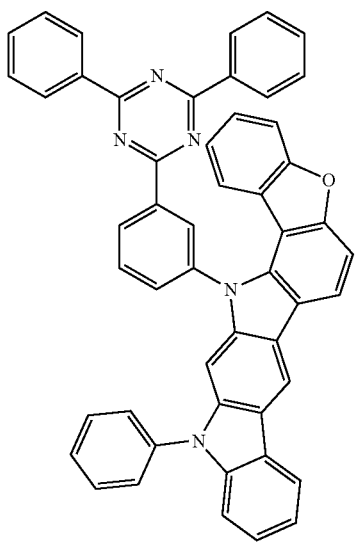

207
-continued
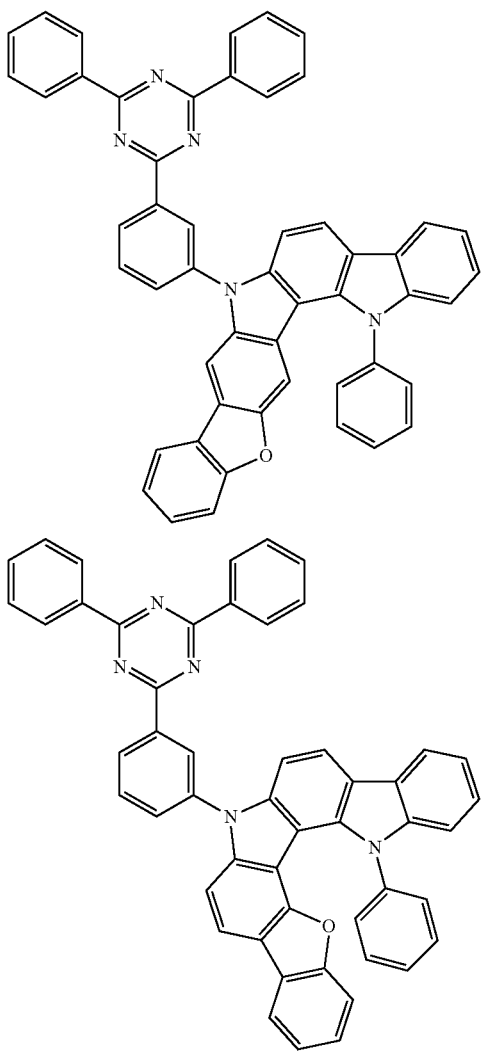
208
-continued
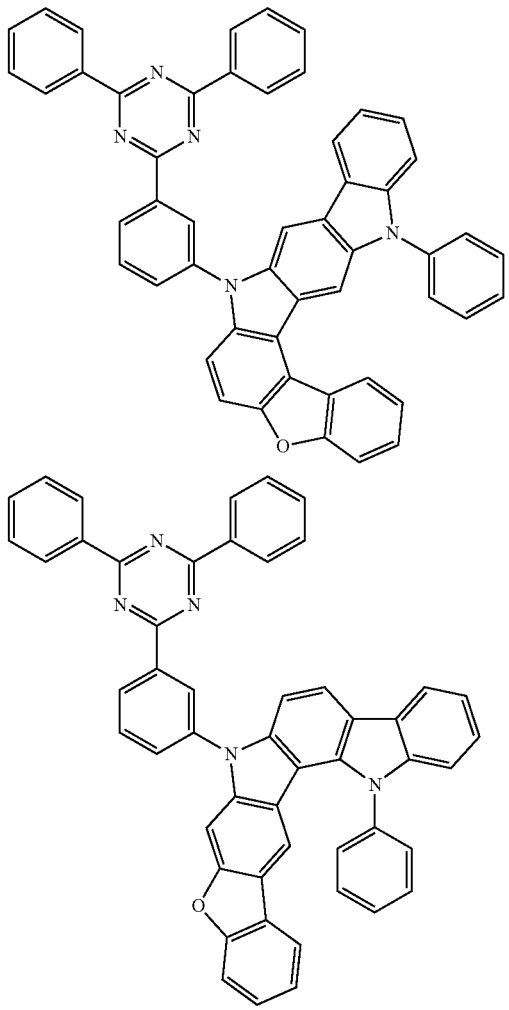
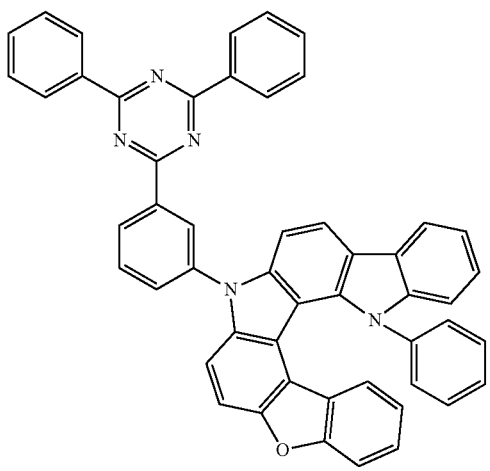
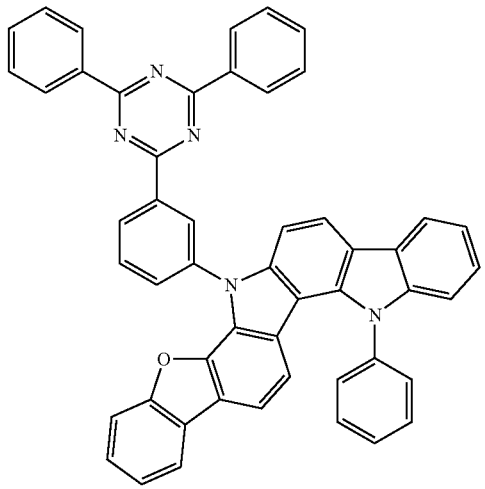

209
-continued
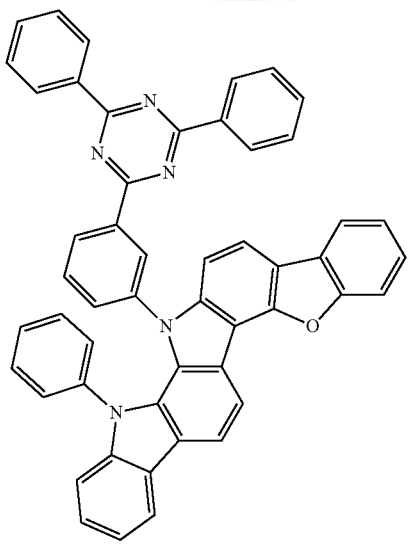
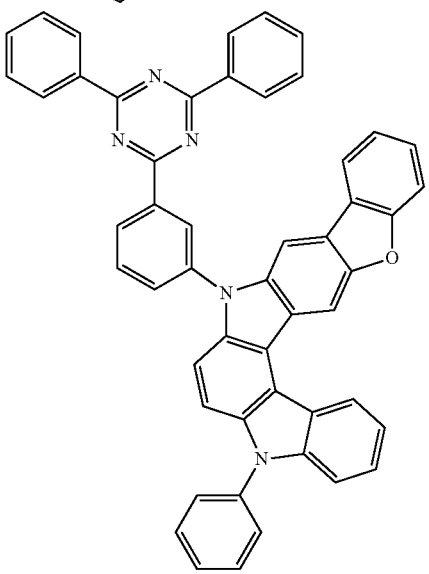
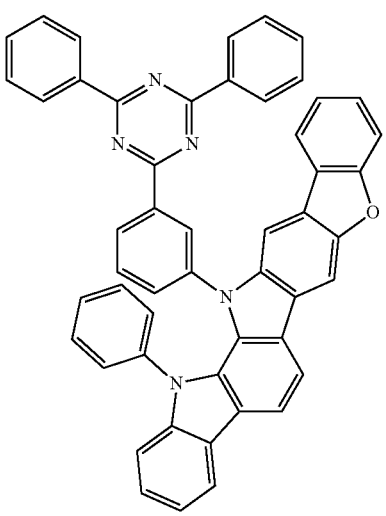
210
-continued
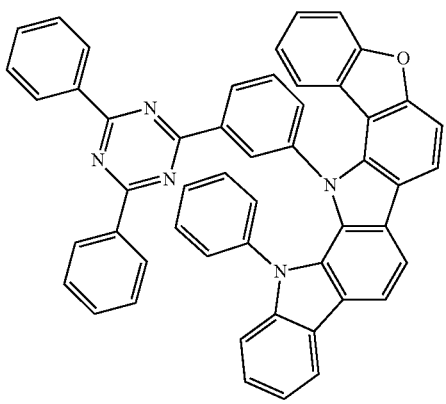
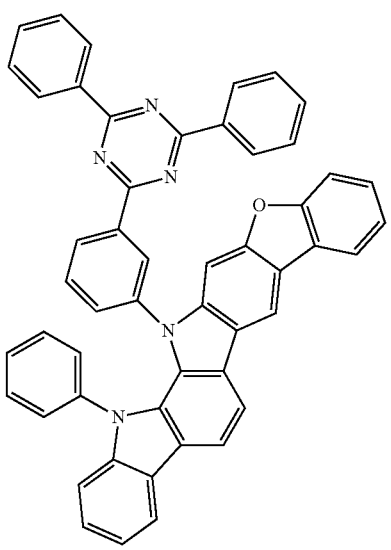
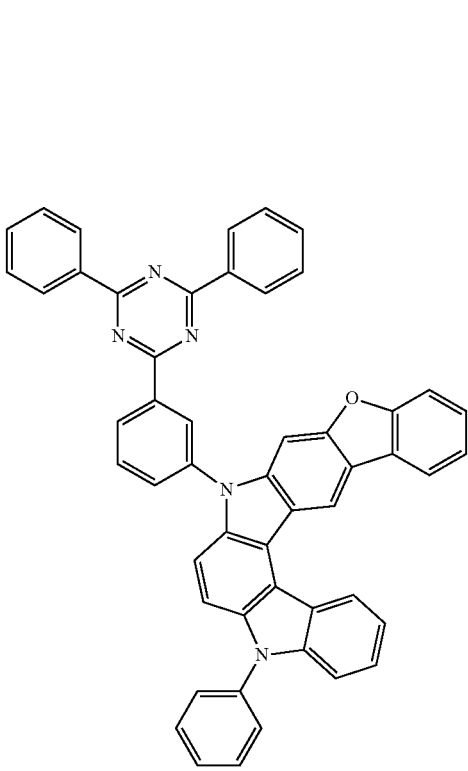

211
-continued
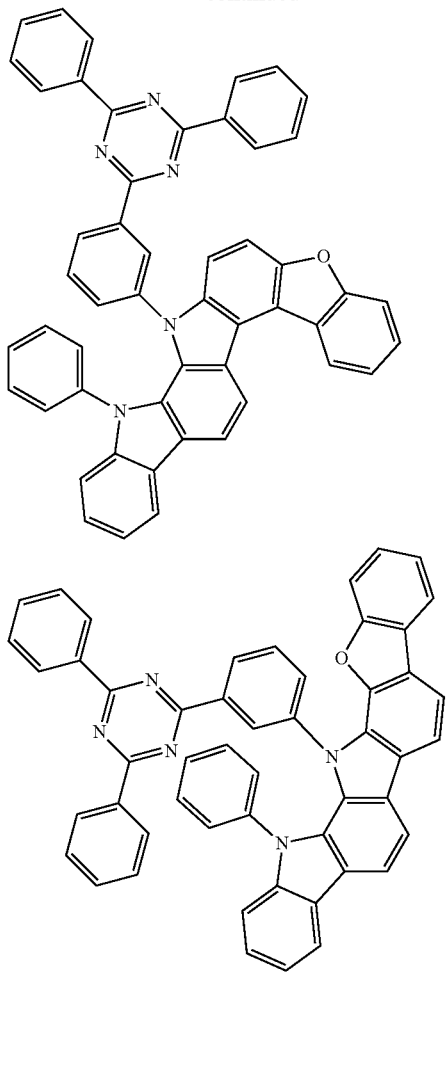
212
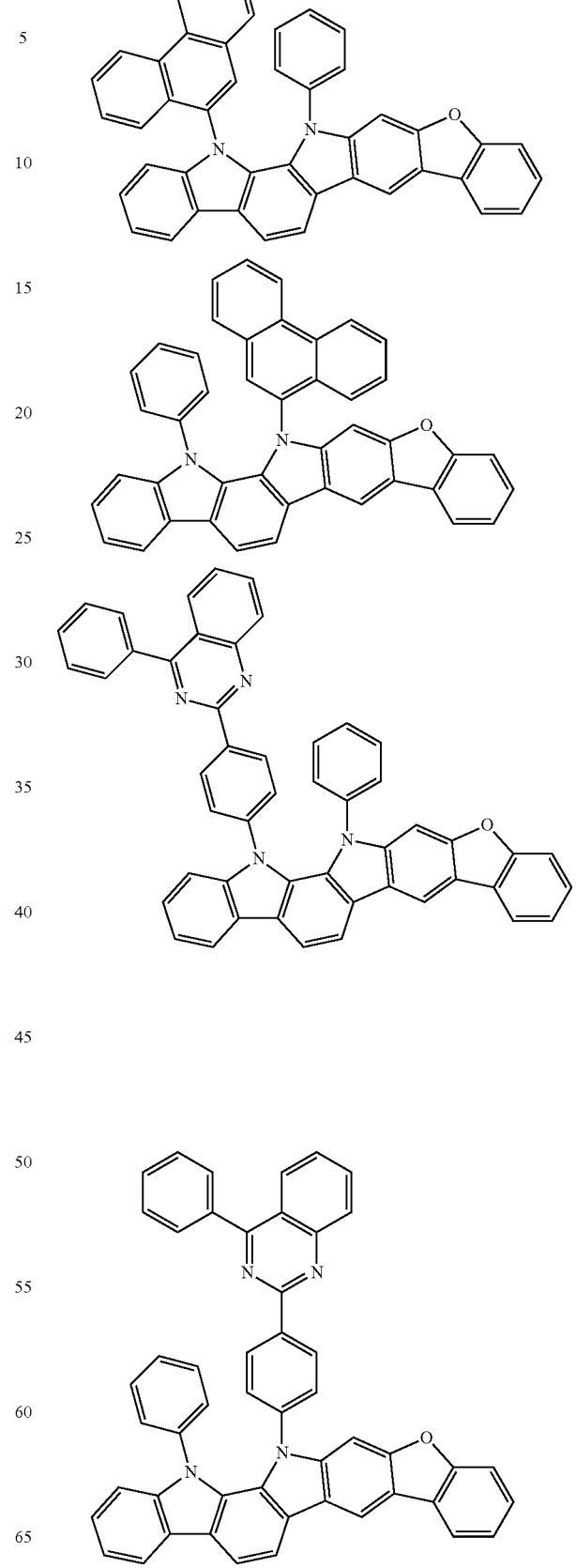

213
-continued
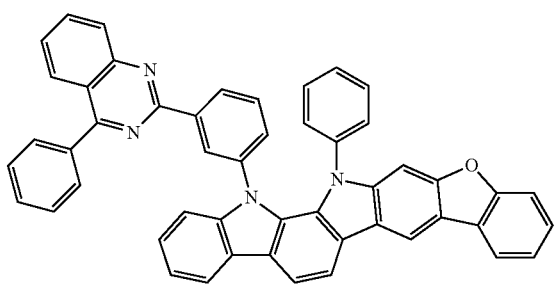
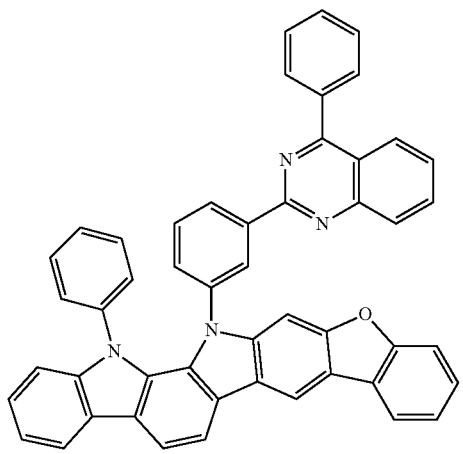
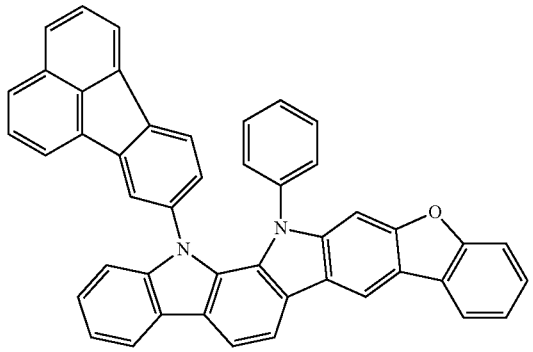
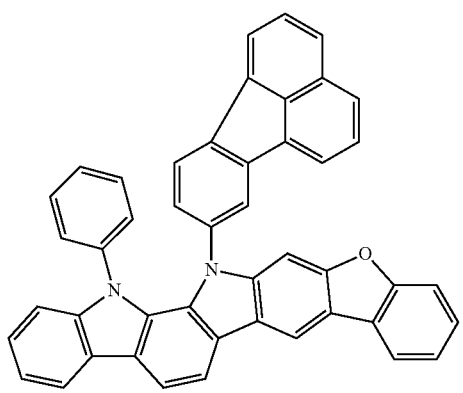
214
-continued
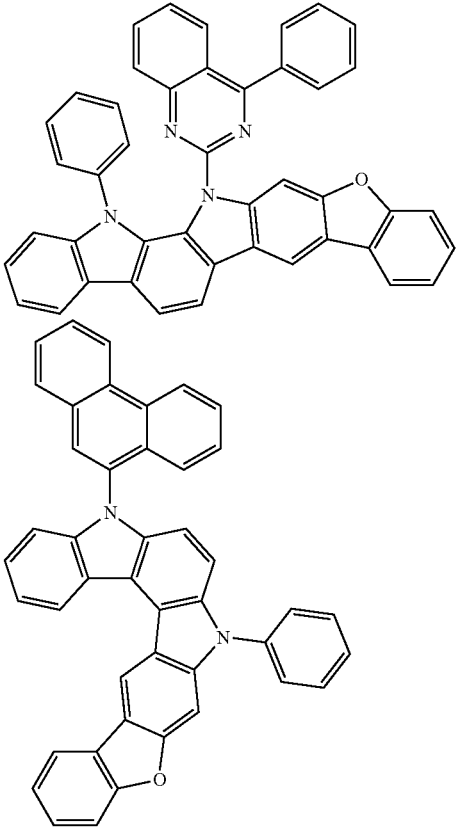
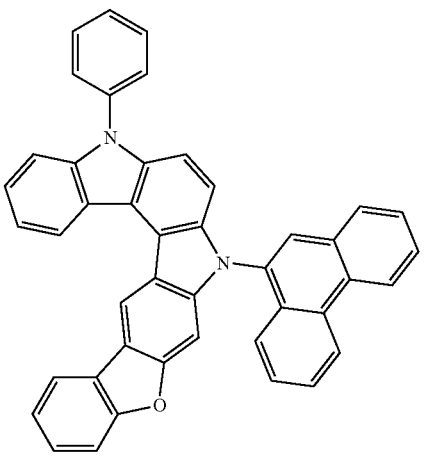

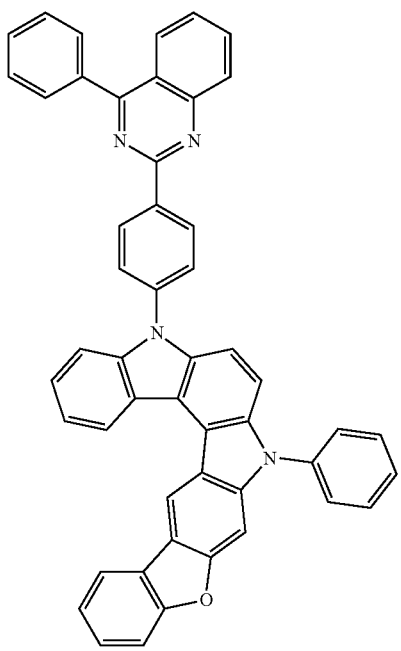
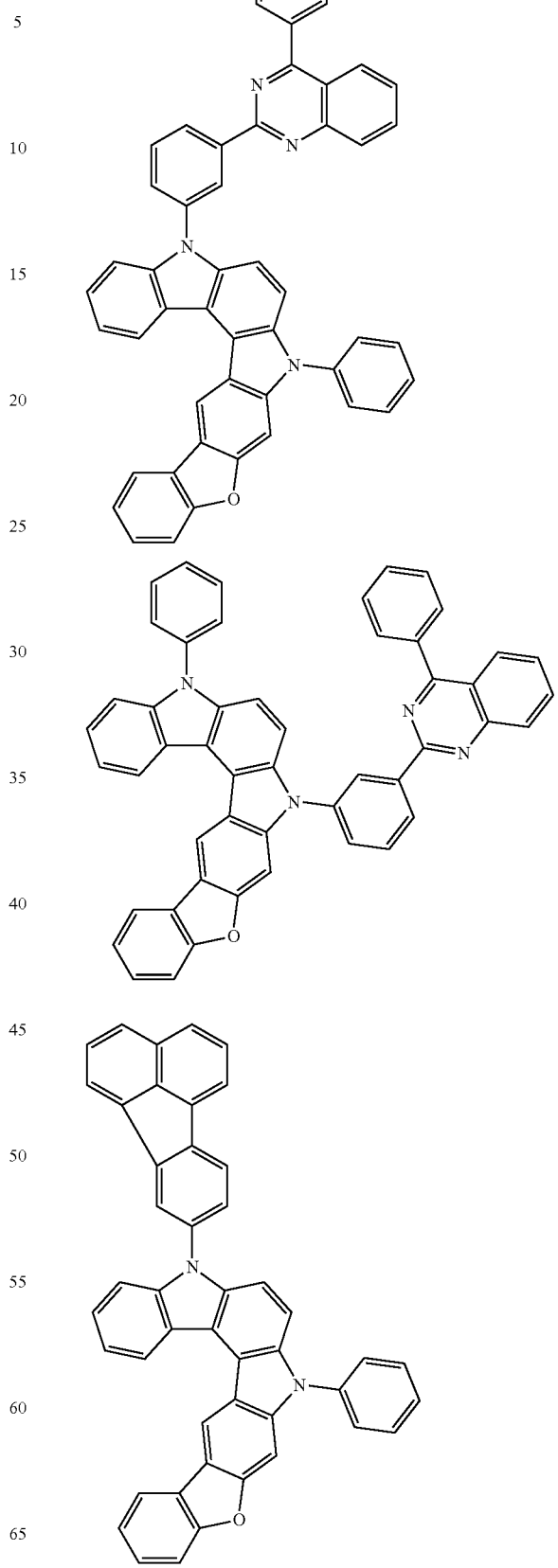
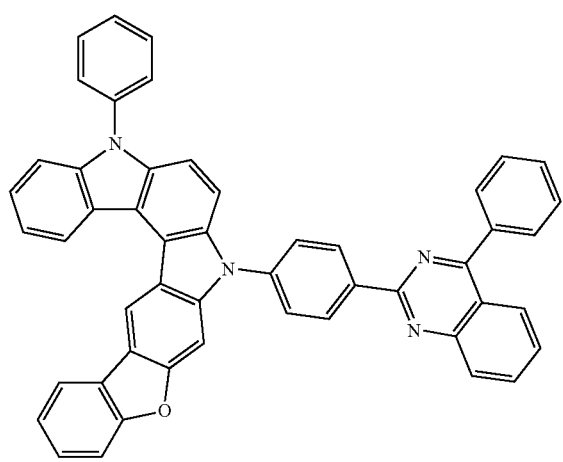

217
-continued
218
-continued
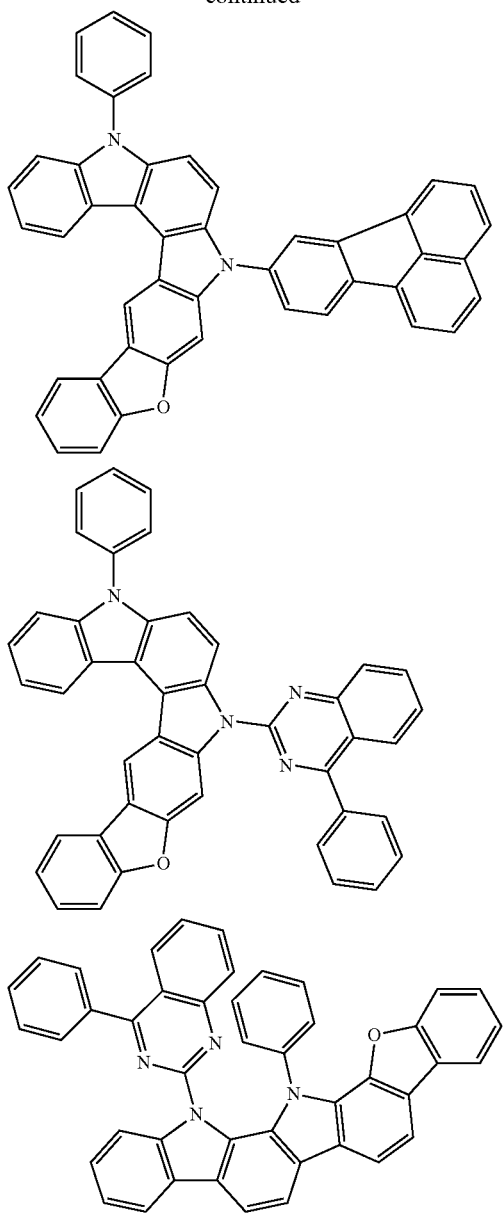
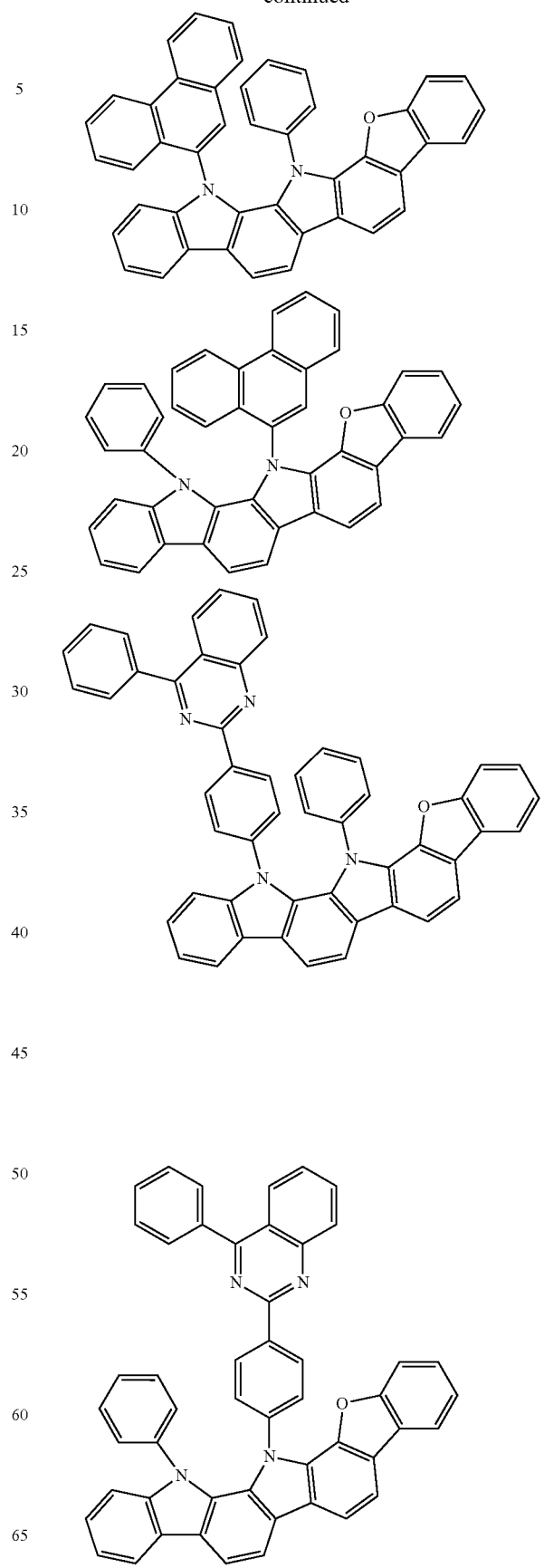

219
-continued
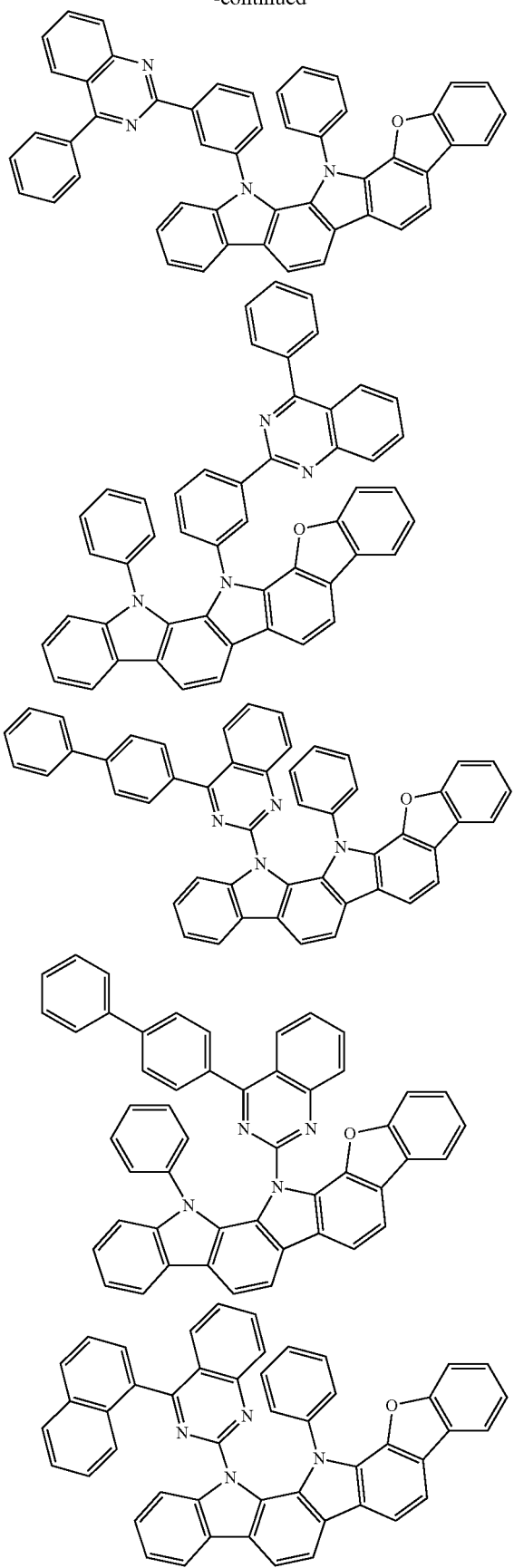
220
-continued
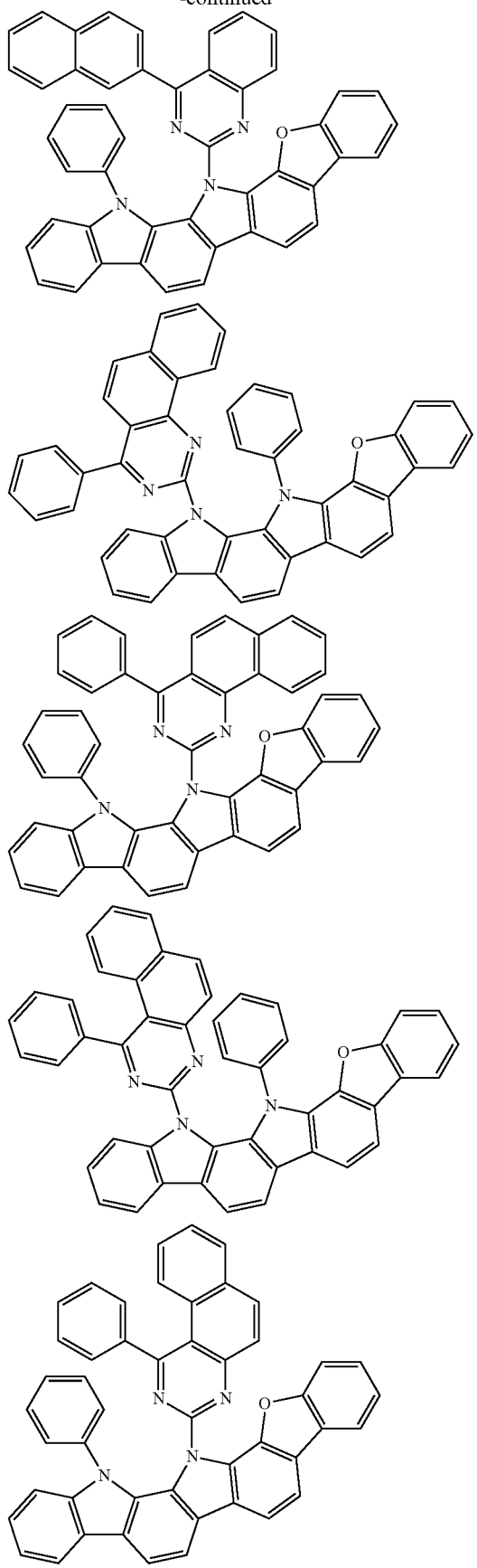

221
-continued
222
-continued
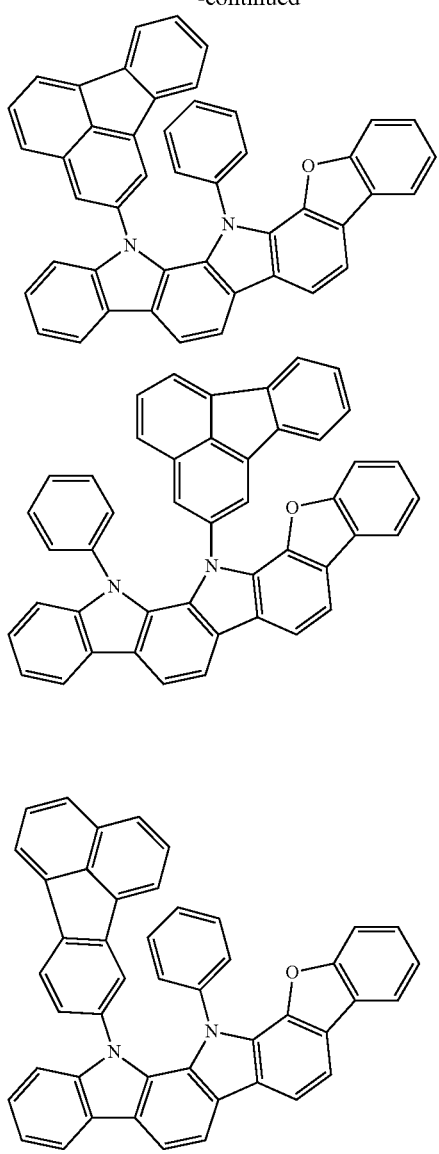
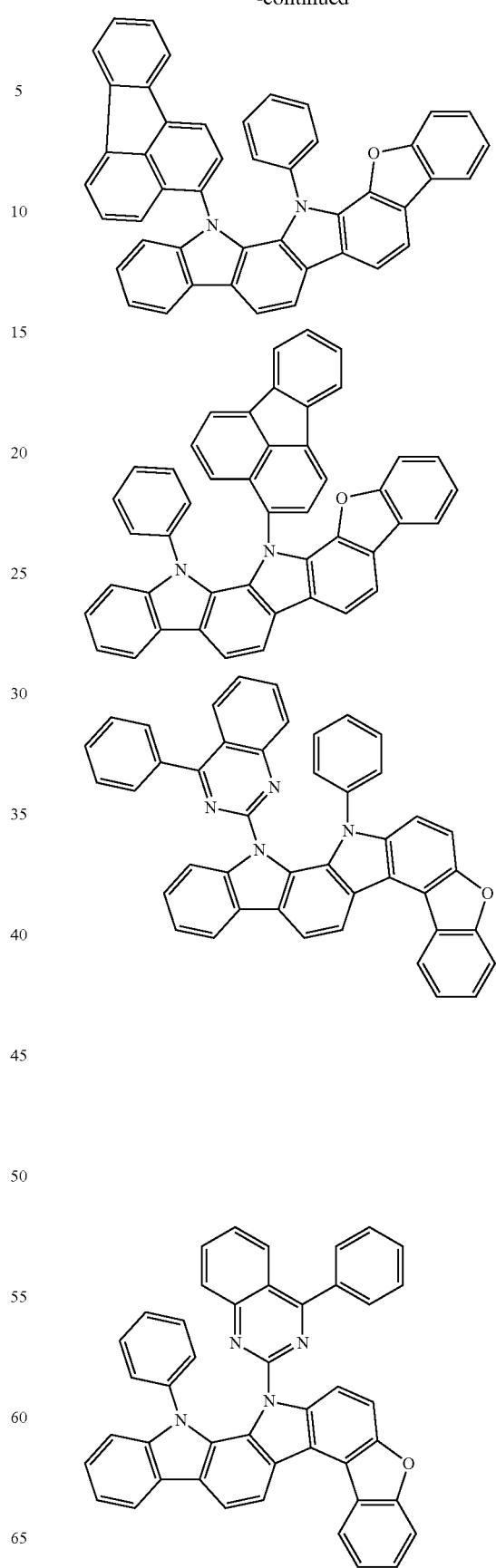

223
-continued
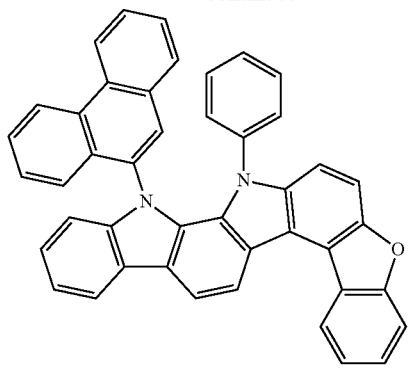
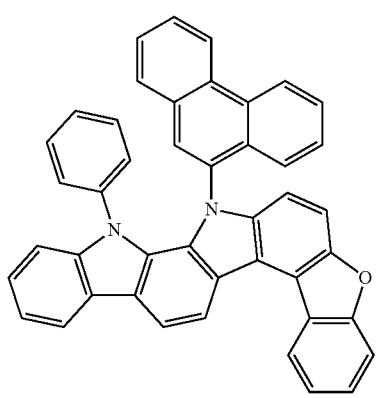
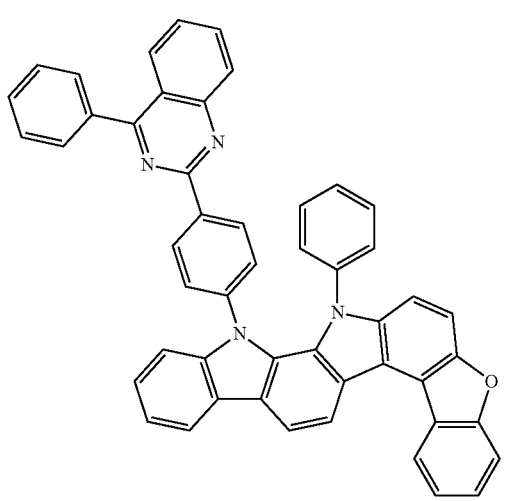
224
-continued
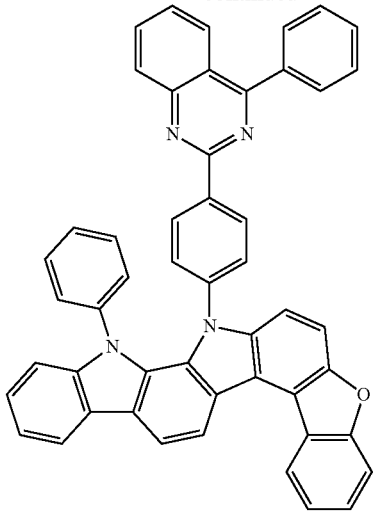
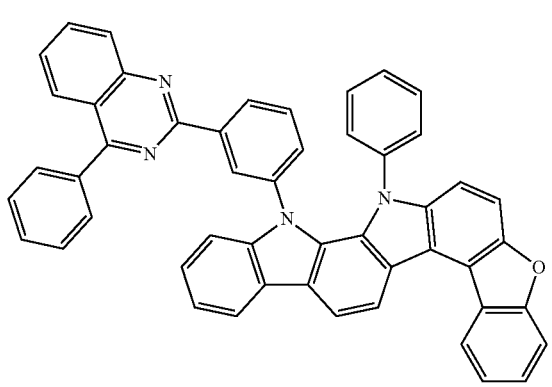
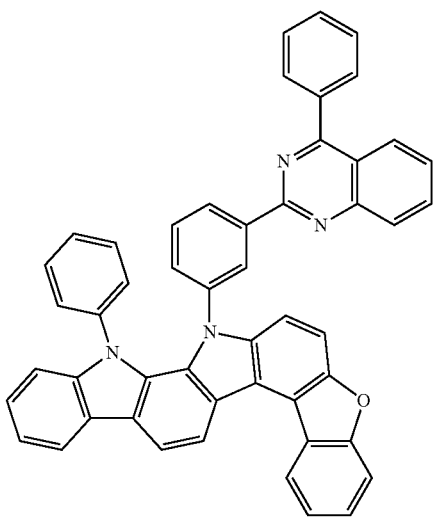

225
-continued
226
-continued
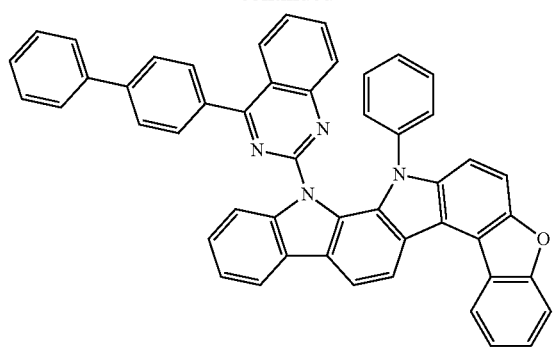
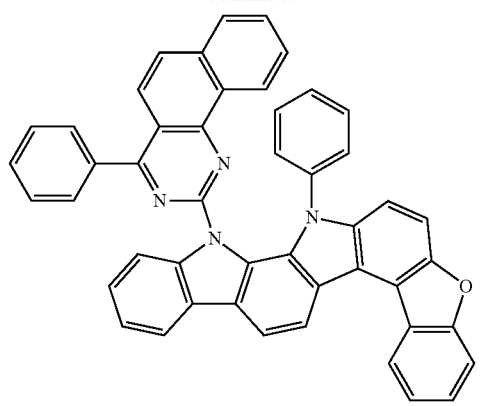
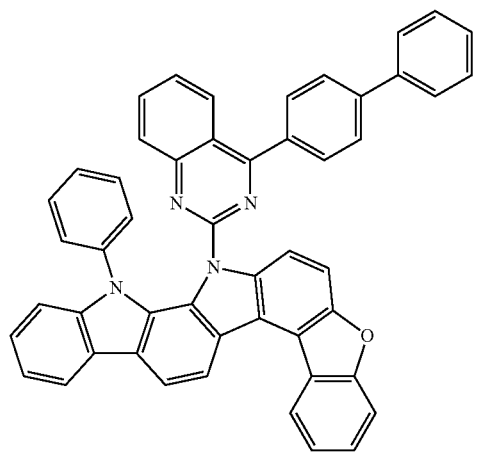
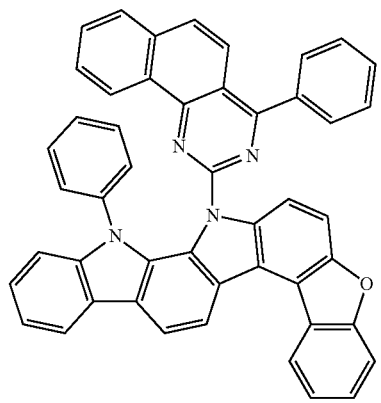
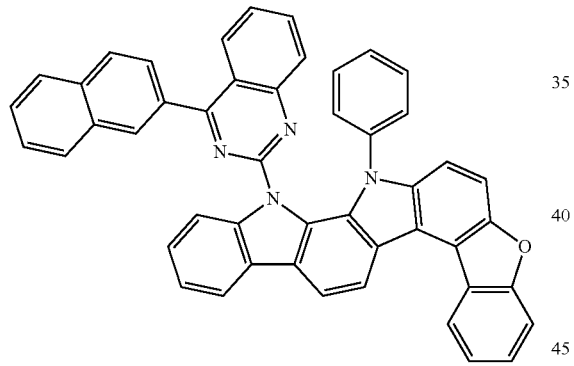
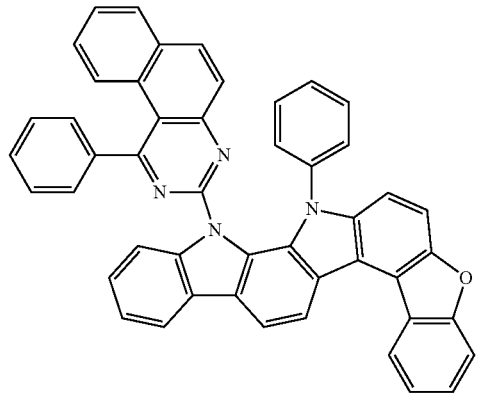
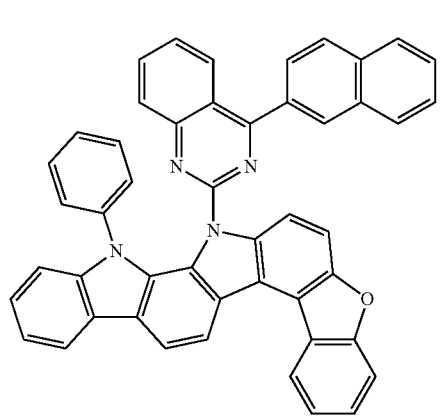
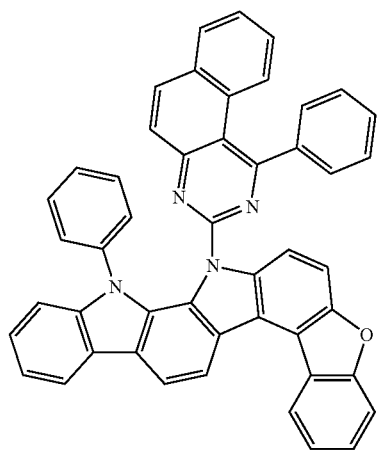

227
-continued
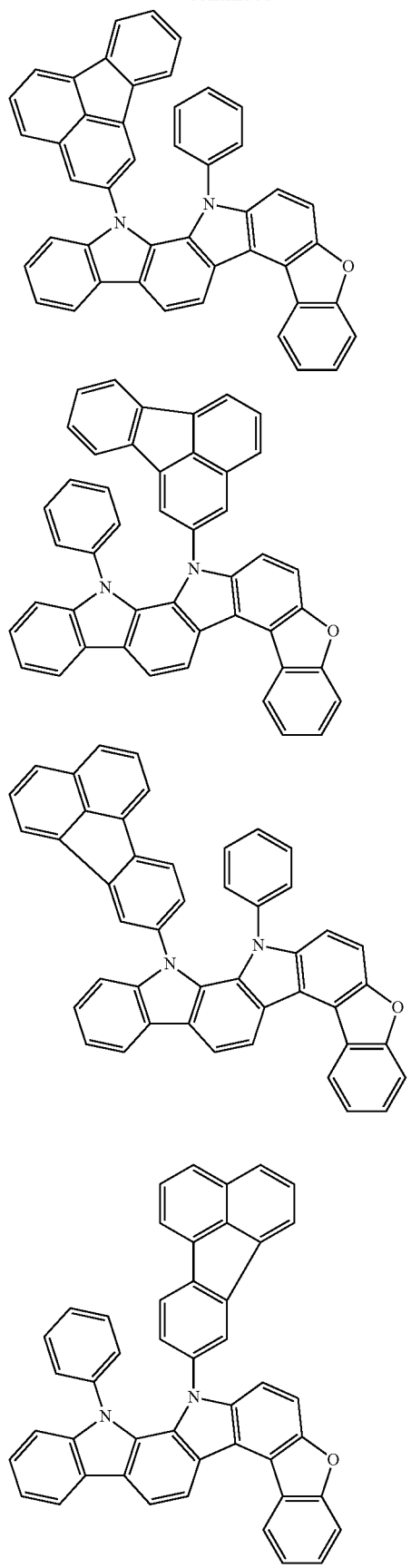
228
-continued
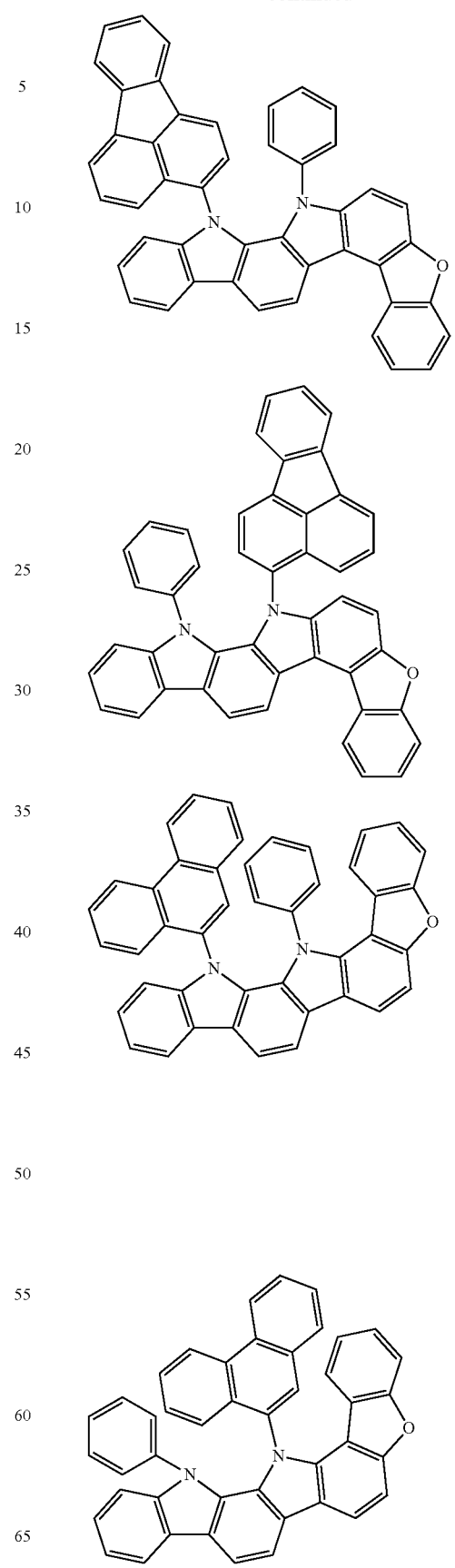

229
-continued
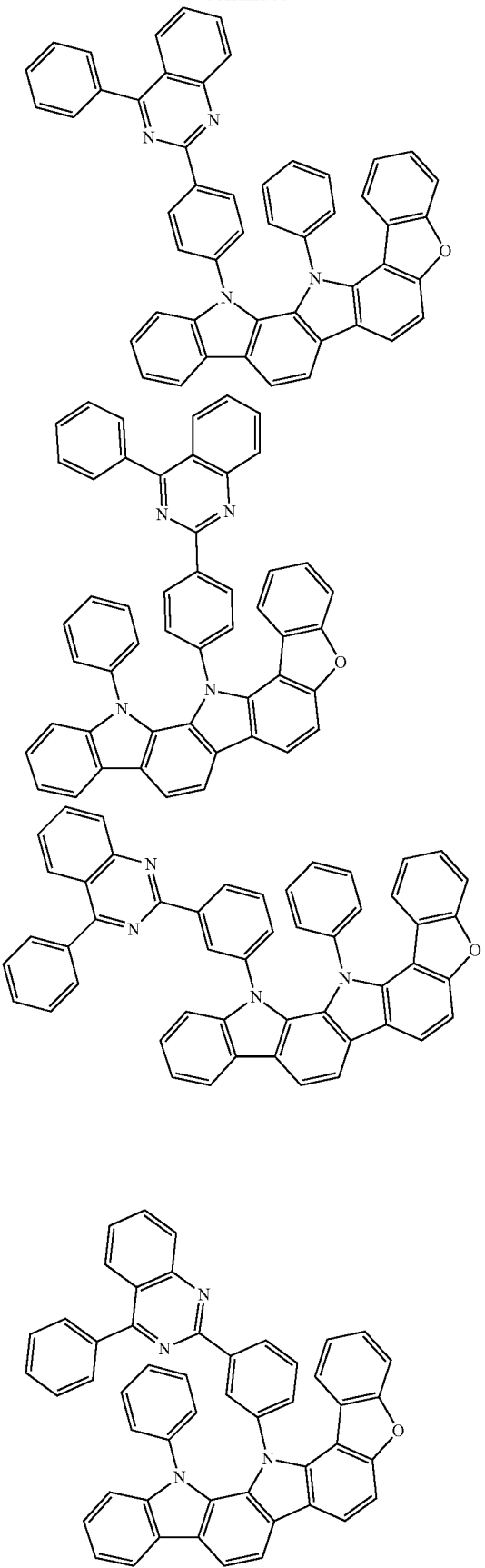
230
-continued
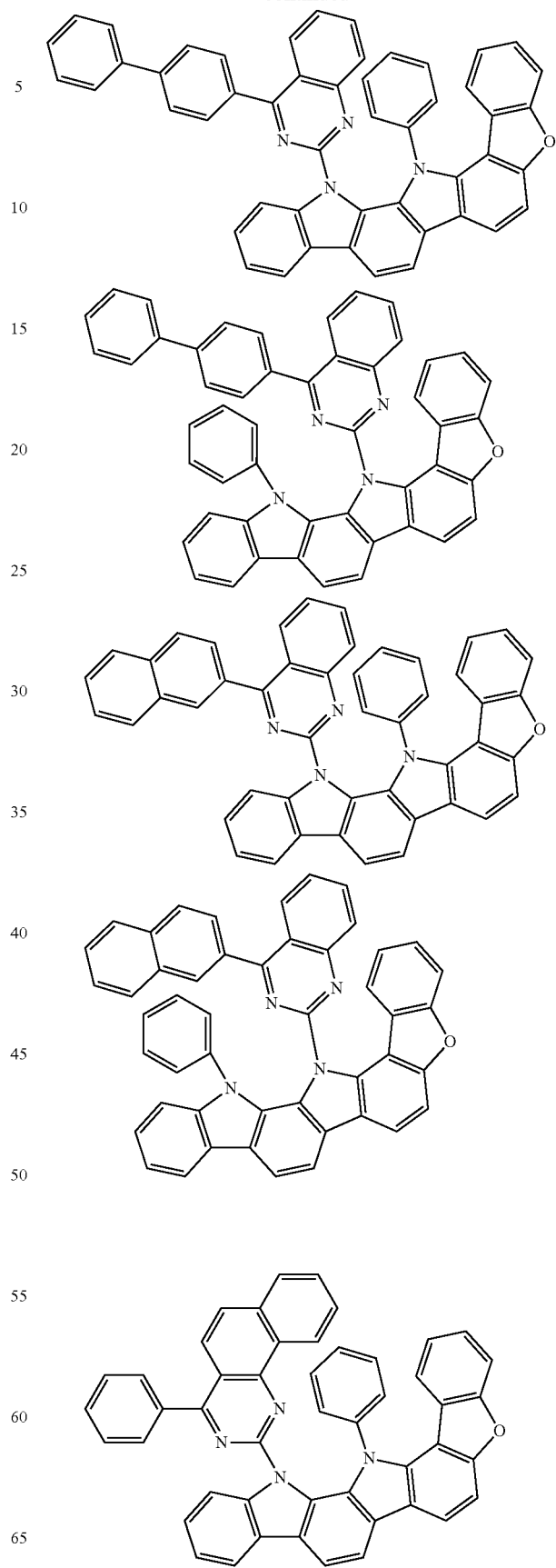

231
-continued
232
-continued
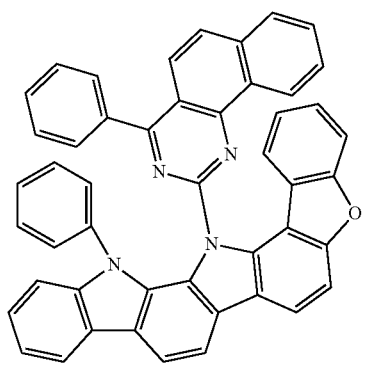
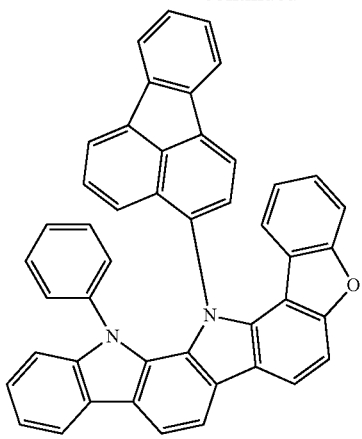
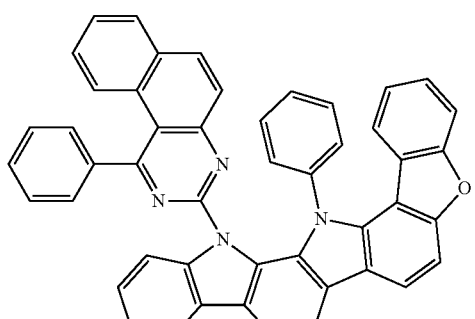
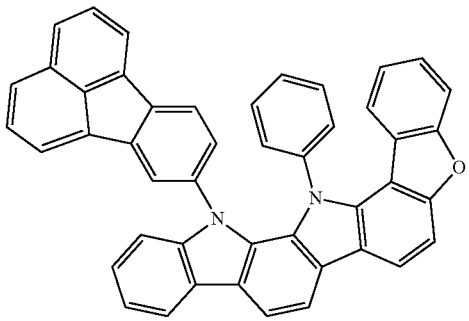
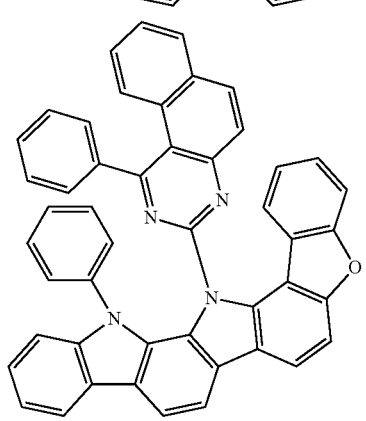
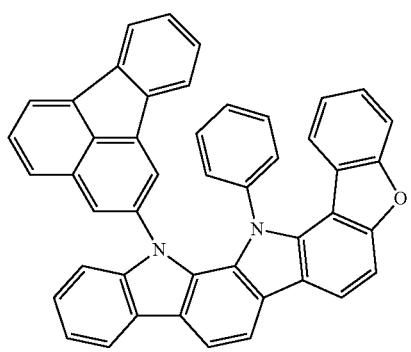

233
-continued
234
-continued
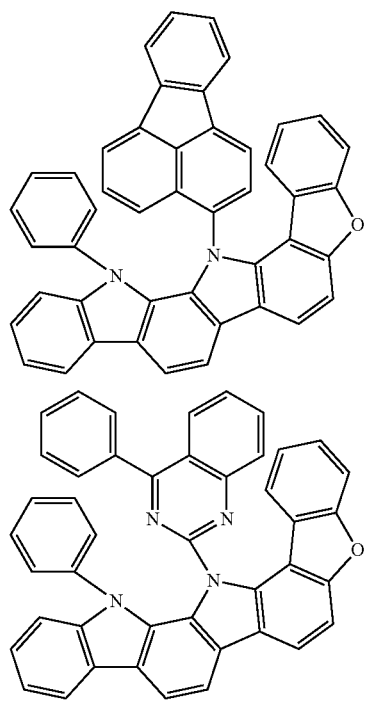
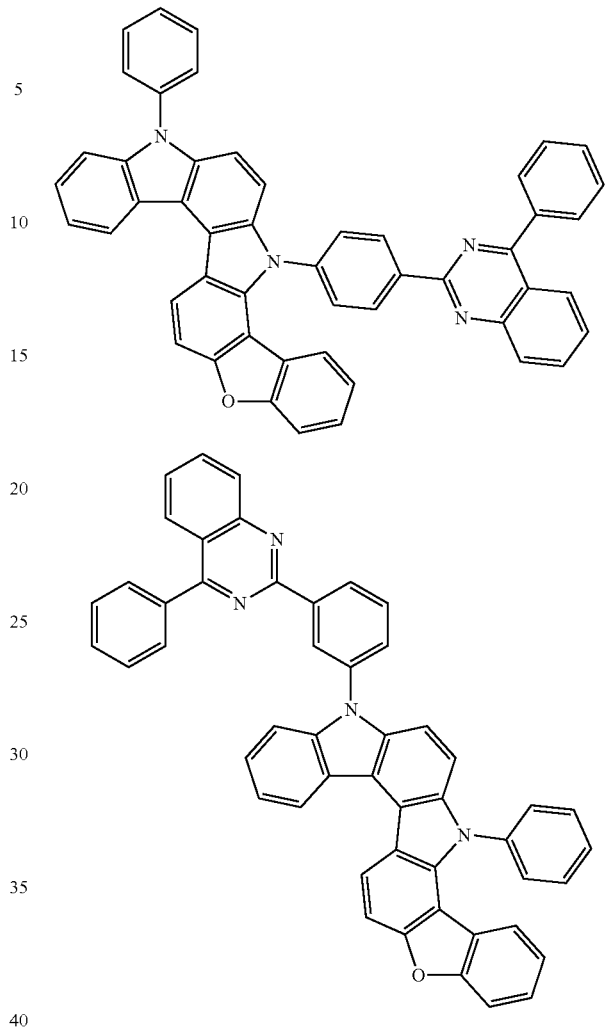
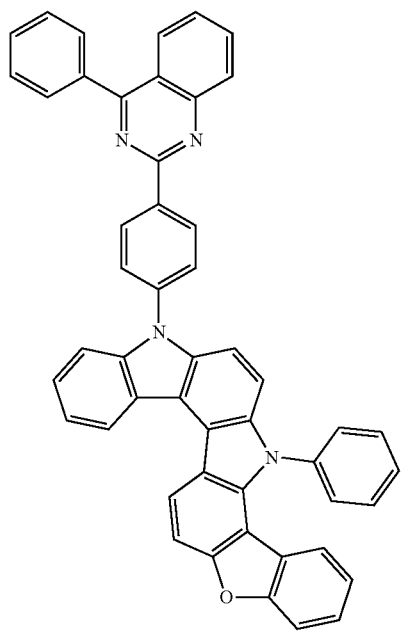

235
-continued
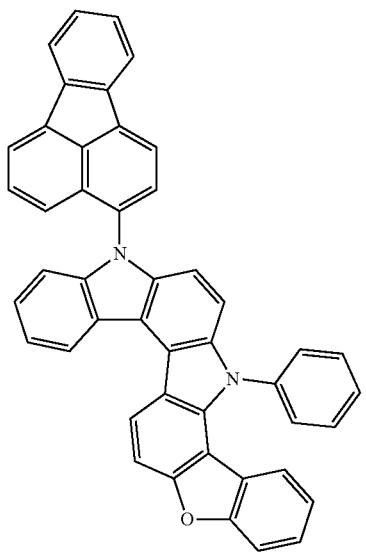
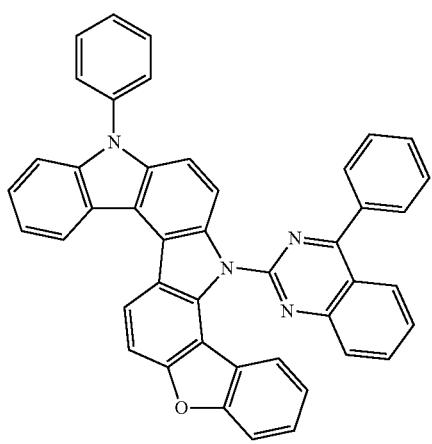
236
-continued
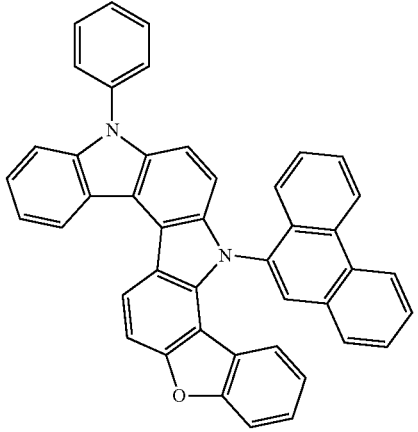
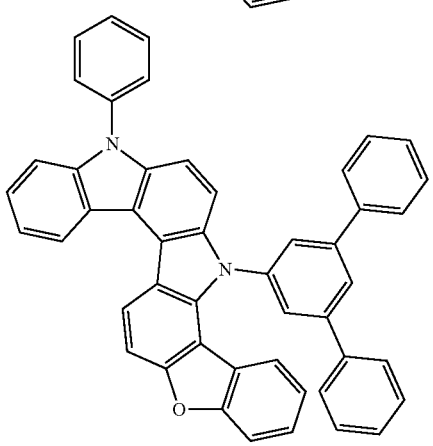
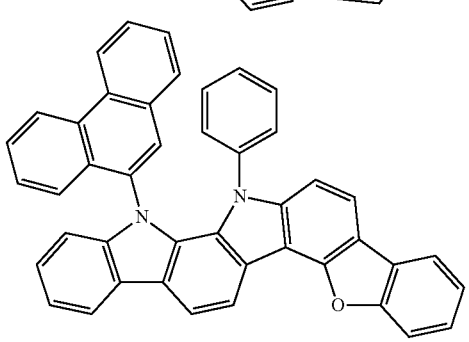
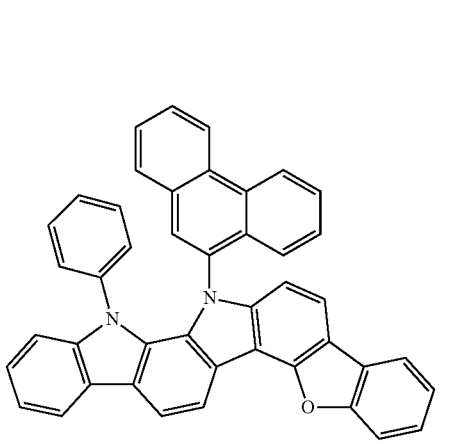

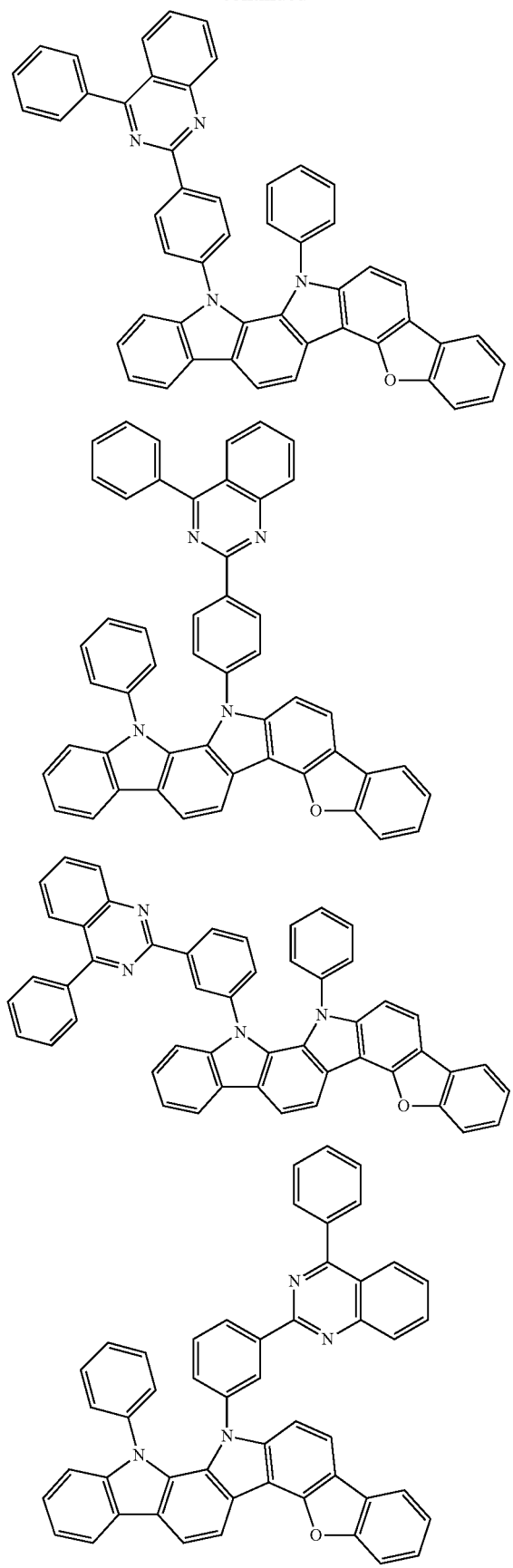
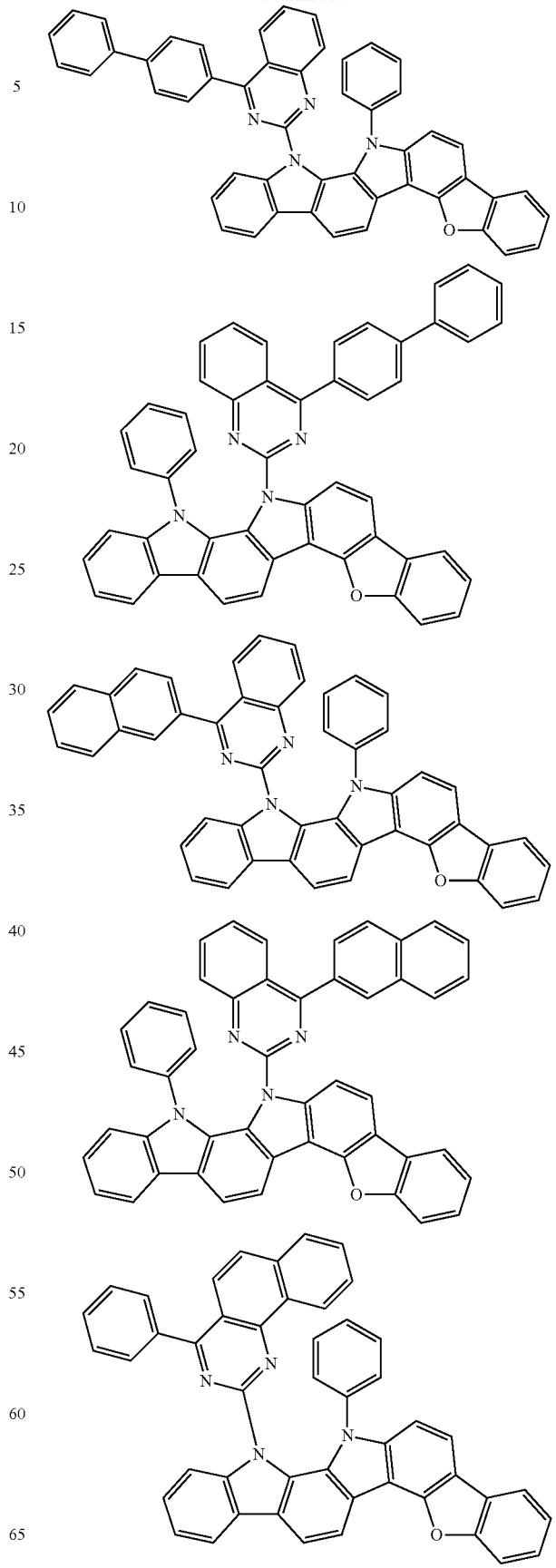

239
-continued
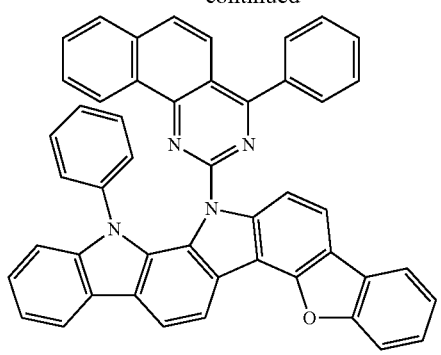
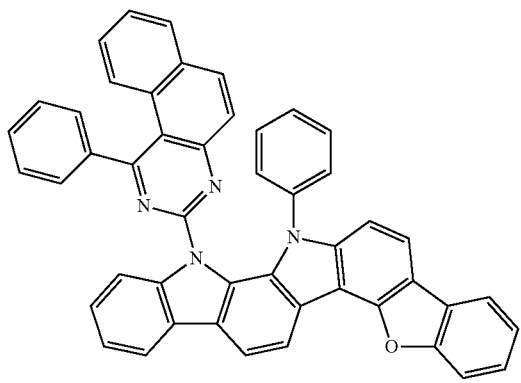
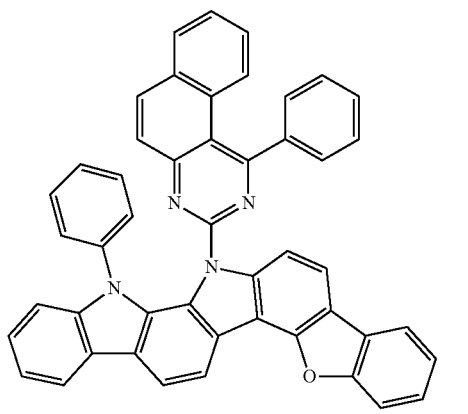
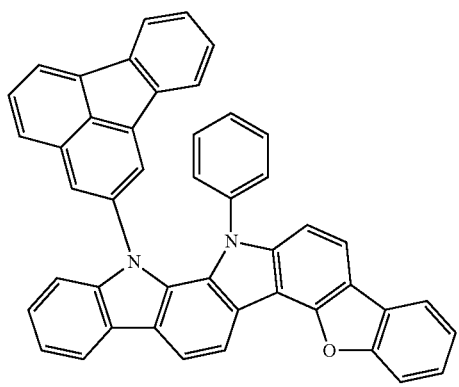
240
-continued
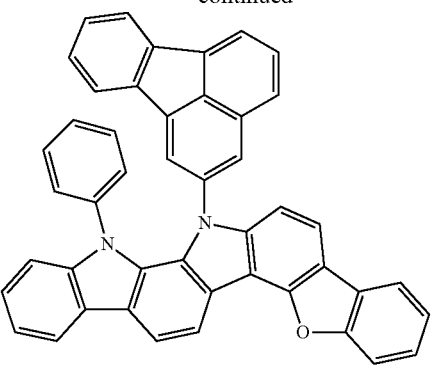
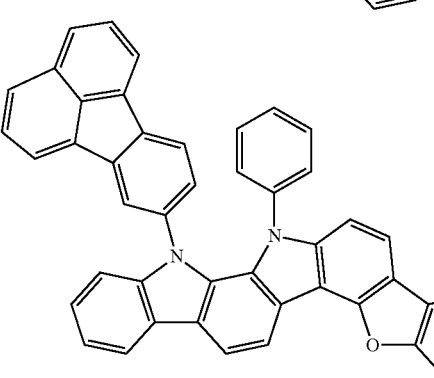
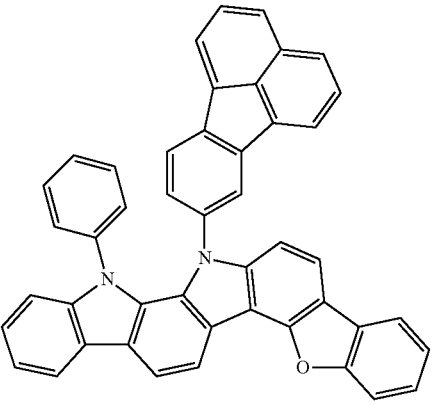
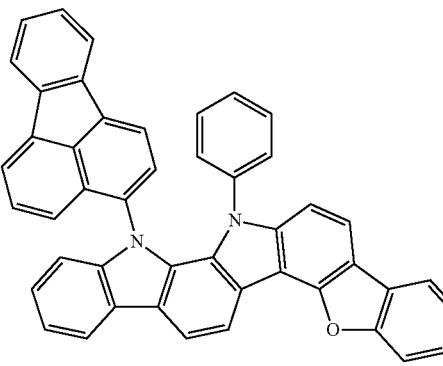

241
-continued
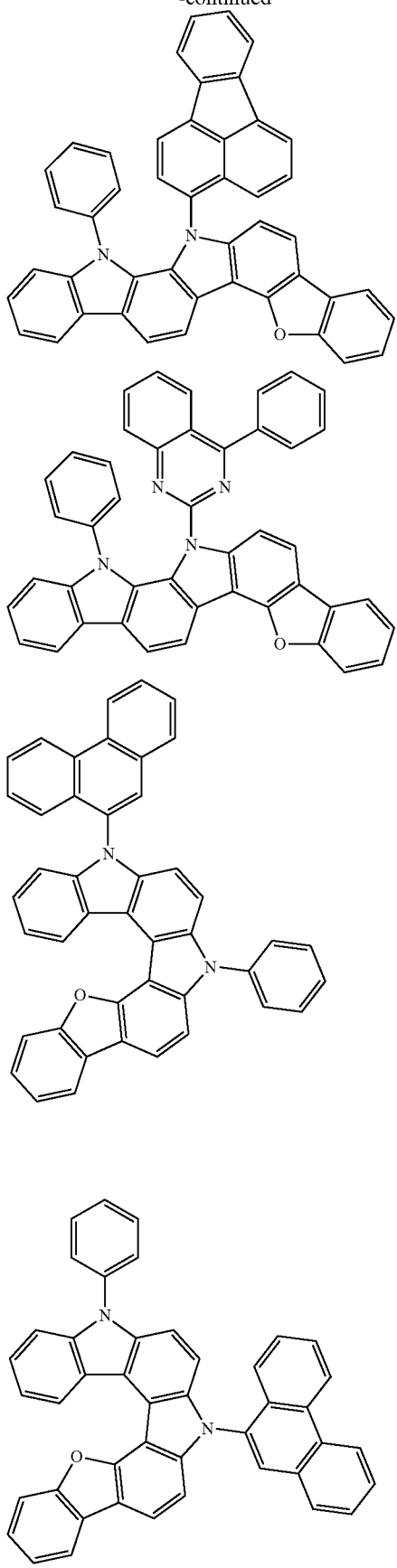
242
-continued
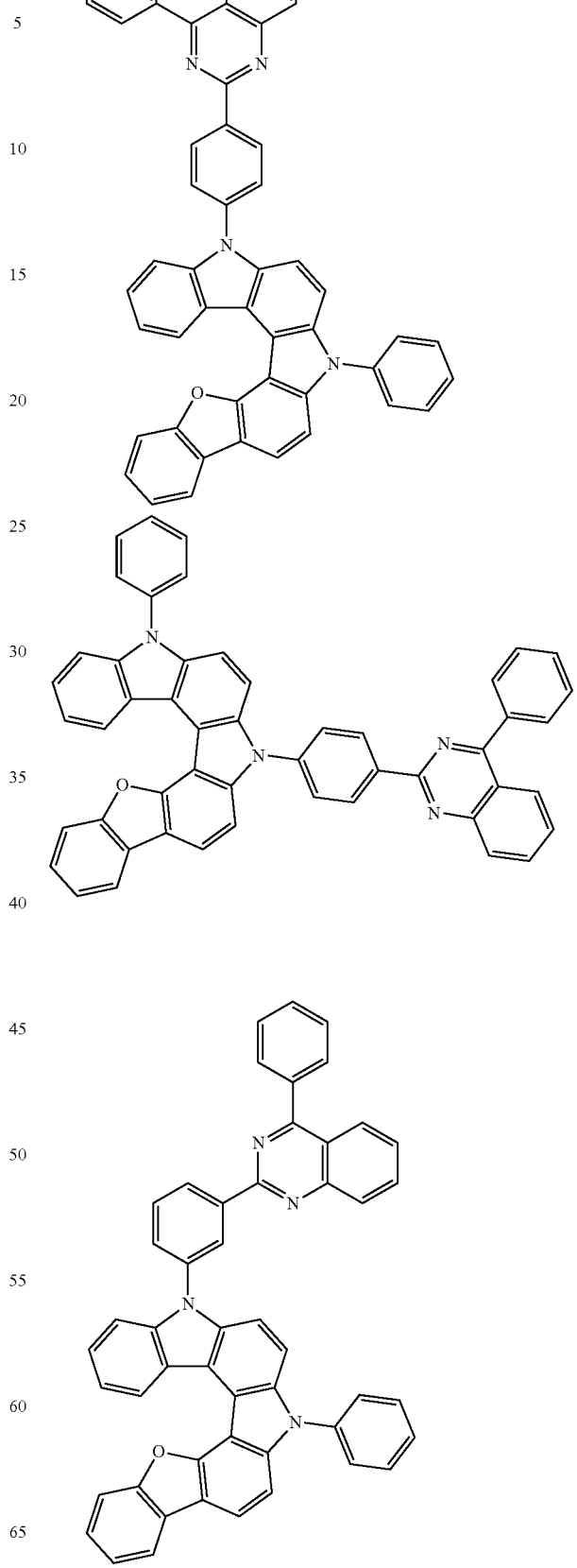

243
-continued
244
-continued
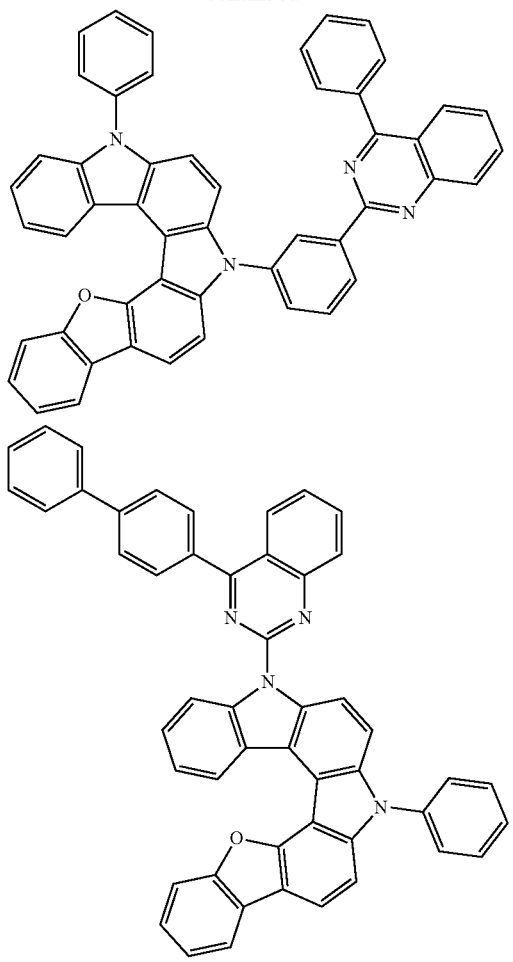
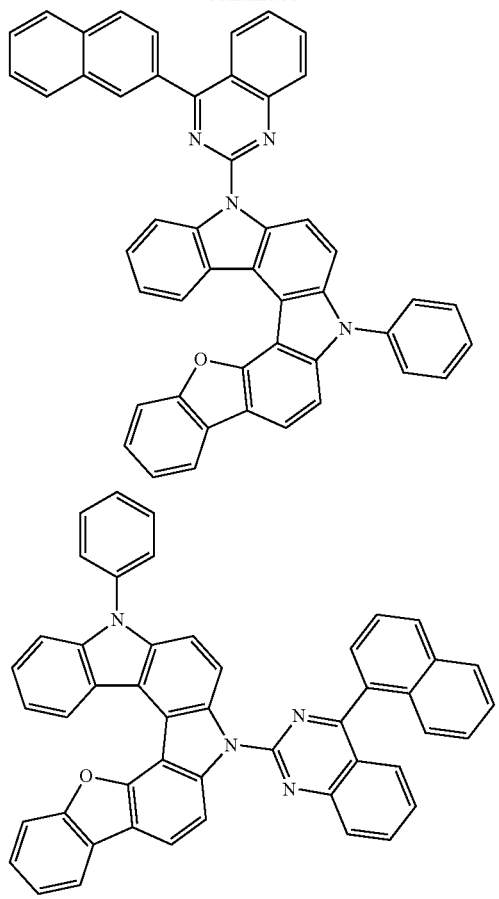
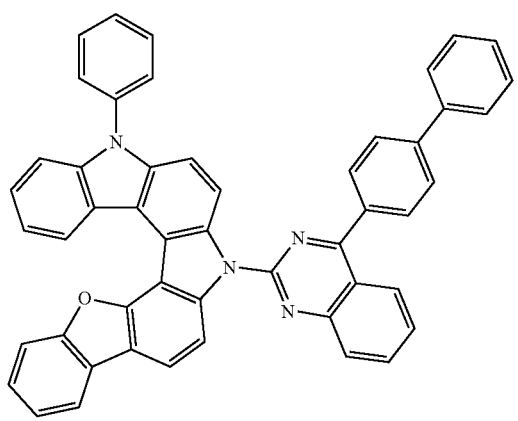
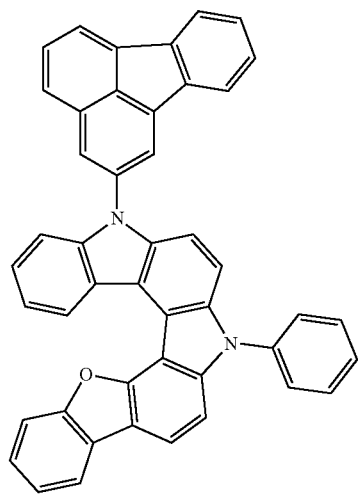

245
-continued
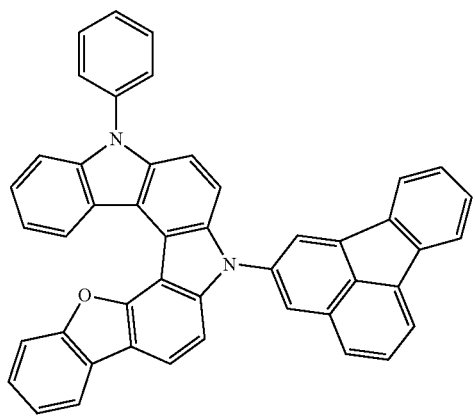
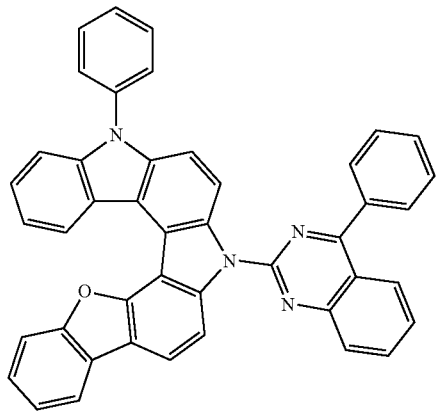
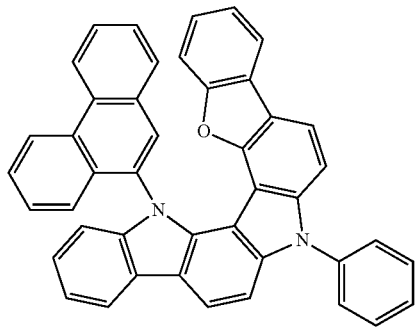
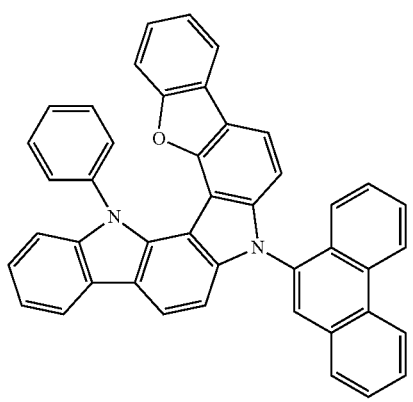
246
-continued
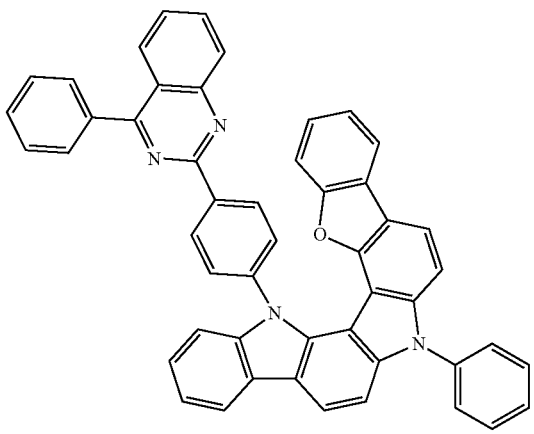
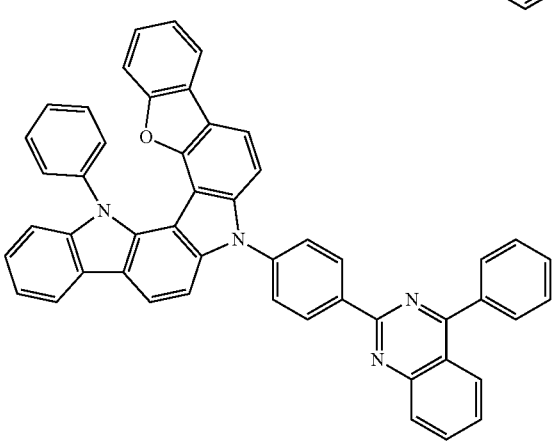
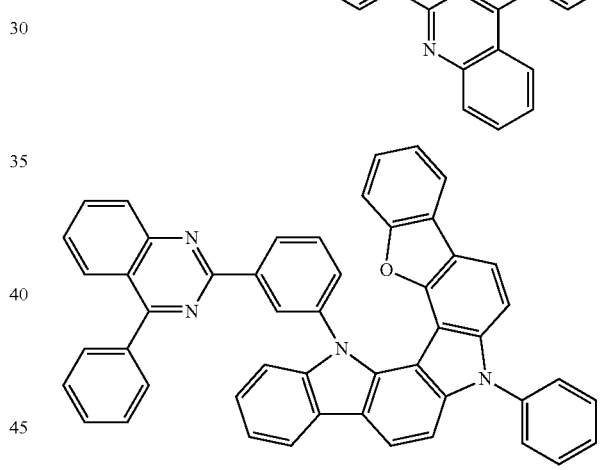
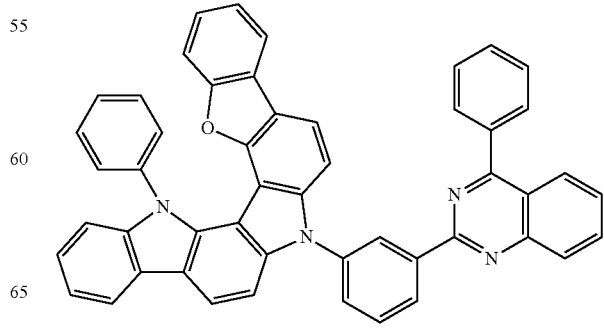

247
-continued
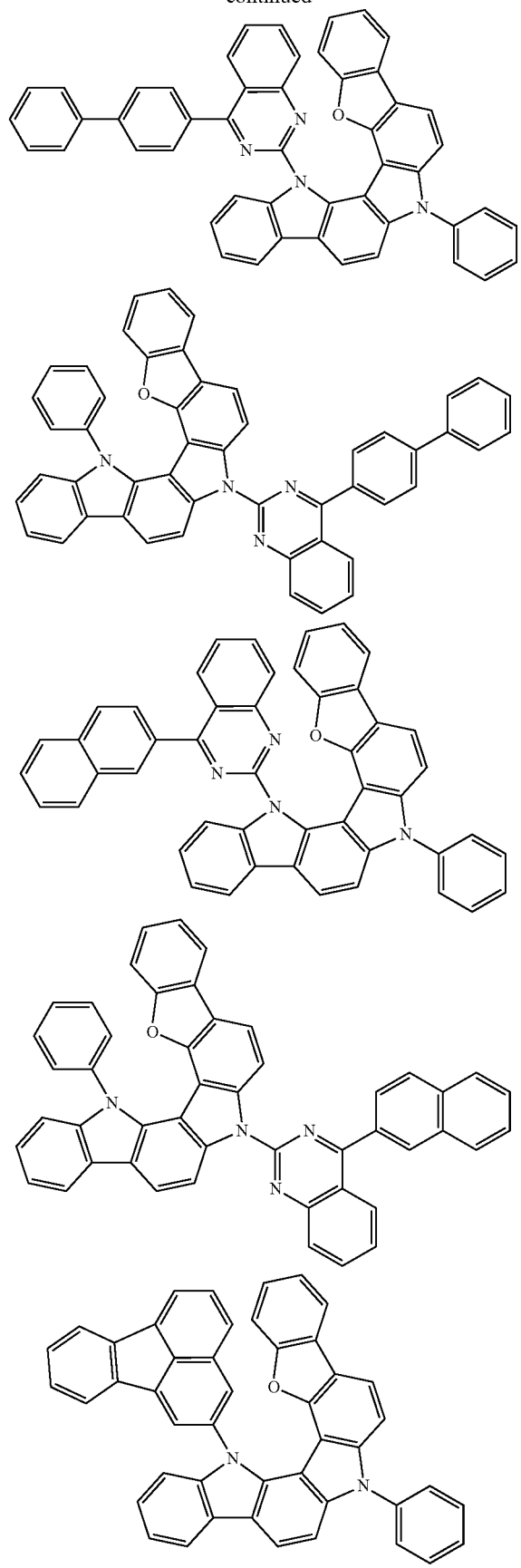
248
-continued
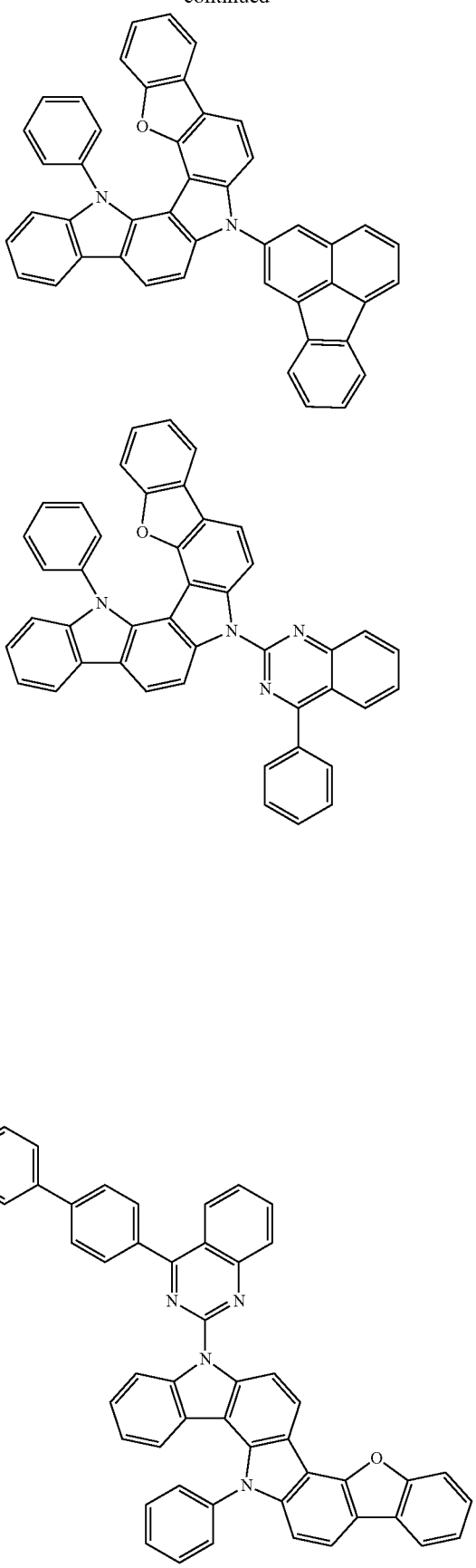

249
-continued
250
-continued
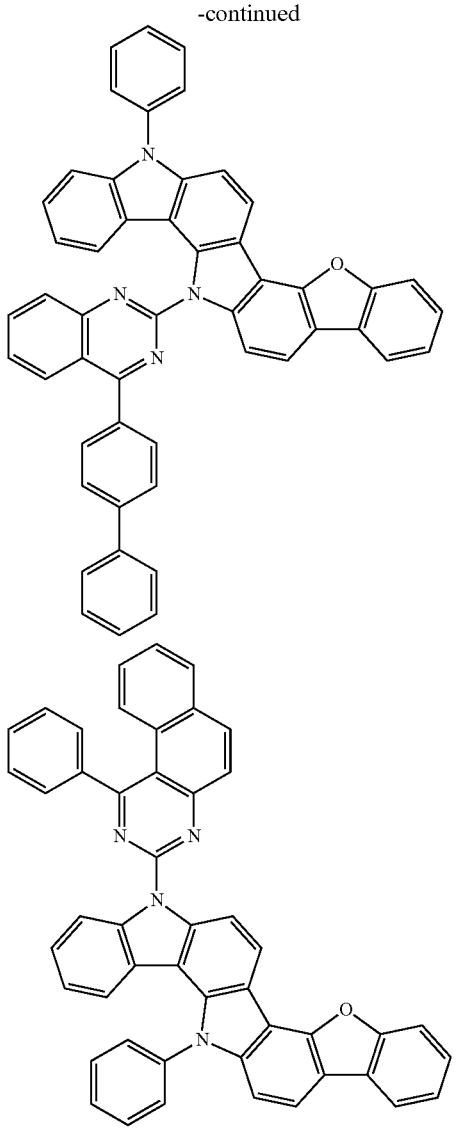
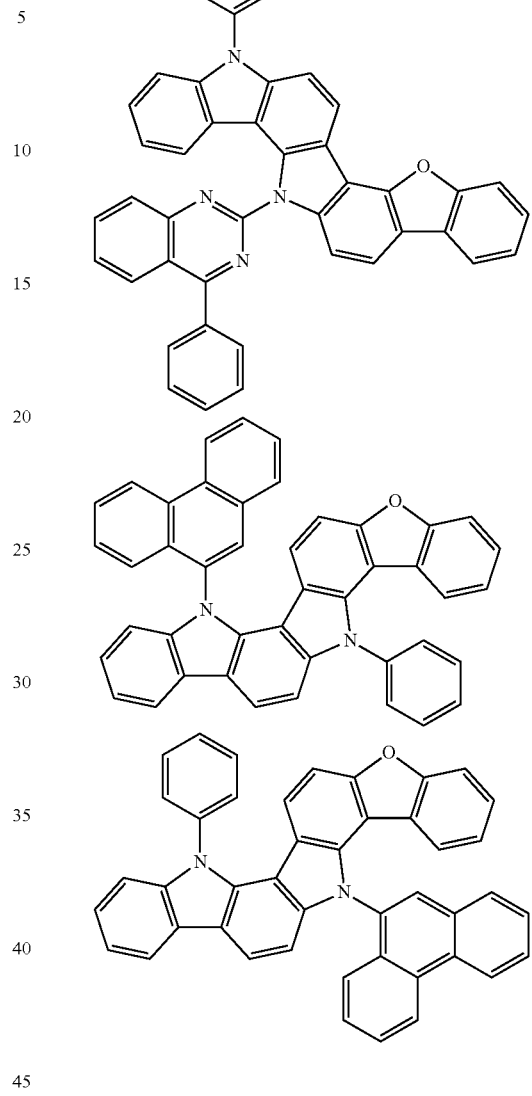
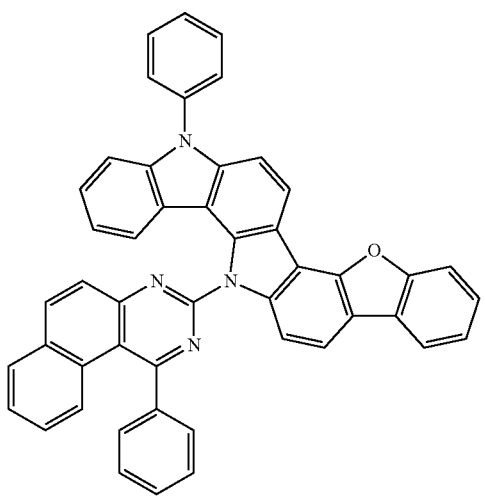

251
-continued
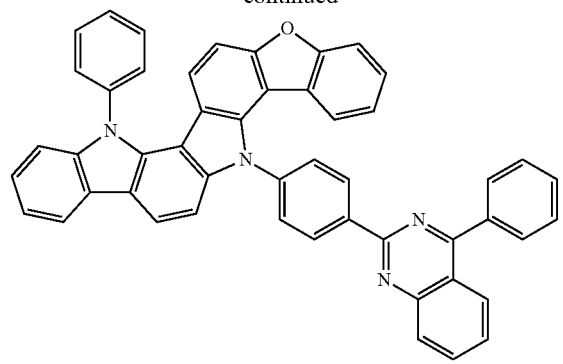
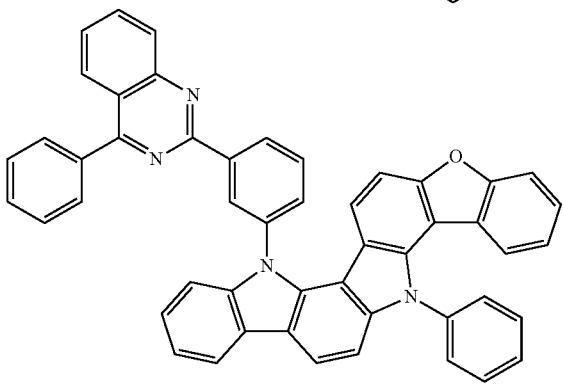
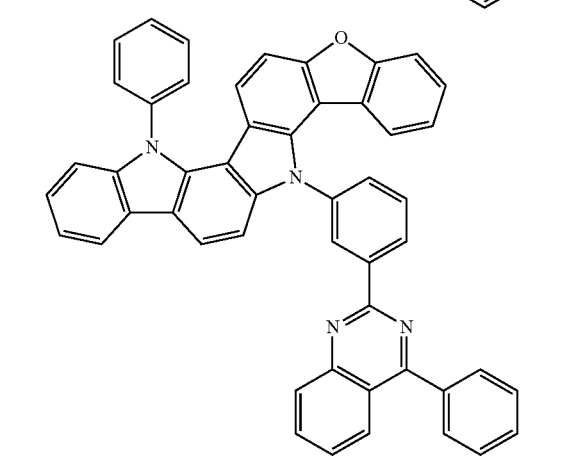
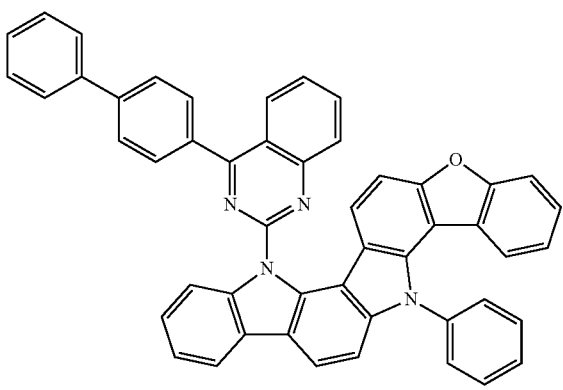
252
-continued
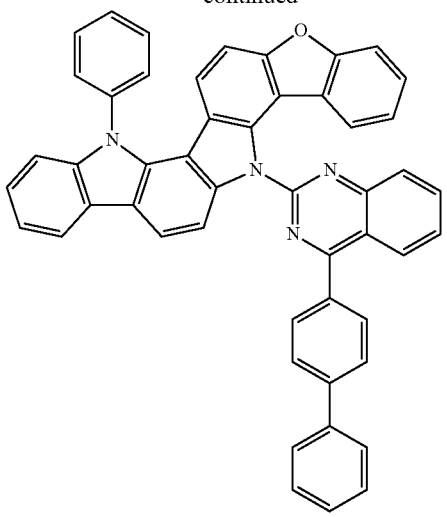
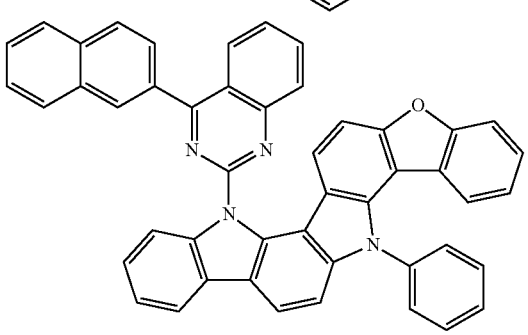
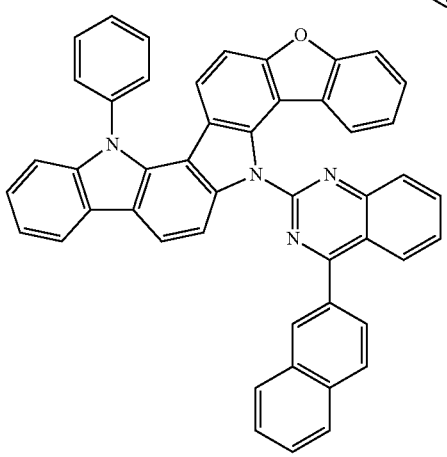
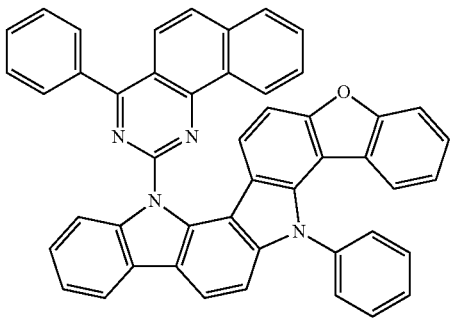

253
-continued
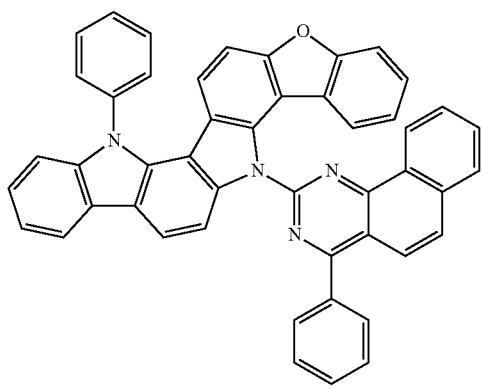
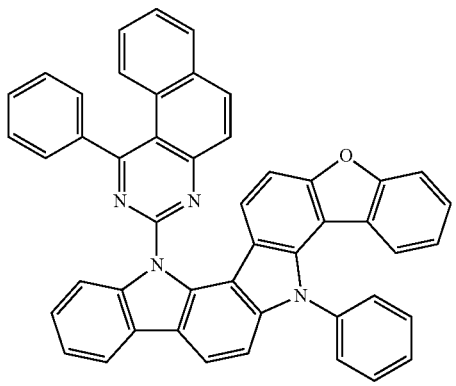
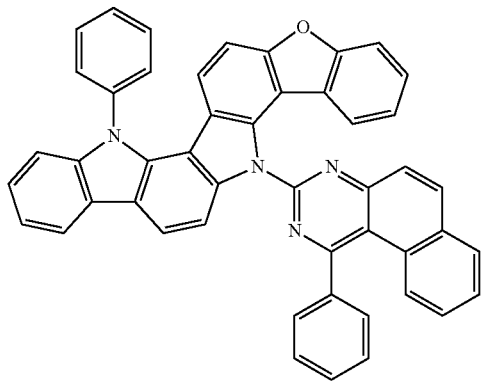
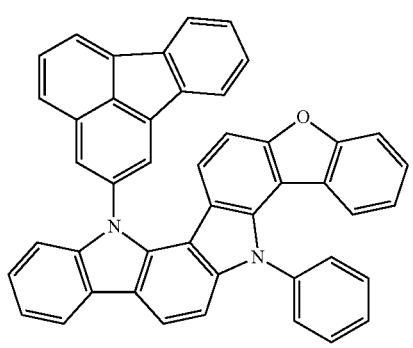
254
-continued
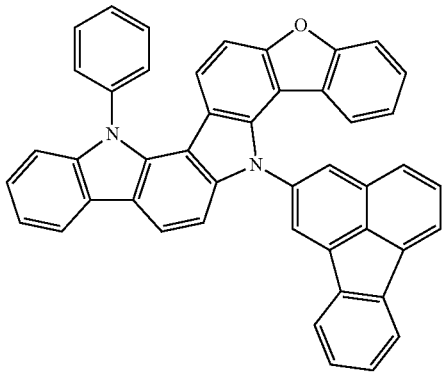
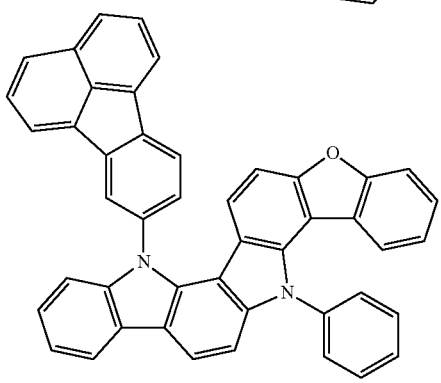
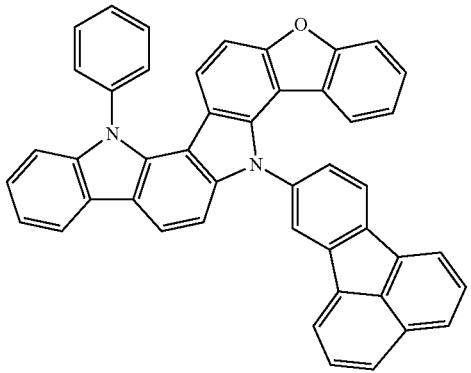
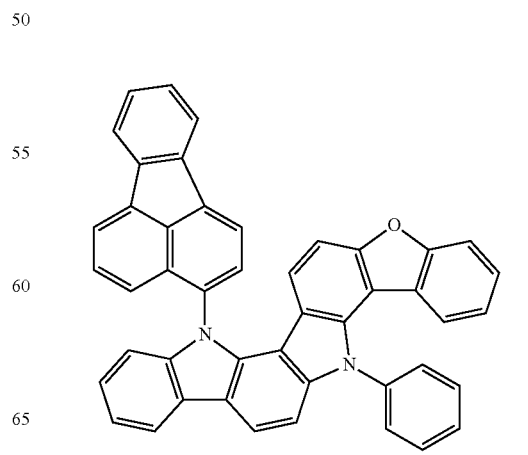

255
-continued
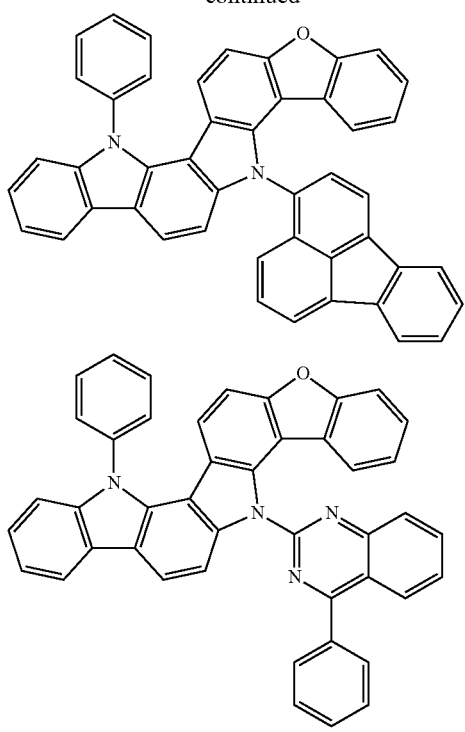
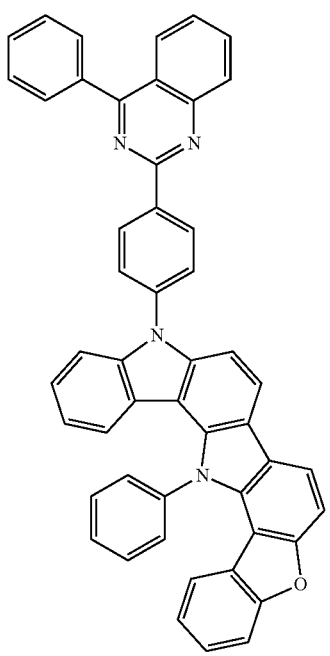
256
-continued
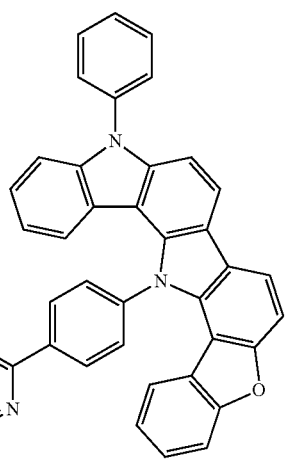
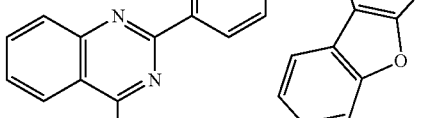
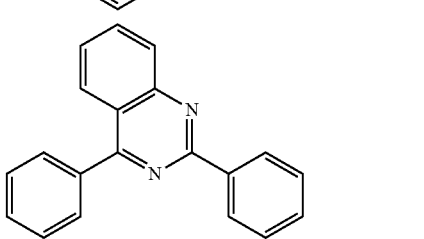
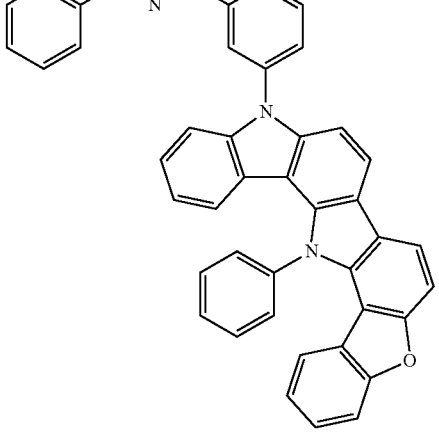
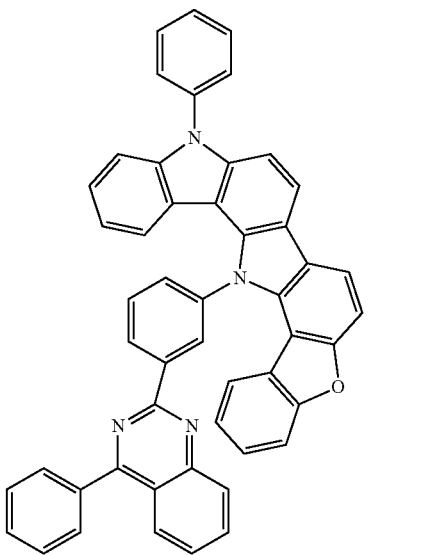

257
-continued
258
-continued
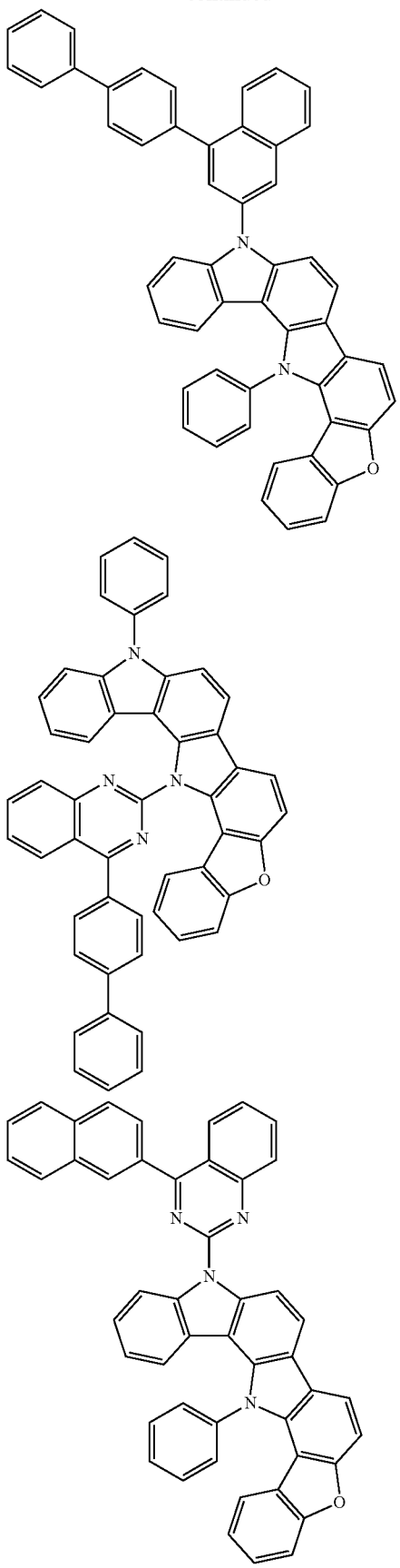
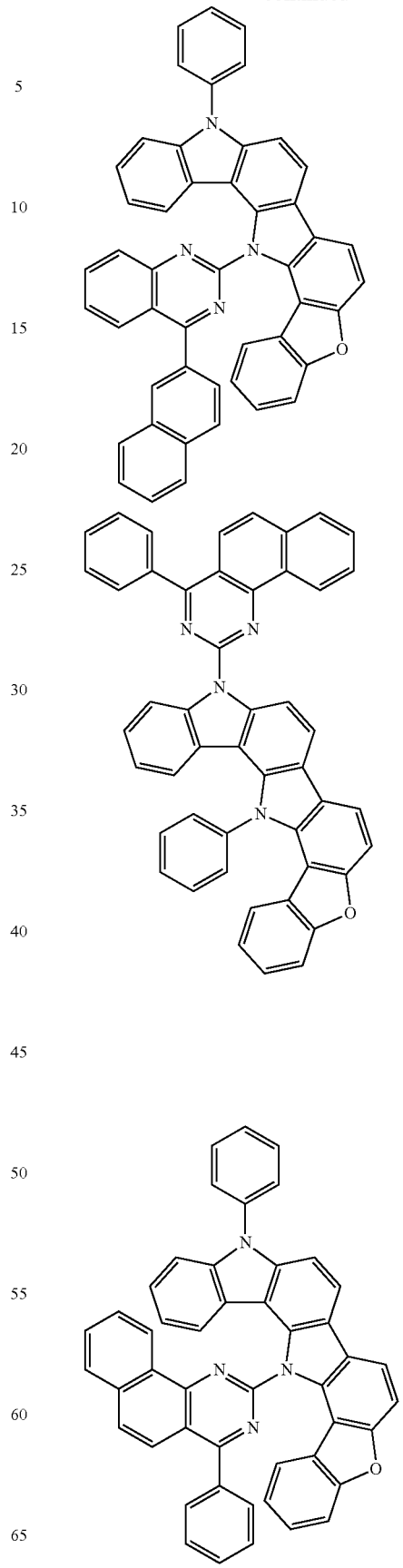

259
-continued
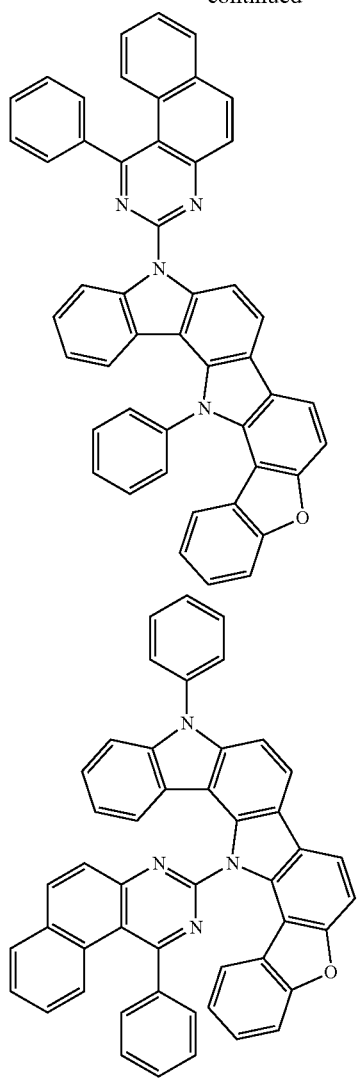
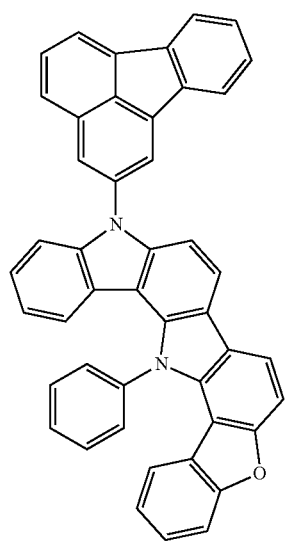
260
-continued
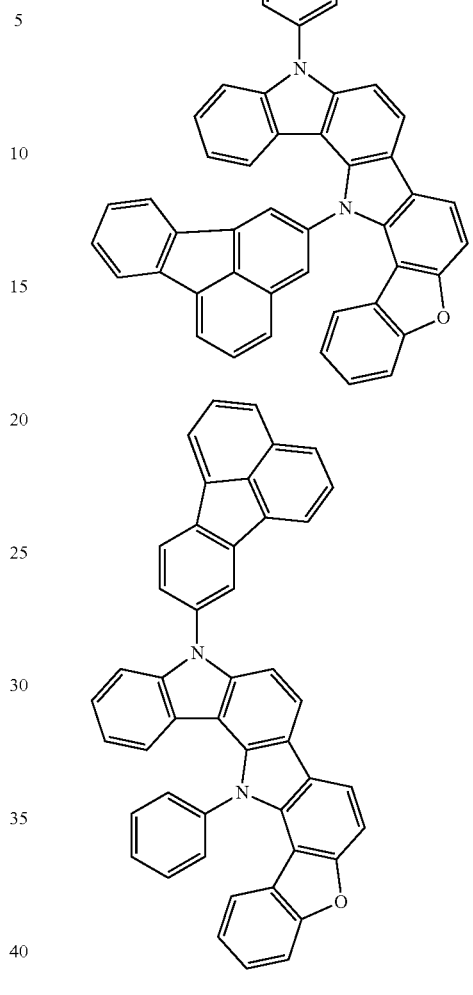
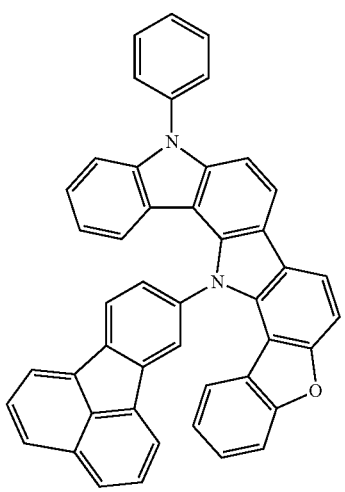

261
-continued
262
-continued
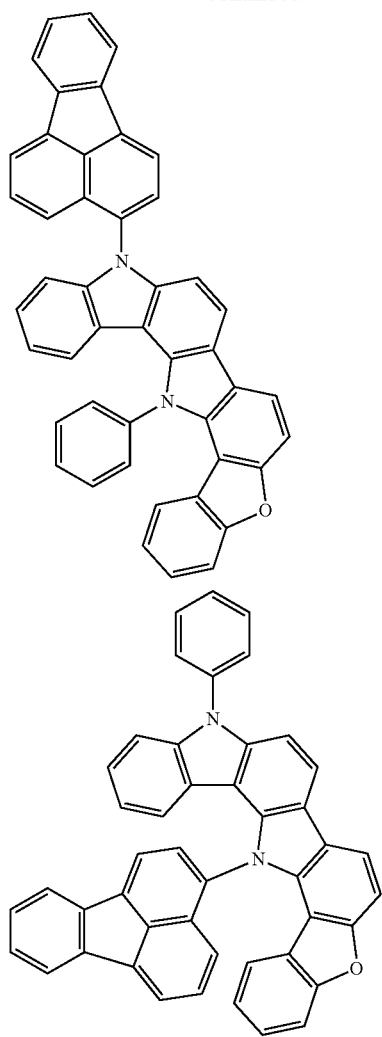
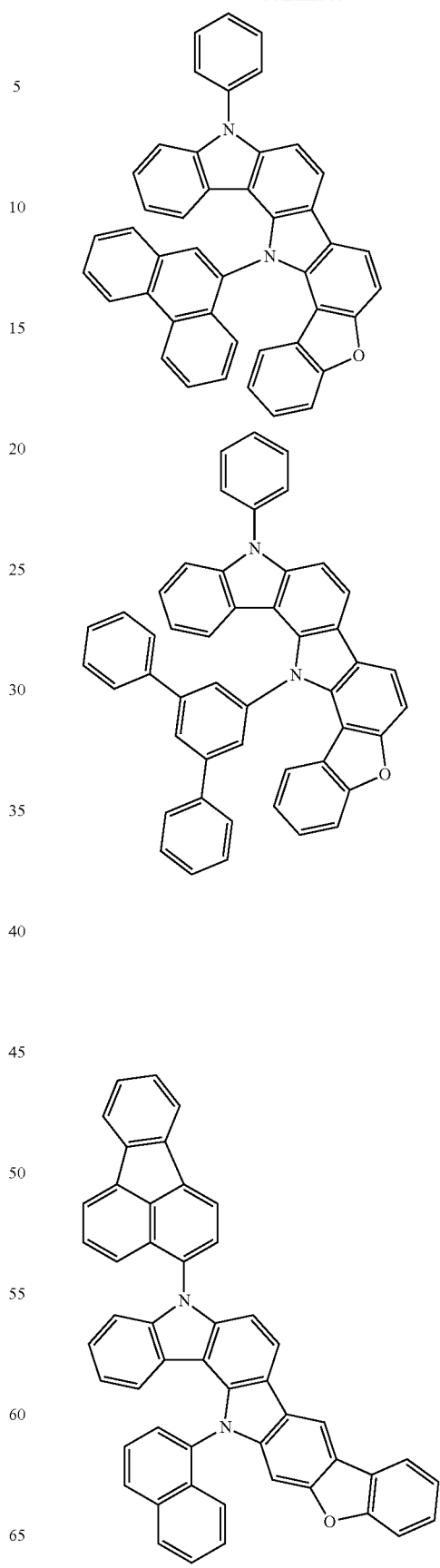

263
-continued
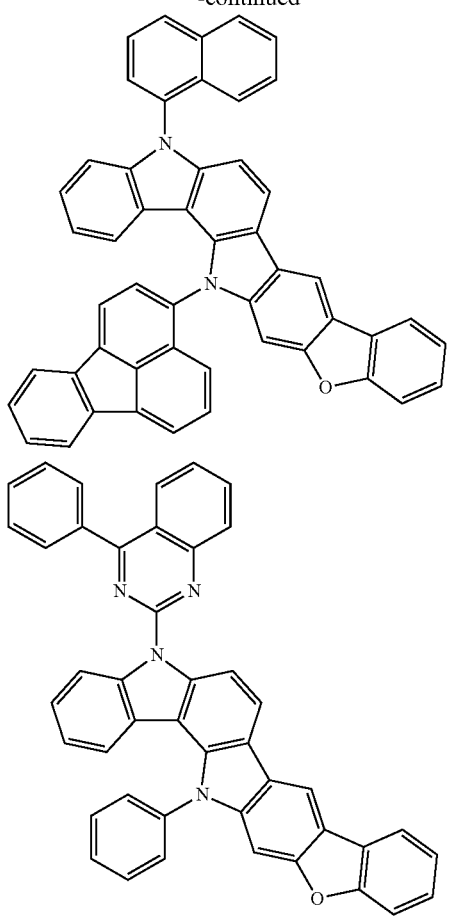
264
-continued
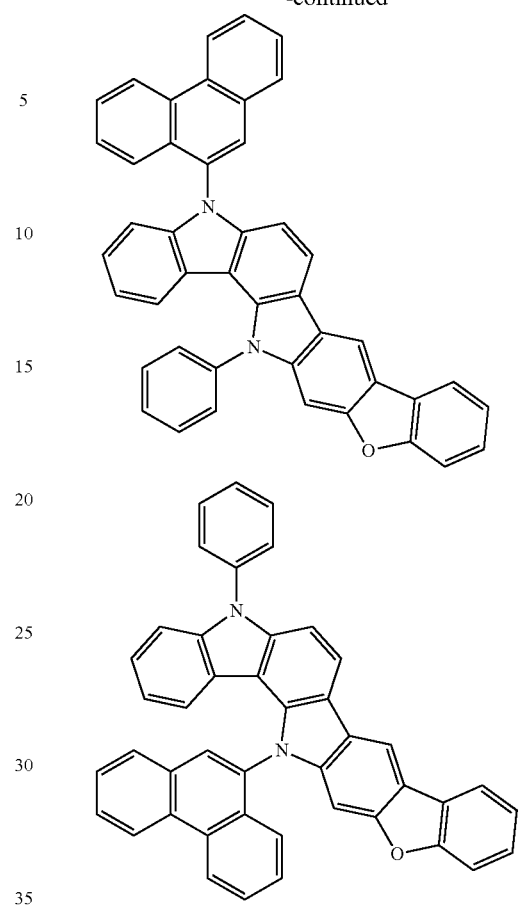
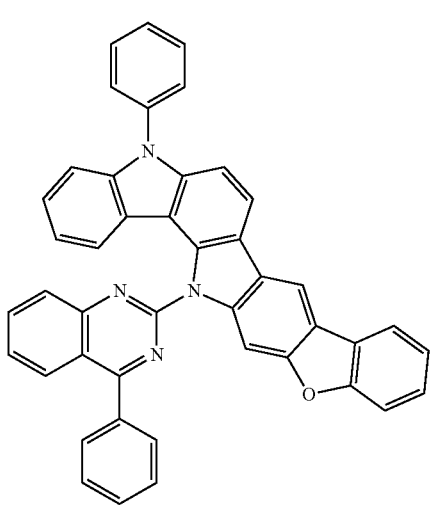
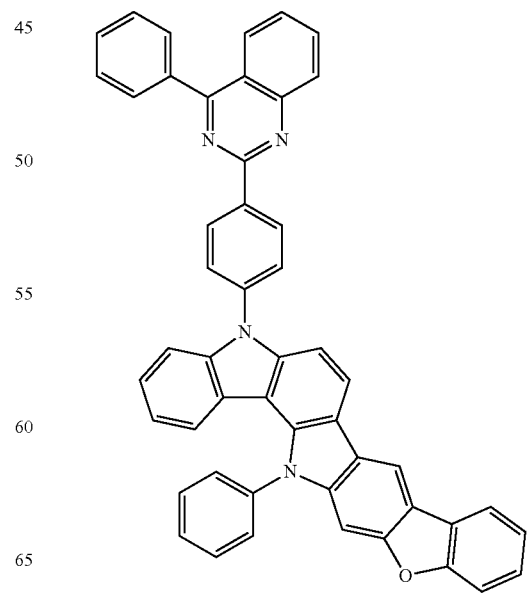

265
-continued
266
-continued
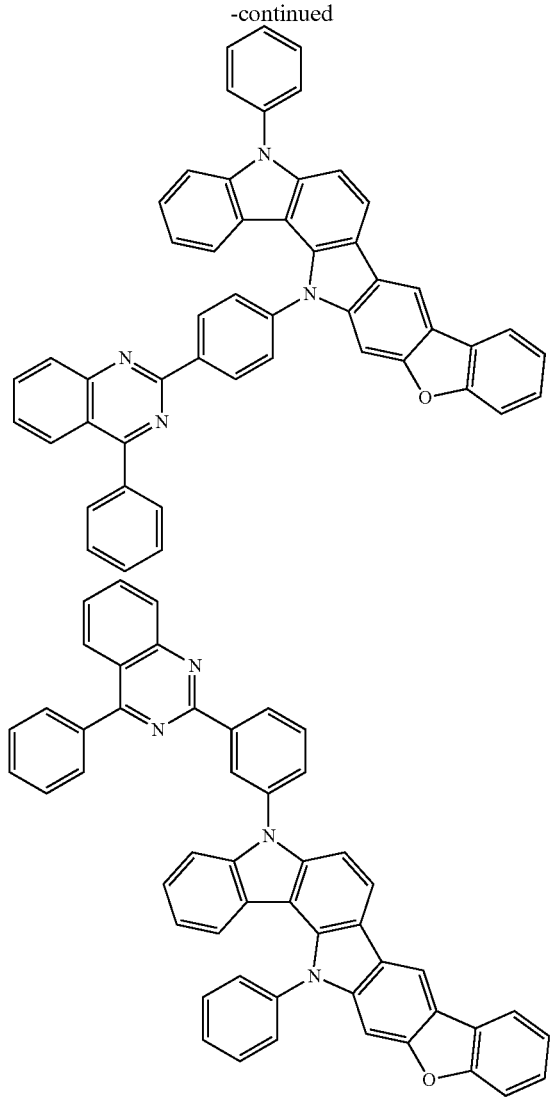
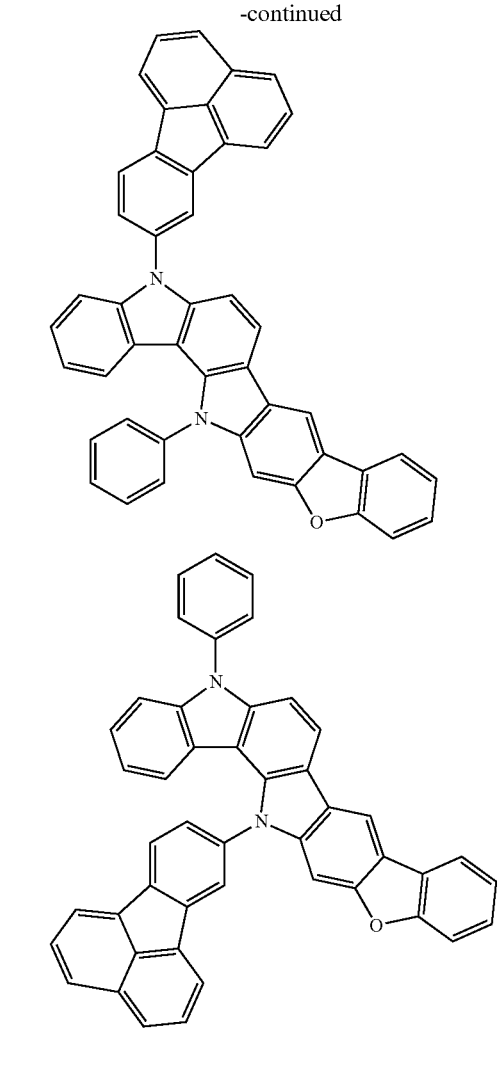
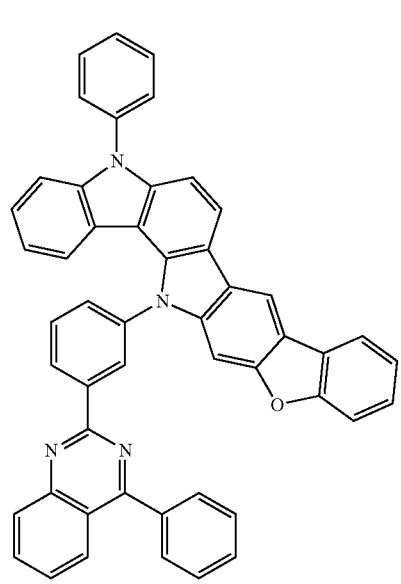
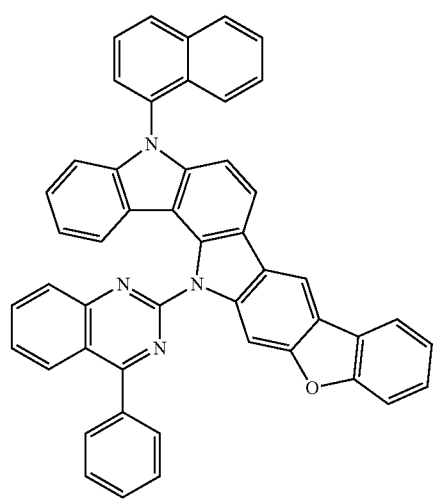

267
-continued
268
-continued
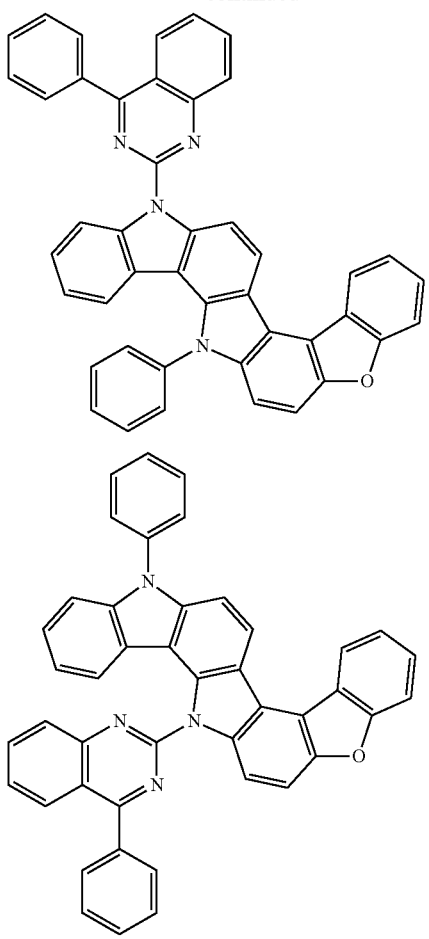
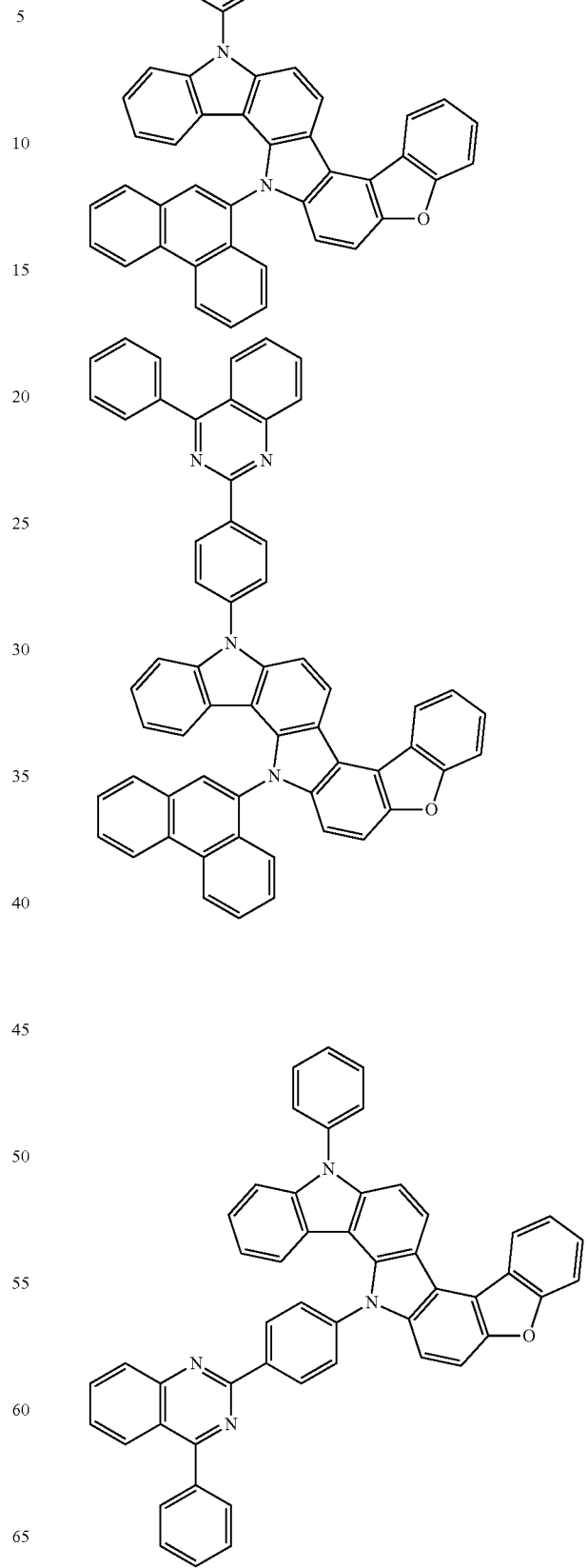
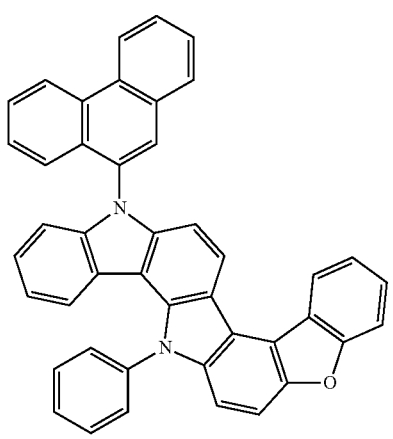

269
-continued
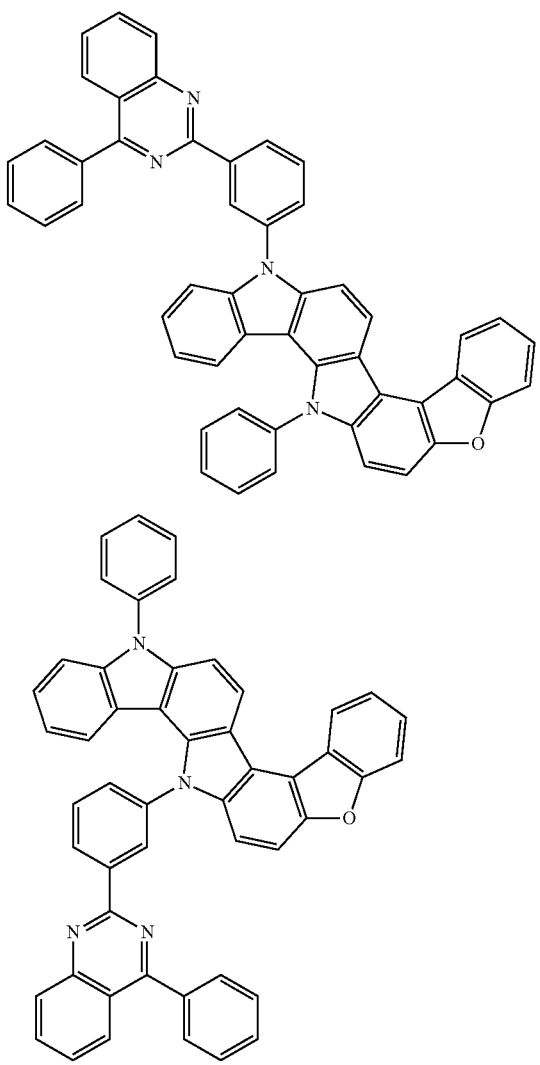
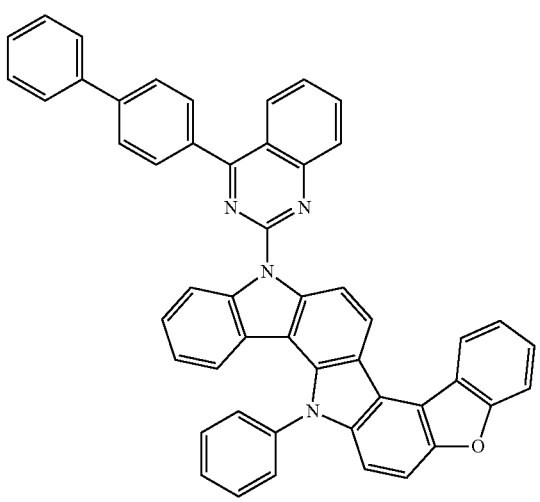
270
-continued
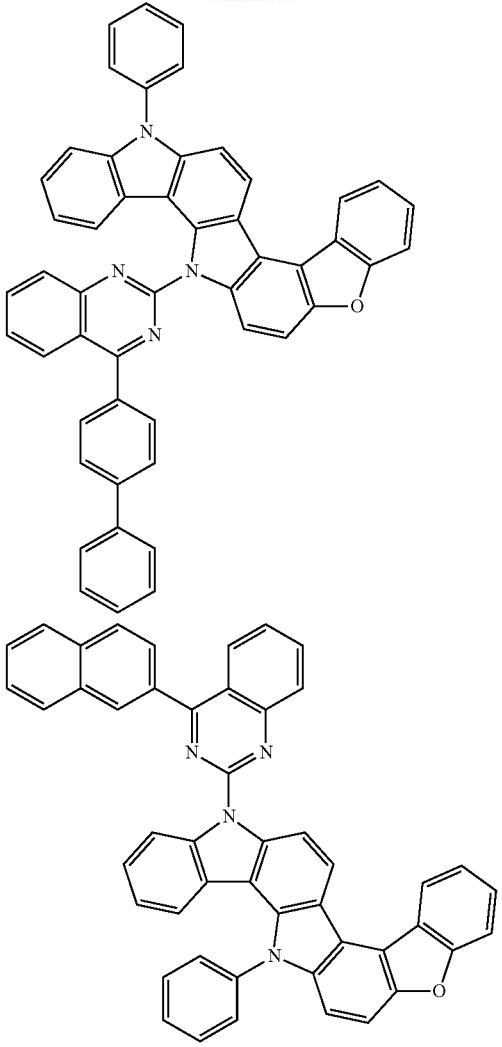
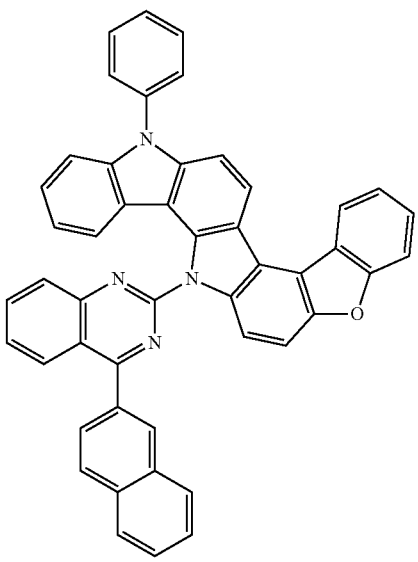

271
-continued
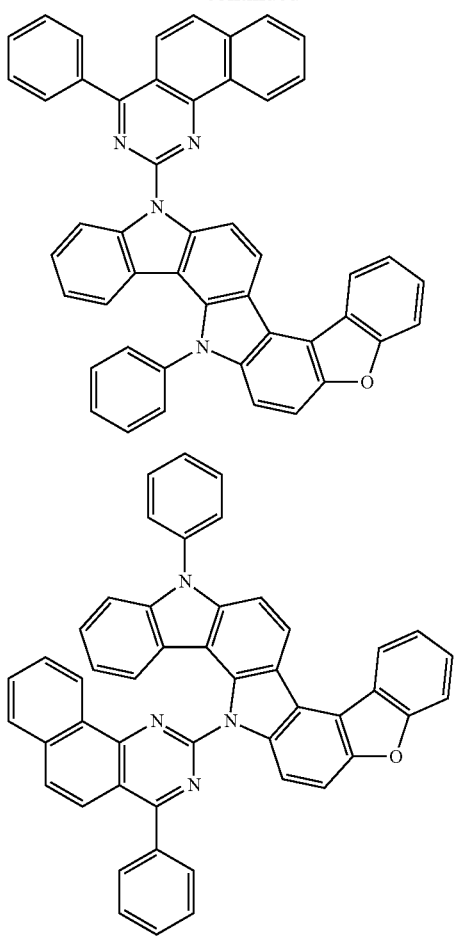
272
-continued
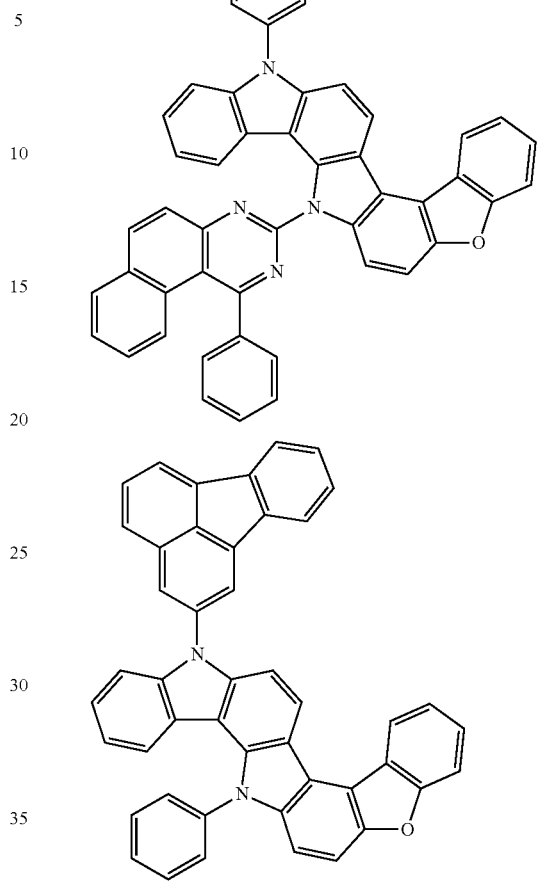
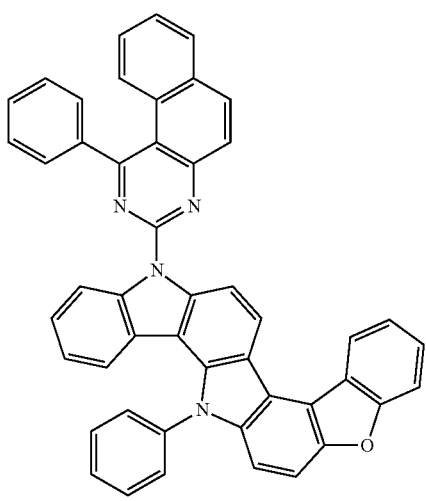
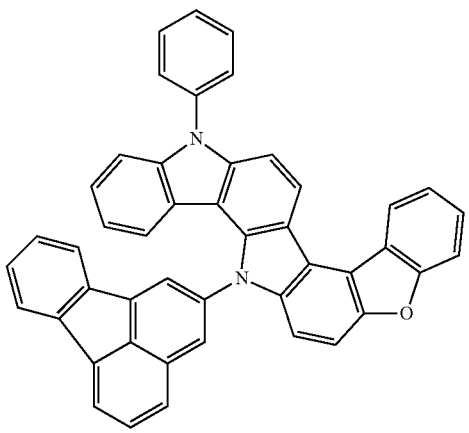

273
-continued
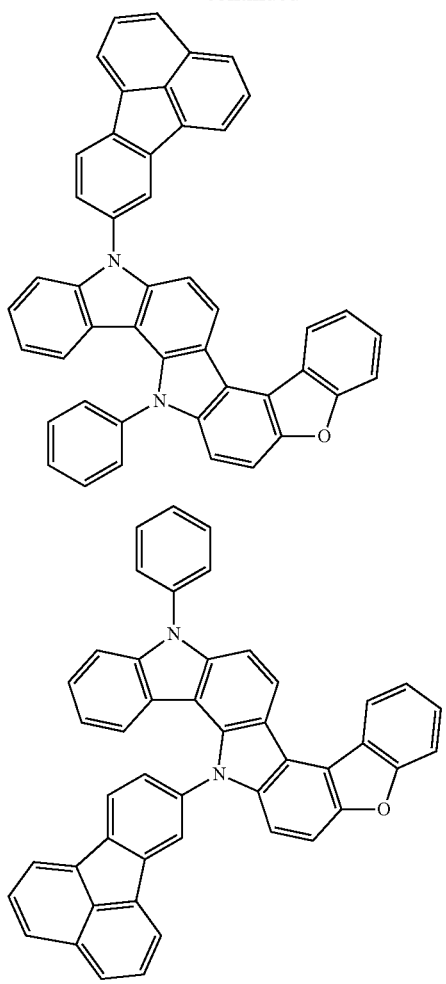
274
-continued
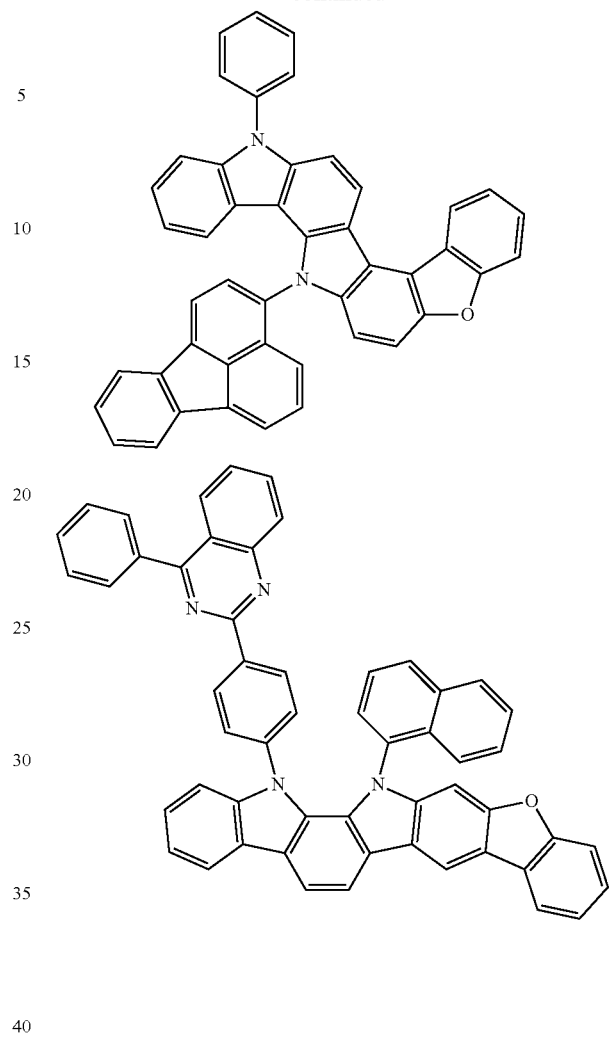
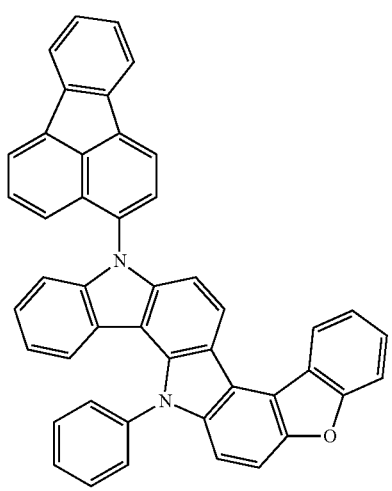
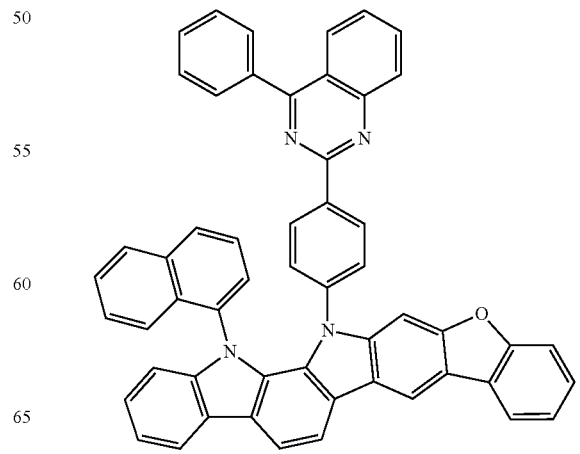

275
-continued
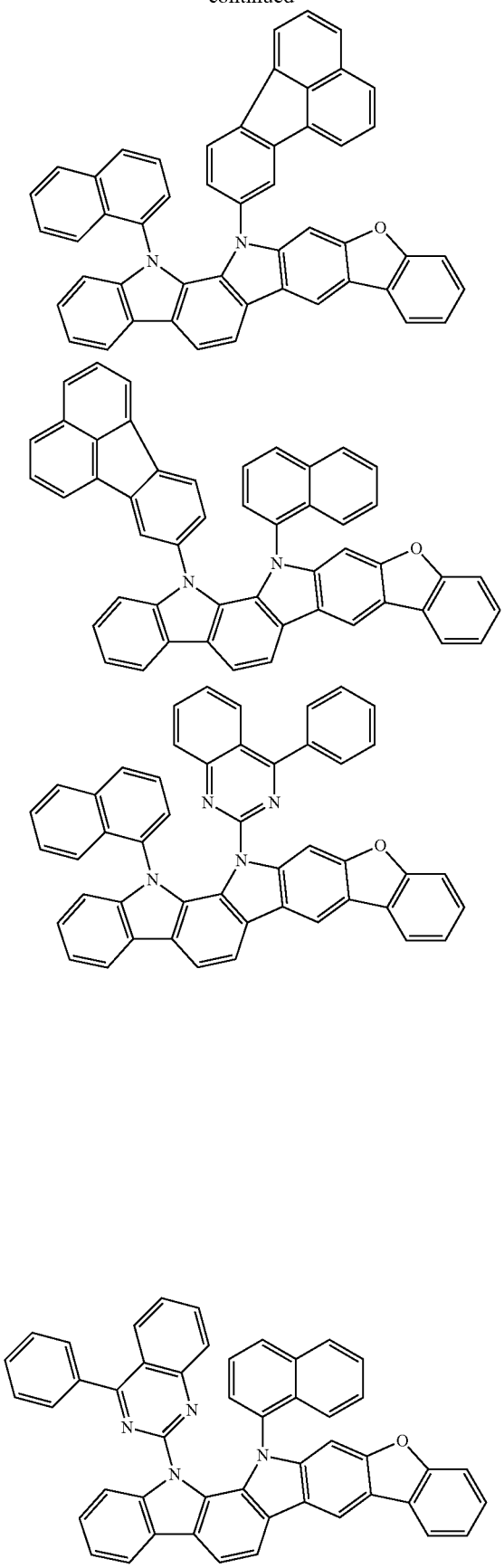
276
-continued
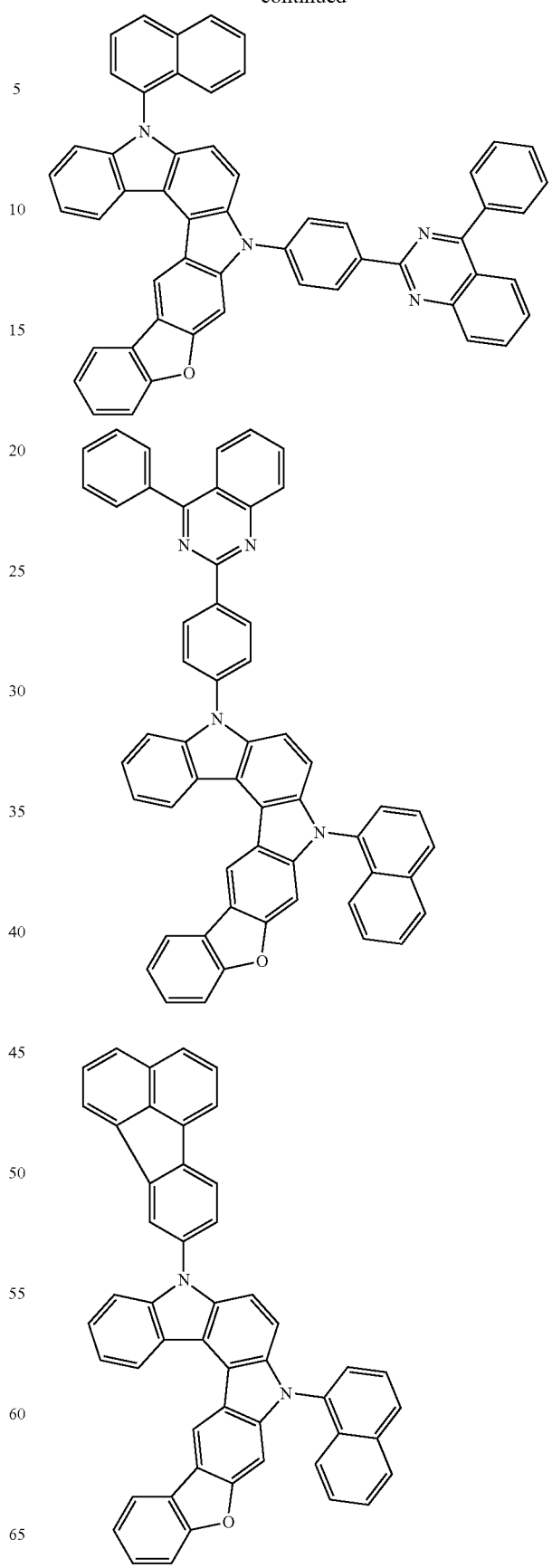

277
-continued
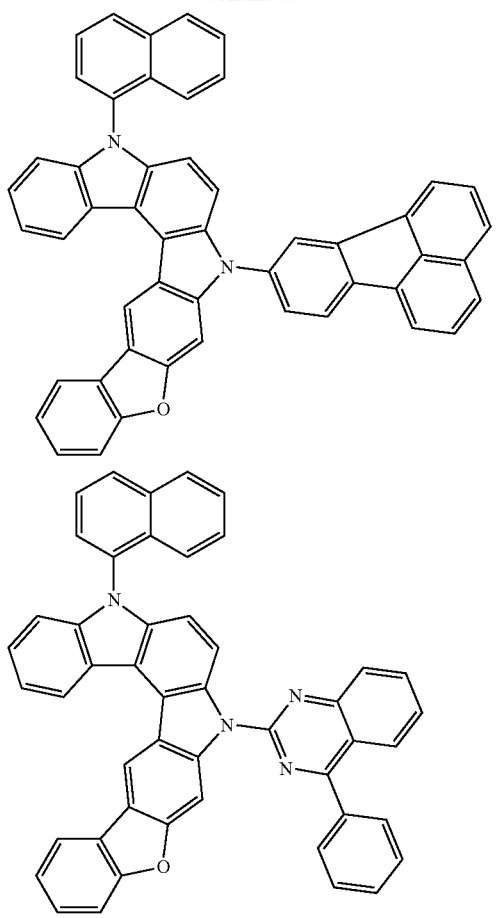
278
-continued
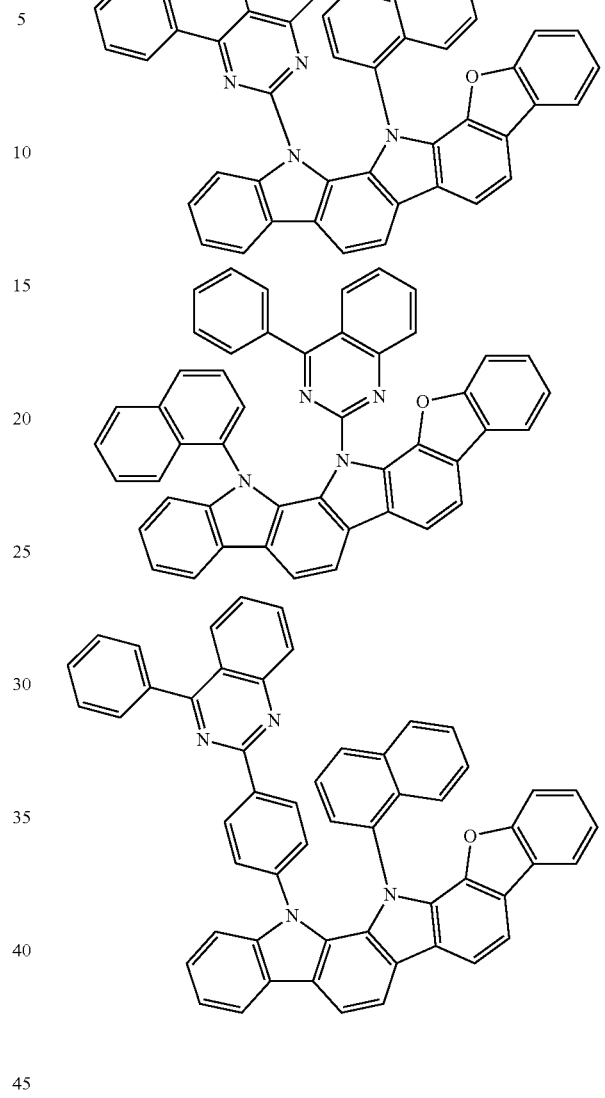
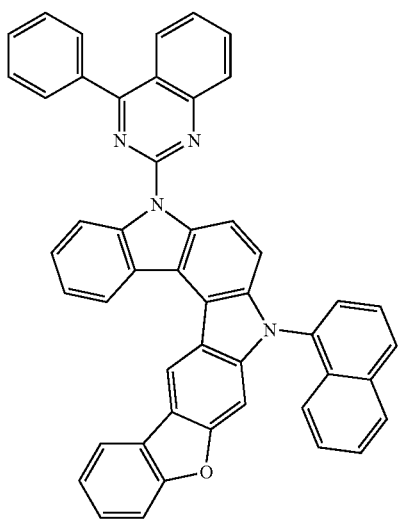
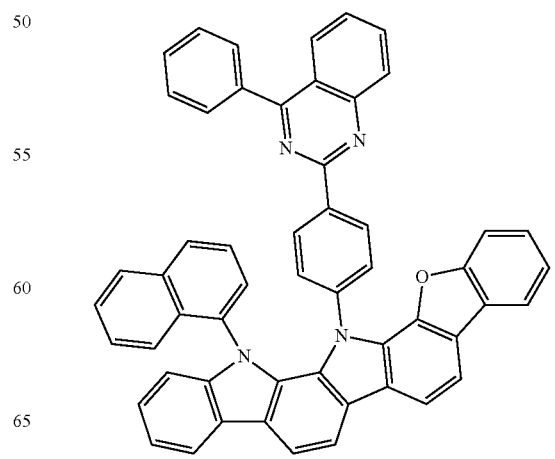

279
-continued
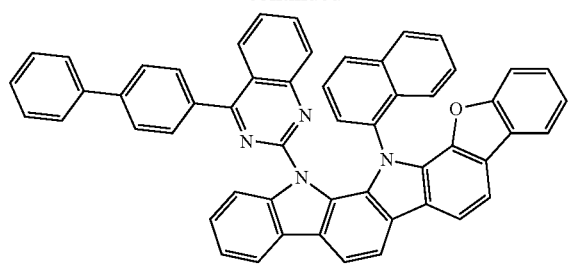
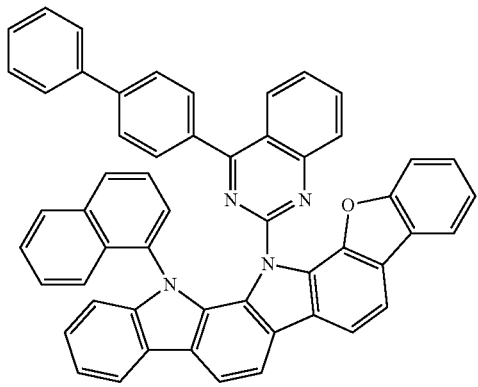
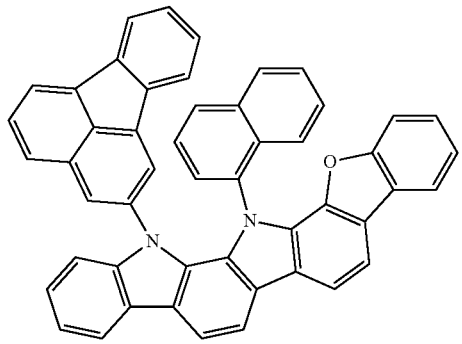
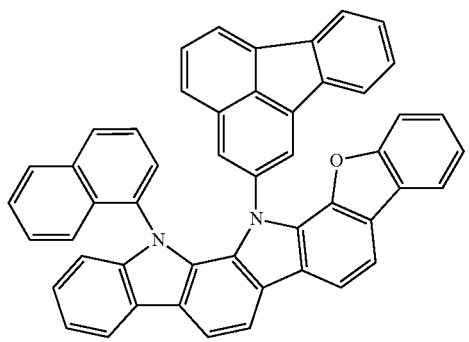
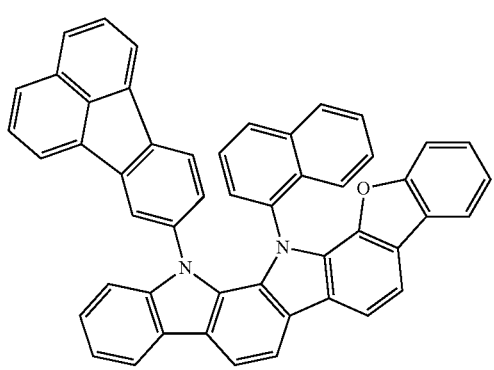
280
-continued
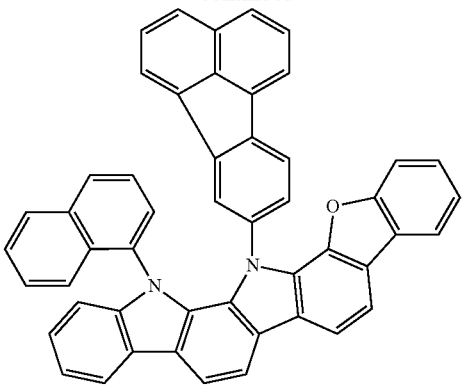
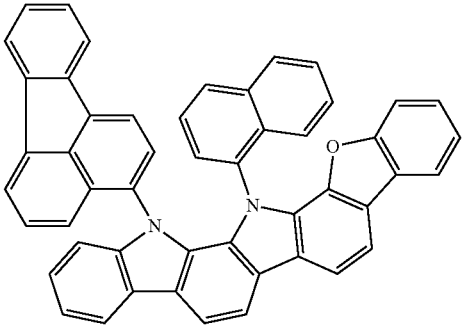
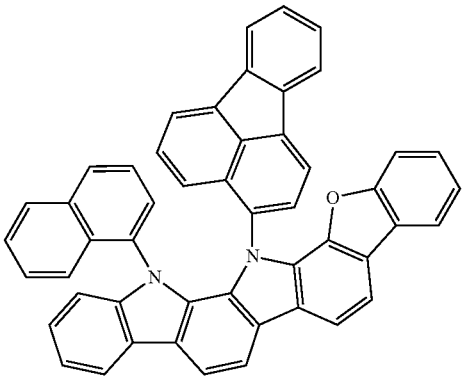
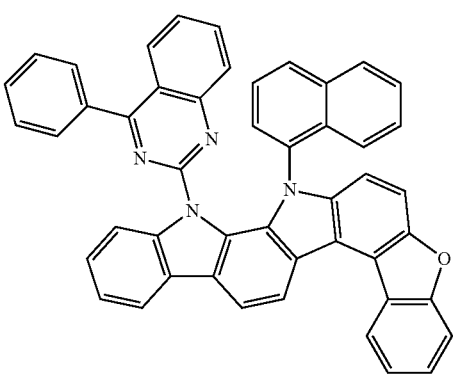

281
-continued
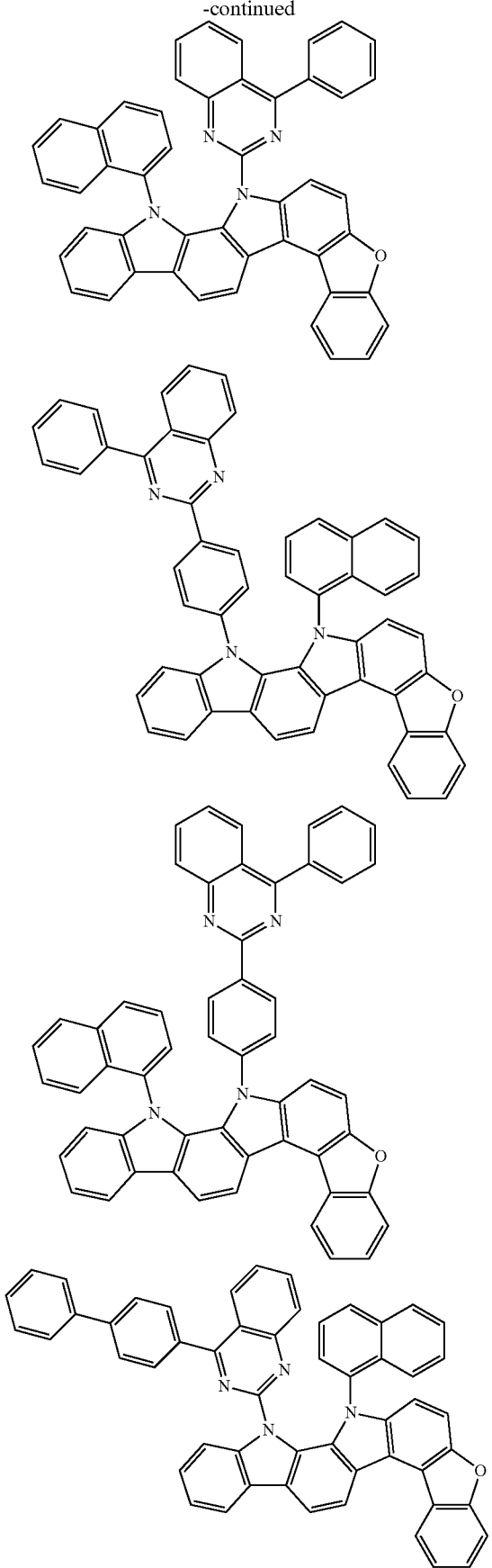
282
-continued
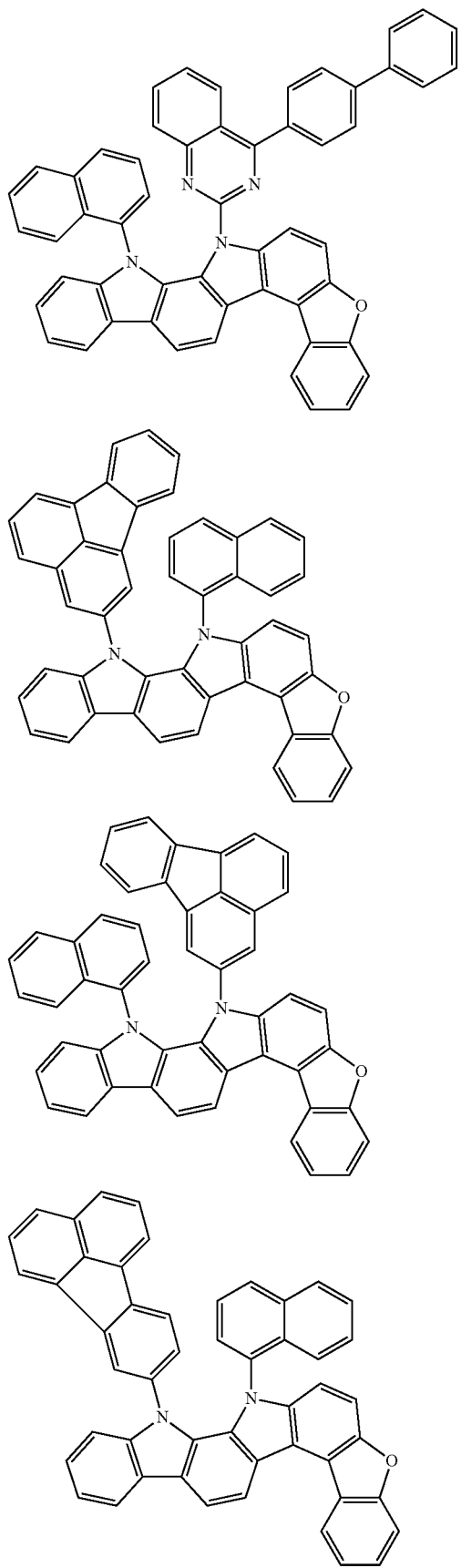

-continued
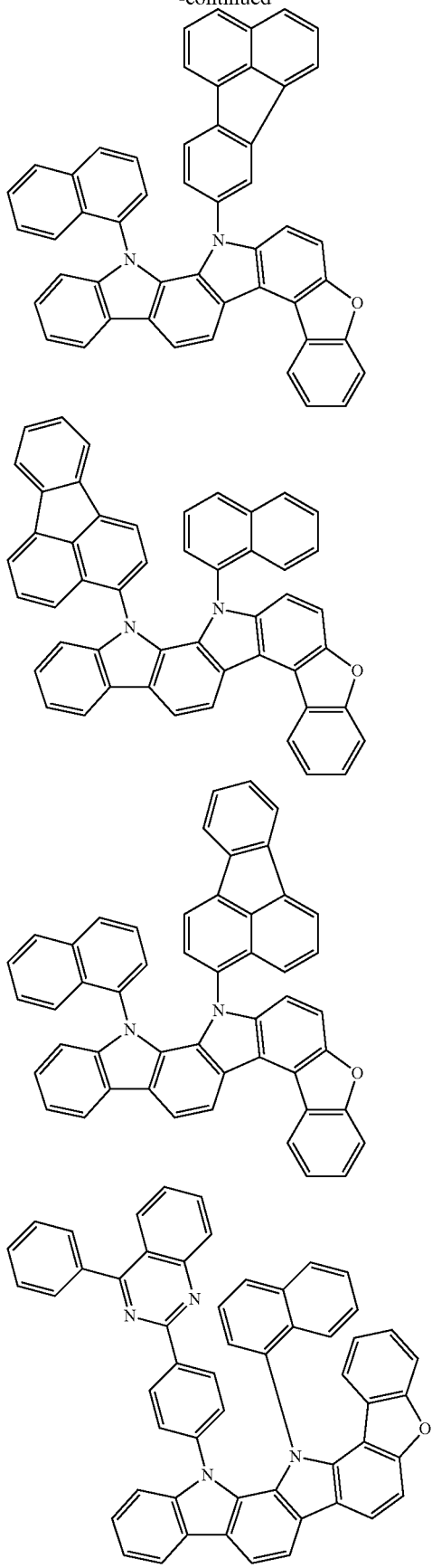
-continued
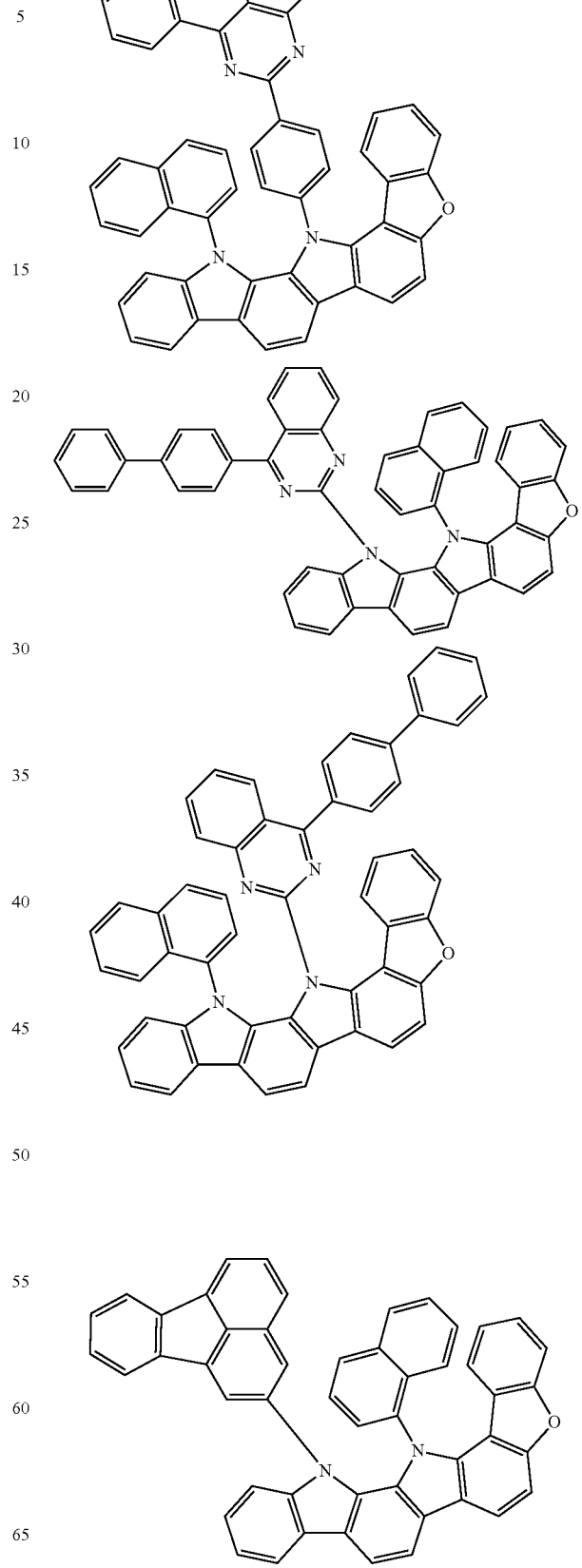

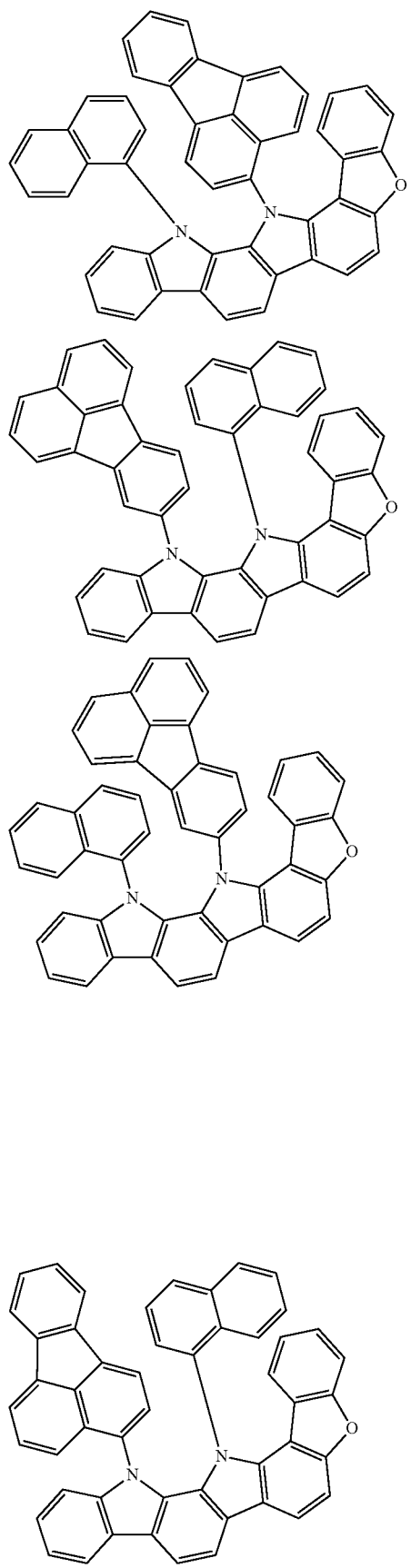
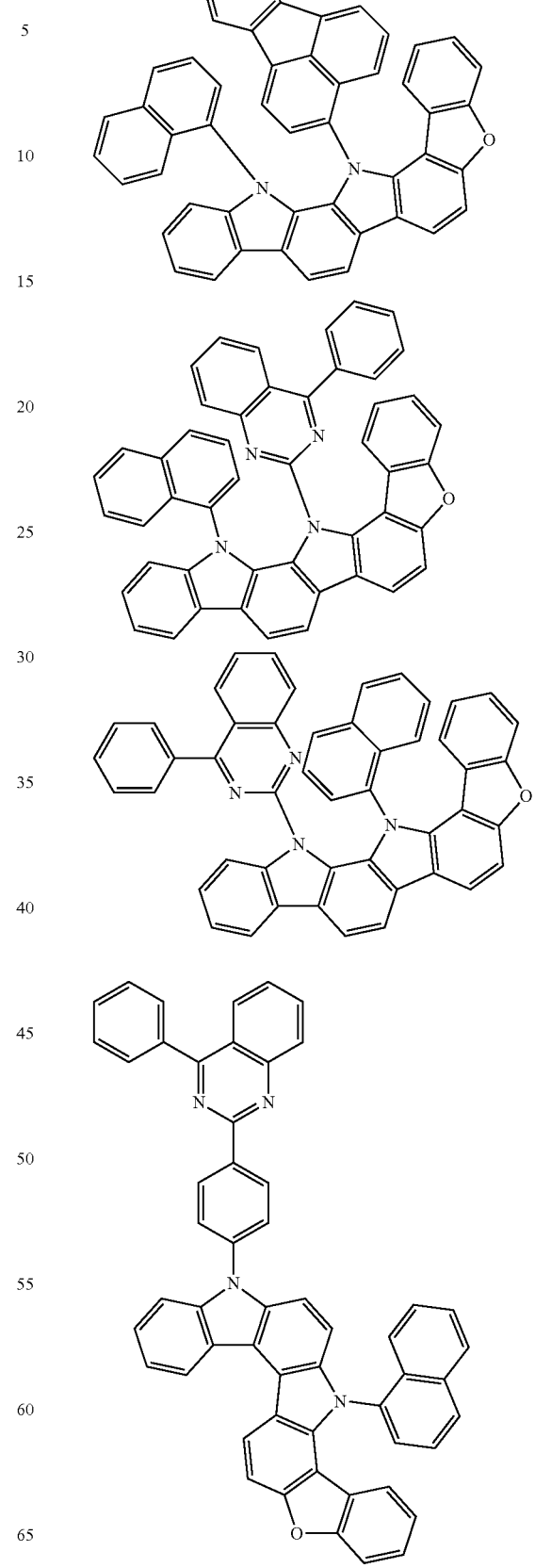

287
-continued
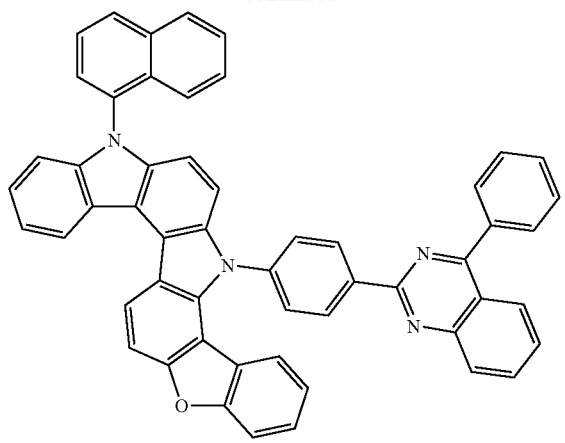
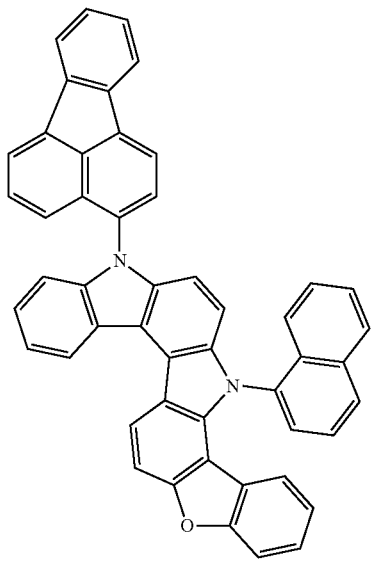
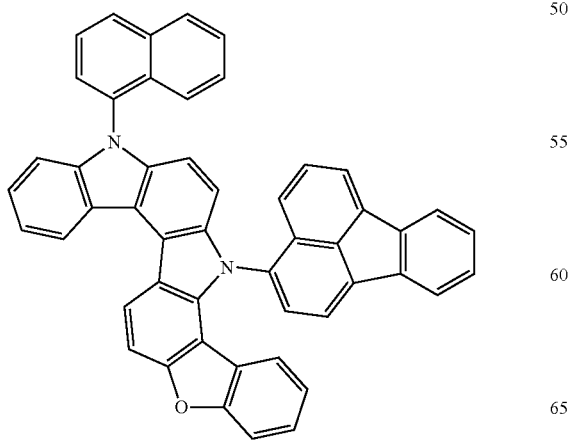
288
-continued
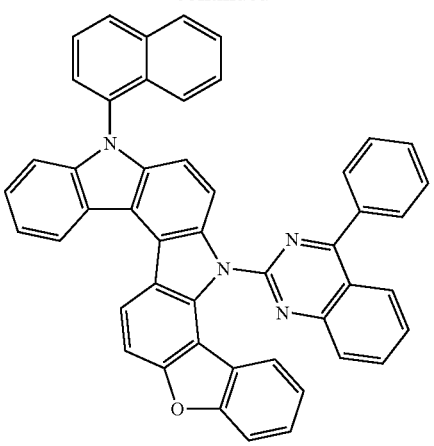
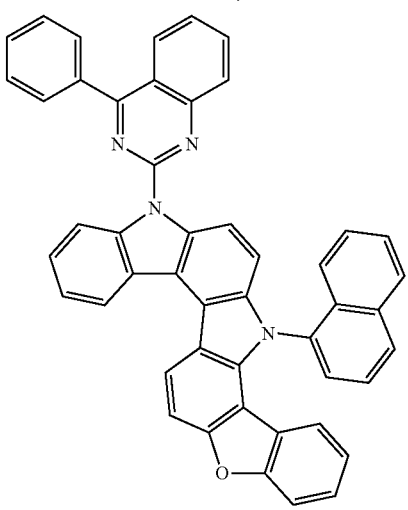
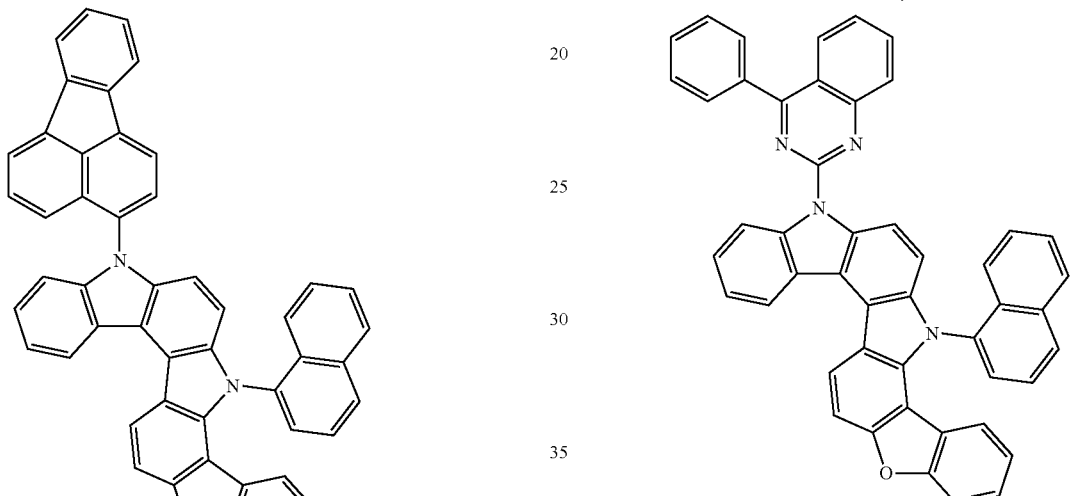

289
-continued

290
-continued

| 291 -continued | 292 -continued |
|---|---|
| 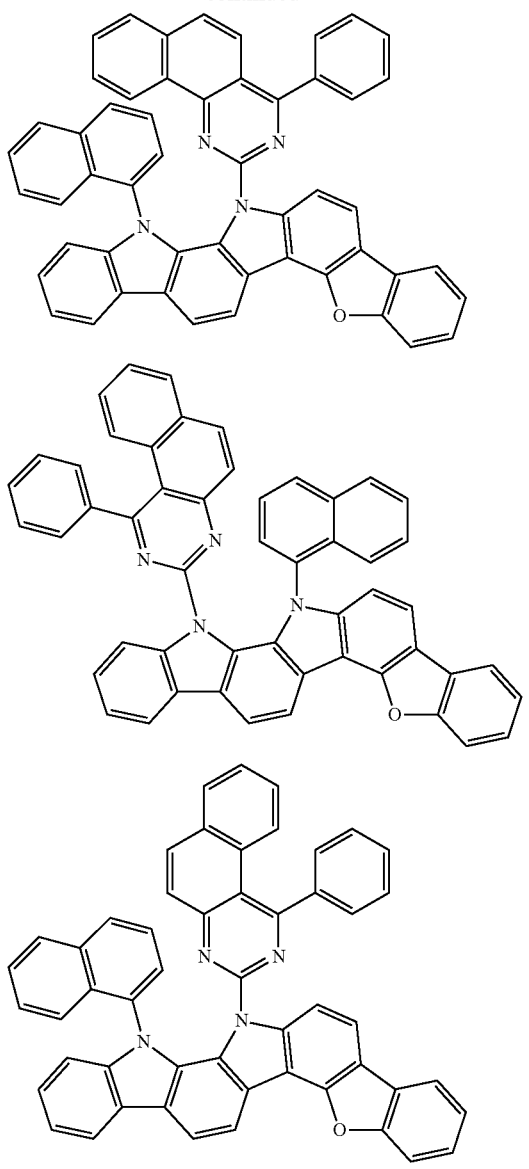 | 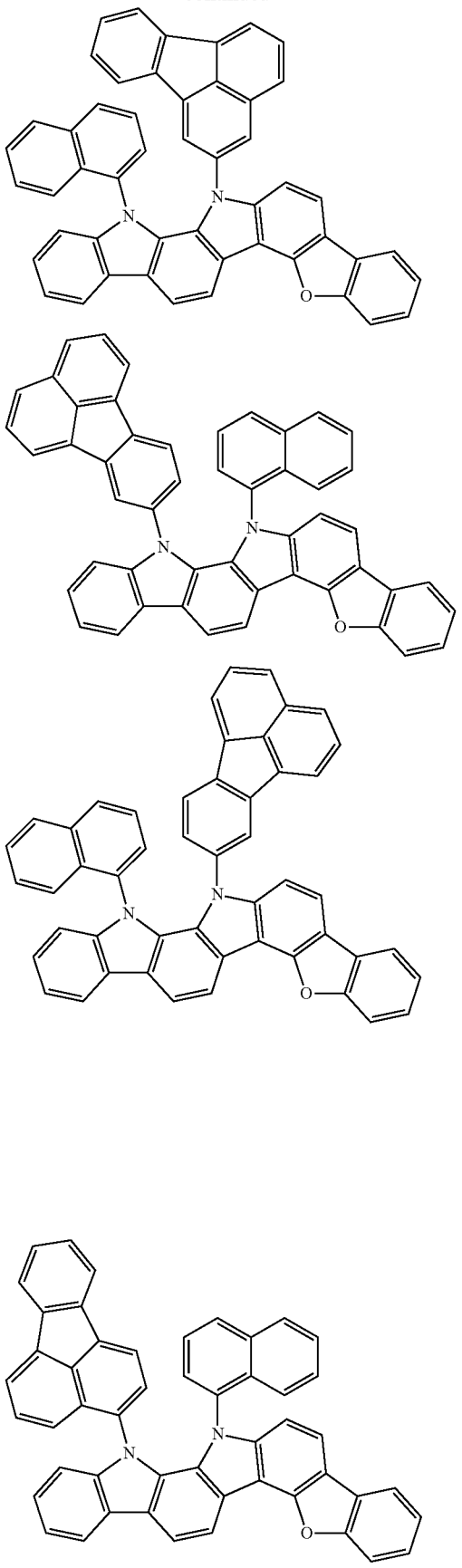 |
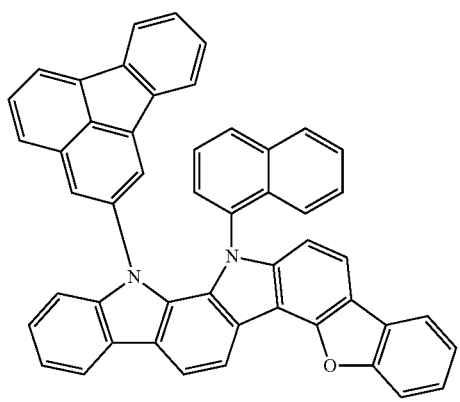

293
-continued
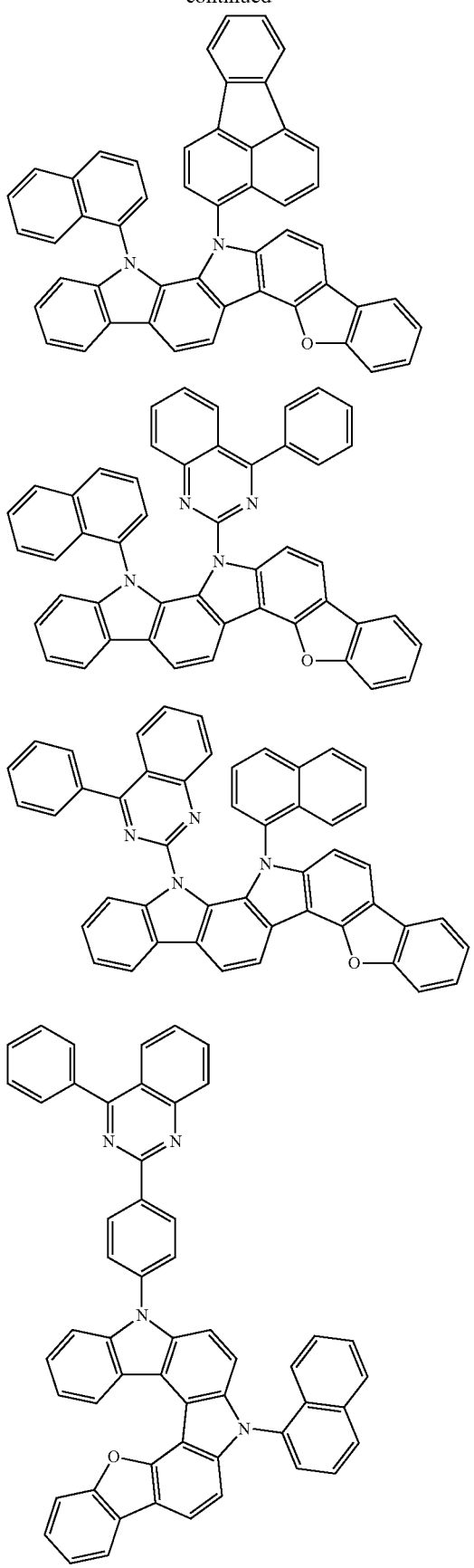
294
-continued
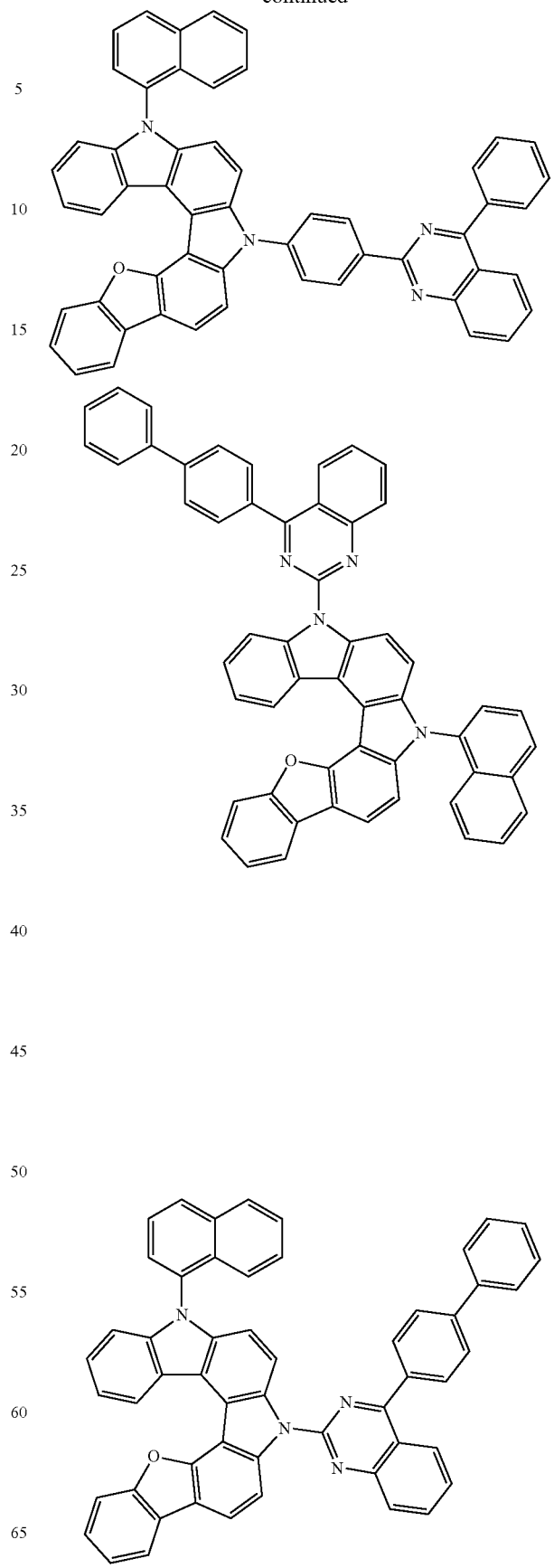

295
-continued
296
-continued
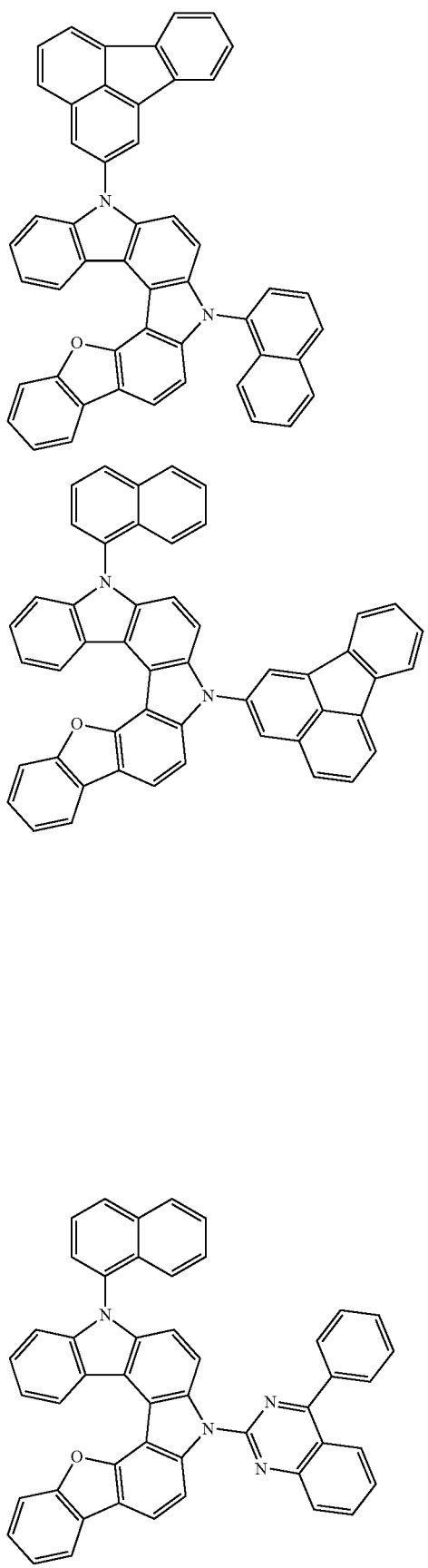
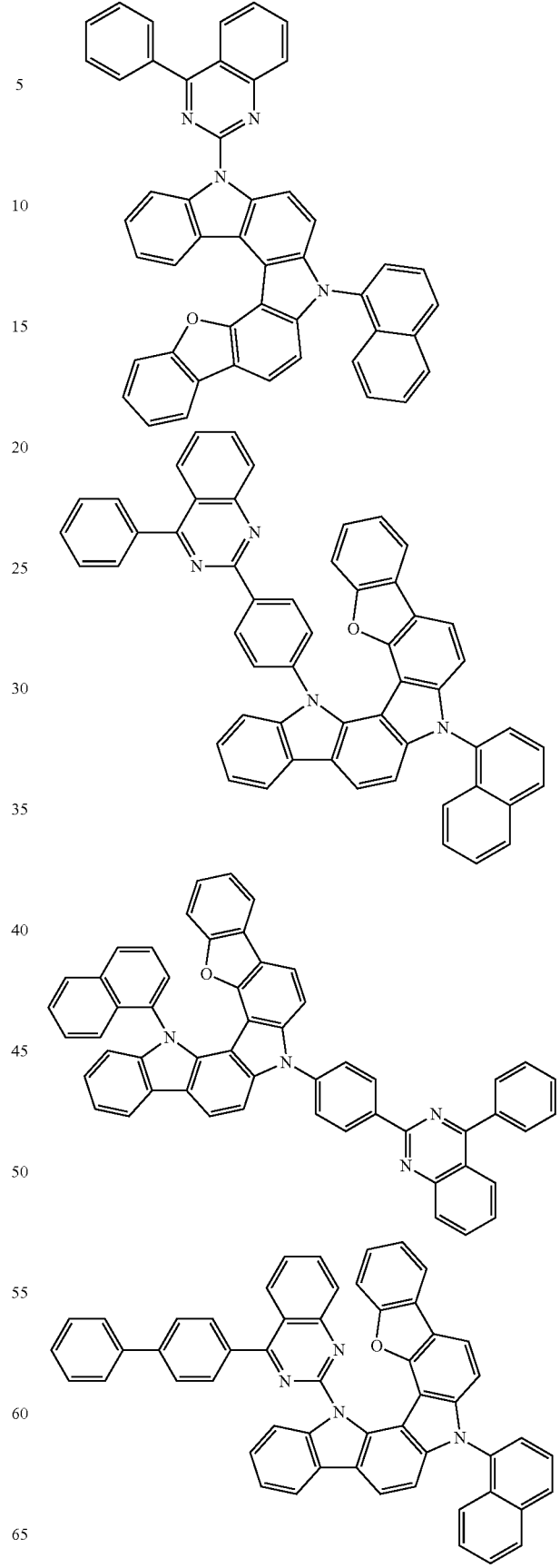

-continued
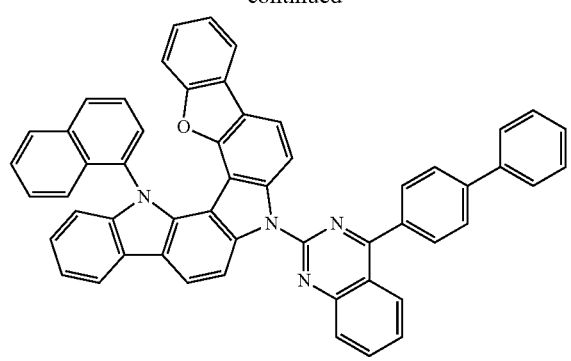
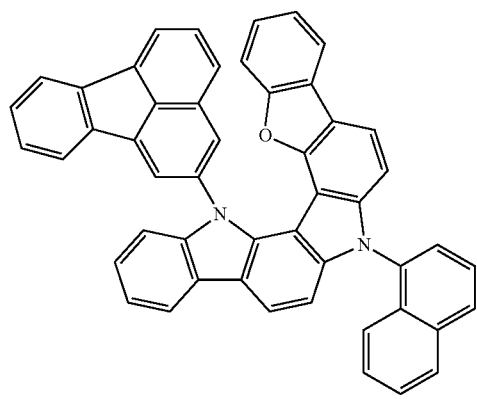
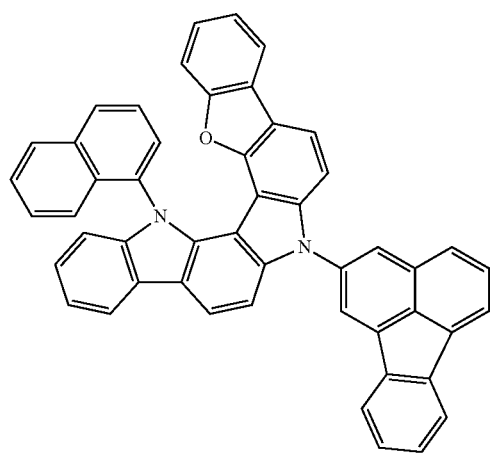
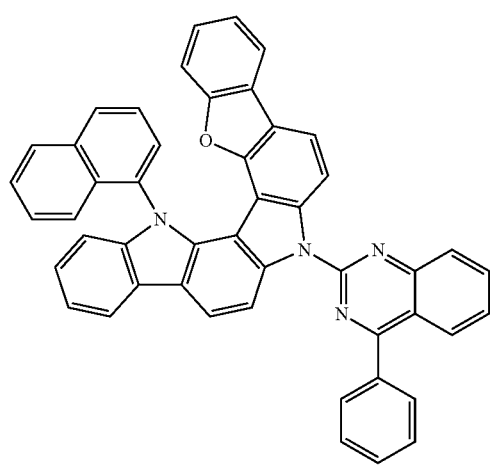 [SMILES: c1ccc(-c2nc(-n3c4ccc5c6ccccc6oc5c4c4c3ccc3c5ccccc5n(-c5ccc6ccccc6c5)c34)nc3ccccc23)cc1]
-continued
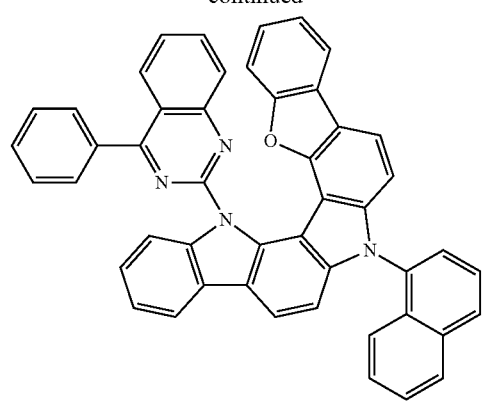
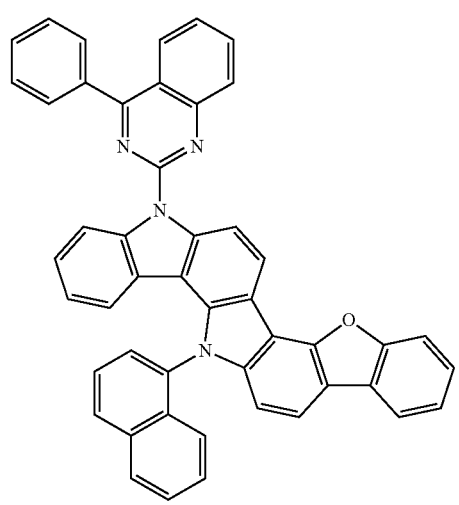
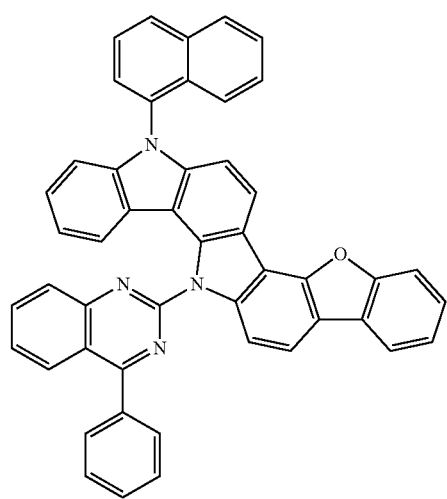

299
-continued
300
-continued
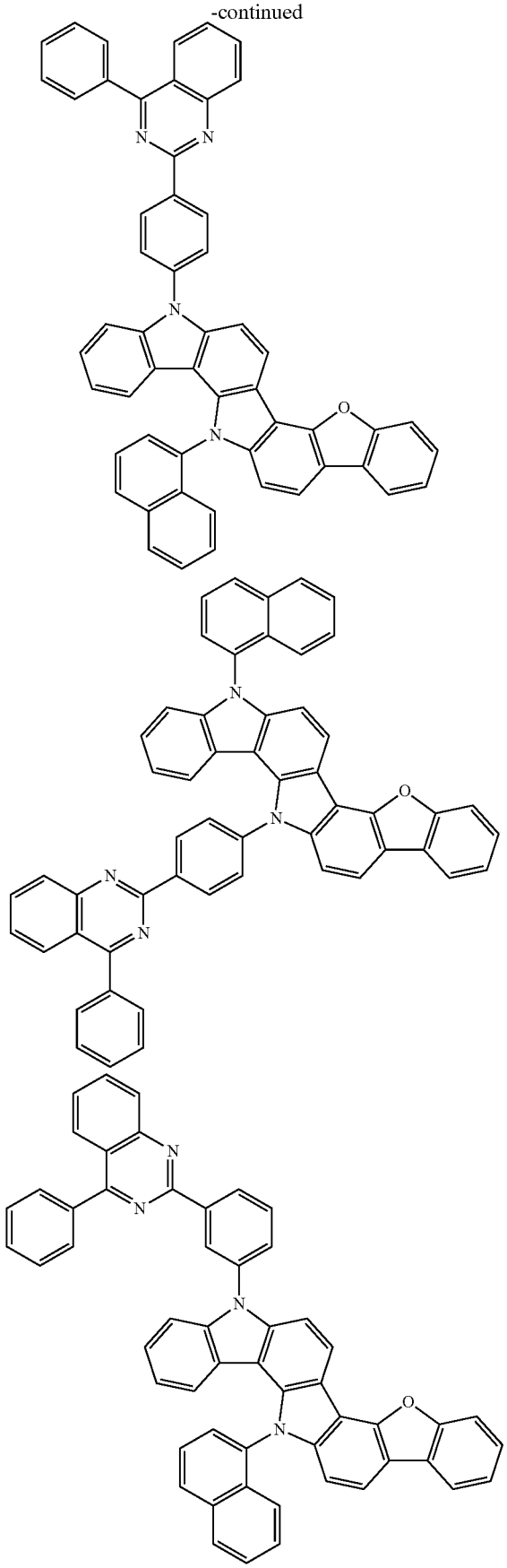
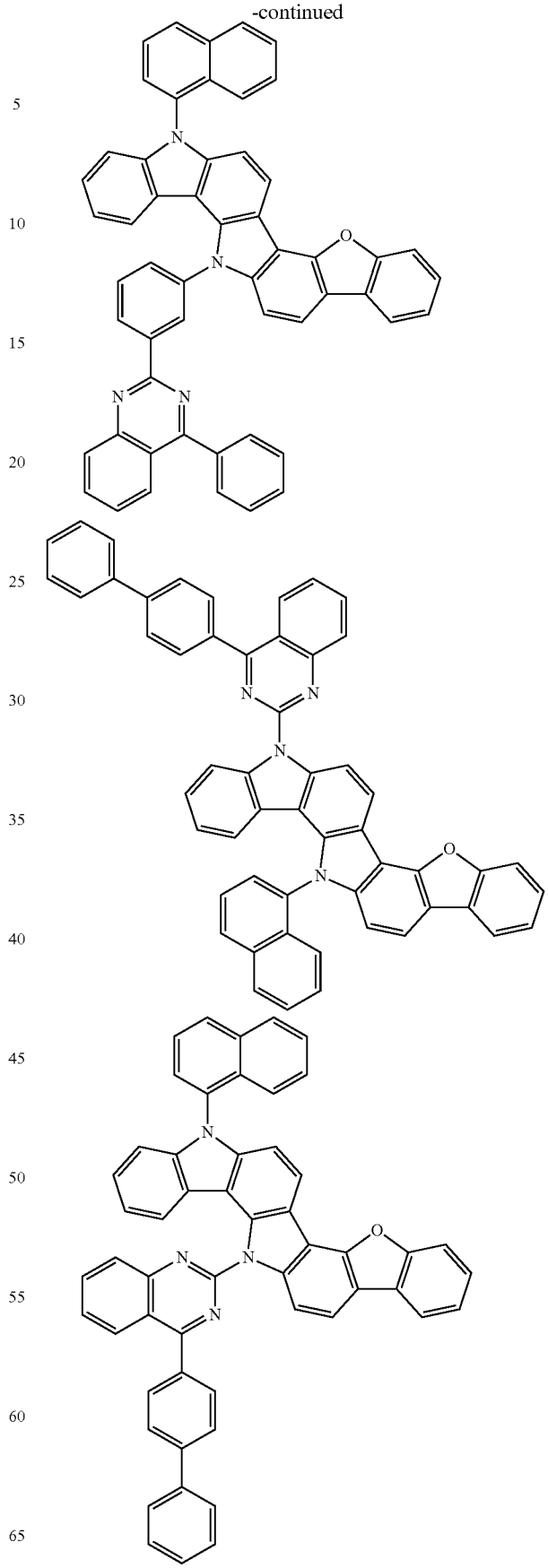

-continued
301
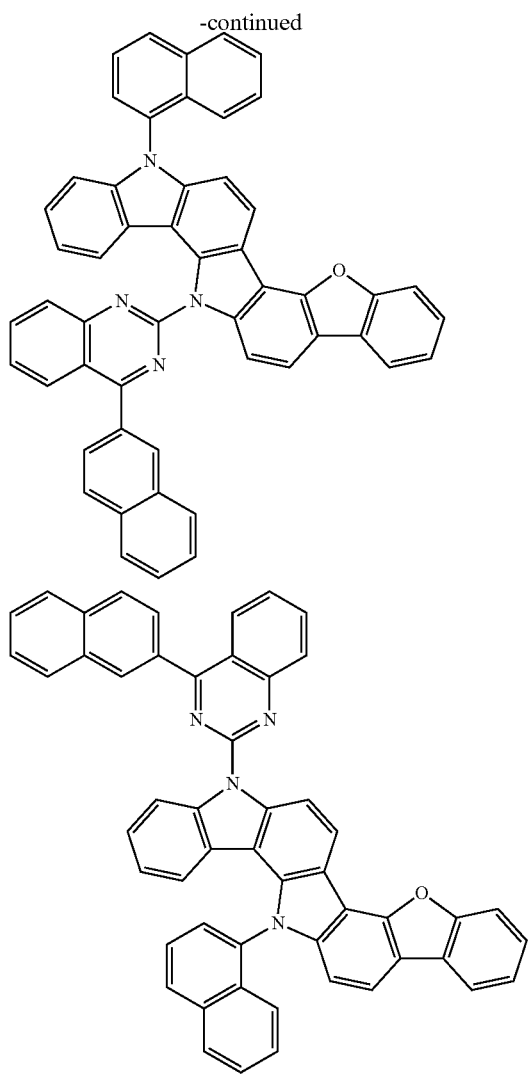
302
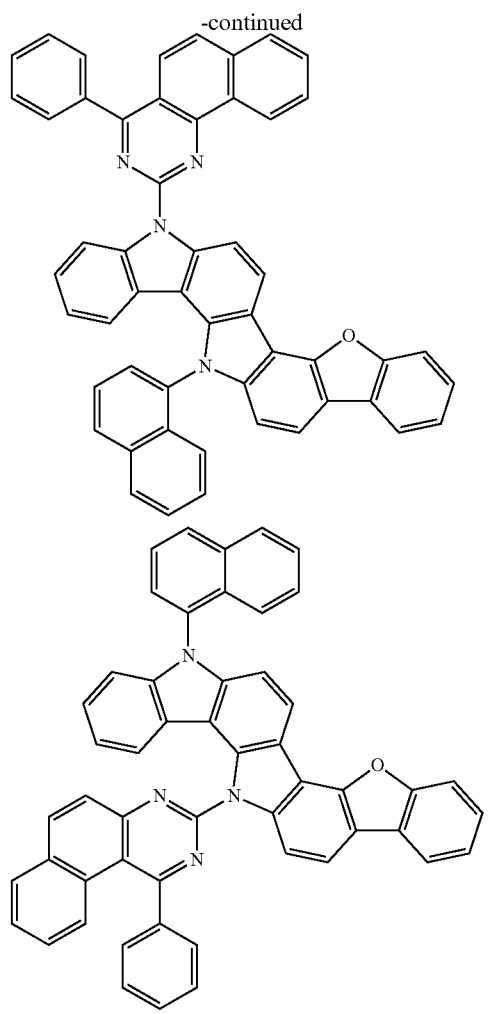
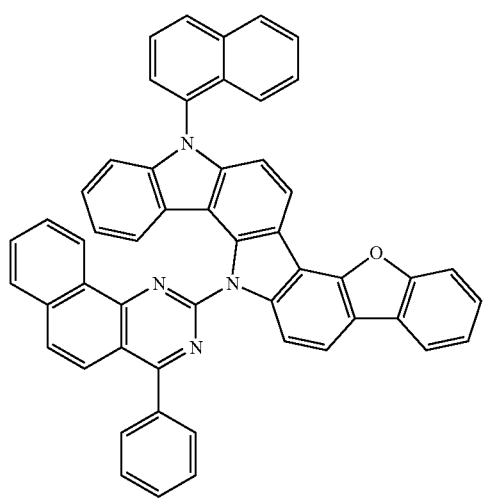
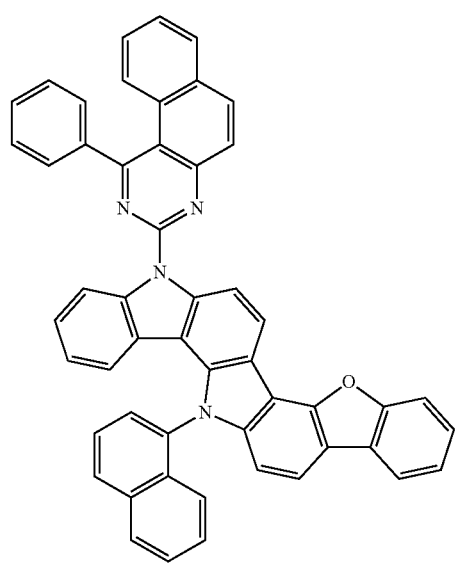

303
-continued
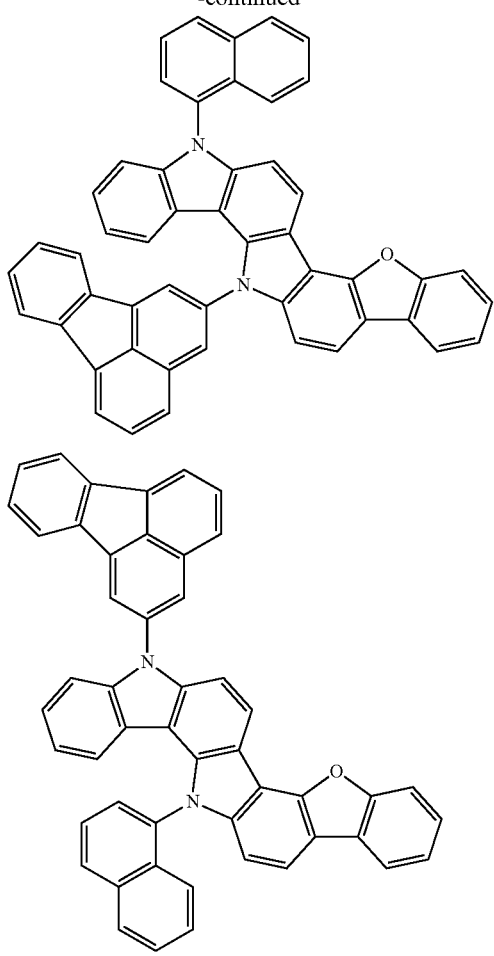
304
-continued
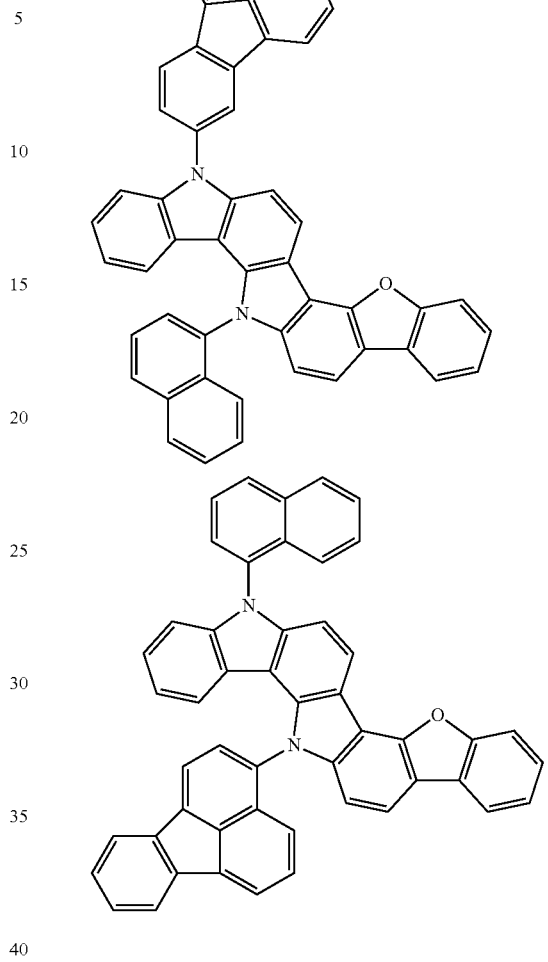
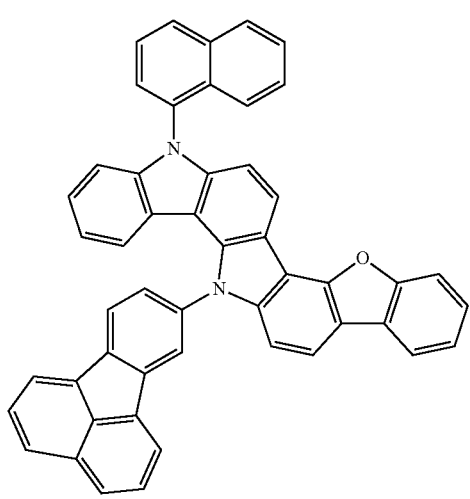
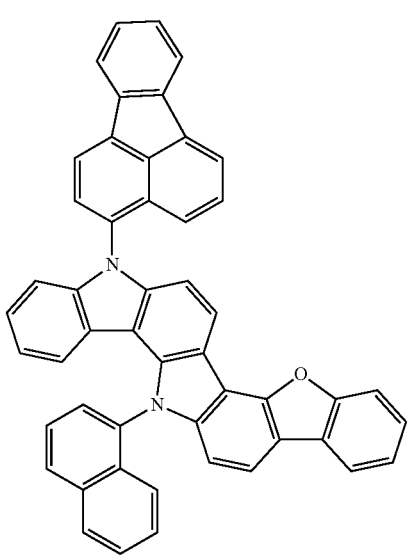

305
-continued
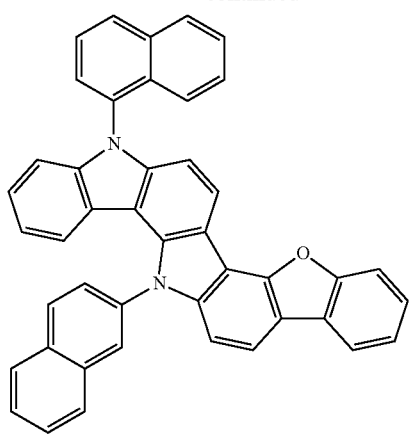
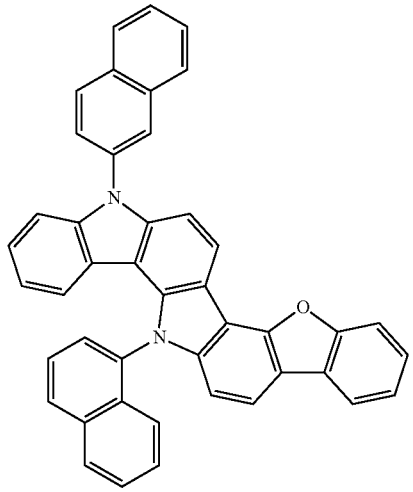
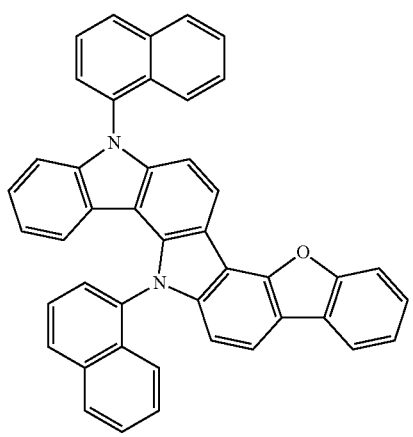
306
-continued
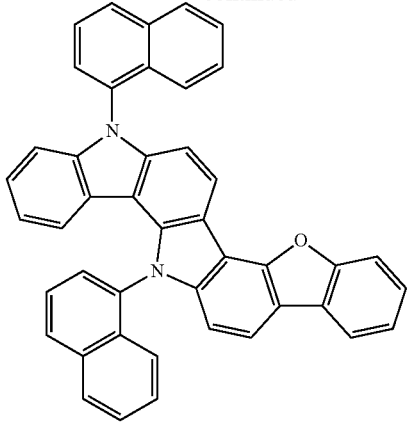
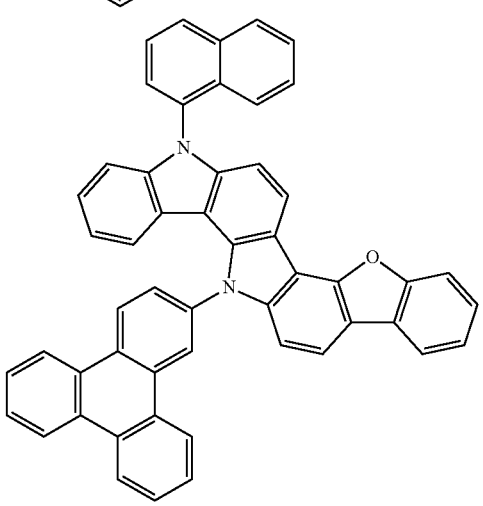
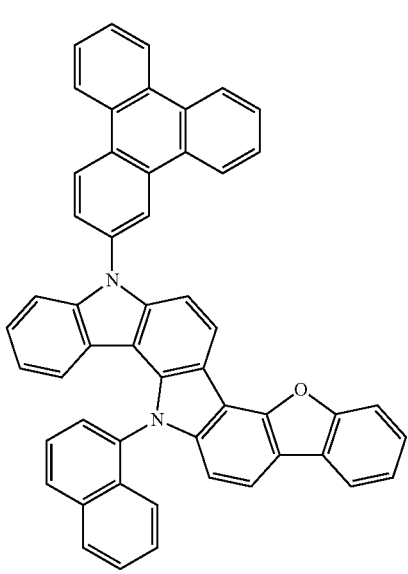

307
-continued
308
-continued
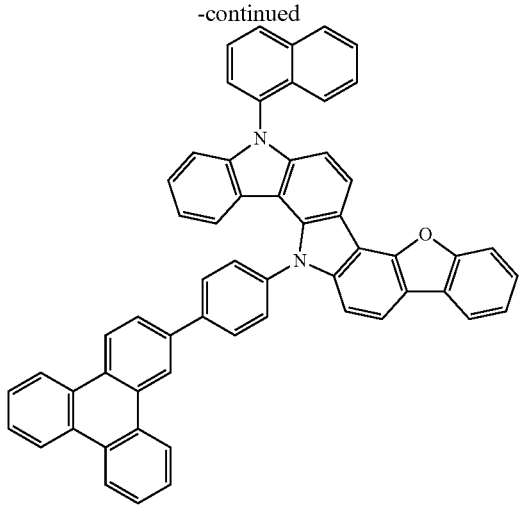
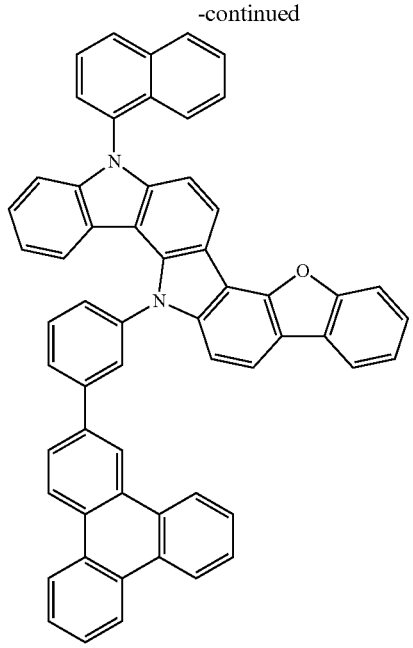
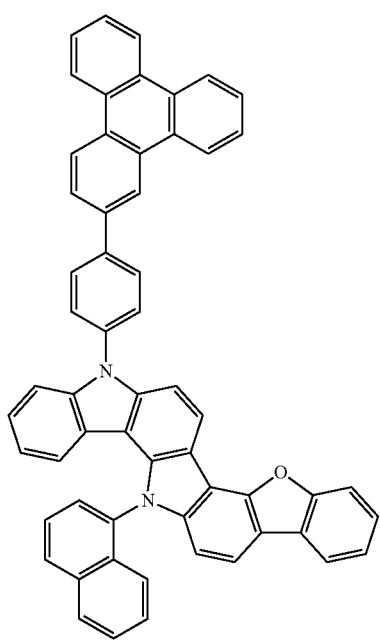

309
-continued
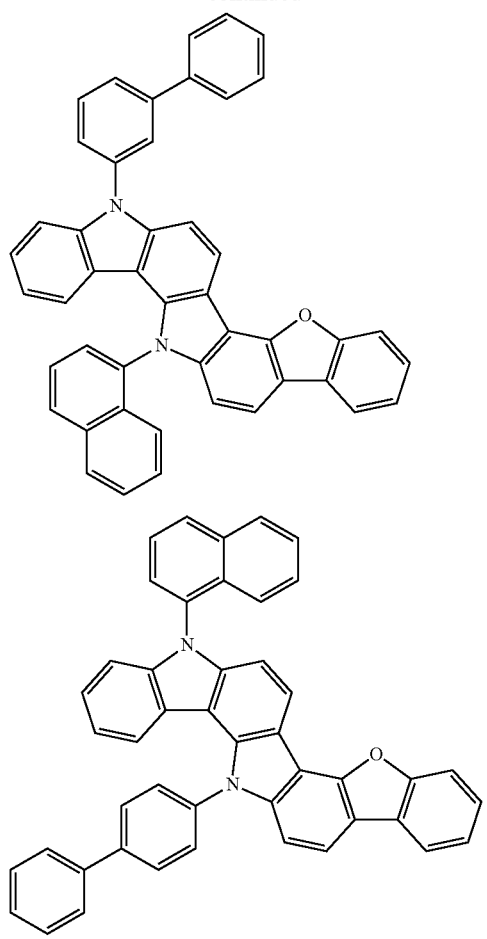
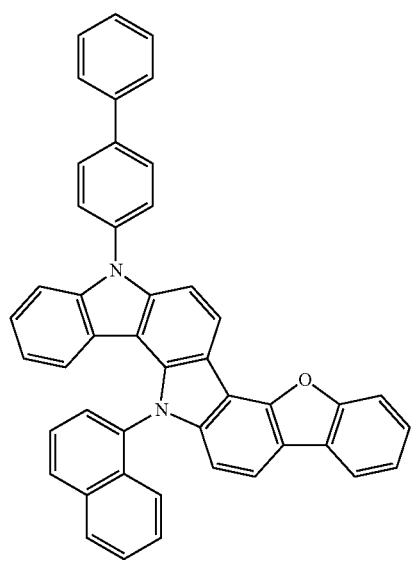
310
-continued
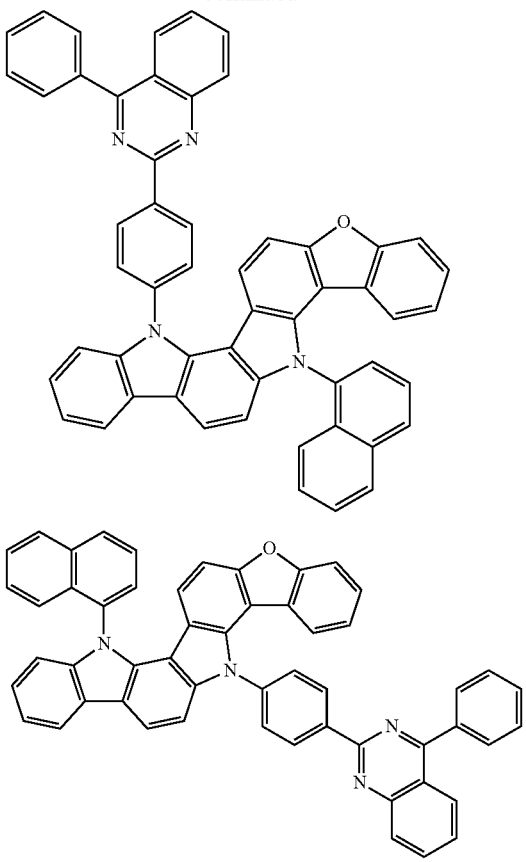
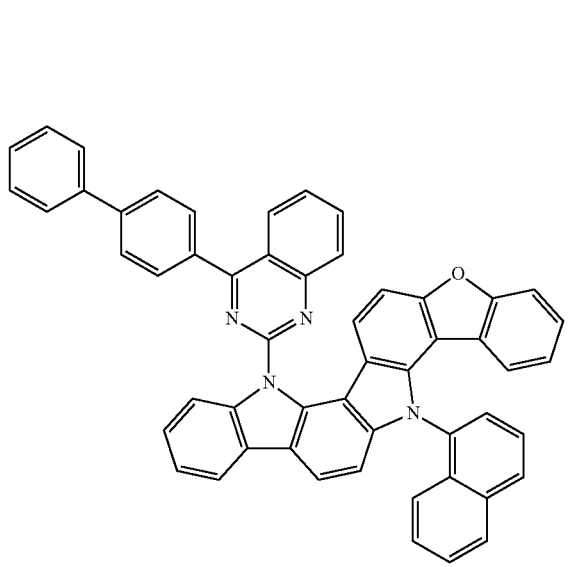

311
-continued
312
-continued
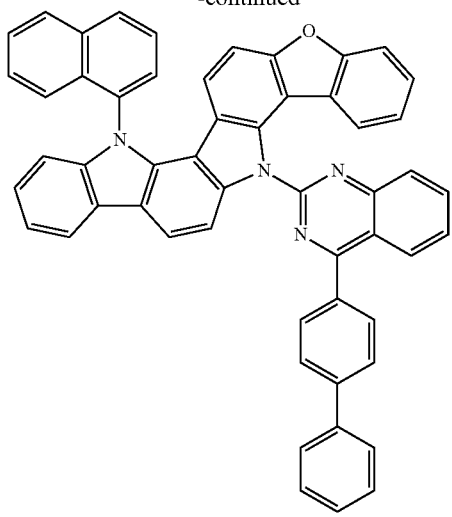
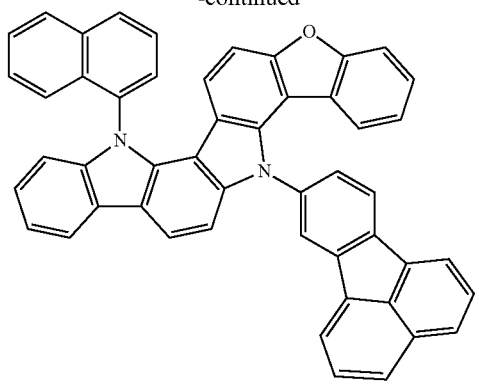
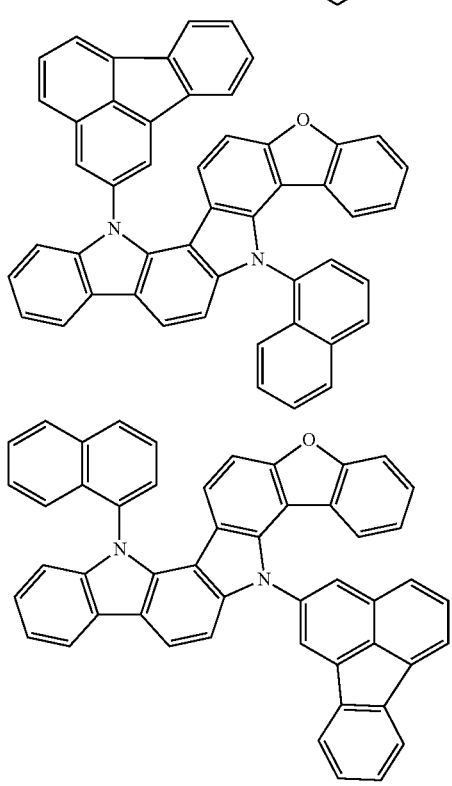
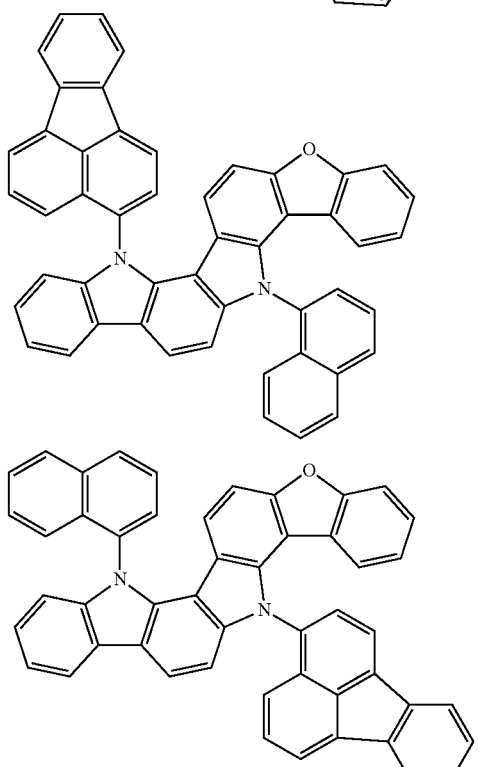
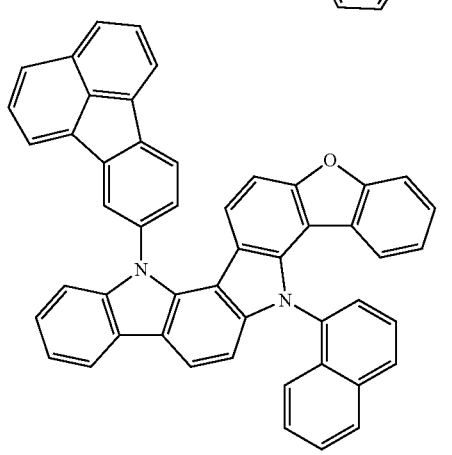
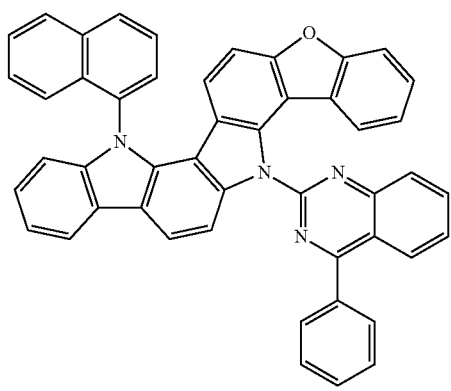

313
-continued
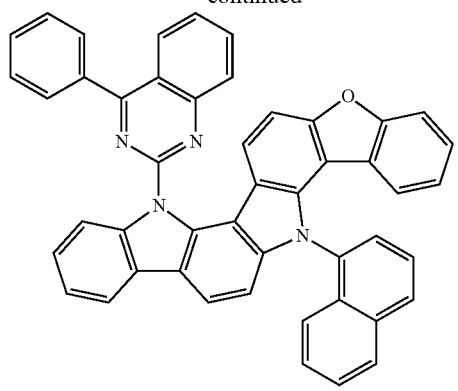
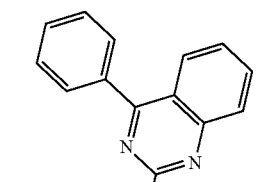
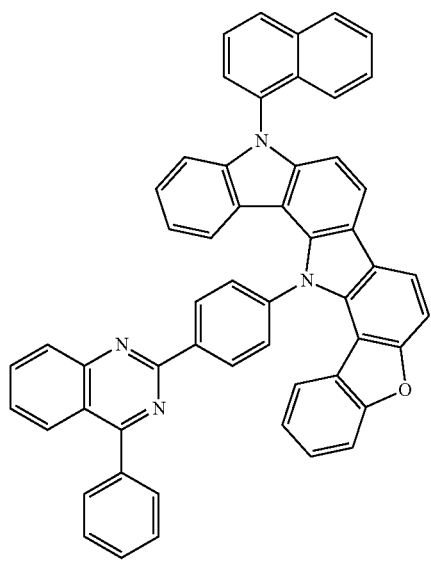
314
-continued
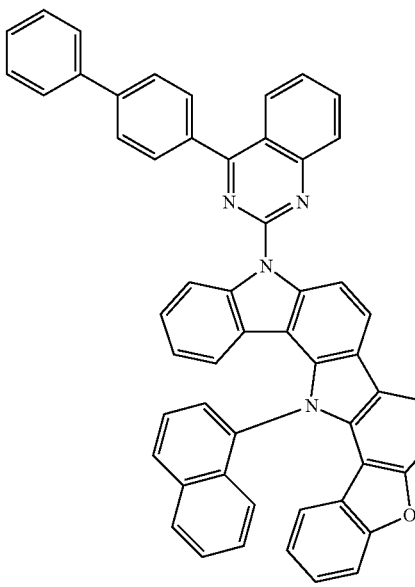
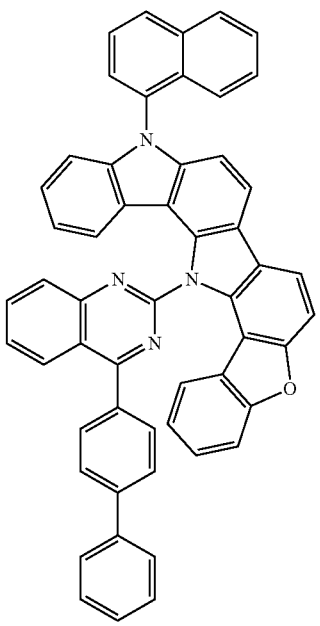

315
-continued
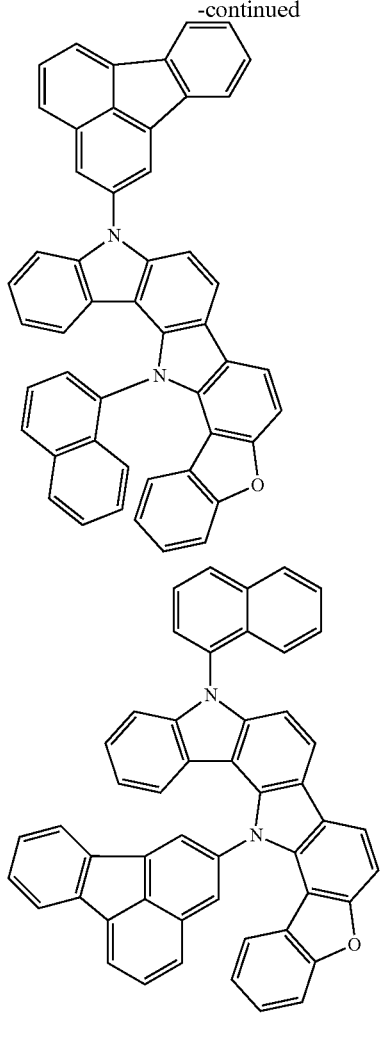
316
-continued
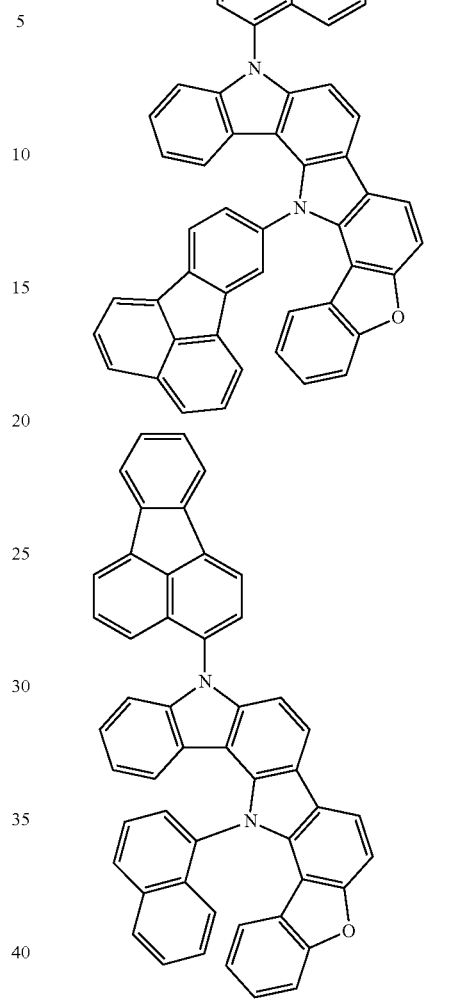
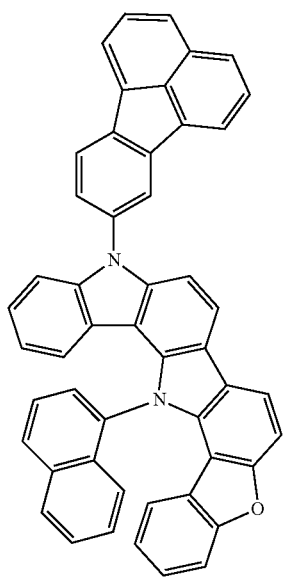
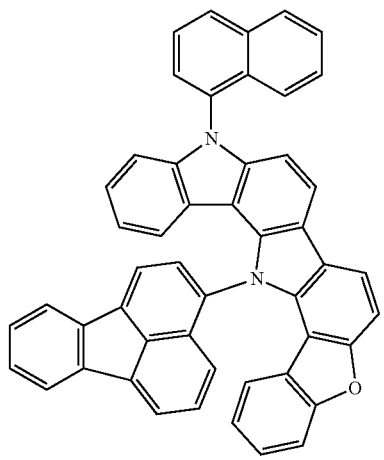

317
-continued
318
-continued
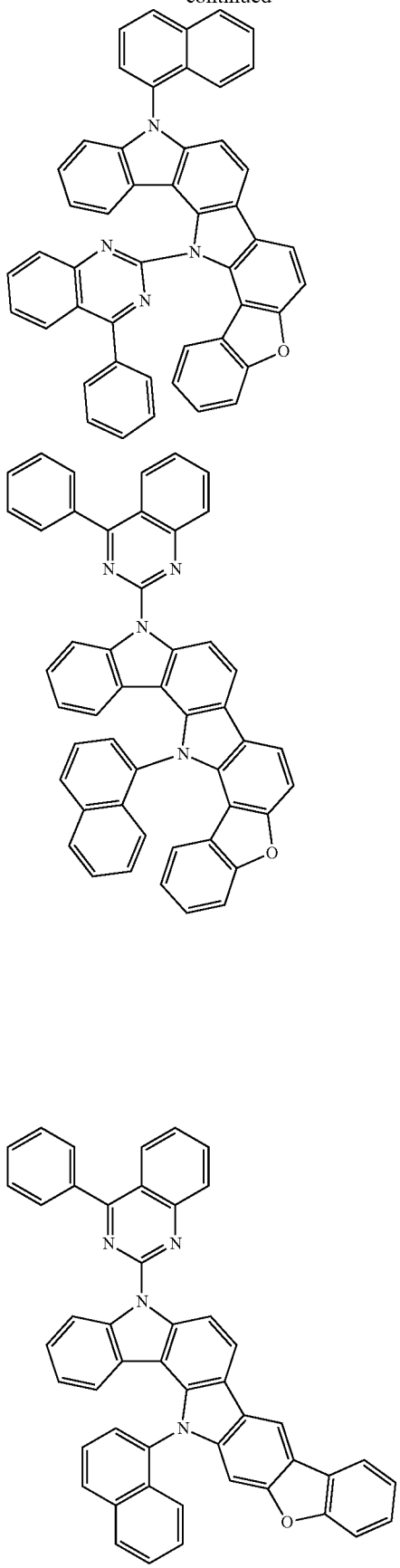
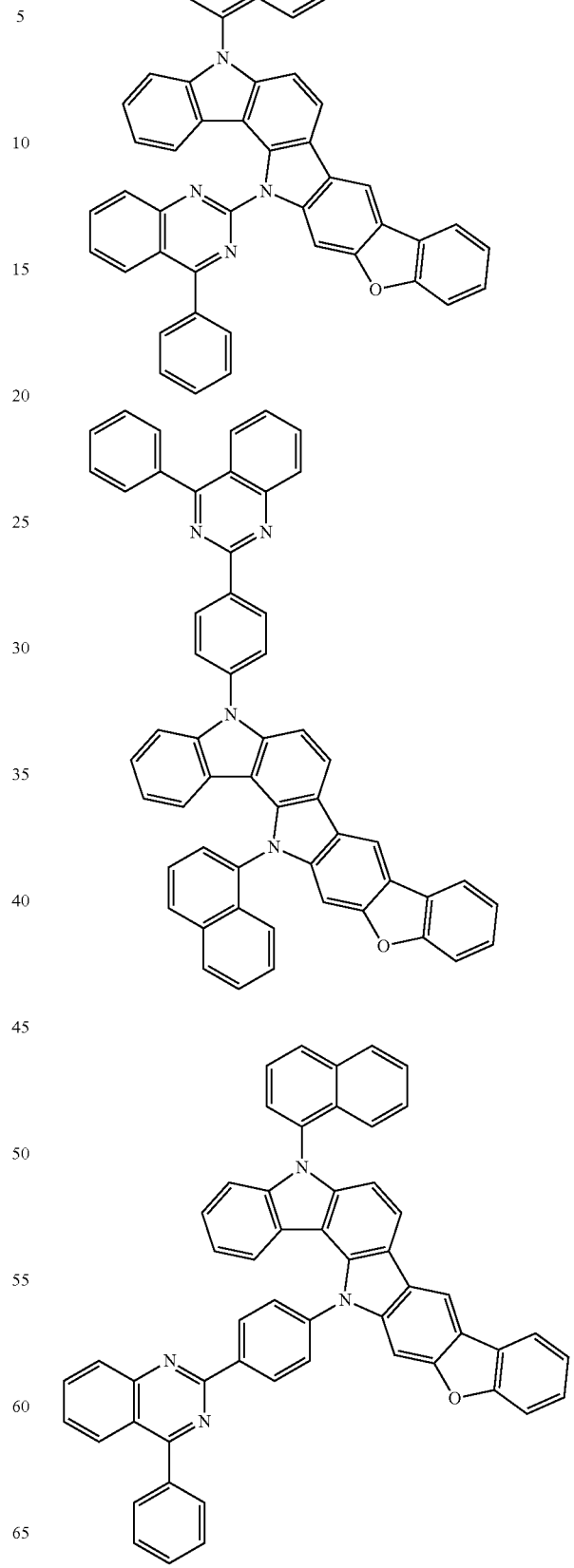

319
-continued
320
-continued
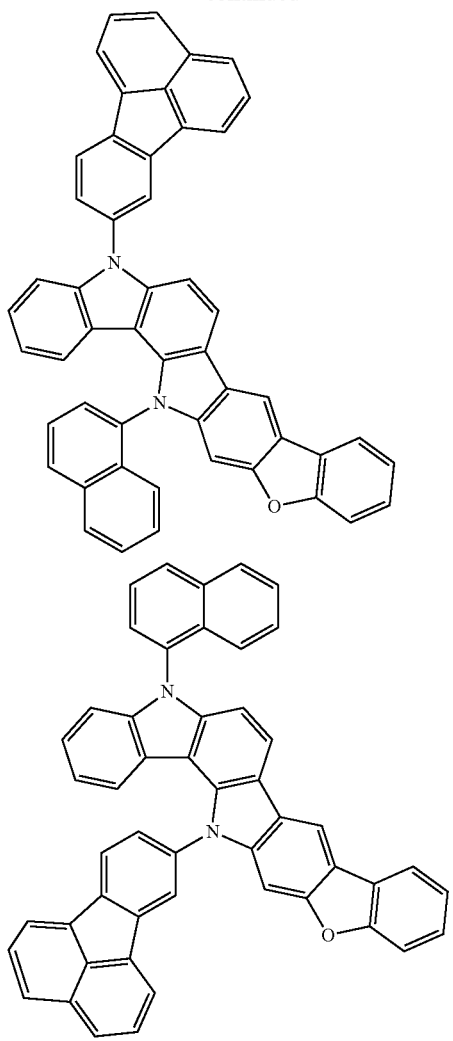
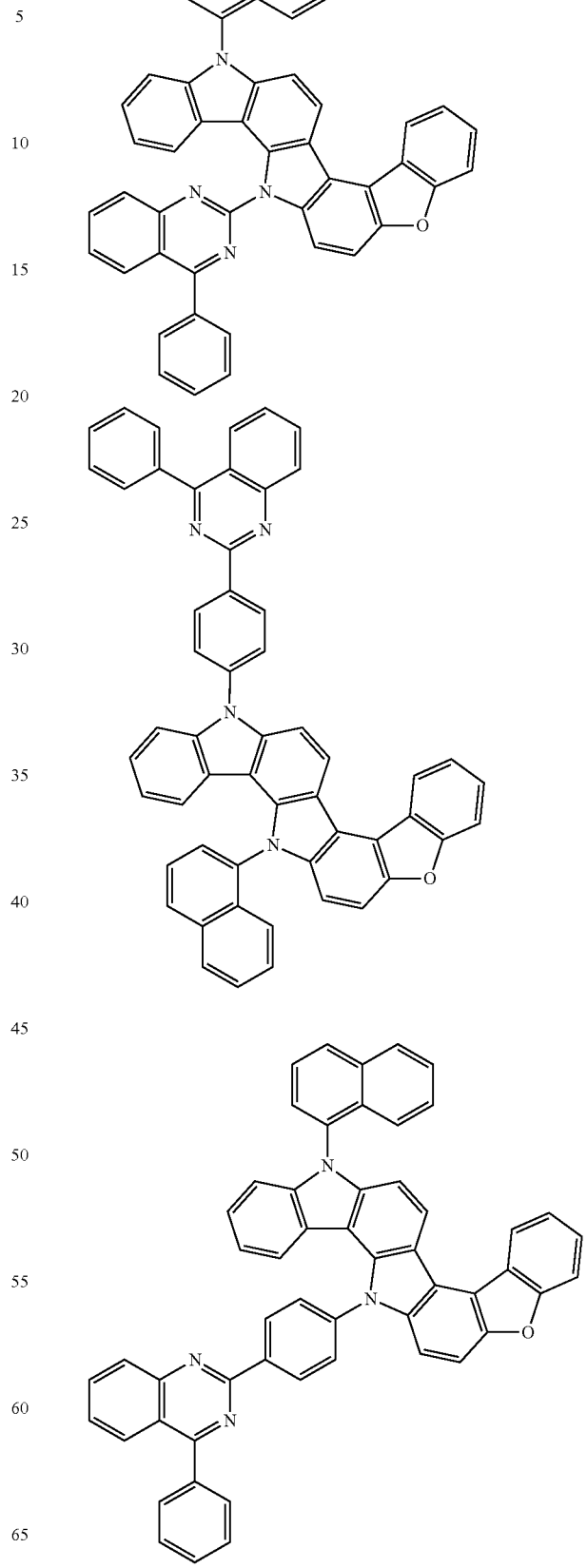

321
-continued
322
-continued
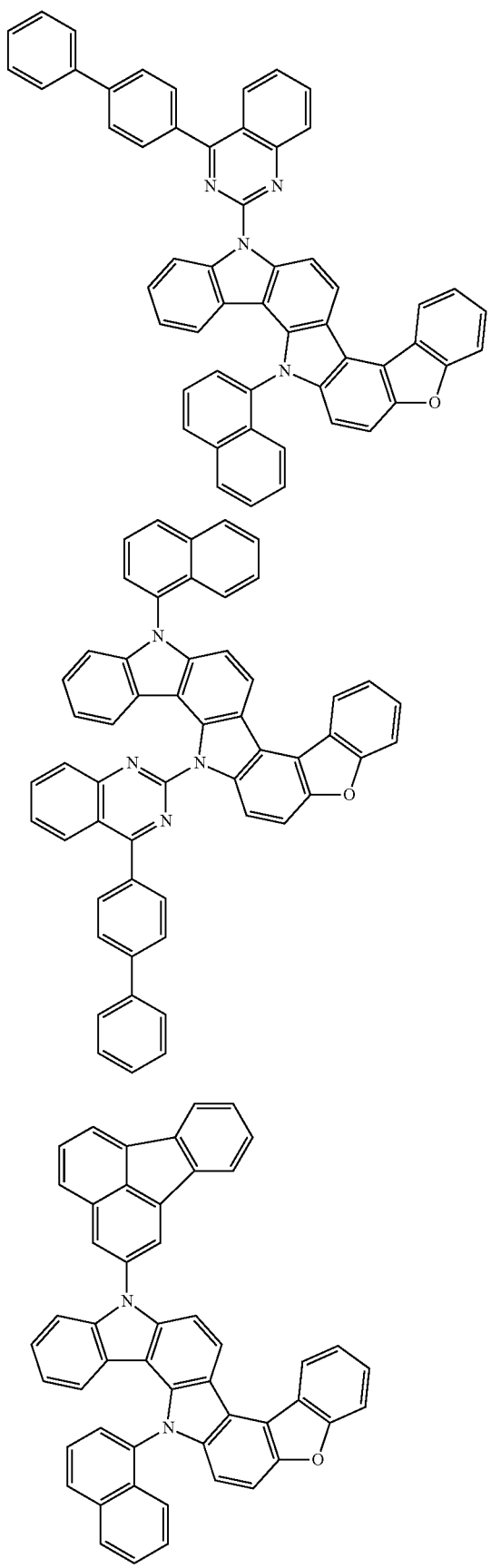
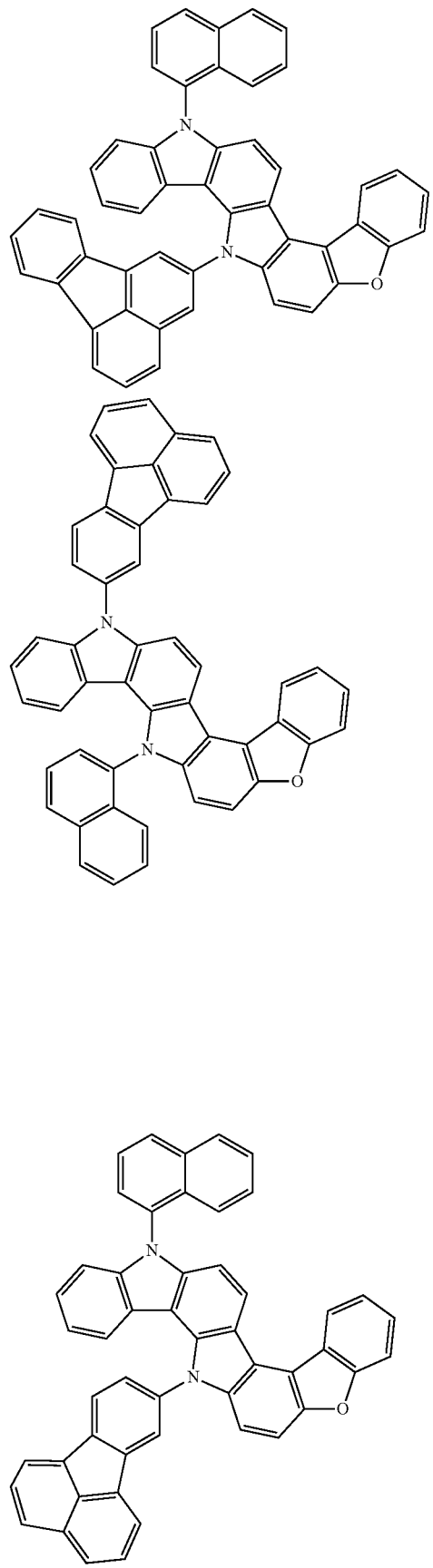

323
-continued
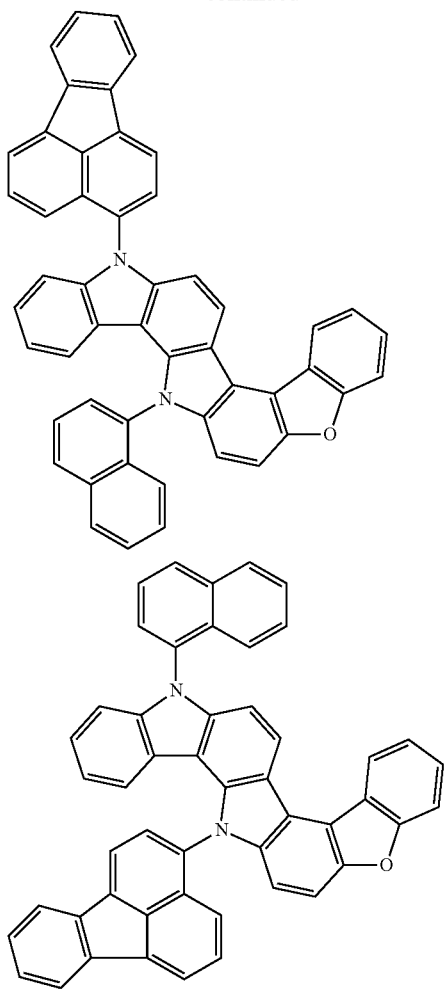
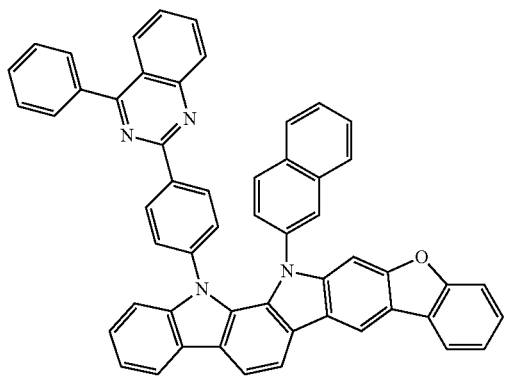
324
-continued
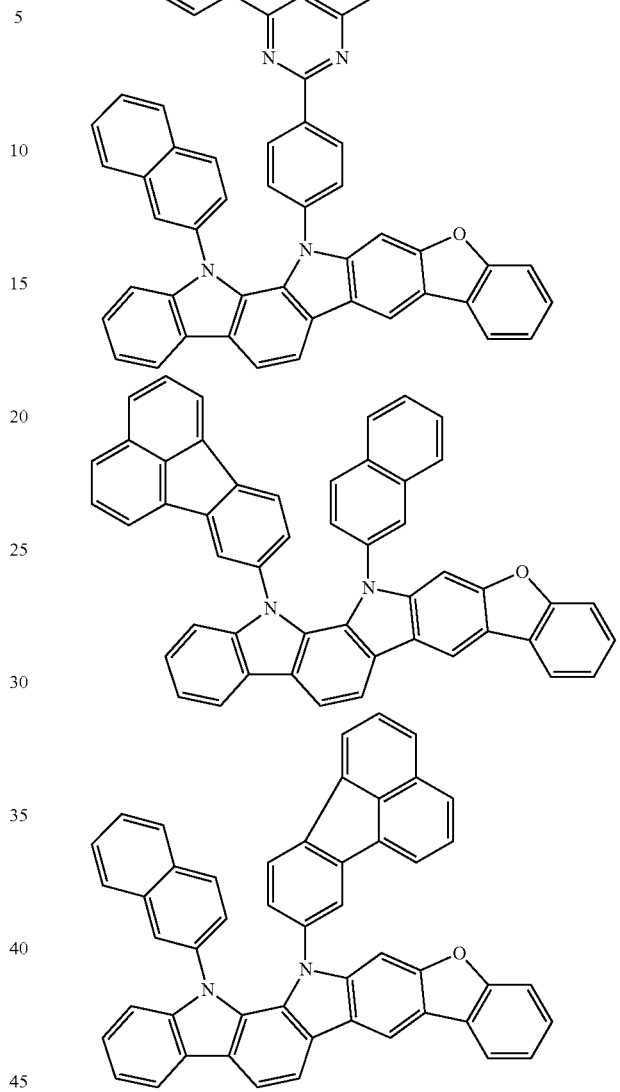
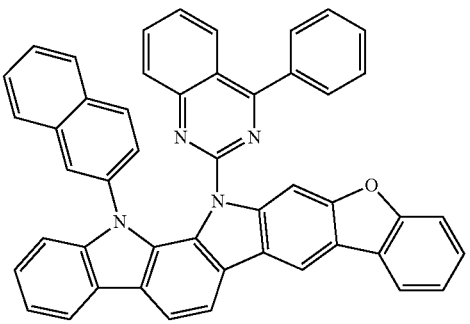

325
-continued
326
-continued
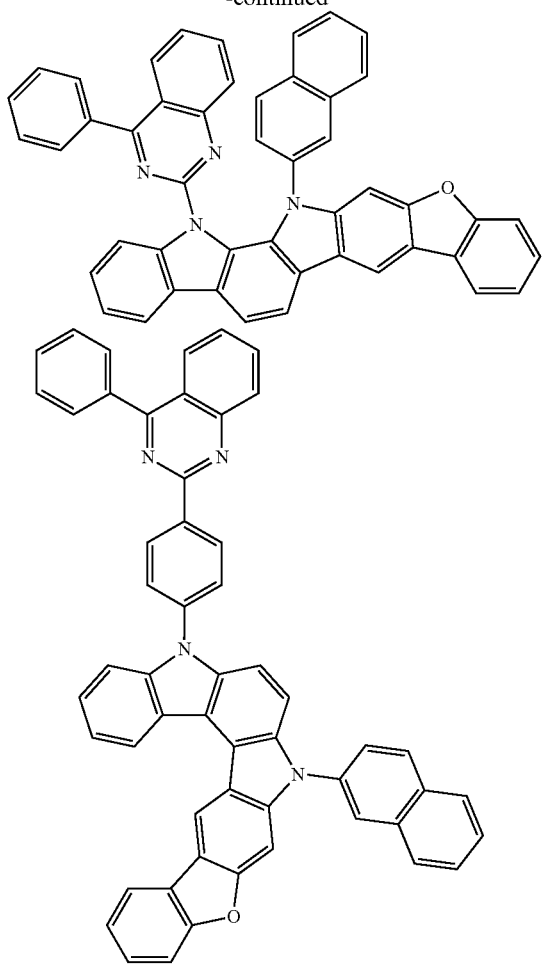
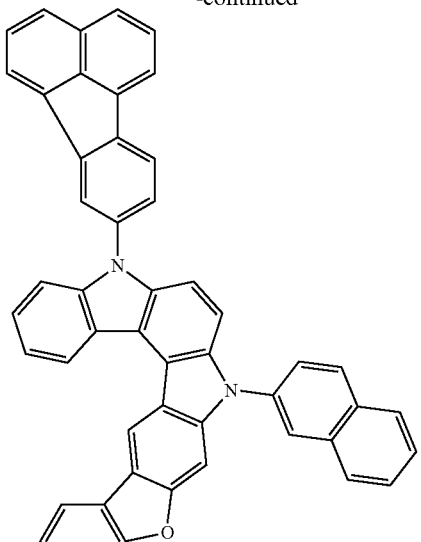
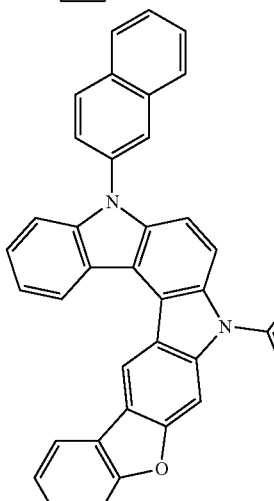
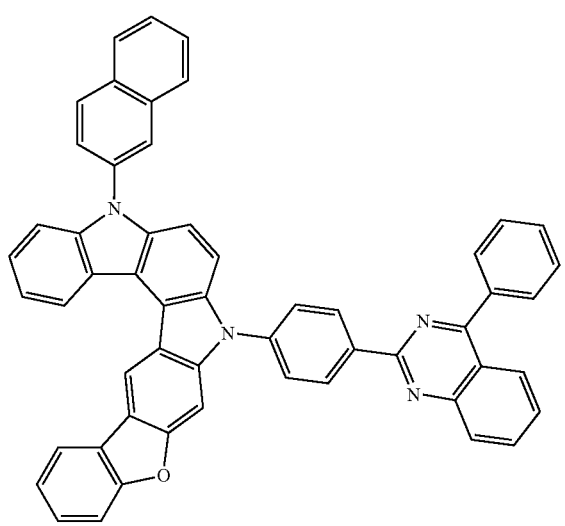
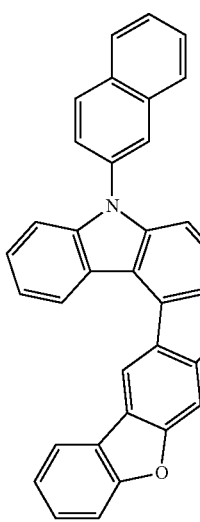

327
-continued
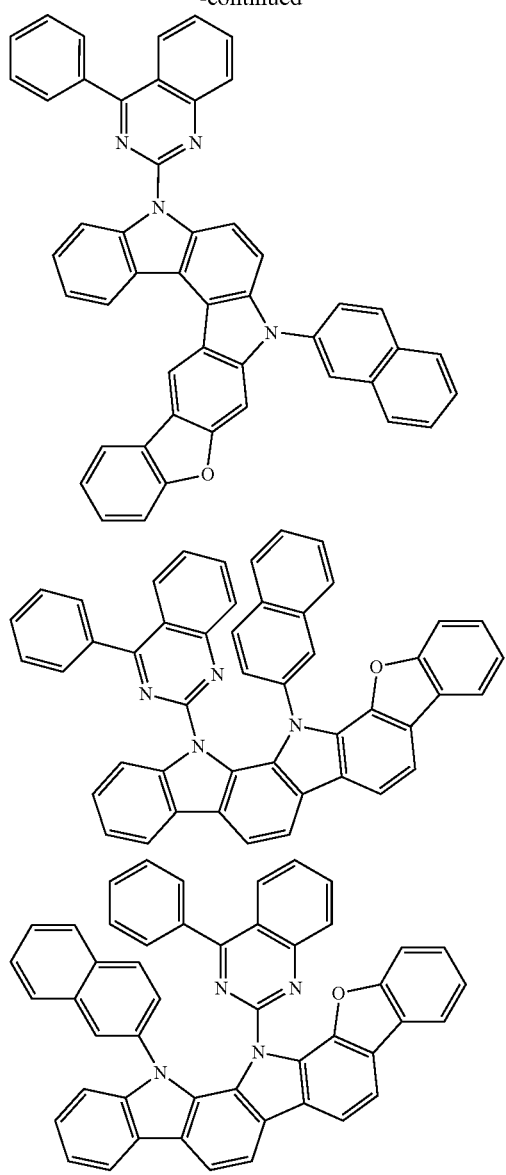
328
-continued
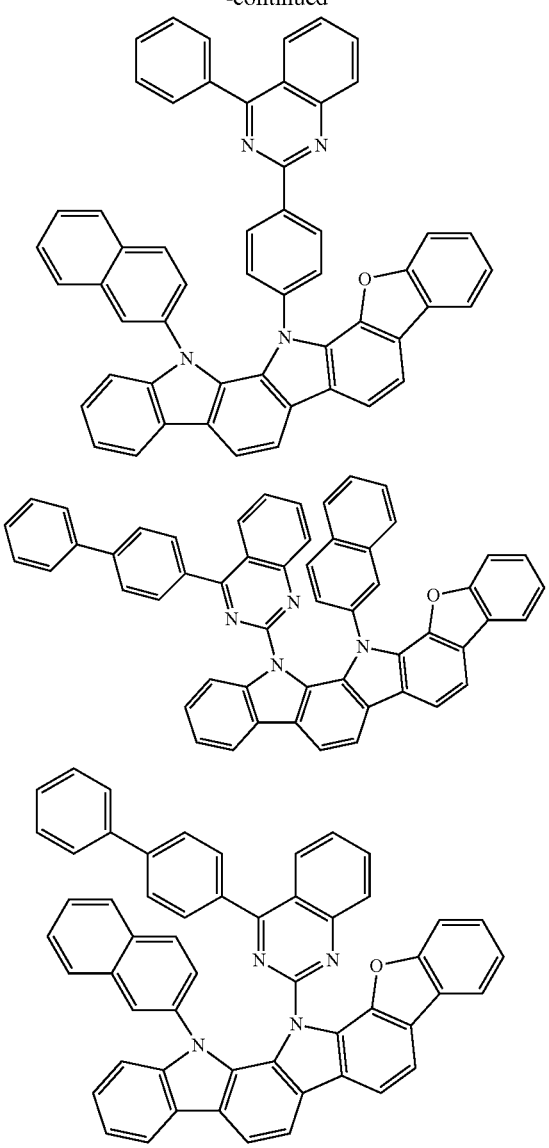
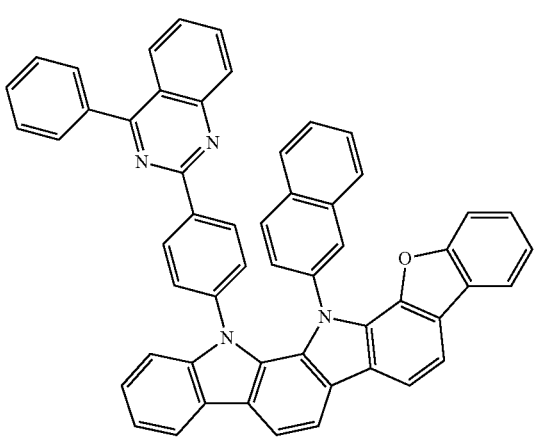
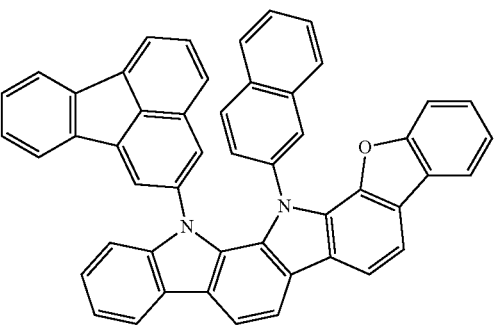

329
-continued
330
-continued
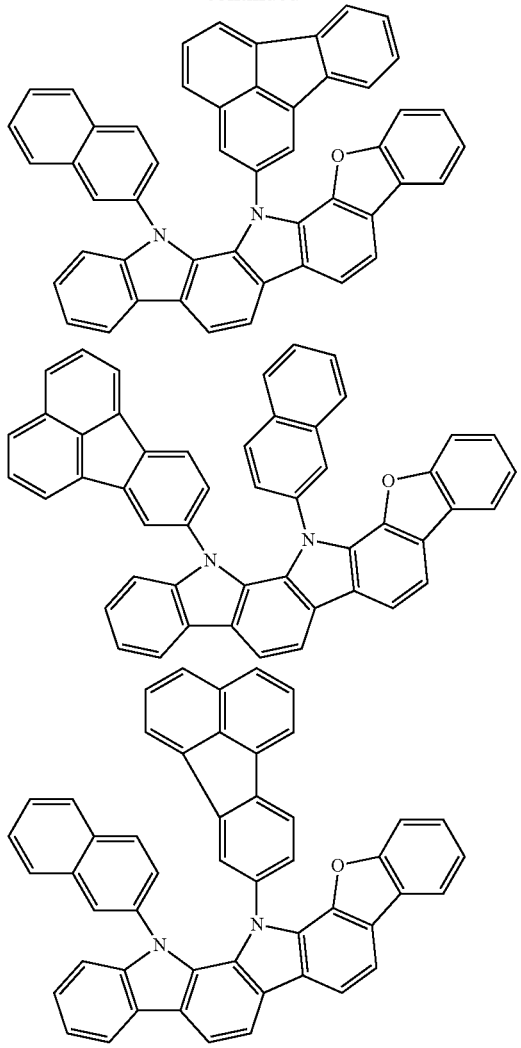
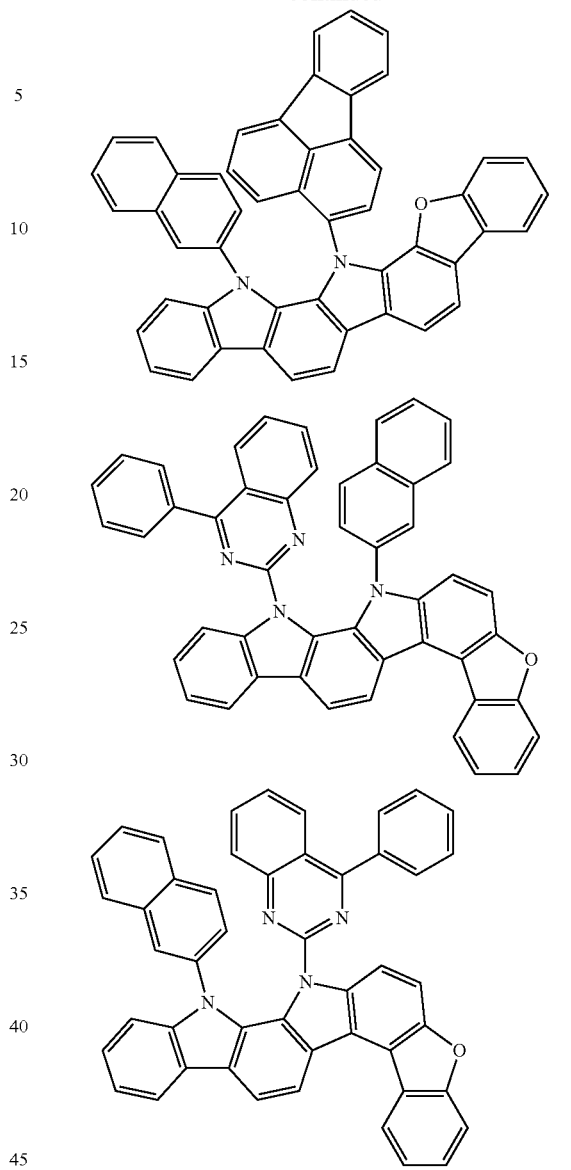
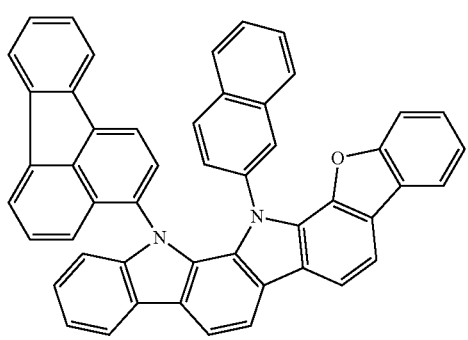
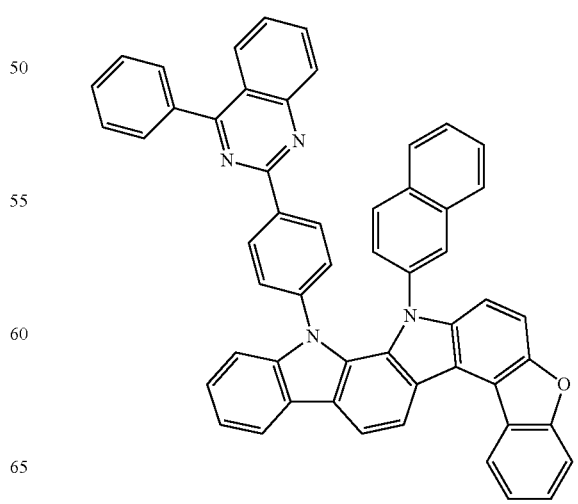

331
-continued
332
-continued
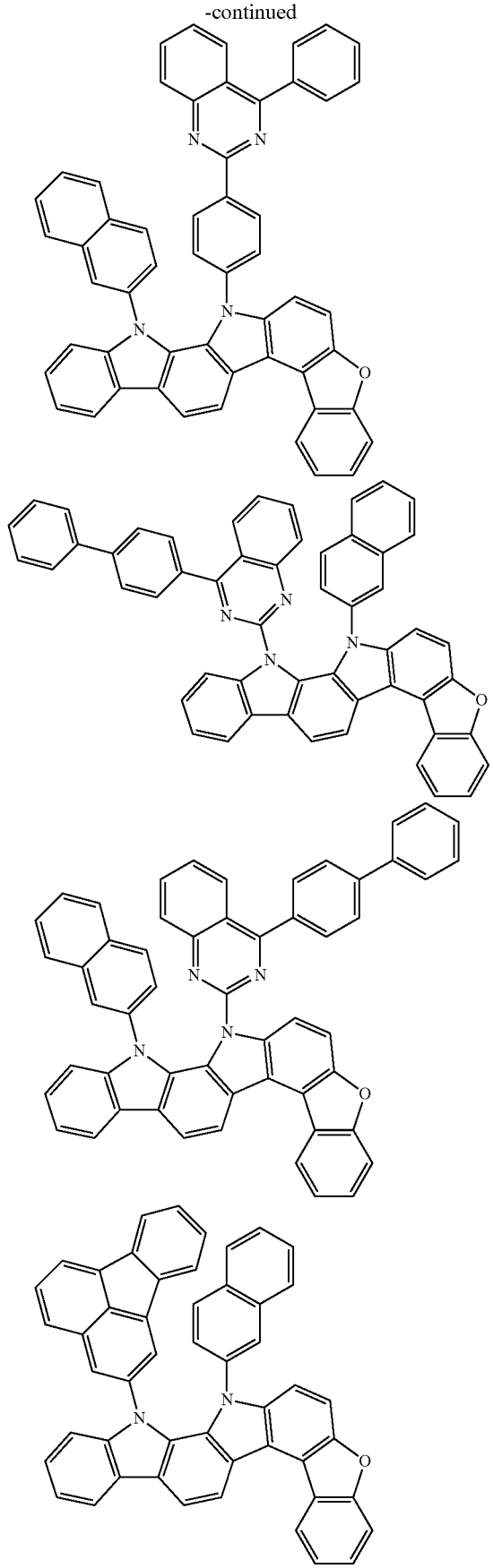
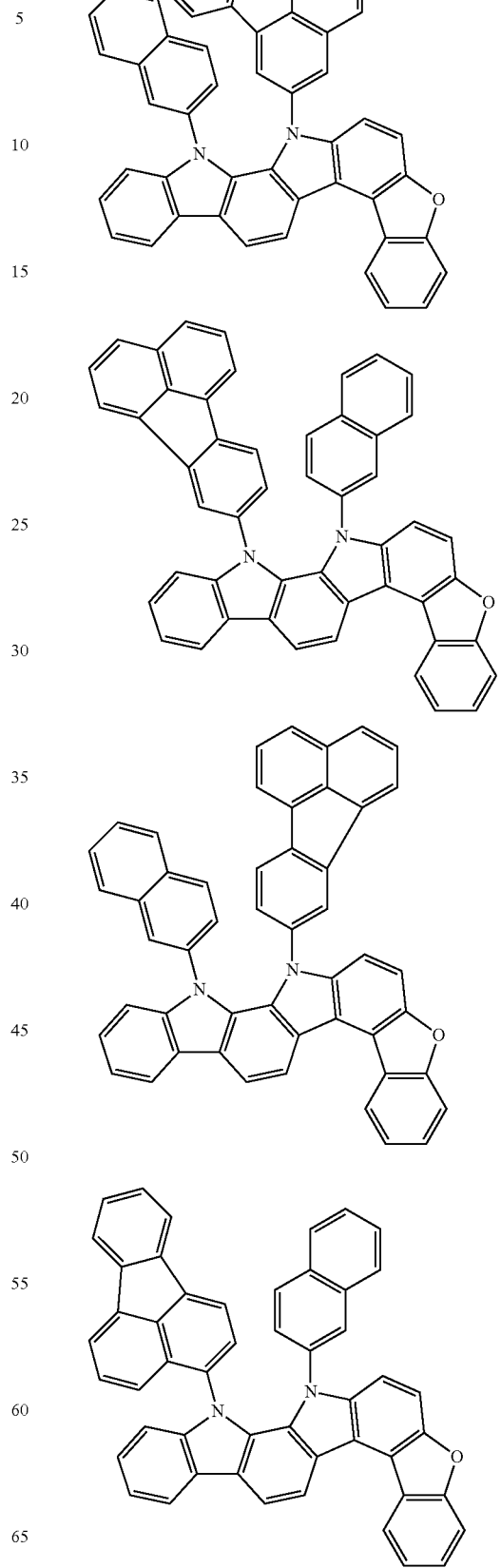

333
-continued
334
-continued
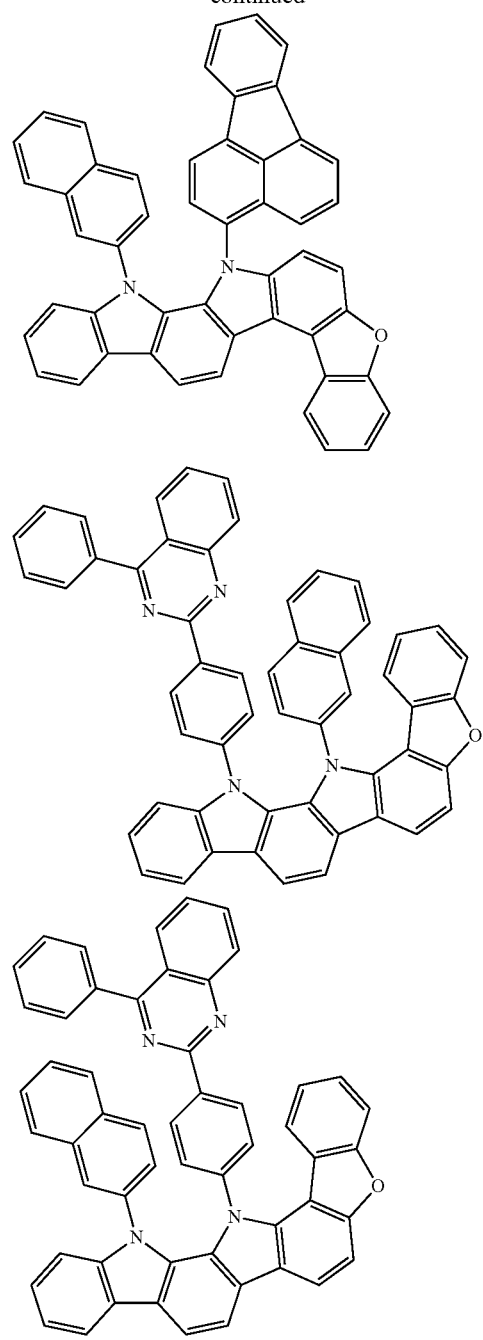
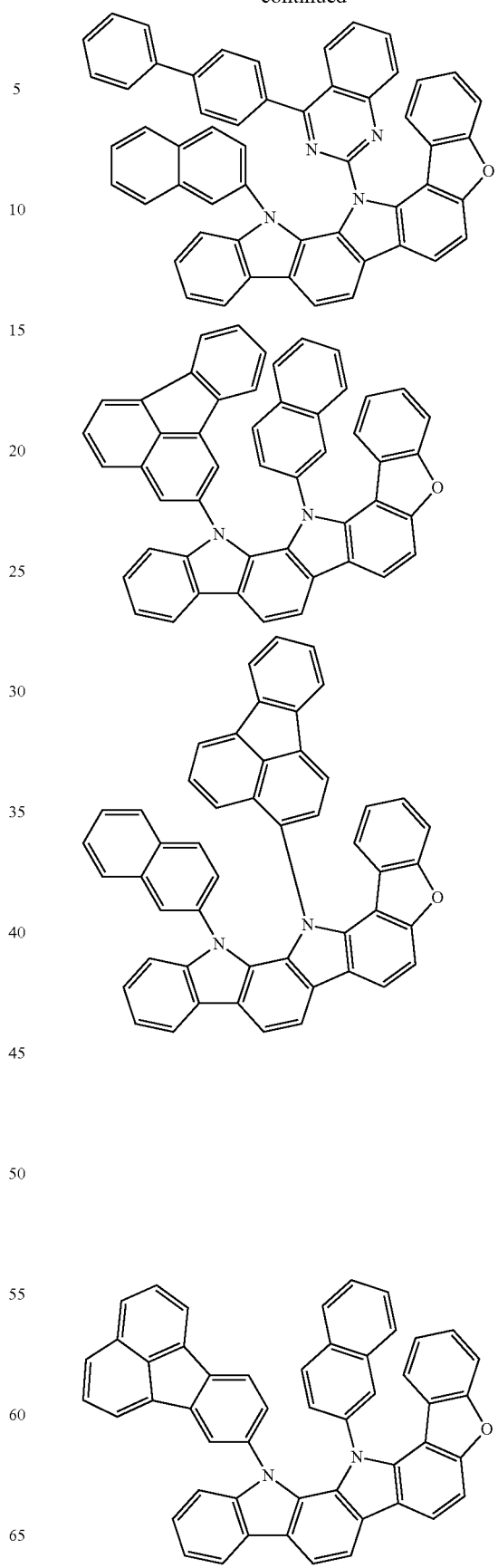

335
-continued
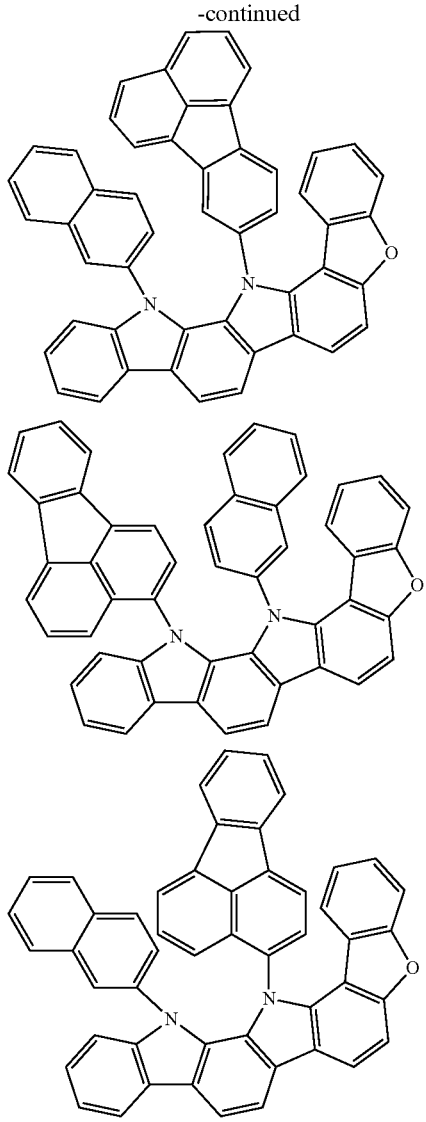
336
-continued
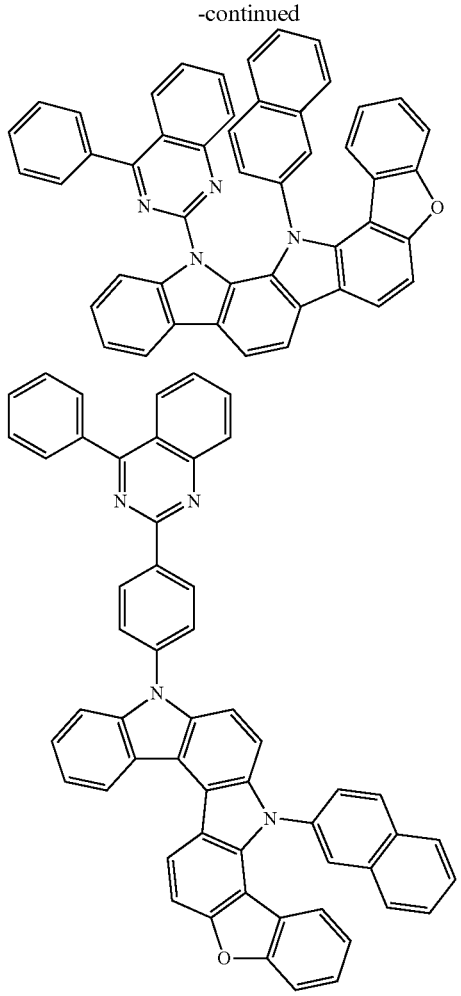
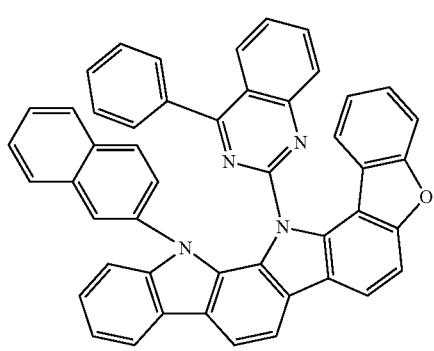
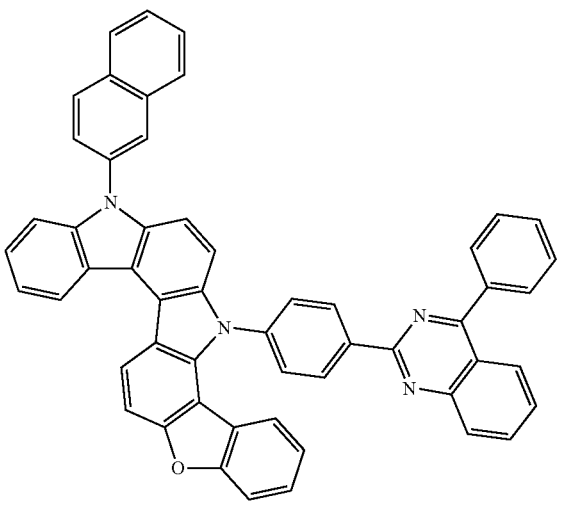

337
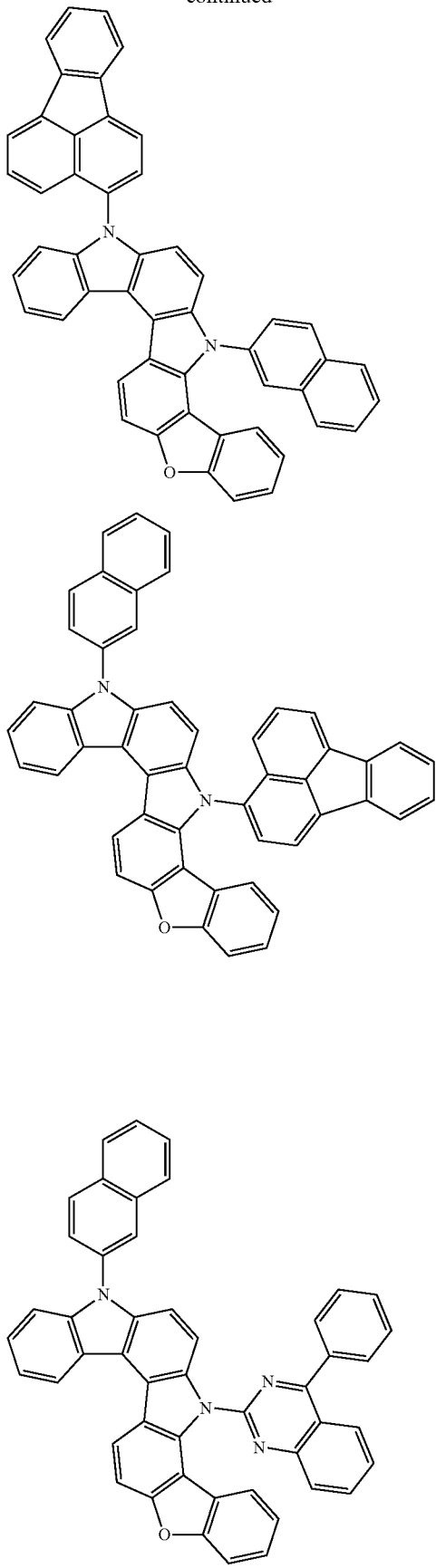
338
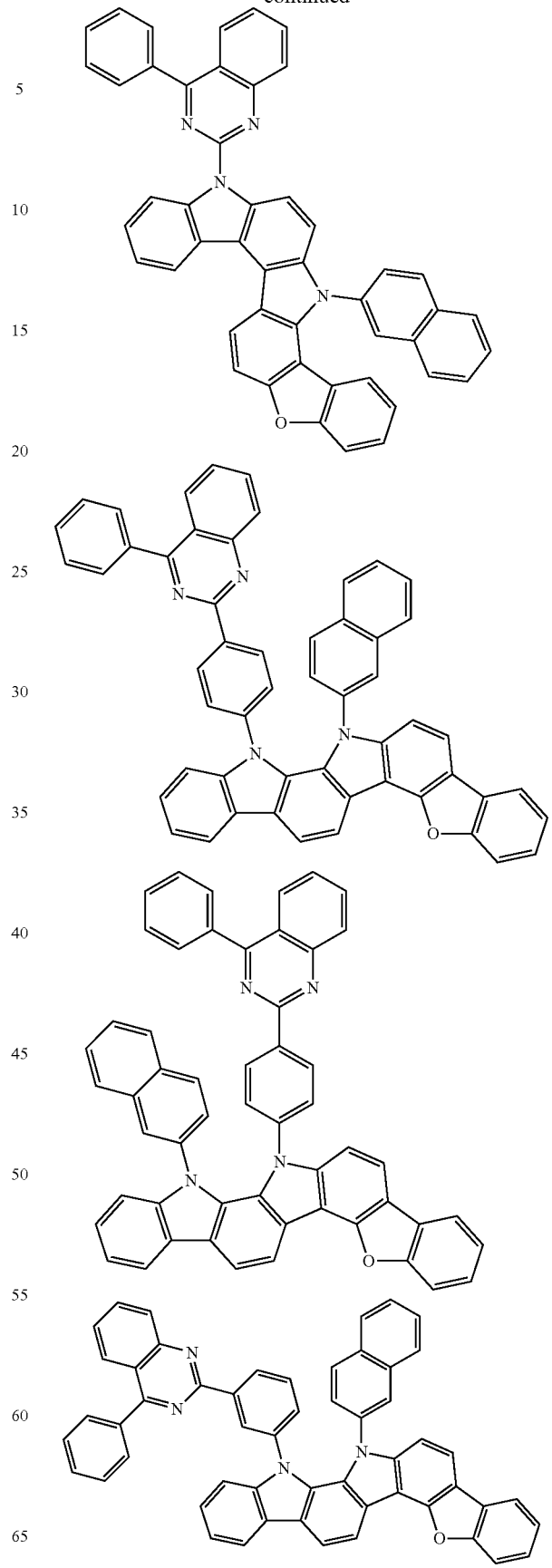

339
-continued
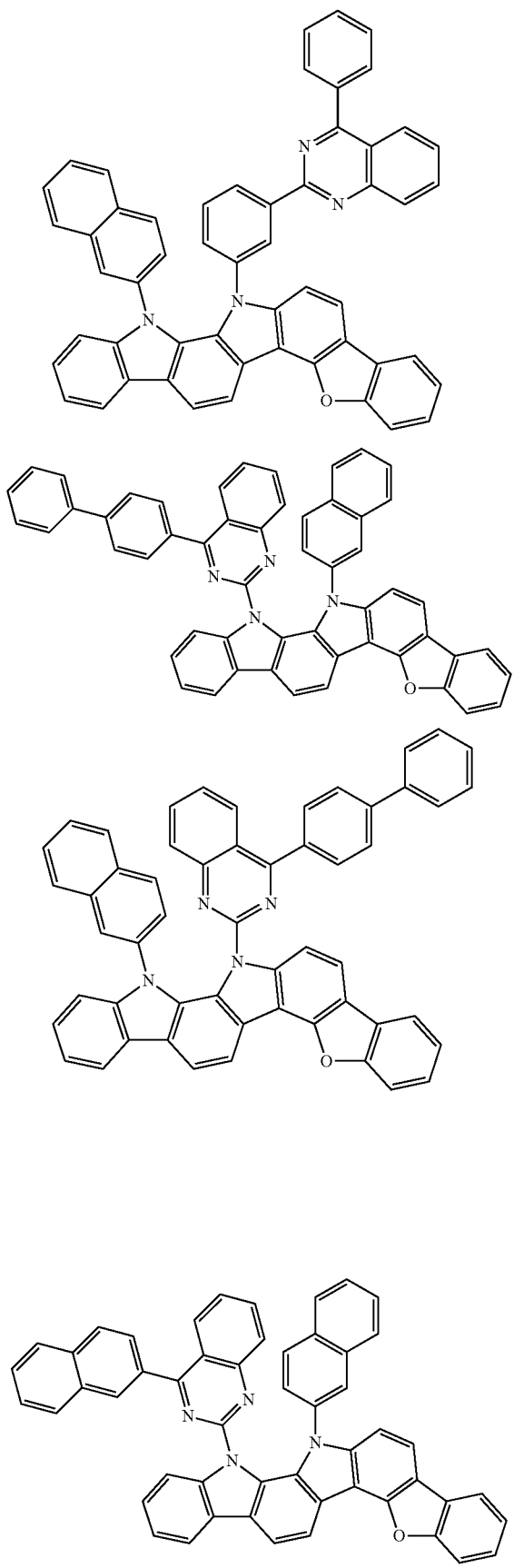
340
-continued
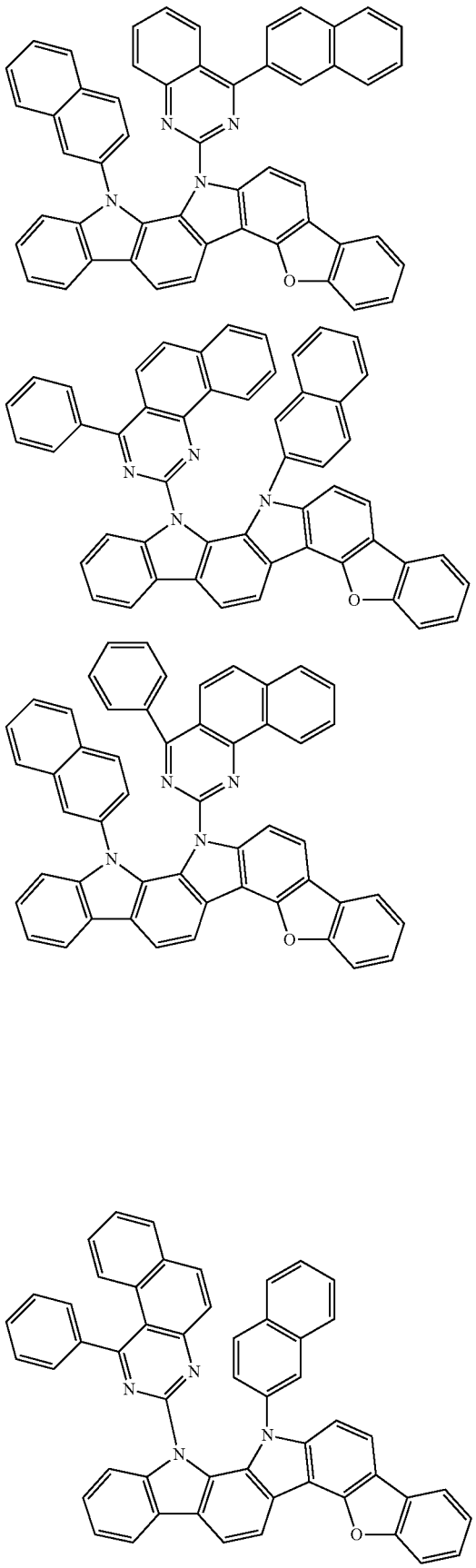

341
-continued
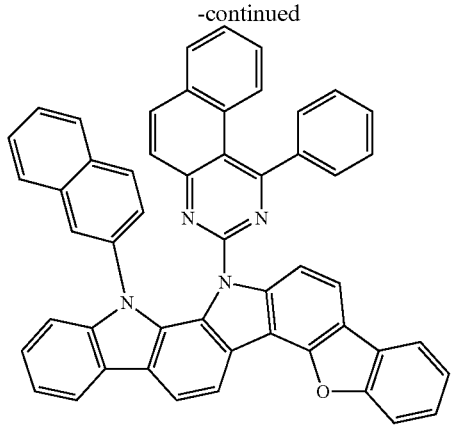
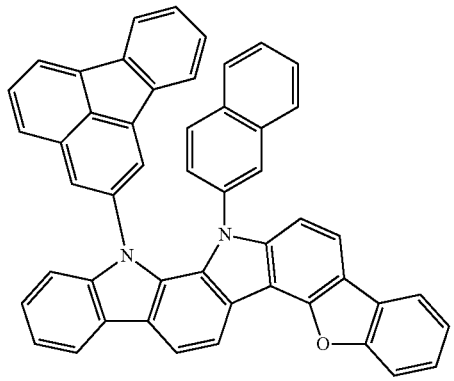
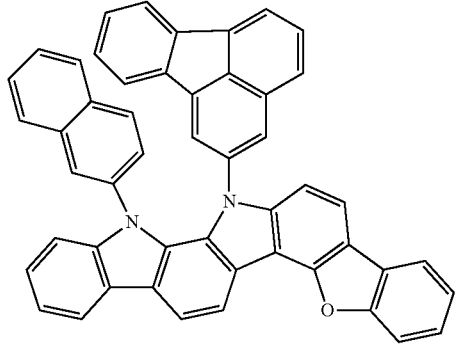
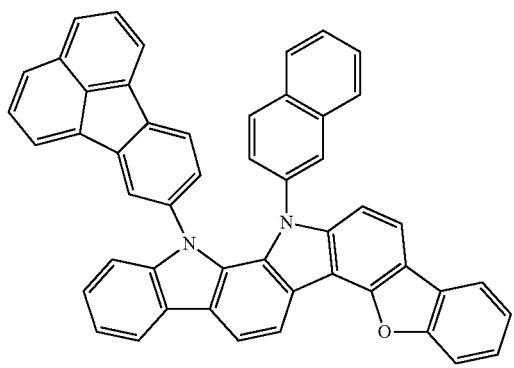
342
-continued
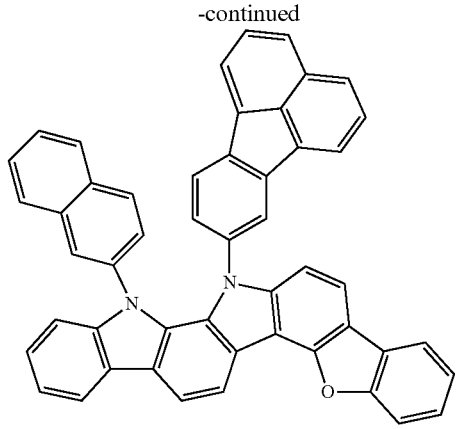
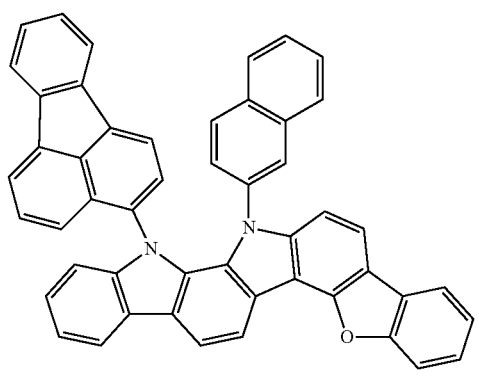
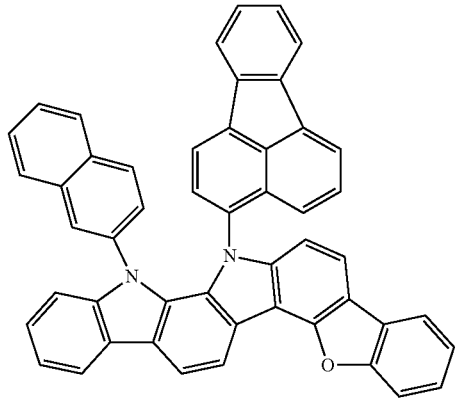
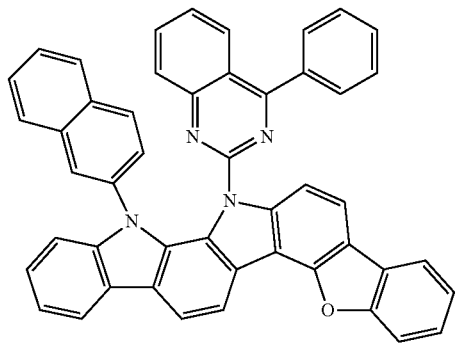

343
-continued
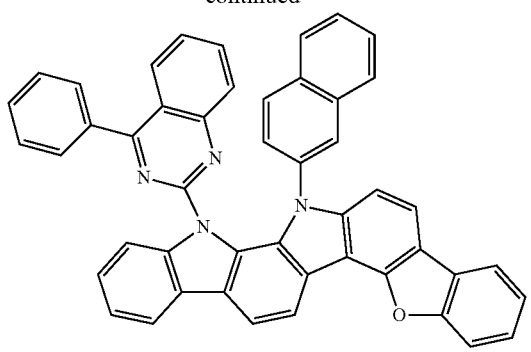
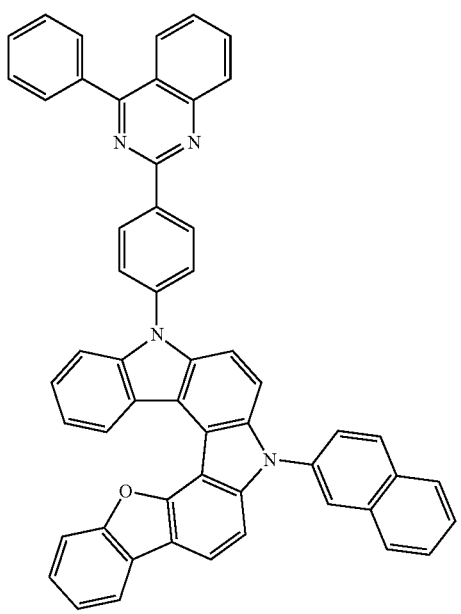
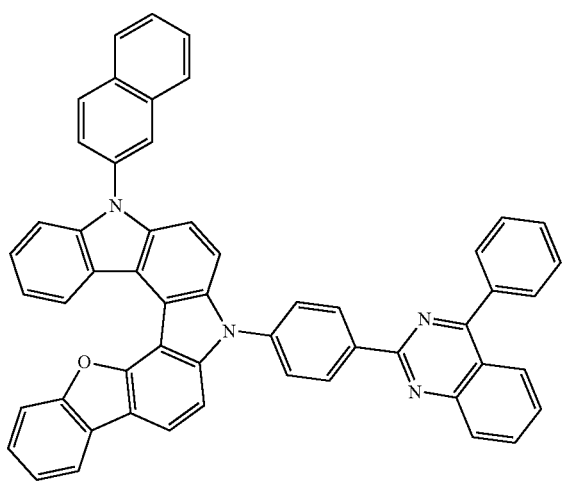
344
-continued
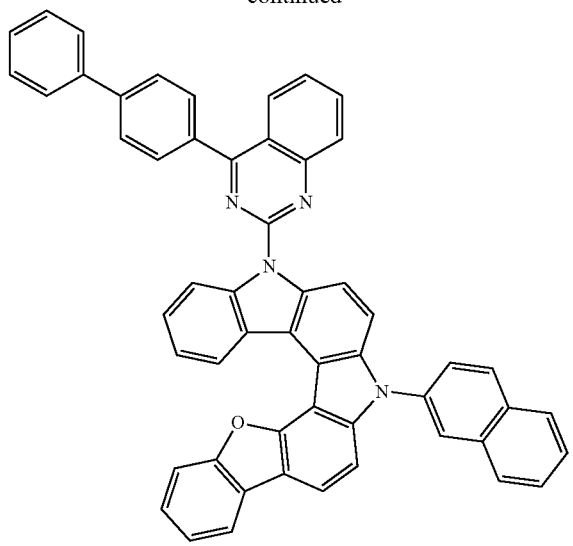
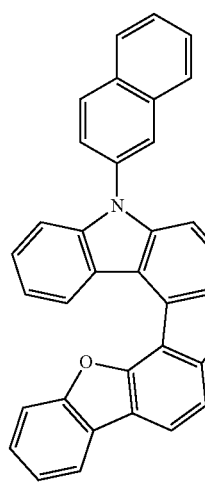
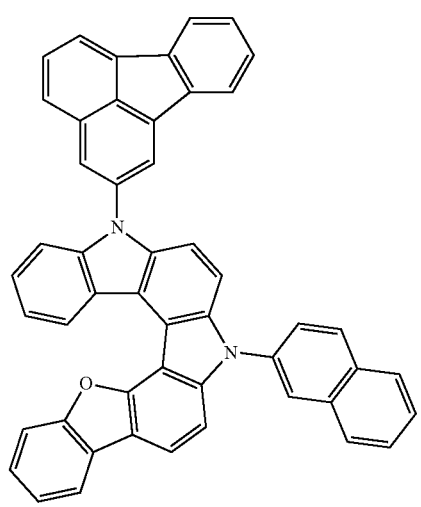

345
-continued
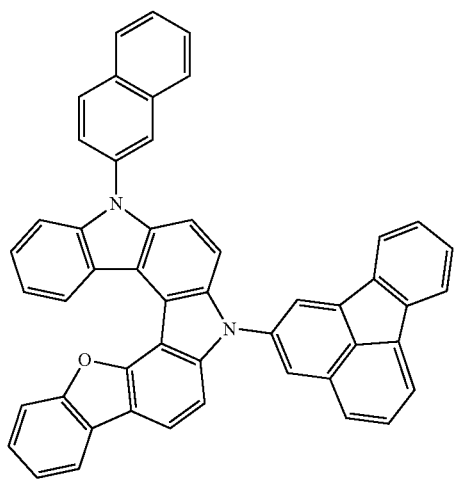
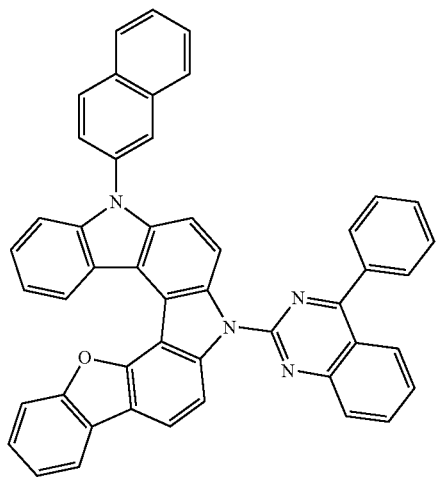
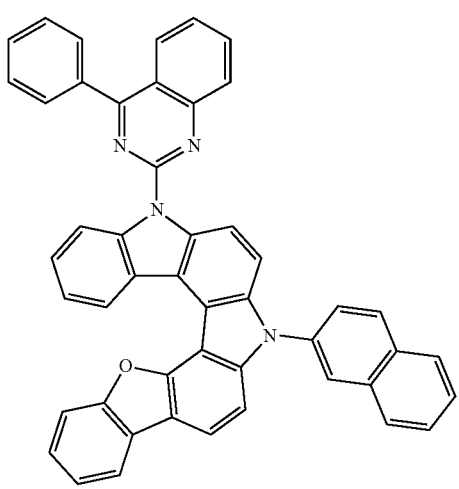
346
-continued
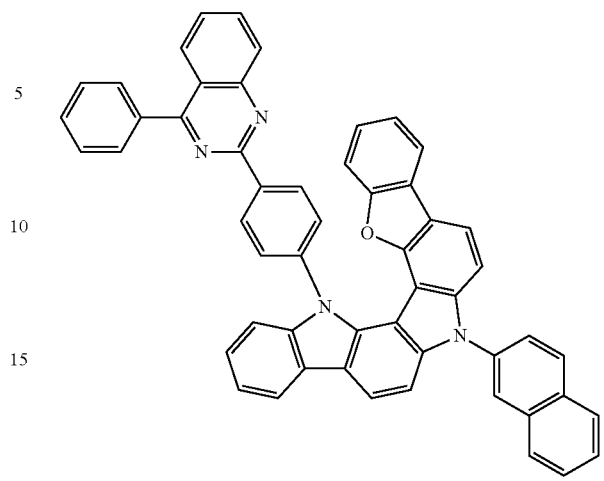
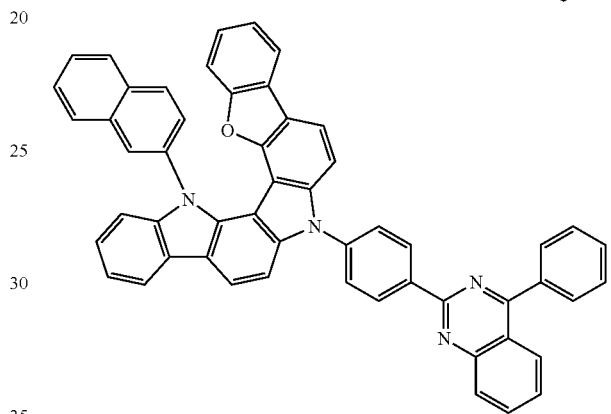
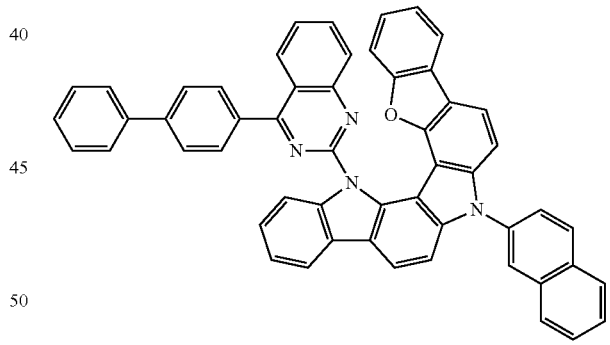
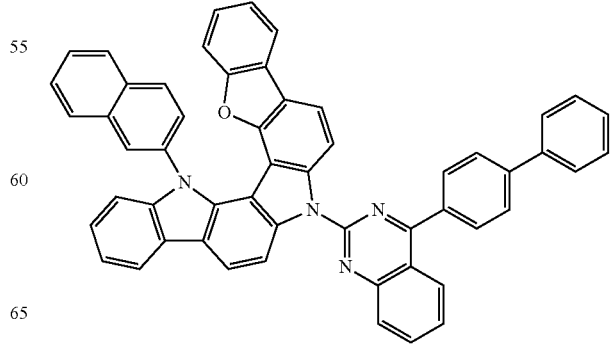

347
-continued
348
-continued
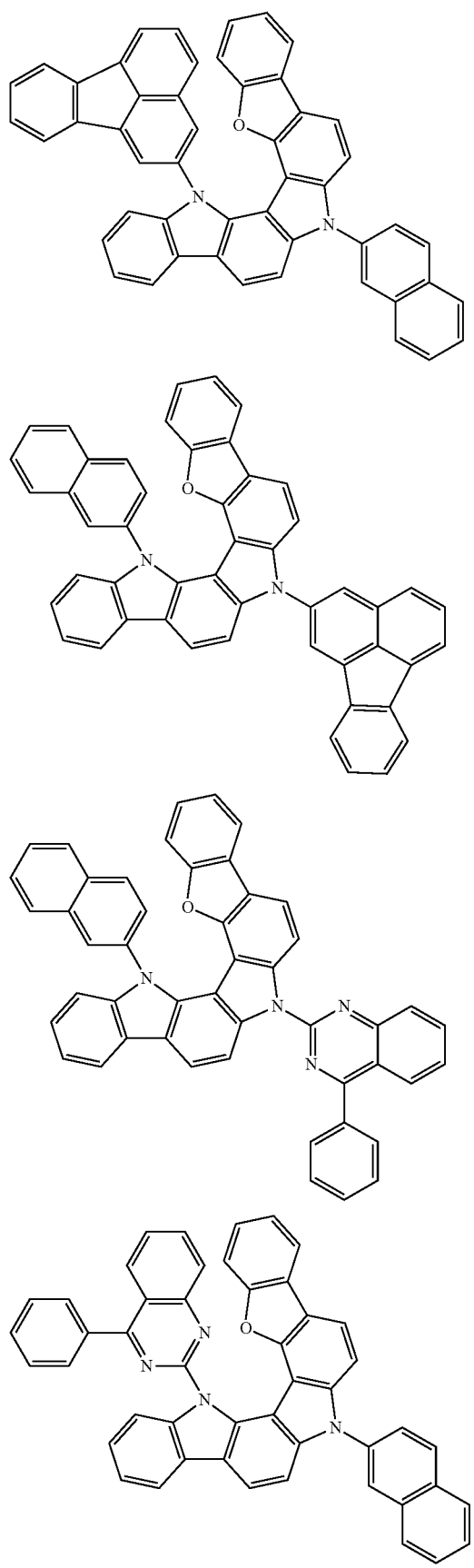
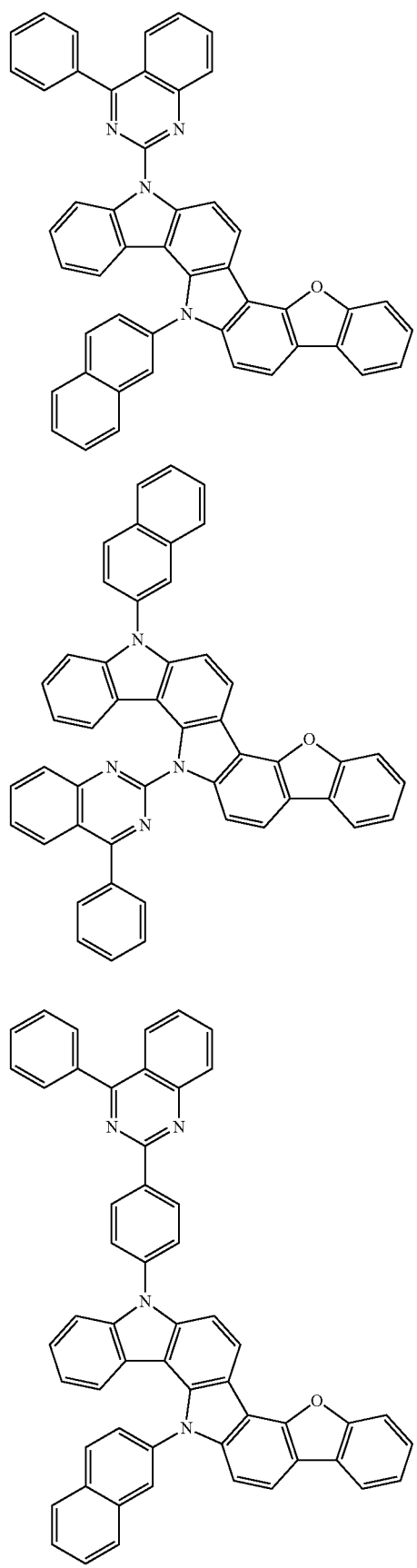

349
-continued
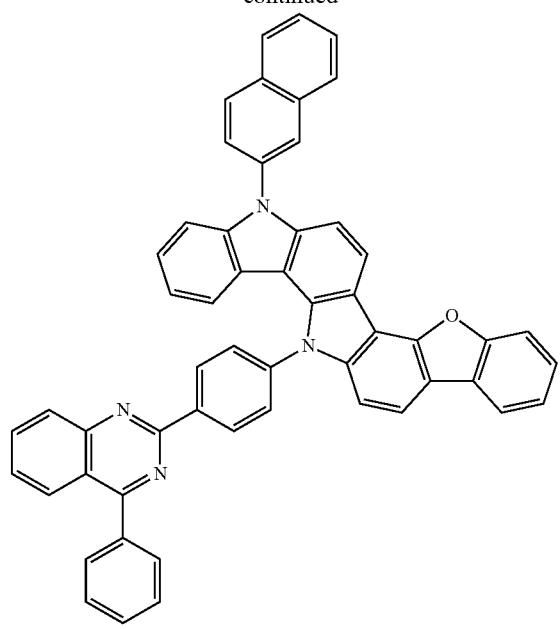
350
-continued
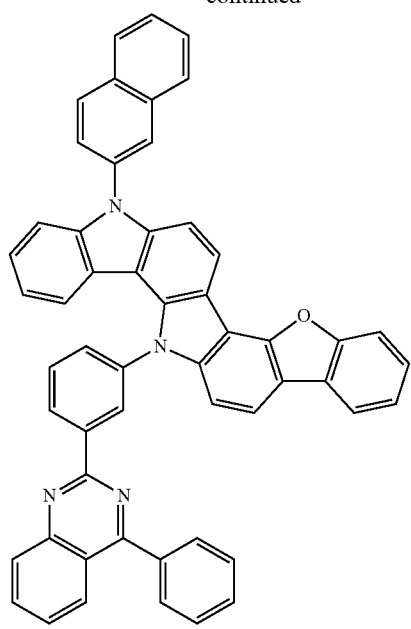
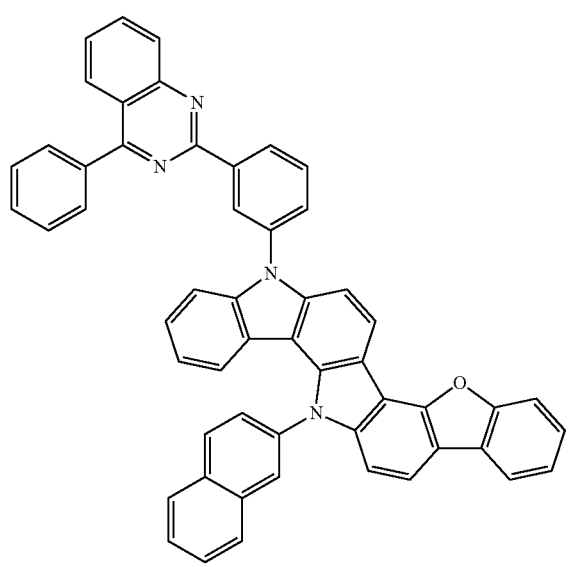
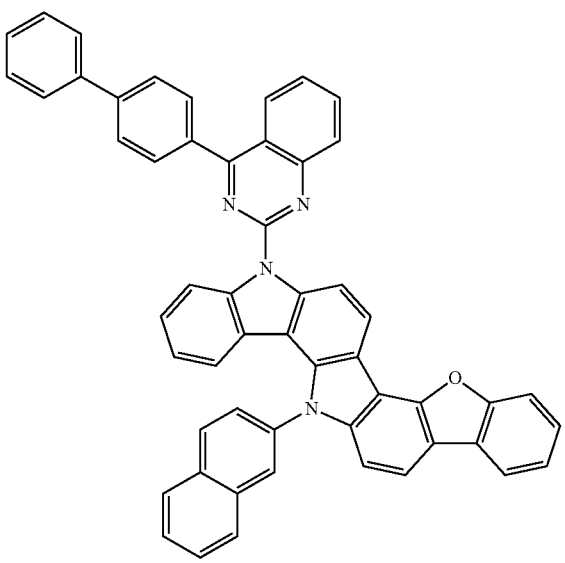

351
-continued
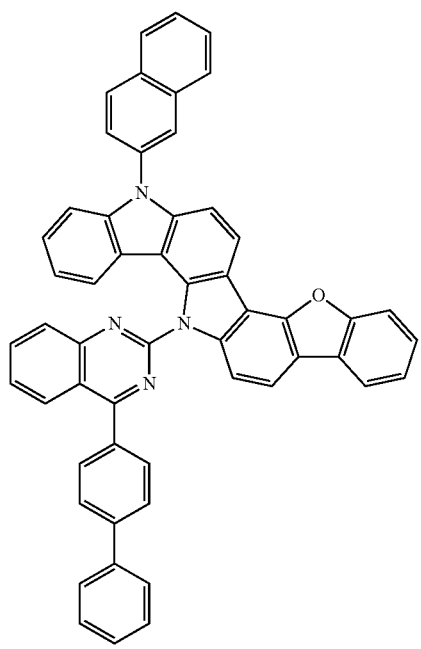
352
-continued
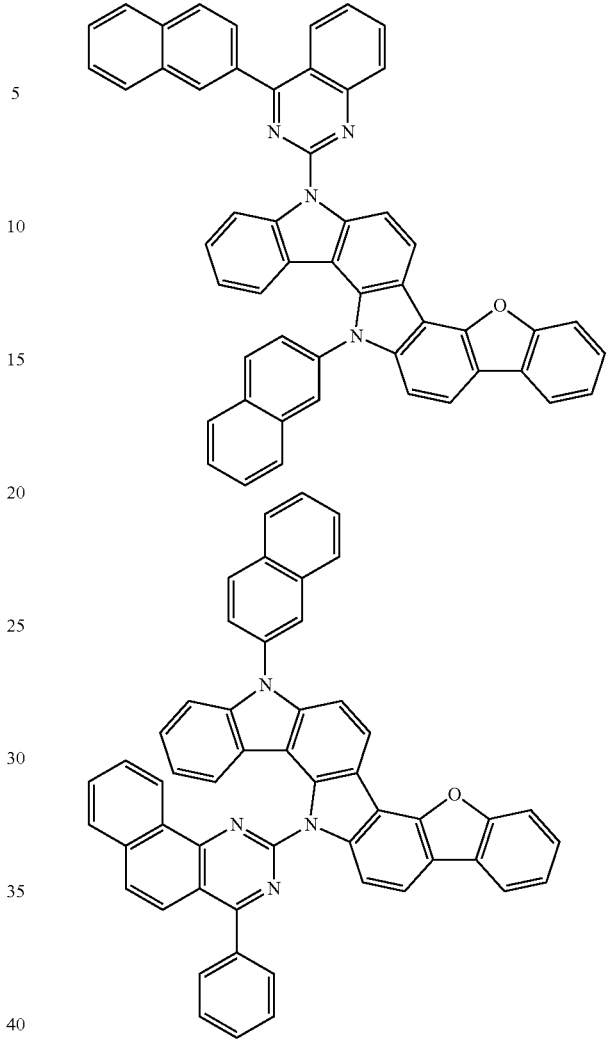
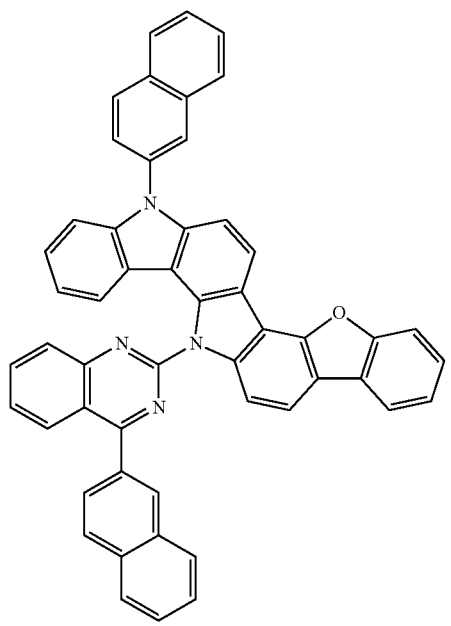
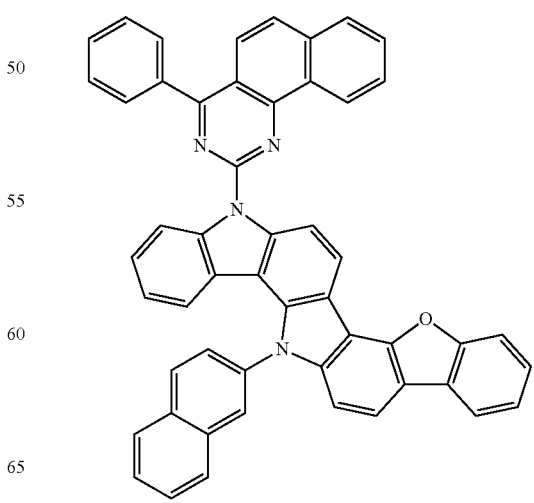

353
-continued
354
-continued
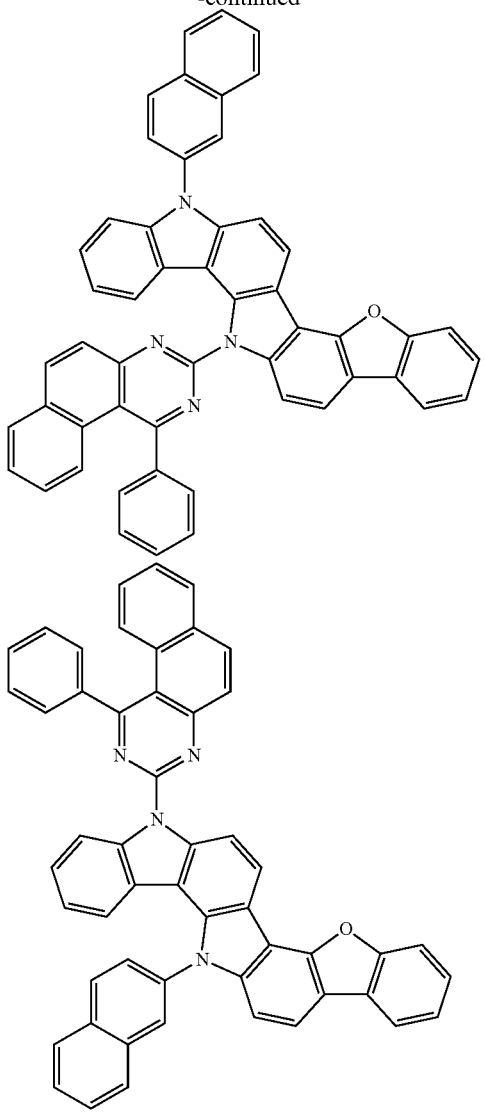
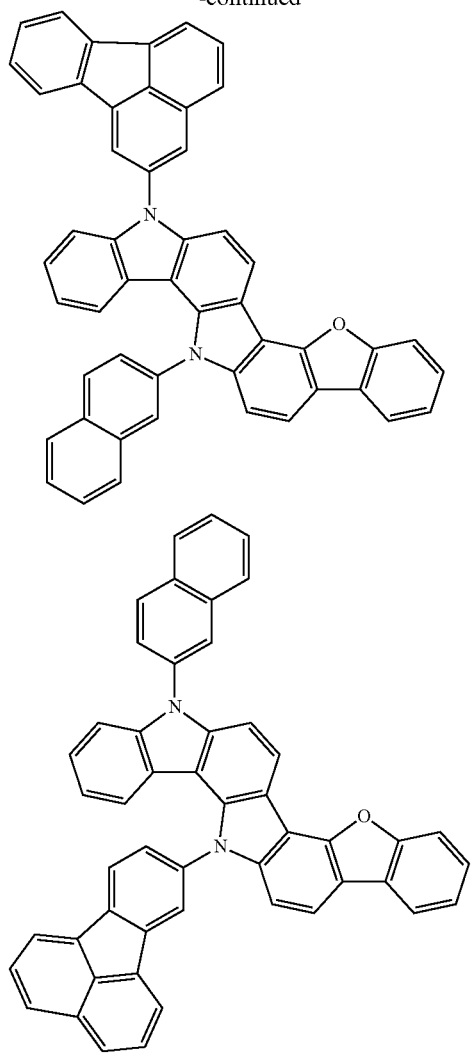
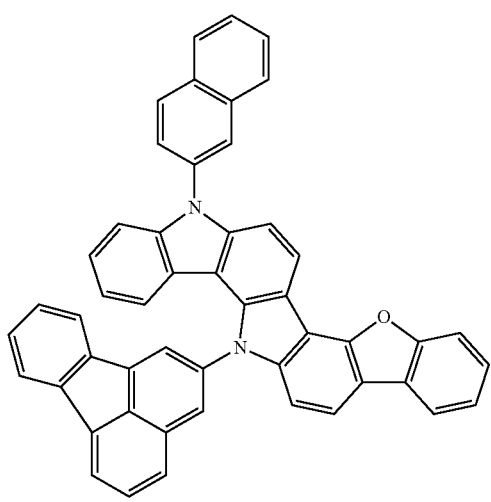

355
-continued
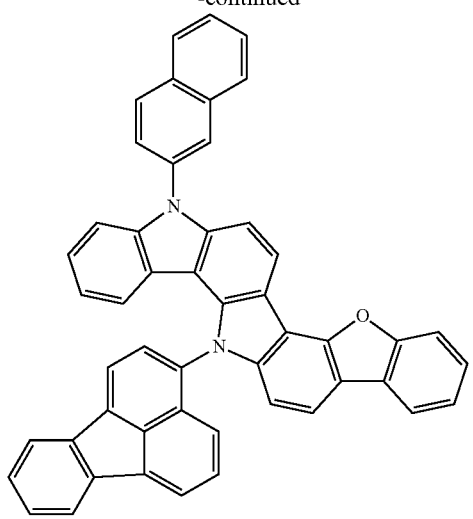
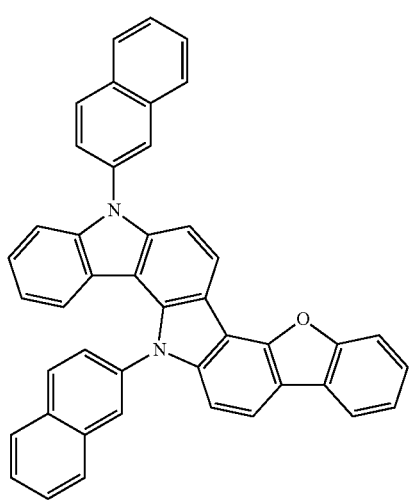
356
-continued
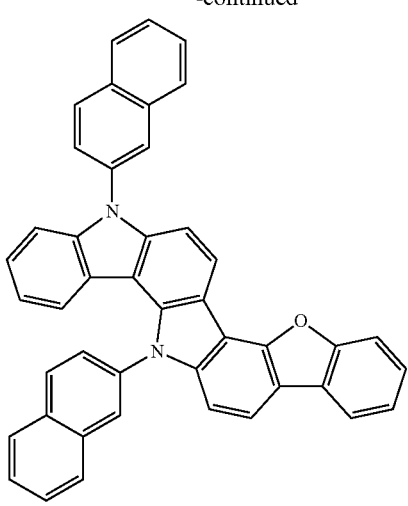
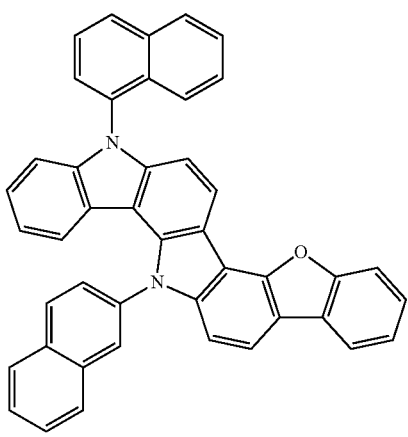

357
-continued
358
-continued
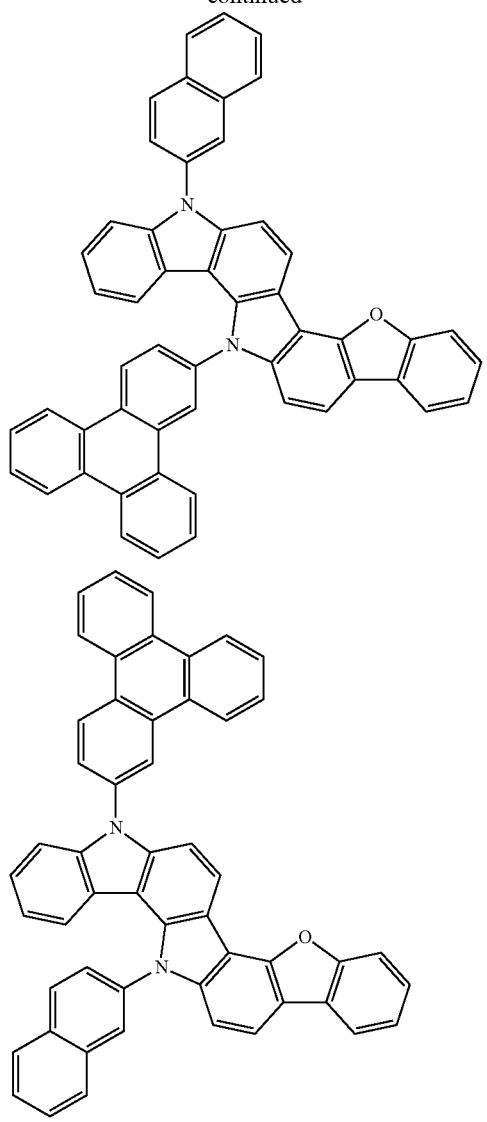
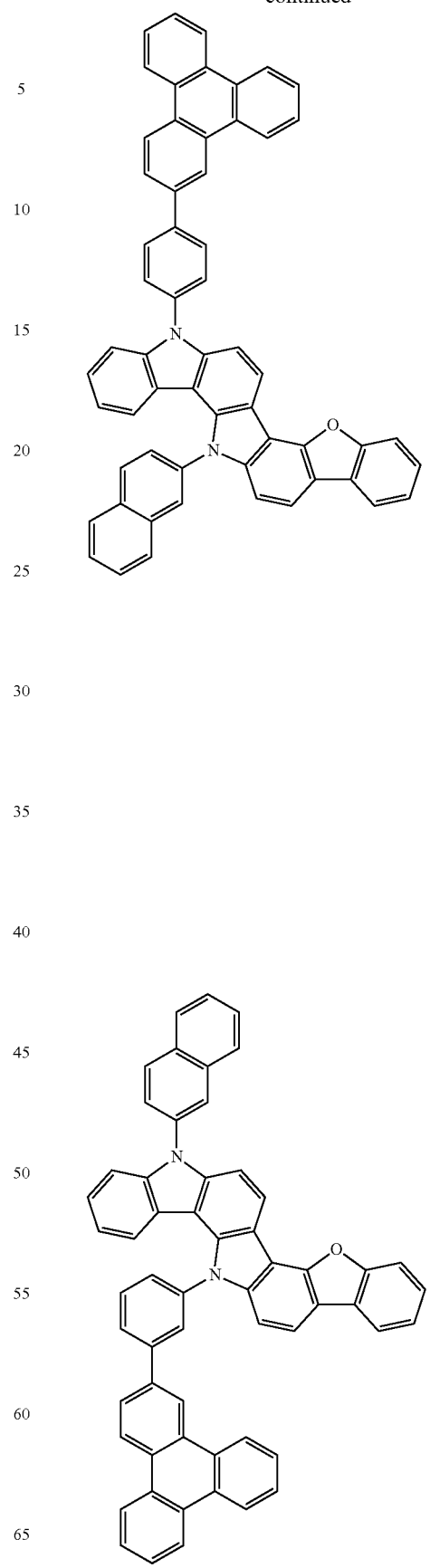

359
-continued
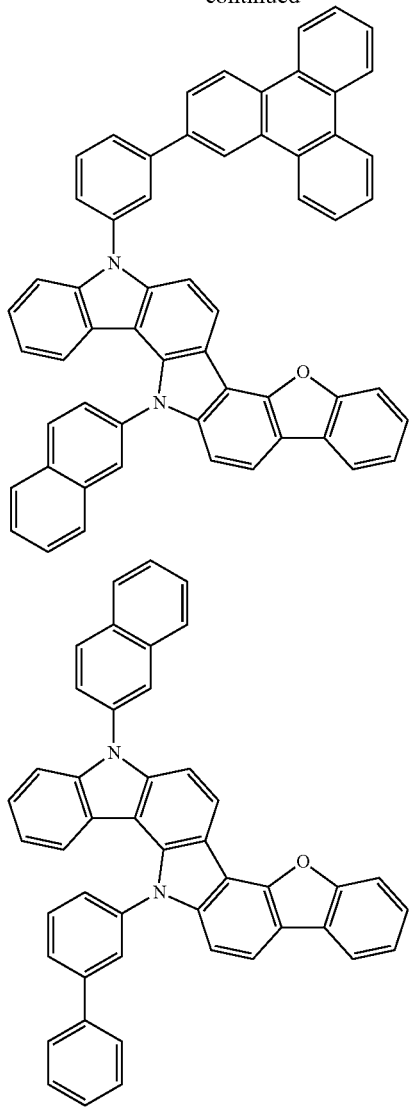
360
-continued
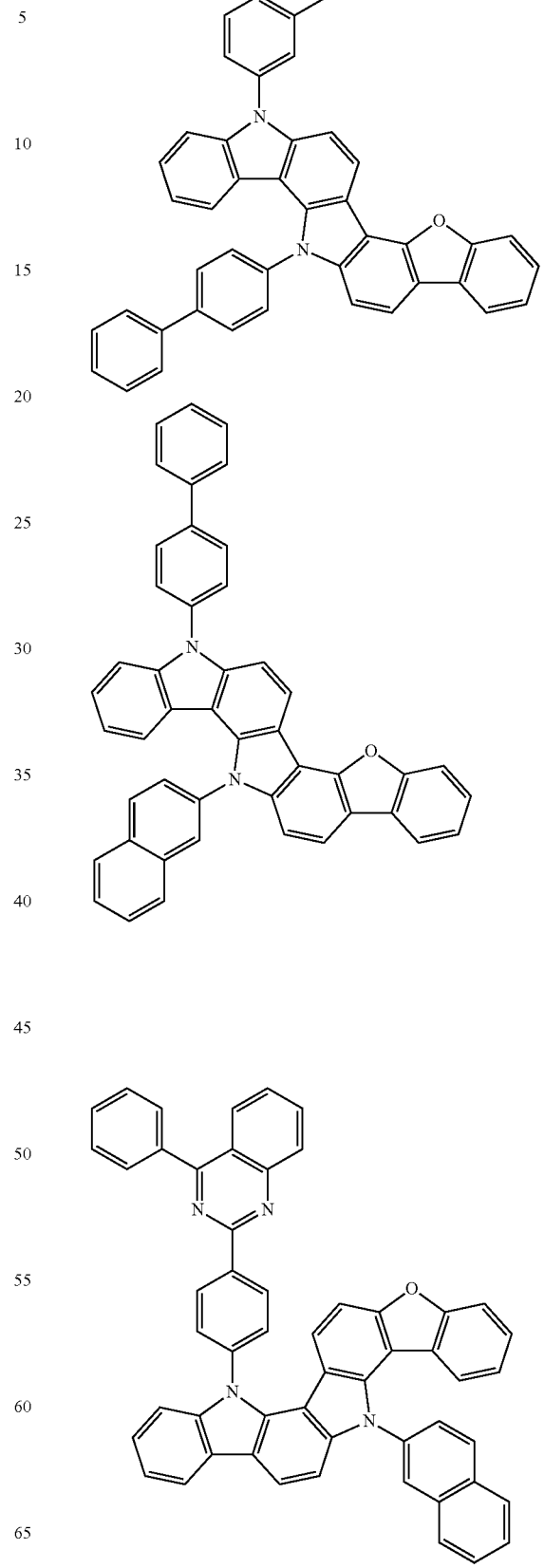

361
-continued
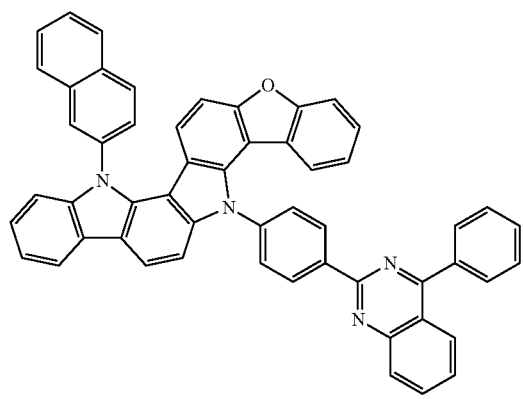
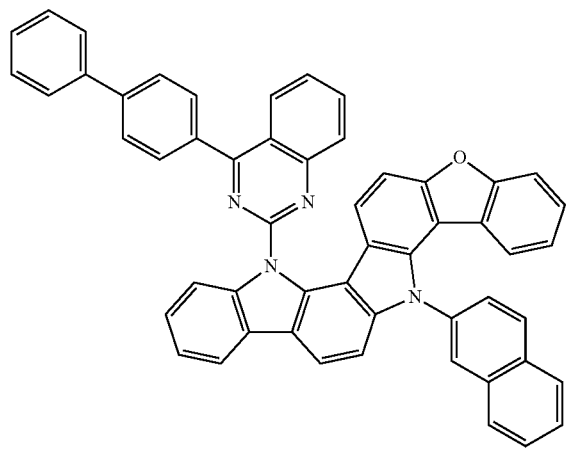
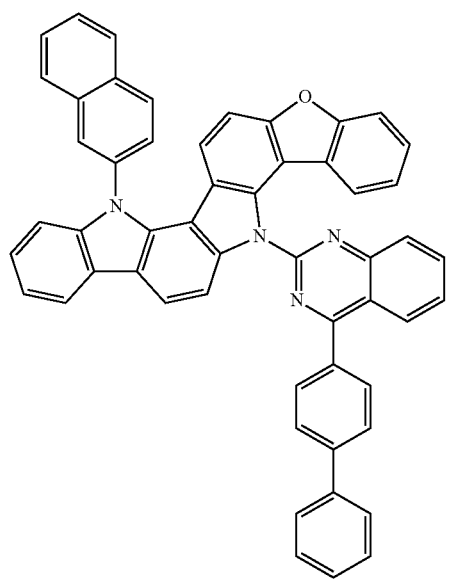
362
-continued
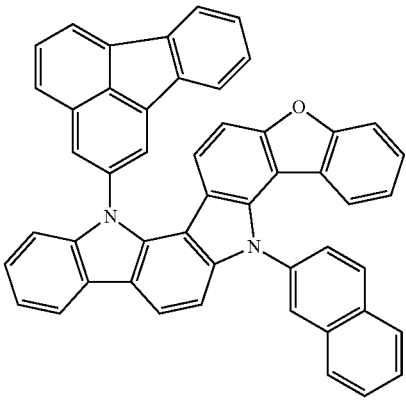
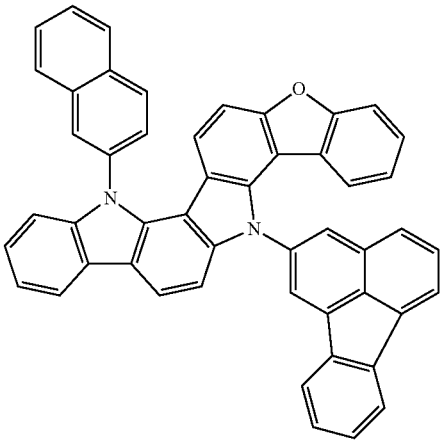
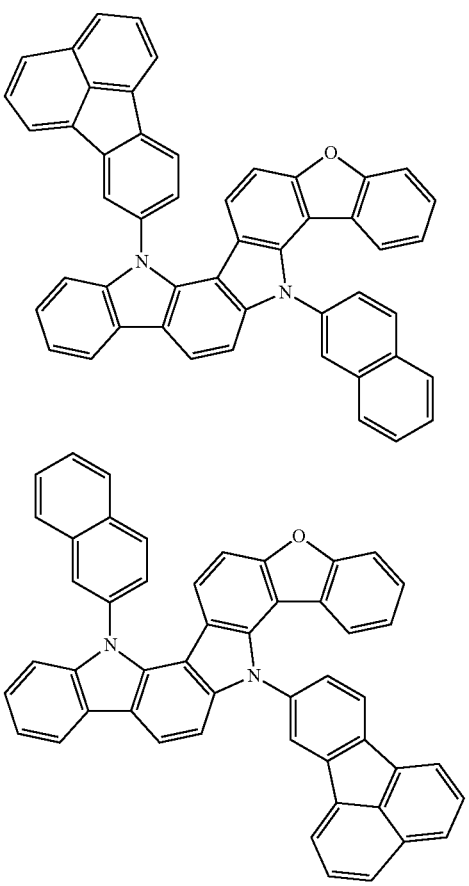

363
-continued
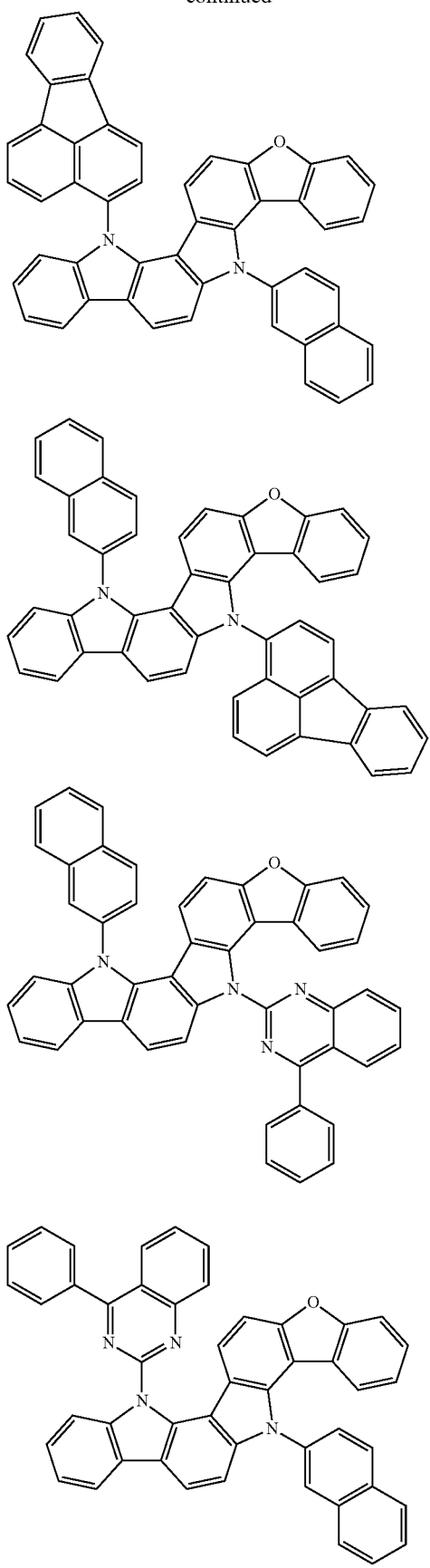
364
-continued
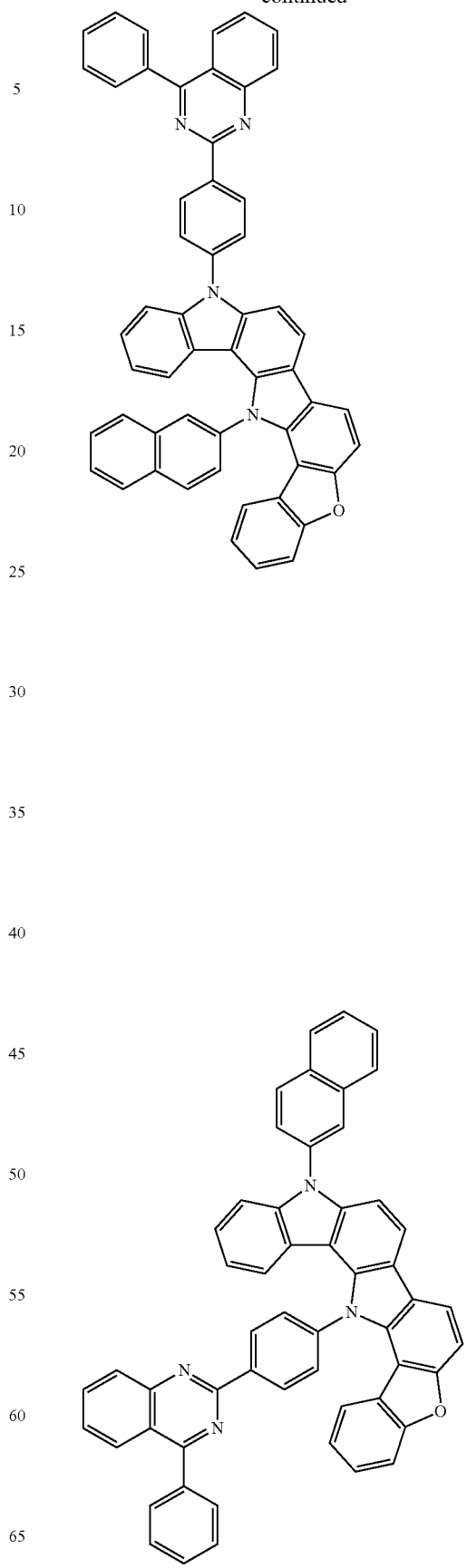

365
-continued
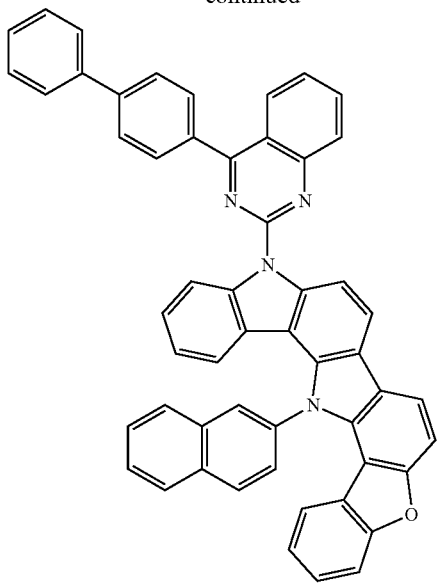
366
-continued
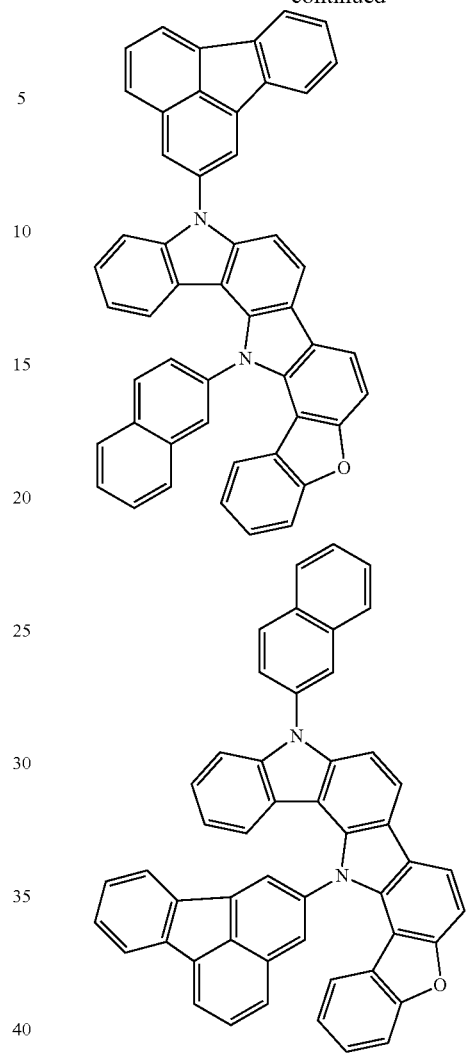
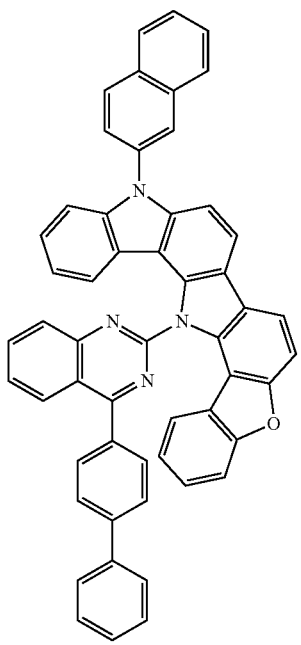

367
-continued
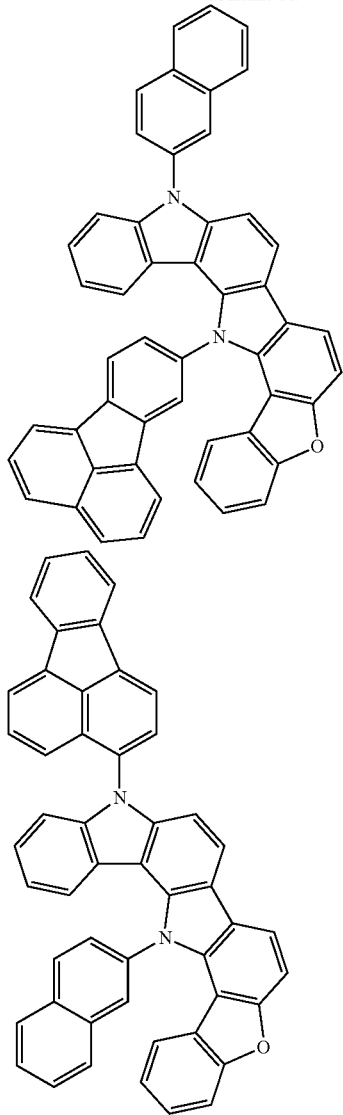
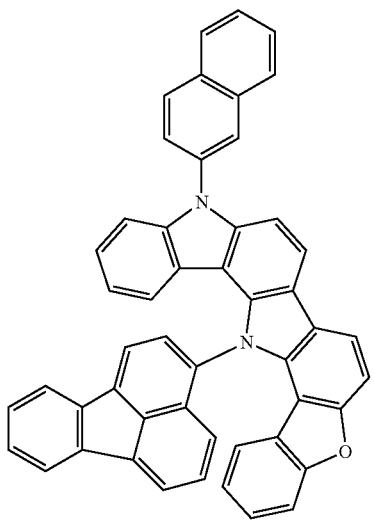
368
-continued
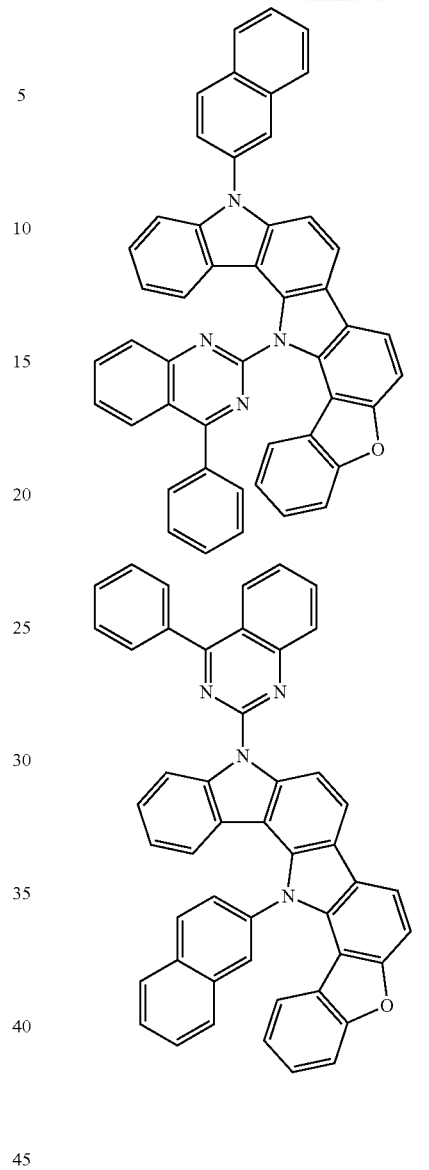
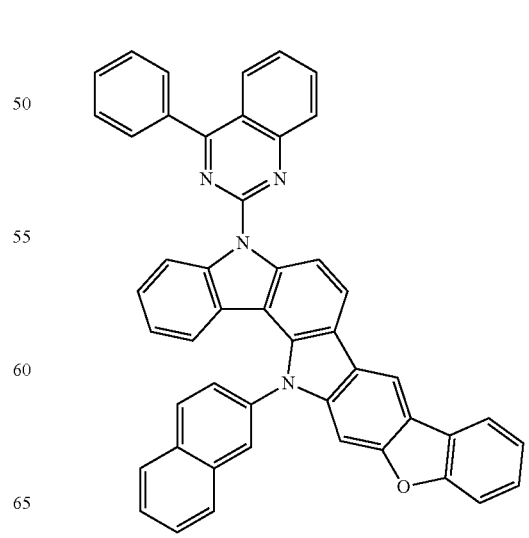

369
-continued
370
-continued
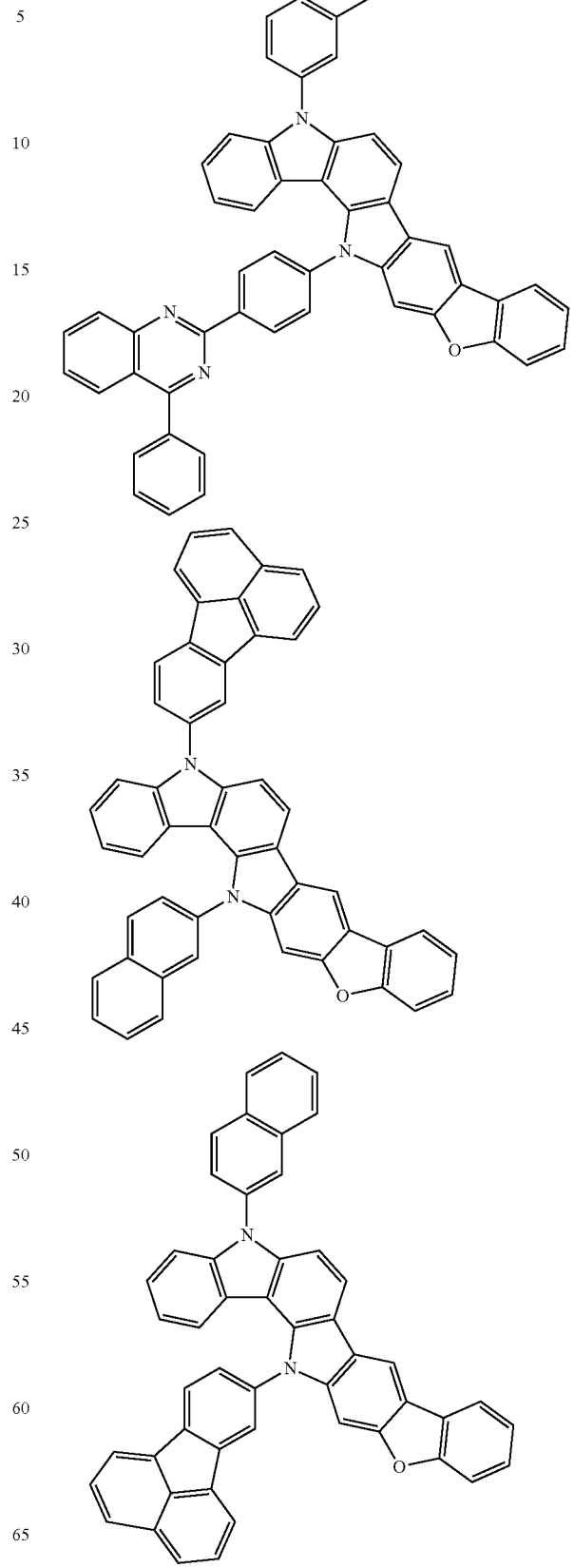

371
-continued
372
-continued
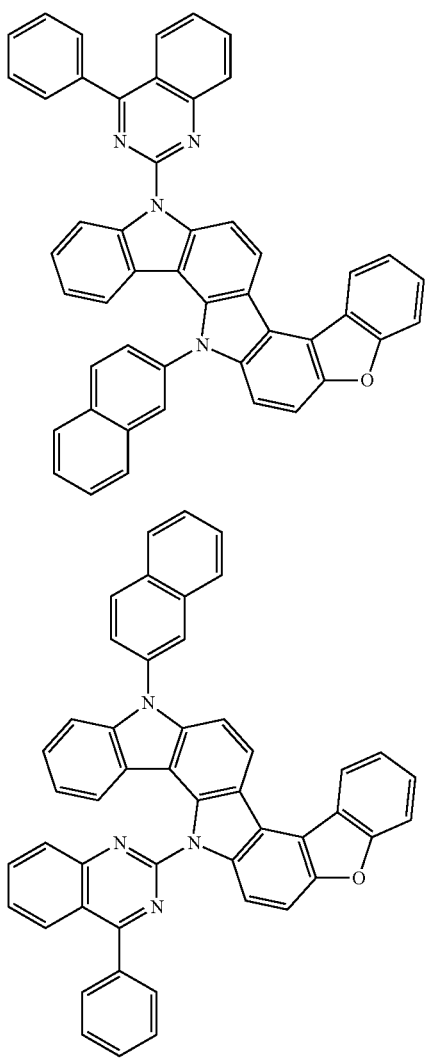
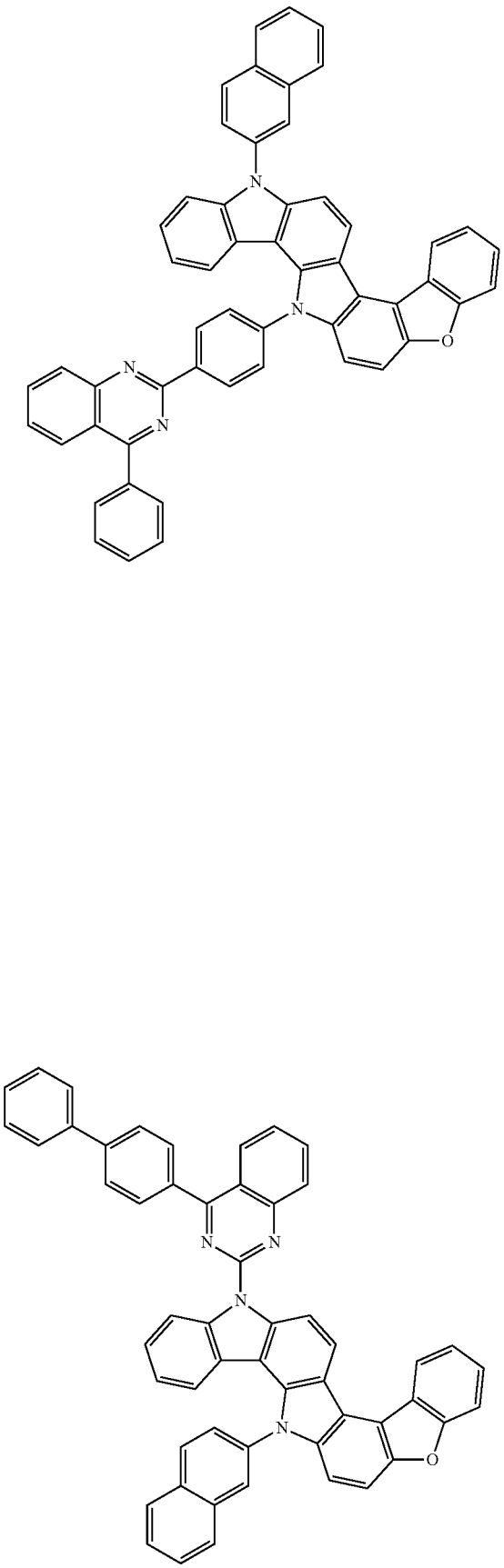

373
-continued
374
-continued
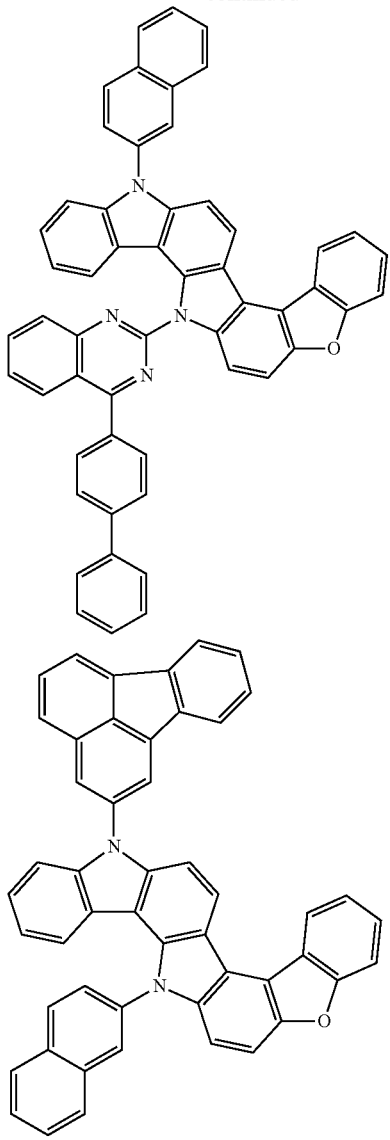
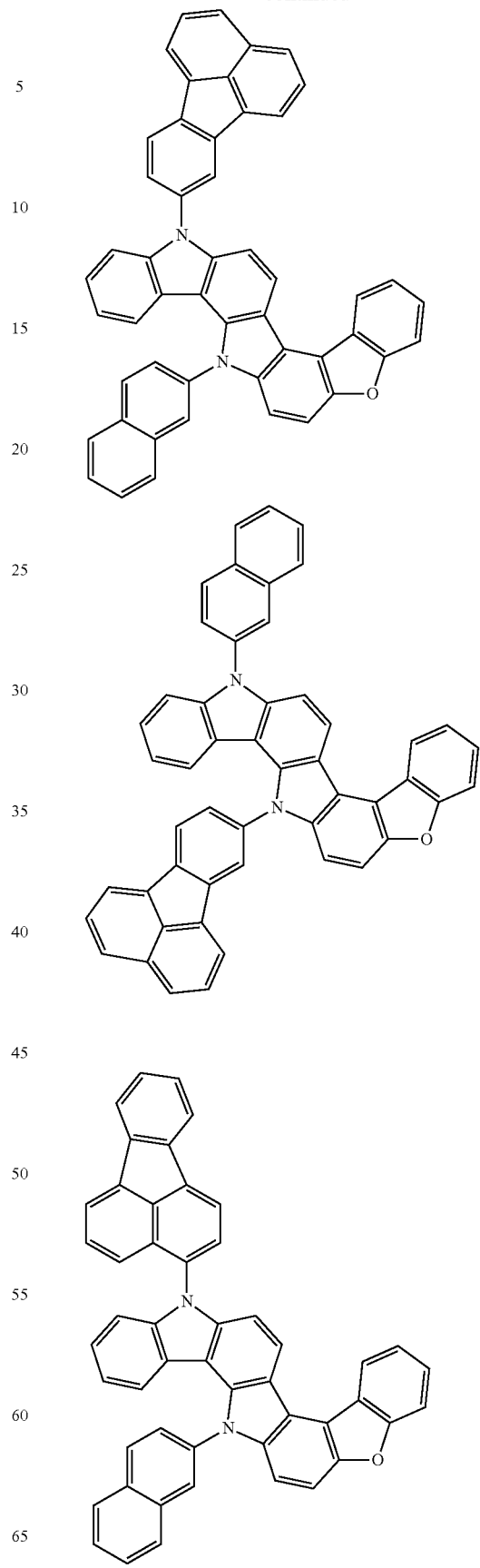

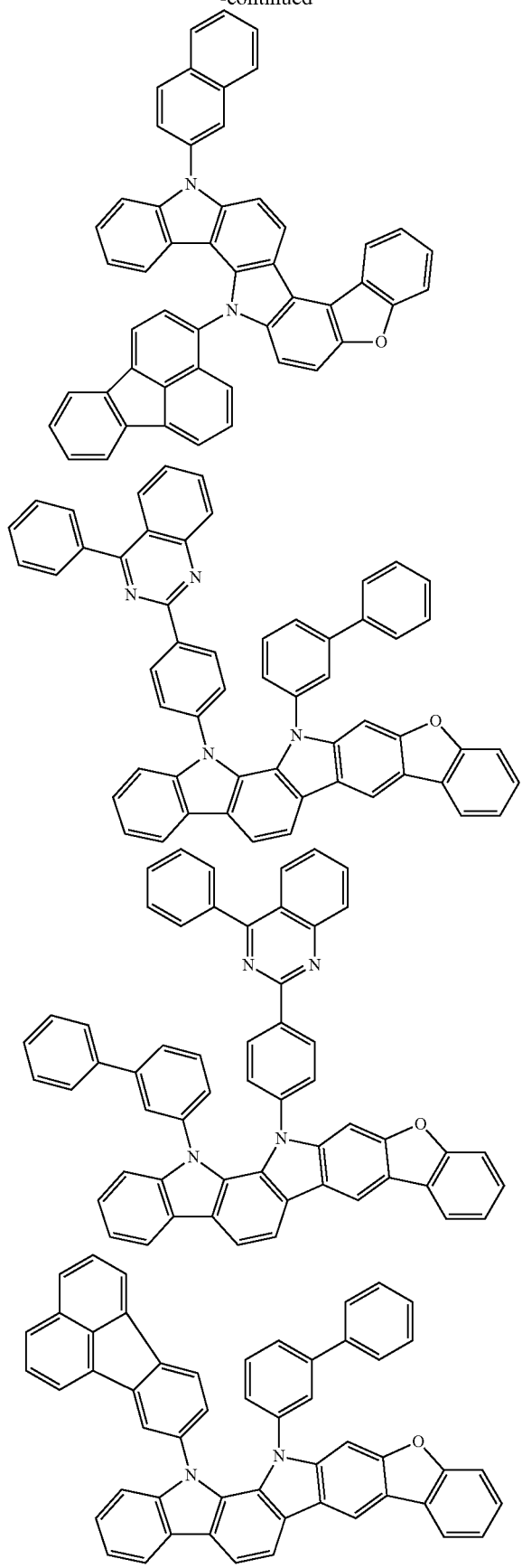
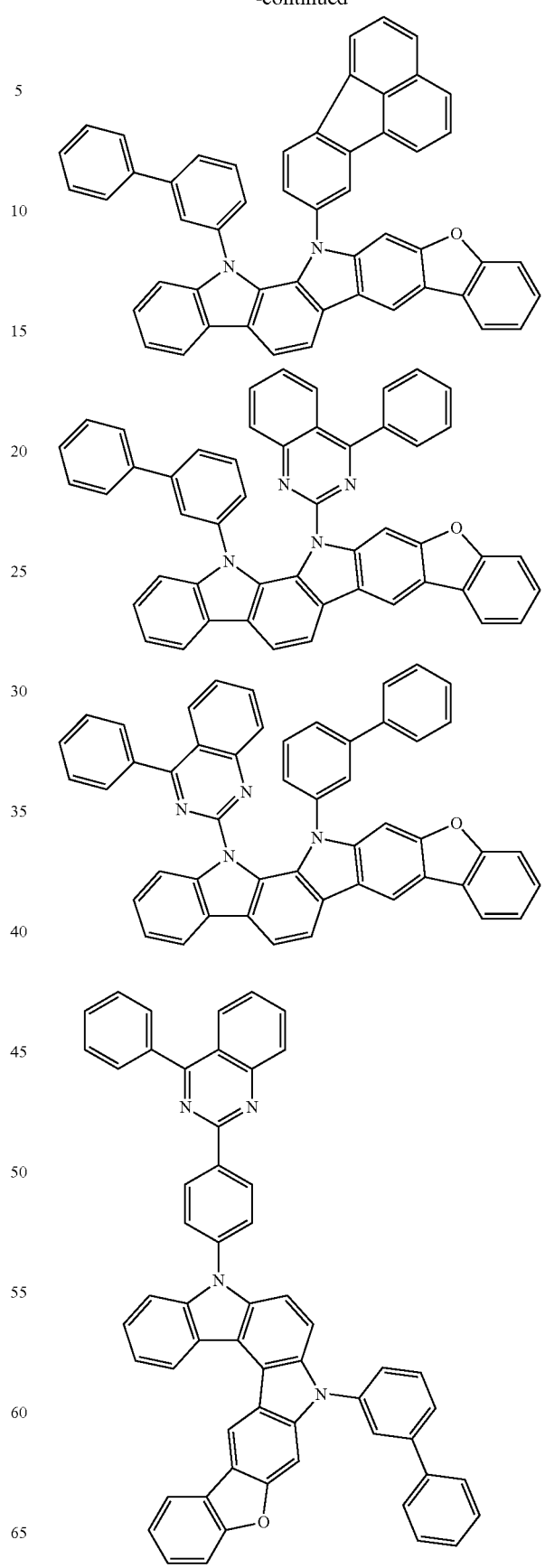

377
-continued
378
-continued
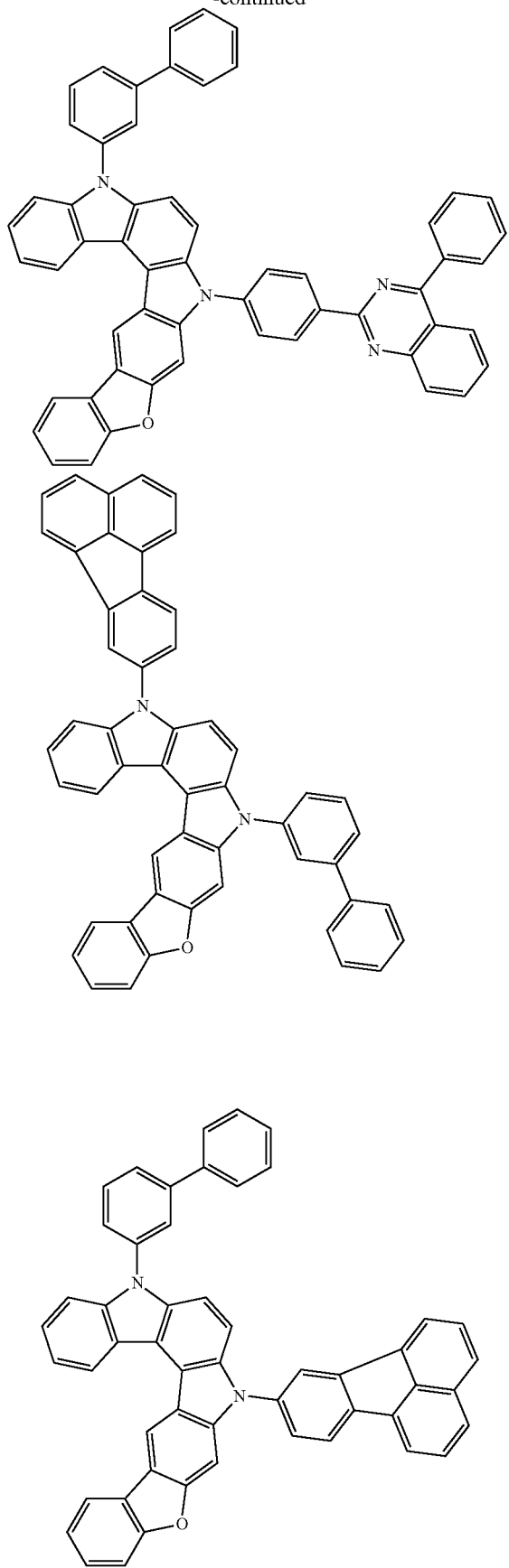
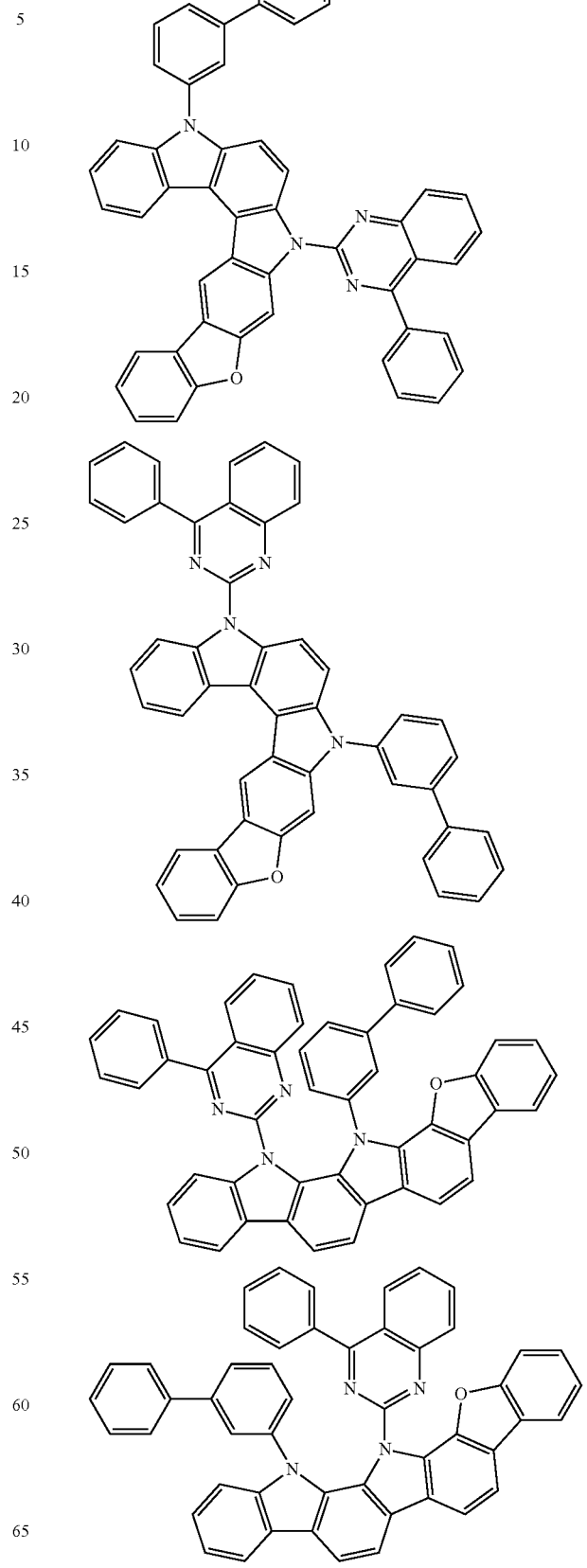

379
-continued
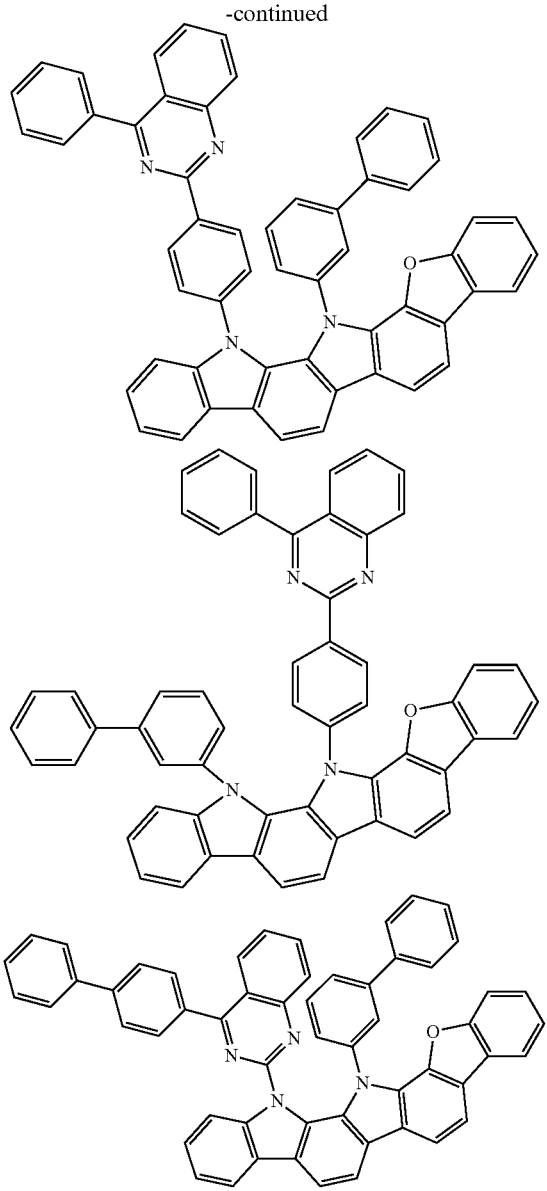
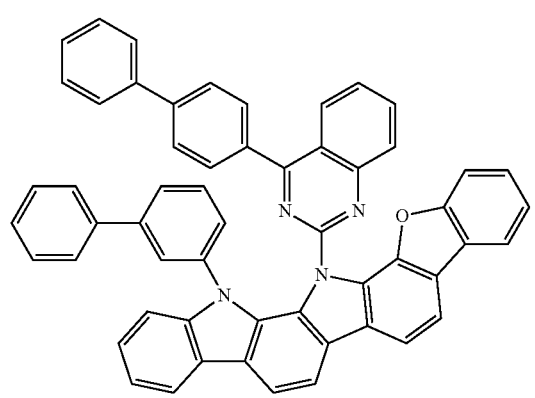
380
-continued
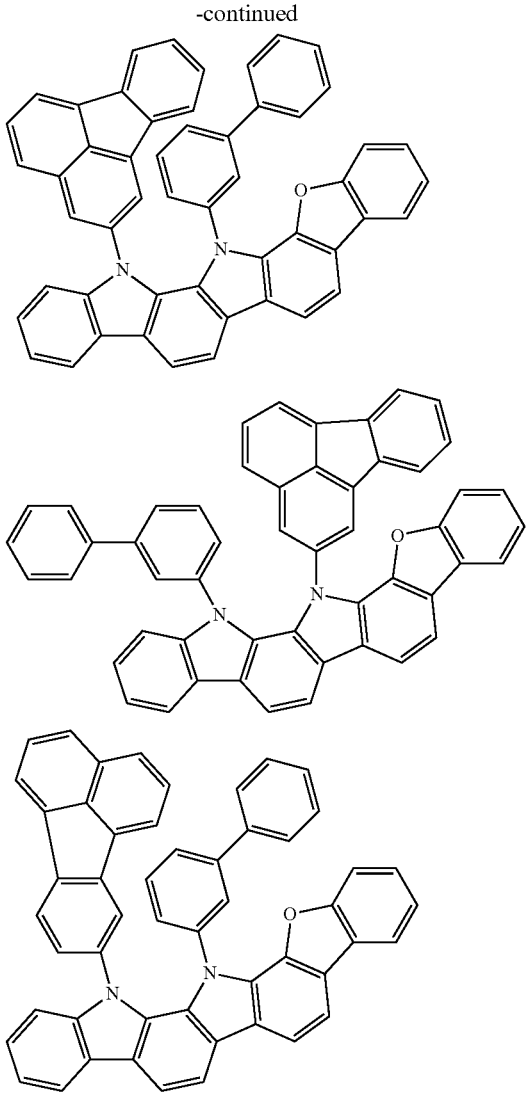
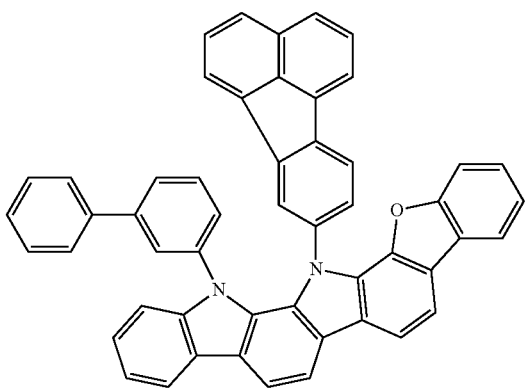

381
-continued
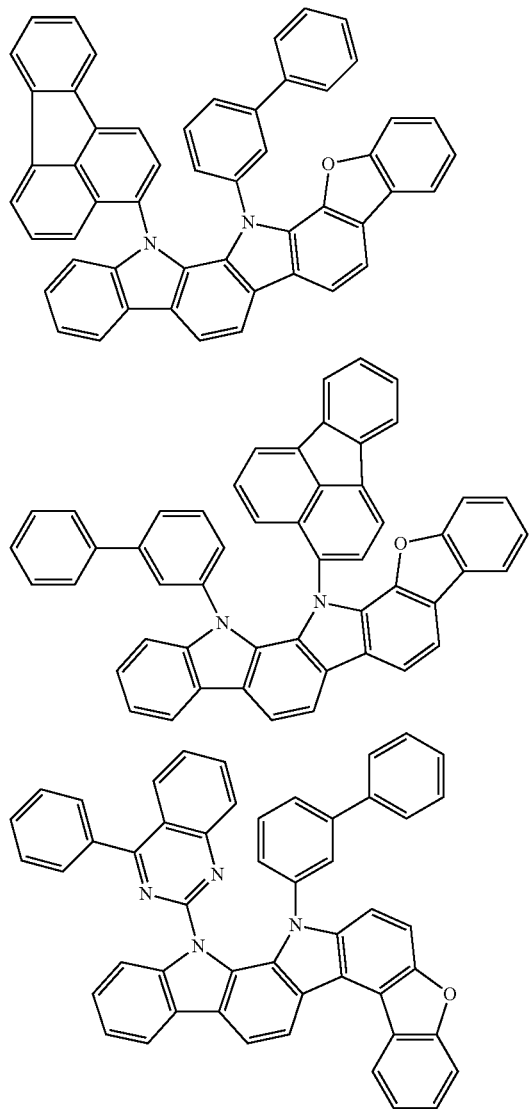
382
-continued
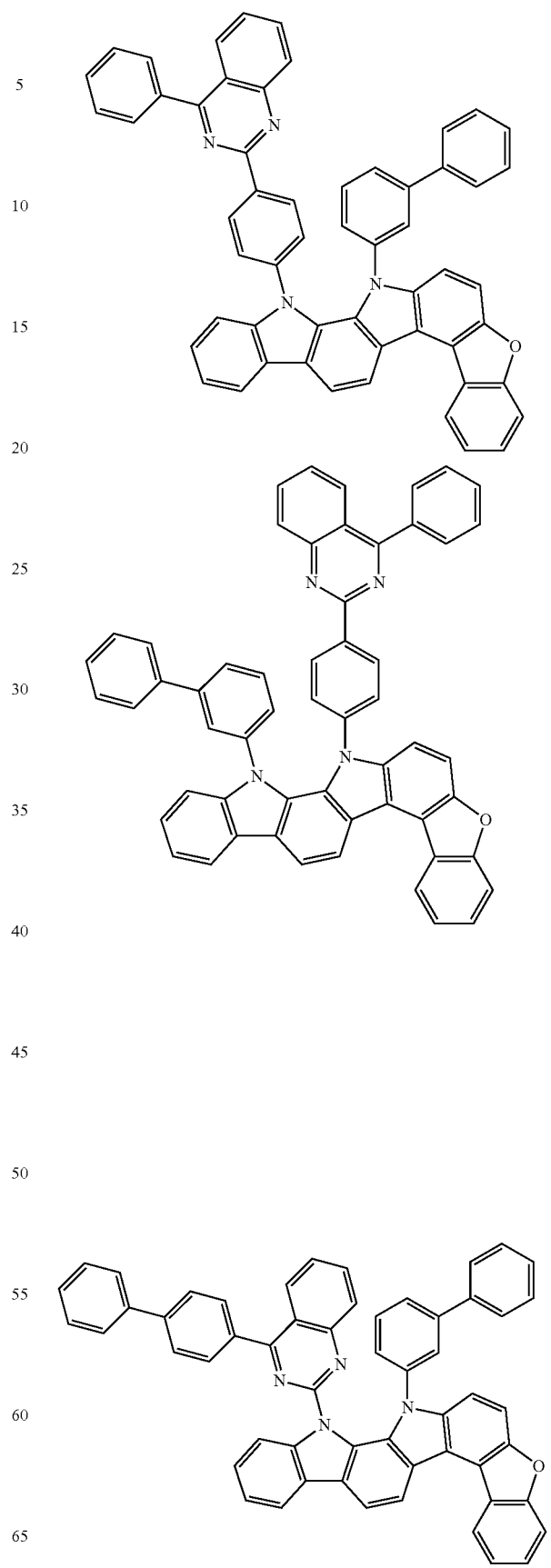

383
-continued
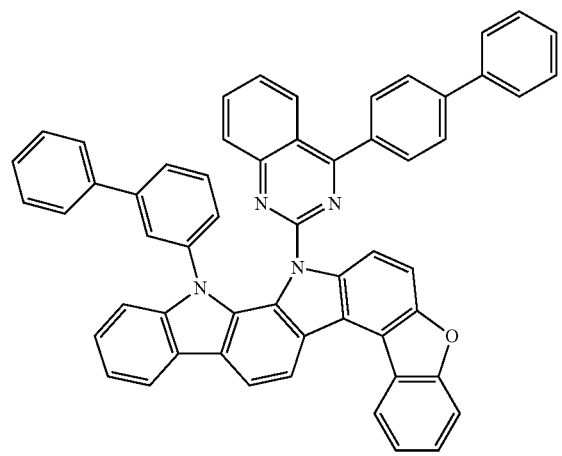
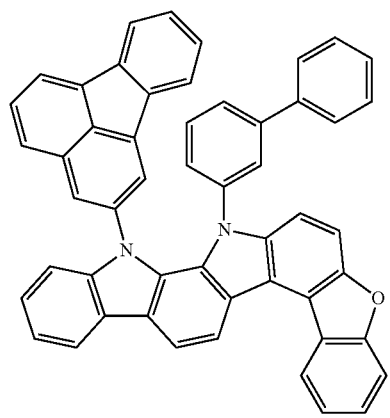
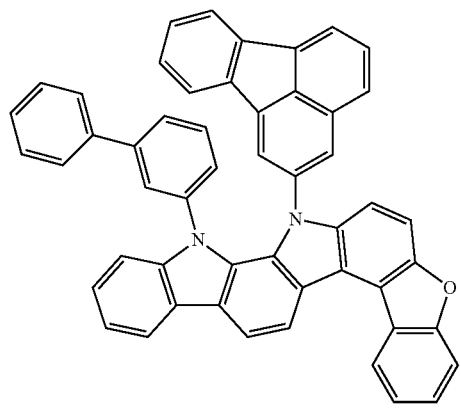
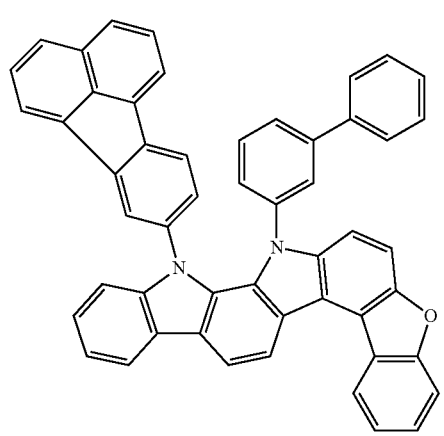
384
-continued
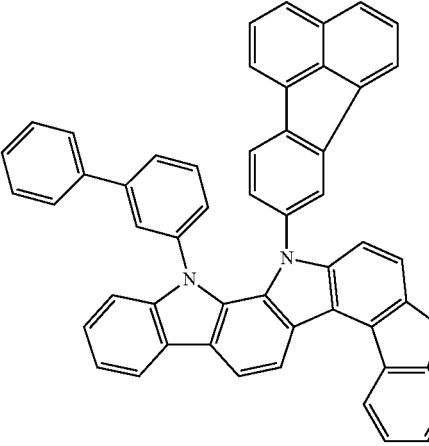
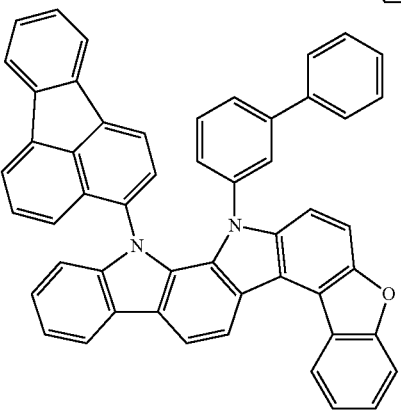
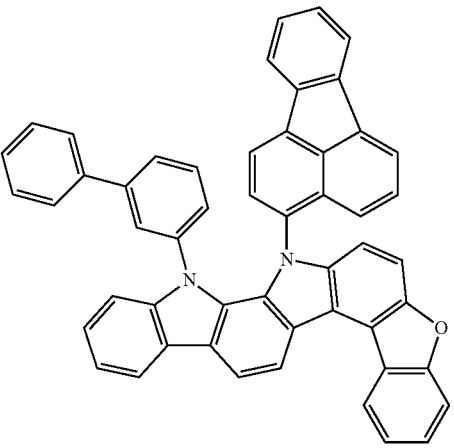
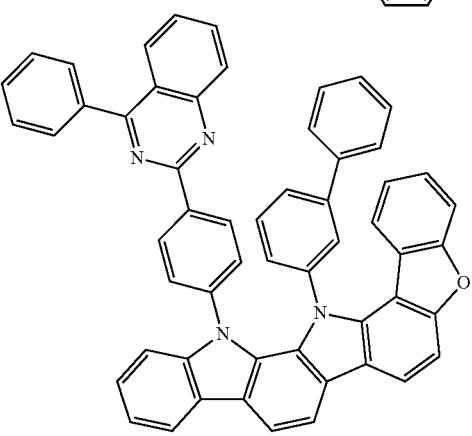

385
-continued
386
-continued
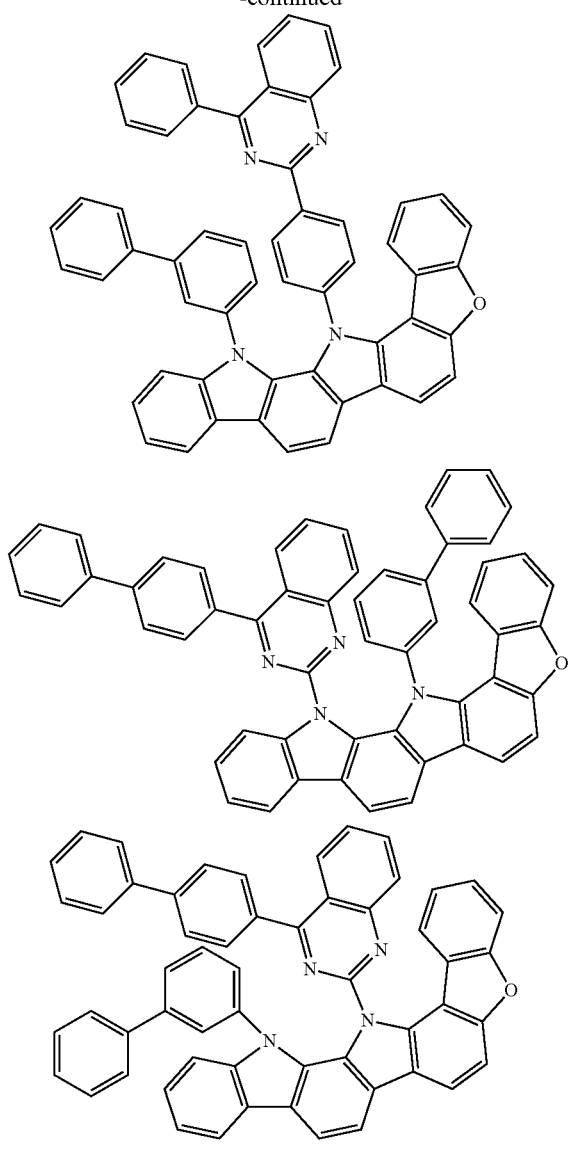
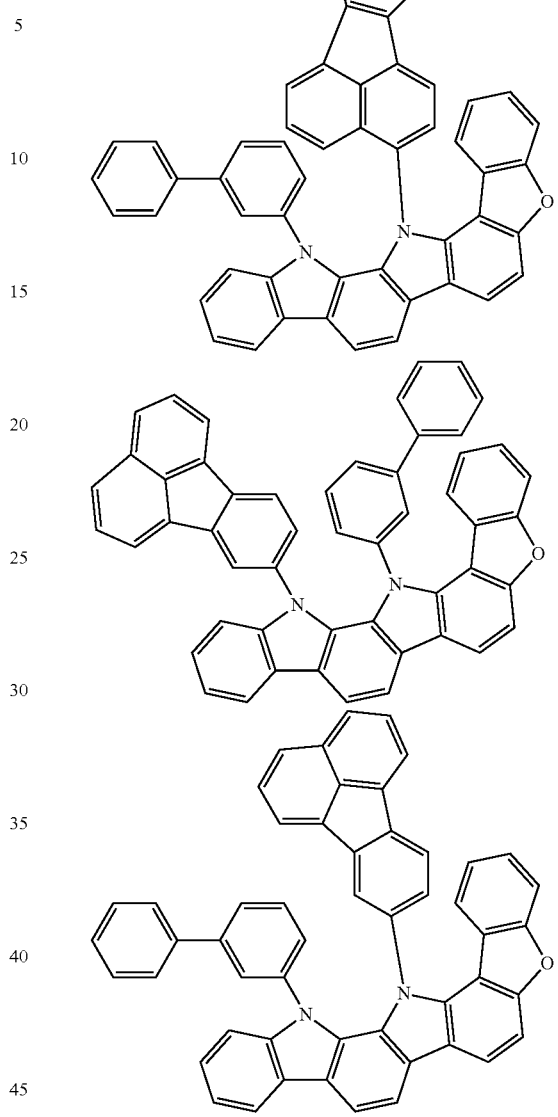
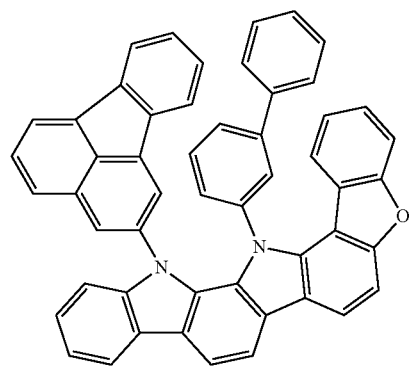
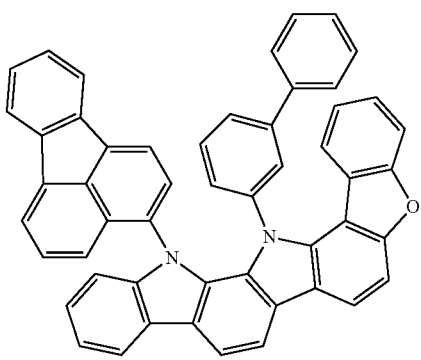

387
-continued
388
-continued
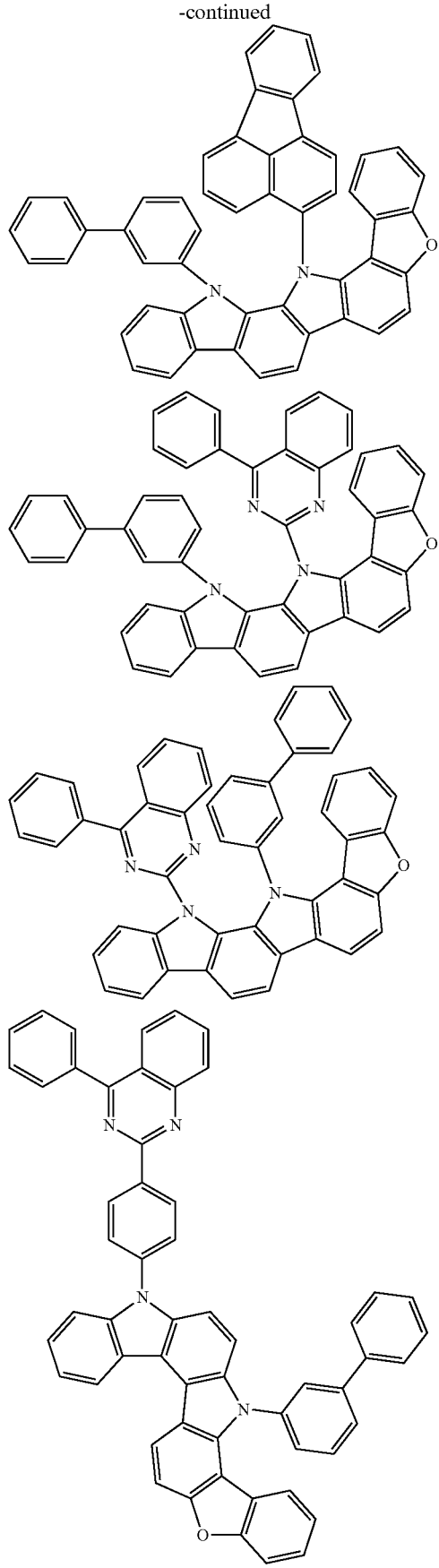
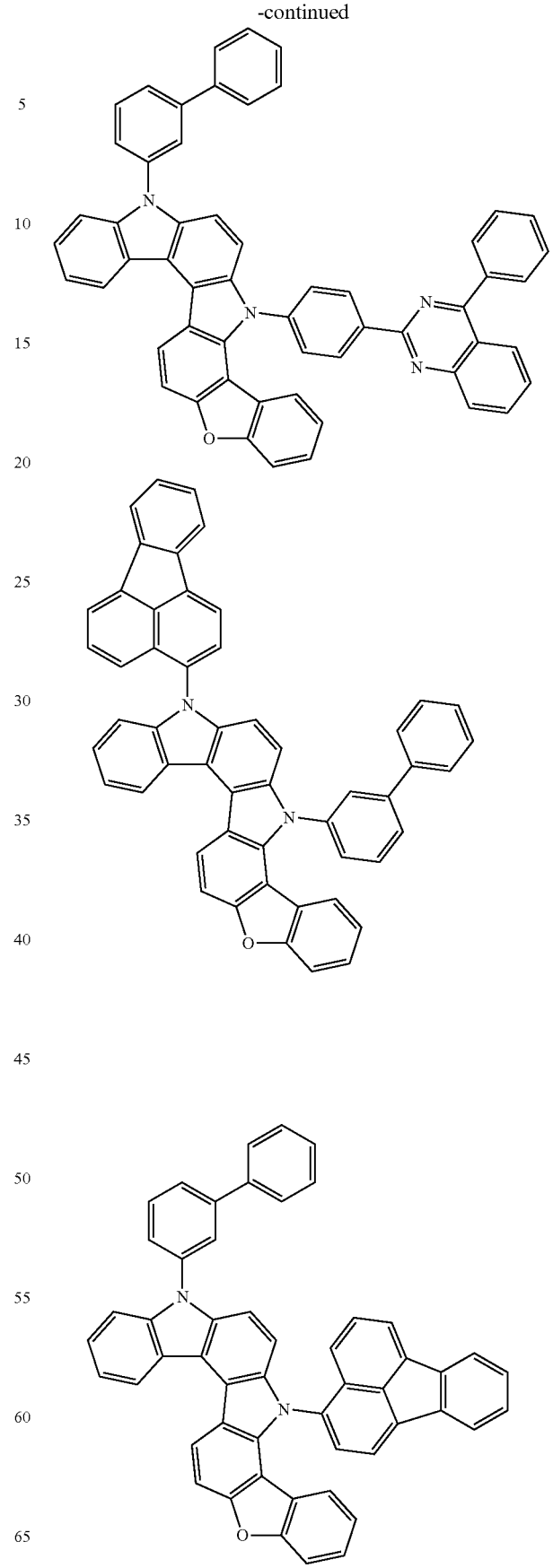

389
-continued
390
-continued
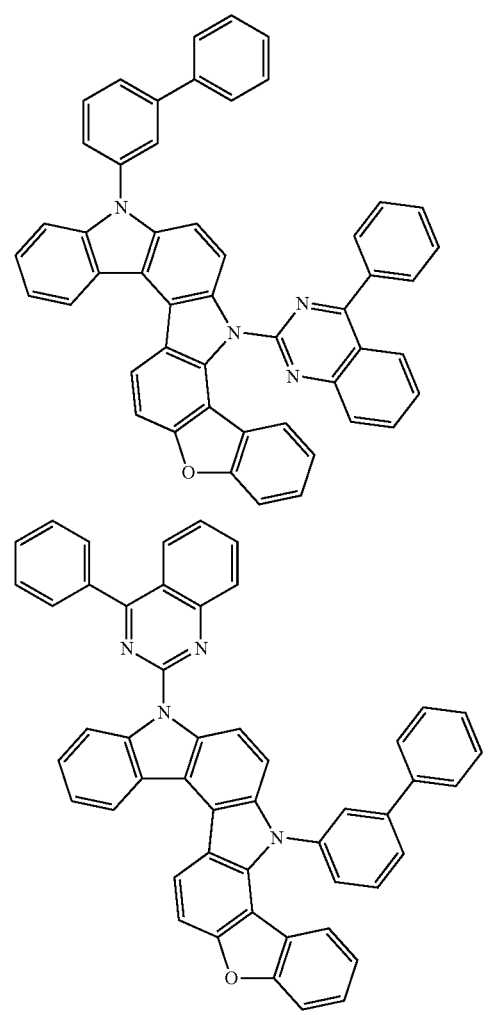
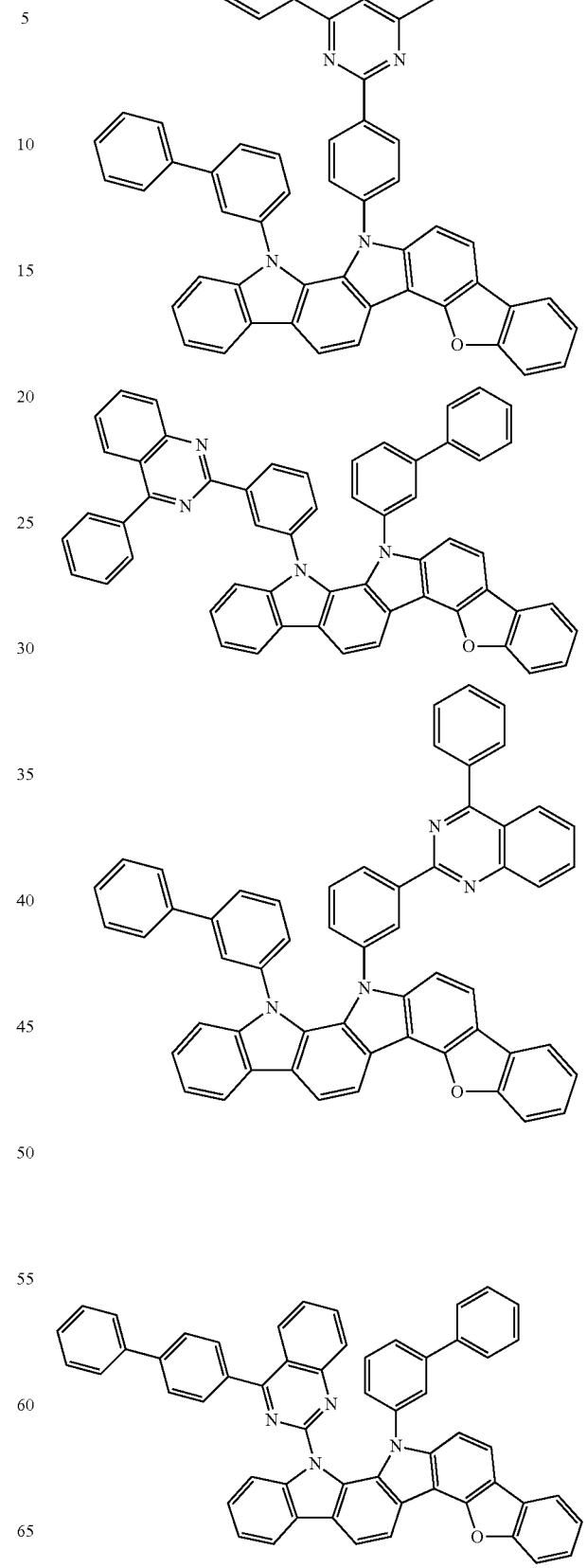

391
-continued
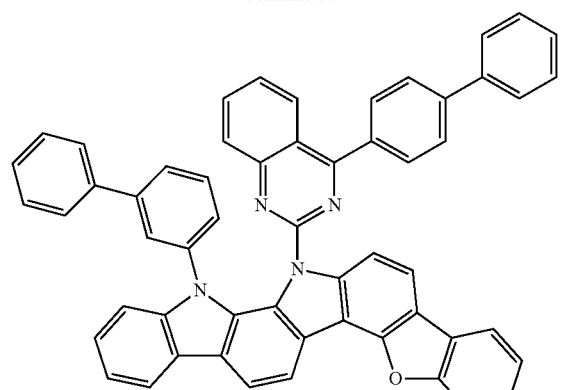
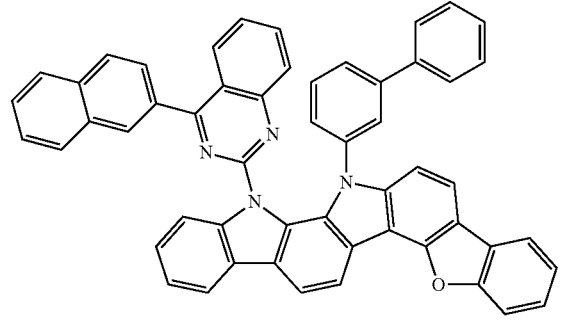
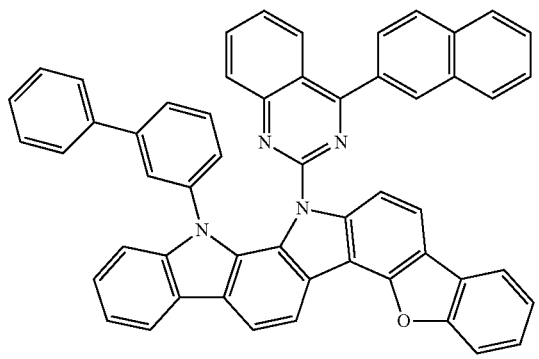
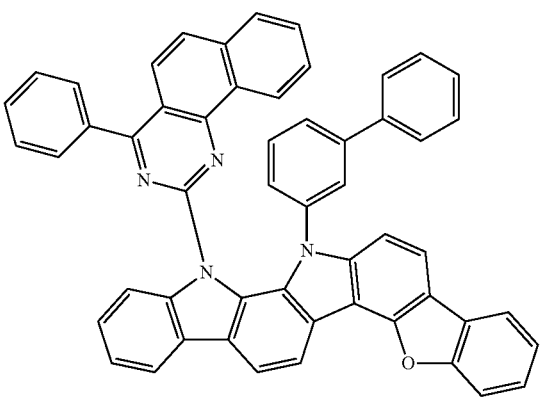
392
-continued
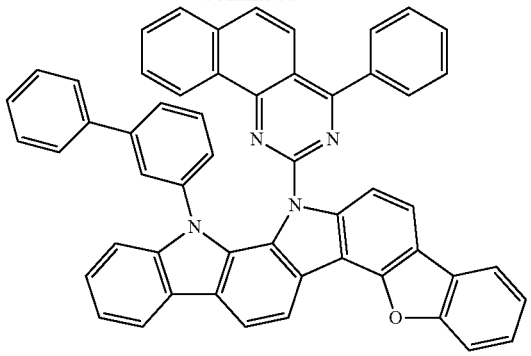
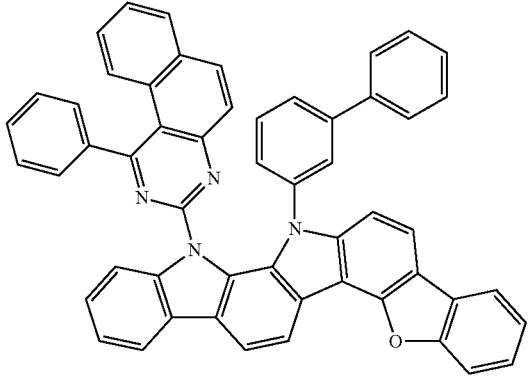
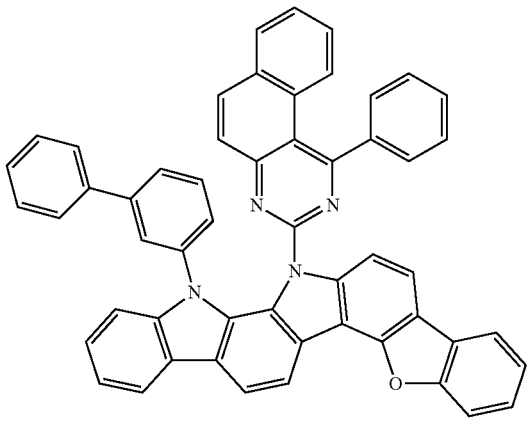
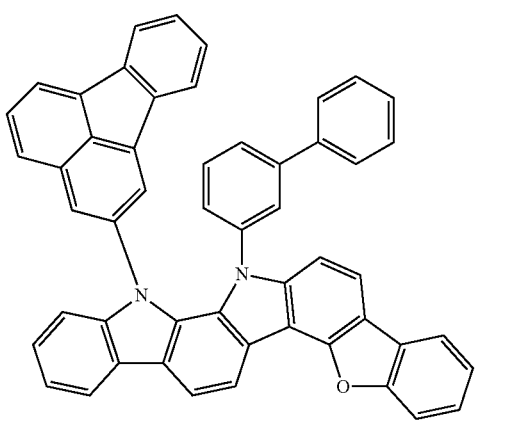

393
-continued
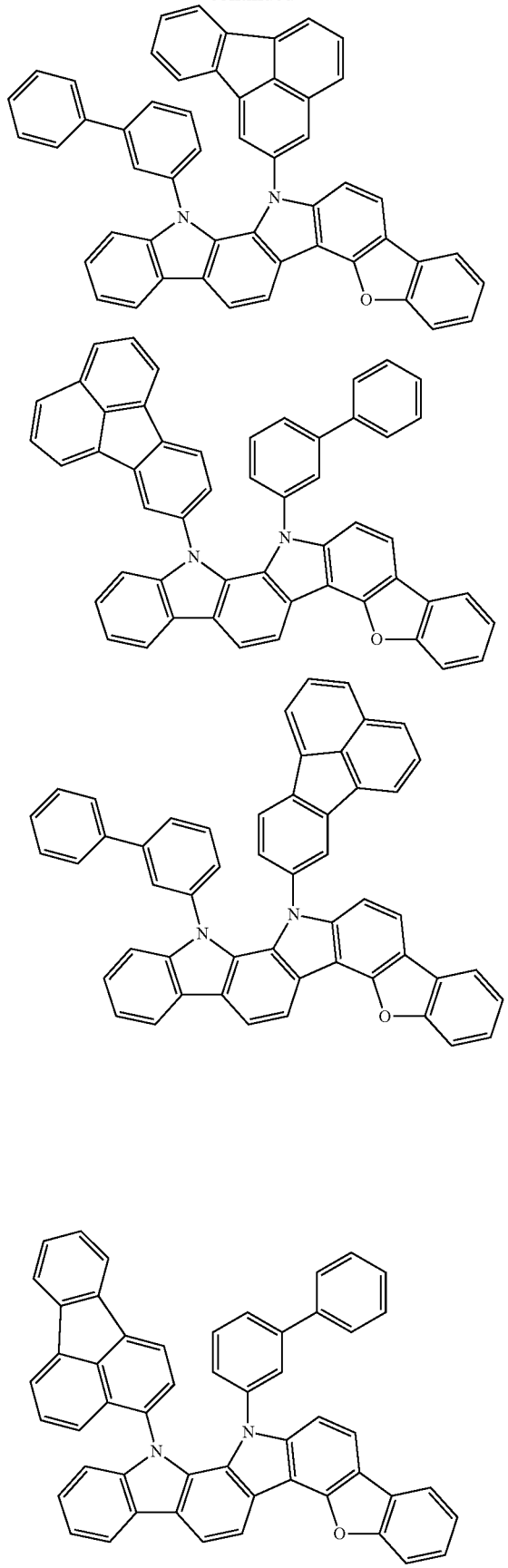
394
-continued
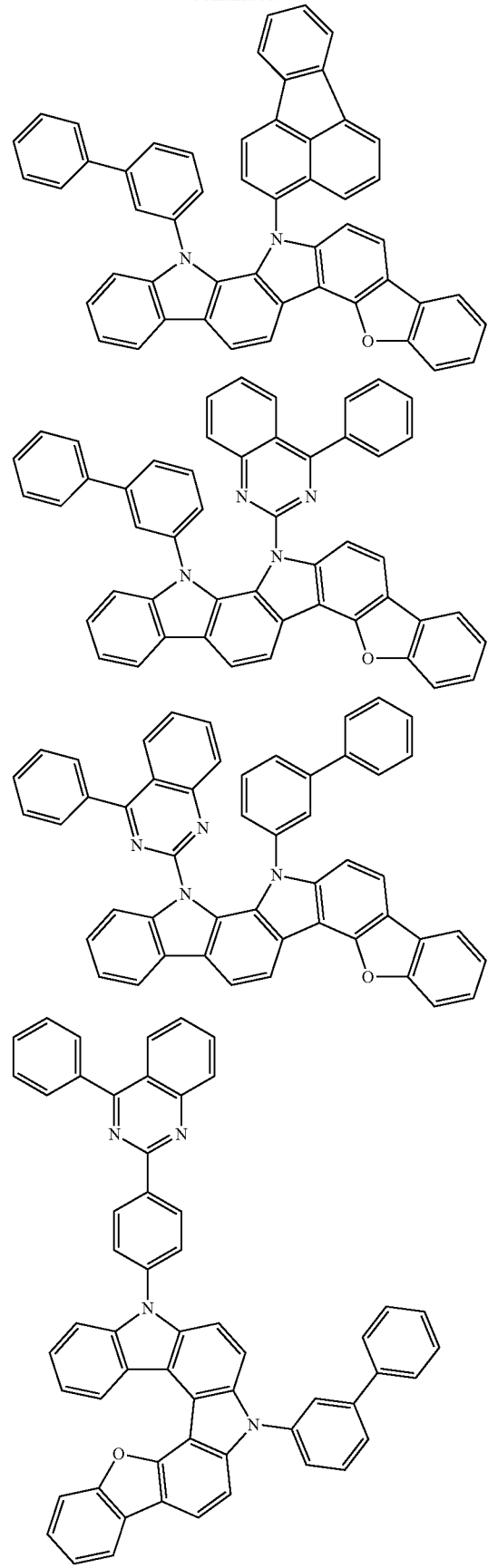

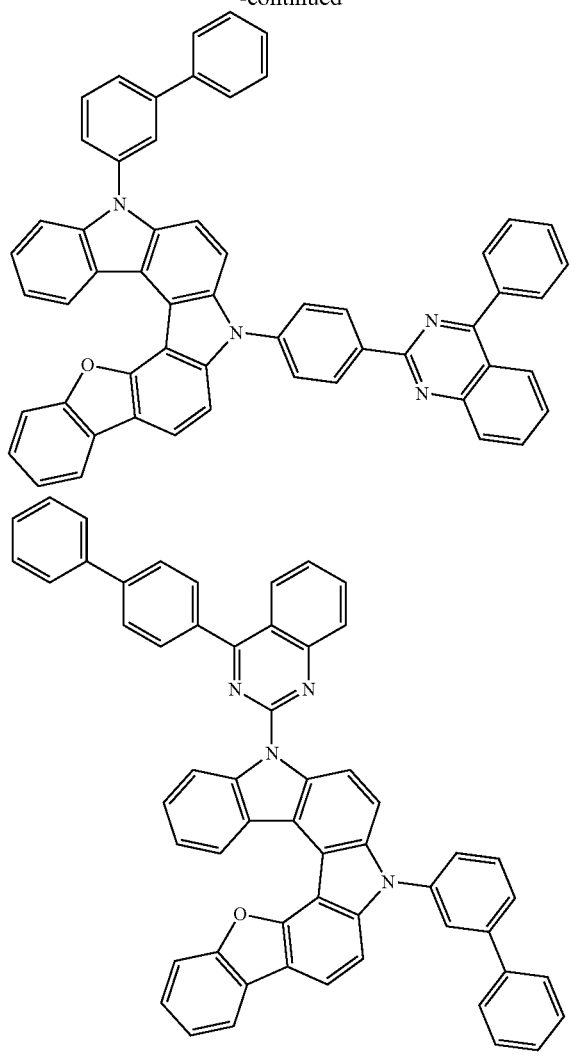
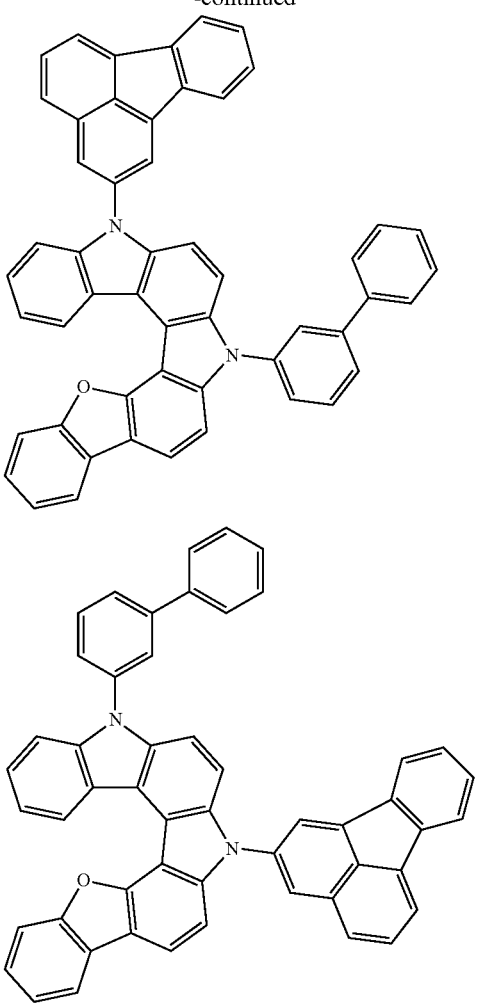
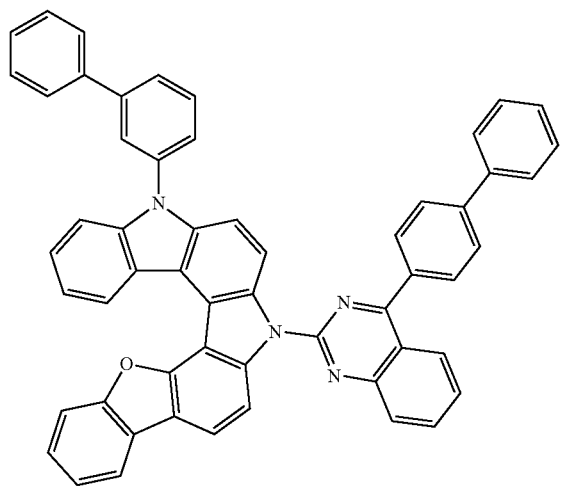
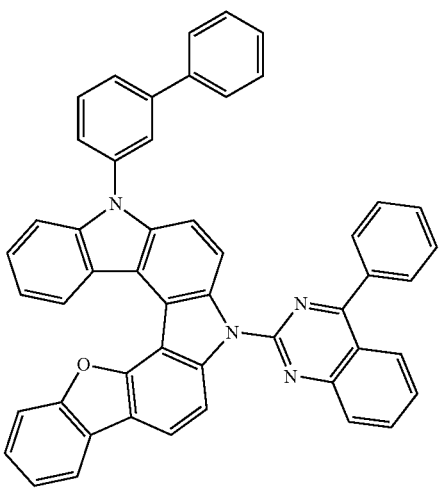

397
-continued
398
-continued
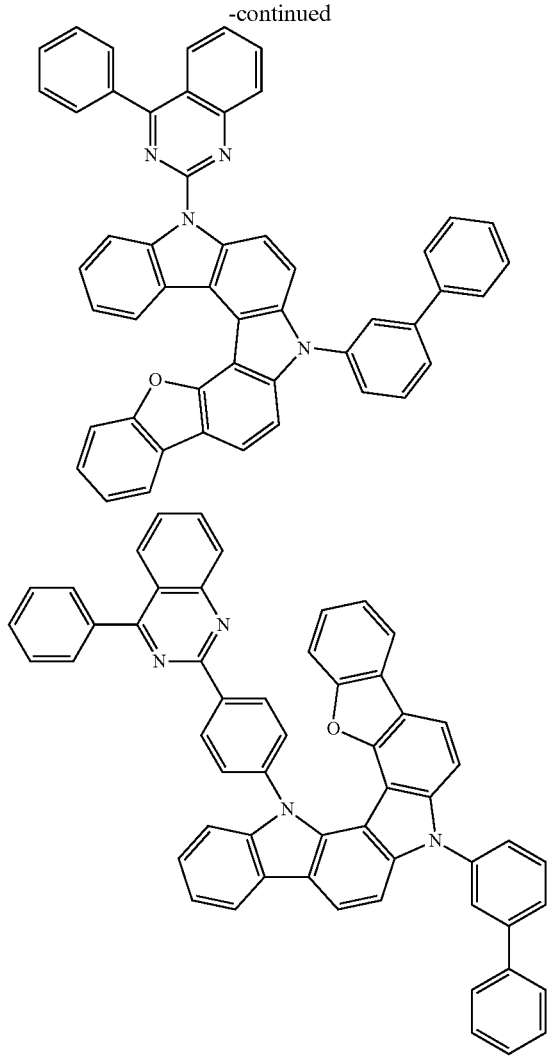
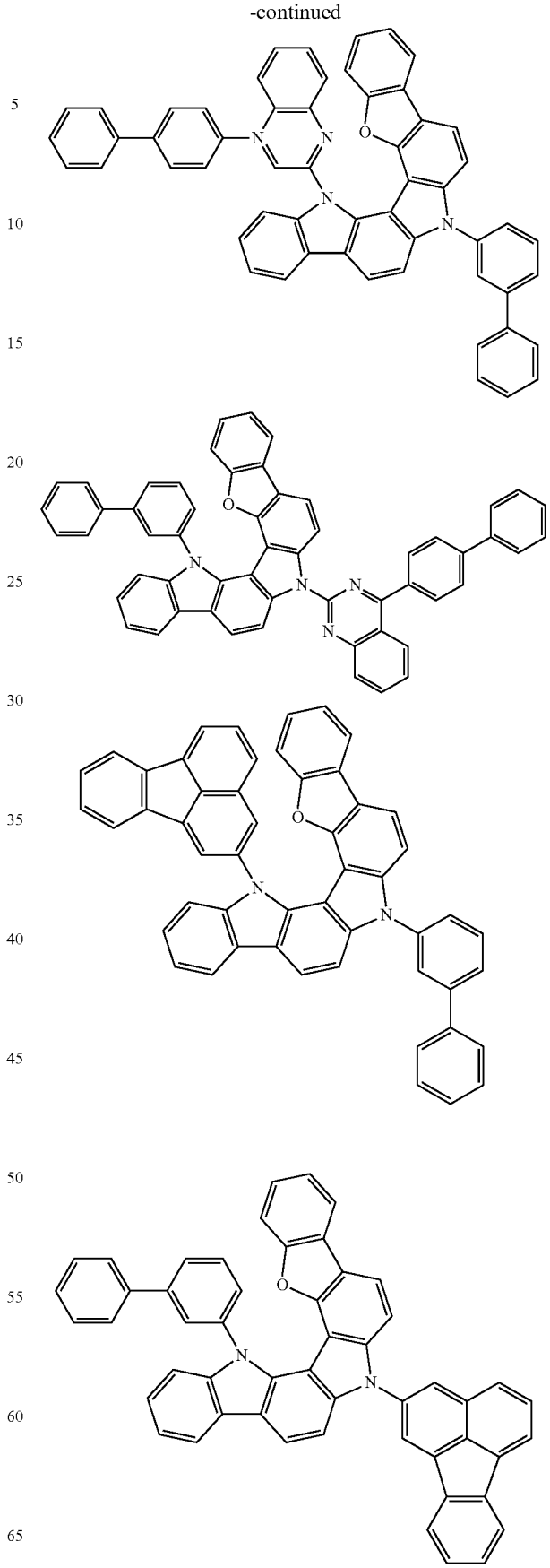

399
-continued
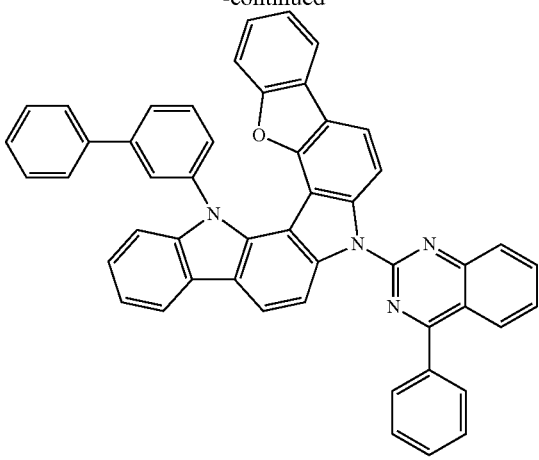
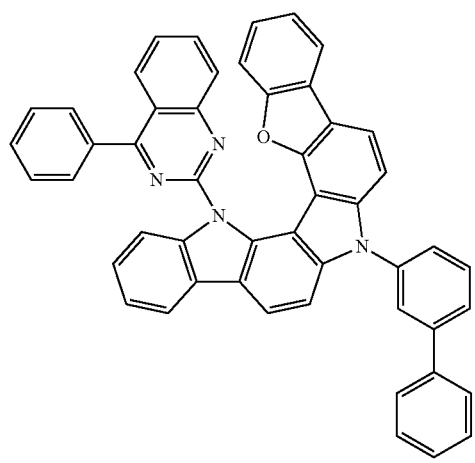
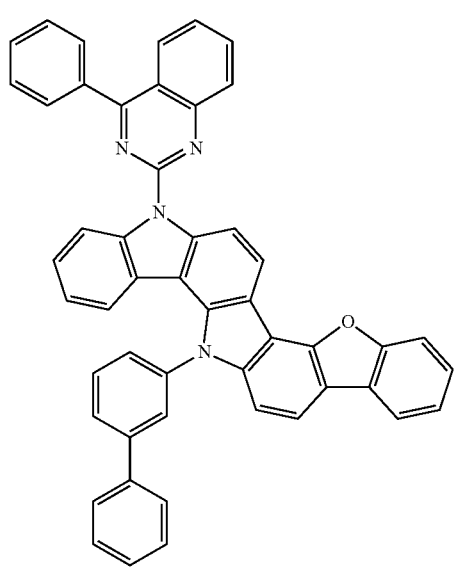
400
-continued
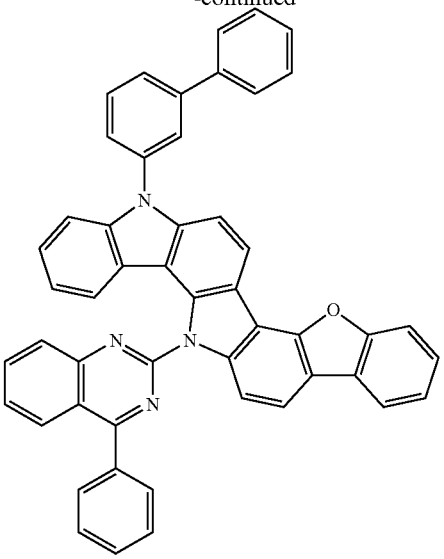
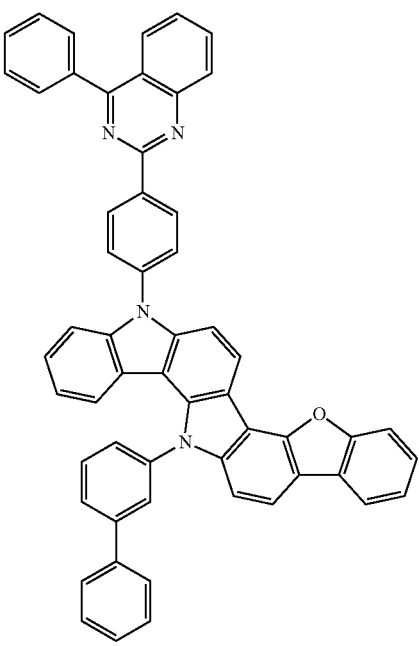

401
-continued
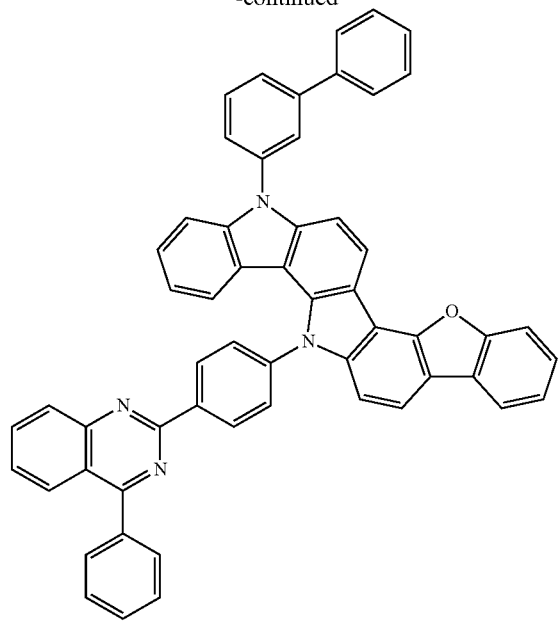
402
-continued
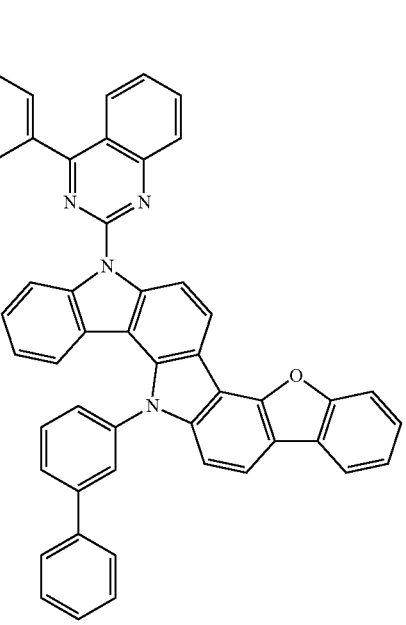
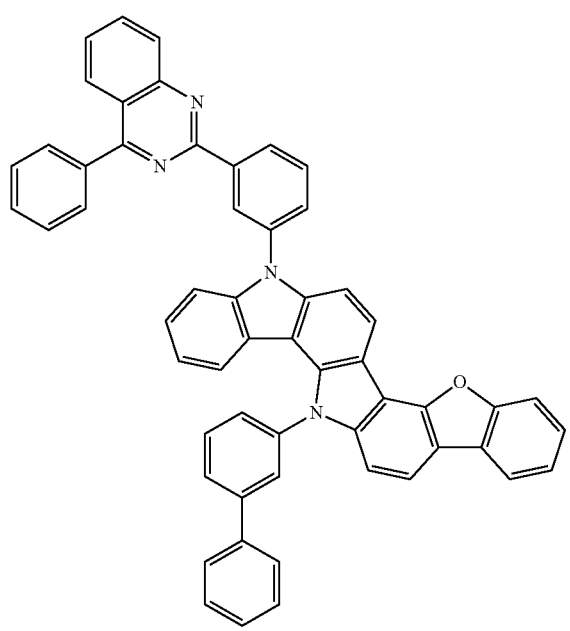
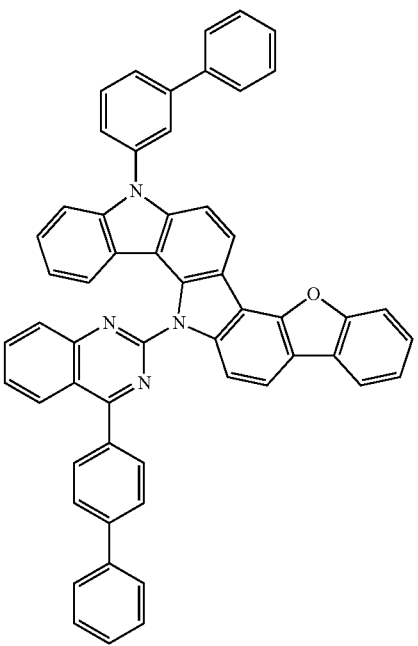

403
-continued
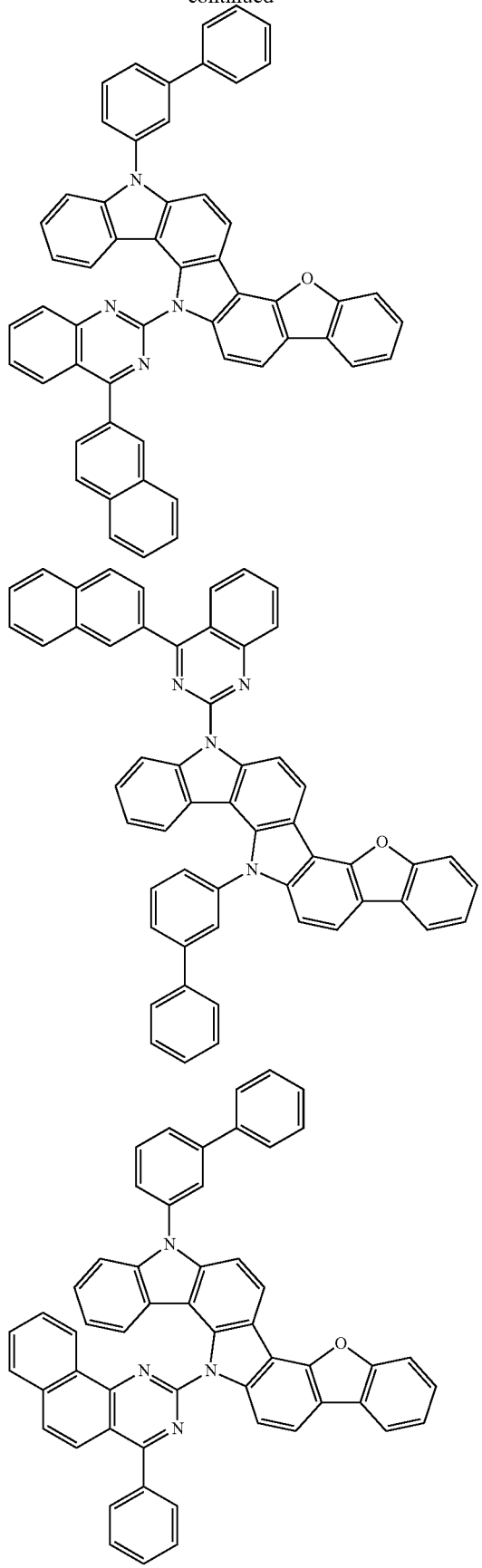
404
-continued
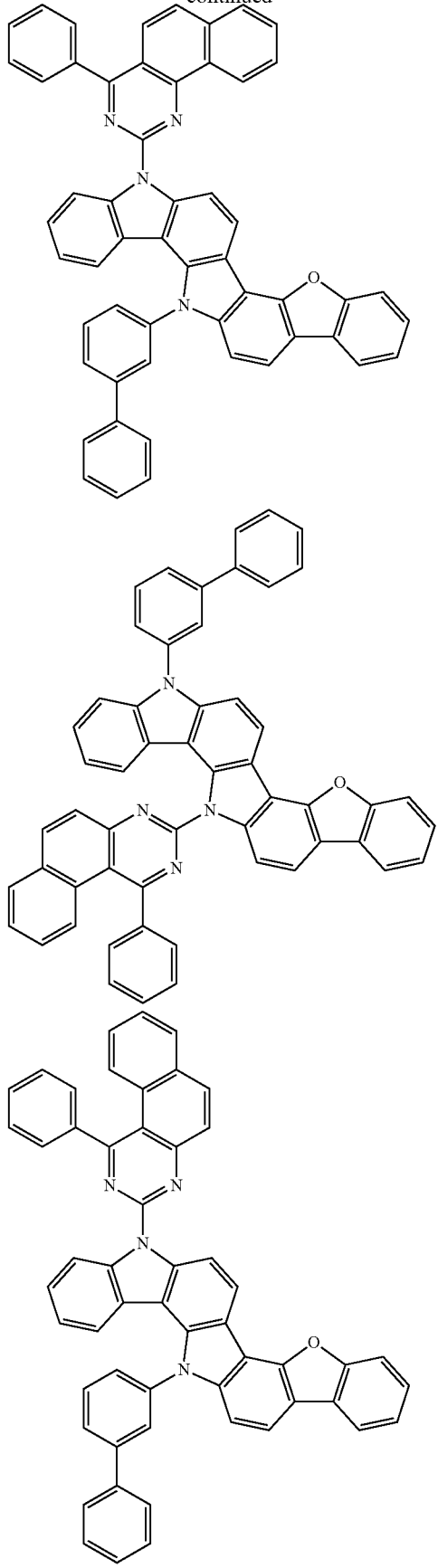

405
-continued
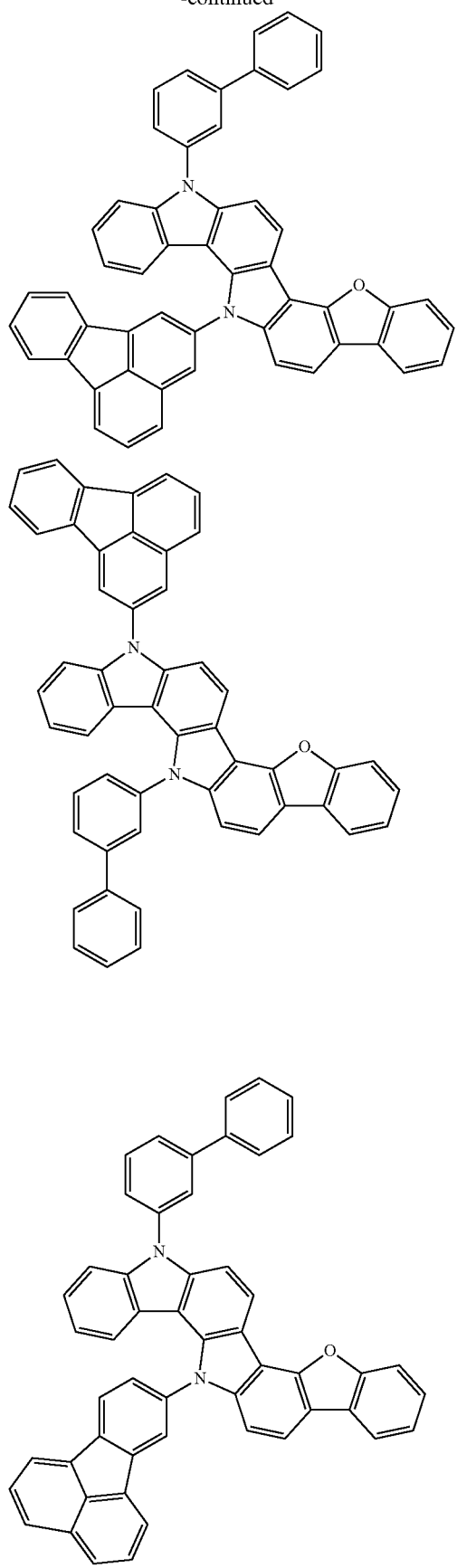
406
-continued
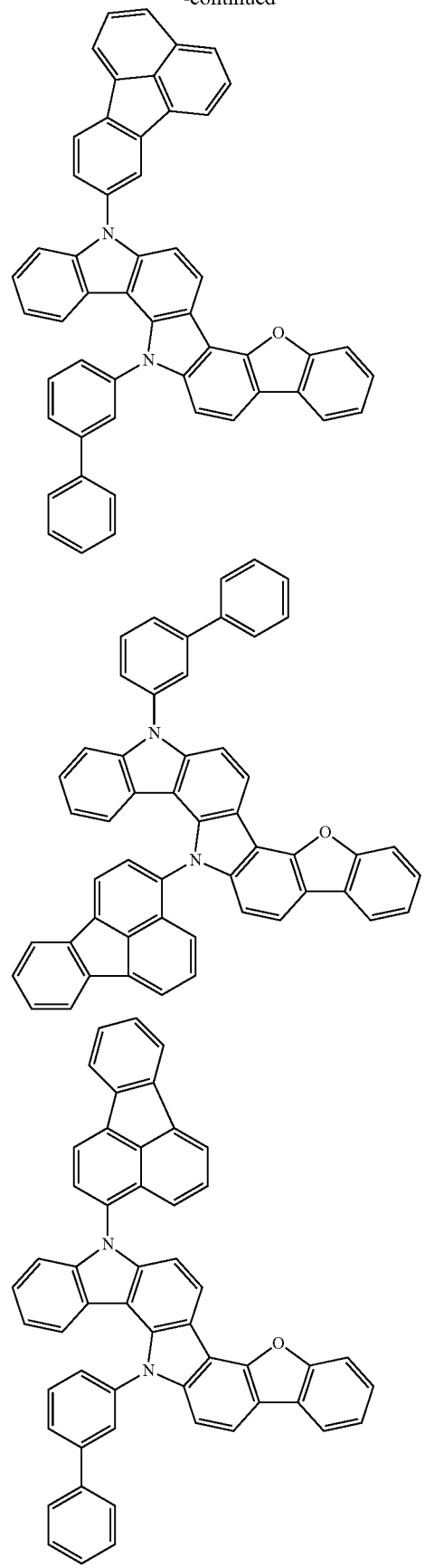

407
-continued
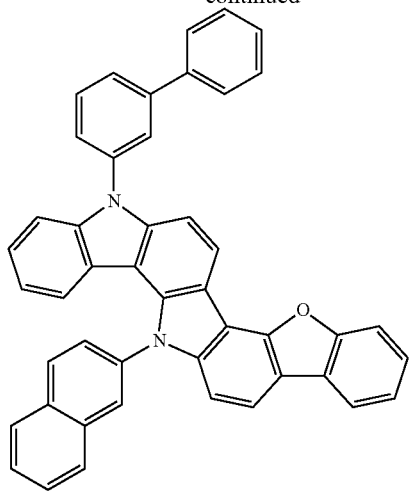
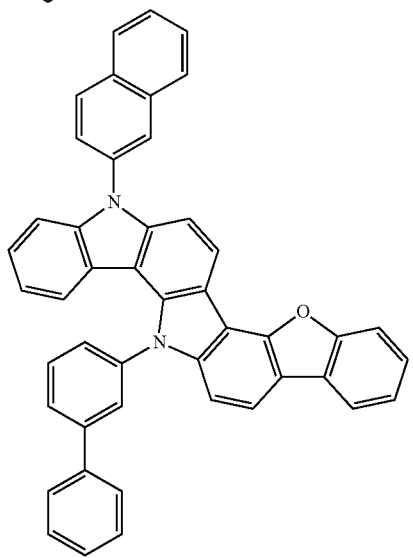
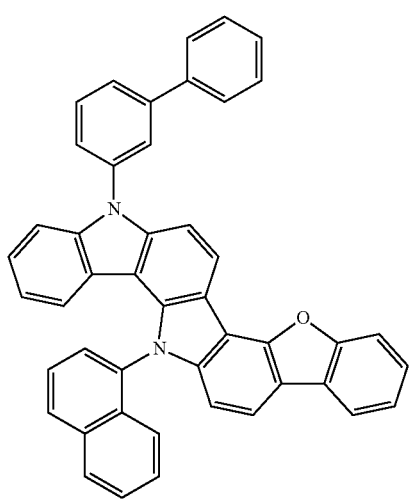
408
-continued
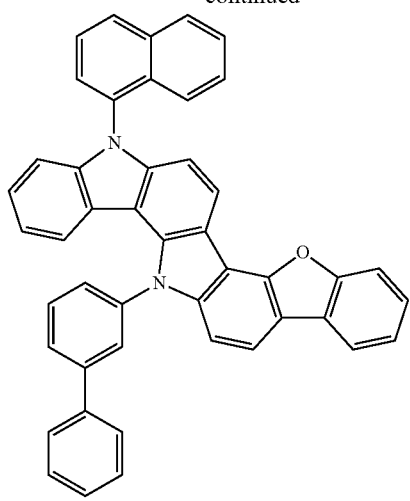
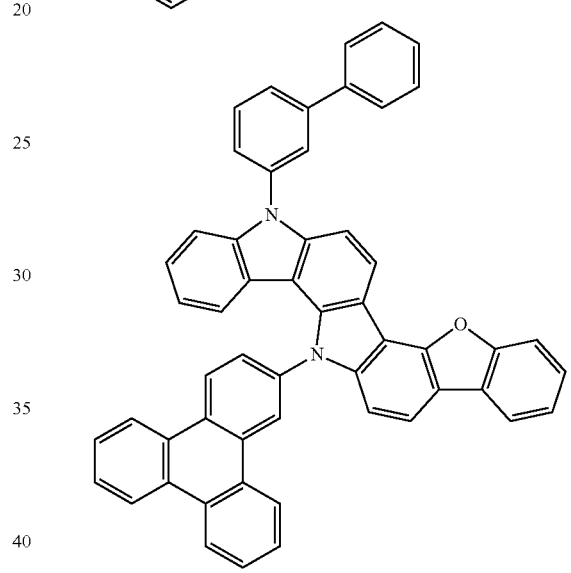
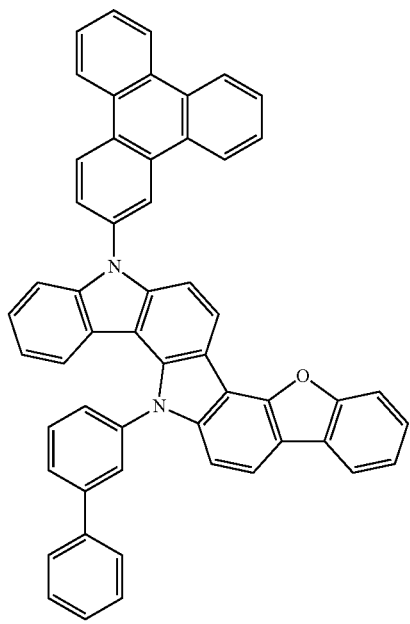

409
-continued
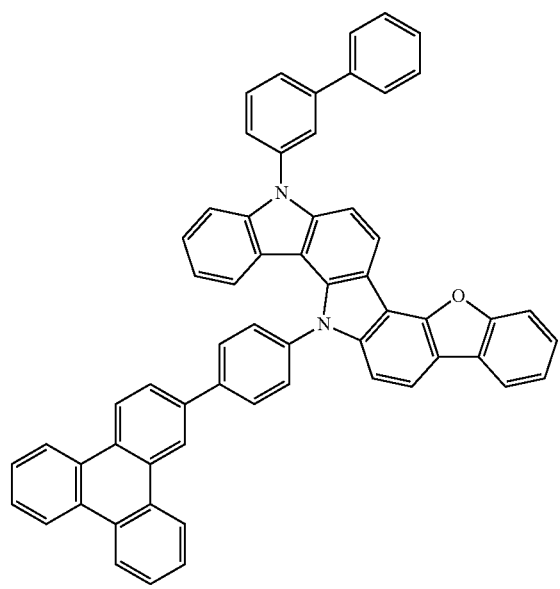
410
-continued
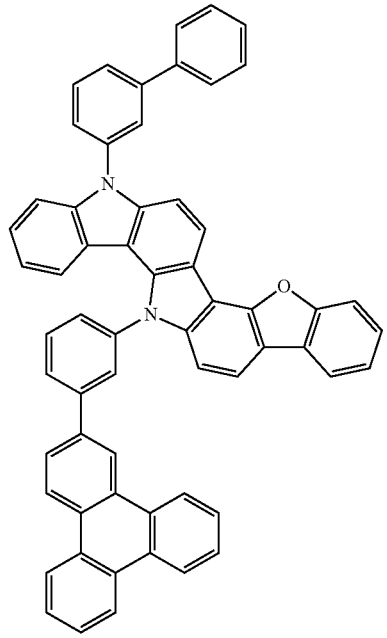
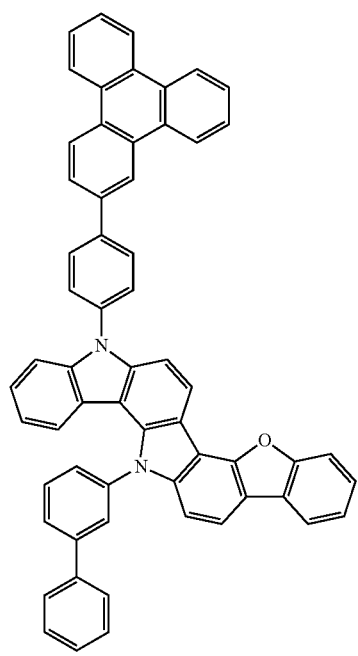
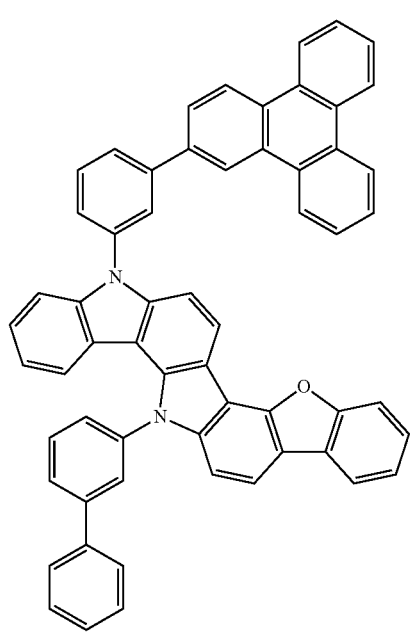 [SMILES: c1ccc(-c2cccc(-n3c4ccc5c6ccccc6oc5c4c4ccc5c(c6ccccc6n5-c5cccc(-c6ccc7c8ccccc8c8ccccc8c7c6)c5)c43)c2)cc1]

411
412
-continued
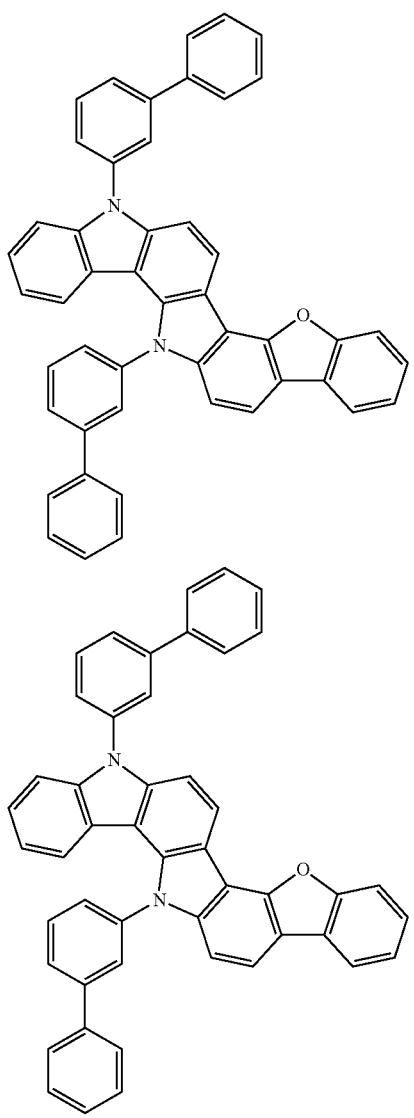
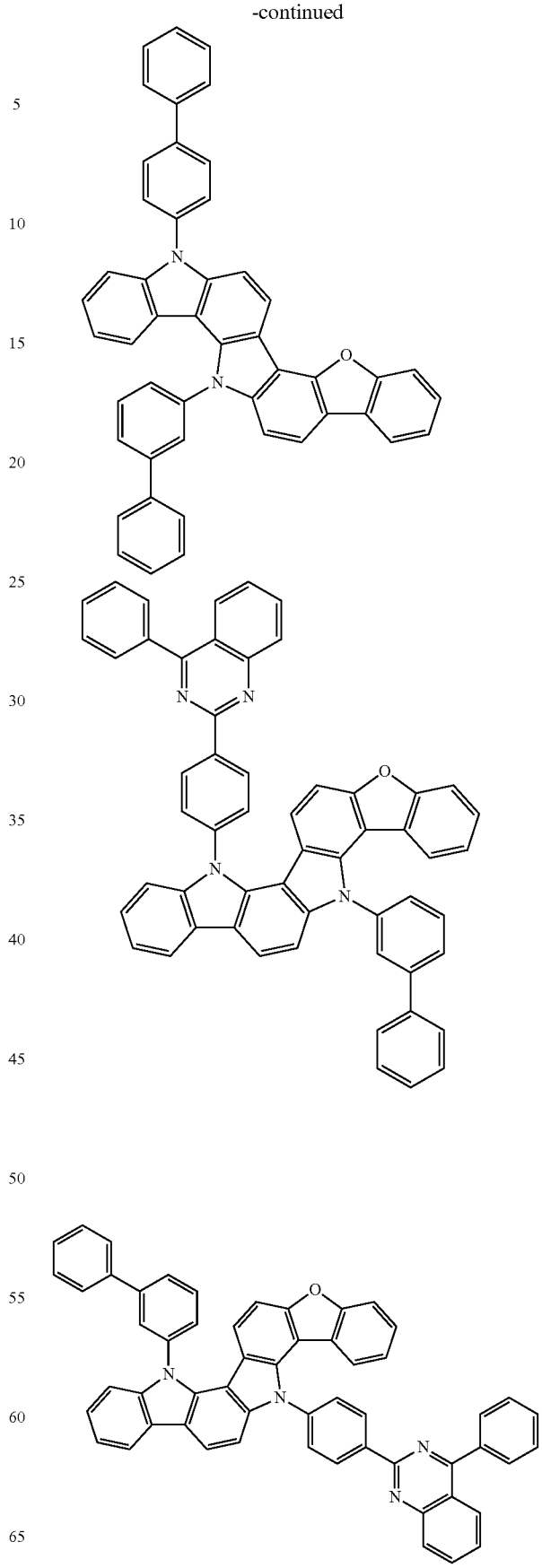

413
-continued
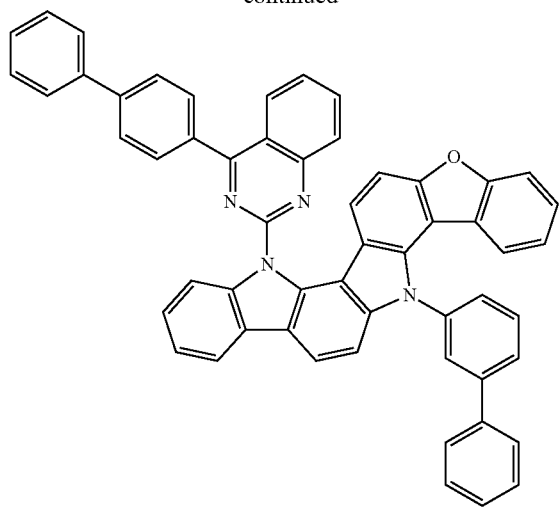
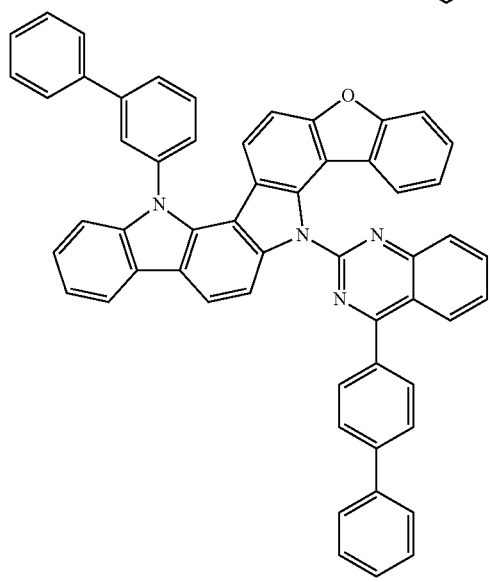
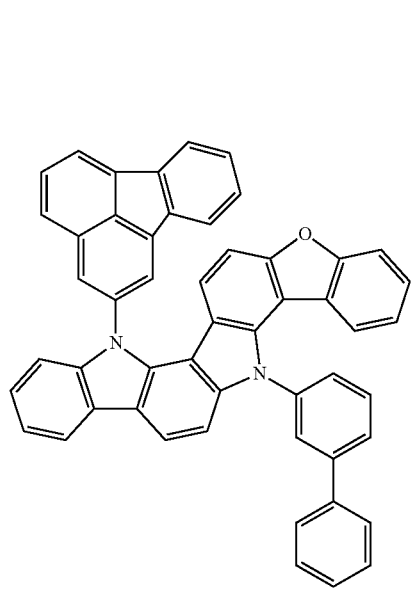
414
-continued
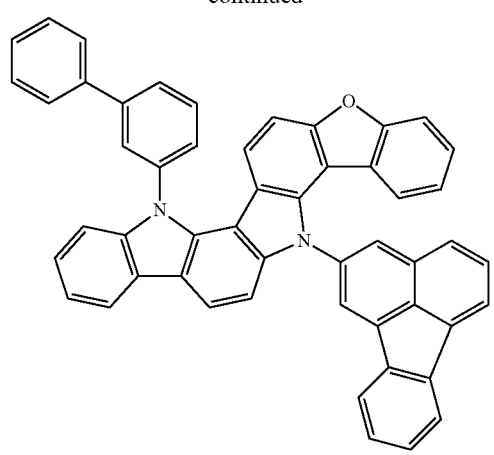
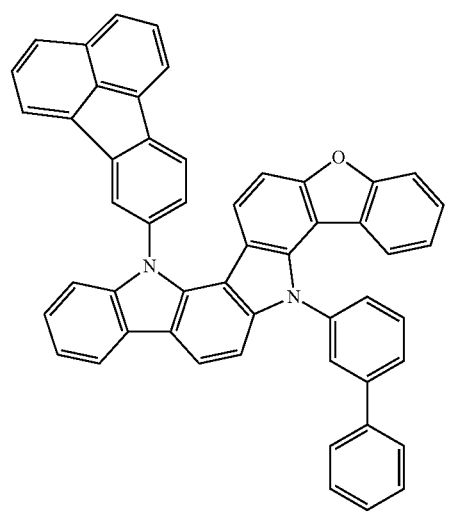
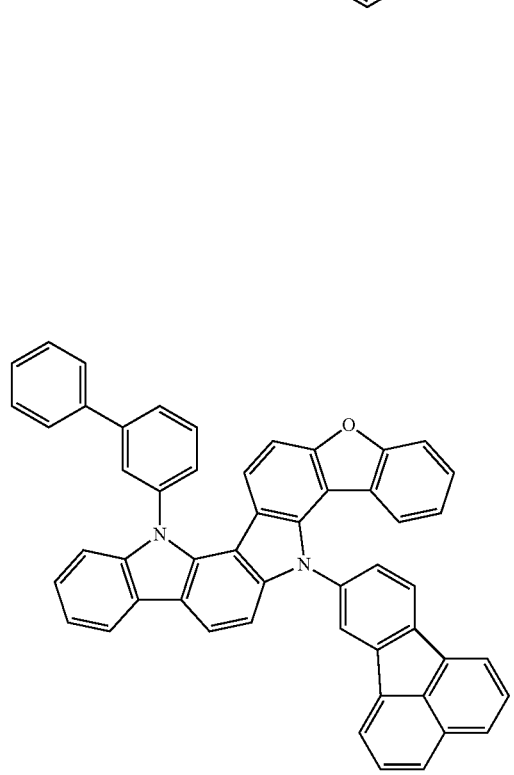

415
-continued
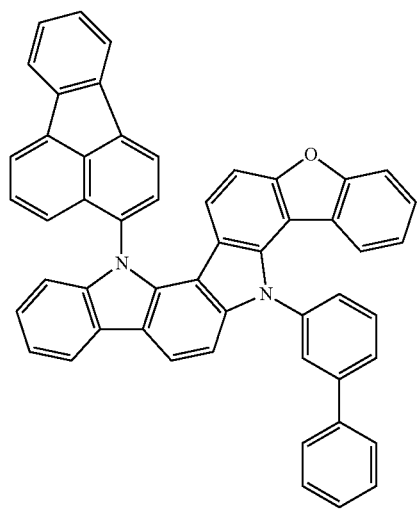
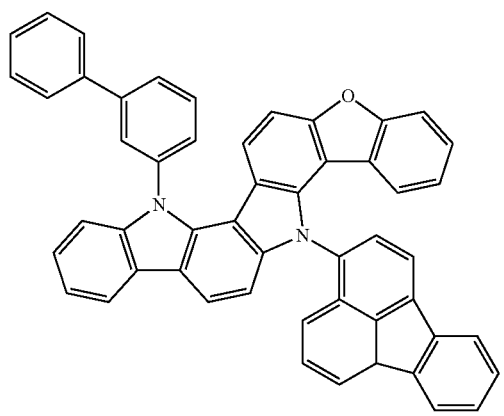
416
-continued
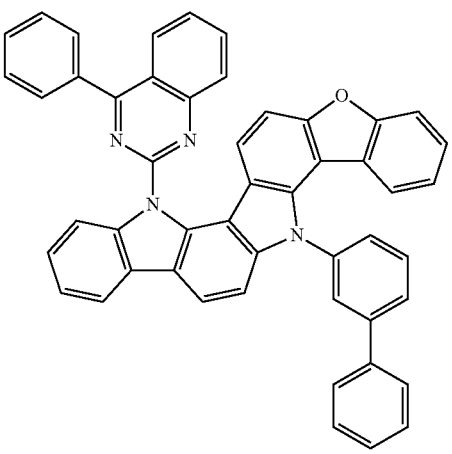
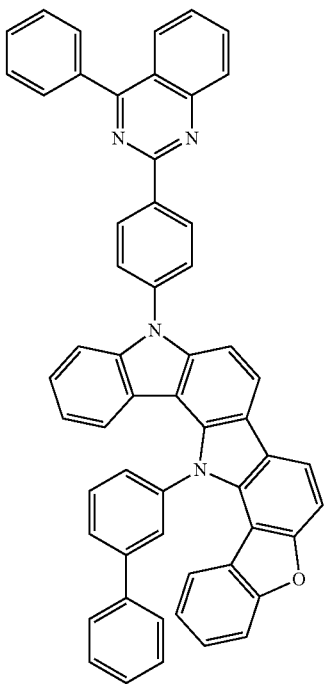

417
-continued
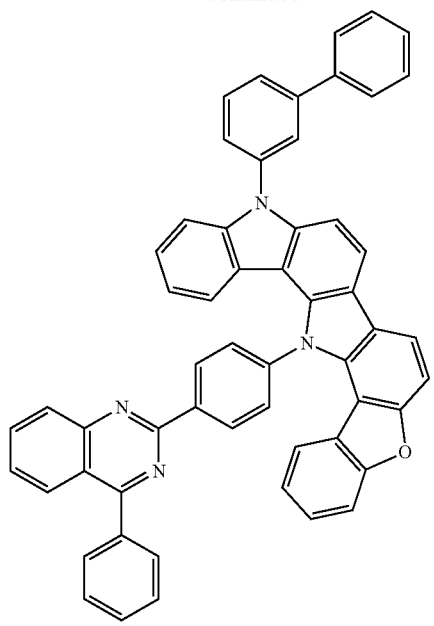
418
-continued
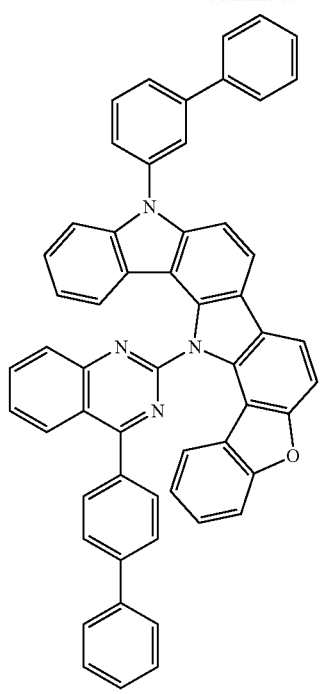
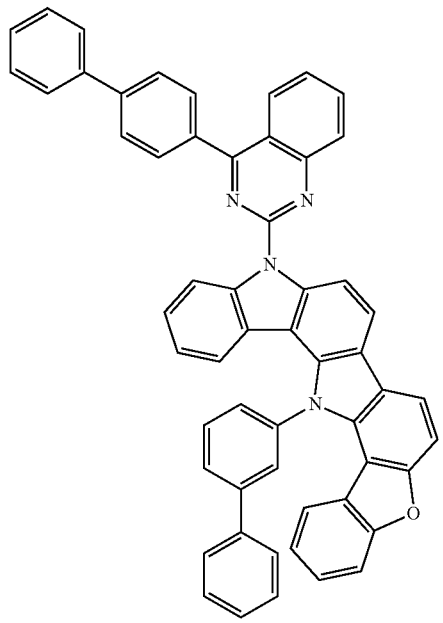
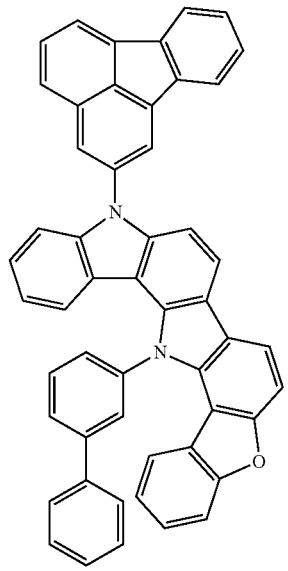

419
-continued
420
-continued
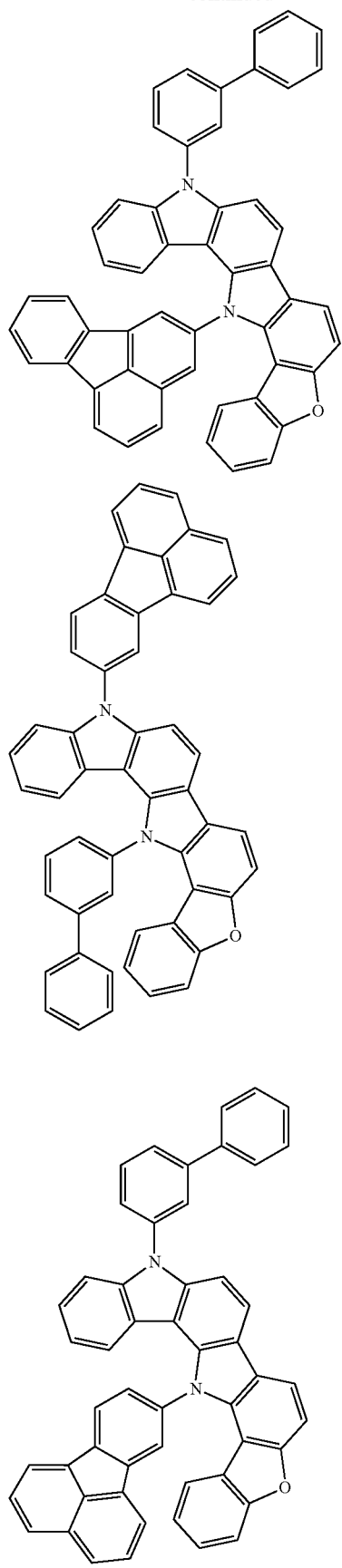
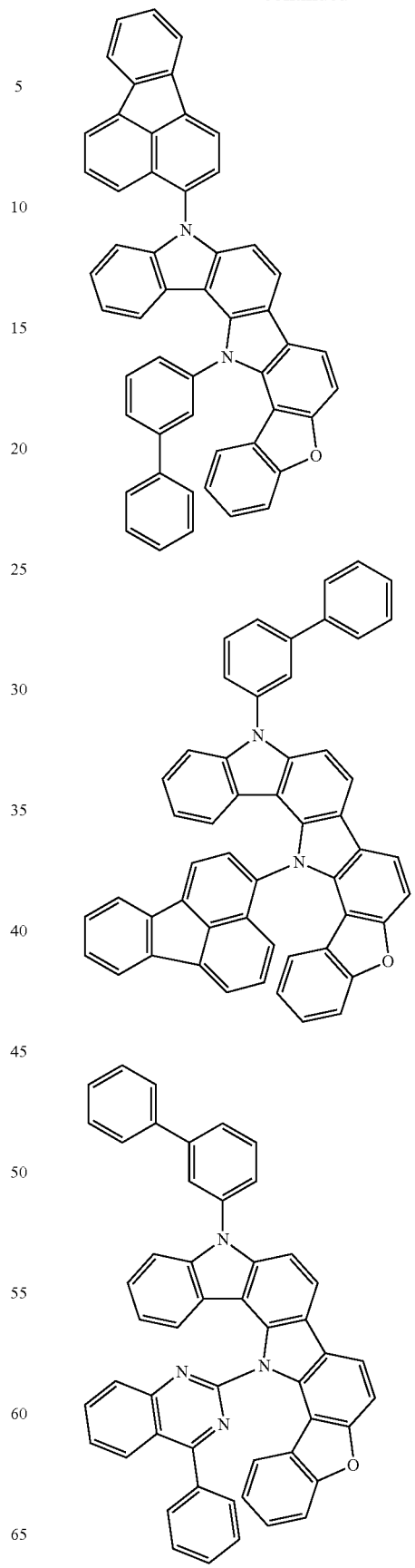

421
-continued
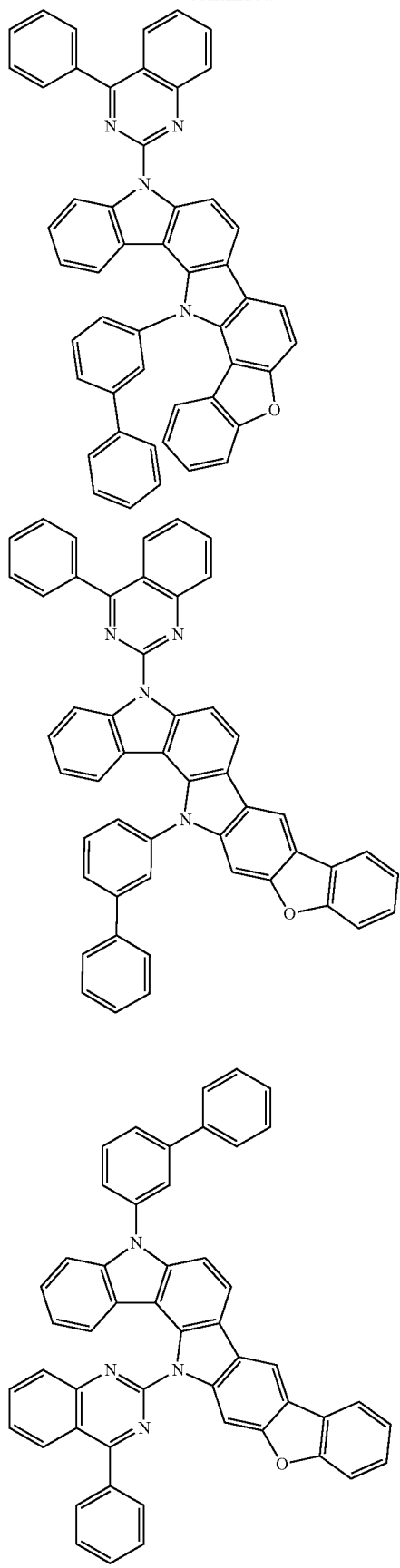
422
-continued
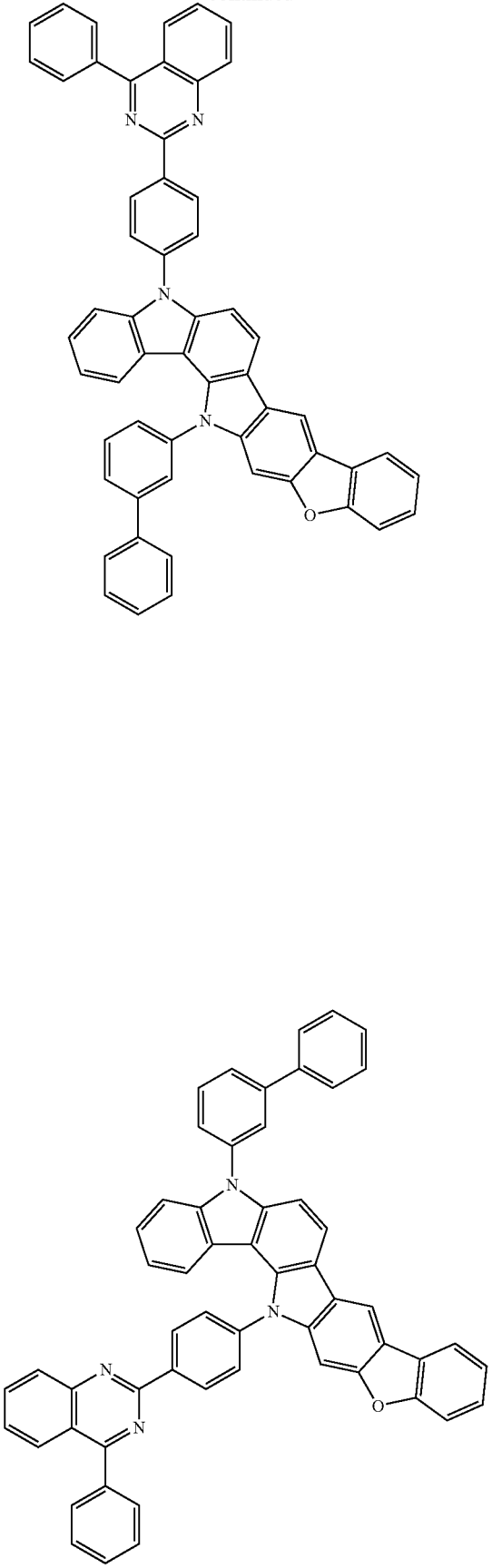

423
-continued
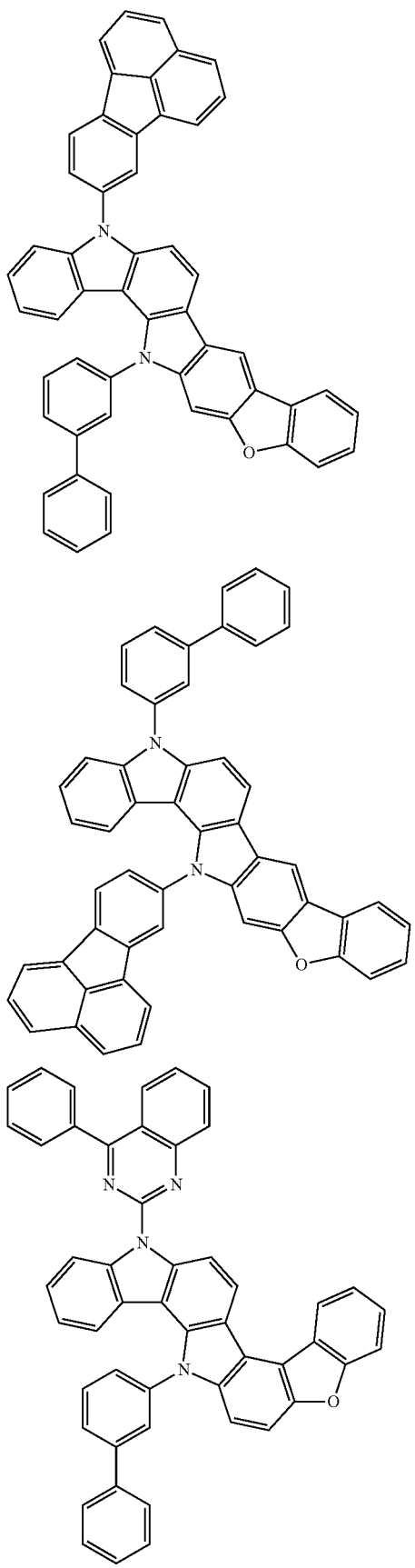
424
-continued
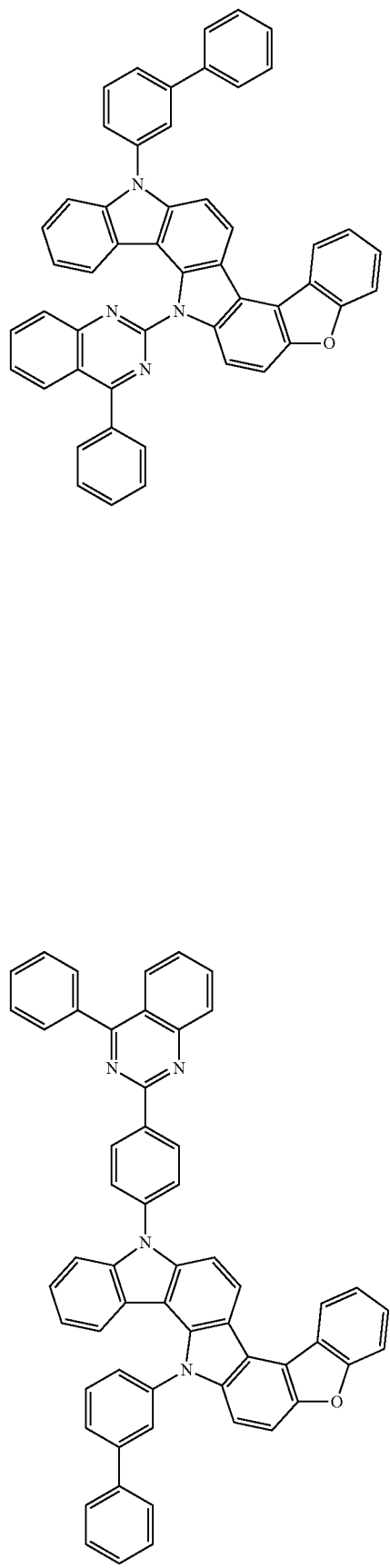

425
-continued
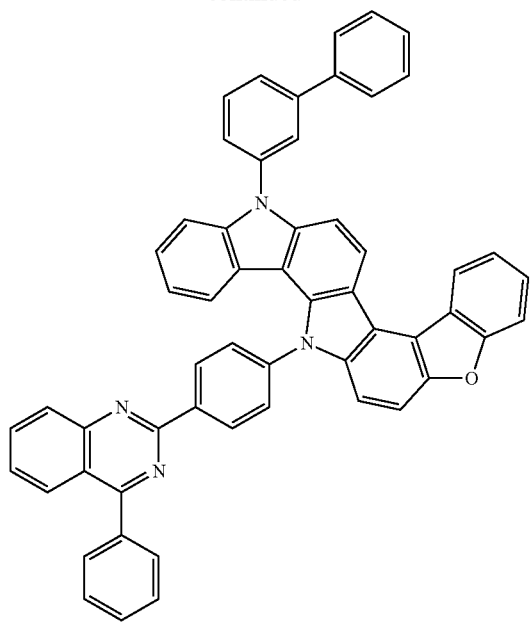
426
-continued
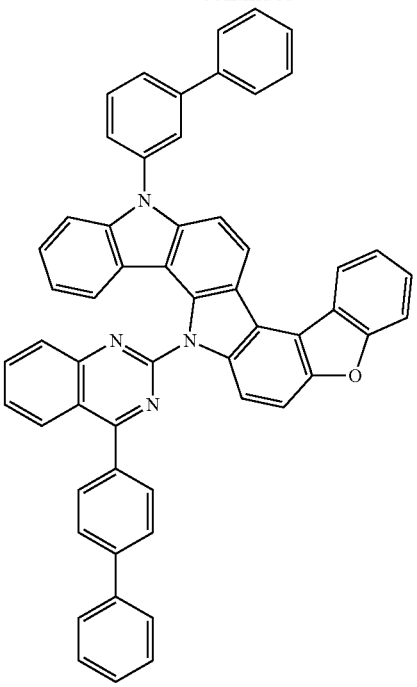
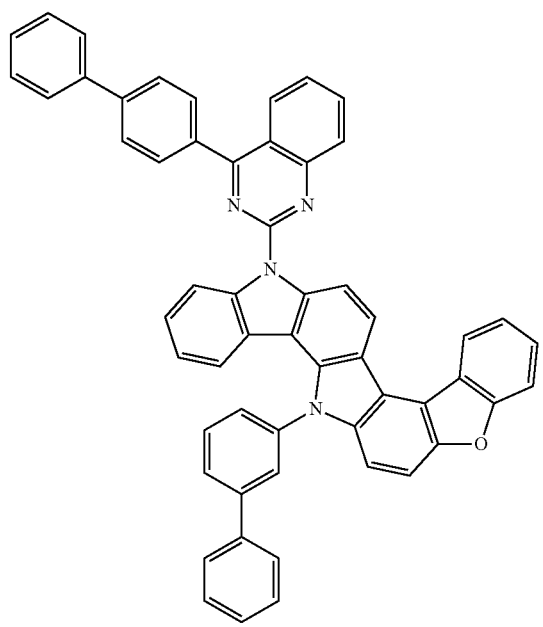
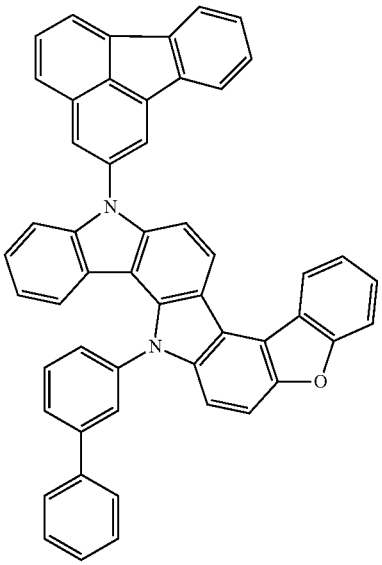

427
-continued
428
-continued
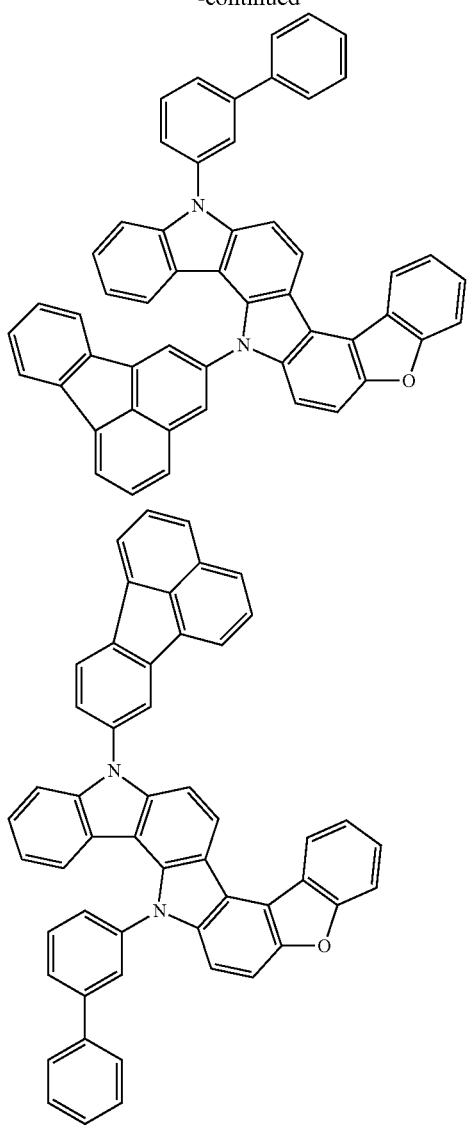
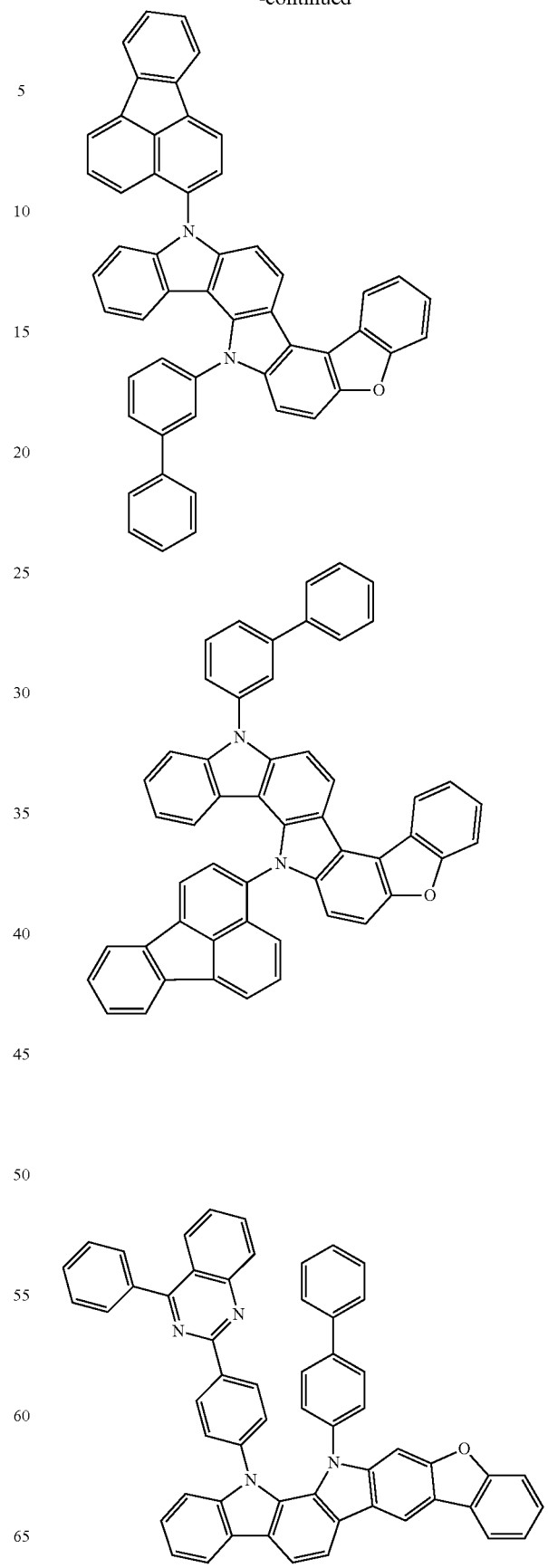

429
-continued
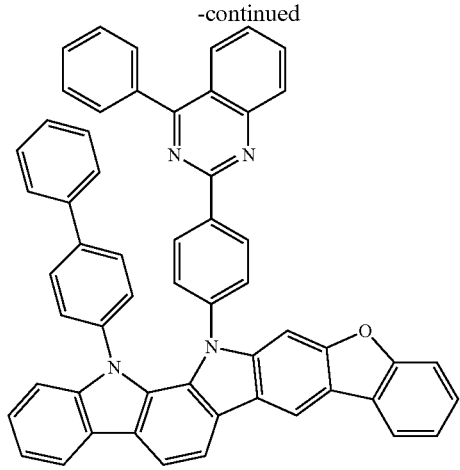
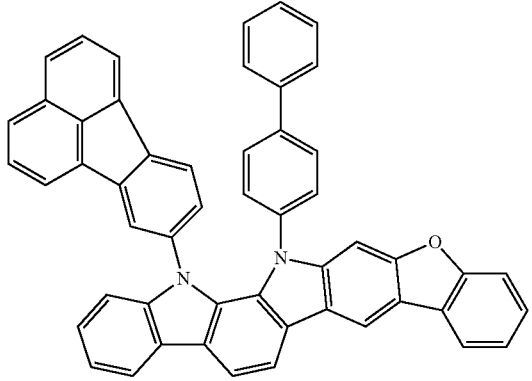
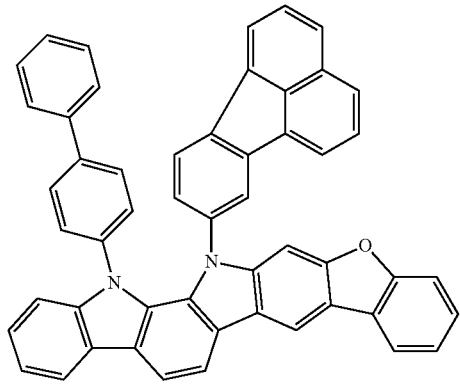
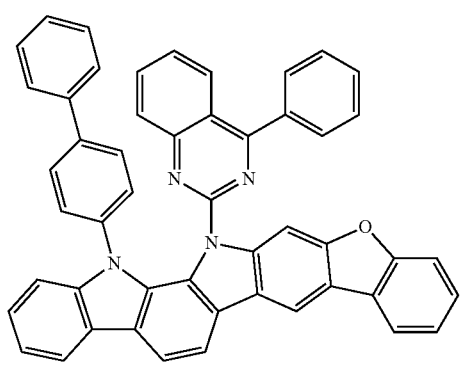
430
-continued
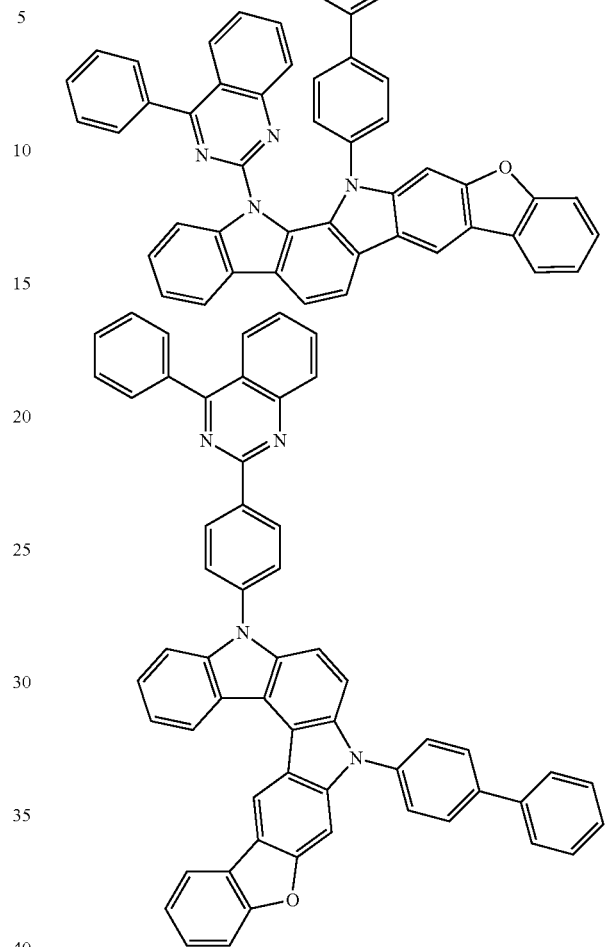
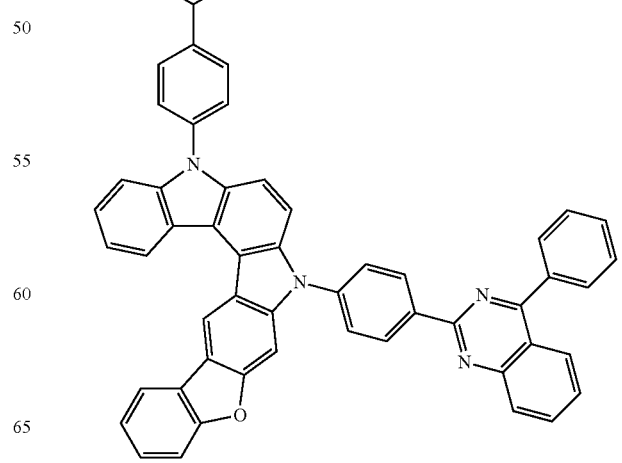

431
-continued
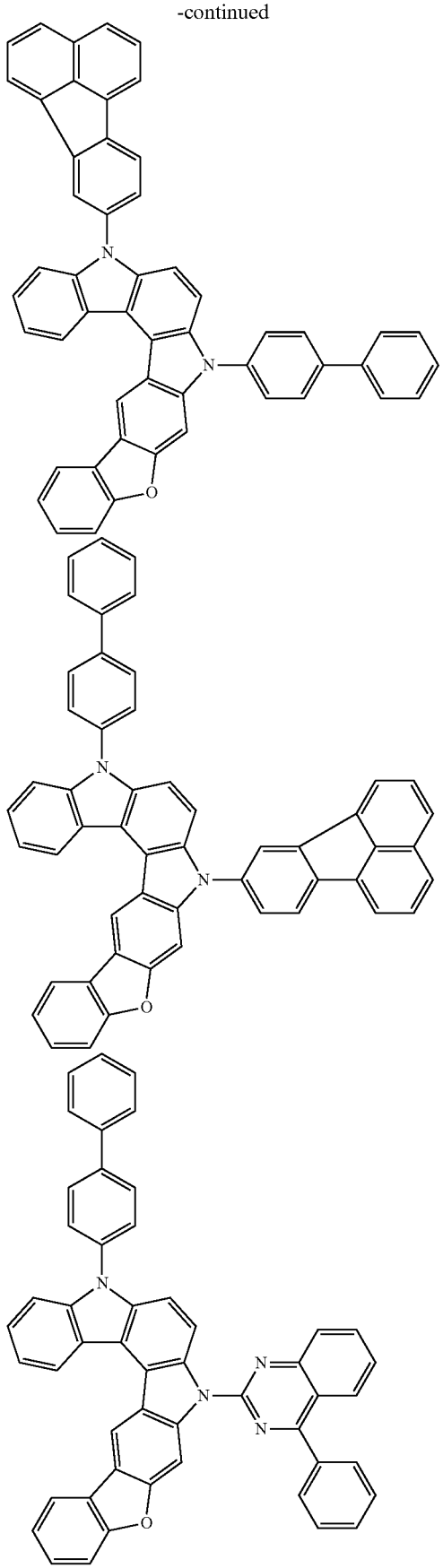
432
-continued
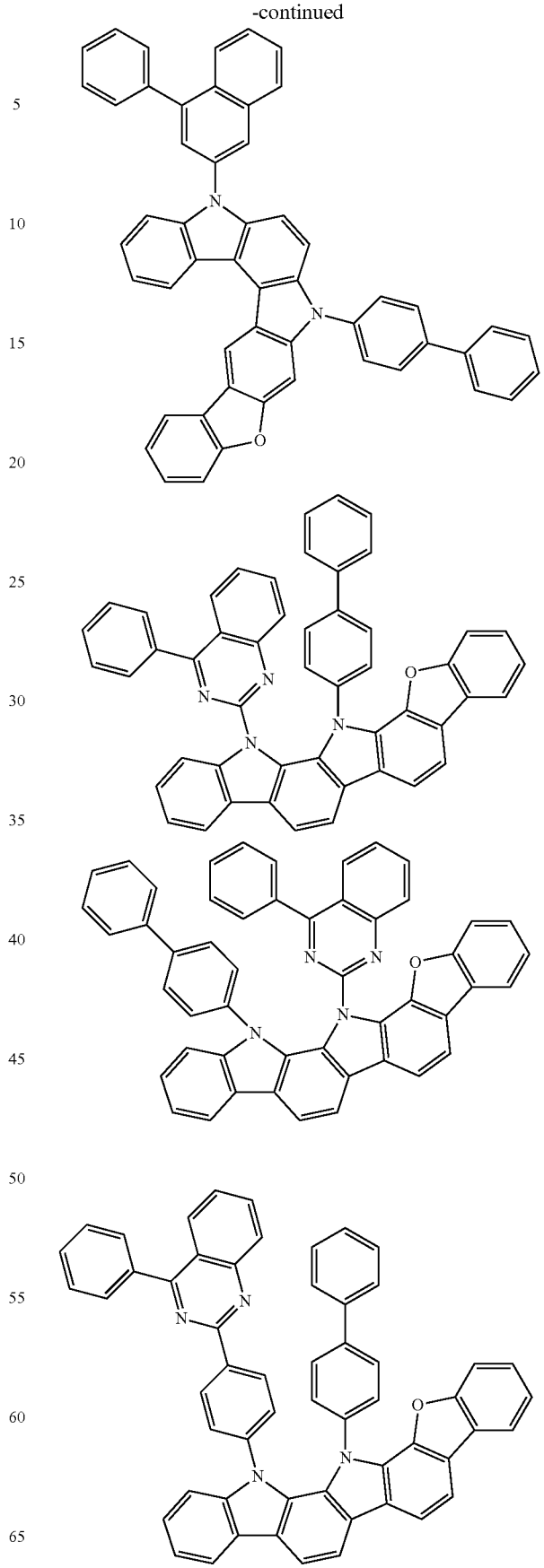

433
-continued
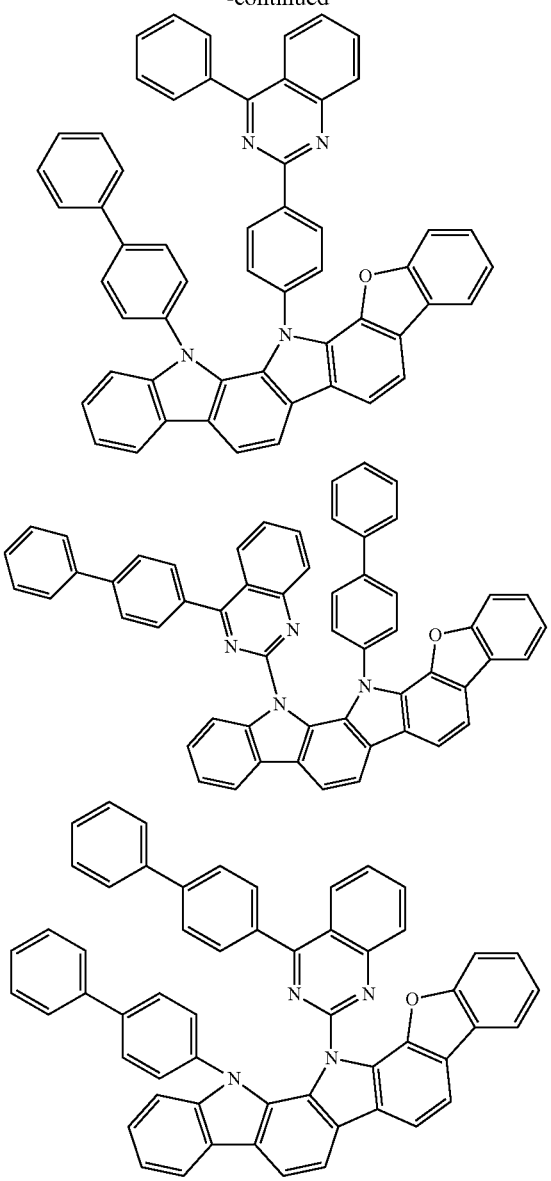
434
-continued
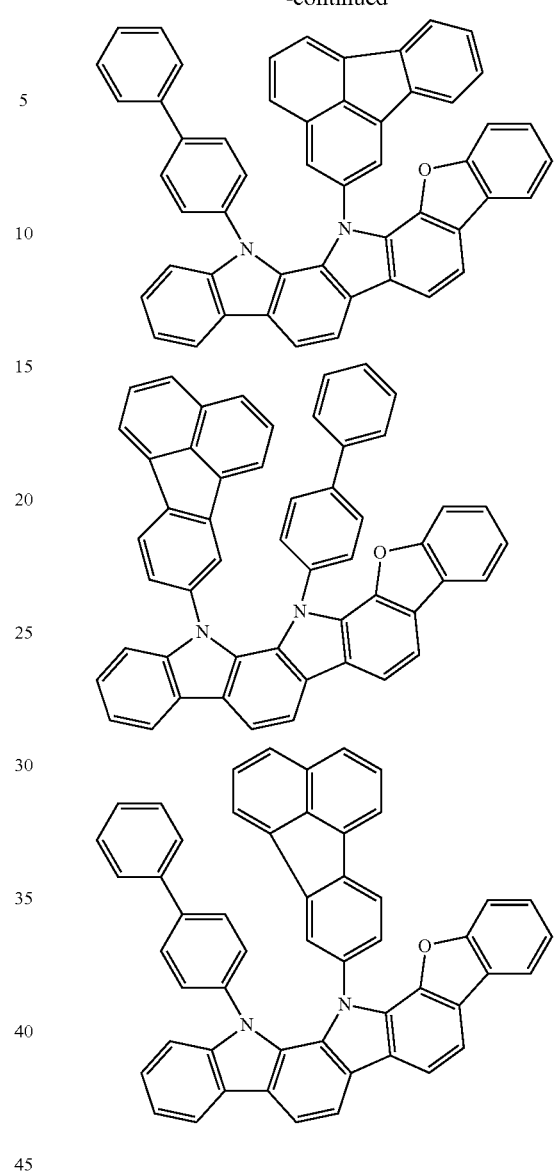
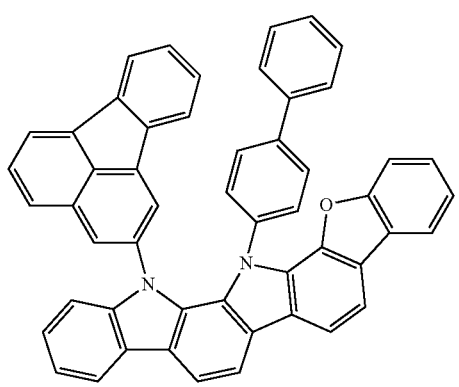
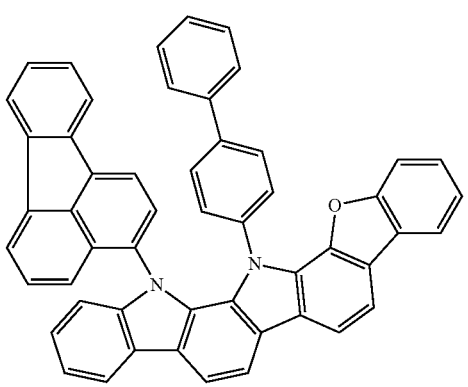

435
-continued
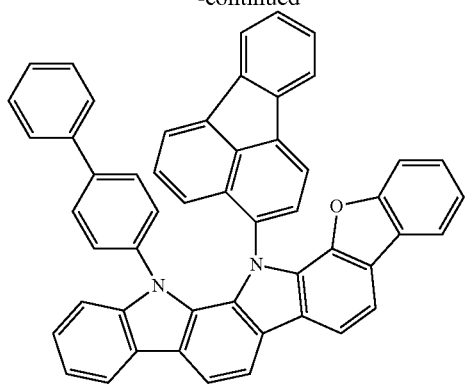
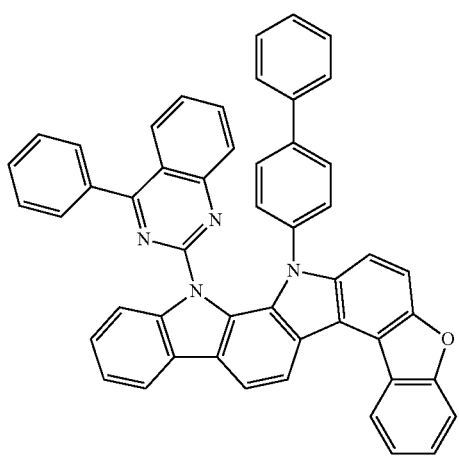
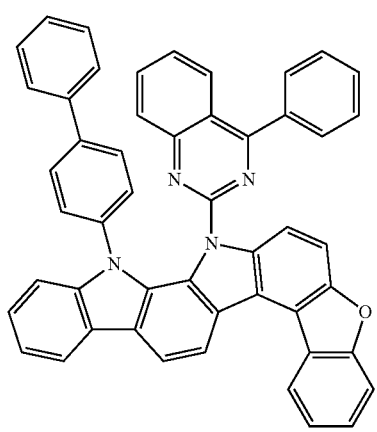
436
-continued
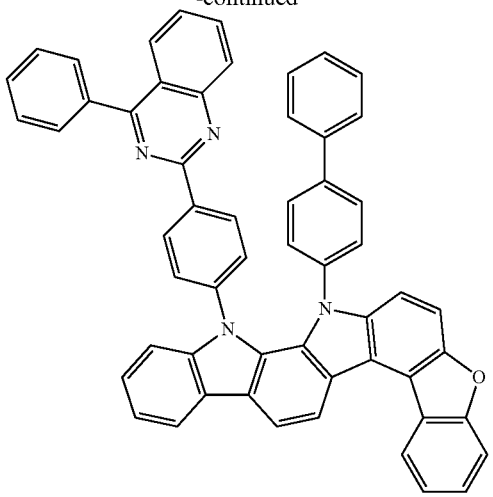
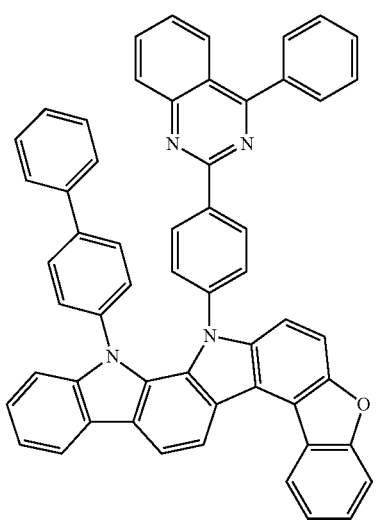
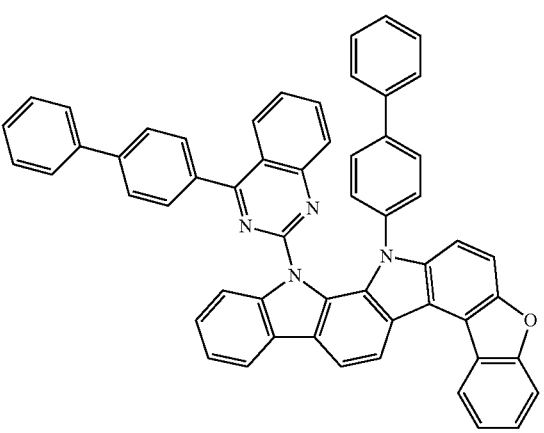

437
-continued
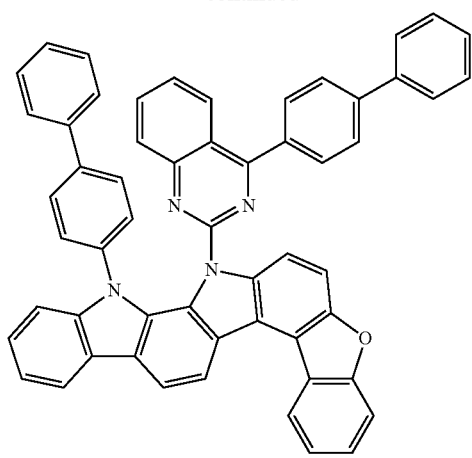
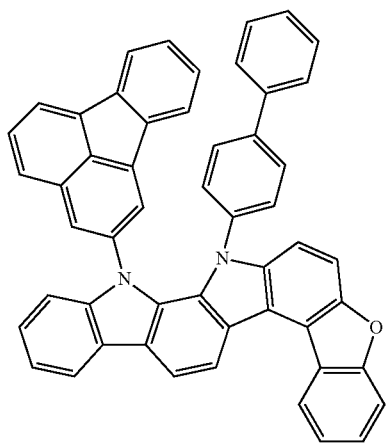
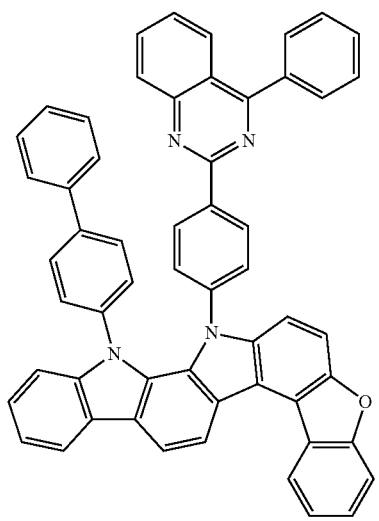
438
-continued
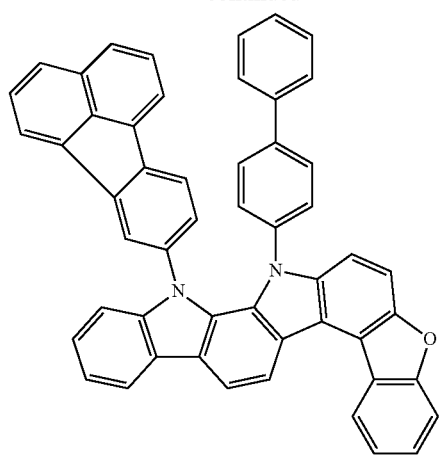
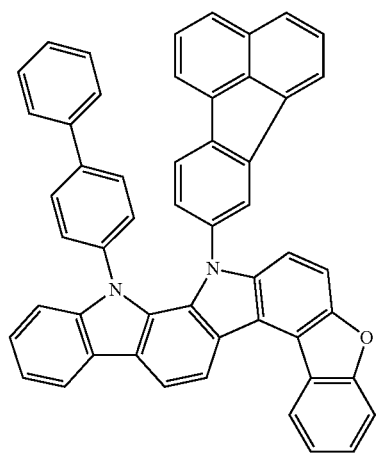
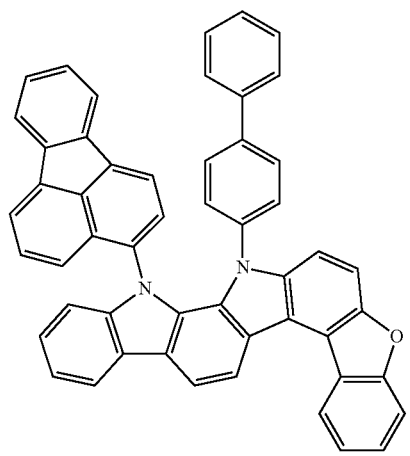

439
-continued
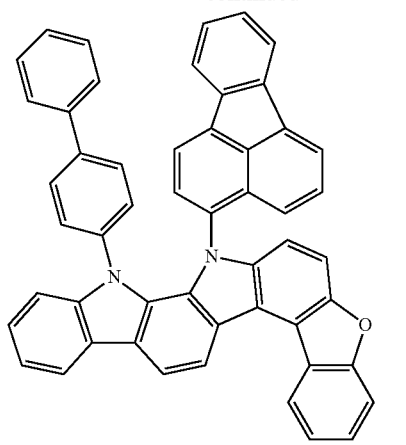
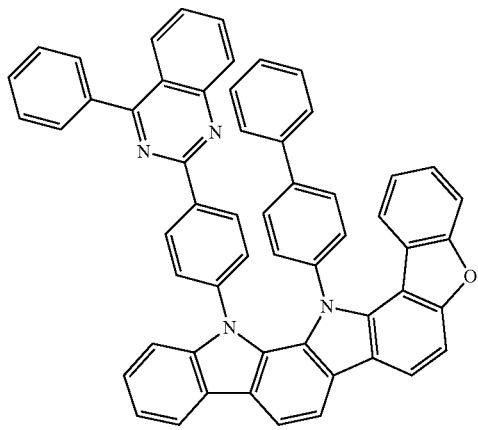
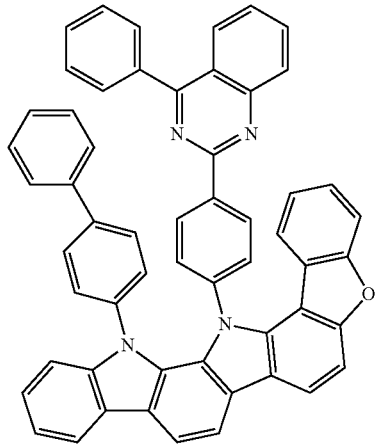
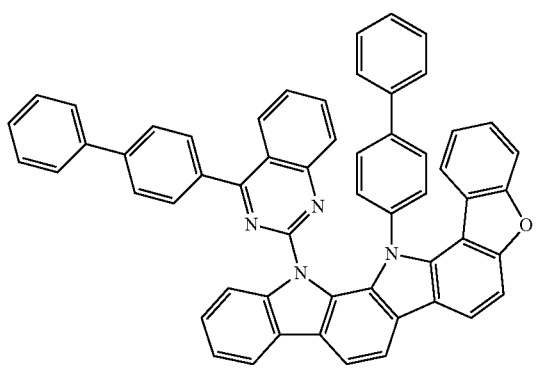
440
-continued
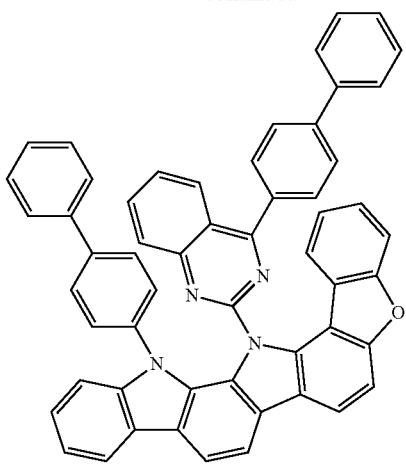
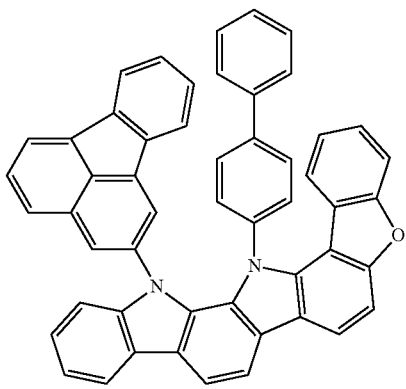
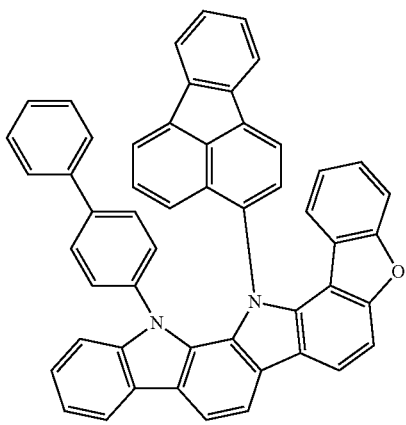
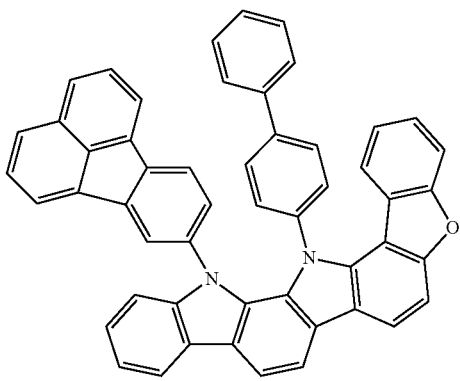

441
-continued
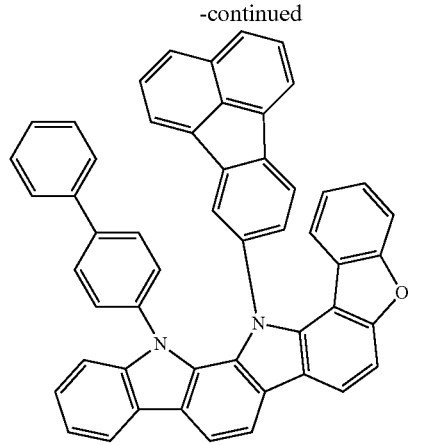
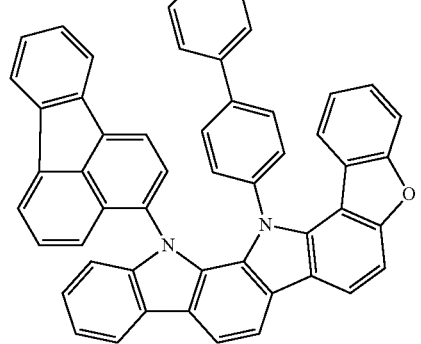
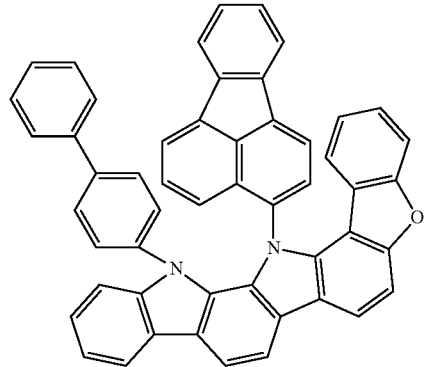
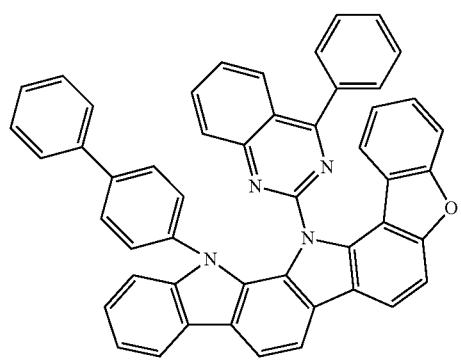
442
-continued
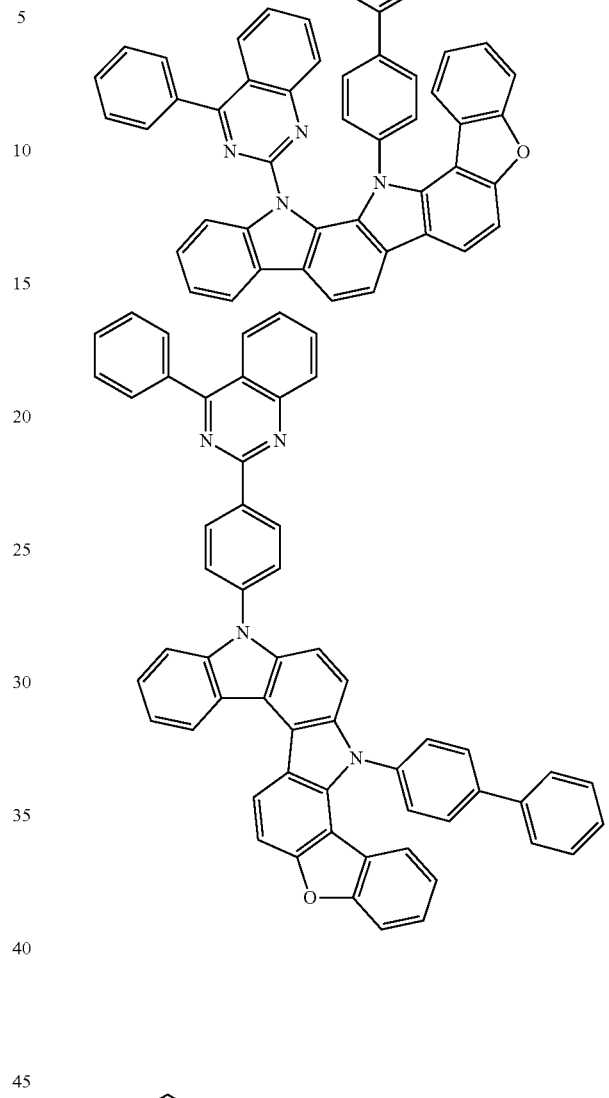
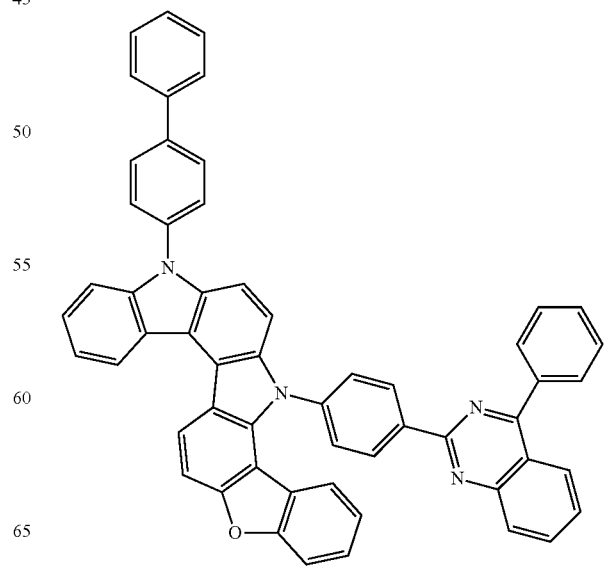

443
-continued
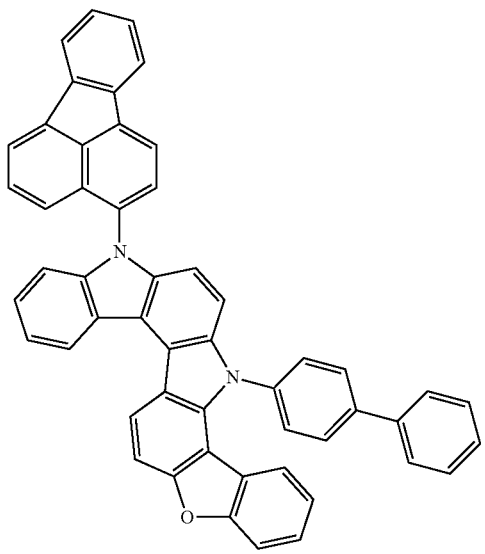
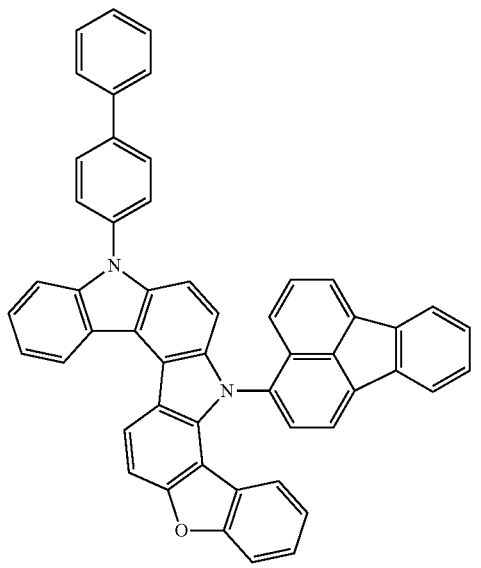
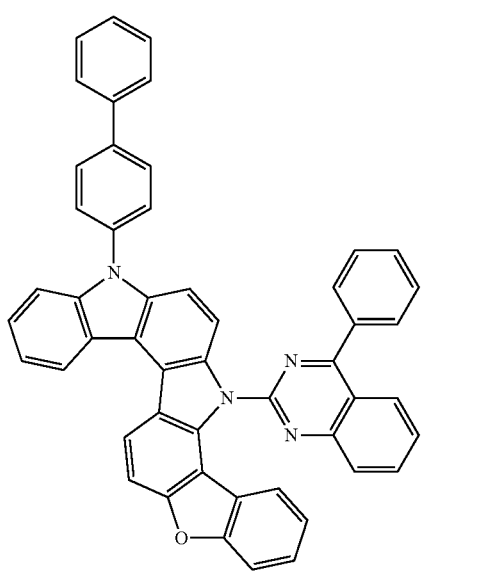
444
-continued
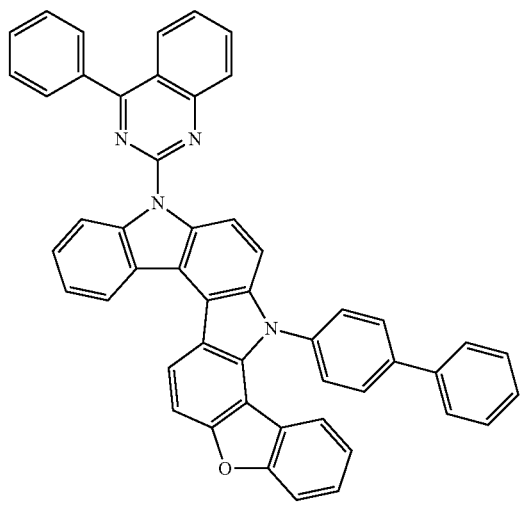
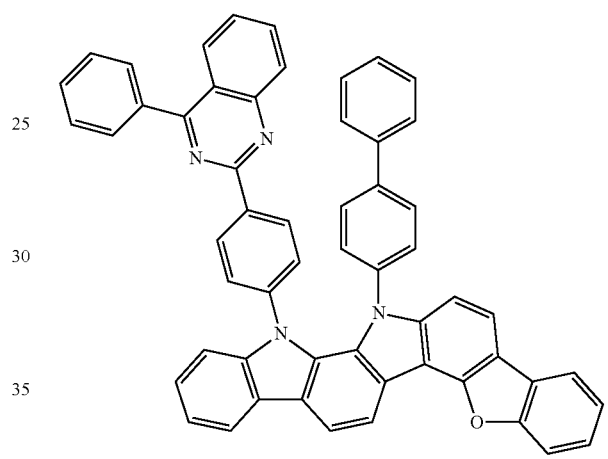
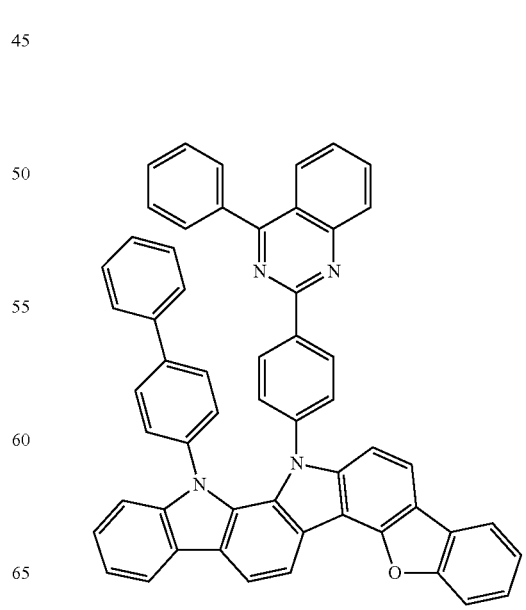

445
-continued
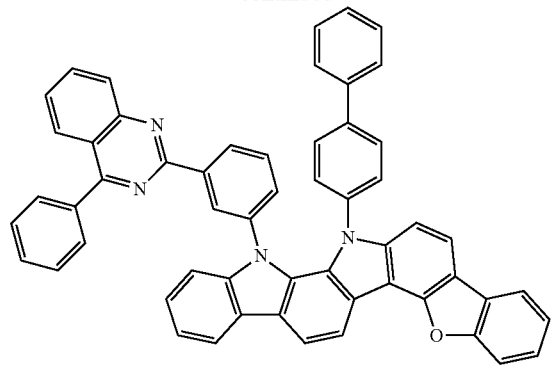
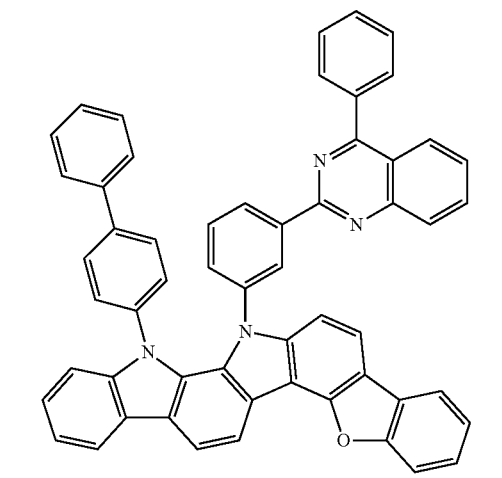
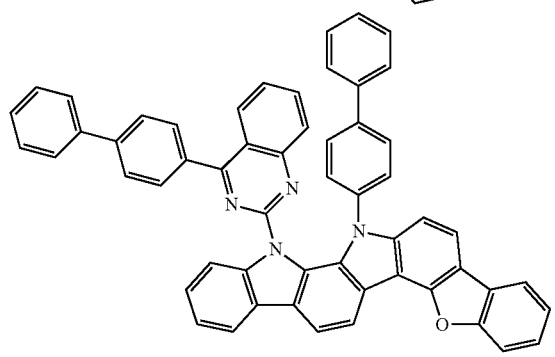
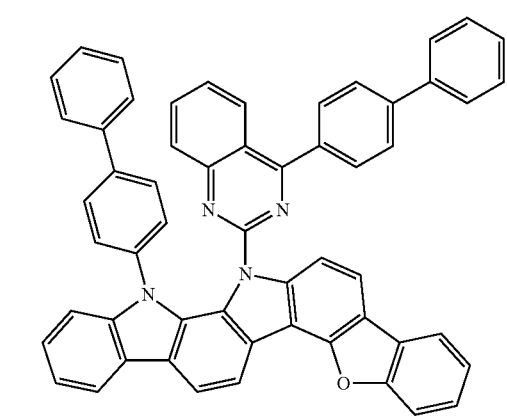
446
-continued
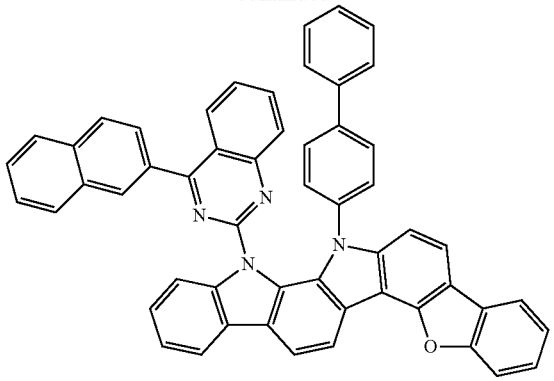
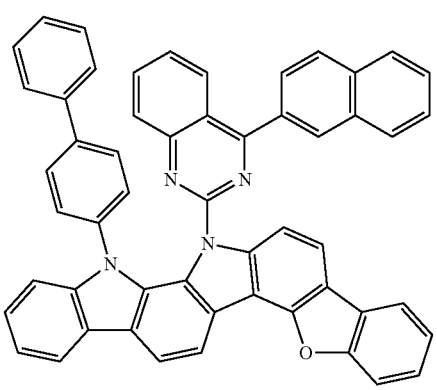
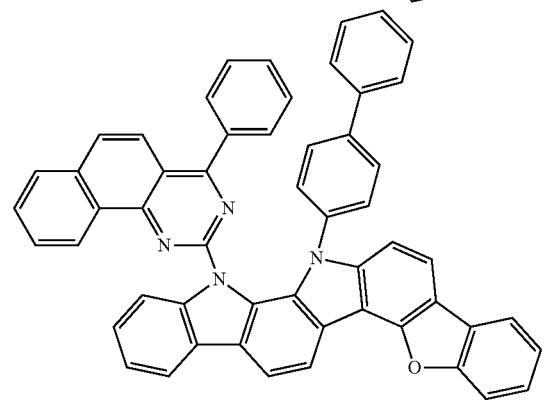
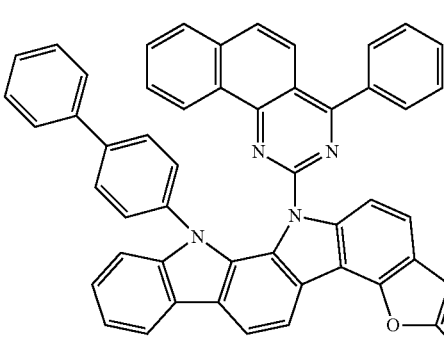

447
-continued
448
-continued
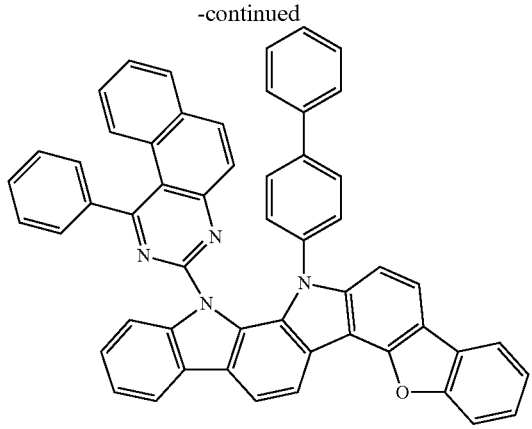
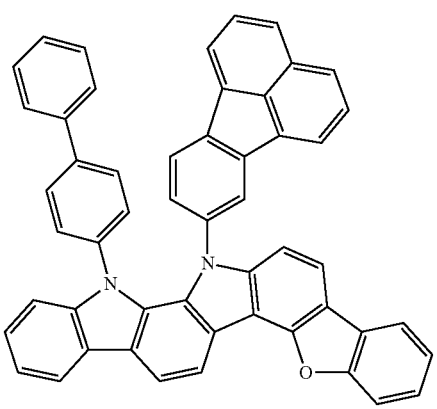
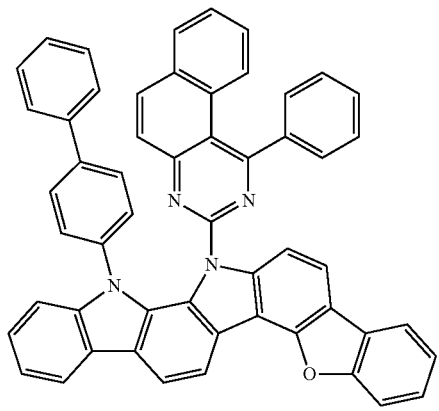
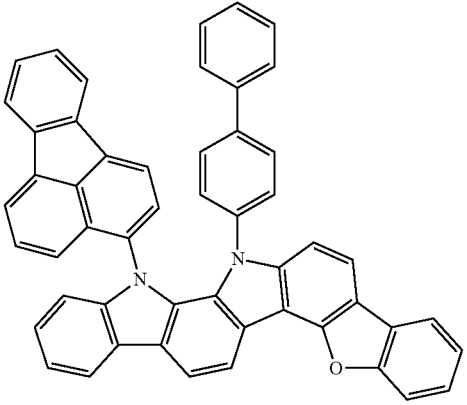
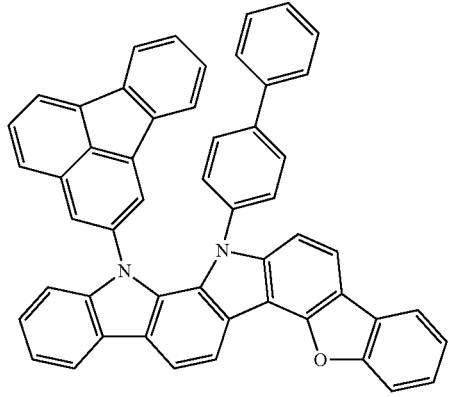
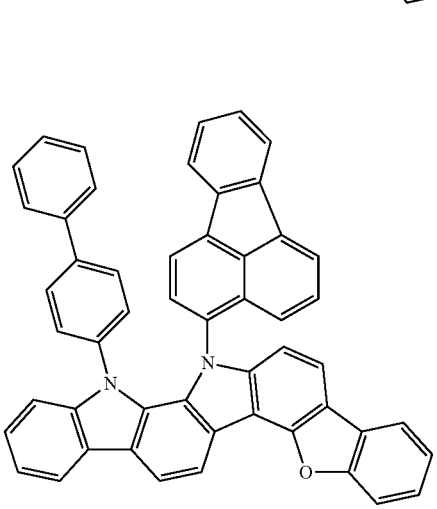
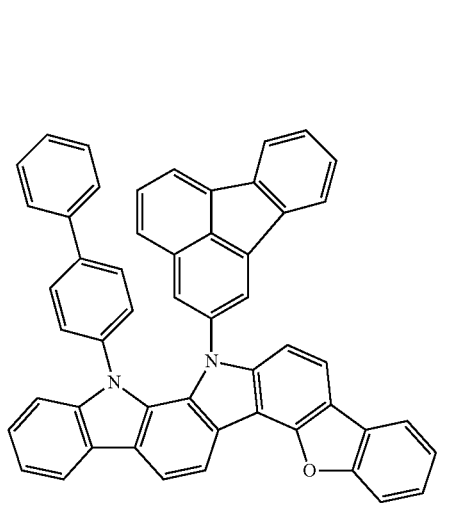
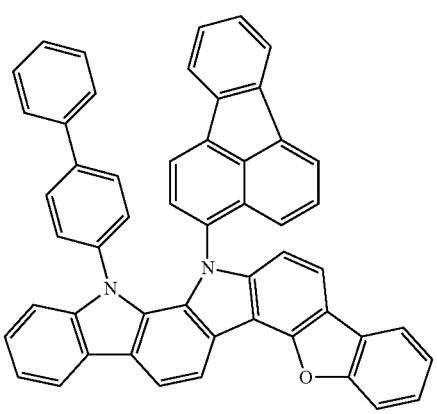

449
-continued
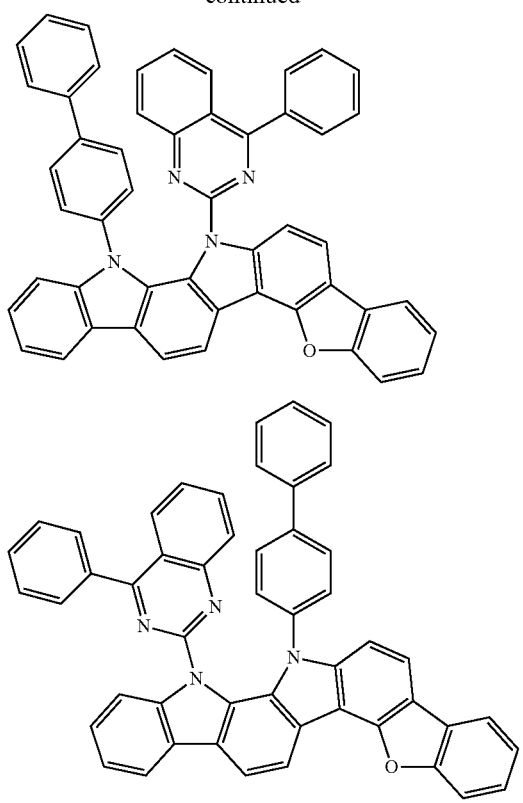
450
-continued
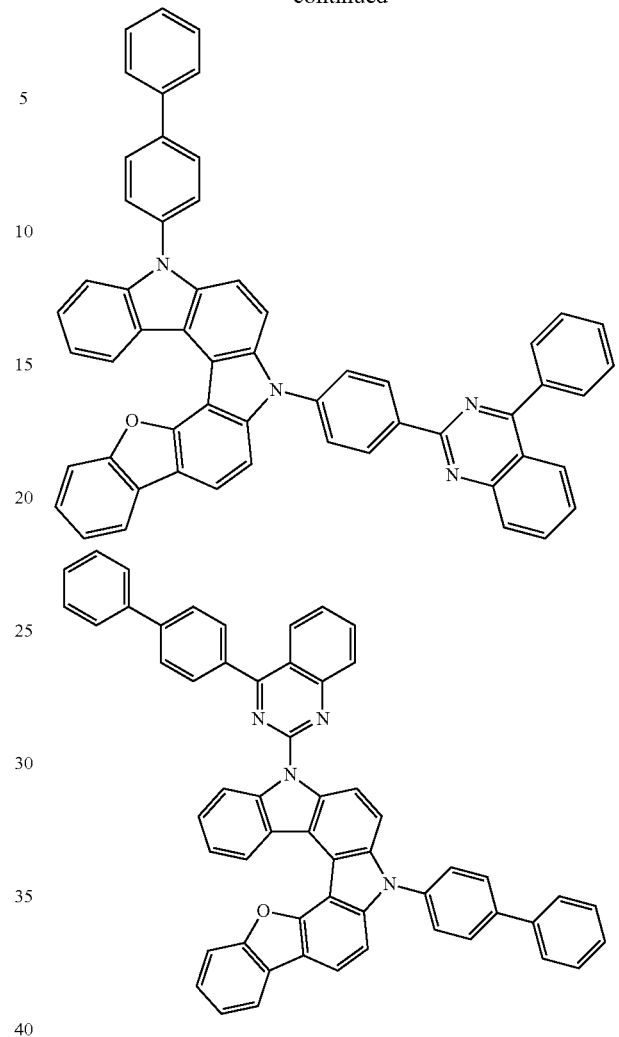
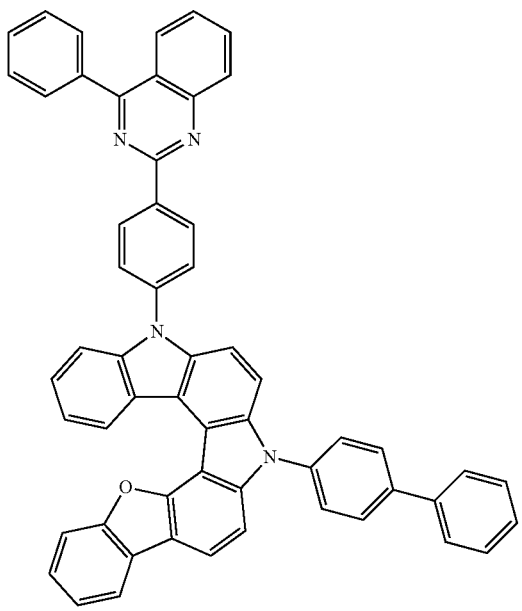

451
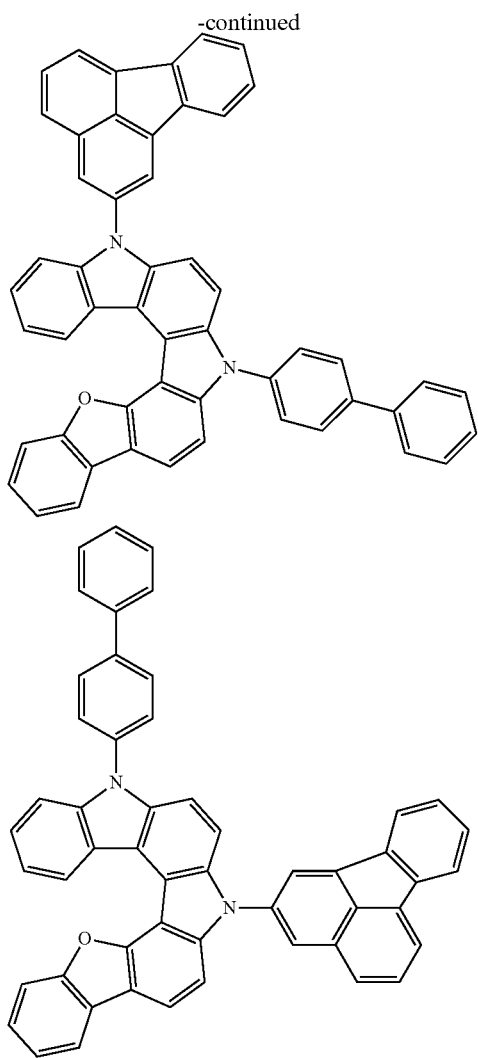
452
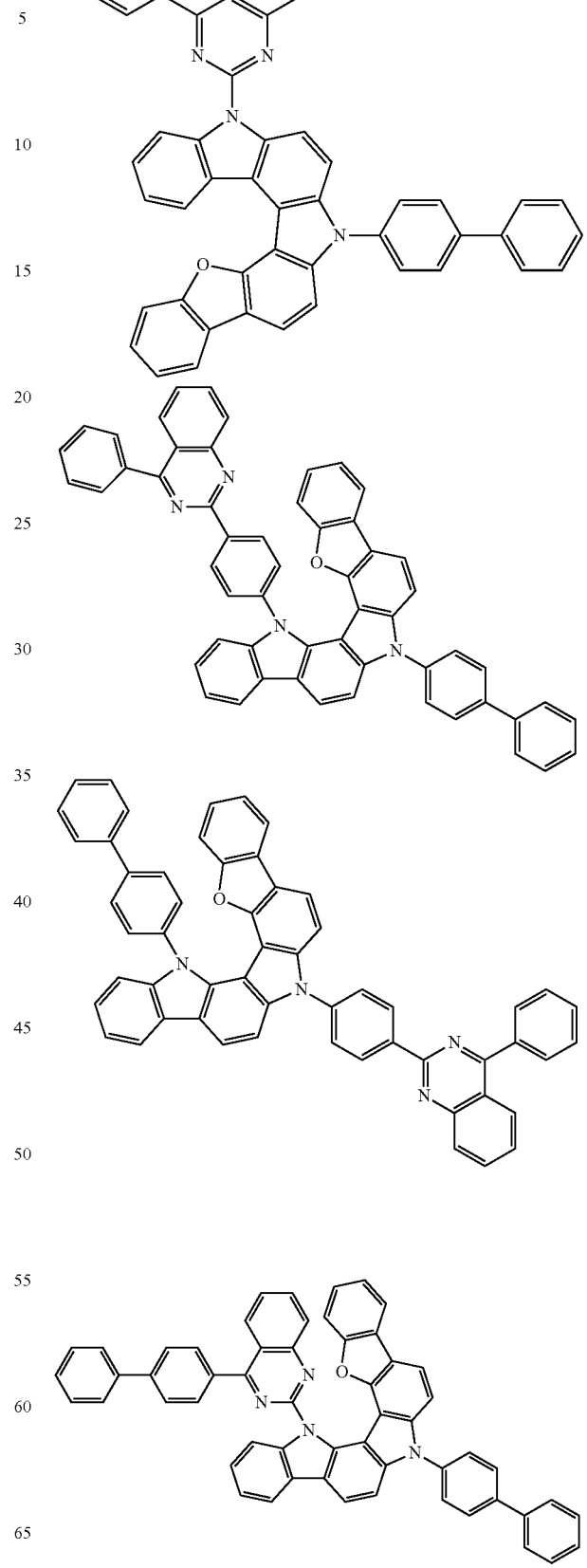

453
-continued
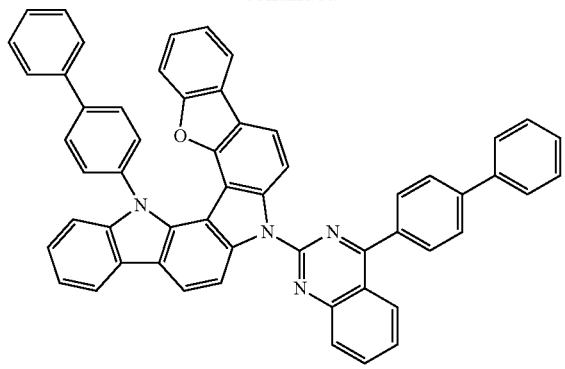
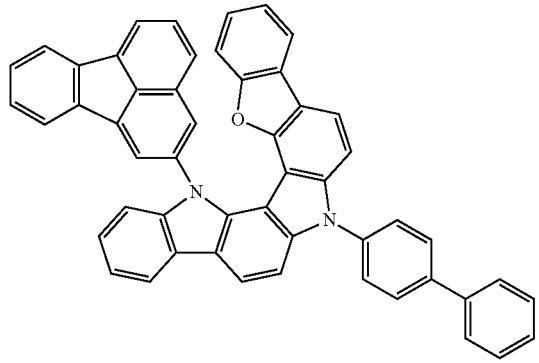
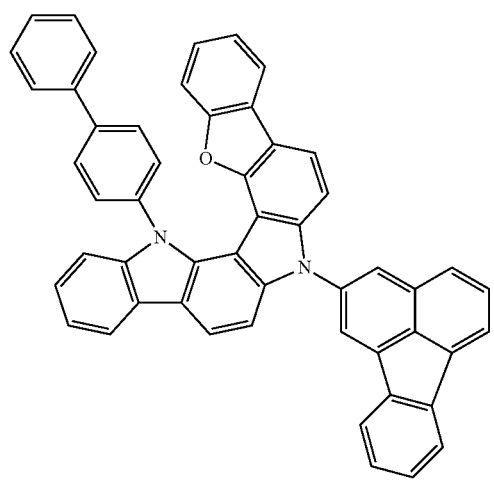
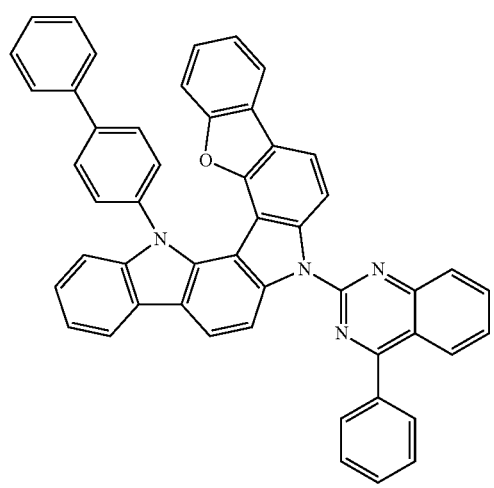
454
-continued
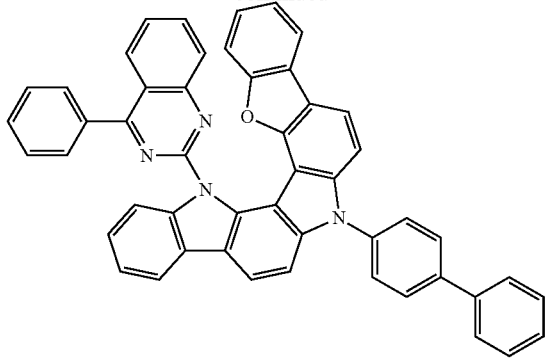
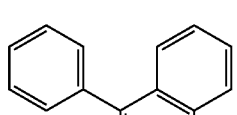
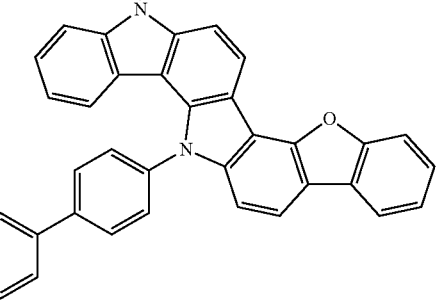
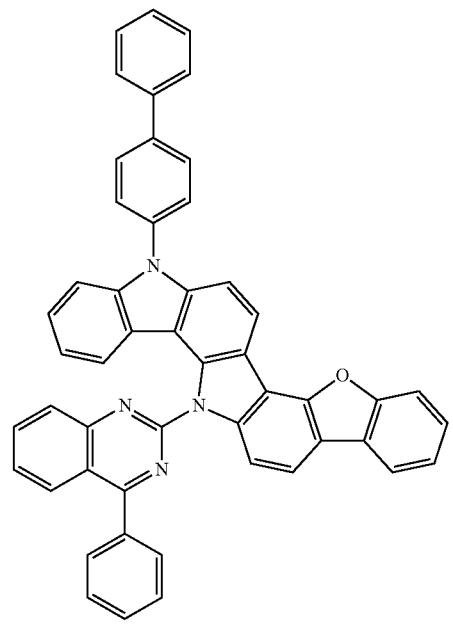

455
-continued
456
-continued
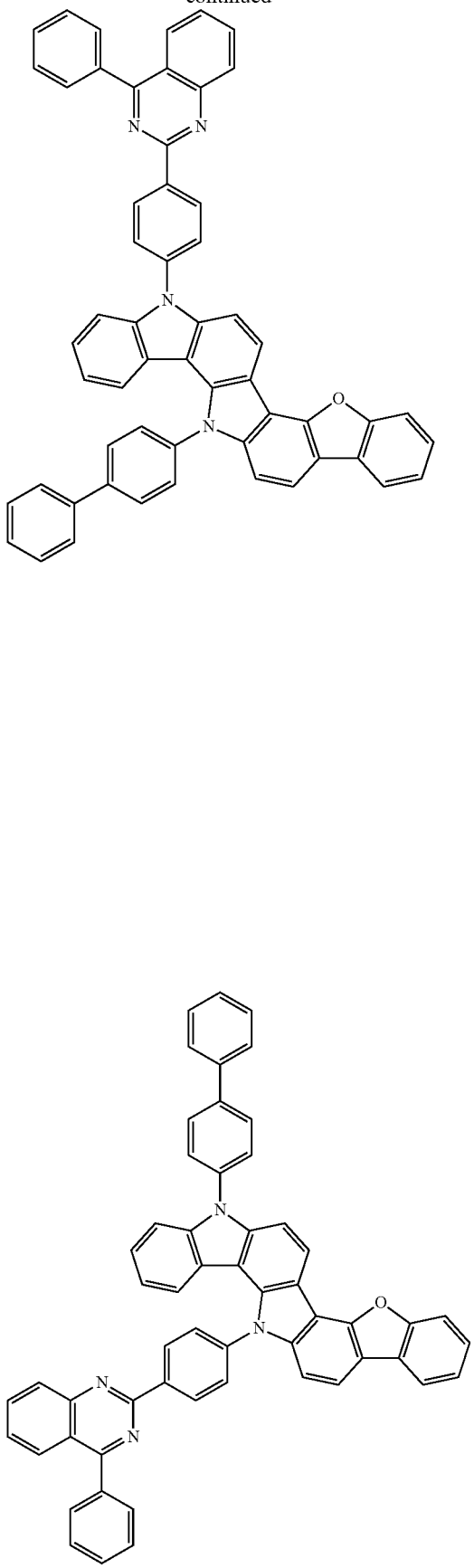
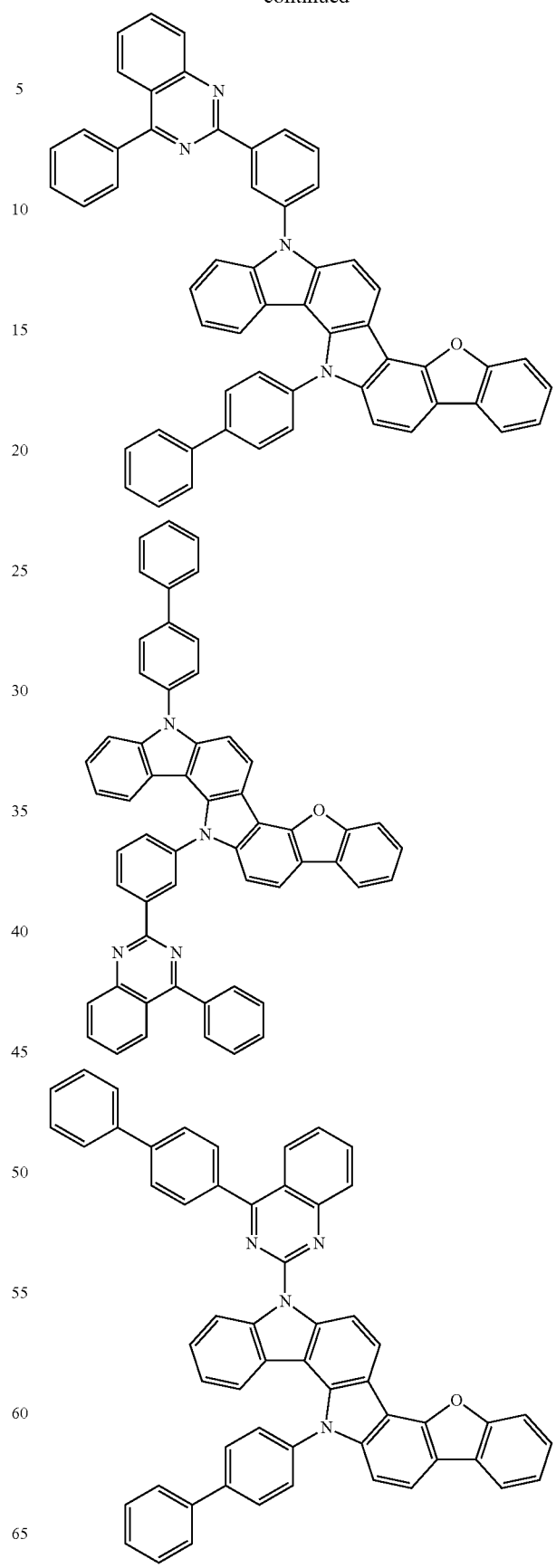

457
-continued
458
-continued
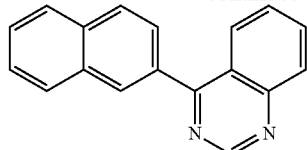
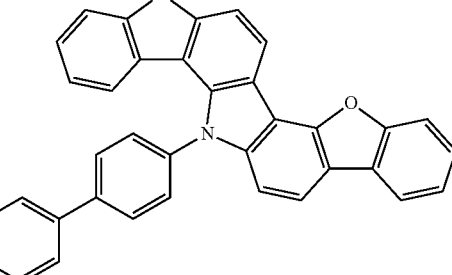
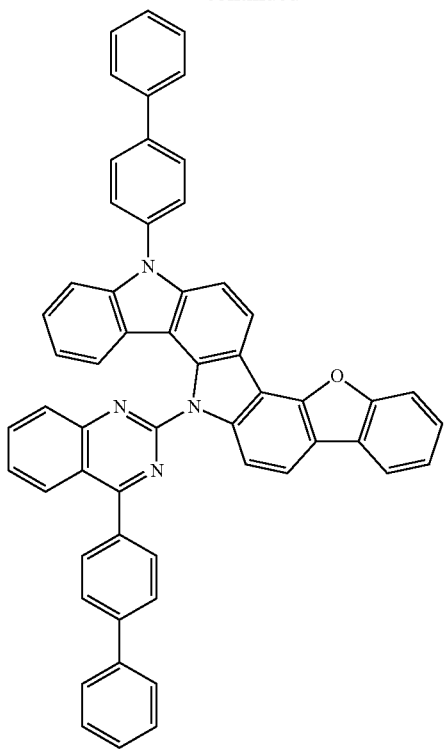
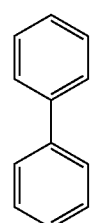
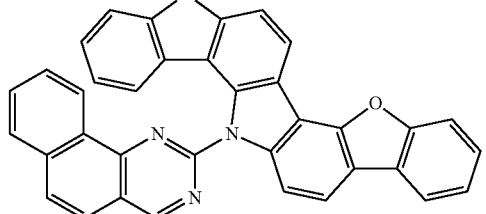
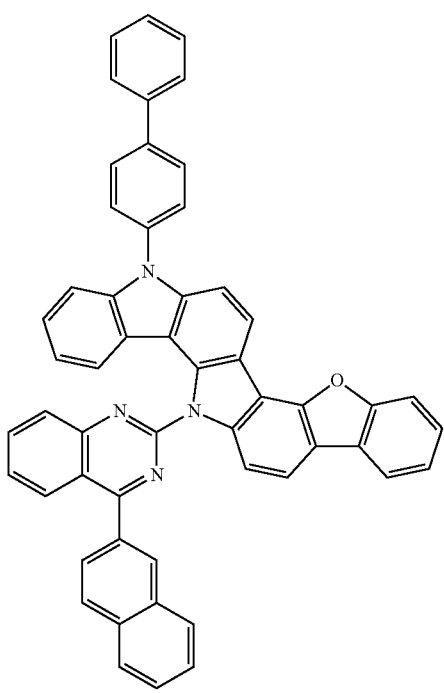
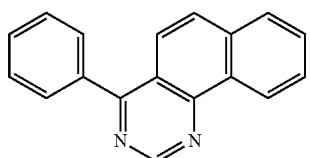
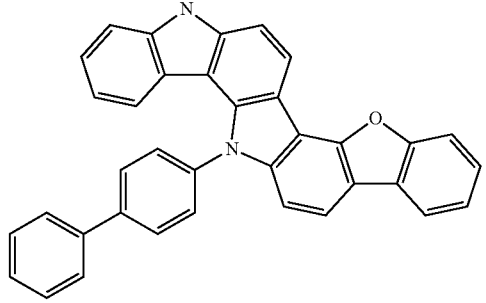

459
-continued
460
-continued
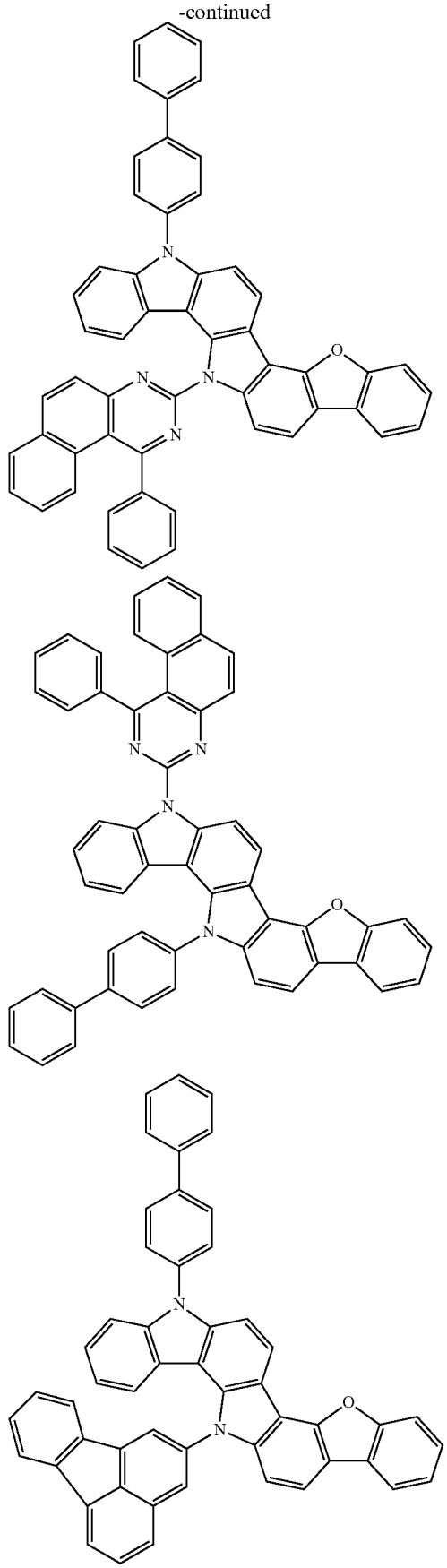
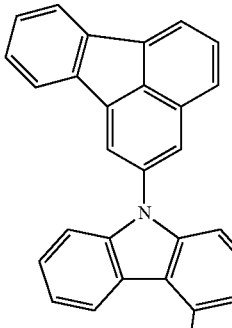
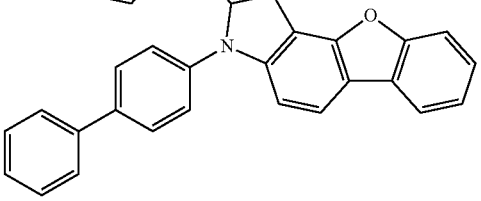
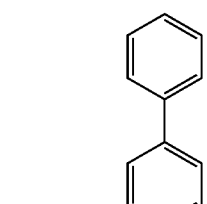
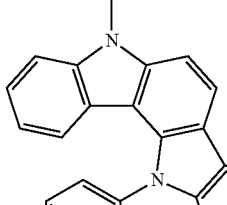
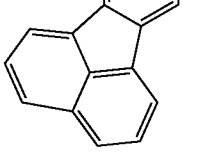
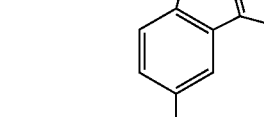
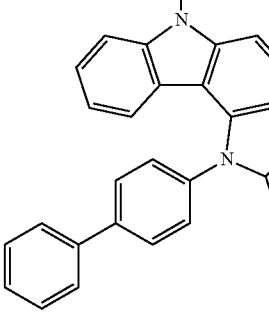

461
-continued
462
-continued
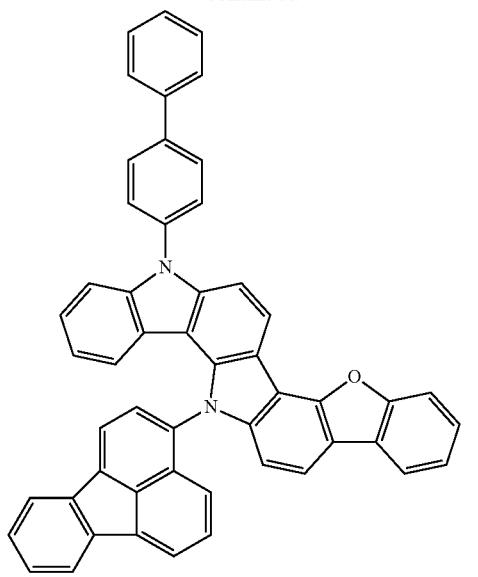
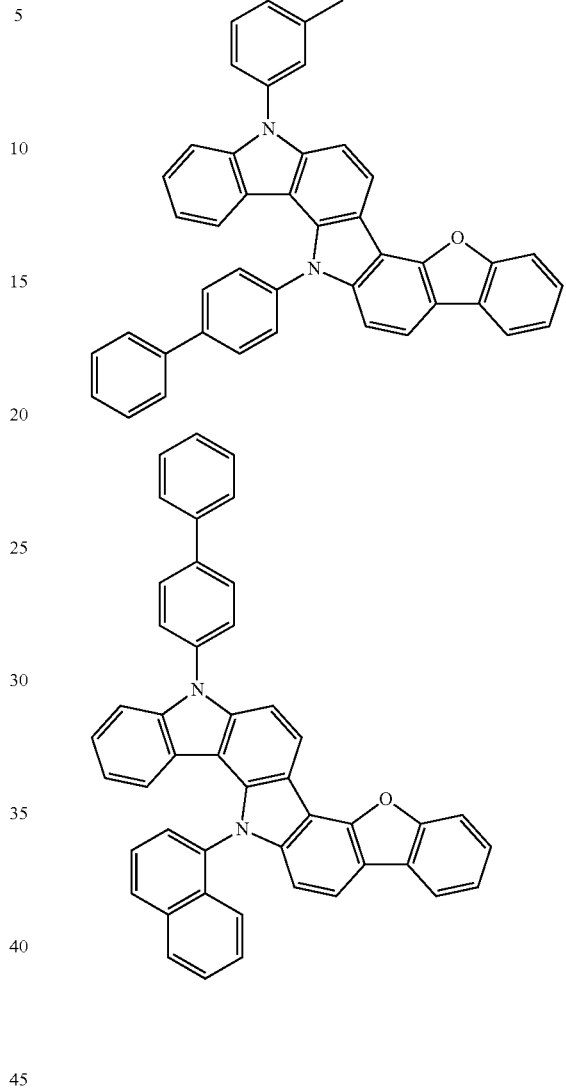
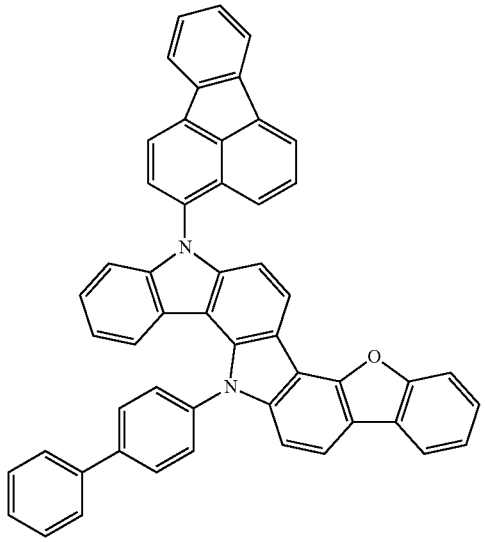
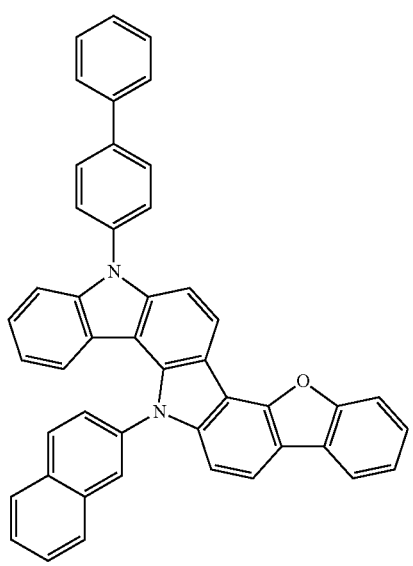
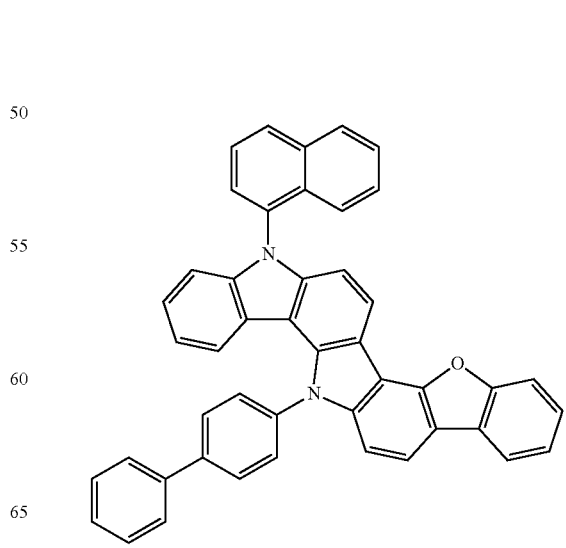

463
-continued
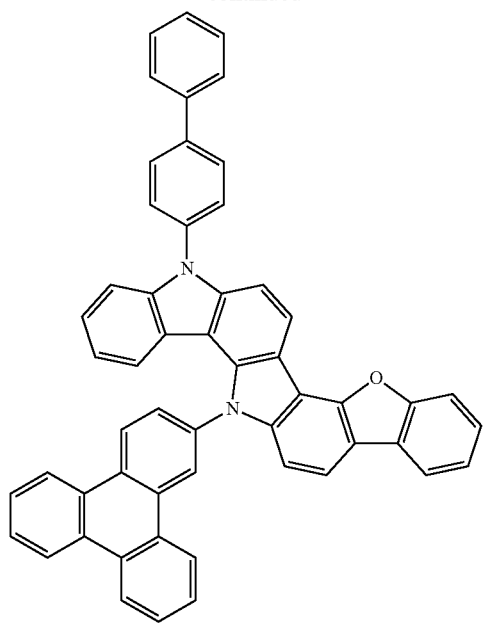
464
-continued
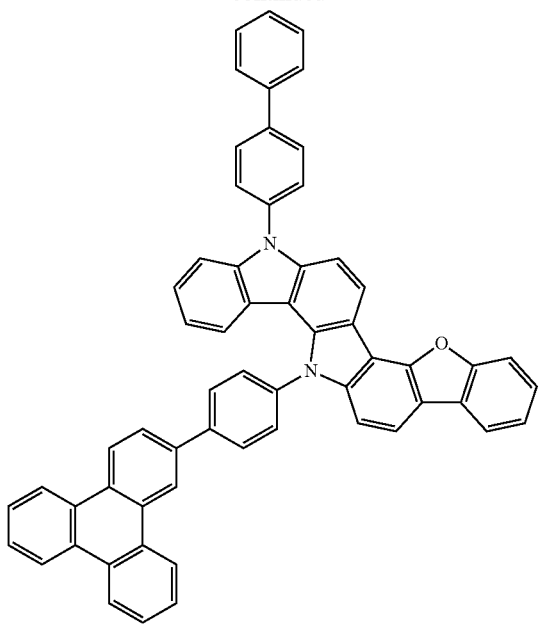
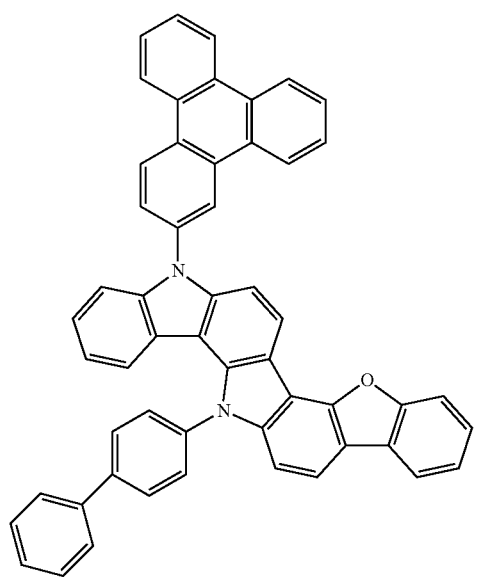

465
-continued
466
-continued
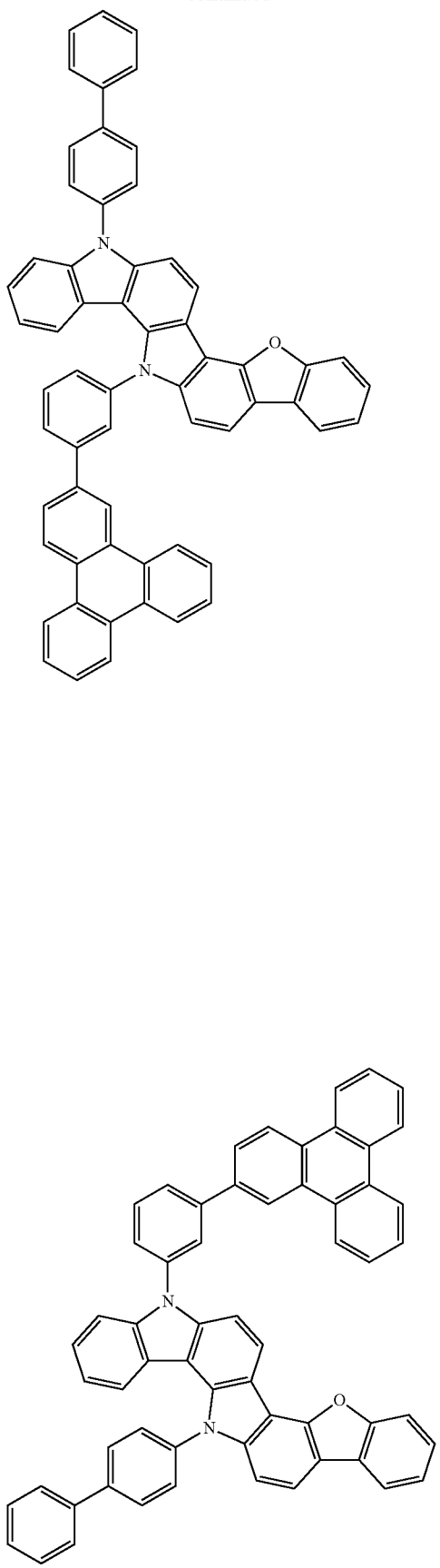
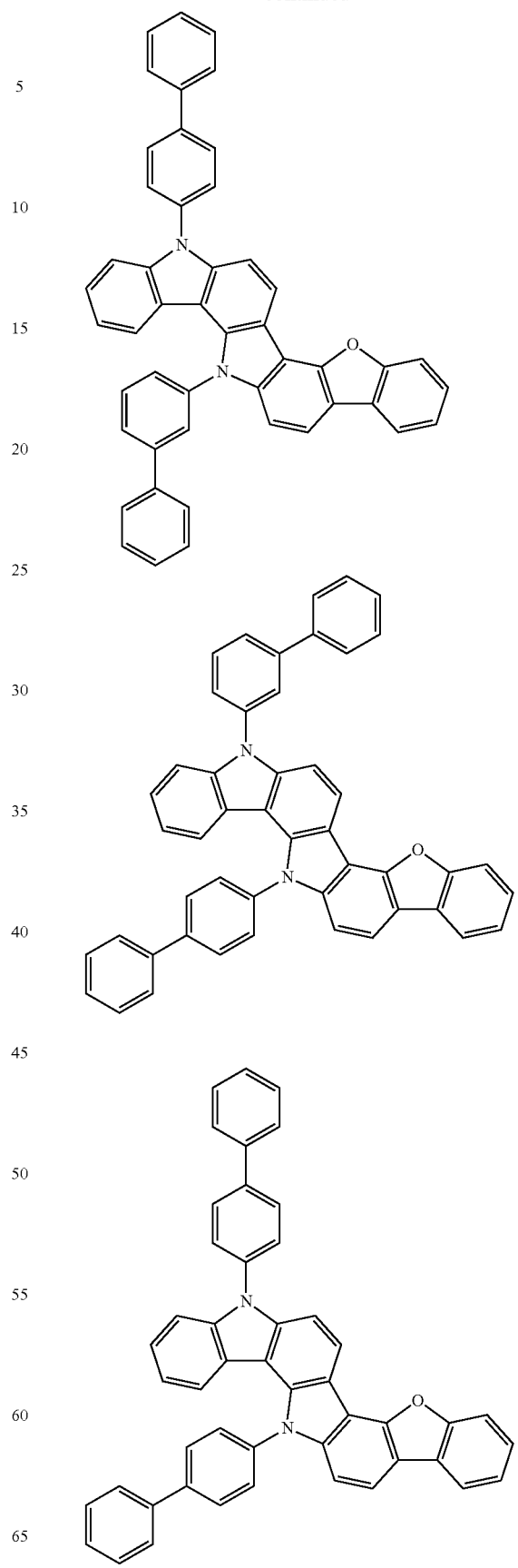

467
-continued
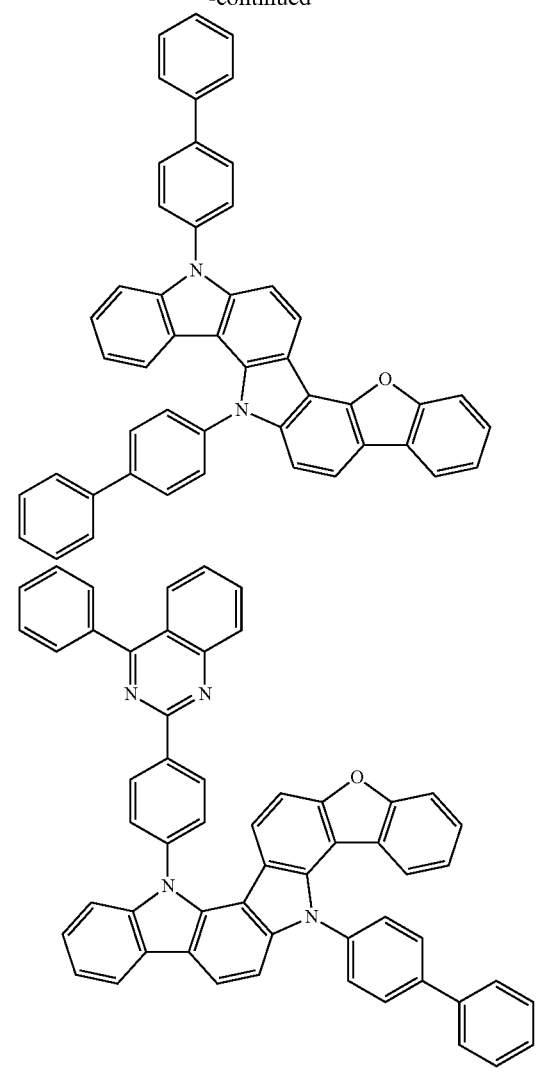
468
-continued
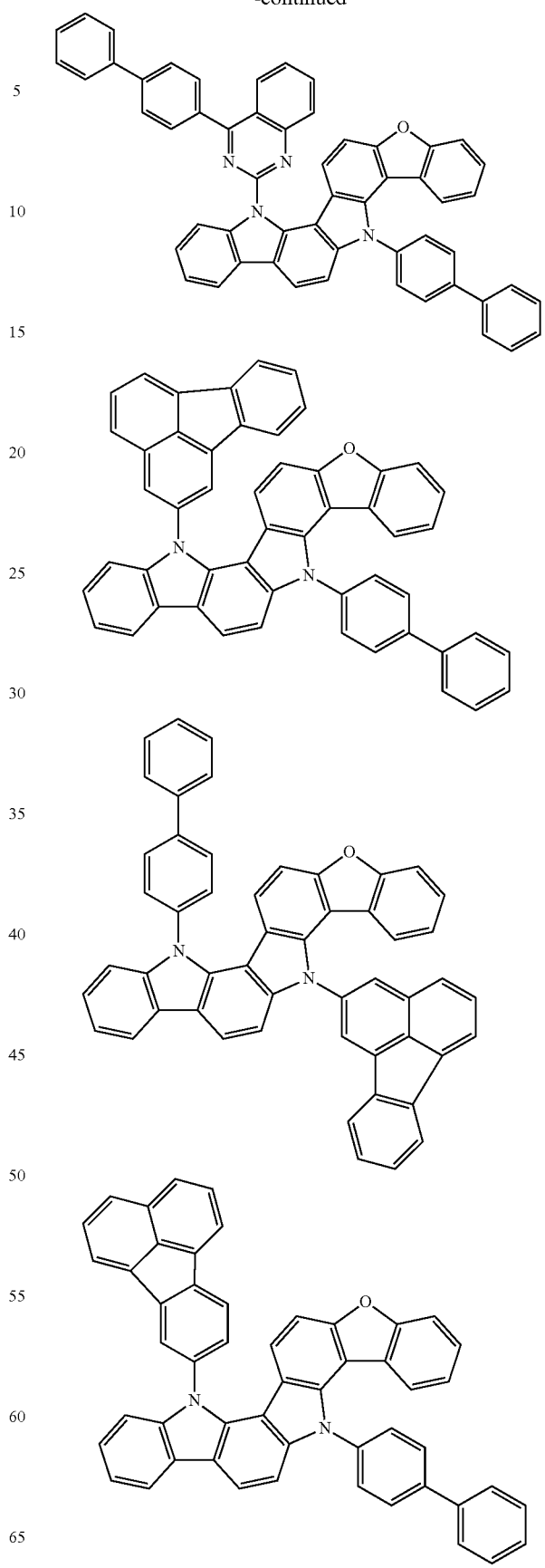

469
-continued
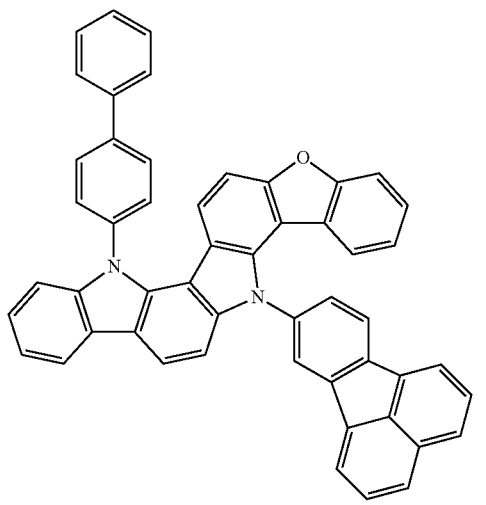
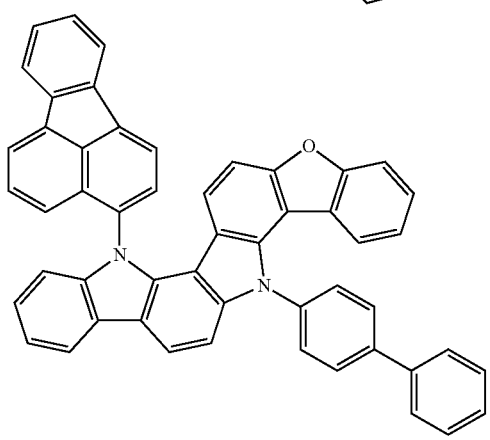
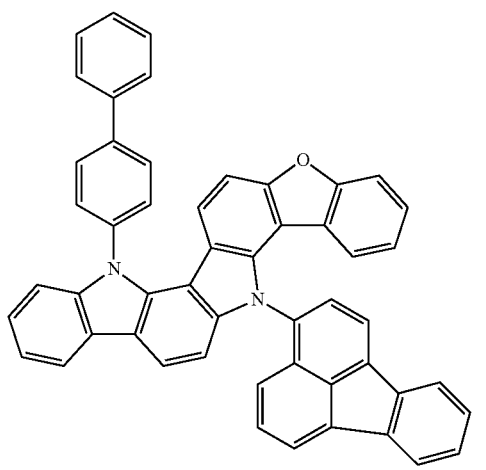
470
-continued
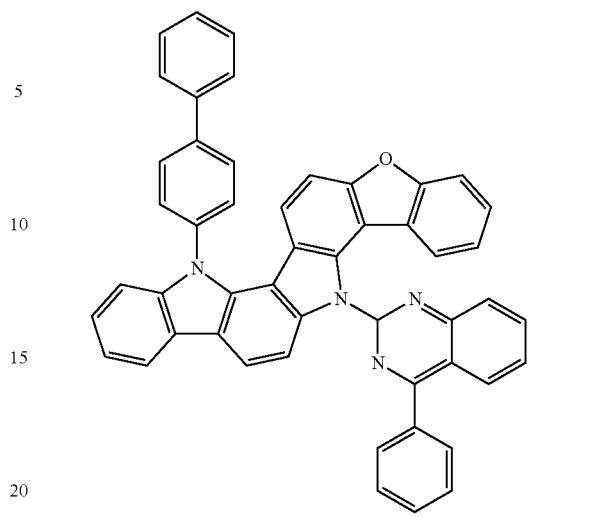
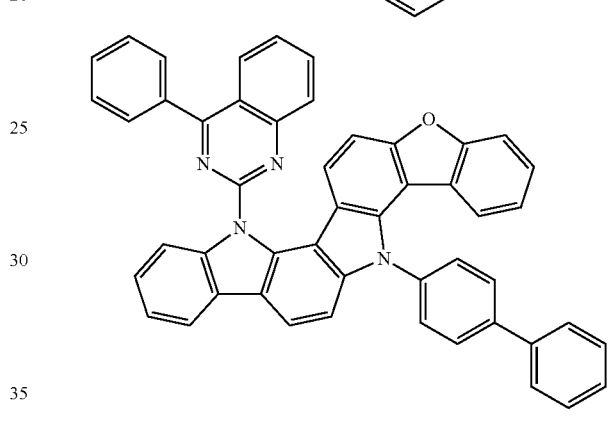
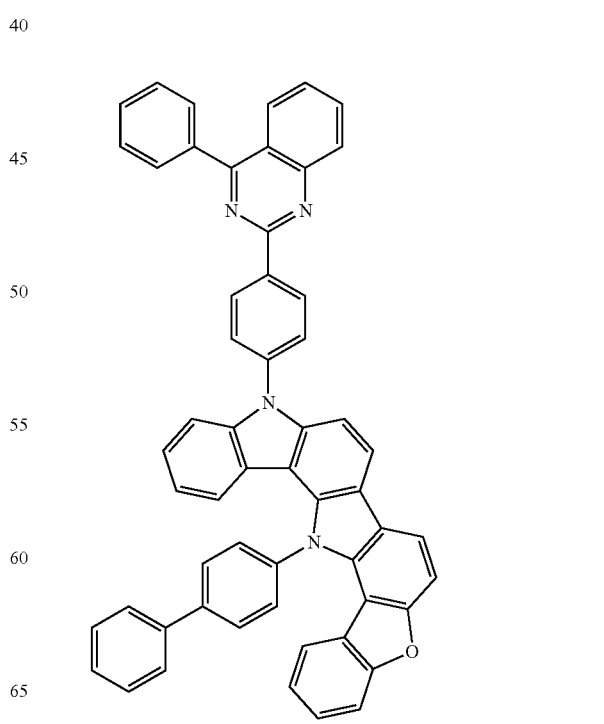

471
-continued
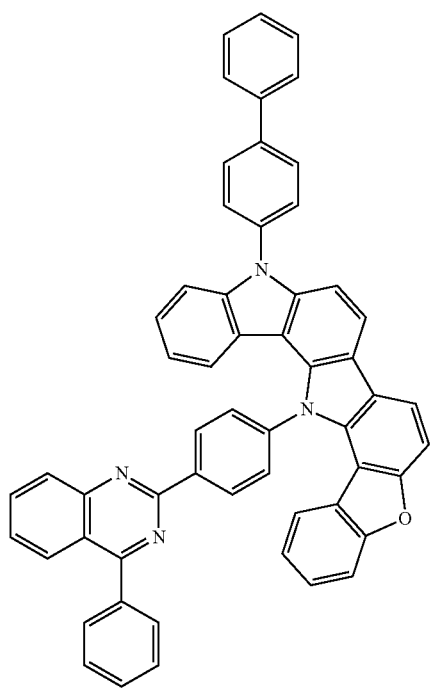
472
-continued
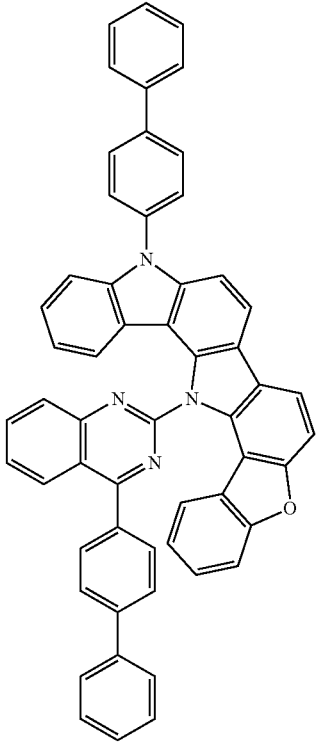
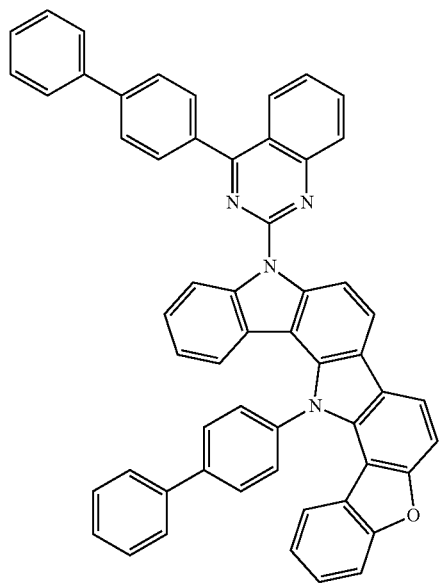
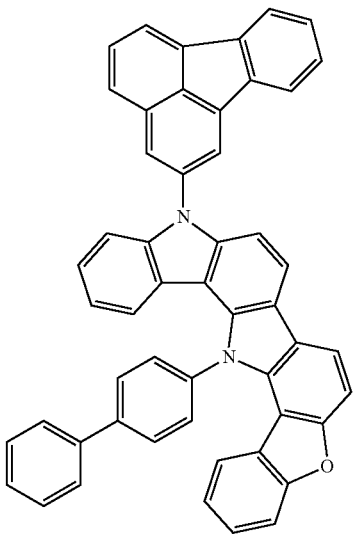

473
-continued
474
-continued
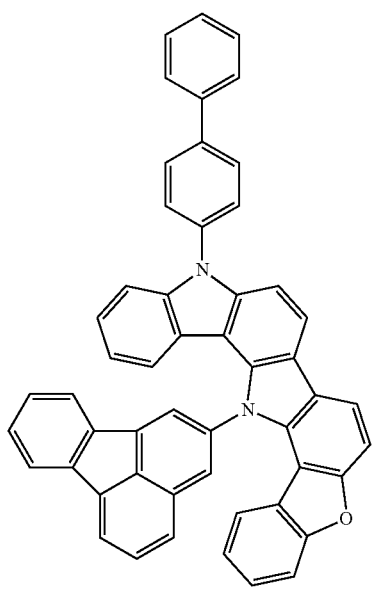
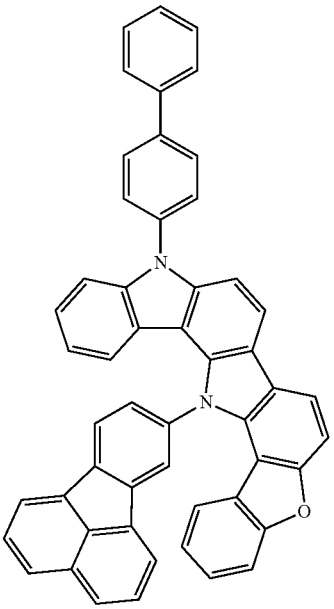

475
-continued
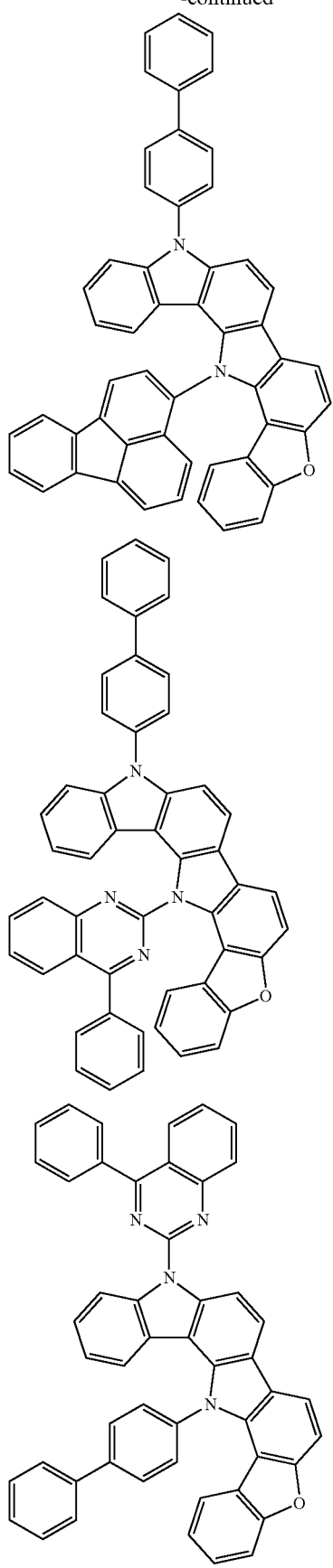
476
-continued
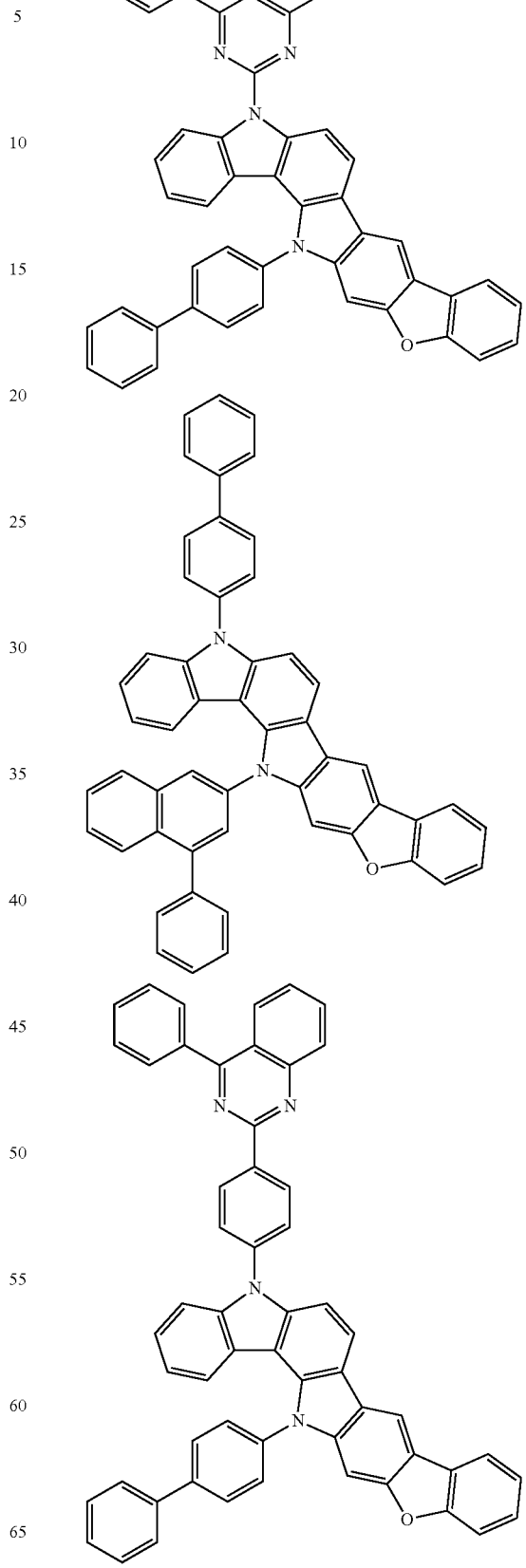

477
-continued
478
-continued
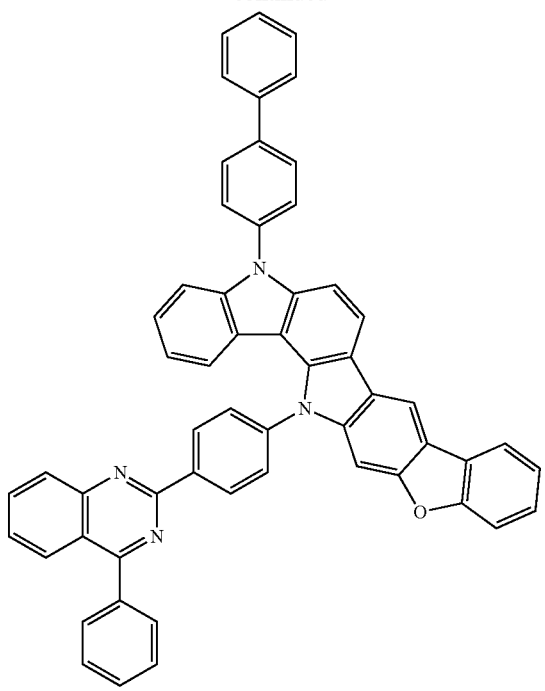
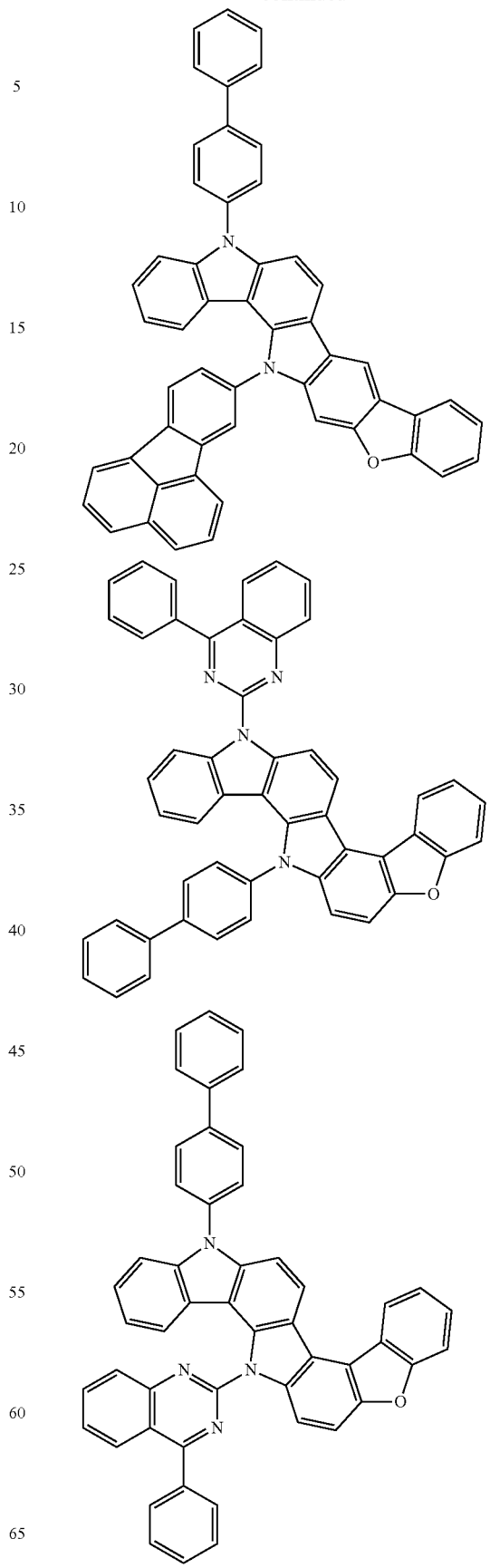

479
-continued
480
-continued
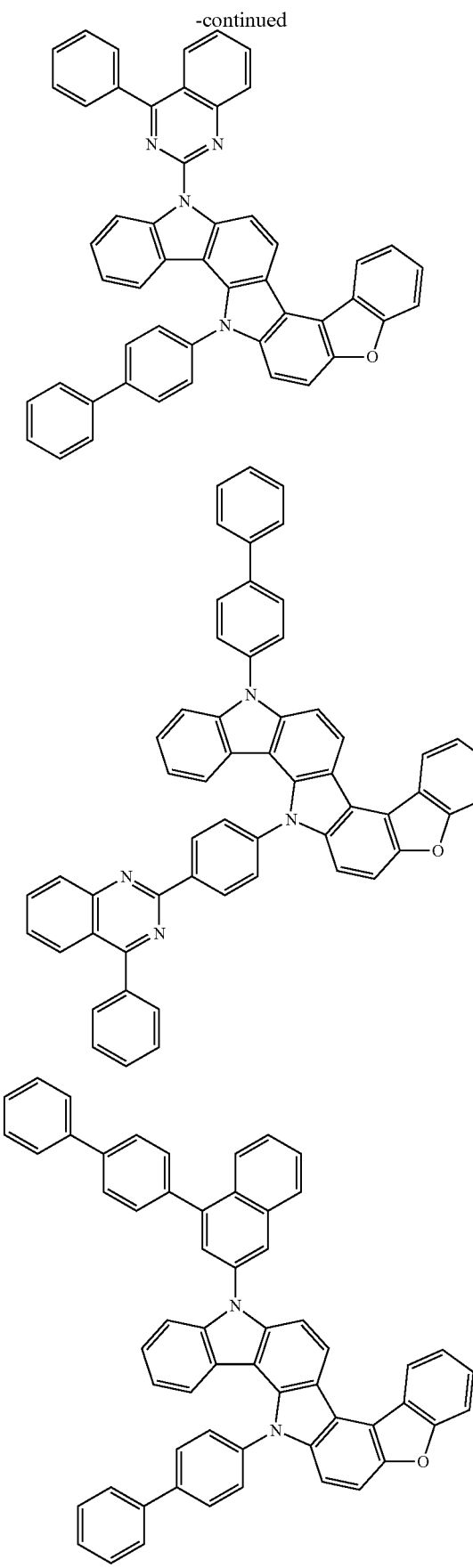
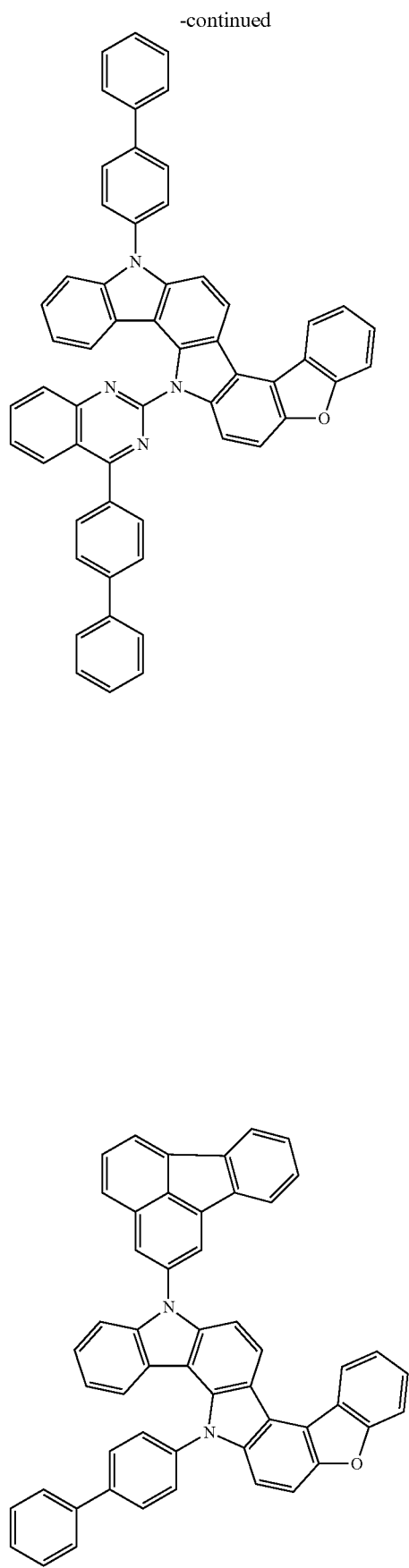

481
-continued

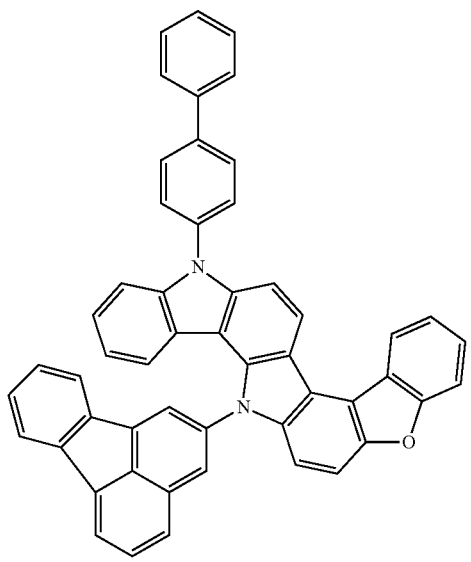

482
-continued

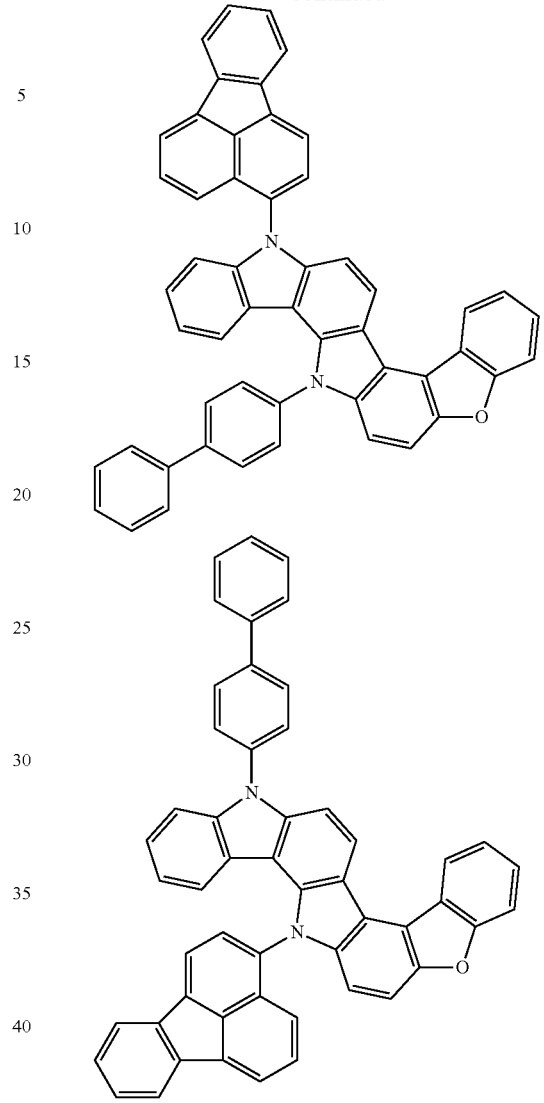

The compound represented by the formula (1) can be produced by a method in the synthesis example mentioned later, and by using known alternative reactions or raw materials that are suited to an intended product.

B. Material for Organic Electroluminescence Device

A material for an organic electroluminescence device as one aspect of the invention (hereinafter referred to as "material for an organic EL device as one aspect of the invention) comprises the compound represented by the formula (1).

The material for an organic EL device as one aspect of the invention may consist only of the compound represented by the formula (1), and may comprise other compounds.

The material for an organic EL device as one aspect of the invention can be used for forming an organic thin film layer such as an emitting layer, a hole-injecting layer, a hole-transporting layer, an electron-injection layer, an electron-transporting layer or the like.

The material for an organic EL device as one aspect of the invention is effective as a phosphorescent host material.

Further, since the compound represented by the formula (1) of the invention has high molecular planarity and has high carrier transporting property, it is effective as a transporting material.

C. Organic Electroluminescent Device

An organic electroluminescence device as one aspect of the invention (hereinafter referred to as "organic EL device as one aspect of the invention") is an organic electroluminescence device that comprises a cathode, an anode and one or more organic thin film layers between the cathode and the anode, wherein the one or more organic thin film layers comprise an emitting layer, and at least one layer of the one or more organic thin film layers comprises a compound represented by the formula (1).

It is preferred that the emitting layer comprise the compound represented by the formula (1).

Further, it is preferred that the emitting layer comprise one or more selected from a fluorescent emitting material and a phosphorescent emitting material. Therefore, the emitting layer may be a phosphorescent emitting layer or a fluorescent emitting layer, but may preferably be a phosphorescent emitting layer. It is preferred that the compound represented by the formula (1) be used as a host material of the emitting layer. In particular, it is preferred that the compound represented by the formula (1) be a host material of a phosphorescent emitting layer.

It is preferred that the one or more organic thin film layers further comprise a hole-transporting layer.

It is preferred that the one or more organic thin film layers further comprise an electron-transporting layer.

Each layer of the organic EL device as one embodiment of the invention may be formed by a dry film-forming method such as vacuum deposition, sputtering, plasma, or ion plating, or a wet film-forming method such as spin coating, dipping, or flow coating. The thickness of each layer is not particularly limited, but it should be adjusted to be an appropriate thickness. If the thickness of each layer is too large, a high voltage is required to be applied to obtain a certain amount of optical output, so that the efficiency may be deteriorated. If the thickness of each layer is too small, pinholes or the like may be generated, so that a sufficient luminance may not be obtained when an electric field is applied. The thickness of each layer is normally 5 nm to 10 μm, and further preferably 10 nm to 0.2 μm.

Hereinbelow, materials or the like of each element constituting the organic EL device of the invention will be explained below.

(Substrate)

The substrate is used as a base of an emitting element. As the substrate, glass, quarts, plastic or the like can be used, for example. A flexible substrate may be used. A flexible substrate is a substrate that can be bent. For example, a plastic substrate made of polycarbonate or polyvinyl chloride or the like can be given.

(Anode)

For an anode formed on the substrate, it is preferable to use a metal, an alloy, an electrically conductive compound having a large work function (specifically, 4.0 eV or more), a mixture thereof or the like. Specifically, indium oxide-tin oxide (ITO: Indium Tin Oxide), indium oxide-tin oxide containing silicon or silicon oxide, indium oxide-zinc oxide, tungsten oxide, indium oxide containing zinc oxide, graphene or the like can be given, for example. In addition, gold (Au), platinum (Pt) or a nitride of a metal material (e.g. titanium nitride) orthe like can be given.

(Hole-Injecting Layer)

A hole-injecting layer is a layer that contains a substance having high hole-injection property. As the substance having high hole-injection property, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, an aromatic amine compound, or a polymer compound (oligomer, dendrimer, polymer, etc.) or the like can be used.

(Hole-Transporting Layer)

A hole-transporting layer is a layer that contains a substance having high hole-transporting property. In the hole-transporting layer, aromatic amine compounds, carbazole derivatives, anthracene derivatives and the like can be used. Polymer compounds such as poly(N-vinylcarbazole) (abbreviation: PVK) or poly(4-vinyltriphenylamine) (abbreviation: PVTPA) can also be used. As long as it has high property of transporting holes rather than electrons, other substances than those mentioned above can be used. The layer containing the substance having high hole-transporting property may be not only a single layer but also a layer obtained by stacking two or more layers containing the above-mentioned substances.

(Guest Material of Emitting Layer)

An emitting layer is a layer that contains a substance having high emitting property, and various materials can be used for the emitting layer. For example, as the substance having high emitting property, a fluorescent compound that emits fluorescence or a phosphorescent compound that emits phosphorescence can be used. A fluorescent compound is a compound that can emit light from the singlet excited state, and a phosphorescent compound is a compound that can emit light from the triplet excited state. These compounds are often referred to as a dopant or a dopant material.

As the blue fluorescent emitting material that can be used in the emitting layer, pyrene derivatives, styrylamine derivatives, chrysene derivatives, fluoranthene derivatives, fluorene derivatives, diamine derivatives, triarylamine derivatives or the like can be used. Specific examples thereof include N,N'-bis[4-(9H-carbazol-9-yl)phenyl]-N,N'-diphenylstilbene-4,4'-diamine (abbreviation: YGA2S), 4-(9H-carbazolyl-9-yl)-4'-(10-phenyl-9-anthryl)triphenylamine (abbreviation: YGAPA), 4-(10-phenyl-9-anthryl)-4'-(9-phenyl-9H-carbazol-3-yl)triphenylamine (abbreviation: PCBAPA) orthe like.

As the green fluorescent emitting material that can be used in the emitting layer, an aromatic amine derivative or the like can be used. Specific examples thereof include N-(9,10-diphenyl-2-anthryl)-N,9-diphenyl-9H-carbazole-3-amine (abbreviation: 2PCAPA), N-[9,10-bis(1,1'-biphenyl-2-yl)-2-anthryl]-N,9-diphenyl-9H-carbazole-3-amine (abbreviation: 2PCABPhA), N-(9,10-diphenyl-2-anthryl)-N,N', N'-triphenyl-1,4-phenylenediamine (abbreviation: 2D-PAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazole-9-yl)phenyl]-N-phenylanthracen-2-amine (abbreviation: 2YGABPhA), N,N,9-triphenylanthracene-9-amine (abbreviation: DPhAPhA) orthe like.

As the red fluorescent emitting material that can be used in the emitting layer, tetracene derivatives, diamine derivatives orthe like can be used. Specific examples thereof include N,N,N',N'-tetrakis(4-methylphenyl tetracene-5,11-diamine (abbreviation: p-mPhTD), 7,14-diphenyl-N,N, N'N'-tetrakis (4-methylphenyl)acenaphtho[1,2-a]fluoranthene-3,10-diamine (abbreviation: p-mPhAFD) or the like.

In one aspect of the invention, it is preferred that the fluorescent emitting material contain at least one selected from an anthracene derivative, a fluoranthene derivative, a styrylamine derivative and an arylamine derivative.

As the blue phosphorescent emitting material that can be used in the emitting layer, a metal complex such as an iridium complex, an osmium complex and a platinum complex can be used. Specific examples include bis[2-(4',6'-difluorophenyl)pyridinato-N,C2']iridium(III)tetrakis(1-pyrazolyl)borate (abbreviation: FIr$_6$), III)tetrakis(1-pyrazolyl)borate (abbreviation: FIr$_6$), bis[2-(4',6'-difluorophenyl)pyridinato-N,C2']iridium (III) picolinato (abbreviation: FIrpic), bis[2-(3'5'-bistrifluoromethylphenyl)pyridinato-N,C2']iridium (III) picolinate (abbreviation: Ir(CF$_3$ppy)$_2$(pic)), bis[2-(4',6'-difluorophenyl)pyridinato-N,C2']iridium (III) acetylacetonate (abbreviation: FIracac) or the like.

As the green-based phosphorescent emitting material, an iridium complex or the like can be used. Tris(2-phenylpyridinato-N,C2)iridium (III) (abbreviation: Ir(ppy)$_3$), bis(2-phenylpyridinato-N,C2)iridium (III) acetylacetonate (abbreviation: Ir(ppy)$_2$(acac), bis(1,2-diphenyl-1H-benzoimidazolate)iridium (III) acetylacetonate (abbreviation: Ir(pbi)$_2$(acac)), bis(benzo[h]quinolinato)iridium (III)acetylacetonato (abbreviation: Ir(bzq)$_2$(acac)) orthe like can be given.

As the red phosphorescent emitting material that can be used in the emitting layer, a metal complex such as an iridium complex, a platinum complex, a terbium complex and an europium complex is used. Specific examples thereof include an organic metal complex such as bis[2-(2'-benzo[4,5-α]thienyl)pyridinato-N,C3']iridium (III) acetyl acetonate (abbreviation: Ir(btp)$_2$(acac)), bis(1-phenylisoquinolinato-N,C2')iridium (III) acetyl acetonate (abbreviation: Ir(piq)$_2$(acac)), (acetyl acetonato) bis[2,3-bis(4-fluorophenyl)quinoxalinato]iridium (III) (abbreviation: Ir(Fdpq)$_2$(acac)), 2,3,7,8,12,13,17,18-octaethyl-21H,23H-porphyline platinum (II) (abbreviation: PtOEP) or the like.

Further, since a rare earth metal complex such as tris(acetyl acetonato)(monophenanthroline)terbium(III) (abbreviation: Tb(acac)$_3$(Phen)), tris(1,3-diphenyl-1,3-propanedionate) (monophenanthroline) europium (III) (abbreviation: Eu(DBM)$_3$(Phen)), tris[1-(2-thenoyl)-3,3,3-trifluoroacetonato](monophenanthroline)europium (III) (abbreviation: Eu(TTA)$_3$(Phen)) emits light from rare earth metal ions (electron transition between different multiplicities), it can be used as a phosphorescent compound.

In one aspect of the invention, the phosphorescent emitting material is preferably an ortho-metalated complex of a metal element selected from iridium (Ir), osmium (Os) and platinum (pt).

A phosphorescent emitting material that is an ortho-metalated complex of a metal element selected from iridium (Ir), osmium (Os) and platinum (Pt) is preferably a complex represented by the following formula (α).

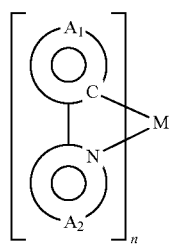

(α)

In the formula (α), M is at least one metal selected from osmium, iridium and platinum, and n is the valence of the metal.

The ring A$_1$ is a substituted or unsubstituted aryl group including 6 to 24 ring carbon atoms or a heteroaryl group including 5 to 30 ring atoms, and the ring A$_2$ is a substituted or unsubstituted heteroaryl group including 5 to 30 ring atoms that contains nitrogen as the ring constituting a hetero ring.

As the aryl group including 6 to 24 ring carbon atoms in the ring A$_1$ in the formula (α), the aryl group in the above-mentioned formula (1) can be given.

As the heteroaryl group including 5 to 30 ring atoms in the ring A$_1$ and the ring A$_2$ in the formula (α), the aryl group in the above-mentioned formula (1) can be given.

The substituent which the ring A$_1$ and the ring A$_2$ in the formula (α) can include is the same as those in the above-mentioned formula (1).

Further, the complex represented by the formula (α) is preferably a complex represented by the following formula (T) or (U).

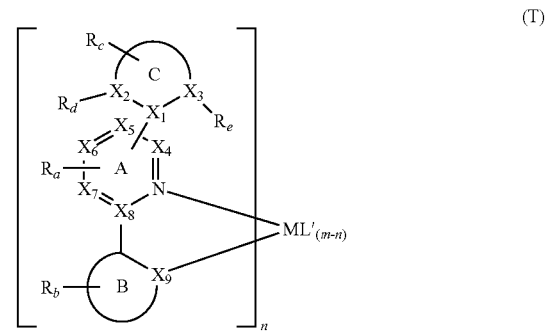

(T)

In the formula (T), M is a metal and the ring B and the ring C are independently an aryl group or a heteroaryl group including 5 or 6 ring atoms.

The ring A-ring B is a bonding pair of the aryl group or the heteroaryl group, and it is coordinated at the metal M through the nitrogen atom in the ring A and the sp$^2$ hybridized atom in the ring B.

The ring A-ring C is a bonding pair of the aryl group or the heteroaryl group.

R$_a$, R$_b$ and R$_c$ are independently any one selected from a hydrogen atom, a substituted or unsubstituted alkyl group including 1 to 25 carbon atoms, a substituted or unsubstituted alkoxy group including 1 to 25 carbon atoms, a substituted or unsubstituted amino group, a substituted or unsubstituted alkenyl group including 2 to 25 carbon atoms, a substituted or unsubstituted alkynyl group including 2 to 25 carbon atoms, a substituted or unsubstituted aralkyl group including 7 to 50 carbon atoms, a substituted or unsubstituted aryl group including 6 to 24 ring carbon atoms and a substituted or unsubstituted heteroaryl group including 5 to 30 ring atoms. They are independently one to four.

X$_1$ to X$_9$ are independently a carbon atom or a nitrogen atom.

R$_d$ and R$_e$ are independently any one selected from the group consisting of a hydrogen atom, a substituted or unsubstituted alkyl group including 1 to 25 carbon atoms, a substituted or unsubstituted alkoxy group including 1 to 25 carbon atoms, a substituted or unsubstituted amino group, a substituted or unsubstituted alkenyl group including 2 to 25 carbon atoms, a substituted or unsubstituted alkynyl group including 2 to 25 carbon atoms, a substituted or unsubstituted aralkyl group including 7 to 50 carbon atoms, a substituted or unsubstituted aryl group including 6 to 24 ring carbon atoms and a substituted or unsubstituted heteroaryl group including 5 to 30 ring atoms, and at least one of R$_c$, R$_d$ and R$_e$ that is bonded with the ring C is not a hydrogen atom.

m shows an oxidization state of the metal M, and n is one or more. L' is a monoanionic bidentate ligand.

In the formula (T), as examples of M, osmium, iridium, platinum or the like can be given, with iridium being preferable.

As the aryl group including 5 or 6 ring atoms represented by the ring B and the ring C, an aryl group in the formula (1) mentioned above can be given.

As the heteroaryl group including 5 or 6 ring atoms represented by the ring B and the ring C, the heteroaryl group mentioned above can be given.

As the substituted or unsubstituted alkyl group including 1 to 25 carbon atoms, the substituted or unsubstituted alkoxy group including 1 to 25 carbon atoms, the substituted or unsubstituted aralkyl group including 7 to 50 carbon atoms, the substituted or unsubstituted aryl group including 6 to 24 ring carbon atoms and the substituted or unsubstituted heteroaryl group including 5 to 30 ring atoms represented by $R_1$, $R_2$, $R_a$, $R_b$ and $R_c$, the same groups as those mentioned above can be given.

As the substituted or unsubstituted alkenyl group including 2 to 25 carbon atoms and the substituted or unsubstituted alkynyl group including 2 to 25 carbon atoms represented by $R_1$, $R_2$, $R_a$, $R_b$ and $R_c$, the same groups as those mentioned above can be given.

As the monoanionic bidentate ligand represented by L', a ligand represented by the following formula (L) can be given.

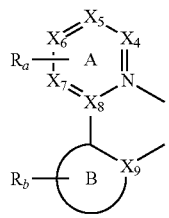

(L')

In the formula (L'), $X_4$ to $X_9$, $R_a$ and $R_b$ are as defined in $X_4$ to $X_9$, $R_a$ and $R_b$ in the formula (T), and preferable aspects are also the same.

Through a solid line extending from $X_9$ to the outside of the ring B and a dotted line extending from nitrogen atom of the ring A to the outside of the ring A, the ligand represented by the formula (L) is coordinated on the metal M represented by the formula (T).

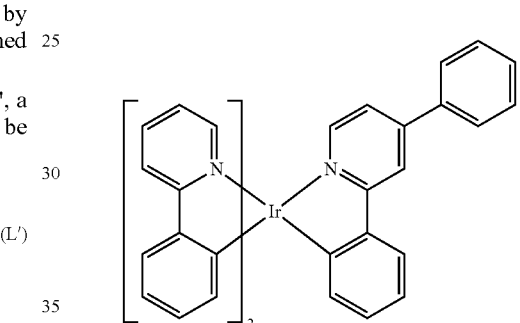

(U)

In the formula (U), X is any selected from NR, an oxygen atom, a sulfur atom, BR and a selenium atom, and R is a hydrogen atom or a substituted or unsubstituted alkyl group including 1 to 25 carbon atoms.

$R_1$, $R_2$, $R_3$ and $R_4$ are independently any selected from a hydrogen atom, a substituted or unsubstituted alkyl group including 1 to 25 carbon atoms and a substituted or unsubstituted aryl group including 6 to 24 ring carbon atoms. They are independently one to four.

In the formula (U), as the alkyl group including 1 to 25 carbon atoms represented by R, $R_1$, $R_2$, $R_3$ and $R_4$, the same groups as those mentioned above can be given, and preferable aspects are also the same.

As the aryl group including 6 to 24 ring carbon atoms represented by $R_1$, $R_2$, $R_3$ and $R_4$, the same groups as those mentioned above can be given, and preferable aspects are also the same.

As the complex represented by the formula (T) or (U), the following compounds are preferable. The complex is not particularly limited to those.

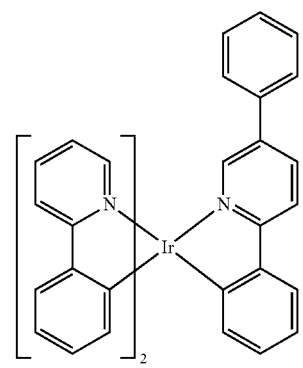

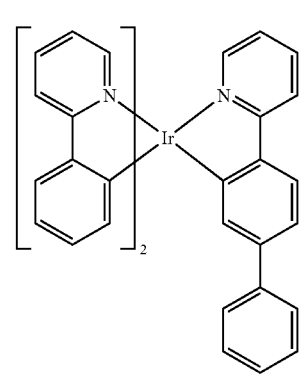

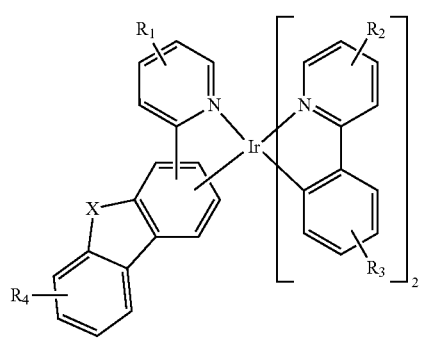

489
-continued
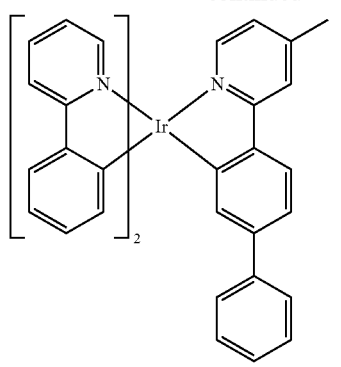
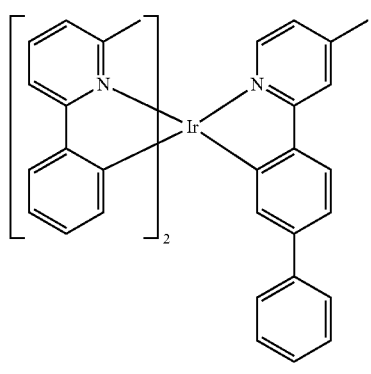
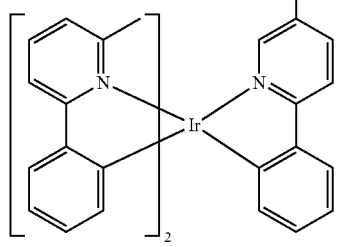
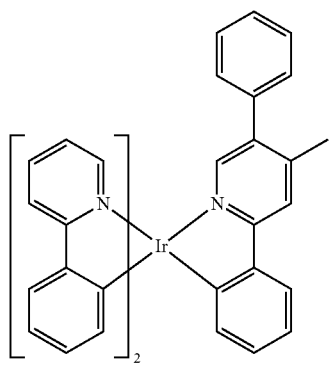
490
-continued
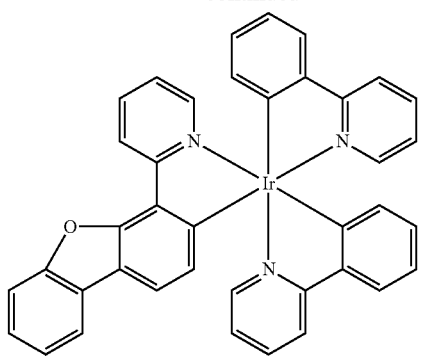
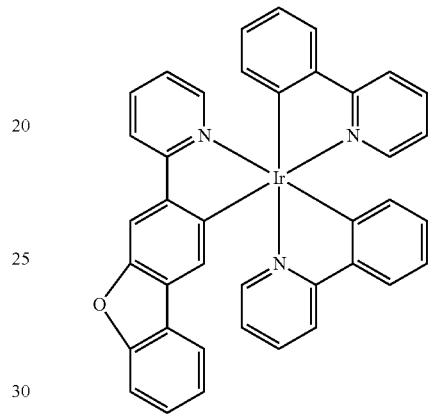
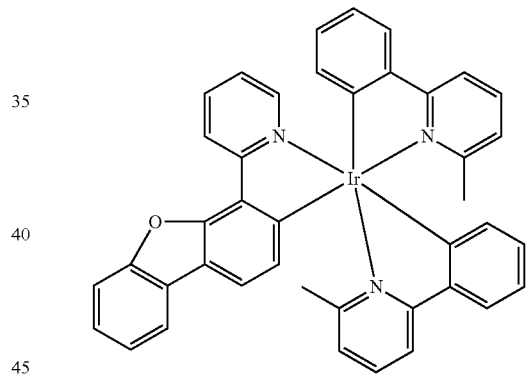
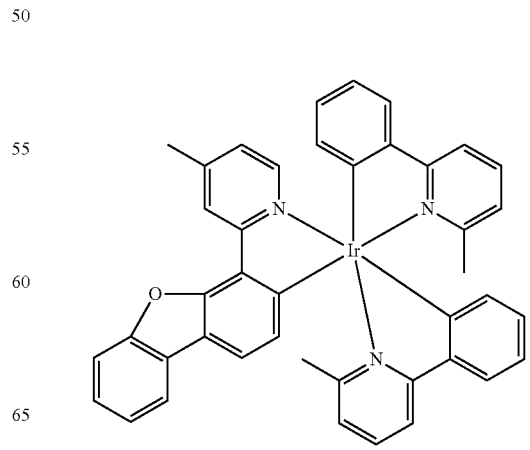

491
-continued
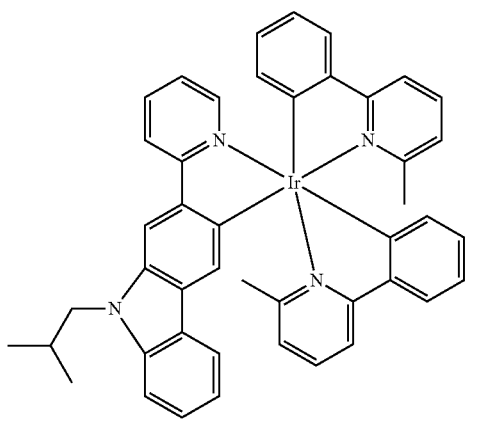
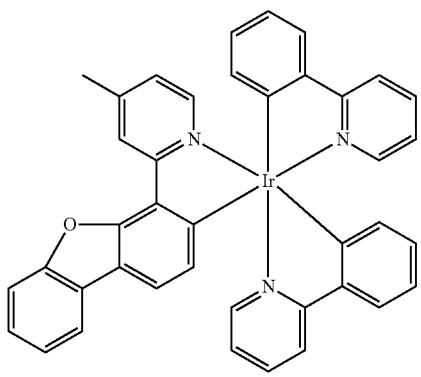
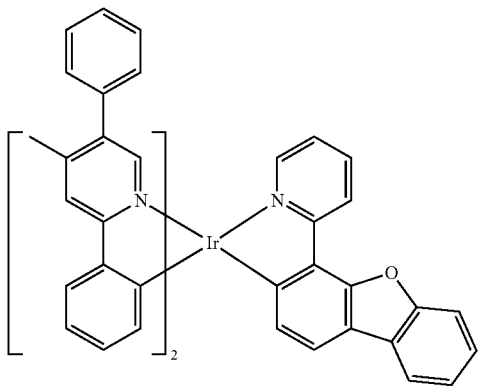
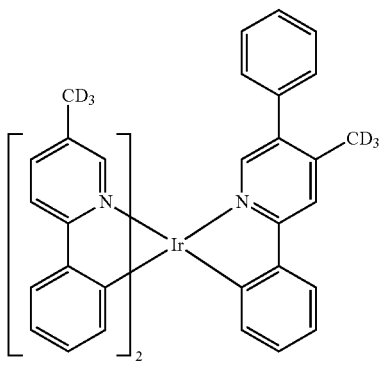
492
-continued
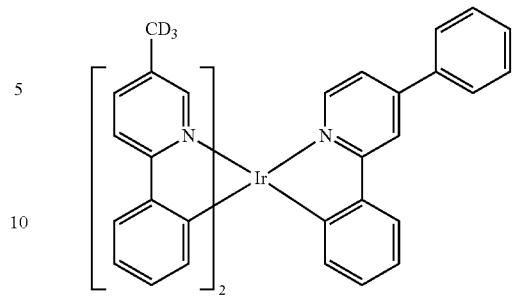
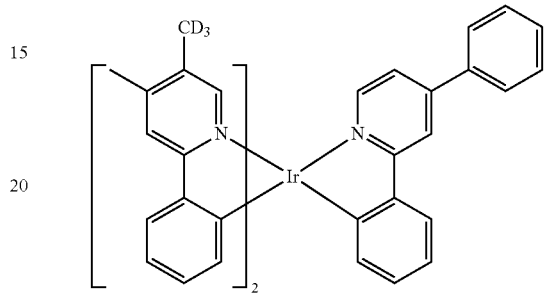
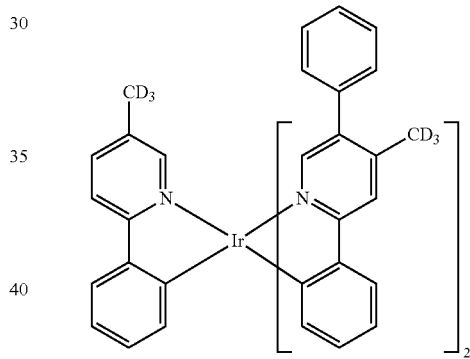
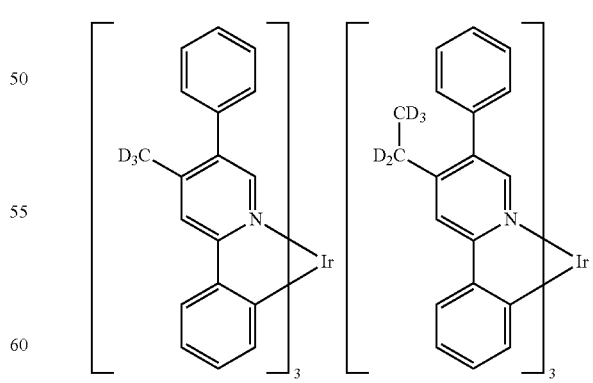
As the complex represented by the formula (α), other than the complex represented by the formula (T) or (U), a complex represented by the following formulas (V), (X), (Y) or (Z) can also be used.

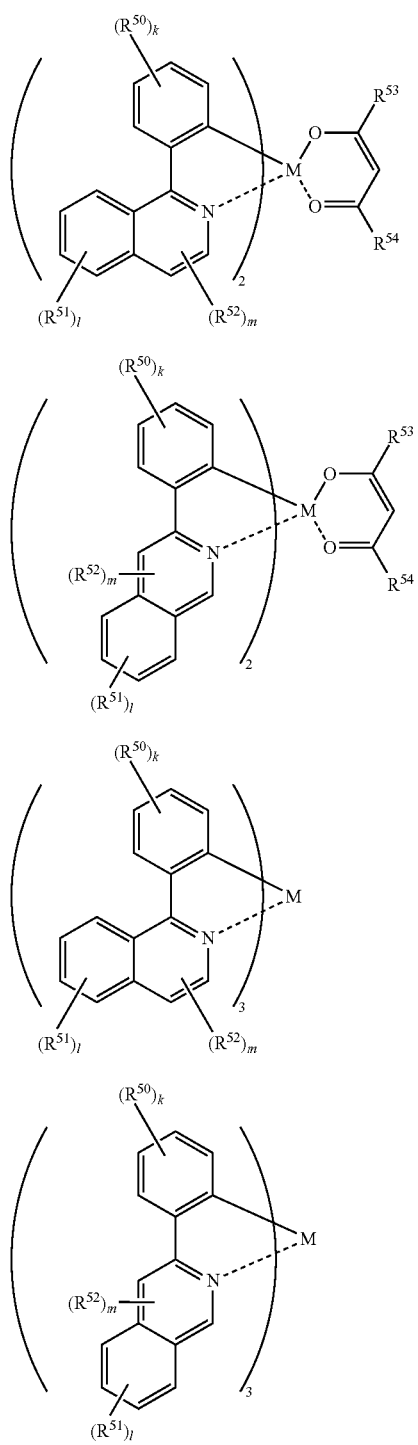

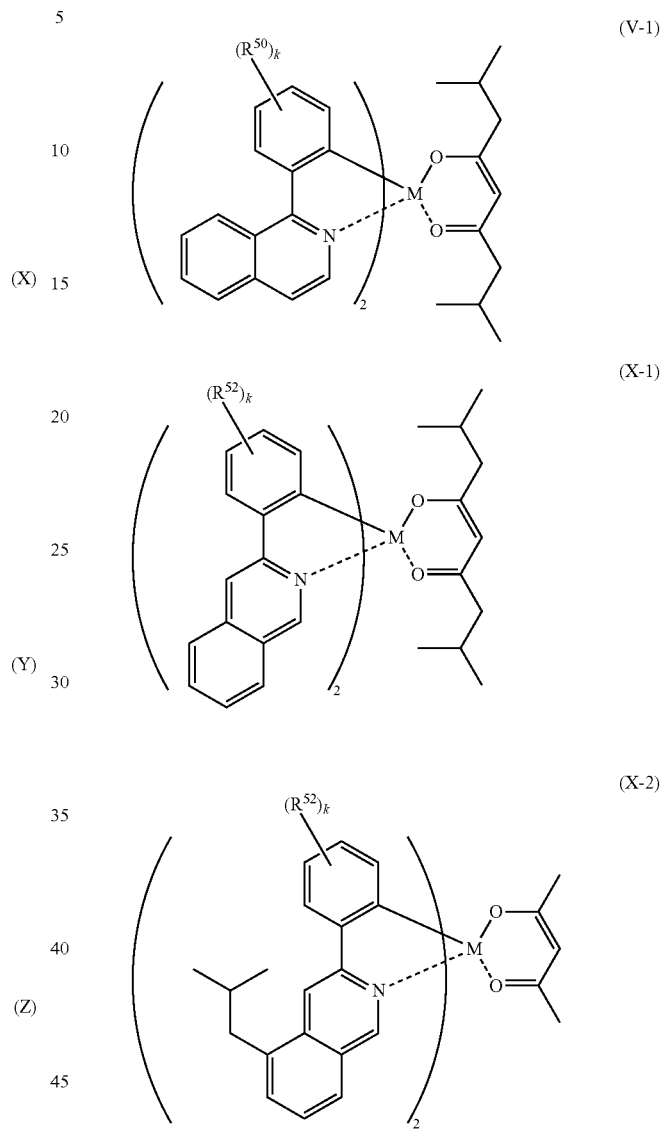

In the formulas (V), (X), (Y) or (Z), $R^{50}$ to $R^{54}$ are a hydrogen atom or a substituent, k is an integer of 1 to 4, l is an integer of 1 to 4, and m is an integer of 1 to 2. M is Ir, Os or Pt.

As the substituent represented by $R^{50}$ to $R^{54}$, the same substituents as those mentioned above can be given.

The complex represented by the formula (V) is preferably a complex represented by the following formula (V-1), and the complex represented by the formula (X) is preferably a complex represented by the following formula (X-1) or (X-2). In the following formulas (V-1), (X-1) and (X-2), $R^{50}$, k and M are the same as $R^{50}$, k and M mentioned above.

The specific examples of the complex represented by the formulas (V), (X), (Y) or (Z) are shown below, but not particularly limited thereto.

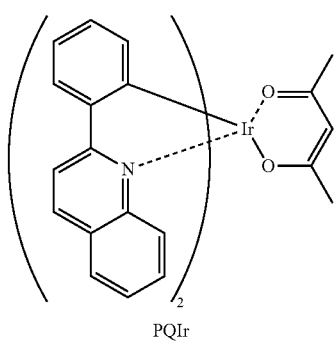

PQIr

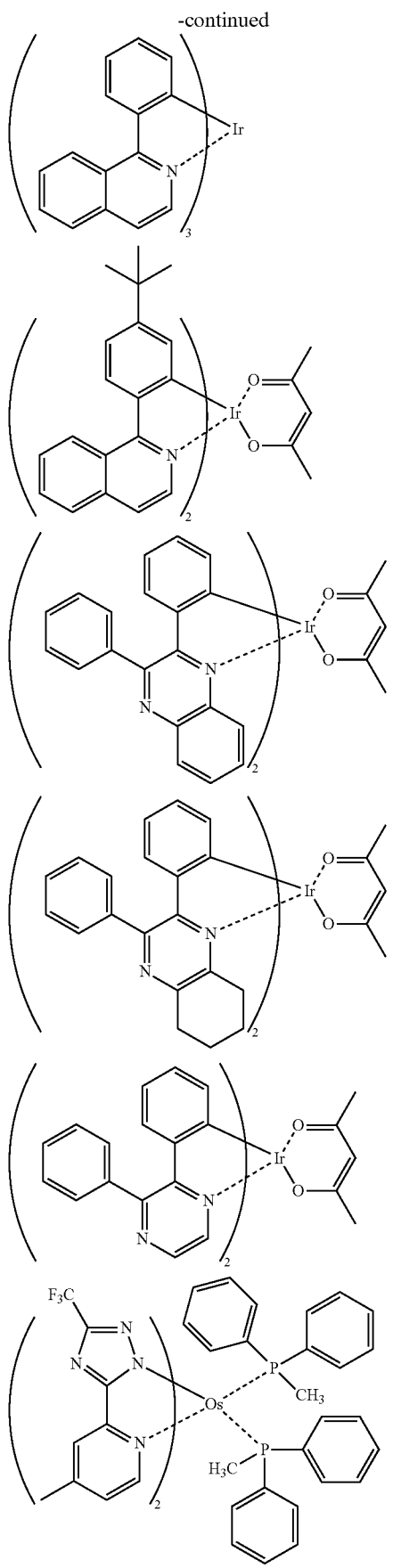
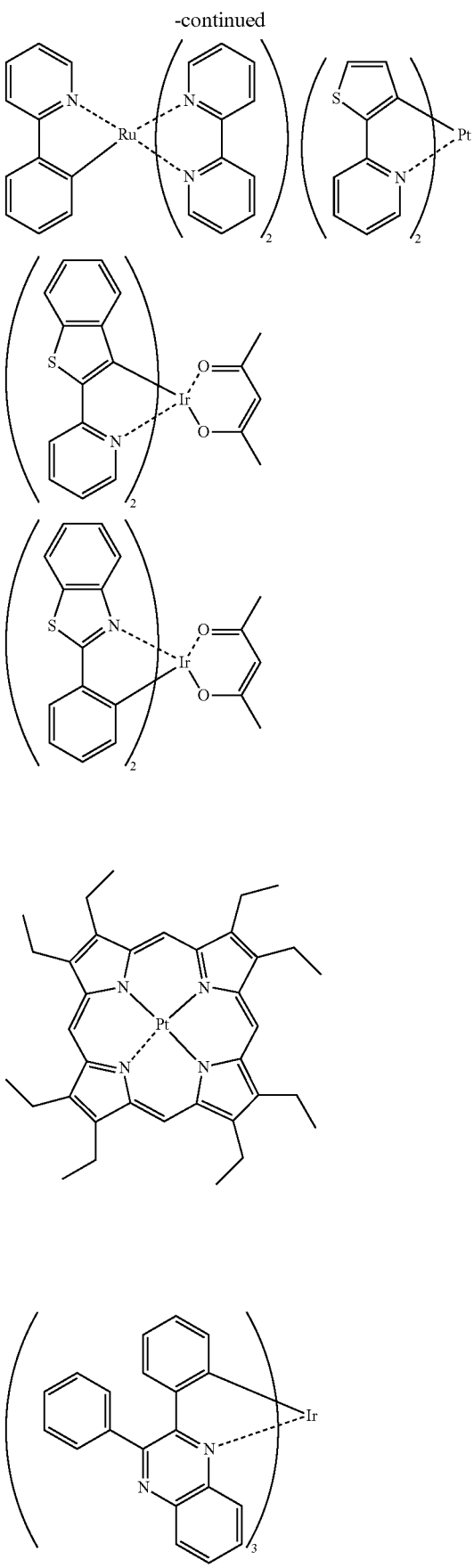

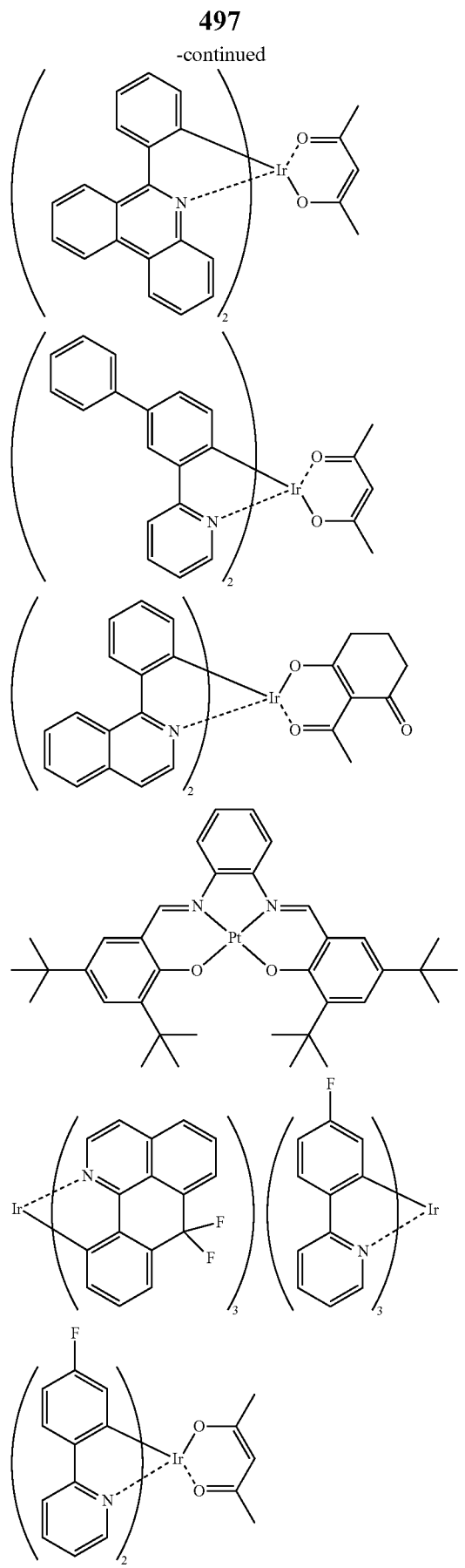
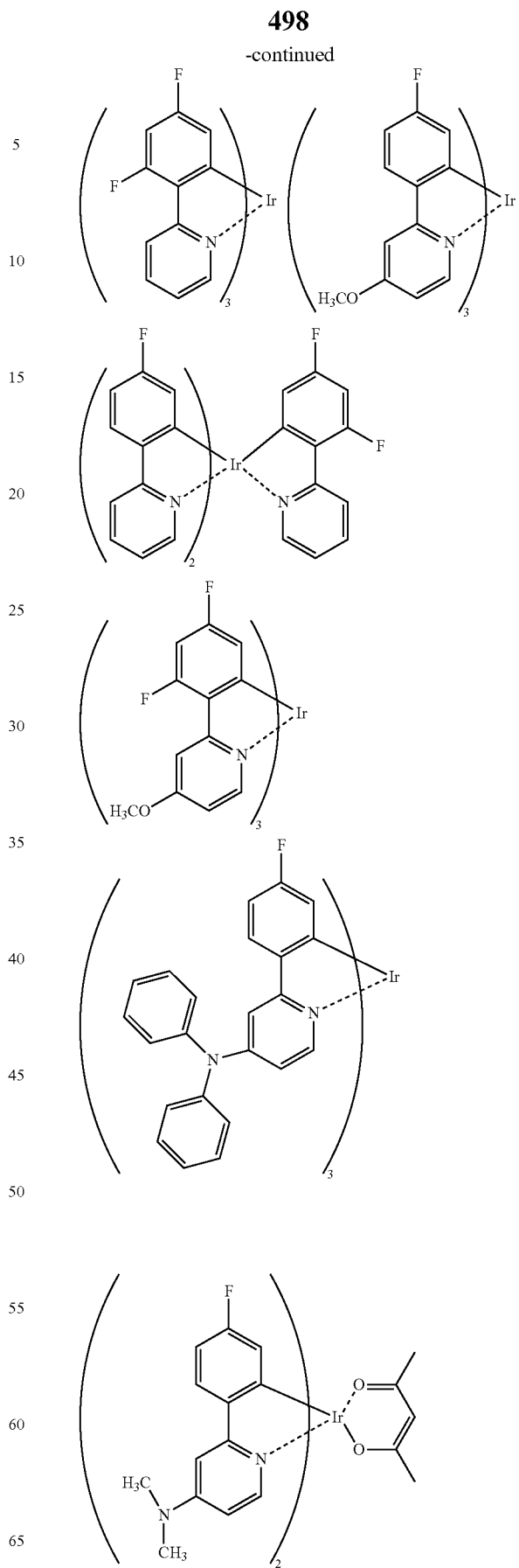

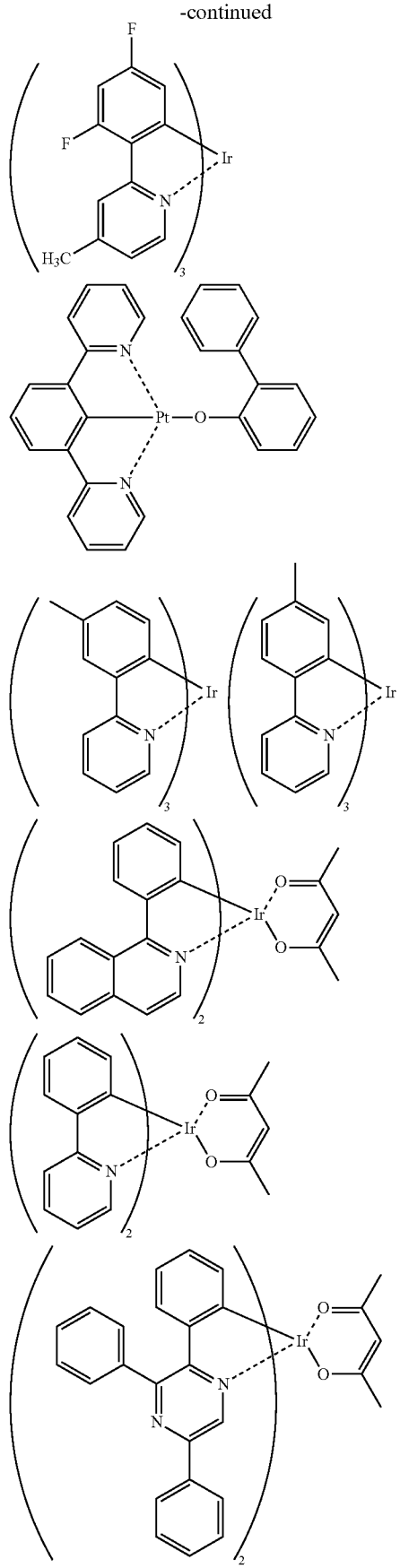
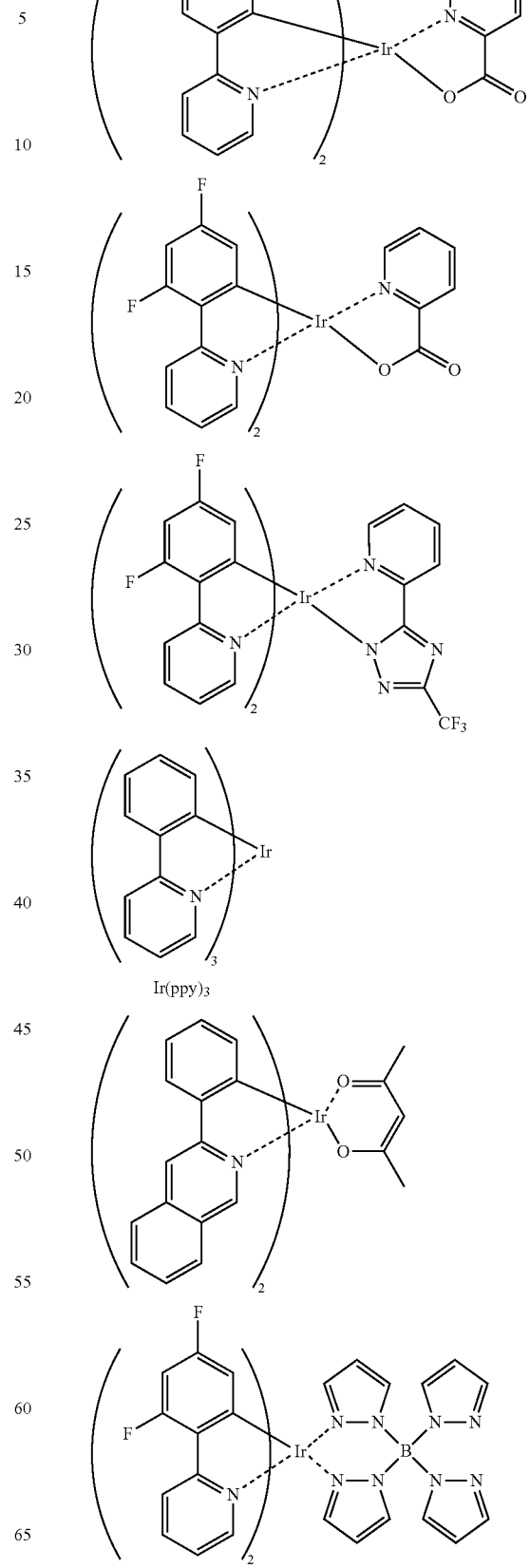

501
-continued
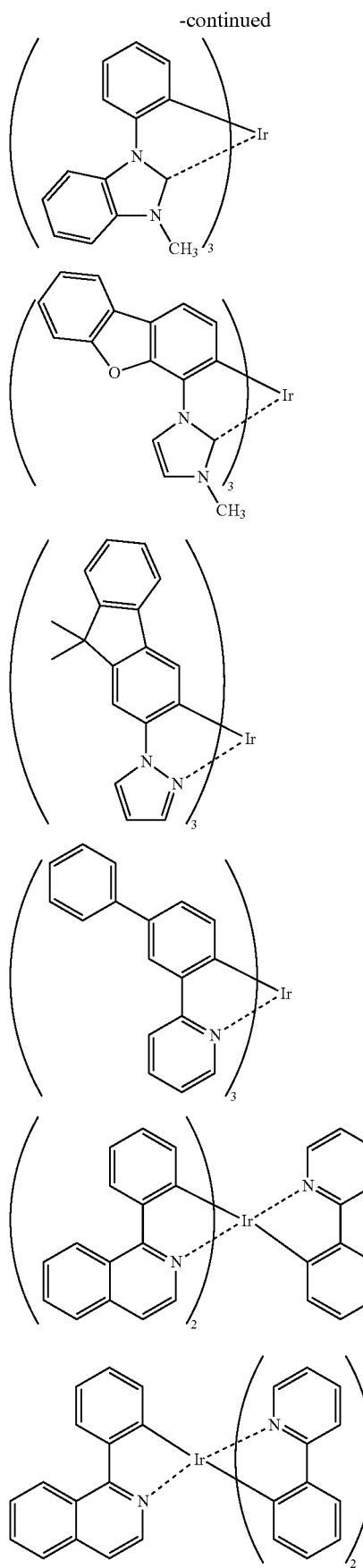
502
-continued
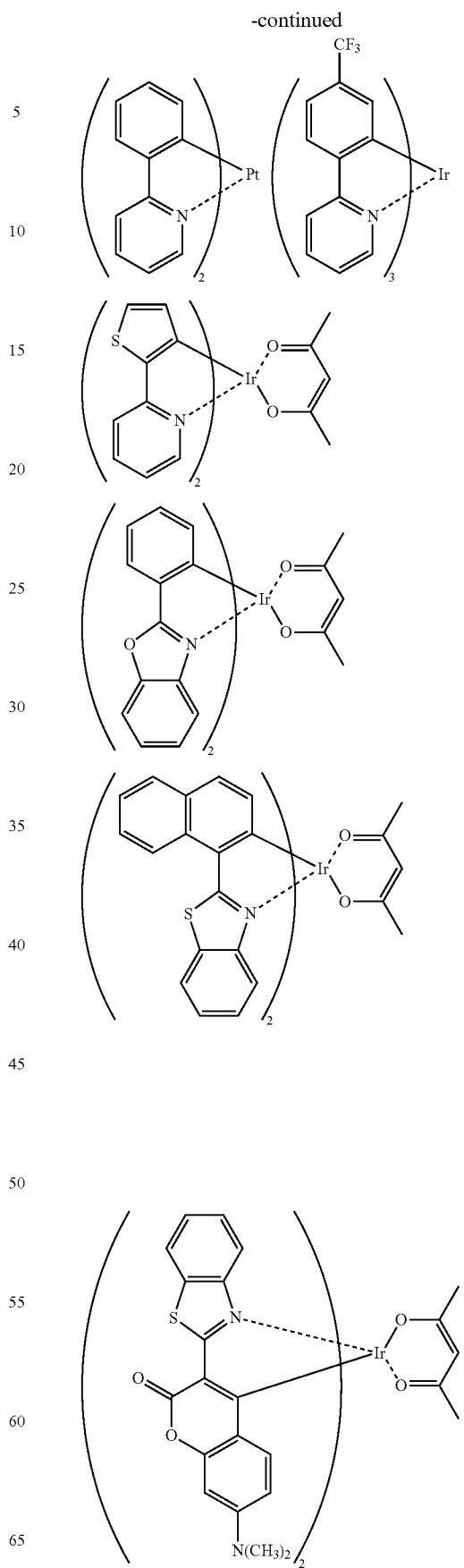

503
-continued

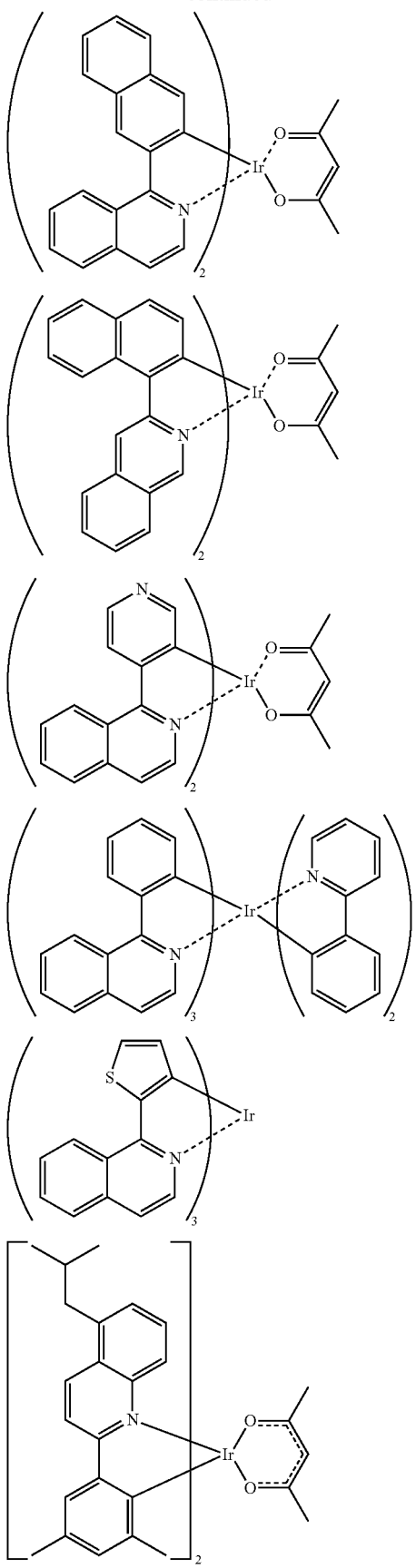

504
-continued

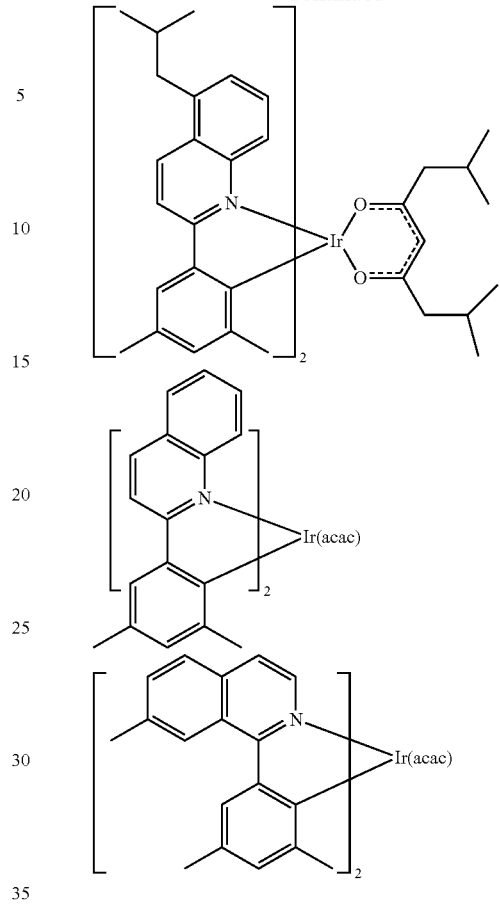

As the phosphorescent emitting material, an iridium complex represented by the following formula (β) is also preferable.

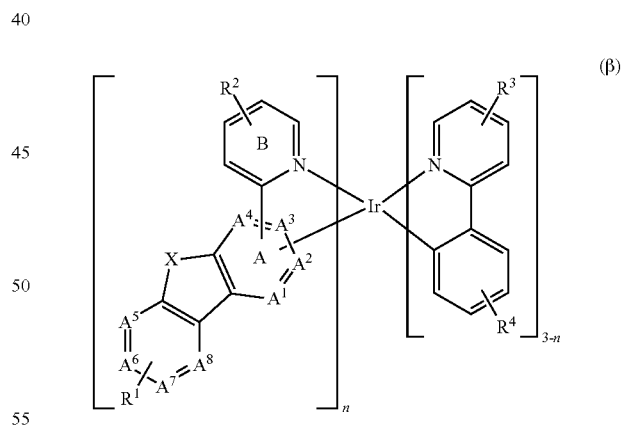

(β)

In the formula (β), $A^1$ to $A^8$ include carbon or nitrogen, and at least one of $A^1$ to $A^8$ is nitrogen, the ring B is bonded with the ring A by a C—C bond, and iridium (Ir) is bonded to the ring A by an Ir—C bond. It is preferred that only one of $A^1$ to $A^8$ be nitrogen, and it is further preferred that only one of $A^5$ to $A^8$ be nitrogen.

X is O, S or Se, with O being preferable.

$R^1$ to $R^4$ are independently a mono-, di-, tri-, or tetra-substituted or unsubstituted. Adjacent $R^1$ to $R^4$ may be bonded to each other to form a ring. $R^1$ to $R^4$ are independently selected from the group consisting of hydrogen, deuterium, halogen, a substituted or unsubstituted alkyl including 1 to 25 carbon atoms, a substituted or unsubstituted cycloalkyl including 3 to 25 ring carbon atoms, a substituted or unsubstituted heteroalkyl including 2 to 25 atoms, a substituted or unsubstituted arylalkyl including 7 to 50 carbon atoms, a substituted or unsubstituted alkoxy including 1 to 25 carbon atoms, a substituted or unsubstituted aryloxy including 6 to 24 ring carbon atoms, a substituted or unsubstituted amino, silyl substituted by one or more groups selected from the group consisting of an alkyl group including 1 to 25 carbon atoms and an aryl group including 6 to 24 ring carbon atoms, a substituted or unsubstituted alkenyl including 2 to 25 carbon atoms, cycloalkenyl including 3 to 25 ring carbon atoms, heteroalkenyl including 3 to 25 atoms, alkynyl including 2 to 25 carbon atoms, aryl including 6 to 24 ring carbon atoms, heteroaryl including 5 to 30 ring atoms, acyl, carbonyl substituted by one or more groups selected from the group consisting of an alkyl group including 1 to 25 carbon atoms and aryl group including 6 to 24 ring carbon atoms, carboxylic acid, ester, nitrile, isonitrile, tolyl, sulfanyl sulfinyl, sulfonyl, phosphino and a combination thereof. $R^1$ to $R^4$ are preferably selected from hydrogen, deuterium, an alkyl group including 1 to 25 carbon atoms and a combination thereof. It is preferred that $R^2$ and/or $R^3$ be an alkyl group including 1 to 25 carbon atoms. It is further preferred that the alkyl group be deuterated or partially deuterated.

n is an integer of 1 to 3, with 1 being preferable.

The iridium complex represented by the formula (IP) is preferably an iridium complex represented by the following formula (β-1).

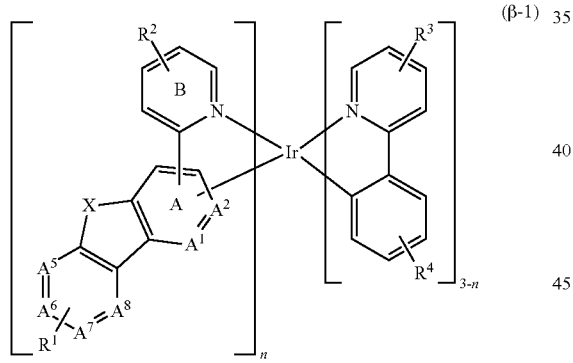

(β-1)

$A^1$, $A^2$, $A^5$ to $A^8$, X, $R^1$ to $R^4$, and n in the formula (⊕-1) are the same as those in the formula (β).

The specific examples of the iridium complex represented by the formula (β) orthe formula (β-1) are shown below, but the iridium complex is not limited thereto.

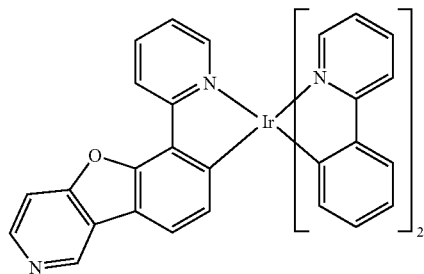

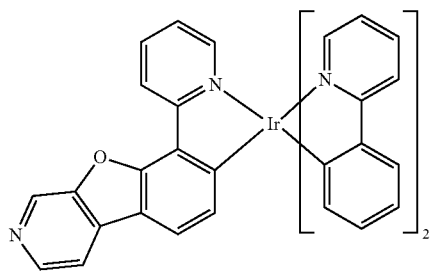

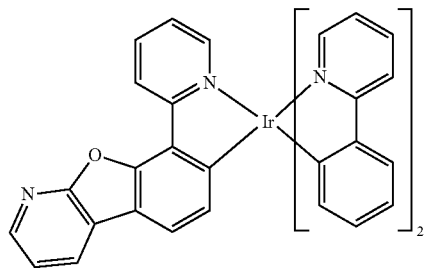

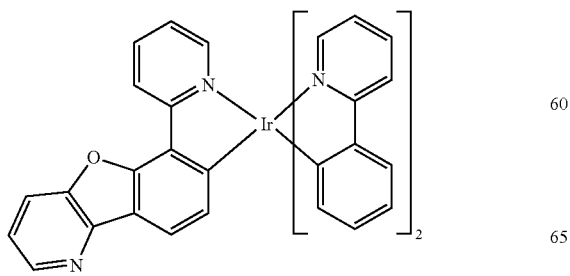

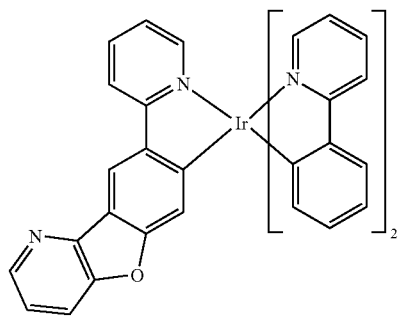

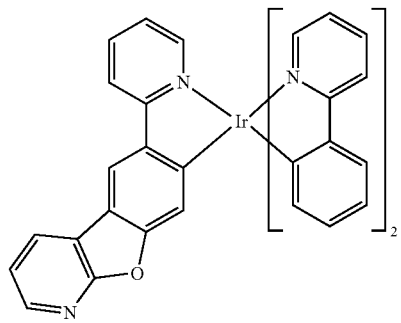

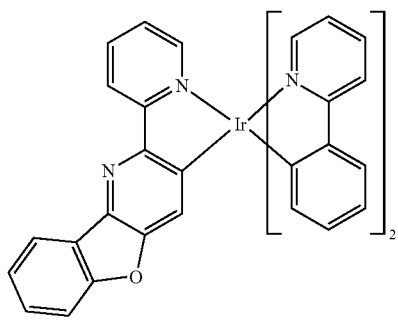

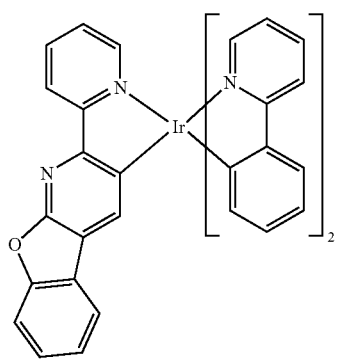

The iridium complex represented by the formula (8) is also preferably an iridium complex represented by the following formula (β-2).

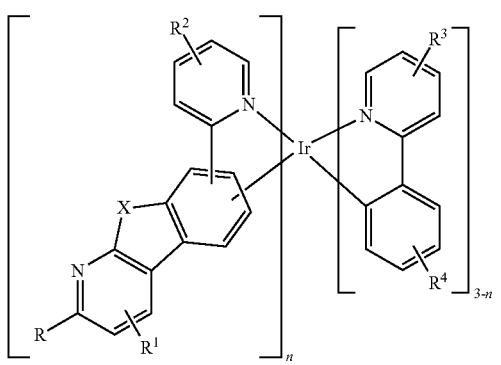

(β-2)

In the formula (β-2), $R^1$ to $R^4$, X and n are the same as in the formula (β).

R is selected from the group consisting of a substituted or unsubstituted alkyl including 1 to 25 carbon atoms, a substituted or unsubstituted cycloalkyl including 3 to 25 ring carbon atoms and a combination thereof. R is preferably a substituted or unsubstituted alkyl including 1 to 25 carbon atoms or a substituted or unsubstituted cycloalkyl including 3 to 25 ring carbon atoms.

The specific examples of the iridium complex represented by the formula (β-2) are shown below, the iridium complex is not limited thereto.

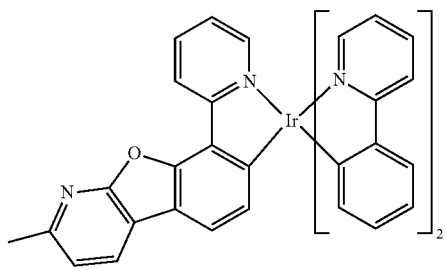

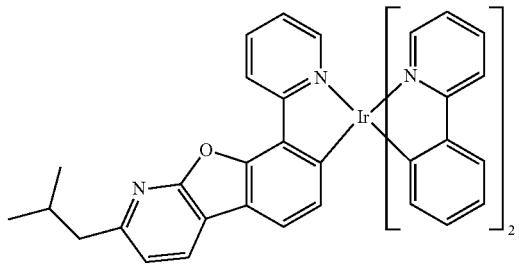

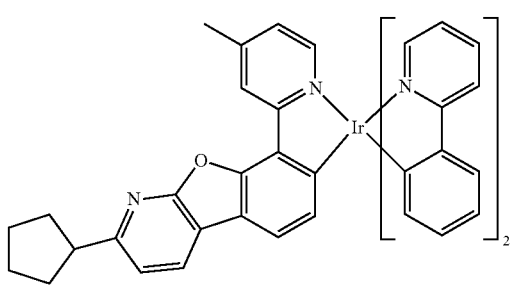

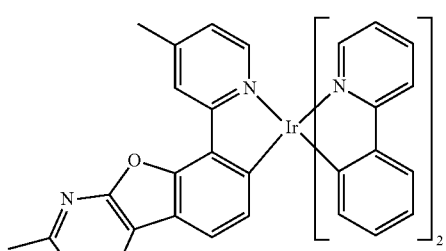

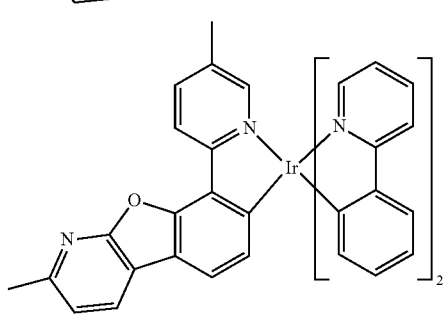

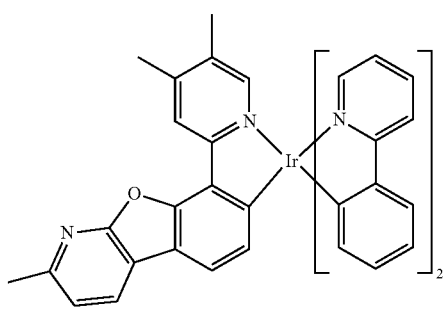

-continued

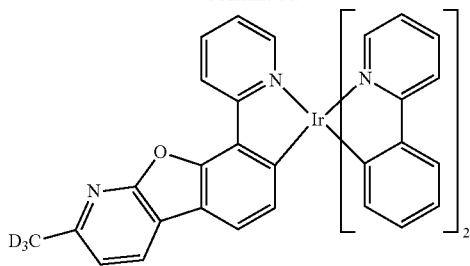
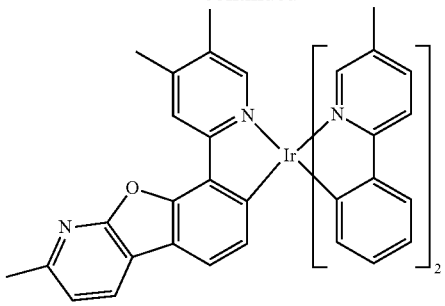
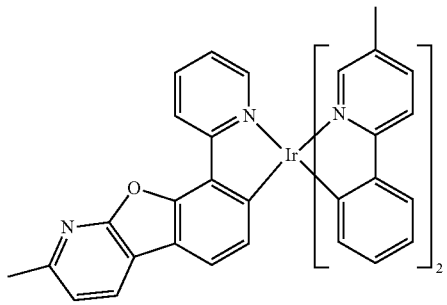
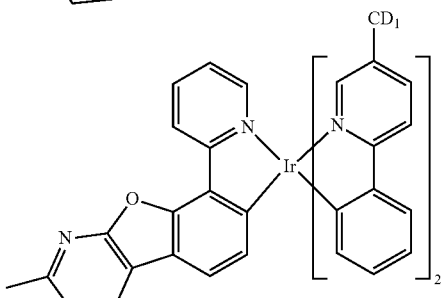
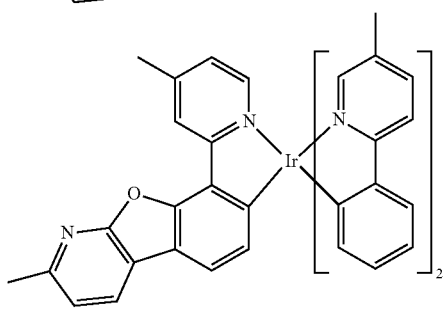
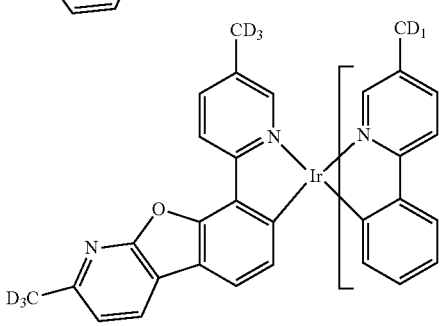

(Host Material of Emitting Layer)

The emitting layer may have a structure in which the above-mentioned substance having high emitting property (guest material) is dispersed in other substances (host material). As the substance for dispersing the substance having high emitting property, various substances can be used. It is preferable to use a substance having a higher lowest unoccupied molecular orbital (LUMO level) than that of the substance having high emitting property, and having a lower highest unoccupied molecular orbital (HOMO level) than that of the substance having high emitting property.

As the substance for dispersing a substance having high emitting property (host material), 1) metal complex such as an aluminum complex, a beryllium complex or a zinc complex, 2) heterocyclic compound such as an oxadiazole derivative, a benzimidazole derivative, a phenanthroline derivative or the like, 3) fused aromatic compound such as a carbazole derivative, an anthracene derivative, a phenanthrene derivative, a pyrene derivative or a chrysene derivative, and 3) aromatic amine compound such as a triarylamine derivative or a fused polycyclic aromatic amine derivative can be used.

(Electron-Transporting Layer)

An electron-transporting layer is a layer containing a substance having high electron-transporting property. In the electron-transporting layer, 1) metal complex such as an aluminum complex, a beryllium complex or a zinc complex; 2) a heteroaromatic compound such as an imidazole derivative, a benzimidazole derivative, an azine derivative, a carbazole derivative and a phenanthroline derivative, and 3) a polymer compound can be used.

(Electron-Injecting Layer)

An electron-injecting layer is a layer containing a substance having high electron injection property. In the electron-injecting layer, an alkali metal such as lithium (Li), lithium fluoride (LiF), cesium fluoride (CsF), calcium fluoride ($CaF_2$), lithium oxide ($LiO_x$); an alkaline earth metal or a compound of those can be used.

(Cathode)

For a cathode, it is preferable to use a metal having a small work function (specifically, 3.8 eV or less), an alloy, an electrically conductive compound, a mixture of those orthe like. As specific examples of the cathode material, an element belonging to Group 1 or Group 2 of the periodic table of the elements, i.e., a rare earth metal such as an alkali metal such as lithium (L) or cesium (Cs), an alkaline earth metal such as magnesium (Mg), alloys containing those (e.g. MgAg, AlLi) and an alloy containing those or the like can be given.

D. Electronic Apparatus

An electronic apparatus according to one aspect of the invention is provided with the organic electroluminescence device as one aspect of the invention.

The organic electroluminescence device as one aspect of the invention can be used in various electronic apparatuses. For example, it can be used in a planar luminous body such as a flat panel display of a wall-hanging TV, a backlight of a copier, a printer and a crystal liquid display, or a light source of instruments, a displaying board, sign lighting orthe like. Further, the compound of the invention can be used not only in an organic EL device but also in the field of an electrophotographic photoreceptor, a photoelectric conversion element, a solar cell, an image sensor or the like.

EXAMPLES

The invention will be explained in more detail with reference to the Examples and the Comparative Examples, which should not be construed as limiting the scope of the invention.

The compound recited in the claims of the invention can be synthesized with reference to the following synthesis reactions and by using known alternative reactions or raw materials suited to an intended product.

Intermediate Synthesis Example 1 (Synthesis of Intermediate 1-A)

The synthesis scheme of the intermediate 1-A is shown below.

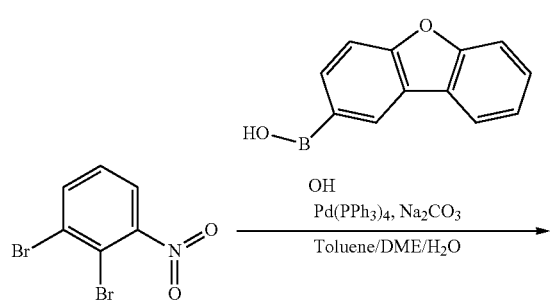

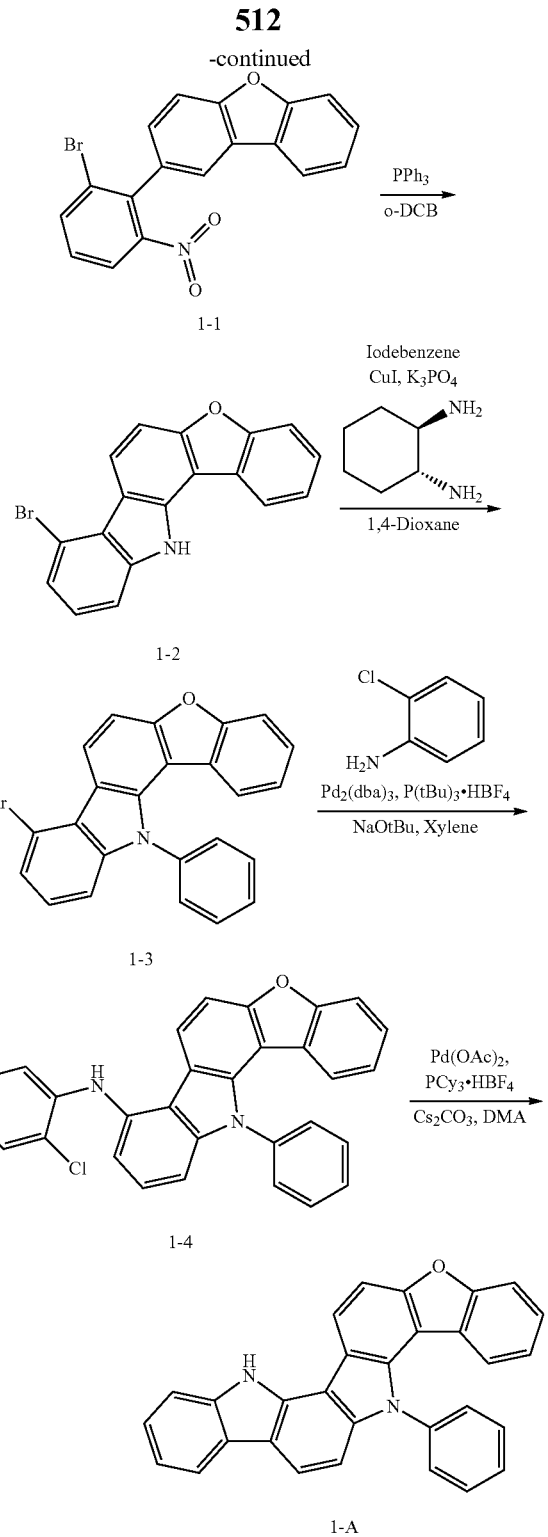

Synthesis of Intermediate 1-1

In argon atmosphere, 2.1 g of 1,2-dibromo-3-nitrobenzene, 1.7 g of dibenzofuran-2-boronic acid, 165 mg of tetrakis (triphenylphosphine) palladium (0), 2.3 g of sodium carbonate, 25 mL of toluene, 5 ml of 1,2-dimethoxyethane, and 5 ml of water were placed in a flask. The resultant was stirred under reflux with heating for 12 hours.

After cooling to room temperature (25° C.), the reaction solution was transferred to a separating funnel, and extracted with toluene. Thereafter, an organic layer was dried with sodium sulfide, filtrated and concentrated. Residues were purified by silica gel chromatography, whereby 2.0 g (yield: 76%) of white solids were obtained.

As a result of an LC-MS analysis, the white solids were identified as intermediate 1-1.

Synthesis of Intermediate 1-2

In an argon atmosphere, 2.0 g of intermediate 1-1, 3.6 g of triphenylphosphine and 50 mL of 1,2-dichlorobenzene were placed in a flask and stirred with heating for 12 hours.

After cooling to room temperature (25° C.), the reaction solution was purified by silica gel chromatography, whereby 1.2 g (yield: 67%) of white solids were obtained.

As a result of an LC-MS analysis, the white solids were identified as intermediate 1-2.

Synthesis of Intermediate 1-3

In an argon atmosphere, 1.2 g of intermediate 1-2, 1.5 g of iodobenzene, 35 mg of copper iodide (I), 62.3 mg of trans-1,2-cyclohexanediamine, 3.1 g of tripotassium phosphate and 20 mL of 1,4-dioxane were placed in a flask, and heated under reflux with stirring for 12 hours.

After cooling to room temperature (25° C.), the reaction solution was transferred to a separating funnel, and water was added and extracted with toluene. Thereafter, an organic layer was dried with sodium sulfide, filtrated and concentrated. Residues were purified by silica gel chromatography, whereby 886 mg (yield: 59%) of white solids were obtained.

As a result of an LC-MS analysis, the white solids were identified as intermediate 1-3.

Synthesis of Intermediate 1-4

In an argon atmosphere, 886 mg of Intermediate 1-3, 329 mg of 2-chloroaniline, 39 mg of tris(dibenzylideneacetone)dipalladium (0), 50 mg of tri-tert-butylphosphonium tetrafluoroborate, 480 mg of sodium tert-butoxide and 8 mL of xylene were placed in a flask, and heated under reflux with stirring for 12 hours.

After cooling to room temperature (25° C.), the reaction solution was concentrated and residues were purified by silica gel chromatography, whereby 808 mg (yield: 82%) of white solids were obtained.

As a result of an LC-MS analysis, the white solids were identified as intermediate 1-4.

Synthesis of Intermediate 1-A

In an argon atmosphere, 808 mg of Intermediate 1-4, 40 mg of palladium (II)acetate, 130 mg of tricyclohexylphosphonium tetrafluoroborate, 1.7 g of cesium carbonate and 15 mL of N,N-dimethylacetamide were placed in a flask, and heated with stirring at 130° C. for 12 hours.

After cooling to room temperature (25° C.), the reaction solution was transferred to a separating funnel, and water was added and extracted with a solution of hexane and ethyl acetate (3:1). Thereafter, an organic layer was dried with sodium sulfide, filtrated and concentrated. Residues were purified by silica gel chromatography, whereby 528 mg (yield: 71%) of white solids were obtained.

As a result of an LC-MS analysis, the white solids were identified as intermediate 1-A.

Intermediate Synthesis Example 2 (Synthesis of Intermediate 2-A)

The synthesis scheme of the intermediate 2-A is shown below.

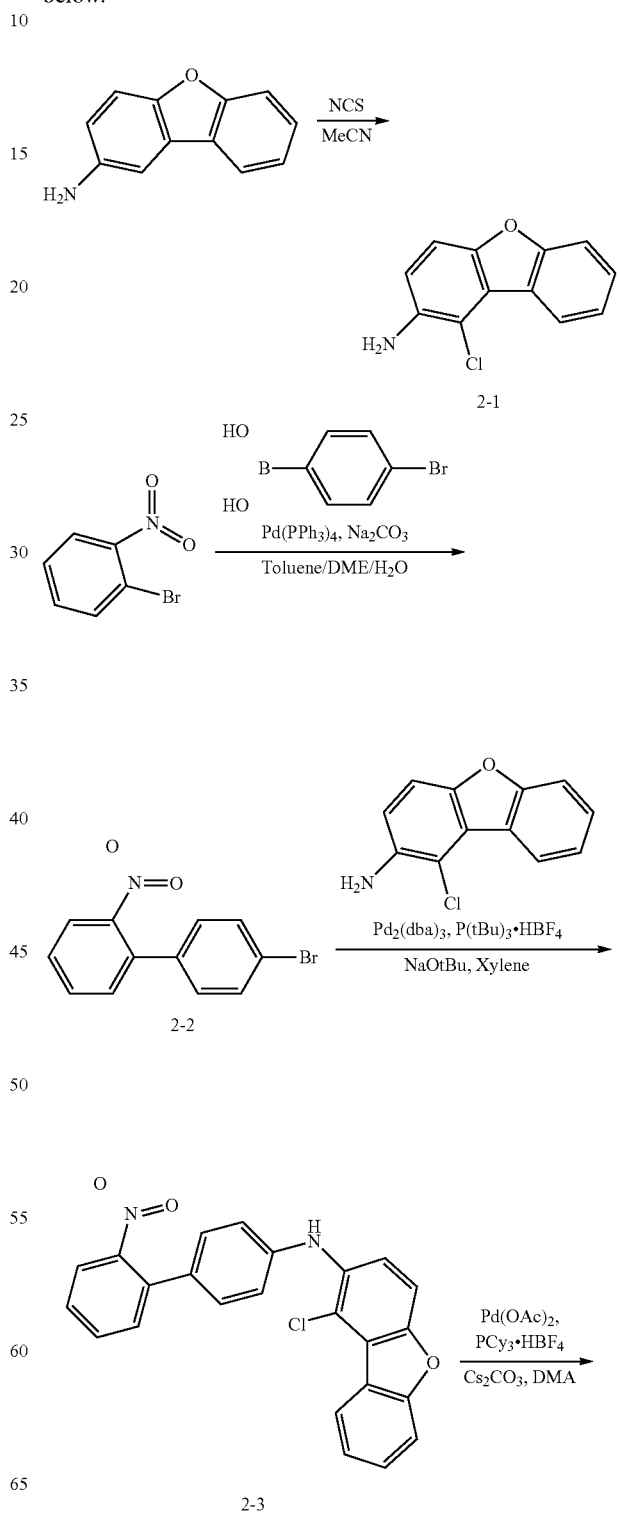

-continued

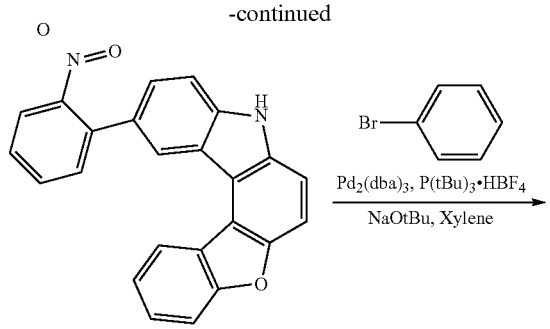

2-4

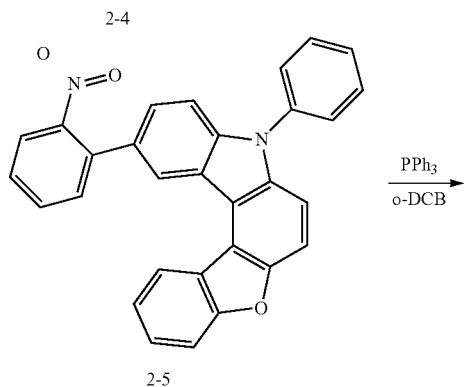

2-5

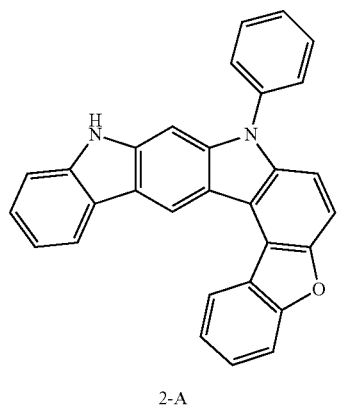

2-A

Synthesis of Intermediate 2-1

In an argon atmosphere, 1.8 g of dibenzofuran-2-amine, 1.3 g of N-chlorosuccinimide and 40 mL of acetonitrile were placed in a flask and stirred at 25° C. for 8 hours.

Thereafter, the reaction solution was transferred to a separating funnel, and water was added and extracted with toluene. Thereafter, an organic layer was dried with sodium sulfide, filtrated and concentrated. Residues were purified by silica gel chromatography, whereby 1.7 g (yield: 76%) of white solids were obtained.

As a result of an LC-MS analysis, the white solids were identified as intermediate 2-1.

Synthesis of Intermediate 2-2

Synthesis was conducted in the same manner as in the synthesis of intermediate 1-1, except that 2-bromonitrobenzene and 4-bromophenylboronic acid were used instead of 1,2-dibromo-3-nitrobenzene and dibenzofuran-2-boronic acid, whereby 1.7 g (yield 61%) of white solids were obtained.

As a result of an LC-MS analysis, the white solids were identified as intermediate 2-2.

Synthesis of Intermediate 2-3

Synthesis was conducted in the same manner as in the synthesis of intermediate 1-4, except that intermediate 2-1 and intermediate 2-2 were used instead of intermediate 1-3 and 2-chloroaniline, whereby 1.9 g (yield 74%) of white solids were obtained.

As a result of an LC-MS analysis, the white solids were identified as intermediate 2-3.

Synthesis of Intermediate 2-4

Synthesis was conducted in the same manner as in the synthesis of intermediate 1-A, except that intermediate 2-3 was used instead of intermediate 1-4, whereby 795 mg (yield 46%) of white solids were obtained.

As a result of an LC-MS analysis, the white solids were identified as intermediate 2-4.

Synthesis of Intermediate 2-5

Synthesis was conducted in the same manner as in the synthesis of intermediate 1-4, except that intermediate 2-4 and bromobenzene were used instead of intermediate 1-3 and 2-chloroaniline, whereby 754 mg (yield 79%) of white solids were obtained.

As a result of an LC-MS analysis, the white solids were identified as intermediate 2-5.

Synthesis of Intermediate 2-A

Synthesis was conducted in the same manner as in the synthesis of intermediate 1-2, except that intermediate 2-5 was used instead of intermediate 1-1, whereby 363 mg (yield 52%) of white solids were obtained.

As a result of an LC-MS analysis, the white solids were identified as intermediate 2-A.

Intermediate Synthesis Example 3 (Synthesis of Intermediate 3-A)

The synthesis scheme of the intermediate 1-A is shown below.

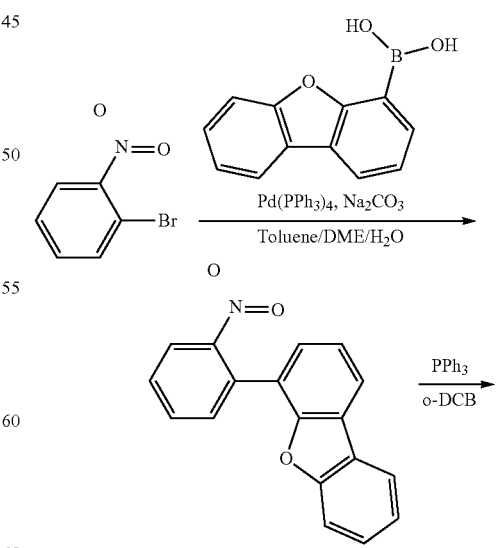

3-1

517
-continued

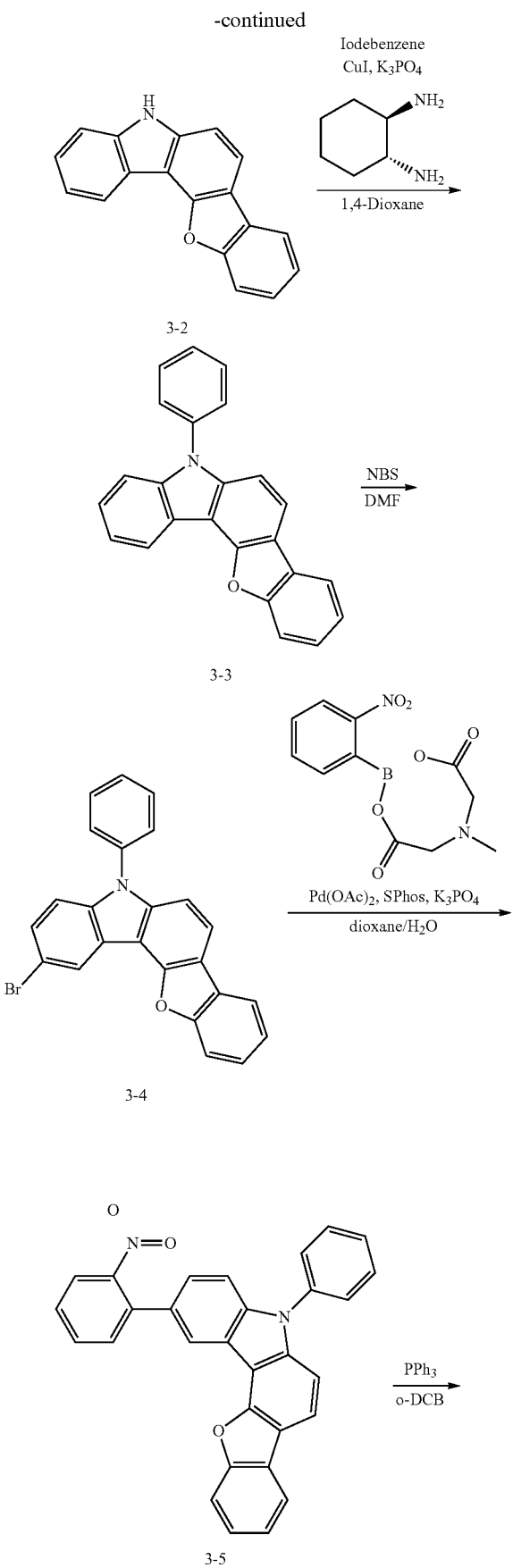

518
-continued

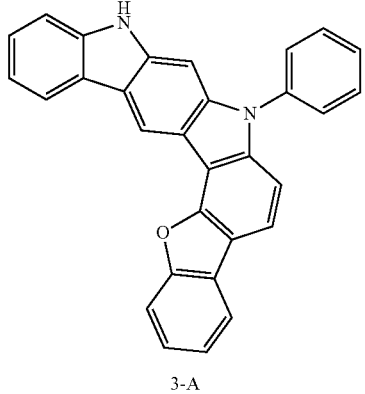

3-A

Synthesis of Intermediate 3-1

Synthesis was conducted in the same manner as in the synthesis of intermediate 1-1, except that 2-bromonitrobenzene and dibenzofuran-4-boronic acid were used instead of 1,2-dibromo-3-nitrobenzene and dibenzofuran-2-boronic acid, whereby 1.9 g (yield 82%) of white solids were obtained.

As a result of an LC-MS analysis, the white solids were identified as intermediate 3-1.

Synthesis of Intermediate 3-2

Synthesis was conducted in the same manner as in the synthesis of intermediate 1-2, except that intermediate 3-1 was used instead of intermediate 1-1, whereby 1.4 g (yield 76%) of white solids were obtained. As a result of an LC-MS analysis, the white solids were identified as intermediate 3-2.

Synthesis of Intermediate 3-3

Synthesis was conducted in the same manner as in the synthesis of intermediate 1-3, except that intermediate 3-2 was used instead of intermediate 1-2, whereby 1.5 g (yield 91%) of white solids were obtained. As a result of an LC-MS analysis, the white solids were identified as intermediate 3-3.

Synthesis of Intermediate 3-4

In an argon atmosphere, 1.5 g of intermediate 3-3, 801 mg of N-bromosuccinimide, and 20 mL of N,N-dimethylformamide were placed in a flask and stirred at 25° C. for 8 hours.

Thereafter, the reaction solution was transferred to a separating funnel, and water was added and extracted with a solution of hexane and ethyl acetate (3:1). Thereafter, an organic layer was dried with sodium sulfide, filtrated and concentrated. Residues were purified by silica gel chromatography, whereby 1.5 g (yield: 82%) of white solids were obtained.

As a result of an LC-MS analysis, the white solids were identified as intermediate 3-4.

Synthesis of Intermediate 3-5

In an argon atmosphere, 1.5 g of intermediate 3-4, 1.5 g of 6-methyl-2-(2-nitrophenyl)-1,3,6,2-dioxazaborocan-4,8-dione, 50 mg of palladium (II) acetate, 182 mg of 2-dicyclohexylphosphino-2',6'-dimethoxybiphenyl, 5.9 g of tripotassium phosphate, 45 ml of 1,4-dioxane and 9 ml of water were placed in a flask, heated under reflux with stirring for 12 hours.

After cooling to room temperature (25° C.), the reaction solution was transferred to a separating funnel, and extracted with toluene. Thereafter, an organic layer was dried with sodium sulfide, filtrated and concentrated. Residues were purified by silica gel chromatography, whereby 1.2 g (yield: 71%) of white solids were obtained.

As a result of an LC-MS analysis, the white solids were identified as intermediate 3-5.

Synthesis of Intermediate 3-A

Synthesis was conducted in the same manner as in the synthesis of intermediate 1-2, except that intermediate 3-5 was used instead of intermediate 1-1, whereby 596 mg (yield 54%) of white solids were obtained.

As a result of an LC-MS analysis, the white solids were identified as intermediate 3-A.

Intermediate Synthesis Example 4 (Synthesis of Intermediate 4-A)

The synthesis scheme of the intermediate 4-A is shown below.

Synthesis of Intermediate 4-2

Synthesis was conducted in the same manner as in the synthesis of intermediate 1-4, except that 9-phenylcarbazole-3-amine and 1-chlorodibenzofuran were used instead of intermediate 1-3 and 2-chloroaniline, whereby 3.1 g (yield 62%) of white solids were obtained.

As a result of an LC-MS analysis, the white solids were identified as intermediate 4-2.

Synthesis of Intermediate 4-A

In an air atmosphere, 3.1 g of Intermediate 4-2, 161 mg of palladium (II) acetate, 99 mg of potassium carbonate and 7.1 g of pivalic acid were placed in a flask and heated with stirring at 130° C. for 12 hours.

After cooling to room temperature (25° C.), toluene was added, and the resulting solution was purified by silica gel chromatography, whereby 977 mg (yield: 32%) of white solids were obtained.

As a result of an LC-MS analysis, the white solids were identified as intermediate 4-A.

Intermediate Synthesis Example 5 (Synthesis of Intermediate 5-A)

The synthesis scheme of the intermediate 5-A is shown below.

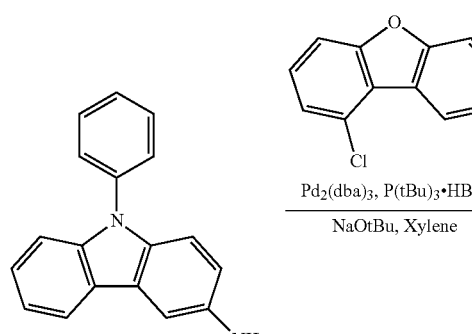

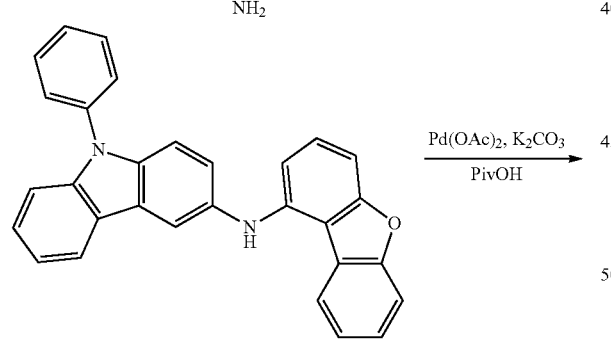

4-2

4-A

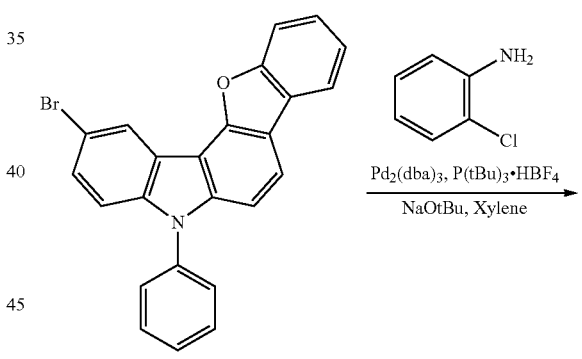

3-4

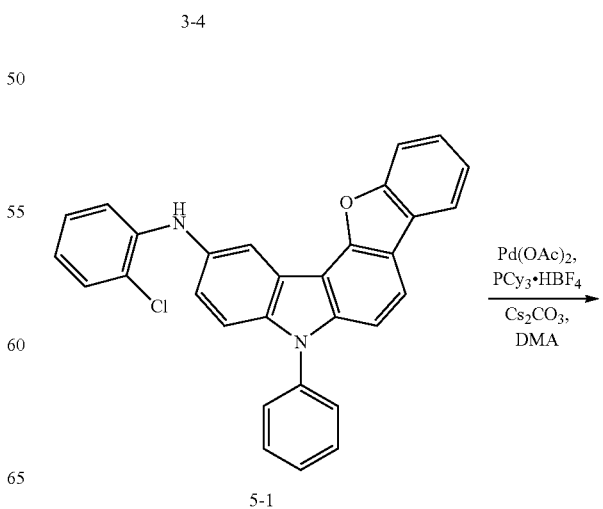

5-1

521

-continued

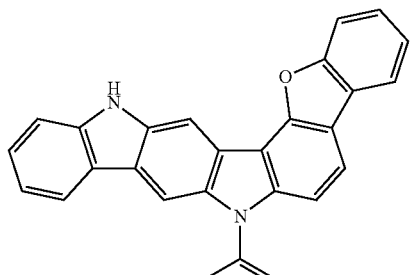

5-A

Synthesis of Intermediate 5-1

Synthesis was conducted in the same manner as in the synthesis of intermediate 1-4, except that intermediate 3-4 was used instead of intermediate 1-3, whereby 2.2 g (yield 88%) of white solids were obtained.

As a result of an LC-MS analysis, the white solids were identified as intermediate 5-1.

Synthesis of Intermediate 5-A

Synthesis was conducted in the same manner as in the synthesis of intermediate 1-A, except that intermediate 5-1 was used instead of intermediate 1-4, whereby 1.2 g (yield 61%) of white solids were obtained.

As a result of an LC-MS analysis, the white solids were identified as intermediate 5-A.

Intermediate Synthesis Example 6 (Synthesis of Intermediate 6-A)

The synthesis scheme of the intermediate 6-A is shown below.

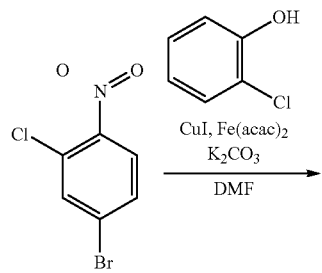

522

-continued

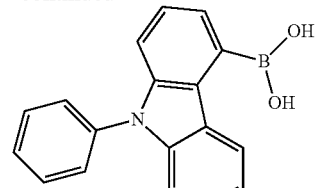

6-1

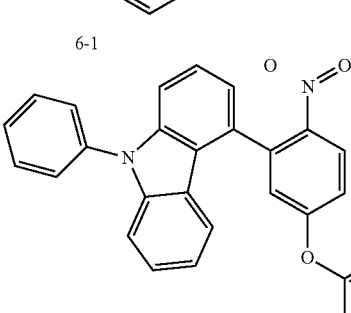

6-2

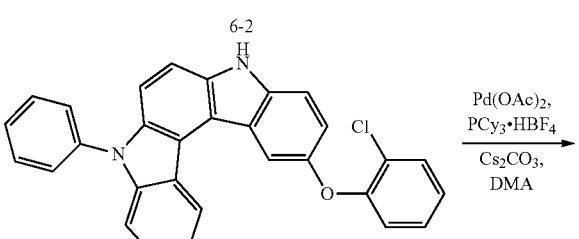

6-3

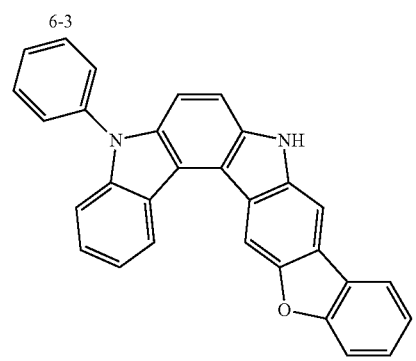

6-A

Synthesis of Intermediate 6-1

In an argon atmosphere, 1.91 g of 4-bromo-2-chloro-1-nitrobenzene, 1.2 ml of 2-chlorophenol, 154 mg of copper iodide, 569 mg of tris(2,4-pentanedionato) iron (III), 2.2 g of potassium carbonate and 15 mL of N,N-dimethylformamide were placed in a flask and heated with stirring at 130° C. for 12 hours.

After cooling the reaction solution to room temperature (25° C.), the reaction solution was filtered. A filtrate was transferred to a separating funnel, and water was added and extracted with a solution of hexane and ethyl acetate (3:1). Thereafter, an organic layer was dried with sodium sulfide, filtrated and concentrated. Residues were purified by silica gel chromatography, whereby 1.4 g (yield: 61%) of white solids were obtained.

As a result of an LC-MS analysis, the white solids were identified as intermediate 6-1.

Synthesis of Intermediate 6-2

Synthesis was conducted in the same manner as in the synthesis of intermediate 1-1, except that intermediate 6-1 and 4-(9-phenylcarbazolyl)boronic acid were used instead of 1,2-dibromo-3-nitrobenzene and dibenzofuran-2-boronic acid, whereby 1.5 g (yield 63%) of white solids were obtained.

As a result of an LC-MS analysis, the white solids were identified as intermediate 6-2.

Synthesis of Intermediate 6-3

Synthesis was conducted in the same manner as in the synthesis of intermediate 1-2, except that intermediate 6-2 was used instead of intermediate 1-1, whereby 812 mg (yield 57%) of white solids were obtained.

As a result of an LC-MS analysis, the white solids were identified as intermediate 6-3.

Synthesis of Intermediate 6-A

Synthesis was conducted in the same manner as in the synthesis of intermediate 1-A, except that intermediate 6-3 was used instead of intermediate 1-4, whereby 368 mg (yield 51%) of white solids were obtained.

As a result of an LC-MS analysis, the white solids were identified as intermediate 6-A.

Intermediate Synthesis Example 7 (Synthesis of Intermediate 7-A)

The synthesis scheme of the intermediate 7-A is shown below.

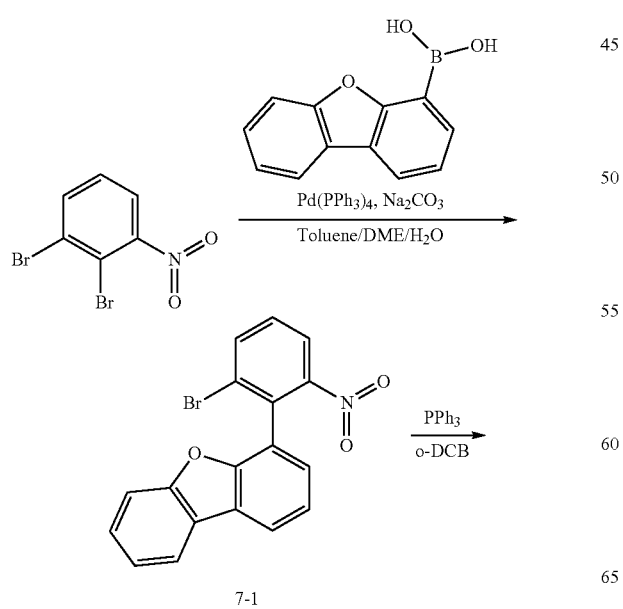

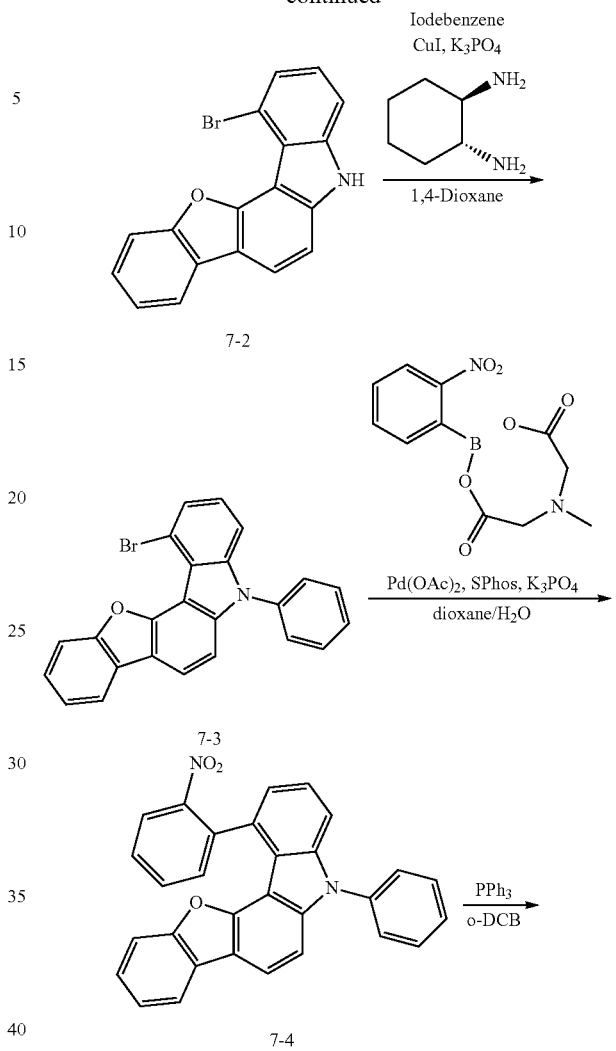

Synthesis of Intermediate 7-1

Synthesis was conducted in the same manner as in the synthesis of intermediate 1-1, except that dibenzofuran-4-boronic acid used instead of dibenzofuran-2-boronic acid, whereby 2.5 g (yield 84%) of white solids were obtained.

As a result of an LC-MS analysis, the white solids were identified as intermediate 7-1.

Synthesis of Intermediate 7-2

Synthesis was conducted in the same manner as in the synthesis of intermediate 1-2, except that intermediate 7-1 was used instead of intermediate 1-1, whereby 1.2 g (yield 54%) of white solids were obtained.

As a result of an LC-MS analysis, the white solids were identified as intermediate 7-2.

Synthesis of Intermediate 7-3

Synthesis was conducted in the same manner as in the synthesis of intermediate 1-3, except that intermediate 7-2 was used instead of intermediate 1-2, whereby 1.3 g (yield 87%) of white solids were obtained.

As a result of an LC-MS analysis, the white solids were identified as intermediate 7-3.

Synthesis of Intermediate 7-4

Synthesis was conducted in the same manner as in the synthesis of intermediate 3-5, except that intermediate 7-3 was used instead of intermediate 3-4, whereby 809 mg (yield 55%) of white solids were obtained.

As a result of an LC-MS analysis, the white solids were identified as intermediate 7-4.

Synthesis of Intermediate 7-A

Synthesis was conducted in the same manner as in the synthesis of intermediate 1-2, except that intermediate 7-4 was used instead of intermediate 1-1, whereby 503 mg (yield 67%) of white solids were obtained.

As a result of an LC-MS analysis, the white solids were identified as intermediate 7-A.

Intermediate Synthesis Example 8 (Synthesis of Intermediate 8-A)

The synthesis scheme of the intermediate 8-A is shown below.

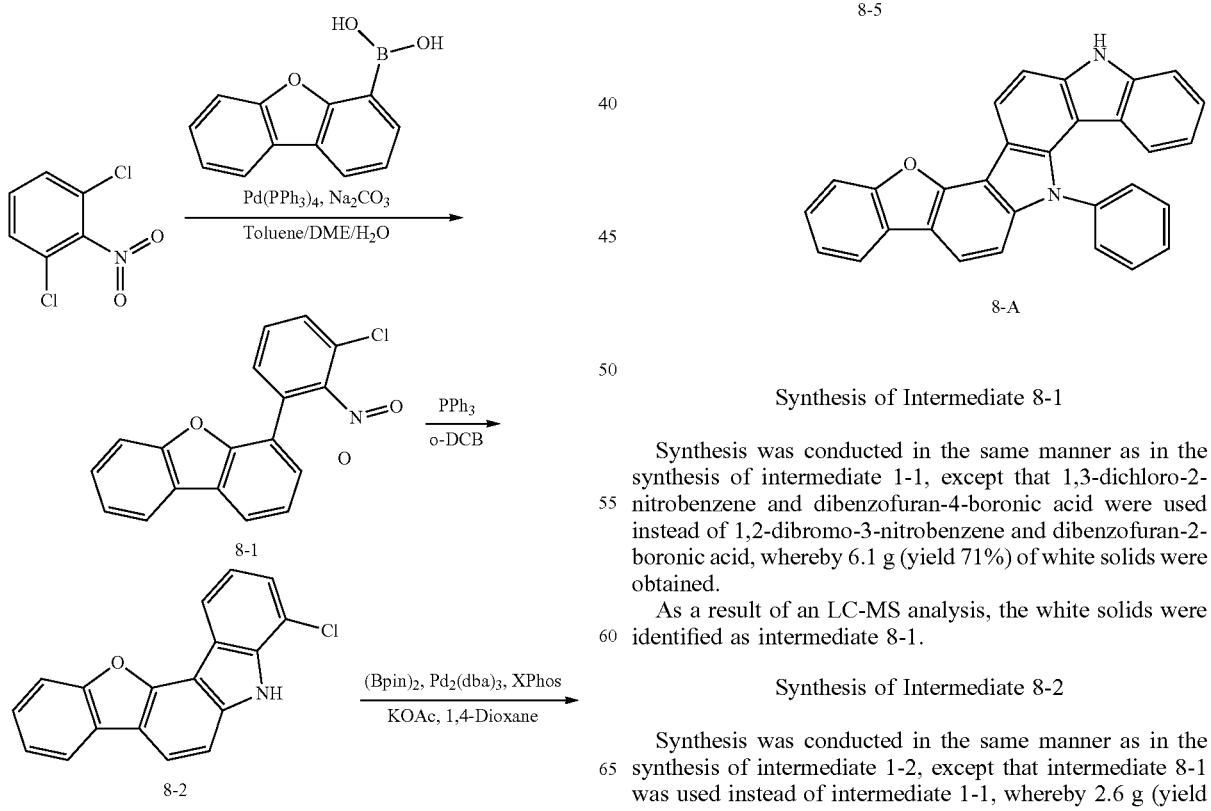

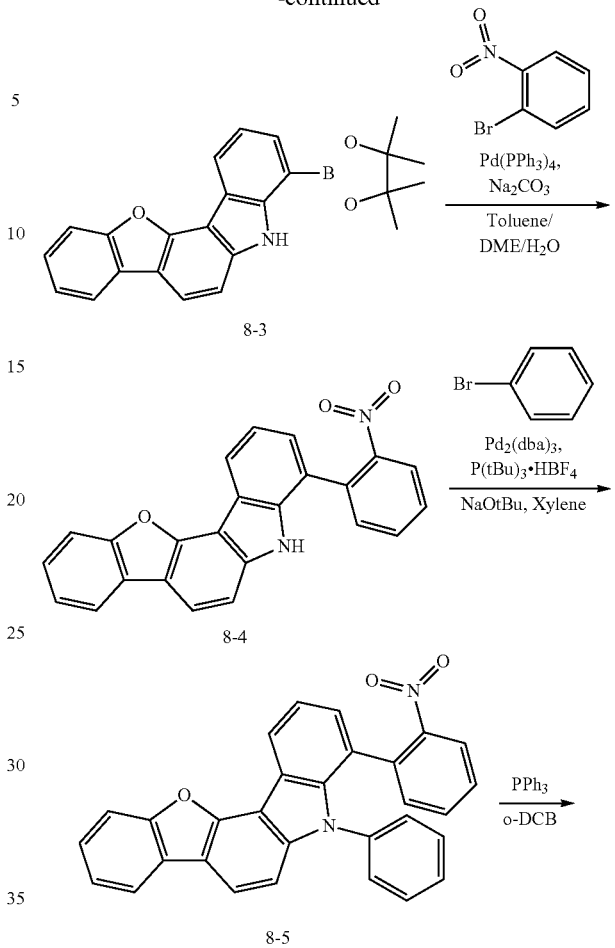

Synthesis of Intermediate 8-1

Synthesis was conducted in the same manner as in the synthesis of intermediate 1-1, except that 1,3-dichloro-2-nitrobenzene and dibenzofuran-4-boronic acid were used instead of 1,2-dibromo-3-nitrobenzene and dibenzofuran-2-boronic acid, whereby 6.1 g (yield 71%) of white solids were obtained.

As a result of an LC-MS analysis, the white solids were identified as intermediate 8-1.

Synthesis of Intermediate 8-2

Synthesis was conducted in the same manner as in the synthesis of intermediate 1-2, except that intermediate 8-1 was used instead of intermediate 1-1, whereby 2.6 g (yield 48%) of white solids were obtained.

As a result of an LC-MS analysis, the white solids were identified as intermediate 8-2.

Synthesis of Intermediate 8-3

In an argon atmosphere, 2.6 g of intermediate 8-2, 6.8 g of bis(pinacolato) diboron, 246 mg of tris(dibenzylideneacetone)dipalladium(0), g of 2-(dicyclohexylphosphino)-2',4',6'-tri-isopropyl-1,1'-biphenyl, 256 mg of potassium acetate and 45 mL of 1,4-dioxane were placed in a flask and heated under reflux with stirring for 12 hours.

After cooling the reaction solution to room temperature (25° C.), the reaction solution was concentrated, and residues were purified by silica gel chromatography, whereby 2.5 g (yield: 74%) of white solids were obtained.

As a result of an LC-MS analysis, the white solids were identified as intermediate 8-3.

Synthesis of Intermediate 8-4

Synthesis was conducted in the same manner as in the synthesis of intermediate 1-1, except that intermediate 8-3 and 2-bromonitrobenezene were used instead of 1,2-dibromo-3-nitrobenzene and dibenzofuran-2-boronic acid, whereby 2.0 g (yield 81%) of white solids were obtained.

As a result of an LC-MS analysis, the white solids were identified as intermediate 8-4.

Synthesis of Intermediate 8-5

Synthesis was conducted in the same manner as in the synthesis of intermediate 1-4, except that intermediate 8-4 and bromobenzene were used instead of intermediate 1-3 and 2-chloroaniline, whereby 1.3 g (yield 54%) of white solids were obtained.

As a result of an LC-MS analysis, the white solids were identified as intermediate 8-5.

Synthesis of Intermediate 8-A

Synthesis was conducted in the same manner as in the synthesis of intermediate 1-2, except that intermediate 8-5 was used instead of intermediate 1-1, whereby 262 mg (yield 62%) of white solids were obtained.

As a result of an LC-MS analysis, the white solids were identified as intermediate 8-A.

Intermediate Synthesis Example 9 (Synthesis of Intermediate 9-A)

The synthesis scheme of the intermediate 9-A is shown below.

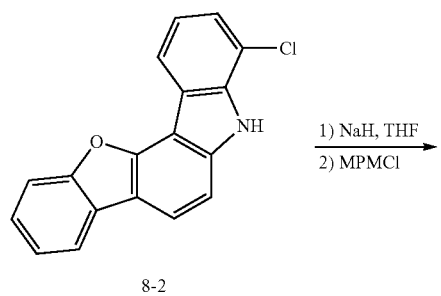

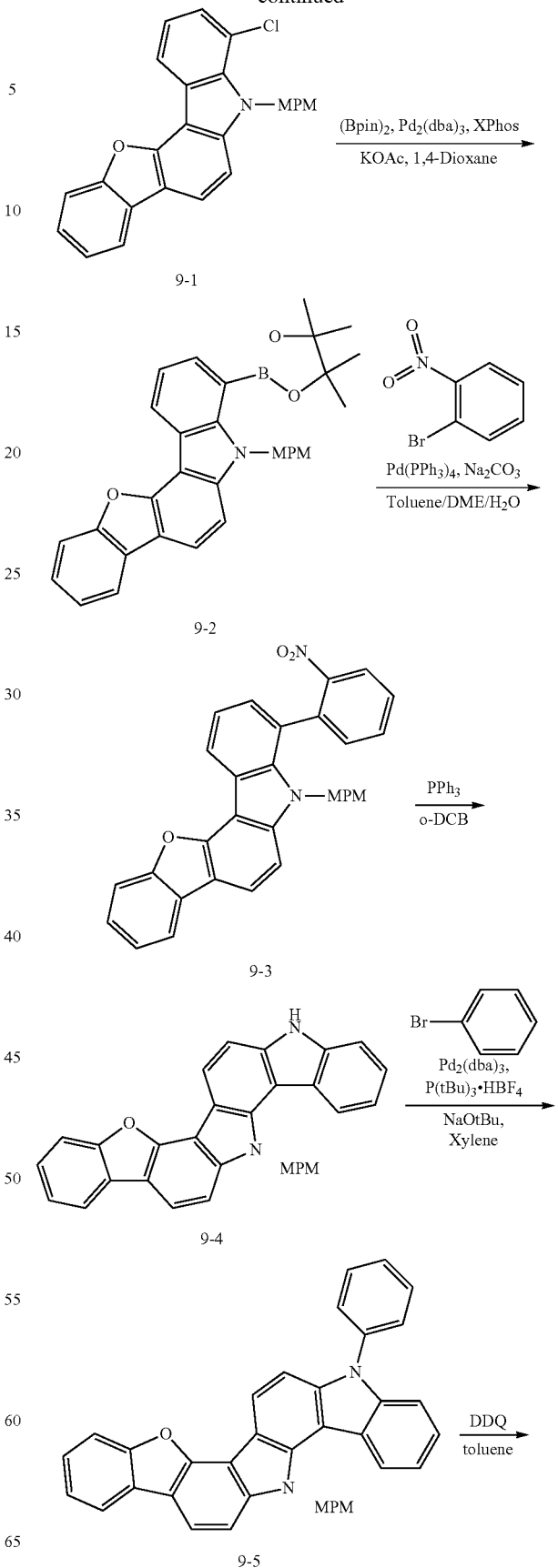

-continued

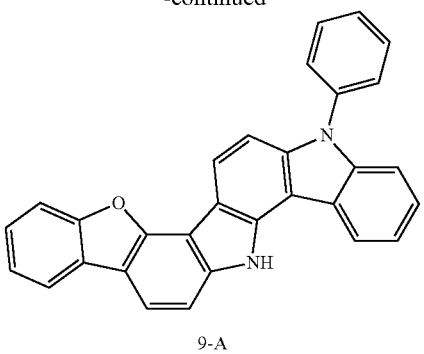

9-A

Synthesis of Intermediate 9-1

In an argon atmosphere, 1.6 g of Intermediate 8-2 and 15 mL of tetrahydrofuran were placed in a flask and cooled with stirring to 0° C. Thereafter, 1.5 g of sodium hydride (60%, dispersed in liquid paraffin) was added and stirred at 0° C. for 30 minutes. Subsequently, 1.3 g of 4-methoxybenzyl chloride (MPM-Cl) was added, and the mixture was stirred at 0° C. for 30 minutes. Thereafter, the temperature was raised to room temperature and stirred for 6 hours.

Subsequently, an aqueous solution of ammonium chloride was added to the reaction solution. The reaction solution was transferred to a separating funnel, and extracted with toluene. Thereafter, an organic layer was dried with sodium sulfate, filtrated and concentrated. Residues were purified by silica gel chromatography, whereby 1.9 g (yield: 86%) of white solids were obtained.

As a result of an LC-MS analysis, the white solids were identified as intermediate 9-1.

Synthesis of Intermediate 9-2

Synthesis was conducted in the same manner as in the synthesis of intermediate 8-3, except that intermediate 9-1 was used instead of intermediate 8-2, whereby 1.5 g (yield 66%) of white solids were obtained.

As a result of an LC-MS analysis, the white solids were identified as intermediate 9-2.

Synthesis of Intermediate 9-3

Synthesis was conducted in the same manner as in the synthesis of intermediate 1-1, except that 2-bromonitrobenzene and intermediate 9-2 were used instead of 1,2-dibromo-3-nitrobenzene and dibenzofuran-2-boronic acid, whereby 1.1 g (yield 69%) of white solids were obtained.

As a result of an LC-MS analysis, the white solids were identified as intermediate 9-3.

Synthesis of Intermediate 9-4

Synthesis was conducted in the same manner as in the synthesis of intermediate 1-2, except that intermediate 9-3 was used instead of intermediate 1-1, whereby 574 mg (yield 58%) of white solids were obtained.

As a result of an LC-MS analysis, the white solids were identified as intermediate 9-4.

Synthesis of Intermediate 9-5

Synthesis was conducted in the same manner as in the synthesis of intermediate 1-4, except that intermediate 9-4 and bromobenzene were used instead of intermediate 1-3 and 2-chloroaniline, whereby 608 mg (yield 91%) of white solids were obtained.

As a result of an LC-MS analysis, the white solids were identified as intermediate 9-5.

Synthesis of Intermediate 9-A

In an argon atmosphere, 608 mg of intermediate 9-5,776 mg of 2,3-dichloro-5,6-dicyano-1,4-benzoquinone and 4 mL of toluene were placed in a flask and heated under reflux with stirring for 12 hours.

After cooling room temperature (25° C.), the reaction solution was filtrated, and a filtrate was concentrated, and residues were purified by silica gel chromatography, whereby 321 mg (yield: 68%) of white solids were obtained.

As a result of an LC-MS analysis, the white solids were identified as intermediate 9-A.

Intermediate Synthesis Example 10 (Synthesis of Intermediate 10-A)

The synthesis scheme of the intermediate 10-A is shown below.

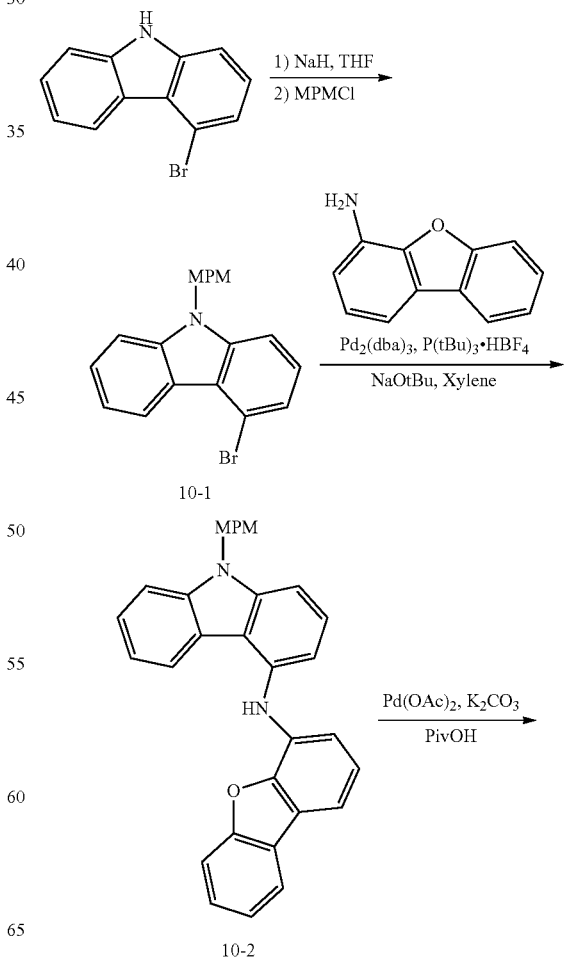

-continued

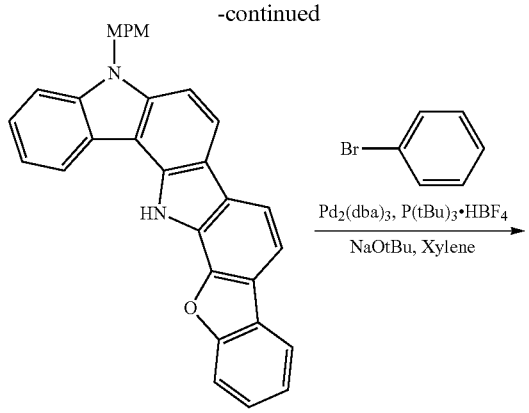

10-3

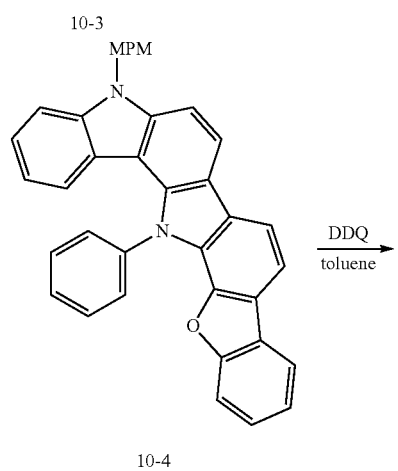

10-4

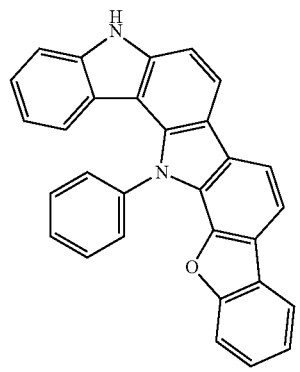

10-A

Synthesis of Intermediate 10-1

Synthesis was conducted in the same manner as in the synthesis of intermediate 1-4, except that 4-bromo-9H-carbazole was used instead of intermediate 8-2, whereby 2.0 g (yield 88%) of white solids were obtained.

As a result of an LC-MS analysis, the white solids were identified as intermediate 10-1.

Synthesis of Intermediate 10-2

Synthesis was conducted in the same manner as in the synthesis of intermediate 1-4, except that intermediate 10-1 and dibenzofuran-4-amine were used instead of intermediate 1-3 and 2-chloroaniline, whereby 2.1 g (yield 82%) of white solids were obtained.

As a result of an LC-MS analysis, the white solids were identified as intermediate 10-2.

Synthesis of Intermediate 10-3

Synthesis was conducted in the same manner as in the synthesis of intermediate 4-A, except that intermediate 10-2 was used instead of intermediate 4-2, whereby 1.3 g (yield 61%) of white solids were obtained.

As a result of an LC-MS analysis, the white solids were identified as intermediate 10-3.

Synthesis of Intermediate 10-4

Synthesis was conducted in the same manner as in the synthesis of intermediate 1-4, except that intermediate 10-3 and bromobenzene were used instead of intermediate 1-3 and 2-chloroaniline, whereby 1.1 g (yield 74%) of white solids were obtained.

As a result of an LC-MS analysis, the white solids were identified as intermediate 10-4.

Synthesis of Intermediate 10-A

Synthesis was conducted in the same manner as in the synthesis of intermediate 9-A, except that intermediate 10-4 was used instead of intermediate 9-5, whereby 706 mg (yield 79%) of white solids were obtained.

As a result of an LC-MS analysis, the white solids were identified as intermediate 10-A.

Intermediate Synthesis Example 11 (Synthesis of Intermediate 11-A)

The synthesis scheme of the intermediate 11-A is shown below.

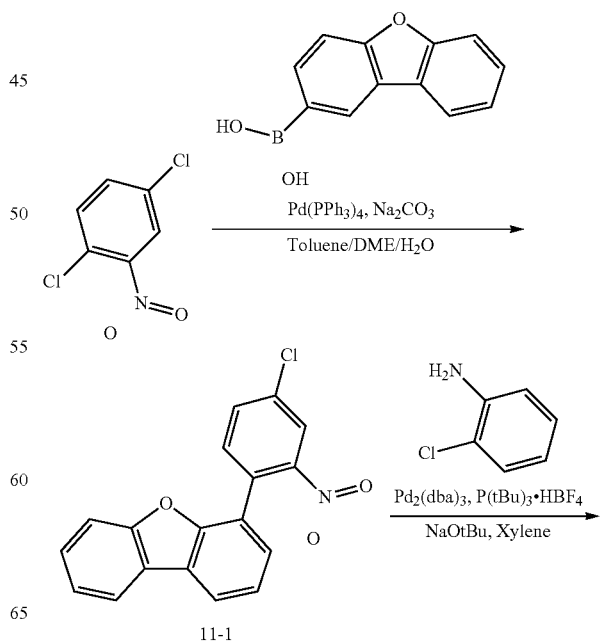

11-1

-continued

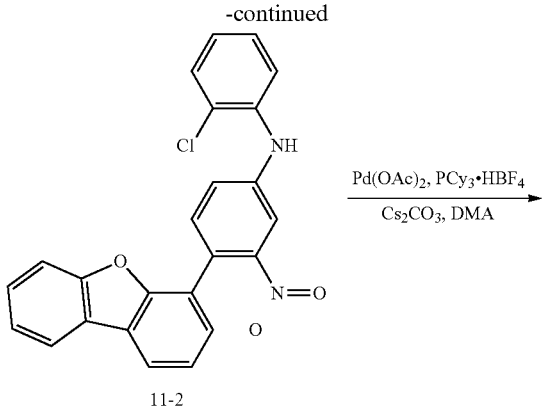

11-2

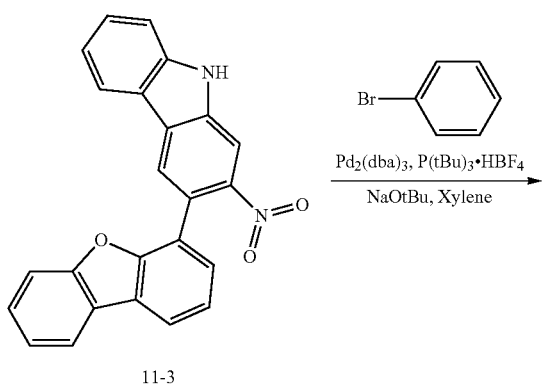

11-3

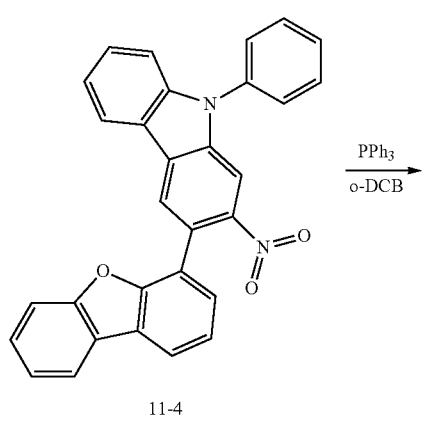

11-4

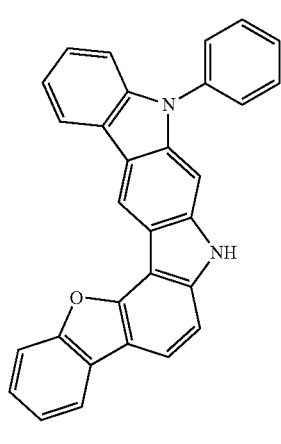

11-A

Synthesis of Intermediate 11-1

Synthesis was conducted in the same manner as in the synthesis of intermediate 1-1, except that 1,4-dichloro-2-nitrobenzene was used instead of 1,2-dibromo-3-nitrobenzene, whereby 2.5 g (yield 83%) of white solids were obtained.

As a result of an LC-MS analysis, the white solids were identified as intermediate 11-1.

Synthesis of Intermediate 11-2

Synthesis was conducted in the same manner as in the synthesis of intermediate 1-4, except that intermediate 11-1 was used instead of intermediate 1-3, whereby 2.3 g (yield 71%) of white solids were obtained.

As a result of an LC-MS analysis, the white solids were identified as intermediate 11-2.

Synthesis of Intermediate 11-3

Synthesis was conducted in the same manner as in the synthesis of intermediate 1-A, except that intermediate 11-2 was used instead of intermediate 1-4, whereby 1.0 g (yield 49%) of white solids were obtained.

As a result of an LC-MS analysis, the white solids were identified as intermediate 11-3.

Synthesis of Intermediate 11-4

Synthesis was conducted in the same manner as in the synthesis of intermediate 1-4, except that intermediate 11-3 and bromobenzene were used instead of intermediate 1-3 and 2-chloroaniline, whereby 690 mg (yield 57%) of white solids were obtained.

As a result of an LC-MS analysis, the white solids were identified as intermediate 11-4.

Synthesis of Intermediate 11-A

Synthesis was conducted in the same manner as in the synthesis of intermediate 1-2, except that intermediate 11-4 was used instead of intermediate 1-1, whereby 334 mg (yield 52%) of white solids were obtained.

As a result of an LC-MS analysis, the white solids were identified as intermediate 11-A.

Intermediate Synthesis Example 12 (Synthesis of Intermediate 12-A)

The synthesis scheme of the intermediate 12-A is shown below.

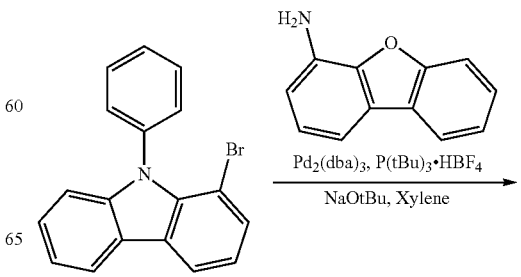

535
-continued

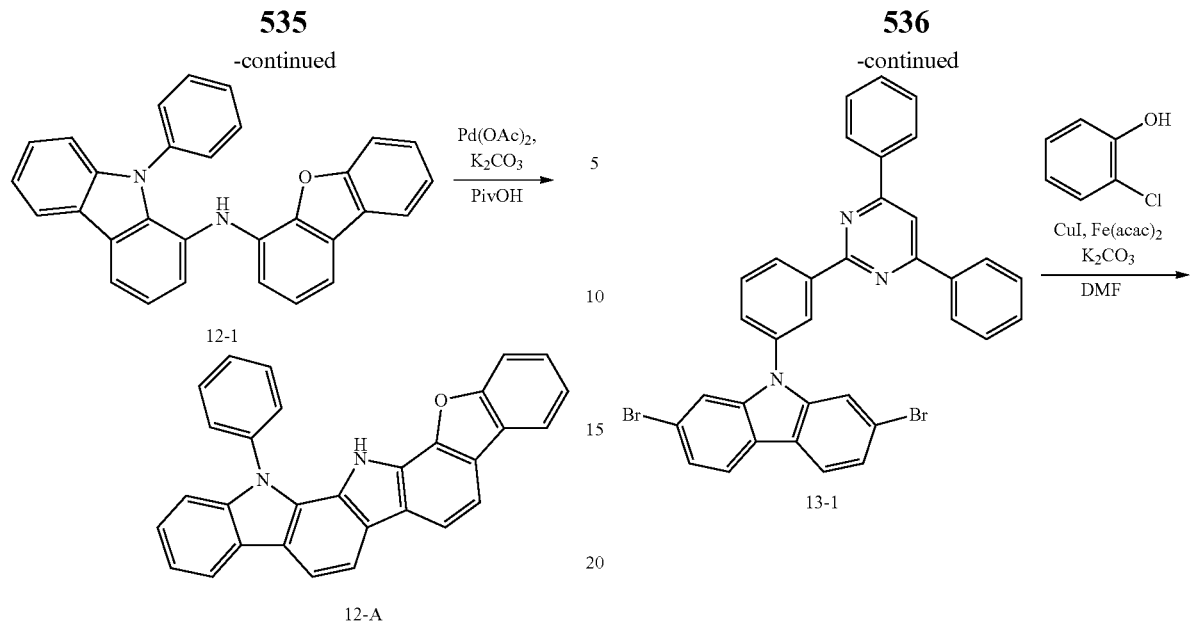

Synthesis of Intermediate 12-1

Synthesis was conducted in the same manner as in the synthesis of intermediate 1-4, except that 1-bromo-9-phenyl-carbazole and dibenzofuran-4-amine were used instead of intermediate 1-3 and 2-chloroaniline, whereby 1.9 g (yield 62%) of white solids were obtained.

As a result of an LC-MS analysis, the white solids were identified as intermediate 12-1.

Synthesis of Intermediate 12-A

Synthesis was conducted in the same manner as in the synthesis of intermediate 4-A, except that intermediate 12-1 was used instead of intermediate 4-2, whereby 887 mg (yield 48%) of white solids were obtained.

As a result of an LC-MS analysis, the white solids were identified as intermediate 12-A.

Intermediate Synthesis Example 13 (Synthesis of Intermediate 13-A)

The synthesis scheme of the intermediate 13-A is shown below.

536
-continued

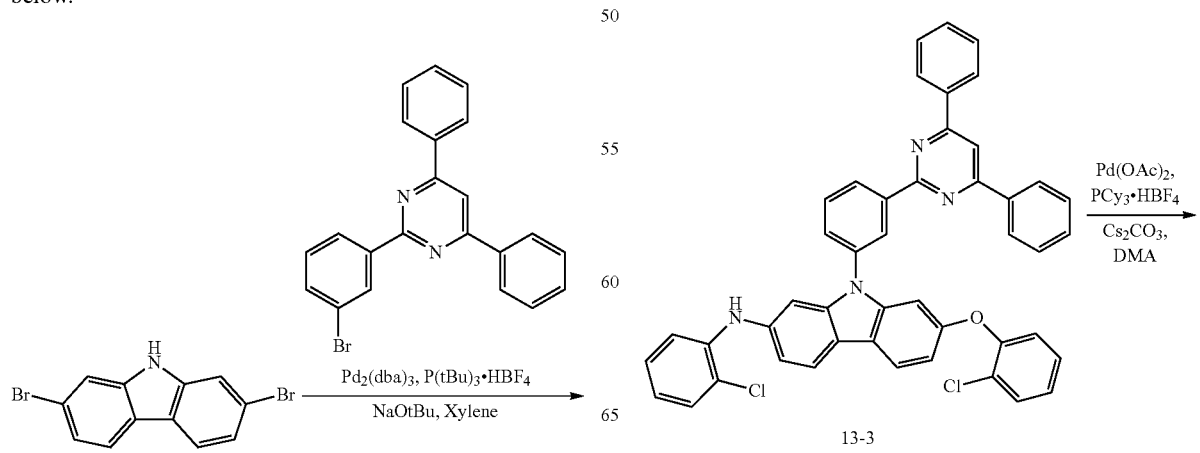

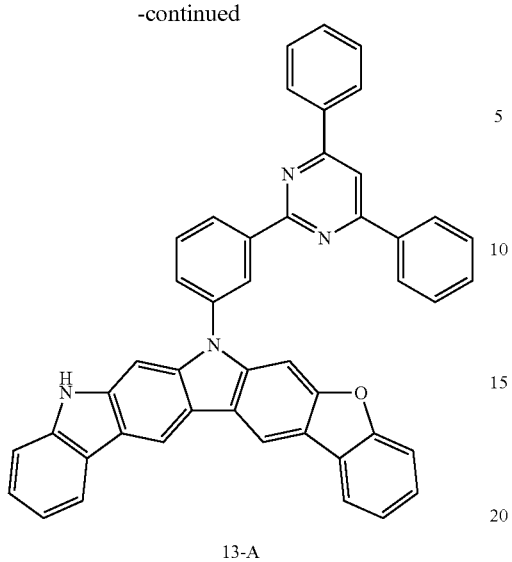

13-A

Synthesis of Intermediate 13-1

Synthesis was conducted in the same manner as in the synthesis of intermediate 1-4, except that 2-(3-bromophenyl)-4,6-diphenylpyrimidine and 2,7-dibromo-9H-carbazole were used instead of intermediate 1-3 and 2-chloroaniline, whereby 7.13 g (yield 78%) of white solids were obtained.

As a result of an LC-MS analysis, the white solids were identified as intermediate 13-1.

Synthesis of Intermediate 13-2

Synthesis was conducted in the same manner as in the synthesis of intermediate 6-1, except that intermediate 12-1 was used instead of 4-bromo-2-chloro-1-nitrobenzene, whereby 3.7 g (yield 48%) of white solids were obtained.

As a result of an LC-MS analysis, the white solids were identified as intermediate 13-2.

Synthesis of Intermediate 13-3

Synthesis was conducted in the same manner as in the synthesis of intermediate 1-4, except that intermediate 12-2 was used instead of intermediate 1-3, whereby 2.6 g (yield 65%) of white solids were obtained.

As a result of an LC-MS analysis, the white solids were identified as intermediate 13-3.

Synthesis of Intermediate 13-4

Synthesis was conducted in the same manner as in the synthesis of intermediate 1-2, except that intermediate 12-3 was used instead of intermediate 1-1, whereby 349 mg (yield 28%) of white solids were obtained.

As a result of an LC-MS analysis, the white solids were identified as intermediate 13-A.

<Synthesis of Compound According to One Aspect of the Invention>

Subsequently, synthesis examples of the following compounds 1 to 34 are shown below.

Compound 1

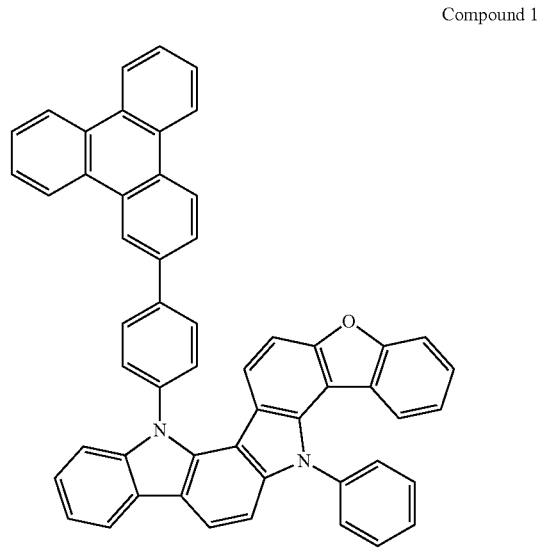

Compound 2

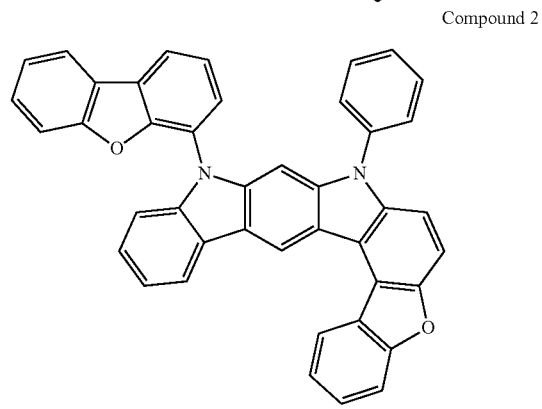

Compound 3

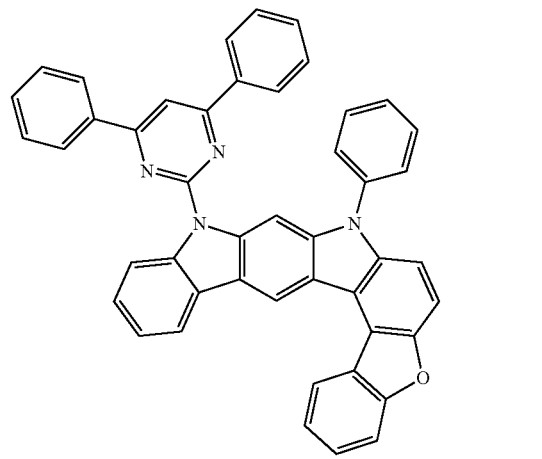

-continued
Compound 4
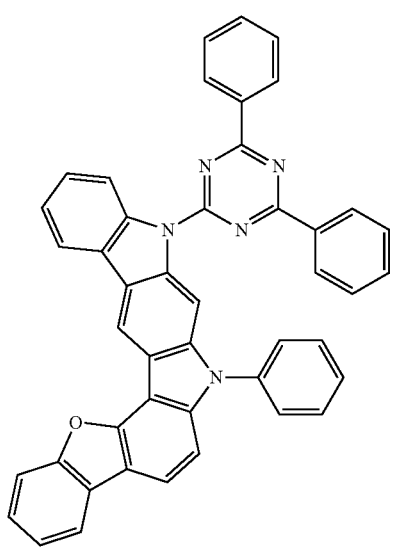
Compound 5
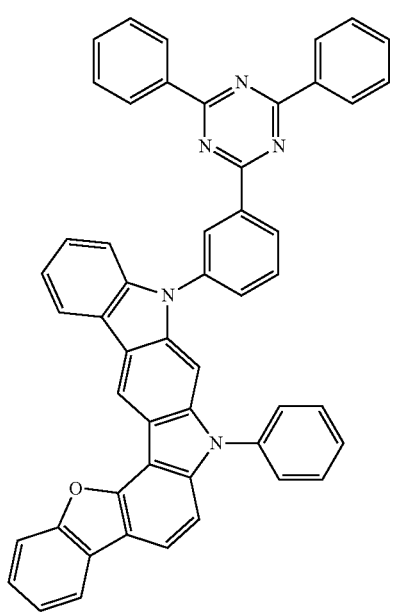
-continued
Compound 6
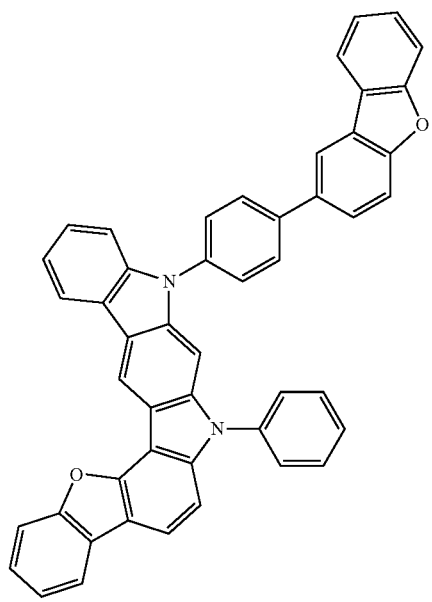
Compound 7
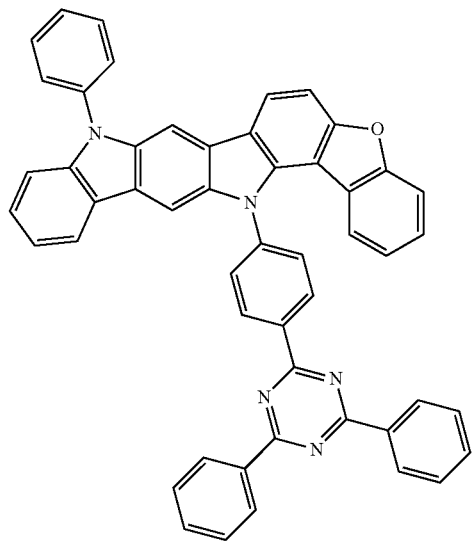

US 10,703,762 B2
-continued
Compound 8
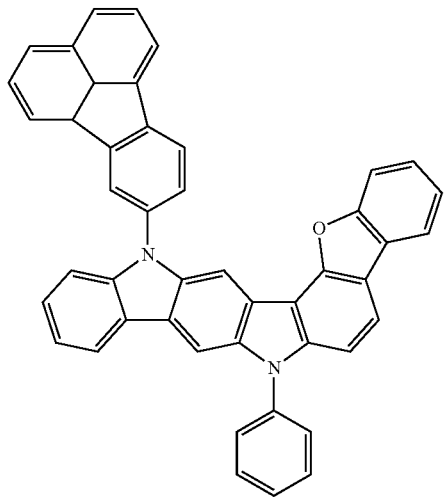
Compound 9
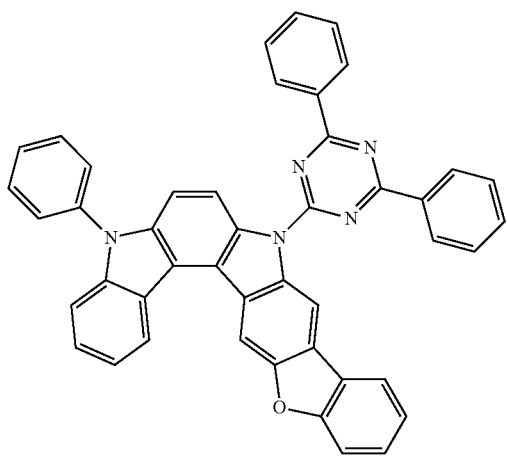
Compound 10
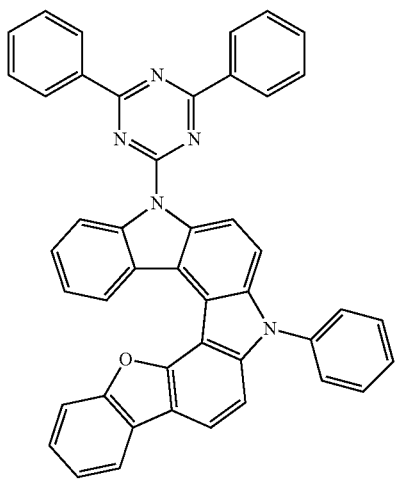
-continued
Compound 11
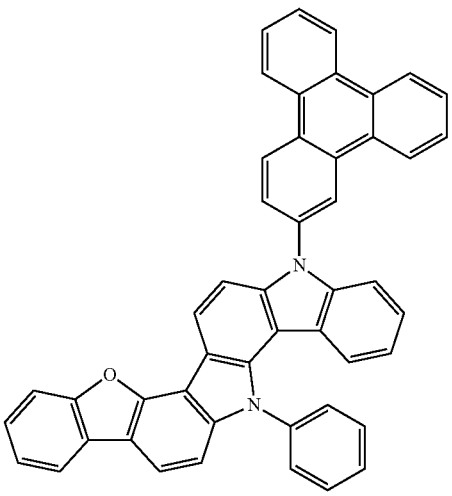
Compound 12
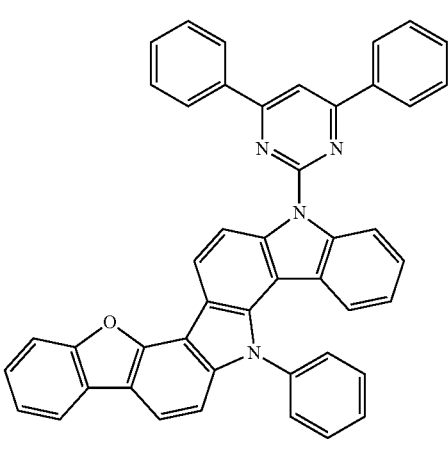
Compound 13
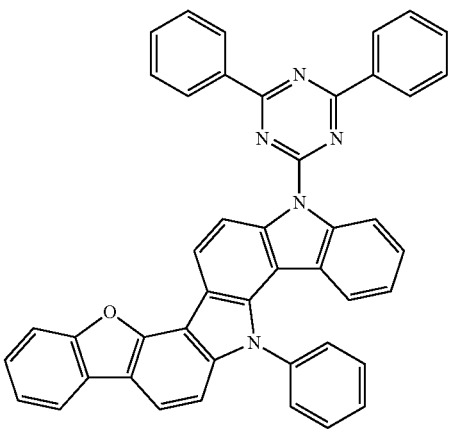

Compound 14
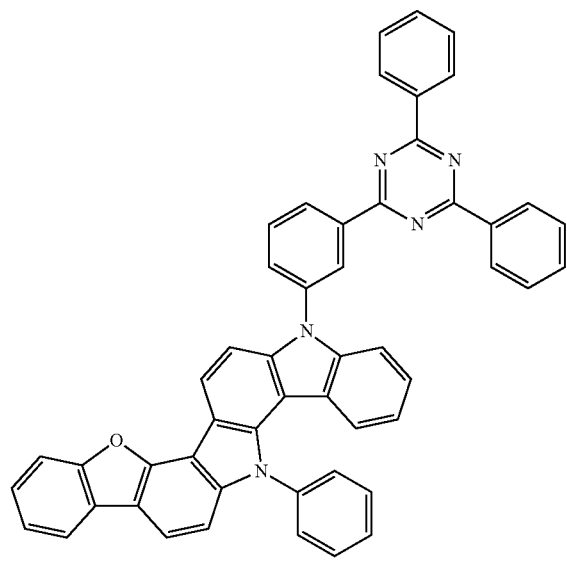
Compound 15
Compound 17
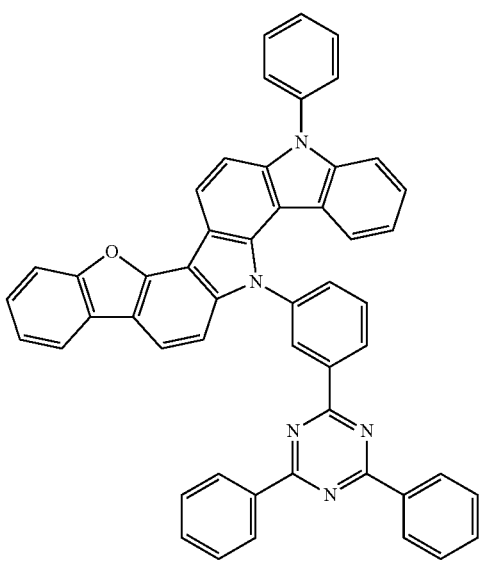
Compound 18
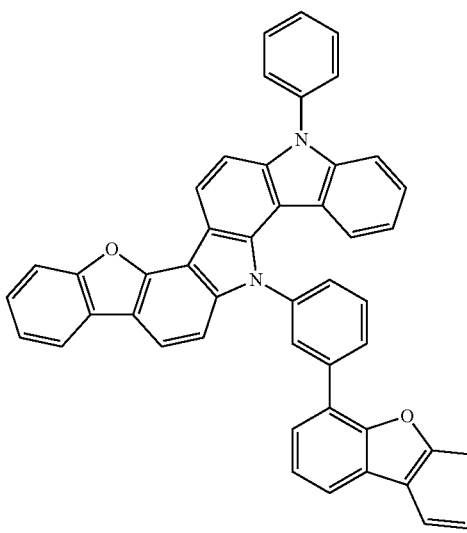
Compound 19
Compound 16
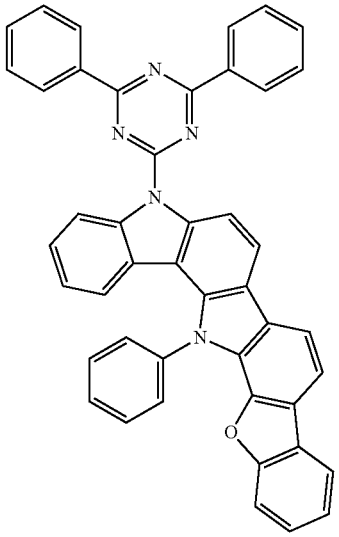

Compound 20
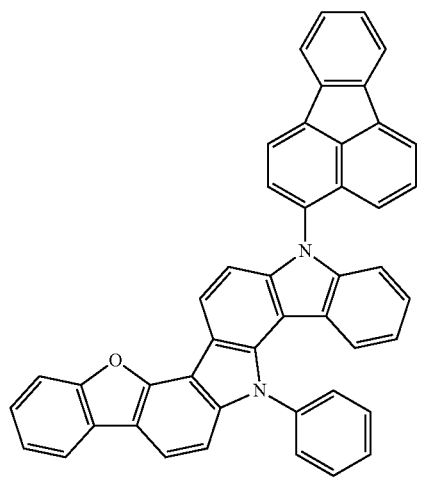
Compound 21
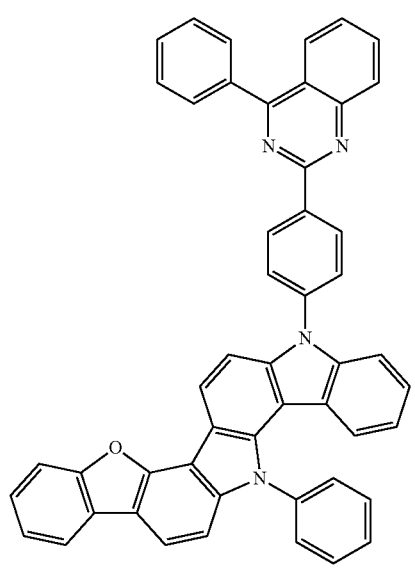
Compound 22
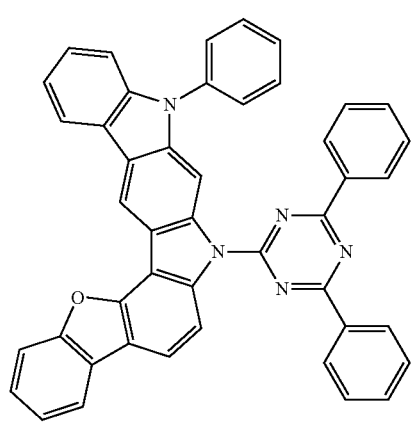
Compound 23
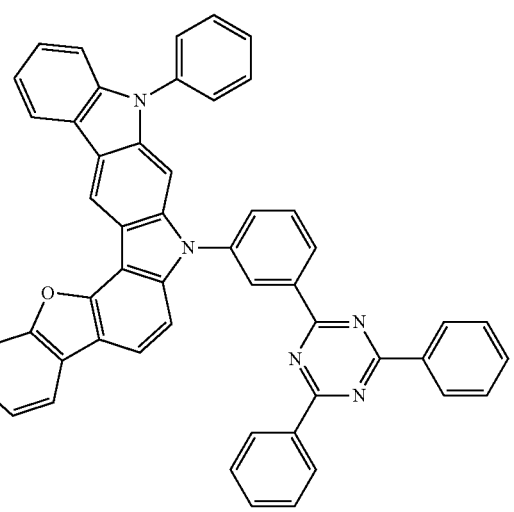
Compound 24
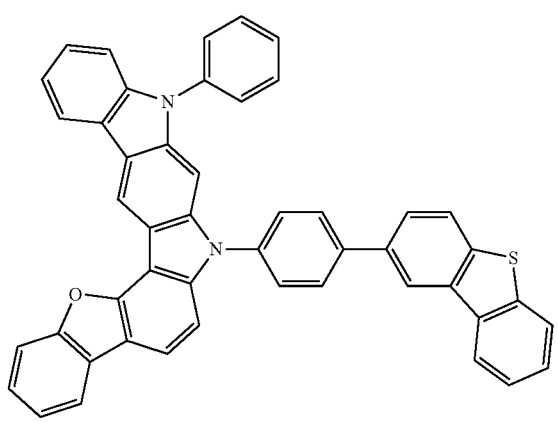
Compound 25
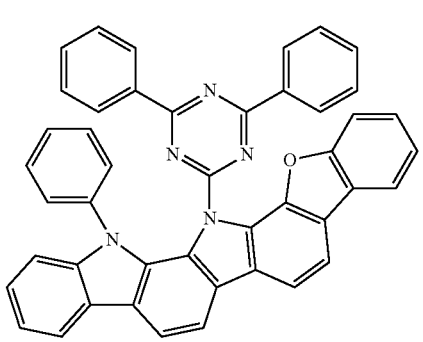

Compound 26
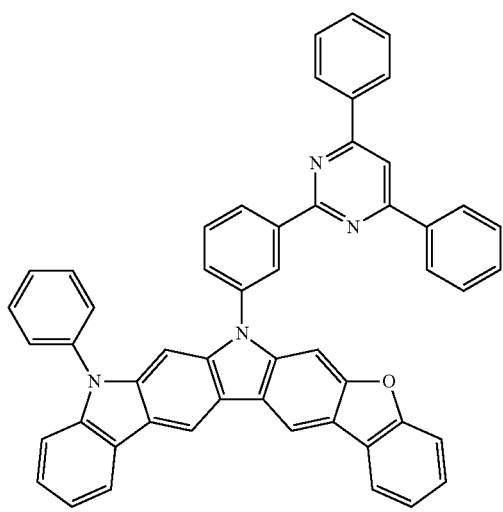
Compound 27
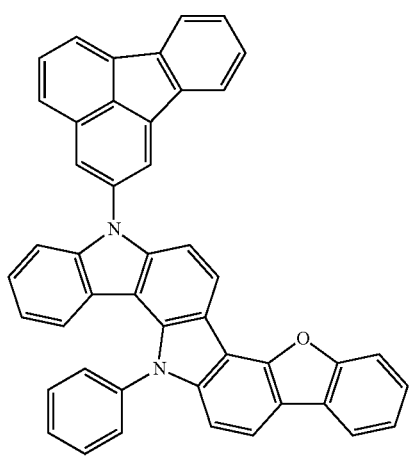
Compound 28
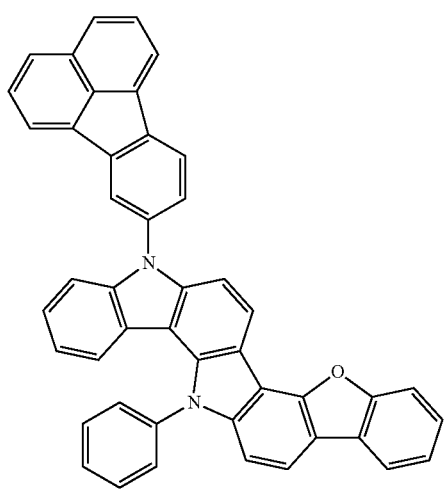
Compound 29
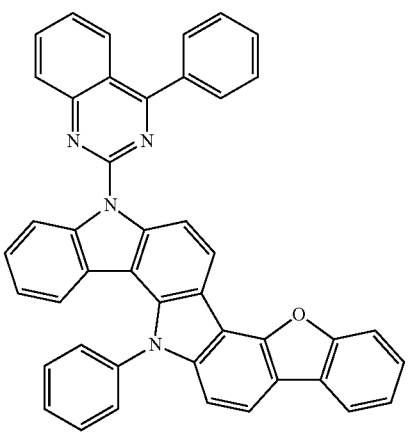
Compound 30
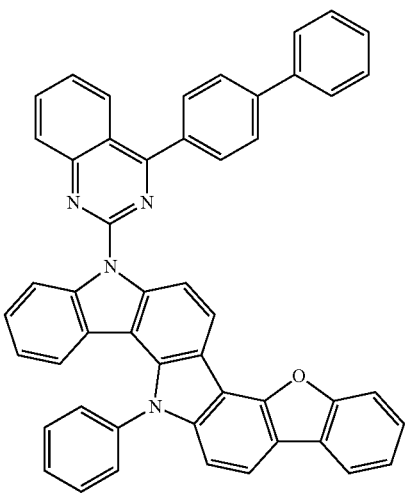
Compound 31
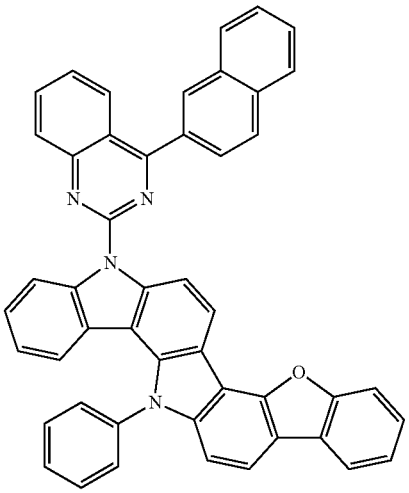

Compound 32

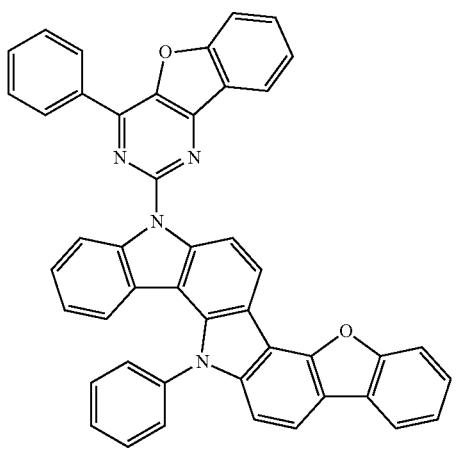

Compound 33

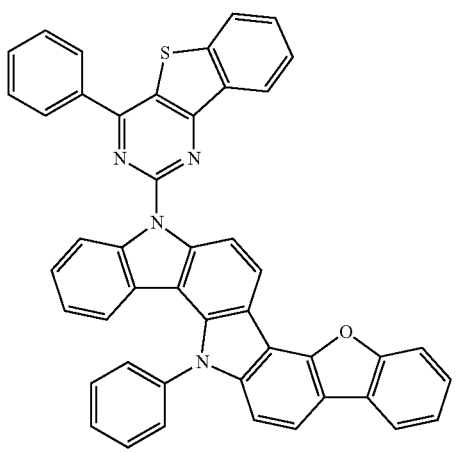

Compound 34

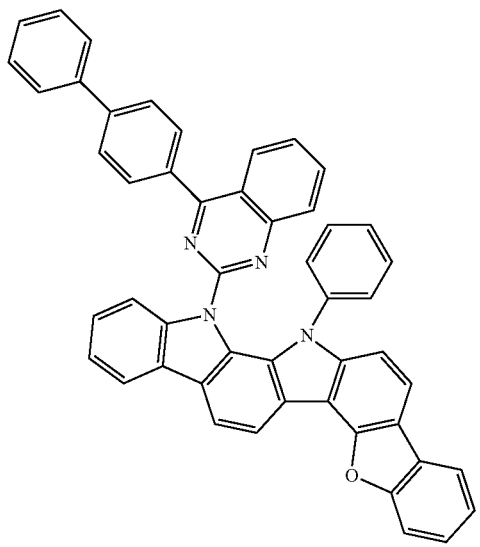

Synthesis Example 1 (Synthesis of Compound 1)

Synthesis was conducted in the same manner as in the synthesis of intermediate 1-4, except that intermediate 1-A and 2-(4-bromophenyl)triphenylene were used instead of 2-chloroaniline and intermediate 1-3, whereby 549 mg (yield 61%) of white solids were obtained.

As a result of an LC-MS analysis, the white solids were identified as compound 1.

Synthesis Example 2 (Synthesis of Compound 2)

Synthesis was conducted in the same manner as in the synthesis of intermediate 1-4, except that intermediate 2-A and 4-bromodibenzofuran were used instead of 2-chloroaniline and intermediate 1-3, whereby 644 mg (yield 73%) of white solids were obtained.

As a result of an LC-MS analysis, the white solids were identified as compound 2.

Synthesis Example 3 (Synthesis of Compound 3)

Synthesis was conducted in the same manner as in the synthesis of intermediate 1-4, except that intermediate 2-A and 2-chloro-4,6-diphenyl-pyrimidine were used instead of 2-chloroaniline and intermediate 1-3, whereby 389 mg (yield 64%) of white solids were obtained.

As a result of an LC-MS analysis, the white solids were identified as compound 3.

Synthesis Example 4 (Synthesis of Compound 4)

Synthesis was conducted in the same manner as in the synthesis of intermediate 1-4, except that intermediate 3-A and 2-chloro-4,6-diphenyl-1,3,5-triazine were used instead of 2-chloroaniline and intermediate 1-3, whereby 391 mg (yield 48%) of white solids were obtained.

As a result of an LC-MS analysis, the white solids were identified as compound 4.

Synthesis Example 5 (Synthesis of Compound 5)

Synthesis was conducted in the same manner as in the synthesis of intermediate 1-4, except that intermediate 3-A and 2-(3-bromophenyl)-4,6-diphenyl-1,3,5-triazine were used instead of 2-chloroaniline and intermediate 1-3, whereby 458 mg (yield 49%) of white solids were obtained.

As a result of an LC-MS analysis, the white solids were identified as compound 5.

Synthesis Example 6 (Synthesis of Compound 6)

Synthesis was conducted in the same manner as in the synthesis of intermediate 1-4, except that intermediate 3-A and 2-(4-bromophenyl)dibenzofuran were used instead of 2-chloroaniline and intermediate 1-3, whereby 719 mg (yield 63%) of white solids were obtained.

As a result of an LC-MS analysis, the white solids were identified as compound 6.

Synthesis Example 7 (Synthesis of Compound 7)

Synthesis was conducted in the same manner as in the synthesis of intermediate 1-4, except that intermediate 4-A and 2-(4-bromophenyl)-4,6-diphenyl-1,3,5-triazine were used instead of 2-chloroaniline and intermediate 1-3, whereby 398 mg (yield 63%) of white solids X were obtained.

As a result of an LC-MS analysis, the white solids were identified as compound 7.

Synthesis Example 8 (Synthesis of Compound 8)

Synthesis was conducted in the same manner as in the synthesis of intermediate 1-4, except that intermediate 5-A and 8-bromofluoranthene were used instead of 2-chloroaniline and intermediate 1-3, whereby 458 mg (yield 63%) of white solids were obtained.

As a result of an LC-MS analysis, the white solids were identified as compound 8.

Synthesis Example 9 (Synthesis of Compound 9)

Synthesis was conducted in the same manner as in the synthesis of intermediate 1-4, except that intermediate 6-A and 2-chloro-4,6-diphenyl-1,3,5-triazine were used instead of 2-chloroaniline and intermediate 1-3, whereby 442 mg (yield 56%) of white solids were obtained.

As a result of an LC-MS analysis, the white solids were identified as compound 9.

Synthesis Example 10 (Synthesis of Compound 10)

Synthesis was conducted in the same manner as in the synthesis of intermediate 1-4, except that intermediate 7-A and 2-chloro-4,6-diphenyl-1,3,5-triazine were used instead of 2-chloroaniline and intermediate 1-3, whereby 299 mg (yield 44%) of white solids were obtained.

As a result of an LC-MS analysis, the white solids were identified as compound 10.

Synthesis Example 11 (Synthesis of Compound 11)

Synthesis was conducted in the same manner as in the synthesis of intermediate 1-4, except that intermediate 8-A and 2-bromotriphenylene were used instead of 2-chloroaniline and intermediate 1-3, whereby 336 mg (yield 63%) of white solids were obtained.

As a result of an LC-MS analysis, the white solids were identified as compound 11.

Synthesis Example 12 (Synthesis of Compound 12)

Synthesis was conducted in the same manner as in the synthesis of intermediate 1-4, except that intermediate 8-A and 2-chloro-4,6-diphenyl-pyrimidine were used instead of 2-chloroaniline and intermediate 1-3, whereby 271 mg (yield 44%) of white solids were obtained.

As a result of an LC-MS analysis, the white solids were identified as compound 12.

Synthesis Example 13 (Synthesis of Compound 13)

Synthesis was conducted in the same manner as in the synthesis of intermediate 1-4, except that intermediate 8-A and 2-chloro-4,6-diphenyl-1,3,5-triazine were used instead of 2-chloroaniline and intermediate 1-3, whereby 394 mg (yield 52%) of white solids were obtained.

As a result of an LC-MS analysis, the white solids were identified as compound 13.

Synthesis Example 14 (Synthesis of Compound 14)

Synthesis was conducted in the same manner as in the synthesis of intermediate 1-4, except that intermediate 8-A and 2-(3-bromophenyl)-4,6-diphenyl-1,3,5-triazine were used instead of 2-chloroaniline and intermediate 1-3, whereby 712 mg (yield 82%) of white solids were obtained.

As a result of an LC-MS analysis, the white solids were identified as compound 14.

Synthesis Example 15 (Synthesis of Compound 15)

Synthesis was conducted in the same manner as in the synthesis of intermediate 1-4, except that intermediate 8-A and 4-(4-bromophenyl)dibenzofuran were used instead of 2-chloroaniline and intermediate 1-3, whereby 531 mg (yield 64%) of white solids were obtained.

As a result of an LC-MS analysis, the white solids were identified as compound 15.

Synthesis Example 16 (Synthesis of Compound 16)

Synthesis was conducted in the same manner as in the synthesis of intermediate 1-4, except that intermediate 9-A and 9-bromophenanthrene were used instead of 2-chloroaniline and intermediate 1-3, whereby 393 mg (yield 54%) of white solids were obtained.

As a result of an LC-MS analysis, the white solids were identified as compound 16.

Synthesis Example 17 (Synthesis of Compound 17)

Synthesis was conducted in the same manner as in the synthesis of intermediate 1-4, except that intermediate 9-A and 2-(3-bromophenyl)-4,6-diphenyl-1,3,5-triazine were used instead of 2-chloroaniline and intermediate 1-3, whereby 376 mg (yield 75%) of white solids were obtained.

As a result of an LC-MS analysis, the white solids were identified as compound 17.

Synthesis Example 18 (Synthesis of Compound 18)

Synthesis was conducted in the same manner as in the synthesis of intermediate 1-4, except that intermediate 9-A and 4-(3-bromophenyl)dibenzofuran were used instead of 2-chloroaniline and intermediate 1-3, whereby 583 mg (yield 62%) of white solids were obtained.

As a result of an LC-MS analysis, the white solids were identified as compound 18.

Synthesis Example 19 (Synthesis of Compound 19)

Synthesis was conducted in the same manner as in the synthesis of intermediate 1-4, except that intermediate 10-A and 2-chloro-4,6-diphenyl-1,3,5-triazine were used instead of 2-chloroaniline and intermediate 1-3, whereby 492 mg (yield 53%) of white solids were obtained.

As a result of an LC-MS analysis, the white solids were identified as compound 19.

Synthesis Example 20 (Synthesis of Compound 20)

Synthesis was conducted in the same manner as in the synthesis of intermediate 1-4, except that intermediate 8-A and 3-bromofluoranthene were used instead of 2-chloroaniline and intermediate 1-3, whereby 583 mg (yield 49%) of white solids were obtained.

As a result of an LC-MS analysis, the white solids were identified as compound 20.

Synthesis Example 21 (Synthesis of Compound 21)

Synthesis was conducted in the same manner as in the synthesis of intermediate 1-4, except that intermediate 8-A and 2-(4-bromophenyl)-4-phenyl-quinazoline were used instead of 2-chloroaniline and intermediate 1-3, whereby 891 mg (yield 77%) of white solids were obtained.

As a result of an LC-MS analysis, the white solids were identified as compound 21.

Synthesis Example 22 (Synthesis of Compound 22)

Synthesis was conducted in the same manner as in the synthesis of intermediate 1-4, except that intermediate 11-A and 2-chloro-4,6-diphenyl-1,3,5-triazine were used instead of 2-chloroaniline and intermediate 1-3, whereby 554 mg (yield 64%) of white solids were obtained.

As a result of an LC-MS analysis, the white solids were identified as compound 22.

Synthesis Example 23 (Synthesis of Compound 23)

Synthesis was conducted in the same manner as in the synthesis of intermediate 1-4, except that intermediate 11-A and 2-(3-bromphenyl)-4,6-diphenyl-1,3,5-triazine were used instead of 2-chloroaniline and intermediate 1-3, whereby 345 mg (yield 48%) of white solids were obtained.

As a result of an LC-MS analysis, the white solids were identified as compound 23.

Synthesis Example 24 (Synthesis of Compound 24)

Synthesis was conducted in the same manner as in the synthesis of intermediate 1-4, except that intermediate 11-A and 2-(4-bromophenyl)dibenzothiophene were used instead of 2-chloroaniline and intermediate 1-3, whereby 711 mg (yield 68%) of white solids were obtained.

As a result of an LC-MS analysis, the white solids were identified as compound 24.

Synthesis Example 25 (Synthesis of Compound 25)

Synthesis was conducted in the same manner as in the synthesis of intermediate 1-4, except that intermediate 12-A and 2-chloro-4,6-diphenyl-1,3,5-triazine were used instead of 2-chloroaniline and intermediate 1-3, whereby 623 mg (yield 73%) of white solids were obtained.

As a result of an LC-MS analysis, the white solids were identified as compound 25.

Synthesis Example 26 (Synthesis of Compound 26)

Synthesis was conducted in the same manner as in the synthesis of intermediate 1-4, except that intermediate 12-4 and bromobenzene were used instead of intermediate 1-3 and 2-chloroaniline, whereby 298 mg (yield 63%) of white solids were obtained.

As a result of an LC-MS analysis, the white solids were identified as compound 26.

Synthesis Example 27 (Synthesis of Compound 27)

In an argon atmosphere, 2.1 g of intermediate 8-A, 1.54 g of 2-bromofluoranthene, 92 mg of tris(dibenzilideneacetone)dipalladium (0), 191 mg of 2,4,6-triisopropylbiphenyl-2'-dicyclohexylphosphine, 673 mg of sodium tert-butoxide were placed in a 60 mL-flask and heated under reflux with stirring overnight. Alter cooling to room temperature (25° C.), the reaction solution was concentrated and residues were purified by silica gel chromatography, whereby 2.31 g (yield 74%) of yellow solids were obtained. As a result of an LC-MS analysis, the yellow solids were identified as compound 27.

Synthesis Example 28 (Synthesis of Compound 28)

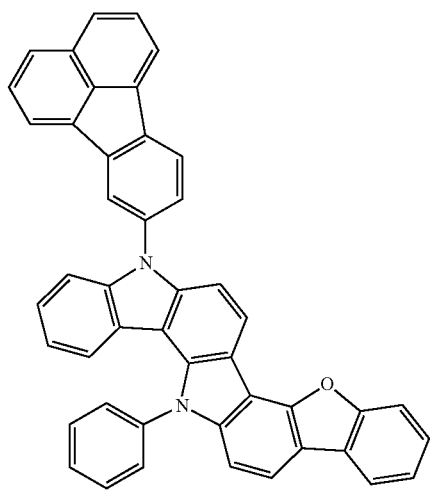

Synthesis was conducted in the same manner as in the synthesis of compound 27, except that 7-chlorofluoranaten was used instead of 2-bromofluoranthene, whereby 2.30 g (yield 78%) of yellow solids were obtained. As a result of an LC-MS analysis, the yellow solids were identified as compound 28.

Synthesis Example 29 (Synthesis of Compound 29)

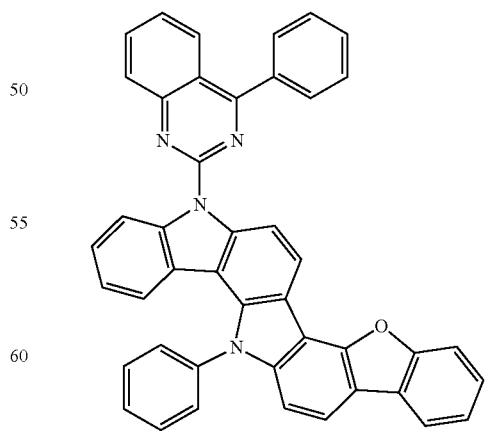

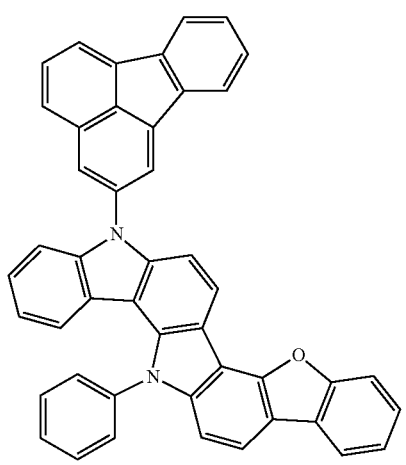 [SMILES: c1ccc(-n2c3ccc4c5ccccc5oc4c3c3ccc4c(c5ccccc5n4-c4cc5c6c(cccc6c4)-c4ccccc4-5)c32)cc1]

Synthesis was conducted in the same manner as in the synthesis of compound 27, except that 2-chloro-4-phenylquinazoline was used instead of 2-bromofluoranthene, whereby 2.45 g (yield 83%) of yellow solids were obtained. As a result of an LC-MS analysis, the yellow solids were identified as compound 29.

Synthesis Example 30 (Synthesis of Compound 30)

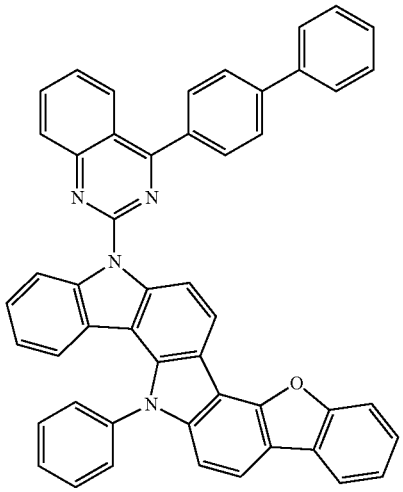 [SMILES: c1ccc(-c2ccc(-c3nc(-n4c5ccccc5c5c4ccc4c6c7oc8ccccc8c7ccc6n(-c6ccccc6)c45)nc4ccccc34)cc2)cc1]

Synthesis was conducted in the same manner as in the synthesis of compound 27, except that 2-chloro-4-[1,1'-biphenyl]quinazoline was used instead of 2-bromofluoranthene, whereby 2.05 g (yield 72%) of yellow solids were obtained. As a result of an LC-MS analysis, the yellow solids were identified as compound 30.

Synthesis Example 31 (Synthesis of Compound 31)

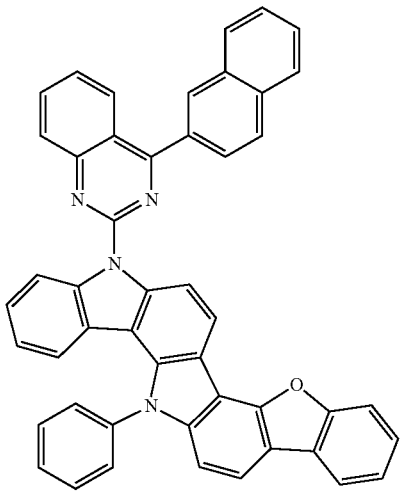 [SMILES: c1ccc(-n2c3ccc4c5ccccc5oc4c3c3ccc4c(c5ccccc5n4-c4nc(-c5ccc6ccccc6c5)c5ccccc5n4)c32)cc1]

Synthesis was conducted in the same manner as in the synthesis of compound 27, except that intermediate 8-A and 2-chloro-4-(2-naphthalenyl)-quinazoline was used instead of 2-bromofluoranthene, whereby 2.05 g (yield 72%) of yellow solids were obtained. As a result of an LC-MS analysis, the yellow solids were identified as compound 31.

Synthesis Example 32 (Synthesis of Compound 32)

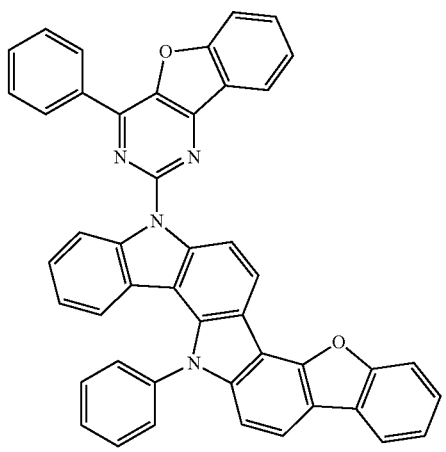 [SMILES: c1ccc(-c2nc(-n3c4ccccc4c4c3ccc3c5c6oc7ccccc7c6ccc5n(-c5ccccc5)c34)nc3c2oc2ccccc23)cc1]

Synthesis was conducted in the same manner as in the synthesis of compound 27, except that 2-chloro-4-phenyl-benzofuro[3,2-d]-pyrimidine was used instead of 2-bromofluoranthene, whereby 2.22 g (yield 65%) of yellow solids were obtained. As a result of an LC-MS analysis, the yellow solids were identified as compound 32.

Synthesis Example 33 (Synthesis of Compound 33)

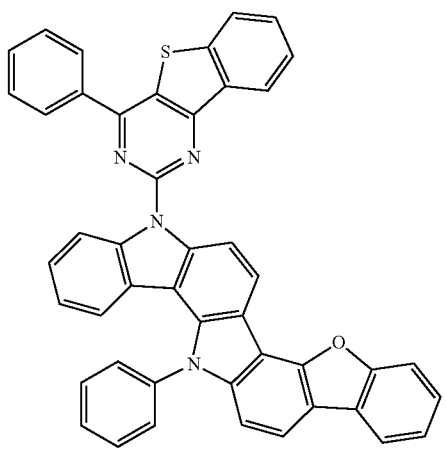

Synthesis was conducted in the same manner as in the synthesis of compound 27, except that intermediate 8-A and 2-chloro-4-phenylbenzothieno[3,2-d]-pyrimidine was used instead of 2-bromofluoranthene, whereby 1.85 g (yield 60%) of yellow solids were obtained. As a result of an LC-MS analysis, the yellow solids were identified as compound 33.

Synthesis Example 34 (Synthesis of Compound 34)

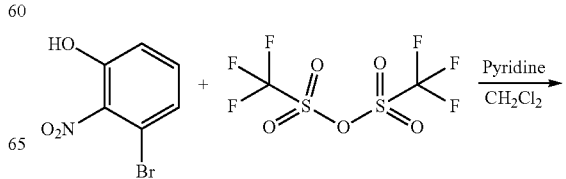

557
-continued

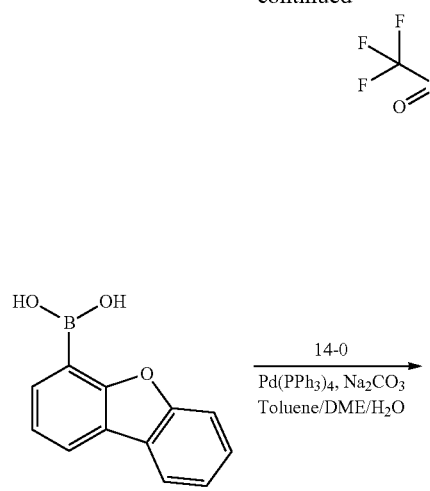

558
-continued

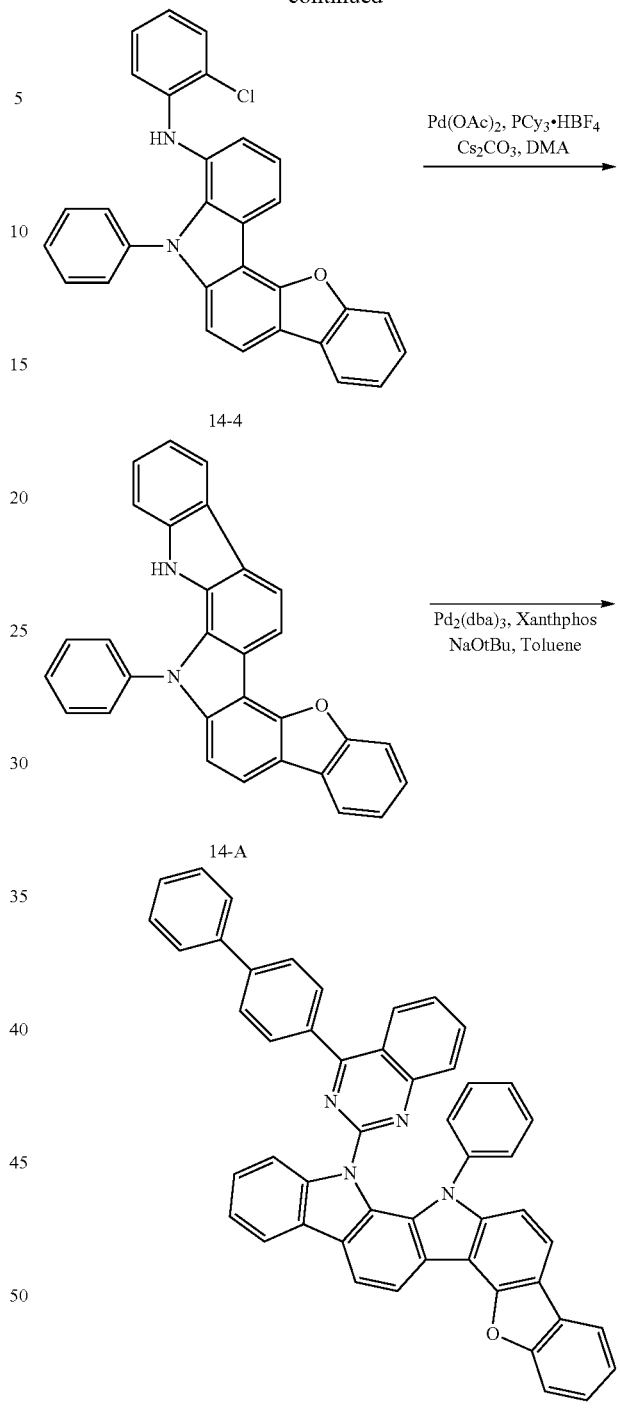

Compound 34

Synthesis of Intermediate 14-0

In a nitrogen atmosphere, 5.01 g of 3-bromo-2-phenol, 9.73 g of trifluoromethylsulfonic acid anhydride and 150 mL of methylene chloride were placed in a flask, and cooled to 0° C. To the solution, 3.7 mL of pyridine was added dropwise, and the mixture was stirred at room temperature for 2 hours. The reaction solution was poured into 300 mL of ice water, and an organic layer was extracted with

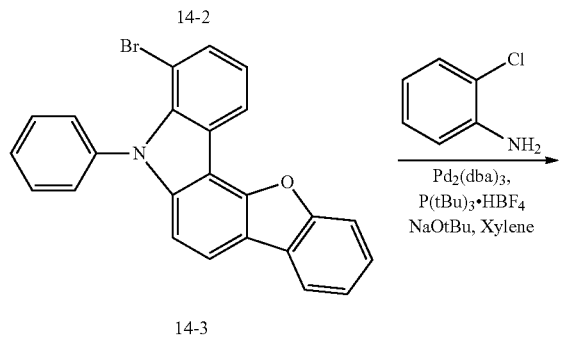

methylene chloride. After drying the organic layer with sodium sulfate, the sodium sulfate was removed and the organic layer was concentrated, whereby 7.73 g of yellow solids were obtained. As a result of an LC-MS analysis, the yellow solids were identified as intermediate 14-0.

Synthesis of Intermediate 14-1

Synthesis was conducted in the same manner as in the synthesis of intermediate 1-2, except that intermediate 14-0 and dibenzofuran-4-boronic acid were used instead of 1,2-dibromo-3-nitrobenzene and dibenzofuran-2-boronic acid, whereby 3.2 g (yield 75%) of white solids were obtained. As a result of an LC-MS analysis, the white solids were identified as intermediate 14-1.

Synthesis of Intermediate 14-2

Synthesis was conducted in the same manner as in the synthesis of intermediate 1-2, except that intermediate 14-1 was used instead of intermediate 1-1, whereby 2.4 g (yield 70%) of white solids were obtained. As a result of an LC-MS analysis, the white solids were identified as intermediate 14-2.

Synthesis of Intermediate 14-3

Synthesis was conducted in the same manner as in the synthesis of intermediate 1-3, except that intermediate 14-2 was used instead of intermediate 1-2, whereby 2.5 g (yield 80%) of white solids were obtained. As a result of an LC-MS analysis, the white solids were identified as intermediate 14-3.

Synthesis of Intermediate 14-4

Synthesis was conducted in the same manner as in the synthesis of intermediate 1-4, except that intermediate 14-3 was used instead of intermediate 1-3, whereby 2.0 g (yield 65%) of white solids were obtained. As a result of an LC-MS analysis, the white solids were identified as intermediate 14-4.

Synthesis of Intermediate 14-A

Synthesis was conducted in the same manner as in the synthesis of intermediate 1-A, except that intermediate 14-4 was used instead of intermediate 1-4, whereby 2.0 g (yield 65%) of white solids were obtained. As a result of an LC-MS analysis, the white solids were identified as intermediate 14-A.

Synthesis of Compound 34

Synthesis was conducted in the same manner as in the synthesis of compound 27, except that 2-chloro-4-[1,1'-biphenyl]-quinazoline was used instead of 2-bromofluoranthene, whereby 2.25 g (yield 70%) of yellow solids were obtained. As a result of an LC-MS analysis, the yellow solids were identified as compound 34.

<Comparative Compound>

Subsequently, comparative compounds 1 to 7 used in the following Comparative Examples are shown below.

Comprarative compound 1

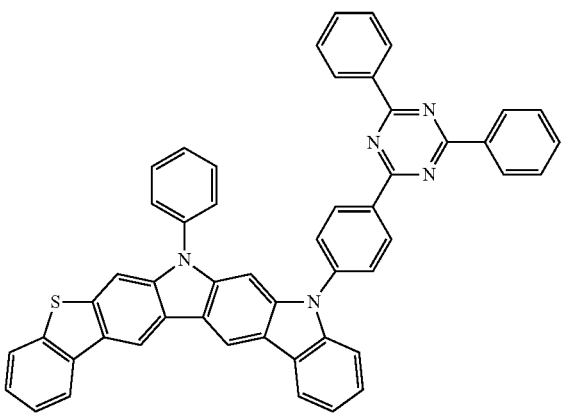

Comparative compound 2

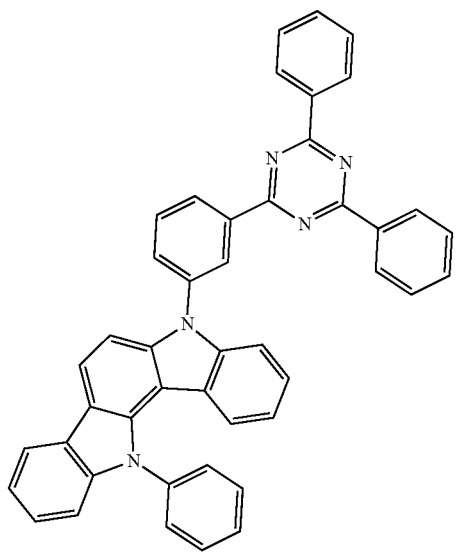

Comparative compound 3

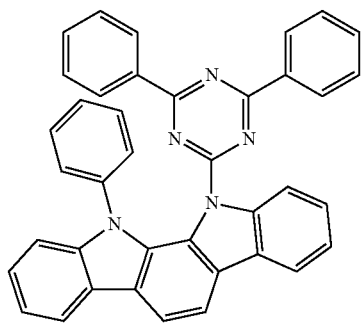

-continued

Comparative compound 4

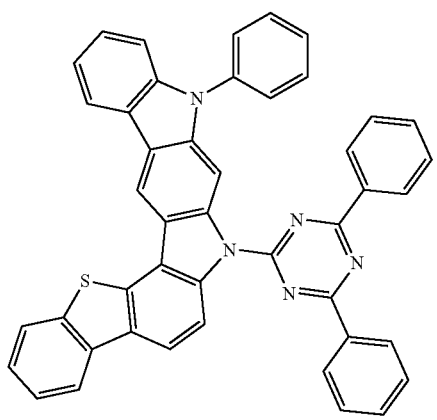

Comparative compound 5

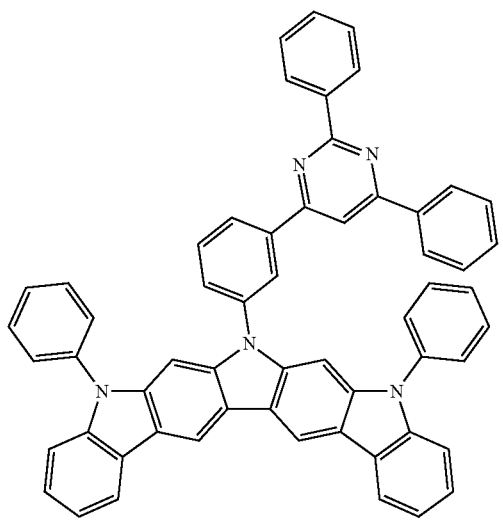

Comparative compound 6

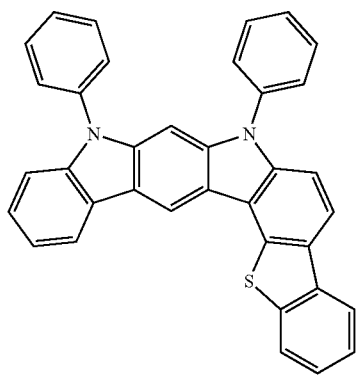

-continued

Comparative compound 7

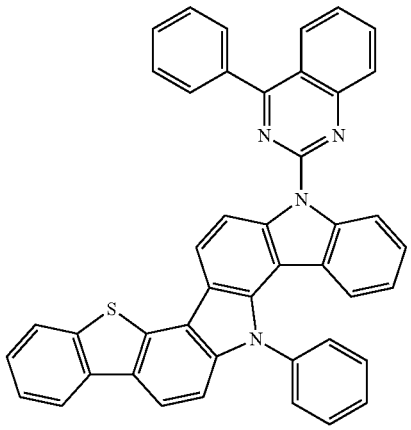

<Fabrication of Organic EL Device According to One Aspect of the Invention>

Materials other than the compounds according to one aspect of the invention and comparative compounds which were used in Examples 1 to 29 and Comparative Examples 1 to 6 are shown below.

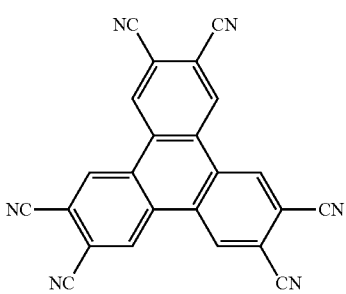

HI1

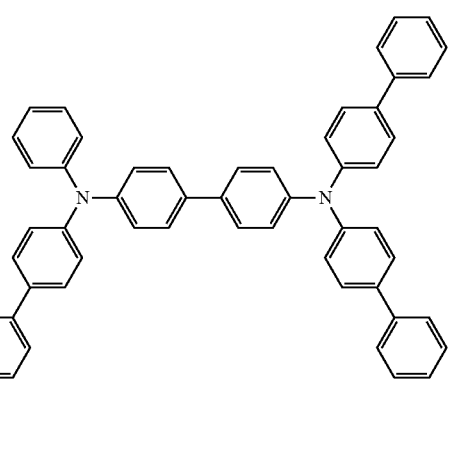

HT1

-continued

HT2

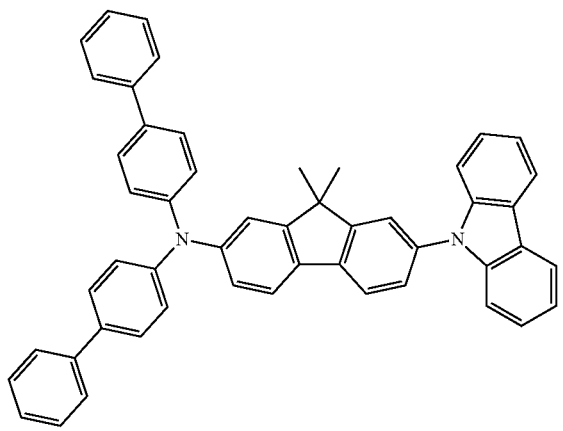

D3

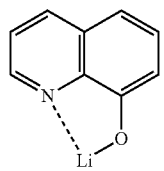

Liq

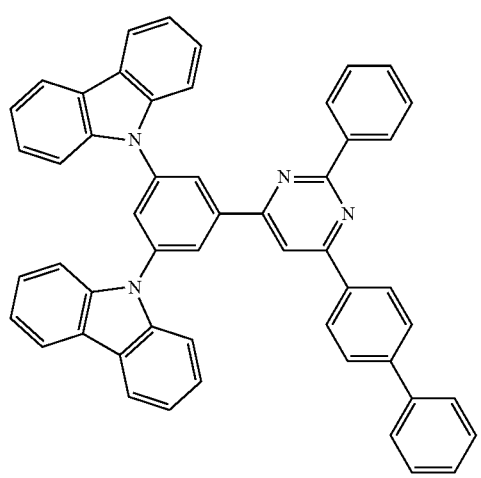

ET1

-continued

D1

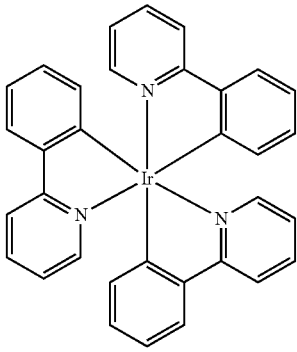

D2

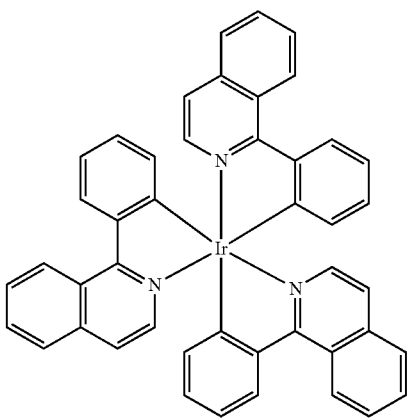

<Yellow Phosphorescent Organic EL Device>

Example 1 (Fabrication of Organic EL Device by Using Compound 25)

A glass substrate with an ITO transparent electrode (anode) having a dimension of 25 mm×75 mm×1.1 mm (manufactured by GEOMATIC Co., Ltd.) was subjected to ultrasonic cleaning in isopropyl alcohol for 5 minutes and then to UV ozone cleaning for 30 minutes. The thickness of ITO was 130 nm.

The cleaned glass substrate with transparent electrode lines was mounted on a substrate holder in a vacuum deposition apparatus. First, compound (HI1) was deposited on the surface on which the transparent electrode lines had been formed so as to cover the transparent electrode, whereby a 5 nm-thick hole-injecting layer was formed.

On this hole-injecting layer formed of compound (HI1), the above-mentioned compound (HT1) was deposited, whereby a first hole-transporting layer having a thickness of 40 nm was formed. Further, on this first hole-injecting layer formed of compound (HT1), the above-mentioned compound (HT2) was deposited, whereby a second hole-transporting layer having a thickness of 10 nm was formed.

Then, on this second hole-transporting layer formed of compound (HT2), the above-mentioned compound 25 and the above-mentioned compound (D3) were co-deposited as the host material and the dopant material, respectively, whereby a 20 nm-thick organic layer (emitting layer) was formed. The concentration of the above-mentioned compound (D3) in the organic layer (emitting layer) was 12 mass %.

On this emitting layer, the above-mentioned compound (ET1) and the above-mentioned compound (Liq) were co-deposited, whereby a 45 nm-thick electron-transporting layer was formed. The concentration of Liq in the organic layer was 50 mass %. This organic layer functions as an electron-transporting layer.

Further, on this electron-transporting layer, the following compound (Liq) was deposited, whereby a 1 nm-thick Liq film was formed. Metal Al was deposited on this Liq film, whereby a 80 nm-thick metal cathode was formed, and as a result, an organic EL device was fabricated.

The device configuration of the organic EL device fabricated in Example 10 was schematically shown as follows.

ITO (130 nm)/HI1 (5 nm)/HT1 (40 nm)/HT2 (10 nm)/compound 25+D3 (12 wt %)(20 nm)/ET1+Liq (50 wt %)(45 nm)/Liq (1 nm)/Al (80 nm)

Examples 2 to 3 and Comparative Examples 1 to 3

Organic EL devices were fabricated in the same manner as in Example 1, except that organic layers (emitting layers) were formed by using compounds 14 and 17 and comparative compounds 1 to 3 instead of compound 25 used as the host material.

<Evaluation of Organic EL Device>

For the organic EL devices fabricated in Examples 1 to 3 and Comparative Examples 1 to 3, the following evaluations were conducted. The results of evaluation are shown in Table 1.

(1) Driving Voltage (V)

A voltage (unit: V) when electric current was passed between the ITO transparent electrode and the metal Al cathode such that the current density became 10 mA/cm$^2$ was measured.

(2) Main Peak Wavelength ($\lambda_p$)

A spectral radiance spectrum when a voltage was applied to the device such that the current density became 10 mA/cm$^2$ was measured by means of a spectroradiometer "CS-1000" (product name, manufactured by Konica Minolta Japan, Ltd.). From the resulting spectral radiance spectrum, a main peak wavelength ($\lambda_p$) (unit: nm) was obtained.

(3) External Quantum Efficiency (EQE)

A spectral radiance spectrum when a voltage was applied to the device such that the current density became 10 mA/cm$^2$ was measured by means of a spectroradiometer "CS-1000" (product name, manufactured by Konica Minolta Japan, Ltd.).

From the resulting spectral radiance spectrum, an external quantum efficiency (EQE) (unit: %) was calculated on the assumption that lambassian radiation was conducted.

TABLE 1

| | Host material | Driving voltage (V) | Main peak wavelength (nm) | External quantum efficiency (%) |
|---|---|---|---|---|
| Example 1 | Compound 25 | 4.0 | 560 | 19.6 |
| Example 2 | Compound 14 | 3.9 | 560 | 21.7 |
| Example 3 | Compound 17 | 4.0 | 561 | 22.2 |
| Comp. Ex 1 | Comp. compound 1 | 4.2 | 561 | 17.9 |
| Comp. Ex 2 | Comp. compound 2 | 4.3 | 560 | 18.5 |
| Comp. Ex 3 | Comp. compound 3 | 4.1 | 561 | 19.1 |

From the results shown in Table 1, it can be assumed that, by using the compound according to one aspect of the invention as a host material, as compared with the case where the comparative compounds were used, since the molecular orbit was widened by fusion of the rings to enable holes to be transported efficiently, the efficiency was increased and the voltage was lowered.

Fabrication of Red Phosphorescent Organic EL Device

Example 4 (Fabrication of Organic EL Device by Using Compound 1)

A glass substrate with an ITO transparent electrode (anode) having a dimension of 25 mm×75 mm×1.1 mm (manufactured by GEOMATIC Co., Ltd.) was subjected to ultrasonic cleaning in isopropyl alcohol for 5 minutes and then to UV ozone cleaning for 30 minutes. The thickness of ITO was 130 nm.

The cleaned glass substrate with transparent electrode lines was mounted on a substrate holder in a vacuum deposition apparatus. First, compound (HI1) was deposited on the surface on which the transparent electrode lines had been formed so as to cover the transparent electrode, whereby a 5 nm-thick hole-injecting layer was formed.

On this hole-injecting layer formed of compound (HI1), the above-mentioned compound (HT1) was deposited, whereby a first hole-transporting layer having a thickness of 200 nm was formed. Further, on this first hole-transporting layer formed of compound (HT1), the above-mentioned compound (HT2) was deposited, whereby a second hole-transporting layer having a thickness of 10 nm was formed.

Then, on this second hole-transporting layer formed of compound (HT2), the above-mentioned compound 1 and the above-mentioned compound (D2) were co-deposited as the host material and the dopant material, respectively, whereby 40 nm-thick organic layer (emitting layer) was formed. The concentration of the above-mentioned compound (D2) in the organic layer (emitting layer) was 2 mass %.

On this emitting layer, the above-mentioned compound (ET1) and the above-mentioned compound (Liq) were co-deposited, whereby a 30 nm-thick electron-transporting layer was formed. The concentration of the Liq in the organic layer was 50 mass %. This organic layer functions as an electron-transporting layer.

Further, on this electron-transporting layer, the above-mentioned compound (Liq) was deposited to form a 1 nm-thick Liq film, and metal Al was deposited on this Liq film, whereby a 80 nm-thick metal cathode was formed, and as a result, an organic EL device was fabricated.

The device configuration of the organic EL device fabricated in Example 4 was schematically shown as follows.

ITO (130 nm)/HI1 (5 nm)/HT1 (200 nm)/HT2 (10 nm)/compound 1+D2 (2 wt %)(40 nm)/ET1+Liq (50 wt %)(30 nm)/Liq (1 nm)/Al (80 nm)

Examples 5 to 28 and Comparative Examples 4 and 5

Organic EL devices were fabricated in the same manner as in Example 4, except that organic layers (emitting layers) were formed by using compounds 2 to 25 and comparative compounds 4 and 1 instead of compound 1 used as a host material.

<Evaluation of Organic EL Device>

For the organic EL devices fabricated in Examples 4 to 28 and Comparative Examples 4 and 5, the following evaluations were conducted. The results of evaluation are shown in Tables 2-1 and 2-2.

(1) Main peak wavelength ($\lambda_p$)

A spectral radiaum spectrum when a voltage was applied to the device such that the current density became 10 mA/cm² was measured by means of a spectroradiometer "CS-1000" (product name, manufactured by Konica Minolta Japan, Ltd.). From the resulting spectral radiance spectrum, a main peak wavelength ($\lambda_p$) (unit: nm) was obtained.

(2) Lifetime (LT90)

A continuous electric current test (DC) was conducted with the initial current density being set as 50 mA/cm². A period of time taken for which the luminance was reduced to 90% as compared with the luminance at the time of starting the test was measured, and the time was taken as lifetime (LT90).

TABLE 2-1

| | Host material | Main peak wavelength (nm) | LT90 (hr) |
|---|---|---|---|
| Example 4 | Compound 1 | 619 | 374 |
| Example 5 | Compound 2 | 621 | 361 |
| Example 6 | Compound 3 | 619 | 217 |
| Example 7 | Compound 4 | 621 | 238 |
| Example 8 | Compound 5 | 617 | 255 |
| Example 9 | Compound 6 | 621 | 321 |
| Example 10 | Compound 7 | 617 | 211 |
| Example 11 | Compound 8 | 620 | 224 |
| Example 12 | Compound 9 | 619 | 245 |
| Example 13 | Compound 10 | 621 | 237 |
| Example 14 | Compound 11 | 621 | 341 |
| Example 15 | Compound 12 | 617 | 269 |
| Example 16 | Compound 13 | 620 | 193 |
| Example 17 | Compound 14 | 619 | 211 |
| Example 18 | Compound 15 | 621 | 319 |
| Example 19 | Compound 16 | 617 | 411 |
| Example 20 | Compound 17 | 621 | 229 |
| Example 21 | Compound 18 | 617 | 340 |
| Example 22 | Compound 19 | 620 | 216 |
| Example 23 | Compound 20 | 620 | 170 |
| Example 24 | Compound 21 | 619 | 182 |
| Example 25 | Compound 22 | 620 | 184 |
| Example 26 | Compound 23 | 619 | 192 |
| Example 27 | Compound 24 | 620 | 245 |
| Example 28 | Compound 25 | 620 | 160 |

TABLE 2-2

| | Host material | Main peak wavelength (nm) | LT90 (hr) |
|---|---|---|---|
| Comp. Ex. 4 | Comp. compound 4 | 621 | 159 |
| Comp. Ex. 5 | Comp. compound 1 | 621 | 122 |

From the results shown in Tables 2-1 and 2-2, it can be assumed that, by using the compound according to one aspect of the invention as a host material, as compared with the case where the comparative compounds were used, the resistance to oxidation was improved, whereby the lifetime was prolonged.

<Green Phosphorescent Organic EL Device>

Example 29 (Fabrication of Organic EL Device by Using Compound 26)

A glass substrate with an ITO transparent electrode (anode) having a dimension of 25 mm×75 mm×1.1 mm (manufactured by GEOMATIC Co., Ltd.) was subjected to ultrasonic cleaning in isopropyl alcohol for 5 minutes and then to UV ozone cleaning for 30 minutes. The thickness of ITO was 130 nm.

The cleaned glass substrate with transparent electrode lines was mounted on a substrate holder in a vacuum deposition apparatus. First, compound (HI1) was deposited on the surface on which the transparent electrode lines had been formed so as to cover the transparent electrode, whereby a 5 nm-thick hole-injecting layer was formed.

On this hole-injecting layer formed of compound (HI1), the above-mentioned compound (HT1) was deposited, whereby a first hole-transporting layer having a thickness of 90 nm was formed. Further, on this first hole-transporting layer formed of compound (HT1), the above-mentioned compound (HT2) was deposited, whereby a second hole-transporting layer having a thickness of 60 nm was formed.

Then, on this second hole-transporting layer formed of compound (HT2), the above-mentioned compound 26 and the above-mentioned compound (D1) were co-deposited as the host material and the dopant material, respectively, whereby a 40 nm-thick organic layer (emitting layer) was formed. The concentration of the above-mentioned compound (D1) in the organic layer (emitting layer) was 5 mass %.

On this emitting layer, the above-mentioned compound (ET1) and the above-mentioned compound (Liq) were co-deposited, whereby a 30 nm-thick electron-transporting layer was formed. The concentration of the Liq in the organic layer was 50 mass %. This organic layer functions as an electron-transporting layer.

Further, on this electron-transporting layer, the above-mentioned compound (Liq) was deposited to form a 1 nm-thick Liq film, and metal Al was deposited on this Liq film, whereby a 80 nm-thick metal cathode was formed, and as a result, an organic EL device was fabricated.

The device configuration of the organic EL device fabricated in Example 4 was schematically shown as follows.
ITO (130 nm)/HI1 (5 nm)/HT1 (90 nm)/HT2 (60 nm)/compound 26+D1 (5 wt %)(40 nm)/ET1+Liq (50 wt %)(30 nm)/Liq (1 nm)/Al (80 nm)

Comparative Example 6

An organic EL device was fabricated in the same manner as in Example 29, except that an organic layer (emitting layer) was formed by using comparative compound 5 instead of compound 26 used as a host material.

<Evaluation of Organic EL Device>

For the organic EL devices fabricated in Example and Comparative Example, the following evaluations were conducted. The results of evaluation are shown in Table 3.

(1) Main peak wavelength ($\lambda_p$)

A spectral radiance spectrum when a voltage was applied to the device such that the current density became 10 mA/cm² was measured by means of a spectroradiometer "CS-1000" (product name, manufactured by Konica Minolta Japan, Ltd.). From the resulting spectral radiance spectrum, a main peak wavelength (A) (unit: nm) was obtained.

(2) External Quantum Efficiency (EQE)

A spectrum radiance spectrum when a voltage was applied to the device such that the current density became 10 mA/cm² was measured by means of a spectroradiometer "CS-1000" (product name, manufactured by Konica Minolta Japan, Ltd.).

From the resulting spectrum radiance spectrum, an external quantum efficiency (EQE) (unit: %) was calculated on the assumption that lambassian radiation was conducted.

TABLE 3

| | Host material | Main peak wavelength (nm) | External quantum efficiency (%) |
|---|---|---|---|
| Example 29 | Compound 26 | 519 | 13.6 |
| Comp. Ex 6 | Comp. compound 5 | 519 | 11.8 |

From the results shown in Table 3, it can be assumed that, by using the compound as one aspect of the invention as a host material, as compared with the case where the comparative compound was used, since a large T1 could be maintained, and as a result, the efficiency was increased due to reduction in emission loss of the dopant.

Materials in Examples 30 to 61 and Comparative Examples 7 to 10, other than the compounds according to one aspect of the invention and comparative compounds, are shown below.

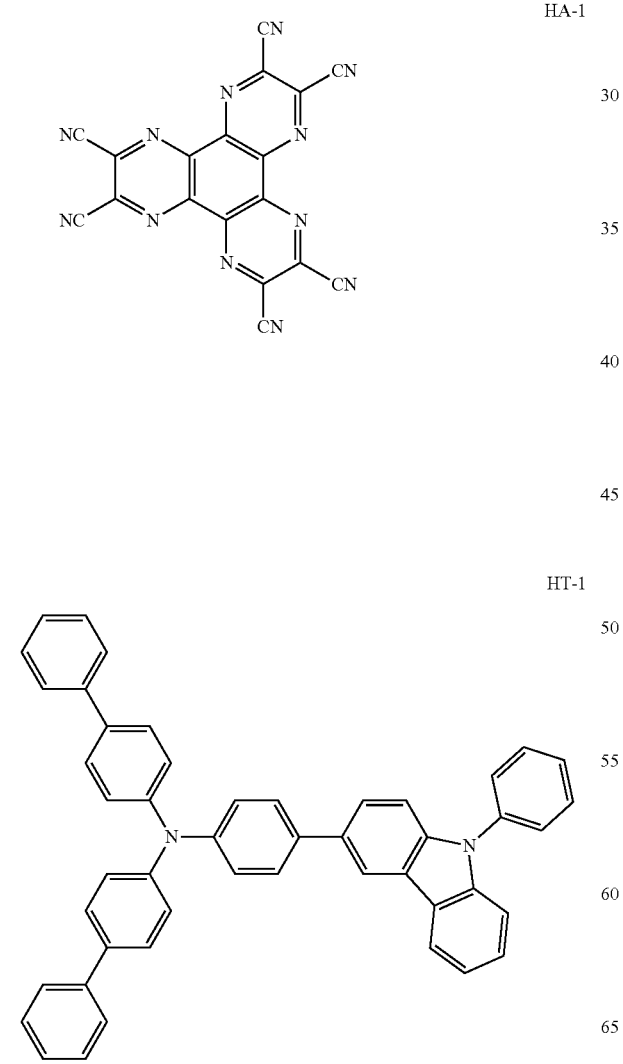

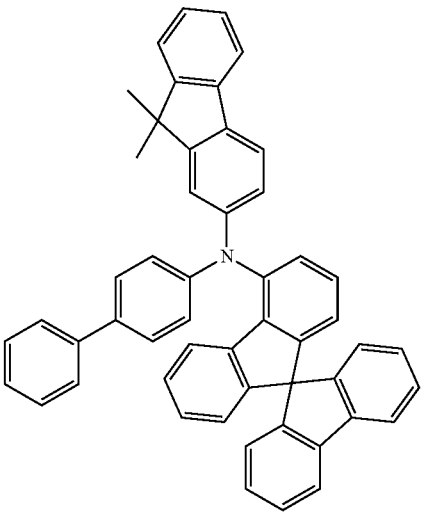

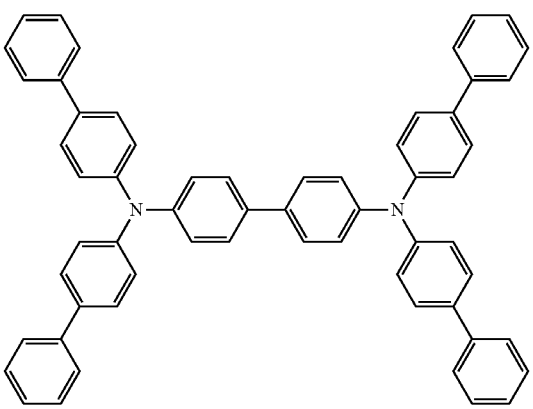

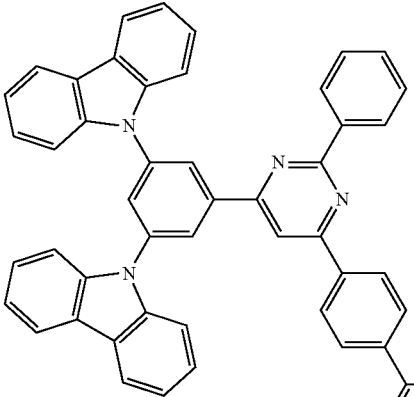

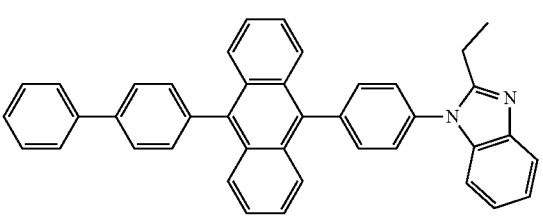

-continued

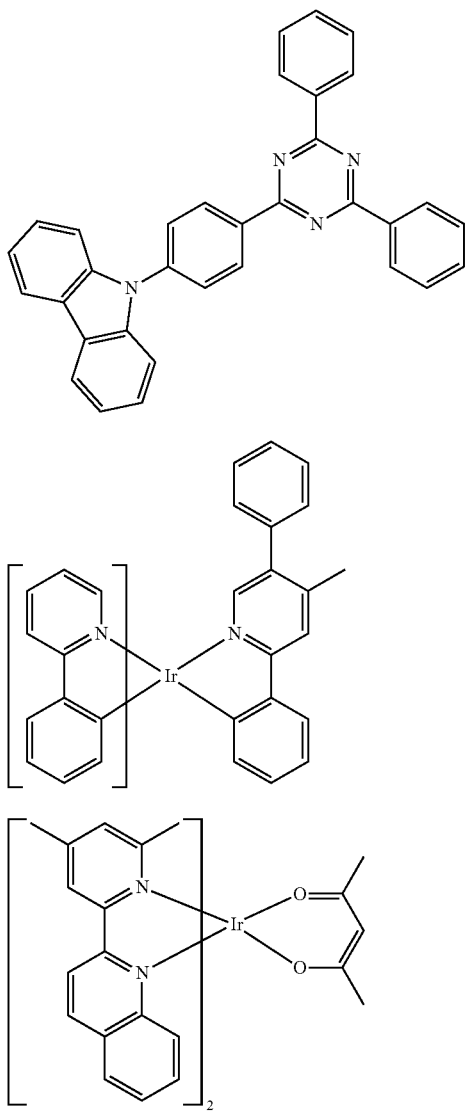

N-1

GD-1

RD-1

Green Phosphorescent Organic EL Device

Example 30

A glass substrate with an ITO transparent electrode (anode) having a dimension of 25 mm×75 mm×1.1 mm (manufactured by GEOMATIC Co., Ltd.) was subjected to ultrasonic cleaning in isopropyl alcohol for 5 minutes and then to UV ozone cleaning for 30 minutes. The thickness of ITO was 130 nm.

The cleaned glass substrate with transparent electrode lines was mounted on a substrate holder in a vacuum deposition apparatus. First, compound HA-1 was deposited on the surface on which the transparent electrode lines had been formed so as to cover the transparent electrode to form a 5 nm-thick HA-1 film, whereby a hole-injecting layer was formed.

Then, on this hole-injecting layer, compound HT-1 was deposited, whereby a 130 nm-thick HT-1 film was formed, whereby a first hole-transporting layer was formed.

Subsequently, on this first hole-transporting layer, compound HT-2 was deposited to form a 20 nm-thick HT-2 fim, whereby a second hole-transporting layer was formed.

Then, on this second hole-transporting layer, the first host (compound 1), the second host (N-1) and GD-1 were co-deposited, whereby a 40 nm-thick emitting layer was formed. The concentration of the first host and the second host in the emitting layer was 50 mass %: 50 mass %, and the concentration of GD-1 in the emitting layer was 5 mass %.

Subsequent to the formation of the emitting layer, compound ET-1 and 8-quinolinolate lithium (Liq) were co-deposited with a mass ratio of 50:50, whereby a 25 nm-thick electron-transporting layer was formed.

On this electron-transporting layer, Liq was deposited, whereby a 1 nm-thick electron-injecting layer was formed.

On this electron-injecting layer, metal Al was deposited to form a 80 nm-thick metal cathode, whereby an organic EL device was fabricated.

The device configuration of the organic EL device fabricated in Example 30 was schematically shown as follows. ITO (130 nm)/HA-1 (5 nm)/HT-1 (130 nm)/HT-2 (20 nm)/compound 1:N-1:GD-1 (47.5 wt %,47.5 wt %,5 wt %)(40 nm)/ET-1+Liq (50 wt %)(25 nm)/Liq (1 nm)/Al (80 nm)

Examples 31 to 37 and Comparative Example 7

Organic EL devices were fabricated in the same manner as in Example 30, except that organic layers (emitting layers) were formed by using compounds shown in the following table 4 instead of compound 1 used as the first host material.

<Evaluation of Organic EL Device>

For the organic EL devices fabricated in Examples 30 to 37 and Comparative Example 7, the external quantum efficiency (EQE) and the lifetime (LT95) were evaluated. The results of evaluation are shown in Table 4.

As for the lifetime (LT95), a continuous electric current test (DC) was conducted with the initial current density being set as 10 mA/cm$^2$. A period of time taken for which the luminance was reduced to 95% as compared with the luminance at the time of starting the test was measured, and the time was taken as lifetime (LT95).

TABLE 4

|  | First host material | Second host material | External quantum efficiency (EQE) (%) | Lifetime (LT95@10 mA/cm$^2$) |
|---|---|---|---|---|
| Example 30 | Compound 1 | N-1 | 18.5 | 150 |
| Example 31 | Compound 2 | N-1 | 18.1 | 90 |
| Example 32 | Compound 6 | N-1 | 18.0 | 90 |
| Example 33 | Compound 11 | N-1 | 18.7 | 130 |
| Example 34 | Compound 15 | N-1 | 18.4 | 150 |
| Example 35 | Compound 16 | N-1 | 18.3 | 140 |
| Example 36 | Compound 18 | N-1 | 18.3 | 130 |
| Example 37 | Compound 24 | N-1 | 18.0 | 90 |
| Comp. Ex. 7 | Comp. compound 6 | N-1 | 17.0 | 70 |

From the results shown in Table 4, it can be understood that, as the first host material, as compared with comparative compound 6 that has heterocyclic five-membered rings in the order of pyrrole(N)-pyrrole(N)-thiophene(S), the compound of the invention that has heterocyclic five-membered rings in the order of pyrrole(N)-pyrrole(N)-furan (O) has a high external quantum efficiency and a long lifetime.

Further, it can be understood that, as compared with compounds 2,6 and 24 in which the bonding position of the second pyrrole (N) is $Y^2$—$Y^3$ in the formula (1), compounds 1, 11, 15, 16 and 18 in which the bonding position is $Y^1$—$Y^2$ or $Y^3$—$Y^4$ have a particularly prolonged device lifetime.

Fabrication of Green Phosphorescent Organic EL Device

Example 38

A glass substrate with an ITO transparent electrode (anode) having a dimension of 25 mm×75 mm×1.1 mm (manufactured by GEOMATIC Co., Ltd.) was subjected to ultrasonic cleaning in isopropyl alcohol for 5 minutes and then to UV ozone cleaning for 30 minutes. The thickness of ITO was 130 nm.

The cleaned glass substrate with transparent electrode lines was mounted on a substrate holder in a vacuum deposition apparatus. First, compound HA-1 was deposited on the surface on which the transparent electrode lines had been formed so as to cover the transparent electrode to form a 5 nm-thick HA-1 film, whereby a hole-injecting layer was formed.

Then, on this hole-injecting layer, compound HT-3 was deposited, whereby a 130 nm-thick HT-3 film was formed, whereby a first hole-transporting layer was formed.

Subsequently, on this first hole-transporting layer, compound HT-2 was deposited to form a 20 nm-thick HT-2 fim, whereby a second hole-transporting layer was formed.

Then, on this hole-transporting layer, the first host (compound 11), the second host (compound 3) shown in the following table and GD-1 were co-deposited, whereby a 40 nm-thick emitting layer was formed. The concentration of the first host and the second host in the emitting layer was 50 mass %:50 mass %, and the concentration of GD-1 in the emitting layer was 5 mass %.

Subsequent to the formation of the emitting layer, compound ET-2 and 8-quinolinolate lithium (Liq) were co-deposited with a mass ratio of 50:50, whereby a 25 nm-thick electron-transporting layer was formed.

On this electron-transporting layer, Liq was deposited, whereby a 1 nm-thick electron-injecting layer was formed.

On this electron-injecting layer, metal Al was deposited to form a 80 nm-thick metal cathode, whereby an organic EL device was fabricated.

The device configuration of the organic EL device fabricated in Example 38 was schematically shown as follows.
ITO (130 nm)/HA-1 (5 nm)/HT-3 (130 nm)/HT-2 (20 nm)/compound 11:compound 3:GD-1 (47.5 wt %,47.5 wt %,5 wt %)(40 nm)/ET-2+Liq (50 wt %)(25 nm)/Liq (1 nm)/Al (80 nm)

Examples 39 to 51 and Comparative Examples 8 and 9

An organic EL device was fabricated in the same manner as in Example 38, except that an organic layer (emitting layer) was formed by using compounds shown in the following table 5 instead of compound 3 used as the second host material.

<Evaluation of Organic EL Device>

For the organic EL devices fabricated in Examples 38 to 51 and Comparative Examples 8 and 9, the external quantum efficiency (EQE) and the lifetime (LT95) were evaluated. The results of evaluation are shown in Table 5.

As for the lifetime (LT95), a continuous electric current test (DC) was conducted with the initial current density being set as 10 mA/cm$^2$. A period of time taken for which the luminance was reduced to 95% as compared with the luminance at the time of starting the test was measured, and the time was taken as lifetime (LT95).

TABLE 5

|  | First host material | Second host material | External quantum efficiency (EQE) (%) | Lifetime (LT95@10 mA/cm$^2$) |
|---|---|---|---|---|
| Example 38 | Compound 11 | Compound 3 | 18.1 | 70 |
| Example 39 | Compound 11 | Compound 4 | 18.0 | 70 |
| Example 40 | Compound 11 | Compound 5 | 18.1 | 70 |
| Example 41 | Compound 11 | Compound 7 | 18.1 | 80 |
| Example 42 | Compound 11 | Compound 9 | 18.8 | 120 |
| Example 43 | Compound 11 | Compound 10 | 18.6 | 110 |
| Example 44 | Compound 11 | Compound 12 | 18.9 | 110 |
| Example 45 | Compound 11 | Compound 13 | 18.8 | 110 |
| Example 46 | Compound 11 | Compound 14 | 18.7 | 110 |
| Example 47 | Compound 11 | Compound 17 | 18.9 | 120 |
| Example 48 | Compound 11 | Compound 19 | 18.6 | 110 |
| Example 49 | Compound 11 | Compound 22 | 18.0 | 70 |
| Example 50 | Compound 11 | Compound 23 | 18.1 | 80 |
| Example 51 | Compound 11 | Compound 25 | 18.6 | 110 |
| Comp. Ex 8 | Compound 11 | Comp. compound 1 | 17.3 | 50 |
| Comp. Ex 9 | Compound 11 | Comp. compound 4 | 17.2 | 50 |

From the results shown in Table 5, it can be understood that, as the second host material, as compared with comparative compounds 1 and 4 that have heterocyclic five-membered rings in the order of pyrrole(N)-pyrrole(N)-thiophene(S), the compound of the invention that has heterocyclic five-membered rings in the order of pyrrole(N)-pyrrole(N)-furan (O) has a high external quantum efficiency and an equivalent or longer lifetime.

Further, it can be understood that, as compared with compounds 3, 4, 5, 7, 22 and 23 in which the bonding position of the second pyrrole (N) is $Y^2$—$Y^3$ in the formula (1), compounds 9, 10, 12, 13, 14, 17, 19 and 25 in which the bonding position is $Y^1$—$Y^2$ or $Y^3$—$Y^4$ have a particularly prolonged device lifetime.

Fabrication of Red Phosphorescent Organic EL Device

Example 52

A glass substrate with an ITO transparent electrode (anode) having a dimension of 25 mm×75 mm×1.1 mm (manufactured by GEOMATIC Co., Ltd.) was subjected to ultrasonic cleaning in isopropyl alcohol for 5 minutes and then to UV ozone cleaning for 30 minutes. The thickness of ITO was 130 nm.

The cleaned glass substrate with transparent electrode lines was mounted on a substrate holder in a vacuum deposition apparatus. First, compound HA-1 was deposited on the surface on which the transparent electrode lines had been formed so as to cover the transparent electrode to form a 5 nm-thick HA-1 film, whereby a hole-injecting layer was formed.

Then, on this hole-injecting layer, compound HT-3 was deposited to form a 210 nm-thick HT-3 film, whereby a first hole-transporting layer was formed.

Then, on this first hole-transporting layer, compound HT-2 was deposited to form a 10 nm-thick HT-2 film, whereby a second hole-transporting layer was formed.

Then, on this hole-transporting layer, compound and RD-1 were co-deposited to form a 40 nm-emitting layer. The concentration of RD-1 in the emitting layer was 2 mass %.

Subsequent to the formation of the emitting layer, compound ET-2 and 8-quinolinolate lithium (Liq) were co-deposited with a mass ratio of 50:50, whereby a 25 nm-thick electron-transporting layer was formed.

On this electron-transporting layer, Liq was deposited to form a 1 nm-thick electron-injecting layer.

On this electron-injecting layer, metal Al was deposited to form a 80 nm-thick metal cathode, whereby an organic EL device was fabricated.

The device configuration of the organic EL device fabricated in Example 52 was schematically shown as follows.
ITO (130 nm)/HA-1 (5 nm)/HT-3 (210 nm)/HT-2 (10 nm)/compound 8+RD-1 (2 wt %)(40 nm)/ET-2+Liq (50 wt %)(25 nm)/Liq (1 nm)/Al (80 nm)

Examples 53 to 61 and Comparative Example 10

Organic EL devices were fabricated in the same manner as in Example 52, except that organic layers (emitting layers) were formed by using compounds shown in the following table 6 instead of compound 8 used as the host material.

<Evaluation of Organic EL Device>

For the organic EL devices fabricated in Examples 52-61 and Comparative Example 10, the external quantum efficiency (EQE) and lifetime (LT95) were evaluated. The results of evaluation are shown in Table 6.

As for the lifetime (LT95), a continuous electric current test (DC) was conducted with the initial current density being set as 50 mA/cm². A period of time taken for which the luminance was reduced to 95% as compared with the luminance at the time of starting the test was measured, and the time was taken as lifetime (LT95).

TABLE 6

|  | Host material | External quantum efficiency (EQE) (%) | Lifetime (LT95@50 mA/cm²) |
|---|---|---|---|
| Example 52 | Compound 8 | 14.5 | 300 |
| Example 53 | Compound 20 | 15.5 | 360 |
| Example 54 | Compound 21 | 15.7 | 340 |
| Example 55 | Compound 27 | 16.1 | 350 |
| Example 56 | Compound 28 | 15.9 | 350 |
| Example 57 | Compound 29 | 15.6 | 380 |
| Example 58 | Compound 30 | 16.2 | 400 |
| Example 59 | Compound 31 | 16.1 | 400 |
| Example 60 | Compound 32 | 16.0 | 360 |
| Example 61 | Compound 33 | 16.1 | 370 |
| Comp. Ex. 10 | Comp. compound 7 | 13.5 | 250 |

From the results shown in Table 6, it can be understood that, as compared with comparative compound 7 that has heterocyclic five-membered rings in the order of pyrrole(N)-pyrrole(N)-thiophene(S), the compound of the invention that has heterocyclic five-membered rings in the order of pyrrole (N)-pyrrole(N)-furan (0) has a high external quantum efficiency and a long life time.

Further, it can be understood that, as compared with compound 8 in which the bonding position of the second pyrrole (N) is $Y^2$—$Y^3$ in the formula (1), compounds 20, 21 and 27 to 33 in which the bonding position is $Y^1$—$Y^2$ or $Y^3$—$Y^4$ have a higher external quantum efficiency and a prolonged device lifetime.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification and the Japanese patent applications claiming the priority under the Paris Convention to the invention are incorporated herein by reference in its entirety.

The invention claimed is:

1. A compound represented by the following formula (1):

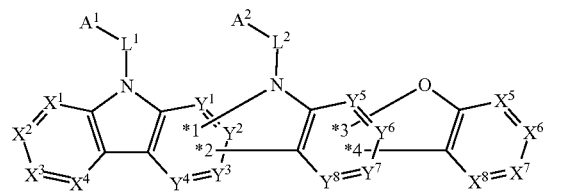

wherein in the formula (1),
at least one of $A^1$ and $A^2$ is a monovalent residue of a compound represented by the following formula (a2):

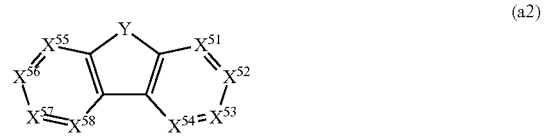

wherein in the formula (a2), $X^{51}$ to $X^{58}$ are independently CH, $C(R^b)$ or N;

$R^b$ is a substituent, and when plural $R^b$s are present, the plural $R^b$s may be the same as or different from each other, and two selected from the plural $R^b$s may be bonded to each other to form a ring;

Y is an oxygen atom, a sulfur atom, or —$NR^d$ and $R^d$, $R^e$ and $R^f$ are independently a hydrogen atom or a substituent $R^b$, and when both $R^e$ and $R^f$ are $R^b$, the $R^b$s may be bonded to each other to form a ring;

$A^1$ or $A^2$ that is not the monovalent residue of a compound represented by the formula (a2) is a substituted or unsubstituted aryl group including 6 to 50 ring carbon atoms or a substituted or unsubstituted heteroaryl group including 5 to 50 ring atoms other than the monovalent residue of a compound represented by the formula (a2);

$L^1$ and $L^2$ are independently a single bond, a substituted or unsubstituted arylene group including 6 to 60 ring carbon atoms or a substituted or unsubstituted heteroarylene group including 5 to 50 ring atoms;

$X^1$ to $X^8$ are independently CH, $C(R^a)$ or N;

*1 to *4 are independently an atomic bonding that forms a single bond;

any adjacent two of $Y^1$ to $Y^4$ are Cs that independently form a single bond with *1 and *2, and remaining two of $Y^1$ to $Y^4$ are independently CH, $C(R^a)$ or N;

any adjacent two of $Y^5$ to $Y^8$ are Cs that independently form a single bond with *3 and *4, and remaining two of $Y^5$ to rare independently CH, $C(R^a)$ or N; and $R^a$ is a substituent, and if plural $R^a$s are present, they may be the same as or different from each other, and two selected from the plural $R^a$s may be bonded to each other to form a ring.

2. The compound according to claim 1, wherein the compound represented by the formula (1) is selected from compounds represented by the following formulas (1-a) to (1-d):

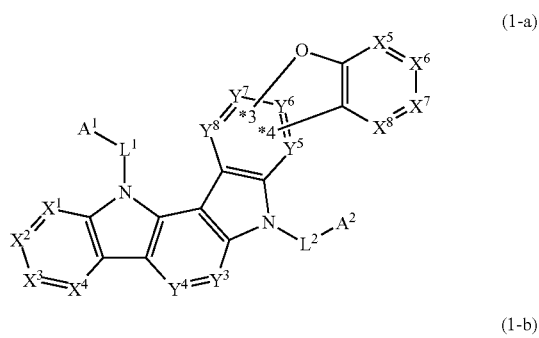

(1-a)

(1-b)

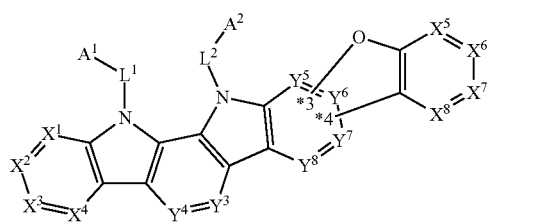

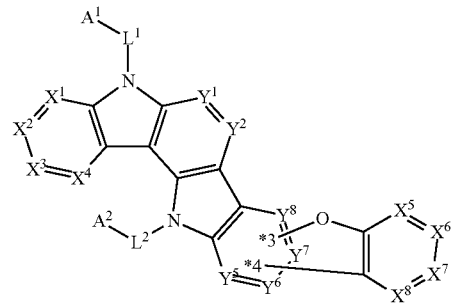

(1-c)

(1-d)

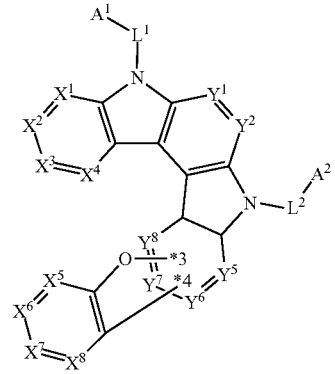

wherein in the formulas (1-a) to (1-d), $A^1$, $A^2$, $L^1$, $L^2$, $X^1$ to $X^8$, $Y^1$ to V, *3 and *4 are as defined in the formula (1).

3. The compound according to claim 1, wherein the compound represented by the formula (1) is a compound represented by the following formula (2):

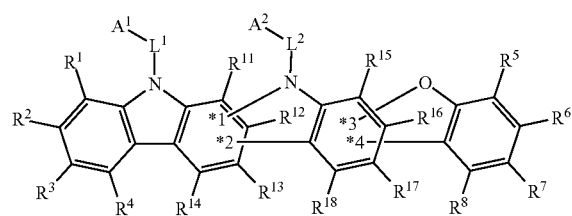

(2)

wherein in the formula (2), $A^1$, $A^2$, $L^1$, $L^2$ and *1 to *4 are as defined in the formula (1);

$R^1$ to $R^8$ are independently a hydrogen atom or a substituent $R^a$;

$R^{11}$ to $R^{14}$ any adjacent two of $R^{11}$ to $R^{14}$ independently form a single bond with *1 and *2, and remaining two of $R^{11}$ to $R^{14}$ care independently a hydrogen atom or a substituent $R^a$;

any adjacent two of $R^{15}$ to $R^{18}$ independently form a single bond with *3 and *4, and remaining two of $R^{15}$ to $R^{18}$ are independently a hydrogen atom or a substituent $R^a$; and $R^a$ is as defined in the formula (1).

4. The compound according to claim 3, wherein the compound represented by the formula (2) is selected from the group consisting of compounds represented by the following formulas (3-1) and (3-4) to (3-6):

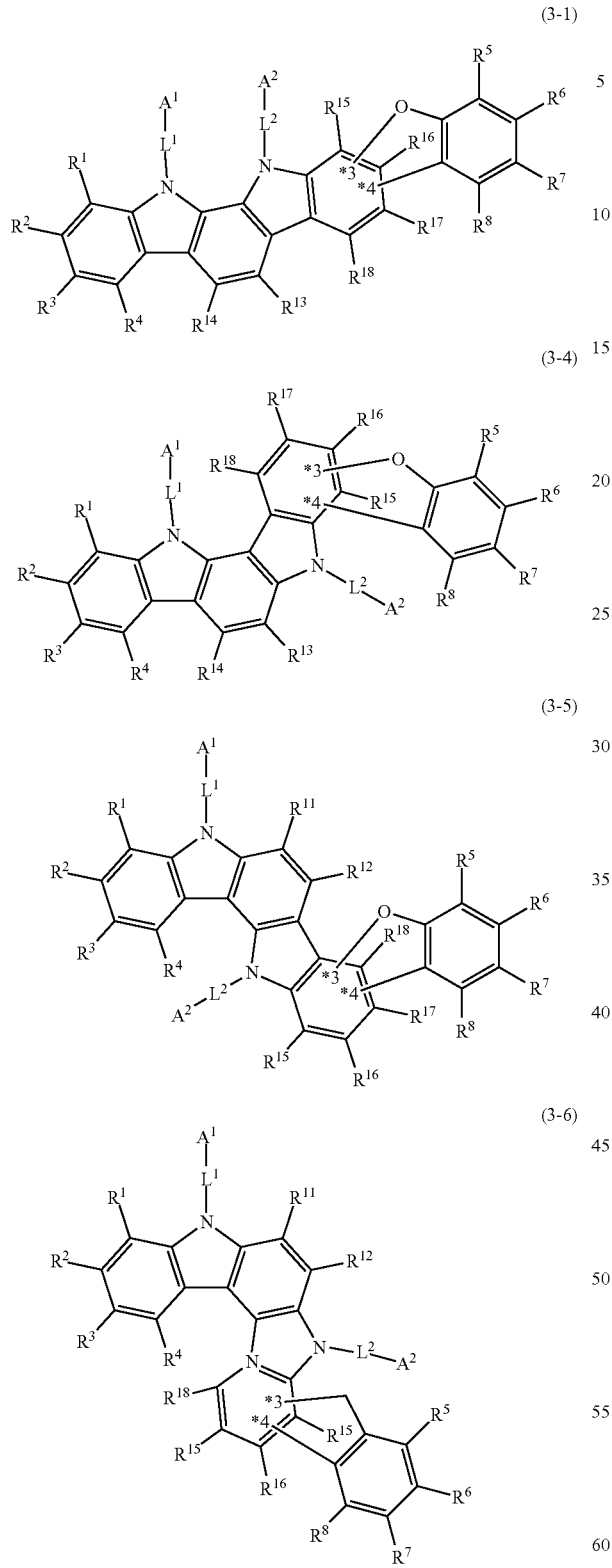
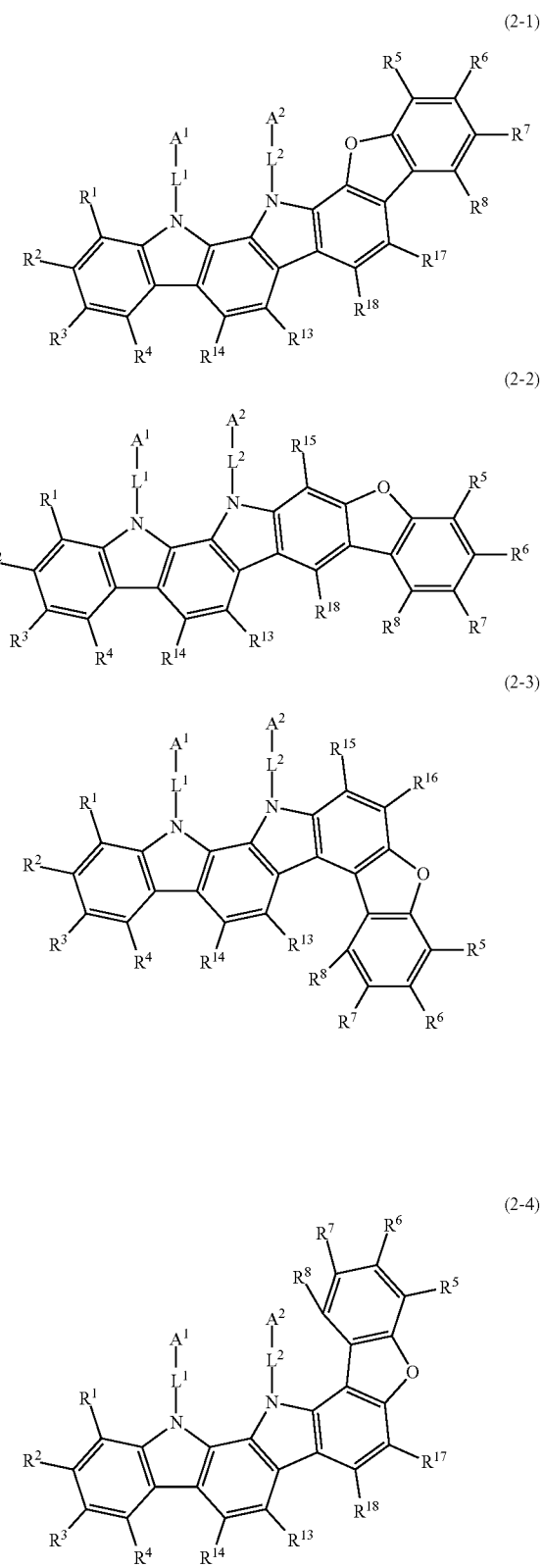
wherein in the formulas (3-1) and (3-4) to (3-6),
$A^1$, $A^2$, $L^1$, $L^2$, *3 and *4 are as defined in the formula (1); and
$R^1$ to $R^8$ and $R^{11}$ to $R^{18}$ are as defined in the formula (2).
5. The compound according to claim 4, wherein the compound represented by the formula (3-1) is selected from the group consisting of compounds represented by the following formulas (2-1) to (2-6):

(2-5)

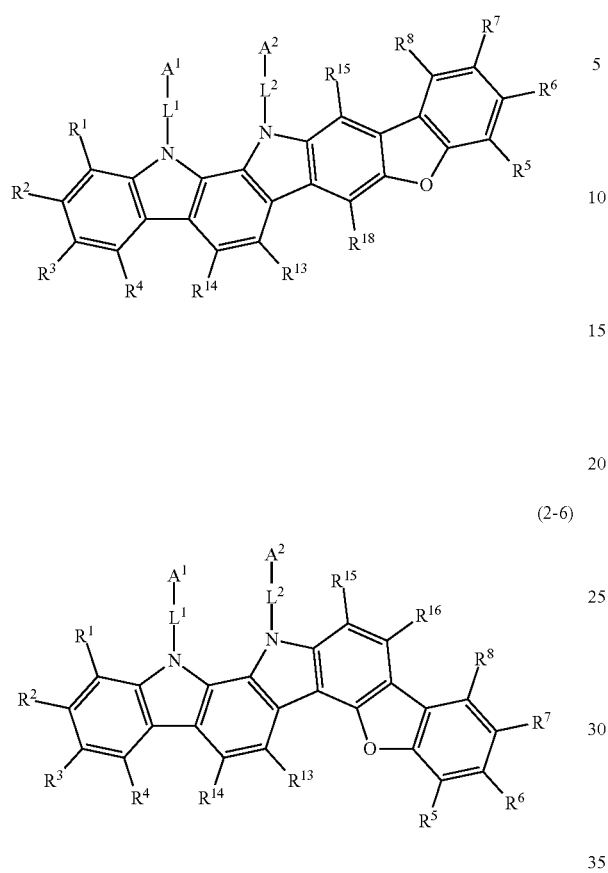

(2-6)

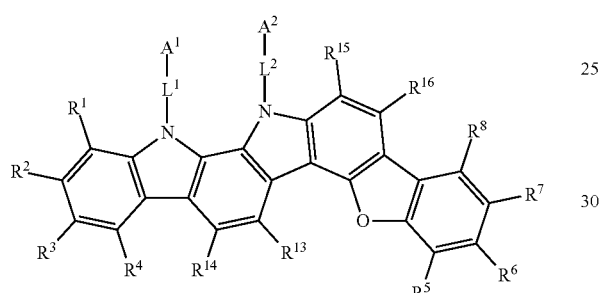

wherein in the formulas (2-1) to (2-6),

A¹, A², L¹ and L² are as defined in the formula (1); and R¹ to R⁸ and R¹¹ to R¹⁸ are as defined in the formula (2).

6. The compound according to claim 5, wherein the compound represented by the formula (3-1) is selected from the group consisting of compounds represented by the formulas (2-2) to (2-4) and (2-6).

7. The compound according to claim 4, wherein the compound represented by the formula (3-4) or (3-5) is selected from the group consisting of compounds represented by the following formulas (2-19) to (2-30):

(2-19)

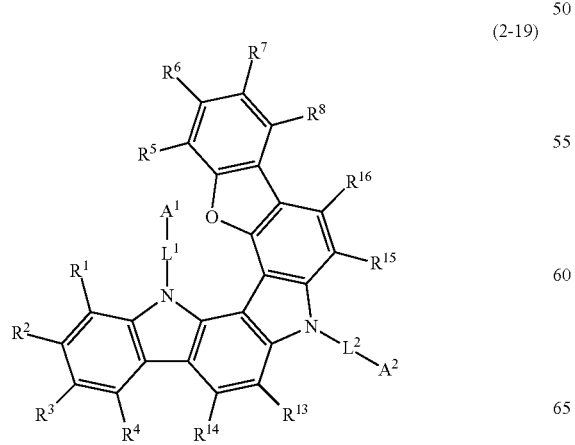

(2-20)

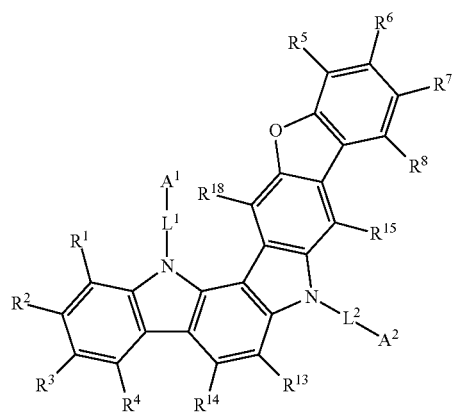

(2-21)

(2-22)

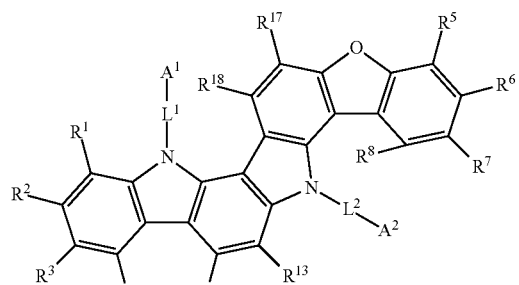

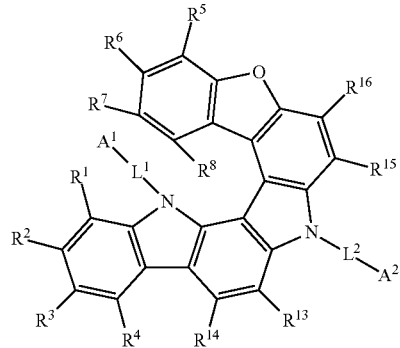

(2-23)

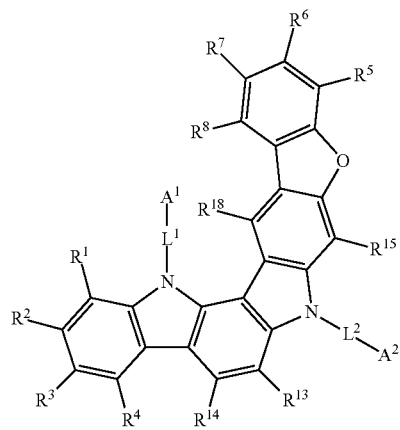

(2-24)
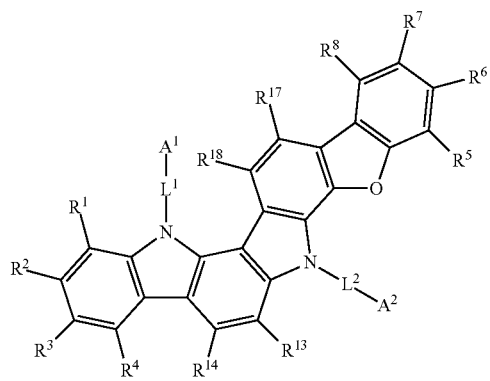
(2-25)
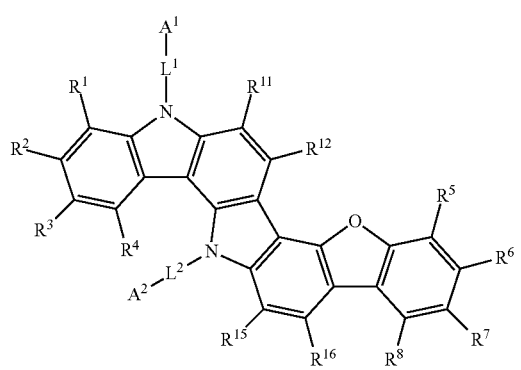
(2-26)
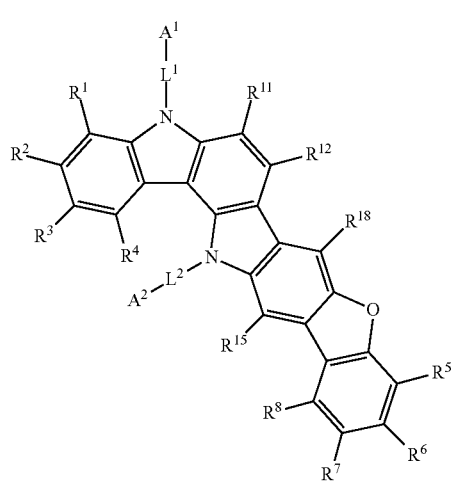
(2-27)
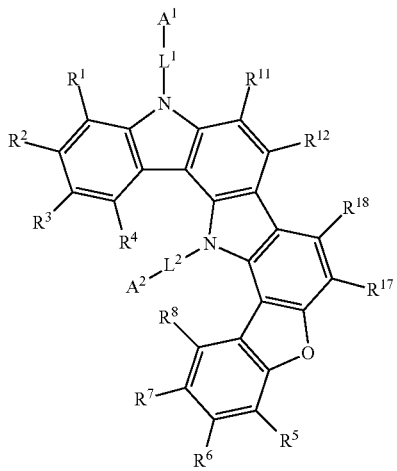
(2-28)
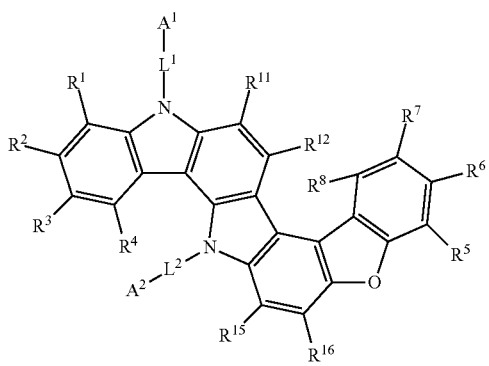
(2-29)
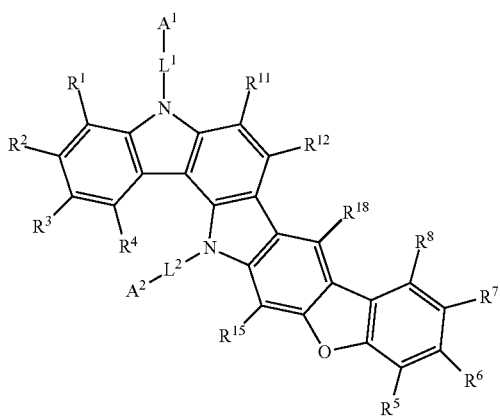

(2-30)
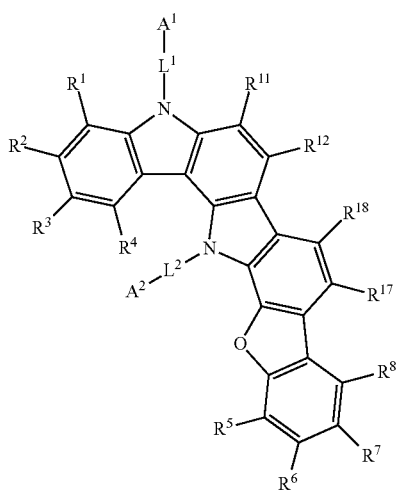
wherein in the formulas (2-19) to (2-30),
$A^1$, $A^2$, $L^1$ and $L^2$ are as defined in the formula (1); and
$R^1$ to $R^8$ and $R^{11}$ to $R^{18}$ are as defined in the formula (2).
8. The compound according to claim 4, wherein the compound represented by the formula (3-6) is selected from the group consisting of compounds represented by the following formulas (2-31) to (2-36):
(2-31)
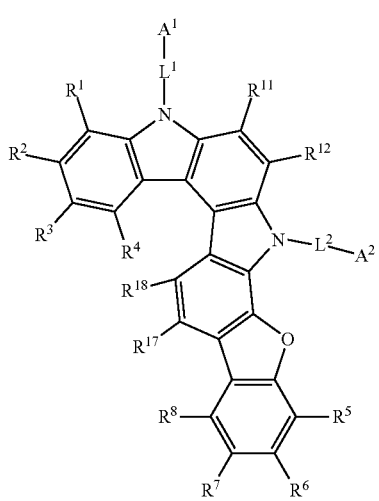
(2-32)
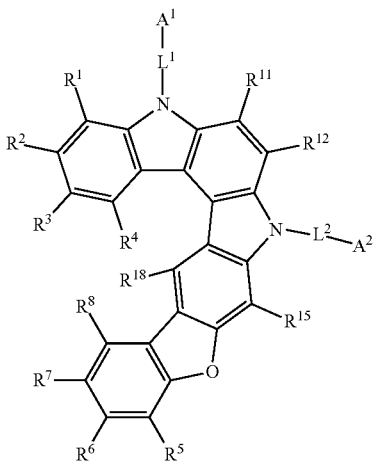
(2-33)
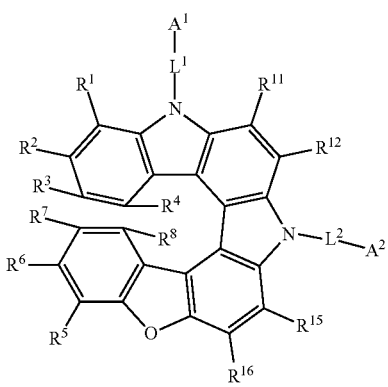
(2-34)
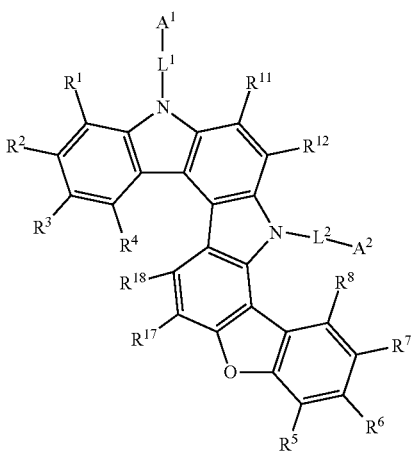

(2-35)

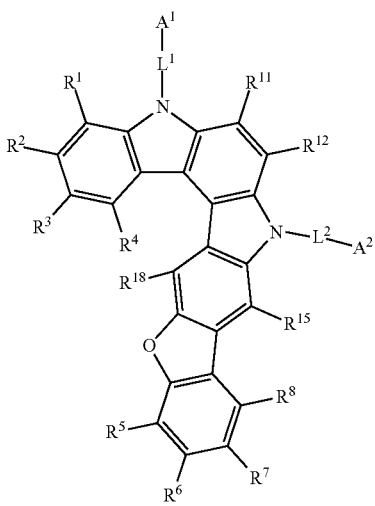

(2-36)

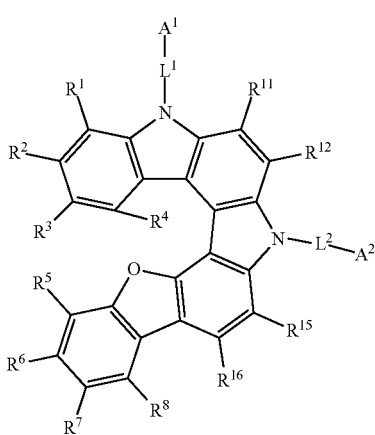

wherein in the formulas (2-31) to (2-36),
$A^1, A^2, L^1$ and $L^2$ are as defined in the formula (1); and
$R^1$ to $R^8$ and $R^{11}$ to $R^{18}$ are as defined in the formula (2).

9. The compound according to claim 3, wherein $R^1$ to $R^8$ are a hydrogen atom.

10. The compound according to claim 4, wherein the compound represented by the formula (3-1) is a compound represented by the following formula (3-1-1):

(3-1-1)

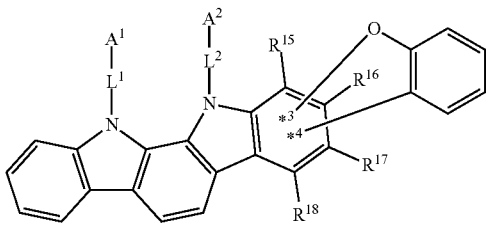

wherein in the formula (3-1-1),
$A^1, A^2, L^1, L^2, *3$ and $*4$ are as defined in the formula (1); and
$R^{15}$ to $R^{18}$ are as defined in the formula (2) and any one selected from $R^{15}$, $R^{17}$ and $R^{18}$ forms a single bond with $*4$.

11. The compound according to claim 4, wherein the compounds represented by the formulas (3-4) and (3-5) are respectively a compound represented by the following formulas (3-4-1) and (3-5-1):

(3-4-1)

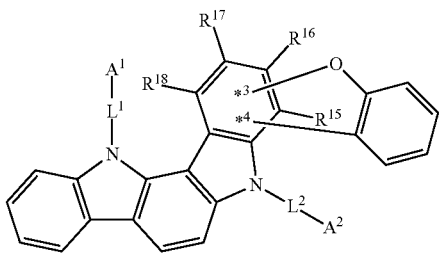

(3-5-1)

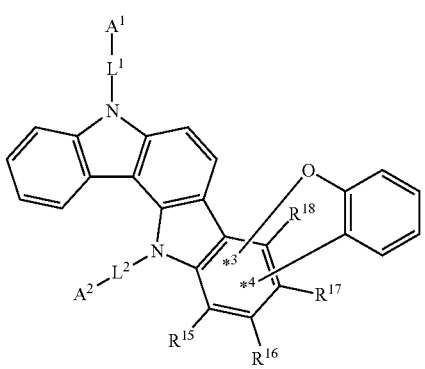

wherein in the formulas (3-4-1) and (3-5-1),
$A^1, A^2, L^1, L^2$ and $*3$ and $*4$ are as defined in the formula (1); and
$R^{15}$ to $R^{18}$ are as defined in the formula (2), and any one selected from $R^{15}$, $R^{17}$ and $R^{18}$ forms a single bond with $*4$.

12. The compound according to claim 4, wherein the compound represented by the formula (3-6) is a compound represented by the following formula (3-6-1), (3-6-1)

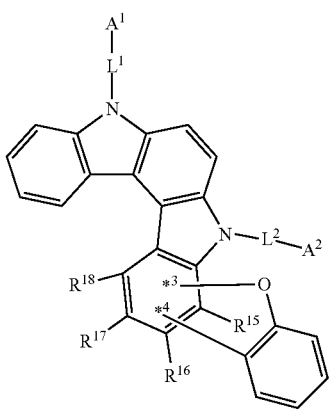

wherein in the formula (3-6-1),
$A^1, A^2, L^1, L^2, *3$ and $*4$ are as defined in the formula (1); and
$R^{15}$ to $R^{18}$ are as defined in the formula (2), and any one selected from $R^{15}$, $R^{17}$ and $R^{18}$ forms a single bond with $*4$.

13. The compound according to claim 1, wherein $A^1$ or $A^2$ that is not the monovalent residue of a compound represented by the formula (a2) is a substituted or unsubstituted aryl group including 6 to 24 ring carbon atoms or a substituted or unsubstituted heteroaryl group including 5 to 24 ring atoms and having, as the ring atom, one or more atoms selected from the group consisting of a nitrogen atom, an oxygen atom and a sulfur atom.

14. The compound according to claim 13, wherein in $A^1$ or $A^2$ that is not the monovalent residue of a compound represented by the formula (a2), the substituted or unsubstituted aryl groups including 6 to 24 ring carbon atoms is a substituted or unsubstituted fused aryl group including 10 to 24 ring carbon atoms.

15. The compound according to claim 14, wherein in $A^1$ or $A^2$ that is not the monovalent residue of a compound represented by the formula (a2), the fused aryl group including 10 to 24 ring carbon atoms is a monovalent residue of a compound represented by the following formula (a1-1) or (a1-2):

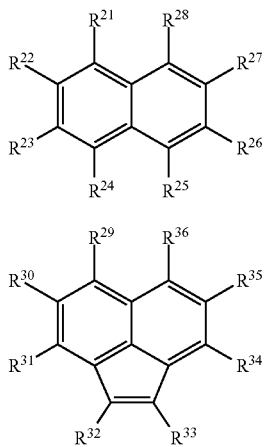

wherein in the formulas (a1-1) and (a1-2),
$R^{21}$ to $R^{36}$ are independently a hydrogen atom or a substituent $R^b$, and when plural $R^b$s are present, the plural $R^b$s may be the same as or different from each other, and two selected from the plural $R^b$s may be bonded to each other to form a ring.

16. The compound according to claim 14, wherein in $A^1$ or $A^2$ that is not the monovalent residue of a compound represented by the formula (a2), the substituted or unsubstituted fused aryl group including 10 to 24 ring carbon atoms is selected from the group consisting of fused rings each being formed of 4 or more rings.

17. The compound according to claim 1, wherein the monovalent residue of the compound represented by the formula (a2) is a monovalent residue of the compound represented by the following formula (a2-1):

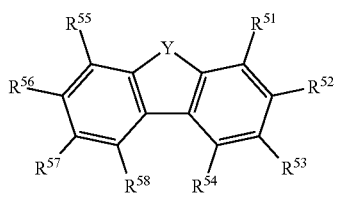

wherein in the formula (a2-1),
Y is as defined in the formula (a2); and
$R^{51}$ to $R^{58}$ are independently a hydrogen atom or a substituent $R^b$, and when plural $R^b$s are present, the plural $R^b$s may be the same as or different from each other, and two selected from the plural $R^b$s may be bonded to each other to form a ring.

18. The compound according to claim 13, wherein in $A^1$ or $A^2$ that is not the monovalent residue of a compound represented by the formula (a2), the heteroaryl groups including 5 to 24 ring atoms and having, as the ring atom, one or more atoms selected from the group consisting of a nitrogen atom, an oxygen atom and a sulfur atom is a monovalent residue of a compound represented by the following formula (a3):

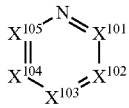

wherein in the formula (a3),
$X^{101}$ to $X^{105}$ are independently CH, C($R^b$) or a nitrogen atom; and
$R^b$ is a substituent, and when plural $R^b$s are present, the plural $R^b$s may be the same as or different from each other, and two selected from the plural $R^b$s may be bonded to each other to form a ring.

19. The compound according to claim 18, wherein the monovalent residue of the compound represented by the formula (a3) is a monovalent residue of a compound represented by the following formula (a3-1):

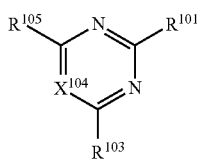

wherein in the formula (a3-1),
$X^{104}$ is as defined in the formula (a3); and
$R^{101}$, $R^{103}$ and $R^{105}$ are independently a hydrogen atom or a substituent $R^b$.

20. The compound according to claim 18, wherein the monovalent residue of the compound represented by the formula (a3) is a monovalent residue of a compound represented by the following formula (a3-2):

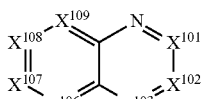

wherein in the formula (a3-2),
$X^{101}$ to $X^{103}$ and $X^{106}$ to $X^{109}$ are independently CH, C($R^b$) or a nitrogen atom; and
$R^b$ is a substituent, and when plural $R^b$s are present, the plural $R^b$s may be the same as or different from each other, and two selected from the plural $R^b$s may be bonded to each other to form a ring.

21. The compound according to claim 20, wherein the monovalent residue of the compound represented by the formula (a3-2) is a monovalent residue of a compound represented by the following formula (a3-2-1):

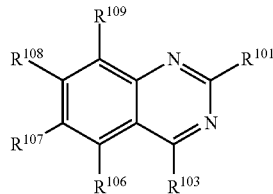
(a3-2-1)

wherein in the formula (a3-2-1), $R^{101}$, $R^{103}$ and $R^{106}$ to $R^{109}$ are independently a hydrogen atom or a substituent $R^b$, and when plural $R^b$s are present, the plural $R^b$s may be the same as or different from each other, and two selected from the plural $R^b$s may be bonded to each other to form a ring.

22. The compound according to claim 1, wherein $A^2$ that is not the monovalent residue of a compound represented by the formula (a2) is a substituted or unsubstituted heteroaryl group including 5 to 50 ring atoms.

23. The compound according to claim 22, wherein $A^2$ that is not the monovalent residue of a compound represented by the formula (a2) is a substituted or unsubstituted heteroaryl group including 5 to 24 ring atoms, and having, as the ring atoms, one or more atoms selected from the group consisting of a nitrogen atom, an oxygen atom and a sulfur atom.

24. The compound according to claim 3, wherein the compound represented by the formula (2) is selected from the group consisting of compounds represented by the following formulas (3-a) to (3-d):

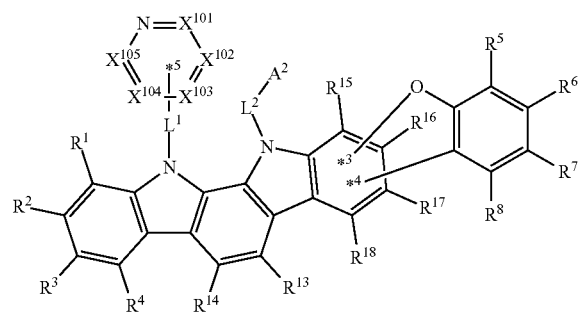
(3-a)

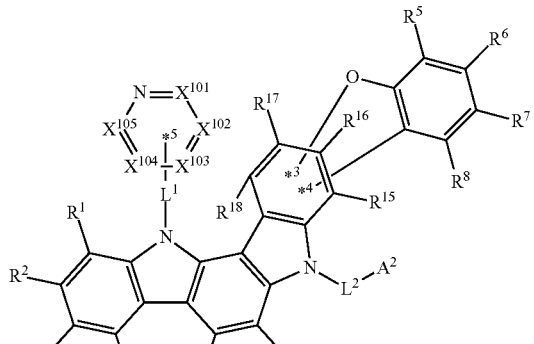
(3-b)

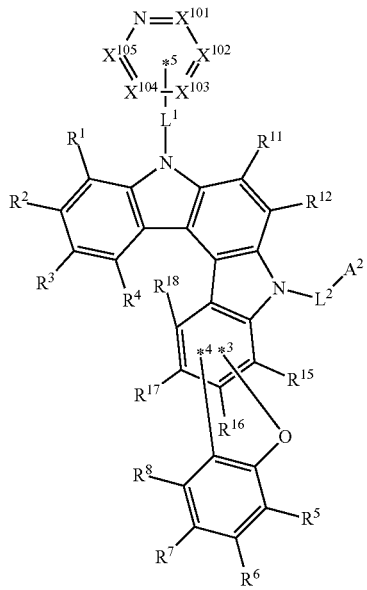
(3-c)

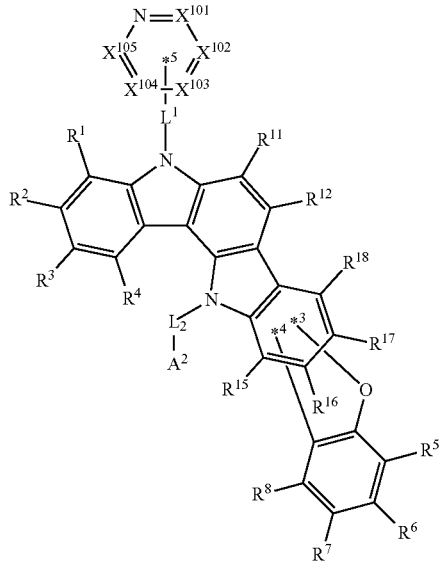
(3-d)

wherein in the formulas (3-a) to (3-d),
$A^2$, $L^1$, $L^2$ and *1 to *4 are as defined in the formula (1);
$R^1$ to $R^8$ and $R^{11}$ to $R^{18}$ are as defined in the formula (2);
$X^{101}$ to $X^{105}$ are as defined in the formula (a3); and \*5 is an atomic bonding that forms a single bond with any one of $X^{101}$ to $X^{105}$.

25. The compound according to claim 24, wherein the compounds represented by the formulas (3-a) to (3-d) are independently compounds represented by the following formulas (4-a) to (4-d):

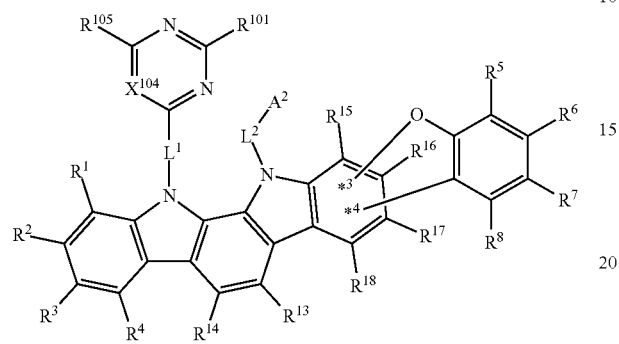
(4-a)

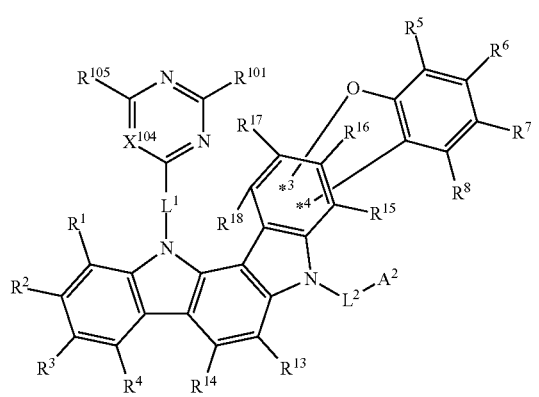
(4-b)

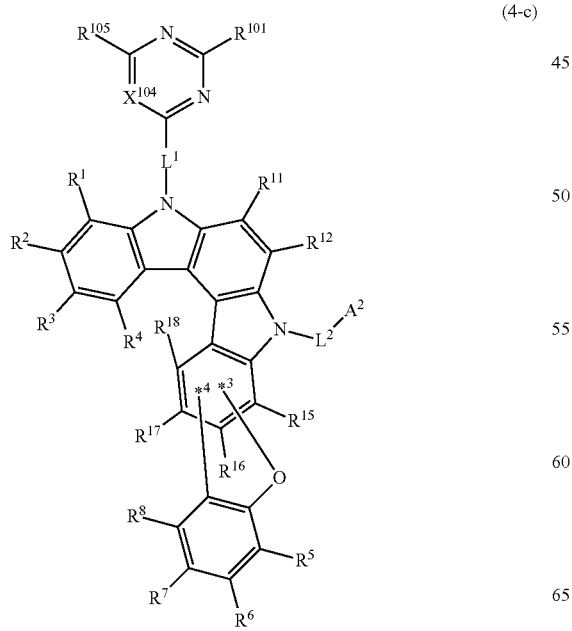
(4-c)

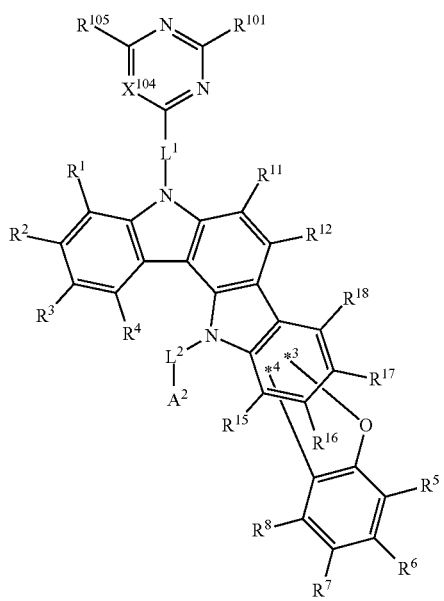
(4-d)

wherein in the formulas (4-a) to (4-d);

$A^2$, $L^1$, $L^2$ and \*1 to \*4 are as defined in the formula (1);

$R^1$ to $R^8$ and $R^{11}$ to $R^{18}$ are as defined in the formula (2);

$X^{104}$ is as defined in the formula (a3); and $R^{101}$ and $R^{105}$ are as defined in the formula (a3-1).

26. The compound according to claim 1, wherein $L^1$ and $L^2$ are independently a single bond or a group selected from the following formulas (i) to (vii):

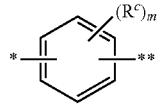
(i)

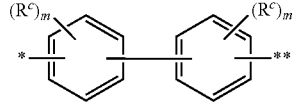
(ii)

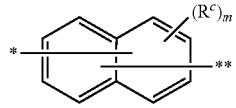
(iii)

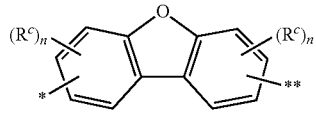
(iv)

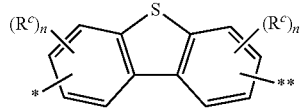
(v)

-continued

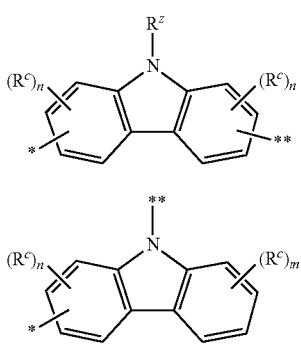

(vi)

(vii)

wherein in the formulas (i) to (vii),

* and ** are independently an atomic bonding that forms a single bond with N and any one of $A^1$ and $A^1$ in the formula (1);

$R^c$ is a substituent, and when plural $R^c$'s are present, the plural $R^c$'s may be the same as or different from each other, and two selected from the plural $R^c$'s may be bonded to each other to form a ring structure;

$R^z$ is a hydrogen atom or a substituent $R^c$; and m is independently an integer of 0 to 4, and n is independently an integer of 0 to 3.

27. The compound according to claim 1, wherein $L^1$ is a substituted or unsubstituted arylene group including 6 to 60 ring carbon atoms.

28. The compound according to claim 26, wherein $L^1$ is selected from the group consisting of the groups represented by the formulas (i) to (iii).

29. A material for an organic electroluminescence device that comprises the compound according to claim 1.

30. An organic electroluminescence device comprising a cathode, an anode and one or more organic thin film layers between the cathode and the anode, wherein
the one or more organic thin film layers include an emitting layer, and at least one layer of the one or more organic thin layers comprises the compound according to claim 1.

31. The organic electroluminescence device according to claim 30, wherein the emitting layer comprises the compound.

32. The organic electroluminescence device according to claim 30, wherein the emitting layer further comprises one or more selected from a fluorescent emitting material and a phosphorescent emitting material.

33. The organic electroluminescence device according to claim 30, wherein the one or more organic thin film layers further include a hole-transporting layer.

34. The organic electroluminescence device according to claim 30, wherein the one or more organic thin film layers further comprise an electron-transporting layer.

35. An electronic apparatus in which the organic electroluminescence device according to claim 30 is mounted.

* * * * *

UNITED STATES PATENT AND TRADEMARK OFFICE
CERTIFICATE OF CORRECTION

PATENT NO. : 10,703,762 B2
APPLICATION NO. : 15/329167
DATED : July 7, 2020
INVENTOR(S) : Yu Kudo et al.

It is certified that error appears in the above-identified patent and that said Letters Patent is hereby corrected as shown below:

In the Claims

Claim 1, Column 577, Line 34:
Please delete:
"of $Y^5$ to rare"
Please replace with:
of $Y^5$ to $Y^8$ are Claim 2, Column 578, Line 32:
Please delete:
"$Y^1$ to V."
Please replace with:
$Y^1$ to $Y^8$ Claim 3, Column 578, Line 57:
Please delete:
"$R^{14}$ care independently"
Please replace with:
$R^{14}$ are independently Signed and Sealed this
Second Day of February, 2021

Drew Hirshfeld
*Performing the Functions and Duties of the*
*Under Secretary of Commerce for Intellectual Property and*
*Director of the United States Patent and Trademark Office*

Please replace Formula (3-6) Claim 4, Column 579, Lines 44-61, with:

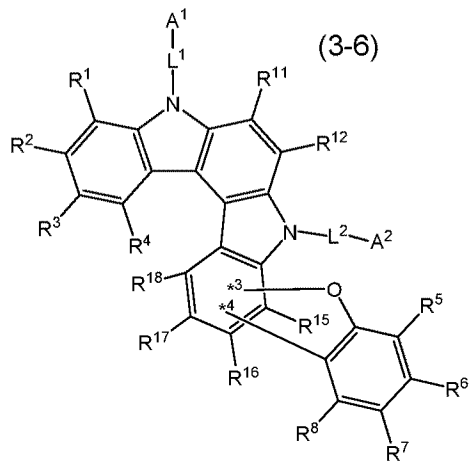

Claim 26, Column 595, Lines 19-23:
Please delete:
"a single bond with N and any one of $A^1$ and $A^1$ in the formula (1);
$R^c$ is a substituent, and when plural $R^c$'s are present, the plural $R^c$'s may be the same as or different from each other, and two selected from the plural $R^c$'s may be bonded to each other to form a ring structure;"
Please replace with:
a single bond with N and any one of $A^1$ and $A^2$ in the formula (1);
$R^c$ is a substituent, and when plural $R^c$s are present, the plural $R^c$s may be the same as or different from each other, and two selected from the plural $R^c$s may be bonded to each other to form a ring structure;